US006849619B2

(12) United States Patent
Robichaud et al.

(10) Patent No.: US 6,849,619 B2
(45) Date of Patent: Feb. 1, 2005

(54) SUBSTITUTED PYRIDOINDOLES AS SEROTONIN AGONISTS AND ANTAGONISTS

(75) Inventors: Albert J. Robichaud, Ringoes, NJ (US); John M. Fevig, Doylestown, PA (US); Ian S. Mitchell, Lafayette, CO (US); Taekyu Lee, Doylestown, PA (US); Wenting Chen, Langhorne, PA (US); Joseph Cacciola, Newark, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/784,064

(22) Filed: Feb. 20, 2004

(65) Prior Publication Data

US 2004/0186094 A1 Sep. 23, 2004

Related U.S. Application Data

(63) Continuation-in-part of application No. 10/026,611, filed on Dec. 19, 2001, now Pat. No. 6,699,852.
(60) Provisional application No. 60/256,740, filed on Dec. 20, 2000.

(51) Int. Cl.[7] .................. A61K 31/33; A61K 31/55; C07D 245/00; C07D 267/02; C07D 223/14
(52) U.S. Cl. ............ 514/183; 514/212.05; 514/214.02; 514/214.03; 514/286; 514/288; 540/468; 540/472; 540/477; 540/544; 540/556; 540/576; 540/596; 540/604; 546/63; 548/421; 548/424; 548/425
(58) Field of Search ............... 514/183, 212.05, 514/214.03, 286, 288; 540/472, 477, 544, 556, 576, 596, 604; 546/63; 548/421, 424, 425

(56) References Cited

U.S. PATENT DOCUMENTS

| | | | |
|---|---|---|---|
| 3,299,078 A | 1/1967 | Pachter | 546/67 |
| 3,914,421 A | * 10/1975 | Rajagopalan | 514/229.5 |
| 4,013,652 A | 3/1977 | Rajogopalan | 544/96 |
| 4,088,647 A | 5/1978 | Glushkov et al. | 544/343 |
| 4,115,577 A | 9/1978 | Rajogopalan | 514/211.1 |
| 4,183,936 A | 1/1980 | Rajogopalan | 514/211.1 |
| 4,219,550 A | 8/1980 | Rajogopalan | 514/221.1 |
| 4,238,607 A | 12/1980 | Rajogopalan | 514/14 |
| 4,997,831 A | 3/1991 | Bays et al. | 514/211.1 |
| 5,100,884 A | 3/1992 | Hamminga et al. | 544/183 |
| 5,223,625 A | 6/1993 | Van Wijngaarden et al. | 546/70 |
| 5,328,905 A | 7/1994 | Hamminga et al. | 514/214.02 |
| 6,407,092 B1 | 6/2002 | Hester et al. | 514/215 |

FOREIGN PATENT DOCUMENTS

| | | |
|---|---|---|
| CA | 2011107 | 8/1991 |
| EP | 0725068 | 8/1996 |
| FR | 2213283 | 2/1974 |
| WO | 0064899 | 11/2000 |
| WO | 0077001 | 12/2000 |

OTHER PUBLICATIONS

Hoyer, D. et al., "VII International Union of Pharmacology Classification of Receptors . . . ", Pharmacological Reviews, vol. 46, No. 2, Jun. 1, 1994, pp. 157–203 XP000604197.

Jenck, F. et al., "The Role of 5–HT2C Receptors in Affective Disorders", Exp. Opin. Ther. Patents, vol. 7, No. 10, 1998, pp. 1587–1599 XP002210253.

Martin, J.R. et al., "5–HT2C Receptor Agonists: Pharmacological Characteristics and Therapeutic Potential", J. Pharmacol. Exp. Ther., vol. 286, No. 2, Aug. 1996, pp. 913–924 XP00221024.

* cited by examiner

Primary Examiner—Richard L. Raymond
Assistant Examiner—Sudhaker B. Patel
(74) Attorney, Agent, or Firm—Sammy G. Duncan, Jr.

(57) ABSTRACT

The present invention is directed to certain novel compounds represented by structural Formula (I)

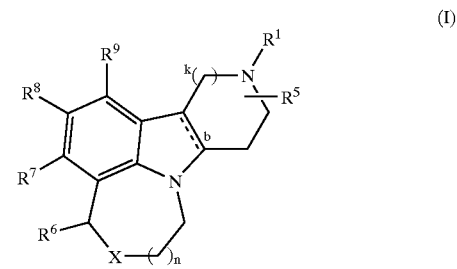

or pharmaceutically acceptable salt forms thereof, wherein $R^1$, $R^5$, $R^6$, $R^7$, $R^8$, $R^9$, X, b, k, and n, and the dashed lines are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

26 Claims, No Drawings

SUBSTITUTED PYRIDOINDOLES AS SEROTONIN AGONISTS AND ANTAGONISTS

RELATED APPLICATIONS

This is a continuation-in-part of U.S. application Ser. No. 10/026,611, filed Dec. 19, 2001, now U.S. Pat. No. 6,699,852, that claims the benefit of U.S. Provisional Application Ser. No. 60/256,740, filed Dec. 20, 2000, the contents of which are herein incorporated by reference.

FIELD OF THE INVENTION

The present invention is directed to certain novel compounds represented by structural Formula (D)

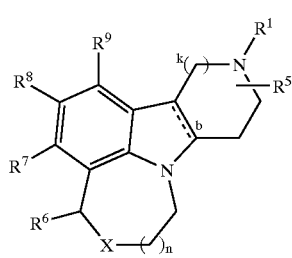

(I)

or pharmaceutically acceptable salt forms thereof, wherein $R^1$, $R^5$, $R^6$, $R^7$, $R^8$, $R^9$, X, b, k, and n, and the dashed line are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

BACKGROUND OF THE INVENTION

There exists a substantial correlation for the relationship between 5-HT2 receptor modulation and a variety of diseases and therapies. To date, three subtypes of the 5-M receptor class have been identified, 5-HT2A, 5-HT2B, and 5-HT2C. Prior to the early 1990's the 5-HT2C and 5-HT2A receptors were referred to as 5-HT1C and 5-HT2, respectively.

The agonism or antagonism of 5-HT2 receptors, either selectively or nonselectively, has been associated with the treatment of various central nervous system (CNS) disorders. Ligands possessing affinity for the 5-HT2 receptors have been shown to have numerous physiological and behavioral effects (Trends in Pharmacological Sciences, 11, 181, 1990). In the recent past the contribution of serotonergic activity to the mode of action of antidepressant drugs has been well documented. Compounds that increase the overall basal tone of serotonin in the CNS have been successfully developed as antidepressants. The serotonin selective reuptake inhibitors (SSRI) function by increasing the amount of serotonin present in the nerve synapse. These breakthrough treatments, however, are not without side effects and suffer from delayed onset of action (Leonard, J. Clin. Psychiatry, 54(suppl), 3, 1993). Due to the mechanism of action of the SSRIs, they effect the activity of a number of serotonin receptor subtypes. This non-specific modulation of the serotonin family of receptors most likely plays a significant role in the side effect profile. In addition, these compounds often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

There is ample evidence to support the role of selective 5-HT2 receptor ligands in a number of disease therapies. Modulation of 5-HT2 receptors has been associated with the treatment of schizophrenia and psychoses (Ugedo, L., et. al., Psychopharmacology, 98, 45, 1989). Mood, behavior and hallucinogenesis can be affected by 5-HT2 receptors in the limbic system and cerebral cortex. 5-HT2 receptor modulation in the hypothalamus can influence appetite, thermoregulation, sleep, sexual behavior, motor activity, and neuroendocrine function (Hartig, P., et. al., Annals New York Academy of Science, 149, 159). There is also evidence indicating that 5-HT2 receptors mediate hypoactivity, effect feeding in rats, and mediate penile erections (Pyschopharmacology, 101, 57, 1990).

Compounds exhibiting selectivity for the 5-HT2B receptor are useful in treating conditions such as tachygastria, hypermotility associated with irritable bowel disorder, constipation, dyspepsia, and other peripherally mediated conditions.

5-HT2A antagonists have been shown to be effective in the treatment of schizophrenia, anxiety, depression, and migraines (Koek, W., Neuroscience and Behavioral reviews, 16, 95, 1996). Aside from the beneficial antipsychotic effects, classical neuroleptic are frequently responsible for eliciting acute extrapyramidal side effects and neuroendocrine disturbances. These compounds generally possess signifcant dopamine D2 receptor affinity (as well as other nuisance receptor affinity) which frequently is associated with extra pyramidal symptoms and tardive dyskinesia, thus detracting from their efficacy as front line treatments in schizophrenia and related disorders. Compounds possessing a more favorable selectivity profile would represent a possible improvement for the treatment of CNS disorders.

U.S. Pat. Nos. 3,914,421; 4,013,652; 4,115,577; 4,183,936; and 4,238,607 disclose pyridopyrrolobenzheterocycles of formula:

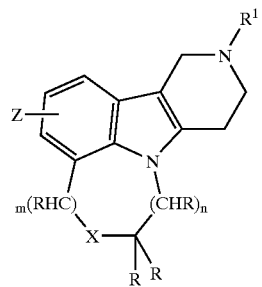

where X is O, S, S(=O), or $SO_2$; n is 0 or 1; m is 0 or 1; R and $R^1$ are various carbon substituents; and Z is a monosubstituent of H, methyl, or chloro.

U.S. Pat. No. 4,219,550 discloses pyridopyrrolo-benzheterocycles of formula:

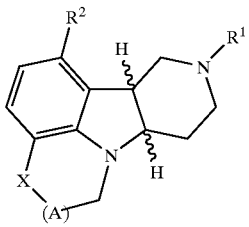

where X is O or S; $R^1$ is $C_{1-4}$ alkyl or cyclopropyl; $R^2$ is H, $CH_3$, $OCH_3$, Cl, Br, F, or $CF_3$; and (A) is —$CH_2$—, —$CH(CH_3)$—, or —$CH_2CH_2$—.

None of the above references suggest or disclose the compounds of the present invention.

There remains a need to discover new compounds useful as serotonin agonists and antagonists which are useful in the control or prevention of central nervous system disorders. As such, the present invention discloses novel compounds which are of low molecular weight, useful as serotonin agonists and antagonists, and provide good in vitro potency.

SUMMARY OF THE INVENTION

One object of the present invention is to provide novel compounds which are useful as agonists or antagonists of 5-HT2 receptors, more specifically 5-HT2A and 5-HT2C receptors, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility comprising administering to a host in need of such treatment a therapeutically effective amount of at least one of the compounds of the present invention or a pharmaceutically acceptable salt or prodrug form thereof. More specifically, the present invention provides a method for treating obesity anxiety, depression, or schizophrenia.

These and other objects, which will become apparent during the following detailed description, have been achieved by the inventors' discovery that compounds of Formula (1):

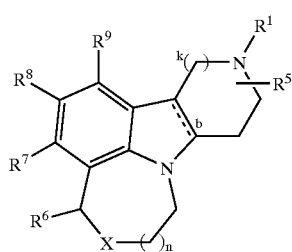

(I)

or pharmaceutically acceptable salt or prodrug forms thereof, wherein $R^1$, $R^5$, $R^6$, $R^7$, $R^8$, $R^9$, X, b, k, and n are defined below, are effective agonists or antagonists of 5-HT2 receptors.

DETAILED DESCRIPTION OF THE EMBODIMENTS

Thus, in a first embodiment, the present invention provides a novel compound of Formula (1):

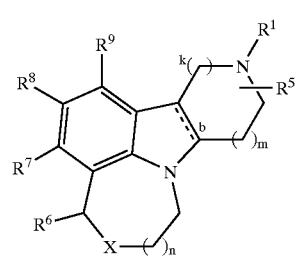

(I)

or stereoisomers or pharmaceutically acceptable salt forms thereof, wherein:

b is a single bond or a double bond;

X is —O—, —S—, —S(=O), —S(=O)$_2$—, or —NR$^{10}$—;

$R^1$ is selected from

H,

C(=O)R$^2$,

C(=O)OR$^2$, $C_{1-8}$ alkyl, $C_{2-8}$ alkenyl, $C_{2-8}$ alkynyl, $C_{3-7}$ cycloalkyl, $C_{1-6}$ alkyl substituted with Z, $C_{2-6}$ alkenyl substituted with Z, $C_{2-6}$ alkynyl substituted with Z, $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{1-3}$ alkyl substituted with Y, $C_{2-3}$ alkenyl substituted with Y, $C_{2-3}$ alkynyl substituted with Y, $C_{1-6}$ alkyl substituted with 0–2 R$^2$, $C_{2-6}$ alkenyl substituted with 0–2 R$^2$, $C_{2-6}$ alkynyl substituted with 0–2 R$^2$, aryl substituted with 0–2 R$^2$, and 5–6 membered heterocyclic ring system containing at least one heteroatom selected from the group consisting of N, O, and S, said heterocyclic ring system substituted with 0–2 R$^2$;

Y is selected from $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{3-6}$ cycloalkyl substituted with —($C_{1-3}$ alkyl)-Z, aryl substituted with —($C_{1-3}$ alkyl)-Z, and 5–6 membered heterocyclic ring system containing at least one heteroatom selected from the group consisting of N, O, and S, said heterocyclic ring system substituted with —($C_{1-3}$ alkyl)-Z;

Z is selected from H,
—CH(OH)$R^2$,
—C(ethylenedioxy)$R^2$,
—$OR^2$,
—$SR^2$,
—$NR^2R^3$,
—C(O)$R^2$,
—C(O)$NR^2R^3$,
—$NR^3$C(O)$R^2$,
—C(O)$OR^2$,
—OC(O)$R^2$,
—CH(=$NR^4$)$NR^2R^3$,
—NHC(=$NR^4$)$NR^2R^3$,
—S(O)$R^2$,
—S(O)$_2R^2$,
—S(O)$_2NR^2R^3$, and —$NR^3$S(O)$_2R^2$;

$R^2$, at each occurrence, is independently selected from
halo,
$C_{1-3}$ haloalkyl,
$C_{1-4}$ alkyl,
$C_{2-4}$ alkenyl,
$C_{2-4}$ alkyl,
$C_{3-6}$ cycloalkyl,
aryl substituted with 0–5 $R^{42}$;
$C_{3-10}$ carbocyclic residue substituted with 03 $R^{41}$, and
5–10 membered heterocyclic ring system containing from 1–4 heteroatoms selected from the group consisting of N, O, and S substituted with 0–3 $R^{41}$;

$R^3$, at each occurrence, is independently selected from
H, $C_{1-4}$ alkyl, $C_{2-4}$ alkenyl, $C_{2-4}$ alkynyl, and
$C_{1-4}$ alkoxy;
alternatively, $R^2$ and $R^3$ join to form a 5- or 6-membered ring optionally substituted with —O— or —N($R^4$)—;

$R^4$, at each occurrence, is independently selected from H and $C_{1-4}$ alkyl;

$R^5$ is H or $C_{1-4}$ alkyl;
$R^6$ is H or $C_{1-4}$ alkyl;
$R^7$ and $R^9$, at each occurrence, are independently selected from
H, halo, —$CF_3$, —$OCF_3$, —OH, —CN, —$NO_2$, —$NR^{46}R^{47}$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^8$ is selected from
H, halo, —$CF_3$, —$OCF_3$, —OH, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^{10}$ is selected from H,
$C_{1-4}$ alkyl substituted with 0–2 $R^{10A}$,
$C_{2-4}$ alkenyl substituted with 0–2 $R^{10A}$,
$C_{2-4}$ alkynyl substituted with 0–1 $R^{10A}$, and
$C_{1-4}$ alkoxy;

$R^{10A}$ is selected from
$C_{1-4}$ alkoxy,
$C_{3-6}$ carbocyclic residue substituted with 0–3 $R^{33}$,
phenyl substituted with 0–3 $R^{33}$, and
5–6 membered heterocyclic ring system containing 1, 2, or 3 heteroatoms selected from the group consisting of N, O, and S; substituted with 0–2 $R^{44}$;

$R^{11}$ is selected from
H, halo, —$CF_3$, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, $C_{3-0}$ cycloalkyl,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^2$C(O)$OR^{15}$, $NR^{12}$S(O)$_2R^{15}$, and $NR^{12}$C(O)$NHR^{15}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
  H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)—;
alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;
$R^{14}$, at each occurrence, is independently selected from H and $C_{1-4}$ alkyl;
$R^{15}$, at each occurrence, is independently selected from
  H, $C_{1-4}$ alkyl, $C_{2-4}$ alkenyl, and $C_{2-4}$ alkynyl;
$R^{16}$, at each occurrence, is independently selected from
  H, OH, halo, CN, $NO_2$, $CF_3$, $SO_2R^{45}$, $NR^{46}R^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, $C_{1-3}$ alkyloxy-, and =O;
$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O), ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O), or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=OC, or ($C_{1-4}$ alkyl)$CO_2$—;
$R^{33}$, at each occurrence, is independently selected from
  H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, (CIA alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;
$R^{41}$, at each occurrence, is independently selected from
  H, $CF_3$, halo, OH, $CO_2H$, $SO_2R^{45}$, $NR^{46}R^{47}$, $NO_2$, CN, =O;
  $C_{2-8}$ alkenyl, $C_{2-8}$ alkynyl, $C_{1-4}$ alkoxy, $C_{1-4}$ haloalkyl
  $C_{1-4}$ alkyl substituted with 0–1 $R^{43}$,
  aryl substituted with 0–3 $R^{42}$, and
  5–10 membered heterocyclic ring system containing from 1–4 heteroatoms selected from the group consisting of N, O, and S substituted with 0–3 $R^{44}$;
$R^{42}$, at each occurrence, is independently selected from
  H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, CH(=NH)$NH_2$, NHC(=NH)$NH_2$,
  $C_{2-6}$ alkenyl, $C_{2-6}$ alkynyl, $C_{1-4}$ alkoxy, $C_{1-4}$ haloalkyl, $C_{3-6}$ cycloalkyl,
  $C_{1-4}$ alkyl substituted with 0–1 $R^{43}$,
  aryl substituted with 0–3 $R^{44}$, and
  5–10 membered heterocyclic ring system containing from 1–4 heteroatoms selected from the group consisting of N, O, and S substituted with 0–3 $R^{44}$;
$R^{43}$ is $C_{3-6}$ cycloalkyl or aryl substituted with 0–3 $R^{44}$;
$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;
$R^{45}$ is $C_{1-4}$alkyl;
$R^{46}$, at each occurrence, is independently selected from H and $C_{1-4}$ alkyl;
$R^{47}$, at each occurrence, is independently selected from H, $C_{1-4}$ alkyl, —C(=O)NH($C_{1-4}$ alkyl), —$SO_2(C_{1-4}$ alkyl), —C(=O)O($C_{1-4}$ alkyl), —C(=O)($C_{1-4}$ alkyl), and —C(=O)H;
k is 1 or 2;
m is 0 or 1; and
n is 1 or 2;
provided that at least one of $R^7$, $R^8$ and $R^9$ is a 5–10 membered heterocyclic ring system containing from 1–4 heteroatoms selected from the group consisting of N, O and S substituted with 0–3 $R^{31}$.

[2]In a preferred embodiment the present invention provides a compound of Formula (I-a):

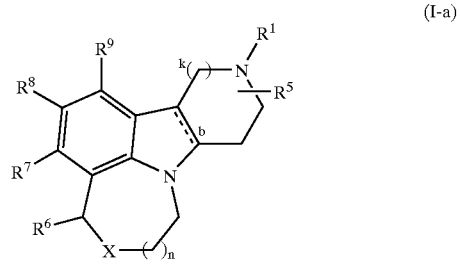

(I-a)

wherein:
X is —O—, —S—, —S(=O)—, —S(O)$_2$—, or —$NR^{10}$—;
$R^1$ is selected from
  H,
  C(=O)$R^2$,
  C(=O)O$R^2$,
  $C_{1-8}$ alkyl,
  $C_{2-8}$ alkenyl,
  $C_{2-8}$ alkynyl,
  $C_{3-7}$ cycloalkyl,
  $C_{1-6}$ alkyl substituted with 0–2 $R^2$,
  $C_{2-6}$ alkenyl substituted with 0–2 $R^2$,
  $C_{2-6}$ alkynyl substituted with 0–2 $R^2$,
  aryl substituted with 0–2 $R^2$, and
  5–6 membered heterocyclic ring system containing at least one heteroatom selected from the group consisting of N, O, and S, said heterocyclic ring system substituted with 0–2 $R^2$;
$R^2$, at each occurrence, is independently selected from
  F, Cl, $CH_2F$, $CHF_2$, $CF_3$,
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{42}$;
  $C_{3-10}$ carbocyclic residue substituted with 0–3 $R^{41}$, and
  5–10 membered heterocyclic ring system containing from 1–4 heteroatoms selected from the group consisting of N, O, and S substituted with 0–3 $R^{41}$;

$R^5$ is H, methyl, ethyl, propyl, or butyl;

$R^6$ is H, methyl, ethyl, propyl, or butyl;

$R^7$ and $R^9$, at each occurrence, are independently selected from

H, halo, —$CF_3$, —$OCF_3$, —OH, —CN, —$NO_2$, —$NR^{46}R^{47}$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^8$ is selected from

H, halo, —$CF_3$, —$OCF_3$, —OH, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^1$ 4)$NR^{12}R^{13}$, NHC(—$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^{10}$ is selected from H, $C_{1-4}$ alkyl, $C_{2-4}$ alkenyl, $C_{2-4}$ alkynyl, and $C_{1-4}$ alkoxy;

$R^{11}$ is selected from

H, halo, —$CF_3$, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^{12}$, at each occurrence, is independently selected from $C_{1-4}$ alkyl substituted with 0–1 $R^{12a}$, $C_{2-4}$ alkenyl substituted with 01 $R^{12a}$, $C_{2-4}$ alkynyl substituted with 0–1 $R^{12a}$, $C_{3-6}$ cycloalkyl substituted with 0–3 $R^{33}$, aryl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from

H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from

H, $C_{1-4}$ alkyl, $C_{2-4}$ alkenyl, and $C_{2-4}$ alkynyl;

$R^{16}$, at each occurrence, is independently selected from

H, OH, halo, CN, $NO_2$, $CF_3$, $SO_2R^{45}$, $NR^{46}R^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, $C_{1-3}$ alkyloxy- and =O;

$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, (CIA alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{33}$, at each occurrence, is independently selected from

H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(—O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{41}$, at each occurrence, is independently selected from

H, $CF_3$, halo, OH, $CO_2H$, $SO_2R^{45}$, $NR^{46}R^{47}$ $NO_2$, CN;

$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $NR^{46}R^{47}$, $NO_2$, CN, $CH(=NH)NH_2$, $NHC(=NH)NH_2$,
$C_{2-6}$ alkenyl, $C_{2-6}$ alkynyl, C 4 alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–1 0 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2; and n is 1 or 2.

[3]In another preferred embodiment the present invention provides a compound of Formula (I-a) wherein:
X is —O—, —S—, or —NH—;
$R^1$ is selected from
H,
$C(=O)R^2$,
$C(=O)OR^2$,
$C_{1-6}$ alkyl,
$C_{2-6}$ alkenyl,
$C_{2-6}$ alkynyl,
$C_{3-6}$ cycloalkyl,
$C_{1-4}$ alkyl substituted with 0–2 $R^2$,
$C_{2-4}$ alkenyl substituted with 0–2 $R^2$, and
$C_{2-4}$ alkynyl substituted with 0–2 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^5$ is H, methyl, ethyl, propyl, or butyl;
$R^6$ is H, methyl, ethyl, propyl, or butyl;
$R^7$ and $R^9$, at each occurrence, are independently selected from
H, halo, —$CF_3$, —$OCF_3$, —OH, —CN, —$NO_2$, —$NR^{46}R^{47}$,
$C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^8$ is selected from
H, halo, —$CF_3$, —$OCF_3$, —OH, —CN, —$NO_2$,
$C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^1$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —CN, —$NO_2$, $C_{1-6}$ alkyl,
$C_{2-6}$ alkenyl, $C_{2-6}$ alkynyl, $C_{1-4}$ haloalkyl, $C_{1-6}$ alkoxy, $C_{3-10}$ cycloalkyl,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^{12}$ at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$);
alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H, methyl, ethyl, propyl, and butyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from
H, OH, F, Cl, CN, $NO_2$, $CF_3$, $SO_2R^{45}$, $NR^{46}R^{47}$, —C(=O)H,
methyl, ethyl, methoxy, ethoxy, trifluoromethyl, trifluoromethoxy and =O;

$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}C$(=O), or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}C$(=O), or ($C_{1-4}$ alkyl)$CO_2$—;

$R^{33}$, at each occurrence, is independently selected from
H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}C$(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}C$(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}C$(=O)—, or ($C_{1-4}$ alkyl)$CO_2$—;

$R^{41}$, at each occurrence, is independently selected from
H, $CF_3$, halo, OH, $CO_2H$, $SO_2R^{45}$, $NR^{46}R^{47}$, $NO_2$, CN, $C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$alkyl;

$R^{46}$, at each occurrence, is independently selected from H and $C_{1-4}$ alkyl;

$R^{47}$, at each occurrence, is independently selected from H and C A4 alkyl;

k is 1 or 2; and n is 1 or 2.

[4] In another preferred embodiment the present invention provides a compound of Formula (I-a) wherein:

X is —S—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic residue substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^6$ is H;

$R^7$ and $R^9$, at each occurrence, are independently selected from
H, halo, —$CF_3$, —$OCF_3$, —OH, —CN, —$NO_2$, —$NR^{46}R^{47}$,
$C_{1-4}$ alkyl, $C_{2-4}$ alkenyl, $C_{2-4}$ alkenyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^8$ is selected from
H, halo, $CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from

H, halo, —$CF_3$, —CN, —$NO_2$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$, $C_{3-10}$ carbocyclic residue substituted with 0–3 $R^{33}$, aryl substituted with 0–5 $R^{33}$, and 5–6 membered heterocyclic ring system containing 1, 2, or 3 heteroatoms selected from the group consisting of N, O, and S substituted with 0–3 $R^{31}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with O—$R^{12a}$, $C_{3-6}$ cycloalkyl substituted with 0–3 $R^{33}$, aryl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from

H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)-;

alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one 0, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from

H, OH, F, Cl, CN, $NO_2$, methyl, ethyl, methoxy, ethoxy, trifluoromethyl, and trifluoromethoxy;

$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{33}$, at each occurrence, is independently selected from

H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{41}$, at each occurrence, is independently selected from

H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{3-6}$ alkyl;

$R^{42}$, at each occurrence, is independently selected from

H, $CF_3$, halo, OH, $CO_2H$, $SO_2R^{45}$, $NR^{46}R^{47}$, $NO_2$, CN, CH(=NH)$NH_2$, NHC(=NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1; and n is 1 or 2.

[5]In another preferred embodiment the present invention provides a compound of Formula (I-a) wherein:

X is —S—;

$R^1$ is selected from

H, $C_{1-4}$ alkyl, $C_{2-4}$ alkenyl, $C_{2-4}$ alkynyl, $C_{3-4}$ cycloalkyl, $C_{1-3}$ alkyl substituted with 0–1 $R^2$, $C_{2-3}$ alkenyl substituted with 0–1 $R^2$, and $C_{2-3}$ alkynyl substituted with 0–1 $R^2$;

$R^2$, at each occurrence, is independently selected from $C_{1-4}$ alkyl, $C_{2-4}$ alkenyl, $C_{2-4}$ alkynyl, $C_{3-6}$ cycloalkyl, phenyl substituted with 0–5 $R^{42}$;

$C_{3-6}$ carbocyclic residue substituted with 0–3 $R^{41}$, and

5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^6$ is H;

$R^7$ and $R^9$, at each occurrence, are independently selected from

H, F, Cl, —$CH_3$, —$OCH_3$, —$CF_3$, —$OCF_3$, —CN, and —$NO_2$, $R^8$ is selected from H, F, Cl, Br, —$CF_3$, —$OCF_3$, —OH, —CN, —$NO_2$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)-;
alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, quinolinyl, tetrahydroquinolinyl, isoquinolinyl, tetrahydroisoquinolinyl; wherein said bicyclic heterocyclic ring system is substituted with 0–1 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)—NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{33}$, at each occurrence, is independently selected from
H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O), $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyloxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O—O, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{41}$, at each occurrence, is independently selected from
H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from
H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1; and n is 1 or 2.

[6] In another preferred embodiment the present invention provides a compound of Formula (I-a) wherein:

X is —S—;

$R^1$ is selected from H,
$C_{1-5}$ alkyl substituted with 0–1 $R^2$,
$C_{2-5}$ alkenyl substituted with 0–1 $R^2$, and
$C_{2-3}$ alkynyl substituted with 0–1 $R^2$;

$R^2$ is $C_{3-6}$ cycloalkyl;

$R^5$ is H, methyl, ethyl, or propyl;

$R^6$ is H;

$R^7$ and $R^9$, at each occurrence, are independently selected from H, F, Cl, —$CH_3$, —$OCH_3$, —$CF_3$, —$OCF_3$, —CN, and —$NO_2$;

$R^8$ is selected from $R^{11}$;
methyl substituted with $R^{11}$;
phenyl substituted with 0–3 $R^{33}$;
pyridyl substituted with 0–2 $R^{33}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
- phenyl-substituted with 0–5 fluoro;
- pyridyl substituted with 0–2 $R^{33}$;
- naphthyl-substituted with 0–2 $R^{33}$;
- 2-($H_3CCH_2C(=O)$)-phenyl-substituted with $R^{33}$;
- 2-($H_3CC(=O)$)-phenyl-substituted with $R^{33}$;
- 2-($HC(=O)$)-phenyl-substituted with $R^{33}$;
- 2-($H_3CCH(OH)$)-phenyl-substituted with $R^{33}$;
- 2-($H_3CCH_2CH(OH)$)-phenyl-substituted with $R^{33}$;
- 2-($HOCH_2$)-phenyl-substituted with $R^{33}$;
- 2-($HOCH_2CH_2$)-phenyl-substituted with $R^{33}$;
- 2-($H_3COCH_2$)-phenyl-substituted with $R^{33}$;
- 2-($H_3COCH_2CH_2$)phenyl-substituted with $R^{33}$;
- 2-($H_3CCH(OMe)$)phenyl-substituted with $R^{33}$;
- 2-($H_3COC(=O)$)phenyl-substituted with $R^{33}$;
- 2-($HOCH_2CH=CH$)-phenyl-substituted with $R^{33}$;
- 2-(($MeOC=O)CH=CH$)-phenyl-substituted with $R^{33}$;
- 2-(methyl)-phenyl-substituted with $R^{33}$;
- 2-(ethyl)-phenyl-substituted with $R^{33}$;
- 2-(i-propyl)-phenyl-substituted with $R^{33}$;
- 2-($F_3C$)-phenyl-substituted with $R^{33}$;
- 2-(NC)phenyl-substituted with $R^{33}$;
- 2-($H_3CO$)-phenyl-substituted with $R^{33}$;
- 2-(fluoro)-phenyl-substituted with $R^{33}$;
- 2-(chloro)-phenyl-substituted with $R^{33}$;
- 3-(NC)-phenyl-substituted with $R^{33}$;
- 3-($H_3CO$)-phenyl-substituted with $R^{33}$;
- 3-(fluoro)-phenyl-substituted with $R^{33}$;
- 3-(chloro)-phenyl-substituted with $R^{33}$;
- 3-($H_3C$)-phenyl-substituted with $R^{33}$;
- 3-($F_3C$)-phenyl-substituted with $R^{33}$;
- 3-($H_3CS$)-phenyl-substituted with $R^{33}$;
- 4-(NC)-phenyl-substituted with $R^{33}$;
- 4-(fluoro)-phenyl-substituted with $R^{33}$;
- 4-(chloro)-phenyl-substituted with $R^{33}$;
- 4-($H_3CS$)-phenyl-substituted with $R^{33}$;
- 4-($H_3CO$)-phenyl-substituted with $R^{33}$;
- 4-(ethoxy)-phenyl-substituted with $R^{33}$;
- 4-(i-propoxy)-phenyl-substituted with $R^{33}$;
- 4-(i-butoxy)-phenyl-substituted with $R^{33}$;
- 4-($H_3CCH_2CH_2C(=O)$)-phenyl-substituted with $R^{33}$;
- 4-(($H_3C)_2CHC(=O)$)-phenyl-substituted with $R^{33}$;
- 4-($H_3CCH_2C(=O)$)phenyl-substituted with $R^{33}$;
- 4-($H_3CC(=O)$)-phenyl-substituted with $R^{33}$;
- 4-($H_3CCH_2CH_2CH(OH)$)-phenyl-substituted with $R^{33}$;
- 4-(($H_3C)_2CHCH(OH)$)-phenyl-substituted with $R^{33}$;
- 4-($H_3CCH_2CH(OH)$)-phenyl-substituted with $R^{33}$;
- 4-($H_3CCH(OH)$)-phenyl-substituted with $R^{33}$;
- 4-(cyclopropyloxy)-phenyl-substituted with $R^{33}$;
- 4-(cyclobutyloxy)-phenyl-substituted with $R^{33}$; and
- 4-(cyclopentyloxy)-phenyl-substituted with $R^{33}$;

$R^{12}$ is selected from
- methyl substituted with $R^{11}$;
- phenyl substituted with 0–5 fluoro;
- pyridyl substituted with 0–2 $R^{33}$;
- naphthyl-substituted with 0–2 $R^{33}$;
- 2-($H_3CCH_2C(=O)$)-phenyl-substituted with $R^{33}$;
- 2-($H_3CC(=O)$)phenyl-substituted with $R^{33}$;
- 2-($HC(=O)$)-phenyl-substituted with $R^{33}$;
- 2-($H_3CCH(OH)$)-phenyl-substituted with $R^{33}$;
- 2-($H_3CCH_2CH(OH)$)-phenyl-substituted with $R^{33}$;
- 2-($HOCH_2$)-phenyl-substituted with $R^{33}$;
- 2-($HOCH_2CH_2$)-phenyl-substituted with $R^{33}$;
- 2-($H_3COCH_2$)-phenyl-substituted with $R^{33}$;
- 2-($H_3COCH_2CH_2$)-phenyl-substituted with $R^{33}$;
- 2-($H_3CCH(OMe)$)-phenyl-substituted with $R^{33}$;
- 2-($H_3COC(=O)$)-phenyl-substituted with $R^{33}$;
- 2-($HOCH_2CH=CH$)-phenyl-substituted with $R^{33}$;
- 2-(($MeOC=O)CH=CH$)-phenyl-substituted with $R^{33}$;
- 2-(methyl)-phenyl-substituted with $R^{33}$;
- 2-(ethyl)-phenyl-substituted with $R^{33}$;
- 2-(i-propyl)-phenyl-substituted with $R^{33}$;
- 2-($F_3C$)-phenyl-substituted with $R^{33}$;
- 2-(NC)-phenyl-substituted with $R^{33}$;
- 2-($H_3CO$)-phenyl-substituted with $R^{33}$;
- 2-(fluoro)-phenyl-substituted with $R^{33}$;
- 2-(chloro)-phenyl-substituted with $R^{33}$;
- 3-NC)-phenyl-substituted with $R^{33}$;
- 3-($H_3CO$)phenyl-substituted with $R^{33}$;
- 3-(fluoro)-phenyl-substituted with $R^{33}$;
- 3-(chloro)-phenyl-substituted with $R^{33}$;
- 3-($H_3C$)-phenyl-substituted with $R^{33}$;
- 3-($F_3C$)-phenyl-substituted with $R^{33}$;
- 3-($H_3CS$)phenyl-substituted with $R^{33}$;
- 4-(fluoro)-phenyl-substituted with $R^{33}$;
- 4-(chloro)-phenyl-substituted with $R^{33}$;
- 4-($H_3CS$)-phenyl-substituted with $R^{33}$;
- 4-($H_3CO$)-phenyl-substituted with $R^{33}$;
- 4-(ethoxy)-phenyl-substituted with $R^{33}$;
- 4-(i-propoxy)-phenyl-substituted with $R^{33}$;
- 4-(i-butoxy)-phenyl-substituted with $R^{33}$;
- 4-($H_3CCH_2CH_2C(=O)$)-phenyl-substituted with $R^{33}$;
- 4-(($H_3C)_2CHC(=O)$)-phenyl-substituted with $R^{33}$;
- 4-($H_3CCH_2C(=O)$)-phenyl-substituted with $R^{33}$;
- 4-($H_3CC(=O)$)-phenyl-substituted with $R^{33}$;
- 4-($H_3CCH_2CH_2CH(OH)$)-phenyl-substituted with $R^{33}$;
- 4-(($H_3C)_2CHCH(OH)$)-phenyl-substituted with $R^{33}$;
- 4-($H_3CCH_2CH(OH)$)-phenyl-substituted with $R^{33}$;
- 4-($H_3CCH(OH)$)-phenyl-substituted with $R^{33}$;
- 4-(cyclopropyloxy)-phenyl-substituted with $R^{33}$;
- 4-(cyclobutyloxy)-phenyl-substituted with $R^{33}$; and
- 4-(cyclopentyloxy)-phenyl-substituted with $R^{33}$;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, quinolinyl, tetrahydroquinolinyl, isoquinolinyl, and tetrahydroisoquinolinyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from
  H, OH, F, Cl, CN, $NO_2$, methyl, ethyl, methoxy, ethoxy, trifluoromethyl, and trifluoromethoxy;

$R^{33}$, at each occurrence, is independently selected from
  H, F, Cl, —$CH_3$, —$CH_2CH_3$, —$OCH_3$, —$SCH_3$, —$CF_3$, —$OCF_3$, —CN, and —$NO_2$;

k is 1; and n is 1 or 2.

[7] In another preferred embodiment the present invention provides a compound of Formula (I-a) wherein:

X is —O—;

$R^1$ is selected from
  H,
  $C_{1-4}$ alkyl,
  $C_{2-4}$ alkenyl,
  $C_{2-4}$ alkynyl,
  $C_{3-4}$ cycloalkyl,
  $C_{1-3}$ alkyl substituted with 0–1 $R^2$,
  $C_{2-3}$ alkenyl substituted with 0–1 $R^2$, and
  $C_{2-3}$ alkynyl substituted with 0–1 $R^2$;

$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{42}$;
  $C_{3-6}$ carbocyclic residue substituted with 0–3 $R^{41}$, and
  5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^6$ is H;

$R^7$ and $R^9$, at each occurrence, are independently selected from
  H, halo, —$CF_3$, —$OCF_3$, —OH, —CN, —$NO_2$, —$NR^{46}R^{47}$,
  $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^{11}$,
  $C_{3-10}$ carbocyclic residue substituted with 0–3 $R^{33}$, aryl substituted with 0–5 $R^{33}$, and
  5–6 membered heterocyclic ring system containing 1, 2, or 3 heteroatoms selected from the group consisting of N, O, and S substituted with 0–3 $R^{31}$;

$R^8$ is selected from
  H, halo, —$CF_3$, —$OCF_3$, —OH, —CN, —$NO_2$,
  $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^{11}$,
  $C_{2-4}$ alkenyl substituted with 0–2 $R^1$,
  $C_{2-4}$ alkynyl substituted with 0–1 $R^{11}$,
  $C_{3-10}$ carbocyclic residue substituted with 0–3 $R^{33}$, aryl substituted with 0–5 $R^{33}$,
  5–6 membered heterocyclic ring system containing 1, 2, or 3 heteroatoms selected from the group consisting of N, O, and S substituted with 0–3 $R^{31}$;
  $OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
  H, halo, —$CF_3$, —CN, —$NO_2$,
  $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
  $C_{3-10}$ cycloalkyl substituted with 0–2 $R^{33}$,
  $C_{3-10}$ carbocyclic residue substituted with 0–3 $R^{33}$,
  aryl substituted with 0–5 $R^{33}$, and
  5–6 membered heterocyclic ring system containing 1, 2, or 3 heteroatoms selected from the group consisting of N, O, and S substituted with 0–3 $R^{31}$;

$R^{12}$ at each occurrence, is independently selected from
  $C_{1-4}$ alkyl substituted with 0–1 $R^{12a}$,
  $C_{2-4}$ alkenyl substituted with O—$R^{12a}$,
  $C_{2-4}$ alkynyl substituted with 0–1 $R^{12a}$,
  $C_{3-6}$ cycloalkyl substituted with 0–3 $R^{33}$,
  aryl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{31}$;

$R^{12a}$, at each occurrence, is independently selected from
  phenyl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{31}$;

$R^{13}$, at each occurrence, is independently selected from
  H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one 0, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from
  H, OH, F, Cl, CN, $NO_2$, methyl, ethyl, methoxy, ethoxy, trifluoromethyl, and trifluoromethoxy;

$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O), or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O), or ($C_{1-4}$ alkyl)$CO_2$—;

$R^{33}$, at each occurrence, is independently selected from
  H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio, $C_{1-4}$ alkyl-C (=O)—, $C_{1-4}$ alkyl-OC(=O)—, $C_{1-4}$ alkyl-C(=O)
O—, $C_{1-4}$ alkyl-C(=O)-NH—, $C_{1-4}$ alkyl-NHC
(=O)—, $(C_{1-4}$ alkyl$)_2$NC(=O)—, $C_{3-6}$ cycloalkyl-
oxy-, $C_{3-6}$ cycloalkylmethyl-oxy-; $C_{1-6}$ alkyl
substituted with OH, methoxy, ethoxy, propoxy,
butoxy, —SO$_2$R$^{45}$, —NR$^{46}$R$^{47}$, NR$^{46}$R$^{47}$C(=O)—, or
($C_{1-4}$ alkyl)CO$_2$—; and $C_{2-6}$ alkenyl substituted with
OH, methoxy, ethoxy, propoxy, butoxy, —SO$_2$R$^{45}$,
—NR$^{46}$R$^{47}$, NR$^{46}$R$^{47}$C(=O)—, or ($C_{1-4}$ alkyl)CO$_2$—;

$R^{41}$, at each occurrence, is independently selected from
H, CF$_3$, halo, OH, CO$_2$H, SO$_2$R$^{45}$, NR$^{46}$R$^{47}$, NO$_2$, CN,
$C_{2-4}$ alkenyl, $C_{2-4}$ alkynyl, $C_{1-3}$ alkoxy, $C_{1-3}$ haloalkyl,
and $C_{1-3}$ alkyl;

$R^{42}$, at each occurrence, is independently selected from
H, CF$_3$, halo, OH, CO$_2$H, SO$_2$R$^{45}$, NR$^{46}$R$^{47}$, NO$_2$, CN,
CH(=NH)NH$_2$, NHC(=NH)NH$_2$,
$C_{2-4}$ alkenyl, $C_{2-4}$ alkynyl, $C_{1-3}$ alkoxy, $C_{1-3}$ haloalkyl,
$C_{3-6}$ cycloalkyl, and $C_{1-3}$ alkyl;

$R^{43}$ is cyclopropyl, cyclobutyl, cyclopentyl, cyclohexyl,
phenyl, or pyridyl, each substituted with 0–3 $R^{44}$;

$R^{44}$, at each occurrence, is independently selected from H,
halo, —OH, NR$^{46}$R$^{47}$, CO$_2$H, SO$_2$R$^{45}$, —CF$_3$, —OCF$_3$,
—CN, —NO$_2$, methyl, ethyl, propyl, butyl, methoxy,
ethoxy, propoxy, and butoxy;

$R^{45}$ is methyl, ethyl, propyl, or butyl;

$R^{46}$, at each occurrence, is independently selected from H,
methyl, ethyl, propyl, and butyl;

$R^{47}$, at each occurrence, is independently selected from from
H, methyl, ethyl, propyl, and butyl;

k is 1; and
n is 1 or 2.

[8] In another preferred embodiment the present invention provides a compound of Formula (I-a) wherein:
X is —O—;
$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic residue substituted with 0–3 $R^{41}$, and
5–6 membered heterocyclic ring system containing 1, 2,
or 3 heteroatoms selected from the group consisting of
N, O, and S substituted with 0–3 $R^{41}$;

$R^5$ is H, methyl, ethyl, propyl, or butyl;
$R^6$ is H;
$R^7$ and $R^9$, at each occurrence, are independently selected
from H, F, Cl, —CH$_3$, —OCH$_3$, —CF$_3$, —OCF$_3$, —CN,
and —NO$_2$;

$R^8$ is selected from
H, F, Cl, Br, —CF$_3$, —OCF$_3$, —OH, —CN, —NO$_2$,
$C_{1-4}$ alkyl, $C_{2-4}$ alkenyl, $C_{2-4}$ alkynyl, $C_{1-4}$ haloalkyl, $C_{1-4}$
alkoxy, ($C_{1-4}$ haloalkyl)oxy, $C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^1$,
$C_{3-10}$ carbocyclic residue substituted with 0–3 $R^{33}$,
aryl substituted with 0–5 $R^{33}$,
5–6 membered heterocyclic ring system containing 1, 2,
or 3 heteroatoms selected from the group consisting of
N, O, and S substituted with 0–3 $R^{31}$;
OR$^{12}$, SR$^{12}$, NR$^{12}$R$^{13}$, NR$^{12}$C(O)R$^{15}$, NR$^{12}$C(O)OR$^{15}$,
NR$^{12}$S(O)$_2$R$^{15}$, and NR$^{12}$C(O)NHR$^{15}$;

$R^{11}$ is selected from
H, halo, —CF$_3$, —CN, —NO$_2$,
$C_{1-4}$ alkyl, $C_{2-4}$ alkenyl, $C_{2-4}$ alkynyl, $C_{1-4}$ haloalkyl, $C_{1-4}$
alkoxy, ($C_{1-4}$ haloalkyl)oxy,
$C_{3-10}$ cycloalkyl substituted with 0–2 $R^{33}$,
$C_{3-10}$ carbocyclic residue substituted with 0–3 $R^{33}$,
aryl substituted with 0–5 $R^{33}$, and
5–6 membered heterocyclic ring system containing 1, 2,
or 3 heteroatoms selected from the group consisting of
N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from
1–4 heteroatoms selected from the group consisting of
N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from
1–4 heteroatoms selected from the group consisting of
N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a 5- or 6-membered
ring optionally substituted with —O— or —N(R$^{14}$);
alternatively, $R^{12}$ and $R^{13}$ when attached to N may be
combined to form a 9- or 10-membered bicyclic heterocyclic ring system containing from 1–3 heteroatoms
selected from the group consisting of N, O, and S;
wherein said bicyclic heterocyclic ring system is selected
from indolyl, indolinyl, indazolyl, benzimidazolyl,
benzimidazolinyl, benztriazolyl, benzoxazolyl,
benzoxazolinyl, benzthiazolyl, quinolinyl,
tetrahydroquinolinyl, isoquinolinyl, and tetrahydroisoquinolinyl; wherein said bicyclic heterocyclic ring system
is substituted with 0–1 $R^{16}$;

$R^{14}$, at each occurrence, is independently selected from H,
methyl, ethyl, propyl, and butyl;

$R^{15}$, at each occurrence, is independently selected from H,
methyl, ethyl, propyl, and butyl;

$R^{16}$, at each occurrence, is independently selected from
H, OH, F, Cl, CN, NO$_2$, methyl, ethyl, methoxy, ethoxy,
trifluoromethyl, and trifluoromethoxy;

$R^{31}$, at each occurrence, is independently selected from CN,
NO$_2$, —OCF$_3$, —OCH$_2$CF$_3$, —C(=O)H, —C(=O)NH$_2$,
—C(=O)OCH$_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-$C_{1-4}$ alkylthio-, $C_{1-4}$ alkyl-C(=O)—, $C_{1-4}$ alkyl-OC(=O)—, $C_{1-4}$ alkyl-C(—O)O—, $C_{1-4}$ alkyl-C(=O)-NH—, $C_{1-4}$ alkyl-NHC(=O)—, $(C_{1-4}$ alkyl$)_2$NC(=O), $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or $(C_{1-4}$ alkyl)CO$_2$—; and $C_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or $(C_{1-4}$ alkyl)CO$_2$—;

$R^{33}$, at each occurrence, is independently selected from
H, OH, halo, CN, NO$_2$, CF$_3$, —OCF$_3$, —OCH$_2$CF$_3$, SO$_2$R$^{45}$, NR$^{46}$R$^{47}$, —C(=O)H, =O, —C(=O)NH$_2$, —C(=O)OCH$_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)-, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, $(C_{1-4}$ alkyl$)_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or $(C_{1-4}$ alkyl)CO$_2$—; and $C_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or $(C_{1-4}$ alkyl)CO$_2$—;

$R^{41}$, at each occurrence, is independently selected from
H, CF$_3$, halo, OH, CO$_2$H, SO$_2$R$^{45}$, NR$^{46}$R$^{47}$, NO$_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from
H, CF$_3$, halo, OH, CO$_2$H, SO$_2$R$^{45}$, NR$^{46}$R$^{47}$, NO$_2$, CN, CH(=NH)NH$_2$, NHC(=NH)NH$_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1; and n is 1 or 2.

[9]In another preferred embodiment the present invention provides a compound of Formula (I-a) wherein:

X is —O—;

$R^1$ is selected from H,
$C_{1-5}$ alkyl substituted with 0–1 $R^2$,
$C_{2-5}$ alkenyl substituted with 0–1 $R^2$, and
$C_{2-3}$ alkynyl substituted with 0–1 $R^2$;

$R^2$ is $C_{3-6}$ cycloalkyl;

$R^5$ is H, methyl, ethyl, or propyl;

$R^6$ is H;

$R^7$ and $R^9$, at each occurrence, are independently selected from H, F, Cl, —CH$_3$, —OCH$_3$, —CF$_3$, —OCF$_3$, —CN, and —NO$_2$;

$R^8$ is selected from $R^{11}$;
methyl substituted with $R^{11}$;
phenyl substituted with 0–3 $R^{33}$;
pyridyl substituted with 0–2 $R^{33}$;
OR$^{12}$, SR$^{12}$, NR$^{12}$R$^{13}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

$R^{11}$ is selected from
phenyl-substituted with 0–5 fluoro;
pyridyl substituted with 0–2 $R^{33}$;
naphthyl-substituted with 0–2 $R^{33}$;
2-(H$_3$CCH$_2$C(=O))-phenyl-substituted with $R^{33}$;
2-(H$_3$CC(=O))-phenyl-substituted with $R^{33}$;
2-(HC(=O))-phenyl-substituted with $R^{33}$;
2-(H$_3$CCH(OH))-phenyl-substituted with $R^{33}$;
2-(H$_3$CCH$_2$CH(OH))phenyl-substituted with $R^{33}$;
2-(HOCH$_2$)-phenyl-substituted with $R^{33}$;
2-(HOCH$_2$CH$_2$)-phenyl-substituted with $R^{33}$;
2-(H$_3$COCH$_2$)-phenyl-substituted with $R^{33}$;
2-(H$_3$COCH$_2$CH$_2$)-phenyl-substituted with $R^{33}$;
2-(H$_3$CCH(OMe))-phenyl-substituted with $R^{33}$;
2-(H$_3$COC(=O))-phenyl-substituted with $R^{33}$;
2-(HOCH$_2$CH=CH)-phenyl-substituted with $R^{33}$;
2-((MeOC=O)CH=CH)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-(F$_3$C)-phenyl-substituted with $R^{33}$;
2-(NC)-phenyl-substituted with $R^{33}$;
2-(H$_3$CO)-phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-(H$_3$CO)-phenyl-substituted with $R^{33}$;
3-(fluoro)-phenyl-substituted with $R^{33}$;
3-(chloro)-phenyl-substituted with $R^{33}$;
3-(H$_3$C)-phenyl-substituted with $R^{33}$;
3-(F$_3$C)-phenyl-substituted with $R^{33}$;
3-(H$_3$CS)-phenyl-substituted with $R^{33}$;
4-(NC)phenyl-substituted with $R^{33}$;
4-(fluoro)-phenyl-substituted with $R^{33}$;
4-(chloro)-phenyl-substituted with $R^{33}$;
4-(H$_3$CS)-phenyl-substituted with $R^{33}$;
4-(H$_3$CO)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-(H$_3$CCH$_2$CH$_2$C(=O))phenyl-substituted with $R^{33}$;
4-((H$_3$C)$_2$CHC(=O))-phenyl-substituted with $R^{33}$;
4-(H$_3$CCH$_2$C(=O))-phenyl-substituted with $R^{33}$;
4-(H$_3$CC(=O))-phenyl-substituted with $R^{33}$;
4-(H$_3$CCH$_2$CH$_2$CH(OH))-phenyl-substituted with $R^{33}$;
4-((H$_3$C)$_2$CHCH(OH))-phenyl-substituted with $R^{33}$;
4-(H$_3$CCH$_2$CH(OH))phenyl-substituted with $R^{33}$;
4-(H$_3$CCH(OH))-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;

$R^{12}$ is selected from
methyl substituted with $R^{11}$;
phenyl substituted with 0–5 fluoro;

pyridyl substituted with 0–2 $R^{33}$;
naphthyl substituted with 0–2 $R^{33}$;
2-($H_3CCH_2C(=O)$)-phenyl-substituted with $R^{33}$;
2-($H_3CC(=O)$)-phenyl-substituted with $R^{33}$;
2-(HC(=O))-phenyl-substituted with $R^{33}$;
2-($H_3CCH(OH)$)-phenyl-substituted with $R^{33}$;
2-($H_3CCH_2CH(OH)$)-phenyl-substituted with $R^{33}$;
2-($HOCH_2$)-phenyl-substituted with $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH(OMe)$)-phenyl-substituted with $R^{33}$;
2-($H_3COC(=O)$)-phenyl-substituted with $R^{33}$;
2-($HOCH_2CH=CH$)-phenyl-substituted with $R^{33}$;
2-(MeOC=O)CH=CH)-phenyl-substituted with $R^{33}$;
2-(methyl)phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-($H_3CO$)phenyl-substituted with $R^{33}$;
3-(fluoro)phenyl-substituted with $R^{33}$;
3-(chloro)-phenyl-substituted with $R^{33}$;
3-($H_3C$)-phenyl-substituted with $R^{33}$;
3-($F_3C$)-phenyl-substituted with $R^{33}$;
3-($H_3CS$)phenyl-substituted with $R^{33}$;
4-(fluoro)-phenyl-substituted with $R^{33}$;
4-(chloro)-phenyl-substituted with $R^{33}$;
4-($H_3CS$)phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C(=O)$)-phenyl-substituted with $R^{33}$;
4-(($H_3C)_2CHC(=O)$)-phenyl-substituted with $R^{33}$;
4-($H_3CCH_2C(=O)$)-phenyl-substituted with $R^{33}$;
4-($H_3CC(=O)$)-phenyl-substituted with $R^{33}$;
4-($H_3CCH_2CH_2CH(OH)$)-phenyl-substituted with $R^{33}$;
4-(($H_3C)_2CHCH(OH)$)-phenyl-substituted with $R^{33}$;
4-($H_3CCH_2CH(OH)$)-phenyl-substituted with $R^{33}$;
4-($H_3CCH(OH)$)-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;
$R^{13}$ is H, methyl, or ethyl;
alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;
alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, quinolinyl, tetrahydroquinolinyl, isoquinolinyl, tetrahydroisoquinolinyl; wherein said bicyclic heterocyclic ring system is substituted with O—$R^{16}$;
$R^{15}$ is H, methyl, ethyl, propyl, or butyl;
$R^{16}$, at each occurrence, is independently selected from H, OH, F, Cl, CN, $NO_2$, methyl, ethyl, methoxy, ethoxy, trifluoromethyl, and trifluoromethoxy;
$R^{33}$, at each occurrence, is independently selected from H, F, Cl, —$CH_3$, —$OCH_3$, —$SCH_3$, —$CF_3$, —$OCF_3$, —CN, and —$NO_2$;
k is 1; and
n is 1 or 2.

[10] In another preferred embodiment the present invention provides a compound of Formula (I-b):

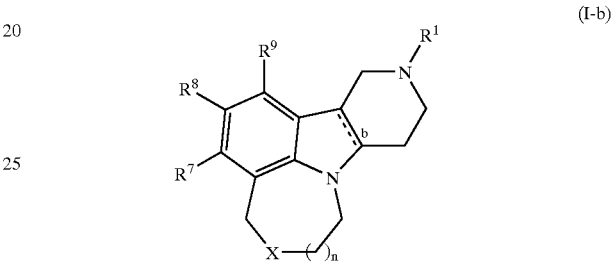

(I-b)

wherein:
b is a single bond or a double bond;
X is —S— or —O—;
$R^1$ is selected from
hydrogen, methyl, ethyl, n-propyl, n-butyl, s-butyl,
t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl,
4-methylpentyl, 2-fluoroethyl, 2,2-difluoroethyl,
2,2,2-trifluoroethyl,
2-propenyl, 2-methyl-2-propenyl, trans-2-butenyl,
3-methyl-2-butenyl, 3-butenyl, trans-2-pentenyl,
cis-2-pentenyl, 4-pentenyl, 4-methyl-3-pentenyl,
3,3-dichloro-2-propenyl, trans-3-phenyl-2-propenyl,
cyclopropyl, cyclobutyl, cyclopentyl, cyclohexyl, cyclopropylmethyl,
cyclobutylmethyl, cyclopentylmethyl, cyclohexylmethyl,
benzyl, 2-methylbenzyl, 3-methylbenzyl, 4-methylbenzyl, 2,5-dimethylbenzyl,
2,4-dimethylbenzyl, 3,5-dimethylbenzyl, 2,4,6-trimethylbenzyl,
3-methoxy-benzyl, 3,5-dimethoxy-benzyl, pentafluorobenzyl, 2-phenylethyl, 1-phenyl-2-propyl,
4-phenylbutyl, 4-phenylbenzyl, 2-phenylbenzyl,
2,6-dimethoxy-benzyl, 2,4-dimethoxy-benzyl,
2,4,6-trimethoxy-benzyl, 2,3-dimethoxy-benzyl,
2,4,5-trimethoxy-benzyl, 2,3,4-trimethoxy-benzyl,
3,4-dimethoxy-benzyl, 3,4,5-trimethoxy-benzyl,
(4-fluoro-phenyl)ethyl,
—CH=$CH_2$, —$CH_2$—CH=$CH_2$, —CH=CH—$CH_3$, —CCH, —C≡C—$CH_3$, and —$CH_2$—C≡CH;
$R^7$, $R^8$, and $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl;

2-Cl-phenyl; 2-F-phenyl; 2-Br-phenyl; 2-CN-phenyl;
2-Me-phenyl; 2-CF$_3$-phenyl; 2-MeO-phenyl; 2-CF$_3$O-phenyl; 2-NO$_2$-phenyl; 2-MeS-phenyl; 2-CHO-phenyl; 2-HOCH$_2$-phenyl;
3-Cl-phenyl; 3-F-phenyl; 3-Br-phenyl; 3-CN-phenyl;
3-Me-phenyl; 3-Et-phenyl; 3-n-Pr-phenyl; 3-isoPr-phenyl;
3-n-Bu-phenyl; 3-CF$_3$-phenyl; 3-MeO-phenyl; 3-MeS-phenyl;
3-isopropoxyphenyl; 3-CF$_3$O-phenyl; 3-NO$_2$-phenyl;
3-CHO-phenyl; 3-HOCH$_2$-phenyl; 3-MeOCH$_2$-phenyl; 3-Me$_2$NCH$_2$-phenyl;
4-Cl-phenyl; 4-F-phenyl; 4-Br-phenyl; 4-CN-phenyl;
4-Me-phenyl; 4-Et-phenyl; 4-n-Pr-phenyl;
4-iso-Pr-phenyl; 4-n-Bu-phenyl; 4-CF$_3$-phenyl;
4-MeO-phenyl; 4-isopropoxyphenyl; 4-CF$_3$O-phenyl;
4-MeS-phenyl;
4-acetylphenyl; 3-acetamidophenyl; 4-pyridyl;
2-furanyl; 2-thiophenyl; 2-naphthyl; 1-pyrrolidinyl,
2,3-diCl-phenyl; 2,3-diF-phenyl; 2,3-diMe-phenyl;
2,3-diCF$_3$-phenyl; 2,3-diMeO-phenyl; 2,3-diCF$_3$O-phenyl;
2,4-diCl-phenyl; 2,4-diF-phenyl; 2,4-diMe-phenyl;
2,4-diCF$_3$-phenyl; 2,4-diMeO-phenyl; 2,4-diCF$_3$O-phenyl;
2,5-diCl-phenyl; 2,5-diF-phenyl; 2,5-diMe-phenyl;
2,5-diCF$_3$-phenyl; 2,5-diMeO-phenyl; 2,5-diCF$_3$O-phenyl;
2,6-diCl-phenyl; 2,6-diF-phenyl; 2,6-diMe-phenyl;
2,6-diCF$_3$-phenyl; 2,6-diMeO-phenyl; 2,6-diCF$_3$O-phenyl;
3,4-diCl-phenyl; 3,4-diF-phenyl; 3,4-diMe-phenyl;
3,4-diCF$_3$-phenyl; 3,4-diMeO-phenyl; 3,4-diCF$_3$O-phenyl;
2,4,6-triCl-phenyl; 2,4,6-triF-phenyl;
2,4,6-triMe-phenyl; 2,4,6-triCF$_3$-phenyl;
2,4,6-triMeO-phenyl; 2,4,6-triCF$_3$O-phenyl;
2,4,5-triMe-phenyl; 2,3,4-triF-phenyl;
2-Me-4-MeO-5-F-phenyl; 2,6-diCl-4-MeO-phenyl;
2,4-diMeO-6-F-phenyl; 2,6-diF-4-Cl-phenyl;
2,3,4,6-tetraF-phenyl; 2,3,4,5,6-pentaF-phenyl;
2-Cl-4-F-phenyl; 2-Cl-6-F-phenyl; 2-Cl-3-Me-phenyl;
2-Cl-4-MeO-phenyl; 2-C$_{1-4}$-EtO-phenyl;
2-C$_{1-4}$-iPrO-phenyl; 2-Cl-4-CF$_3$-phenyl;
2-Cl-4-CF$_3$O-phenyl; 2-C$_{14}$—(CHF$_2$)O-phenyl;
2-F-3-Cl-phenyl; 2-F-4-MeO-phenyl; 2-F-5-Me-phenyl;
2-Me-3-Cl-phenyl; 2-Me-3-CN-phenyl; 2-Me-4-Cl-phenyl;
2-Me-4-F-phenyl; 2-Me-4-CN-phenyl; 2-Me-4-MeO-phenyl;
2-Me-4-EtO-phenyl; 2-Me-4-MeS-phenyl;
2-Me-4-H$_2$NCO-phenyl; 2-Me-4-MeOC(=O)-phenyl;
2-Me-4-CH$_3$C(=O)-phenyl; 2-Me-5-F-phenyl;
2-Et-4-MeO-phenyl; 2-MeO-5-F-phenyl;
2-MeO-4-isopropyl-phenyl; 2-CF$_3$-4-Cl-phenyl;
2-CF$_3$-4-F-phenyl; 2-CF$_3$-4-MeO-phenyl;

2-CF$_3$-4-EtO-phenyl; 2-CF$_3$-4-iPrO-phenyl;
2-CF$_3$-4-CN-phenyl; 2-CF$_3$-6-F-phenyl;
2-CHO-4-MeO-phenyl; 2-MeOC(=O)-3-MeO-phenyl;
2-CH$_3$CH(OH)-4-MeO-phenyl; 2-CH$_3$CH(OH)-4-F-phenyl;
2-CH$_3$CH(OH)-4-Cl-phenyl; 2-CH$_3$CH(OH)-4-Me-phenyl;
2-CH$_3$CH(OMe)-4-MeO-phenyl; 2-CH$_3$C(=O)-4-MeO-phenyl;
2-CH$_3$C(=O)-4-F-phenyl; 2-CH$_3$C(=O)$_4$—Cl-phenyl;
2-CH$_3$C(=O)-4-Me-phenyl; 2-H$_2$C(OH)-4-MeO-phenyl;
2-H$_2$C(OMe)-4-MeO-phenyl; 2-H$_3$CCH$_2$CH(OH)-4-MeO-phenyl;
2-H$_3$CCH$_2$C(=O)-4-MeO-phenyl; 2-CH$_3$CO$_2$CH$_2$CH$_2$-4-MeO-phenyl;
(Z)-2-HOCH$_2$CH=CH-4-MeO-phenyl;
(E)-2-HOCH$_2$CH=CH-4-MeO-phenyl;
(Z)-2-CH$_3$CO$_2$CH=CH-4-MeO-phenyl;
(E)-2-CH$_3$CO$_2$CH=CH MeO-phenyl;
2-CH$_3$OCH$_2$CH$_2$-4-MeO-phenyl;
3-CN-4-F-phenyl; 3-H$_2$NCO-4—F-phenyl;
(2-Cl-phenyl)-CH=CH—; (3-Cl-phenyl)-CH=CH—;
(2,6-diF-phenyl)-CH=CH—; phenyl-CH=CH—;
(2-Me$_4$-MeO-phenyl)-CH=CH—;
cyclohexyl; cyclopentyl; cyclohexylmethyl; benzyl;
2-F-benzyl; 3-F-benzyl; 4-F-benzyl; 3-MeO-benzyl;
3-OH-benzyl; 2-MeO-benzyl; 2-OH-benzyl;
tetrahydroquinolin-1-yl;
tetrahydroindolin-1-yl;
tetrahydroisoindolin-1-yl;
phenyl-S—; phenyl-NH—; pyrid-3-yl-NH—;
(4-Me-pyrid-3-yl)-NH—; (1-naphthyl)-NH—;
(2-naphthyl)-NH—; (2-Me-naphth-1-yl)-NH—;
(3-quinolinyl)-NH—;
(2-[1,1'-biphenyl])—NH—; (3-[1,1'-biphenyl])—NH—;
(4-[1,1'-biphenyl])—NH—; (2-F-phenyl)-NH—;
(2-Cl-phenyl)-NH—; (2-CF$_3$-phenyl)-NH—;
(2-CH$_3$-phenyl)-NH—; (2-OMe-phenyl)-NH—;
(2-CN-phenyl)-NH—; (2-OCF$_3$-phenyl)-NH—;
(2-SMe-phenyl)-NH—; (3-F-phenyl)-NH—;
(3-Cl-phenyl)-NH—; (3-CF$_3$-phenyl)-NH—;
(3-CH$_3$-phenyl)-NH—; (3-OMe-phenyl)-NH—;
(3-CN-phenyl)-NH—; (3-OCF$_3$-phenyl)-NH—;
(3-SMe-phenyl)-NH—; (4-F-phenyl)-NH—;
(4-Cl-phenyl)-NH—; (4-CF$_3$-phenyl)-NH—;
(4-CH$_3$-phenyl)-NH—; (4-OMe-phenyl)-NH—;
(4-CN-phenyl)-NH—; (4-OCF$_3$-phenyl)-NH—;
(4-SMe-phenyl)-NH—; (2,3-diCl-phenyl)-NH—;
(2,4-diCl-phenyl)-NH—; (2,5-diCl-phenyl)-NH—;
(2,6-diCl-phenyl)-NH—; (3,4-diCl-phenyl)-NH—;
(3,5-diCl-phenyl)-NH—; (2,3-diF-phenyl)-NH—;
(2,4-diF-phenyl)-NH—; (2,5-diF-phenyl)-NH—;
(2,6-diF-phenyl)-NH—; (3,4-diF-phenyl)-NH—;
(3,5-diF-phenyl)-NH—; (2,3-diCH$_3$-phenyl)-NH—;
(2,4-diCH$_3$-phenyl)-NH—; (2,5-diCH$_3$-phenyl)-NH—;
(2,6-diCH$_3$-phenyl)-NH—; (3,4-diCH$_3$-phenyl)-NH—;
(3,5-diCH$_3$-phenyl)-NH—; (2,3-diCF$_3$-phenyl)-NH—;

(2,4-diCF$_3$-phenyl)-NH—; (2,5-diCF$_3$-phenyl)-NH—; (2,6-diCF$_3$-phenyl)-NH—; (3,4-diCF$_3$-phenyl)-NH—; (3,5-diCF$_3$-phenyl)-NH—; (2,3-diOMe-phenyl)-NH—; (2,4-diOMe-phenyl)-NH—; (2,5-diOMe-phenyl)-NH—; (2,6-diOMe-phenyl)-NH—; (3,4-diOMe-phenyl)-NH—; (3,5-diOMe-phenyl)-NH—; (2-F-3-Cl-phenyl)-NH—; (2-F-4-Cl-phenyl)-NH—; (2-F—S-Cl-phenyl)-NH—; (2-F-6-Cl-phenyl)-NH—; (2-F-3-CH$_3$-phenyl)-NH—; (2-F-4-CH$_3$-phenyl)-NH—; (2-F-5-CH$_3$-phenyl)-NH—; (2-F-6-CH$_3$-phenyl)-NH—; (2-F-3-CF$_3$-phenyl)-NH—; (2-F-4-CF$_3$-phenyl)-NH—; (2-F-5-CF$_3$-phenyl)-NH—; (2-F-6-CF$_3$-phenyl)-NH—; (2-F-3-OMe-phenyl)-NH—; (2-F-4-OMe-phenyl)-NH—; (2-F-5-OMe-phenyl)-NH—; (2-F-6-OMe-phenyl)-NH—; (2-Cl-3-F-phenyl)-NH—; (2-Cl-4-F-phenyl)-NH—; (2-Cl-5-F-phenyl)-NH—; (2-Cl-6-F-phenyl)-NH—; (2-Cl-3-CH$_3$-phenyl)-NH—; (2-Cl-4-CH$_3$-phenyl)-NH—; (2-Cl-5-CH$_3$-phenyl)-NH—; (2-Cl-6-CH$_3$-phenyl)-NH—; (2-Cl-3-CF$_3$-phenyl)-NH—; (2-Cl-4-CF$_3$-phenyl)-NH—; (2-Cl-5-CF$_3$-phenyl)-NH—; (2-Cl-6-CF$_3$-phenyl)-NH—; (2-Cl-3-OMe-phenyl)-NH—; (2-Cl-4-OMe-phenyl)-NH—; (2-Cl-5-OMe-phenyl)-NH—; (2-Cl-6-OMe-phenyl)-NH—; (2-CH$_3$-3-F-phenyl)-NH—; (2-CH$_3$-4-F-phenyl)-NH—; (2-CH$_3$-5-F-phenyl)-NH—; (2-CH$_3$-6-F-phenyl)-NH—; (2-CH$_3$-3-F-phenyl)-NH—; (2-CH$_3$-4-CF-phenyl)-NH—; (2-CH$_3$-5-Cl-phenyl)-NH—; (2-CH$_3$-6-Cl-phenyl)-NH—; (2-CH$_3$-3-CF$_3$-phenyl)-NH—; (2-CH$_3$-4-CF$_3$-phenyl)-NH—; (2-CH$_3$-5-CF$_3$-phenyl)-NH—; (2-CH$_3$-6-CF$_3$-phenyl)-NH—; (2-CH$_3$-3-OMe-phenyl)-NH—; (2-CH$_3$-6-OMe-phenyl)-NH—; (2-CH$_3$-5-OMe-phenyl)-NH—; (2-CH$_3$-6-OMe-phenyl)-NH—; (2-CF$_3$-3-F-phenyl)-NH—; (2-CF$_3$-4-F-phenyl)-NH—; (2-CF$_3$-5-F-phenyl)-NH—; (2-CF$_3$-6-F-phenyl)-NH—; (2-CF$_3$-3-Cl-phenyl)-NH—; (2-CF$_3$-4-Cl-phenyl)-NH—; (2-CF$_3$-5-Cl-phenyl)-NH—; (2-CF$_3$-6-Cl-phenyl)-NH—; (2-CF$_3$-3-CH$_3$-phenyl)-NH—; (2-CF$_3$-4-CH$_3$-phenyl)-NH—; (2-CH$_3$-5-CF$_3$-phenyl)-NH—; (2-CF$_3$-6-CH$_3$-phenyl)-NH—; (2-CF$_3$-3-OMe-phenyl)-NH—; (2-CF$_3$-4-OMe-phenyl)-NH—; (2-CF$_3$-5-OMe-phenyl)-NH—; (2-CF$_3$-6-OMe-phenyl)-NH—; (2-OMe-3-F-phenyl)-NH—; (2-OMe-4-F-phenyl)-NH—; (2-OMe-5-F-phenyl)-NH—; (2-OMe-6-F-phenyl)-NH—; (2-OMe-3-Cl-phenyl)-NH—; (2-OMe-4-phenyl)-NH—; (2-OMe-5-Cl-phenyl)-NH—; (2-OMe-6-Cl-phenyl)-NH—; (2-OMe-4-CN-phenyl)-NH—; (2-OMe-4-CHO-phenyl)-NH—; (2-OMe-3-CH$_3$-phenyl)-NH—; (2-OMe-4-CH$_3$-phenyl)-NH—; (2-OMe-5-CH$_3$-phenyl)-NH—; (2-OMe-6-CH$_3$-phenyl)-NH—; (2-OMe-3-CF$_3$-phenyl)-NH—; (2-OMe-4-CF$_3$-phenyl)-NH—; (2-OMe-5-CF$_3$-phenyl)-NH—; (2-OMe-6-CF$_3$-phenyl)-NH—; (2-acetyl-4-Cl-phenyl)-NH—; (2-acetyl-4-Me-phenyl)-NH—; (2-acetyl-4-MeO-phenyl)-NH—; (2-CH$_3$CH(OH)$_4$—Cl-phenyl)-NH—; (2-CH$_3$CH(OH)-4-Me-phenyl)-NH—; (2-CH$_3$CH(OH)-4-MeO-phenyl)-NH—; (3-CF$_3$-4-Cl-phenyl)-NH—; (3-F-4-CHO-phenyl)-NH—; (3-CH$_3$-4-CN-phenyl)-NH—; (3-CH$_3$-4-MeO-phenyl)-NH—; (3-CH$_3$-4-Cl-phenyl)-NH—; (3-CH$_3$-4-F-phenyl)-NH—; (3-CH$_3$-4-CO$_2$-Me-phenyl)-NH—; (3-CF$_3$-4-C(O)CH$_3$-phenyl)-NH—; (3-CHO-4—OMe-phenyl)-NH—; (4-F-3-CF$_3$-phenyl)-NH—; (2,3,5-triCl-phenyl)-NH—; (2,4,5-triF-phenyl)-NH—; (2,6-diCl-3-Me-phenyl)-NH—; (3,5-diMe-4-MeO-phenyl)-NH—; (2-F-3-Cl-6-CF$_3$-phenyl)-NH—; benzyl-NH—; (3-quinolinyl)CH$_2$NH—; (2-F-phenyl)CH$_2$NH—; (2-Cl-phenyl)CH$_2$NH—; (2-CF$_3$-phenyl)CH$_2$NH—; (2-CH$_3$-phenyl)CH$_2$NH—; (2-OMe-phenyl)CH$_2$NH—; (2-CN-phenyl)CH$_2$NH—; (2-OCF$_3$-phenyl)CH$_2$NH—; (2-SMe-phenyl)CH$_2$NH—; (3-F-phenyl)CH$_2$NH—; (3-Cl-phenyl)CH$_2$NH—; (3-CF$_3$-phenyl)CH$_2$NH—; (3-CH$_3$-phenyl)CH$_2$NH—; (3-OMe-phenyl)CH$_2$NH—; (3-CN-phenyl)CH$_2$NH—; (3-OCF$_3$-phenyl)CH$_2$NH—; (3-SMe-phenyl)CH$_2$NH—; (4-F-phenyl)CH$_2$NH—; (4-Cl-phenyl)CH$_2$NH—; (4-CF$_3$-phenyl)CH$_2$NH—; (4-CH$_3$-phenyl)CH$_2$NH—; (4-OMe-phenyl)CH$_2$NH—; (4-CN-phenyl)CH$_2$NH—; (4-OCF$_3$-phenyl)CH$_2$NH—; (4-SMe-phenyl)CH$_2$NH—; (2,3-diCl-phenyl)CH$_2$NH—; (2,4-diCl-phenyl)CH$_2$NH—; (2,5-diCl-phenyl)CH$_2$NH—; (2,6-diCl-phenyl)CH$_2$NH—; (3,4-diCl-phenyl)CH$_2$NH—; (3,5-diCl-phenyl)CH$_2$NH—; (2,3-diF-phenyl)CH$_2$NH—; (2,4-diF-phenyl)CH$_2$NH—; (2,5-diF-phenyl)CH$_2$NH—; (2,6-diF-phenyl)CH$_2$NH—; (3,4-diF-phenyl)CH$_2$NH—; (3,5-diF-phenyl)CH$_2$NH—; (2,3-diCH$_3$-phenyl)CH$_2$NH—; (2,4-diCH$_3$-phenyl)CH$_2$NH—; (2,5-diCH$_3$-phenyl)CH$_2$NH—; (2,6-diCH$_3$-phenyl)CH$_2$NH—; (3,4-diCH$_3$-phenyl)CH$_2$NH—; (3,5-diCH$_3$-phenyl)CH$_2$NH—; (2,3-diCF$_3$-phenyl)CH$_2$NH—; (2,4-diCF$_3$-phenyl)CH$_2$NH—; (2,5-diCF$_3$-phenyl)CH$_2$NH—; (2,6-diCF$_3$-phenyl)CH$_2$NH—; (3,4-diCF$_3$-phenyl)CH$_2$NH—; (3,5-diCF$_3$-phenyl)CH$_2$NH—; (2,3-diOMe-phenyl)CH$_2$NH—;

(2,4-diOMe-phenyl)CH$_2$NH—; (2,5-diOMe-phenyl)CH$_2$NH—;
(2,6-diOMe-phenyl)CH$_2$NH—; (3,4-diOMe-phenyl)CH$_2$NH—;
(3,5-diOMe-phenyl)CH$_2$NH—; (2-F-3-Cl-phenyl)CH$_2$NH—;
(2-F-4-Cl-phenyl)CH$_2$NH—; (2-F-5-Cl-phenyl)CH$_2$NH—;
(2-F-6-Cl-phenyl)CH$_2$NH—; (2-F-3-CH$_3$-phenyl)CH$_2$NH—;
(2-F-4-CH$_3$-phenyl)CH$_2$NH—; (2-F-5-CH$_3$-phenyl)CH$_2$NH—;
(2-F-4-CH$_3$-phenyl)CH$_2$NH—; (2-F-3-CF$_3$-phenyl)CH$_2$NH—;
(2-F-4-CF$_3$-phenyl)CH$_2$NH—; (2-F-5-CF$_3$-phenyl)CH$_2$NH—;
(2-F-6-CF$_3$-phenyl)CH$_2$NH—; (2-F-3-OMe-phenyl)CH$_2$NH—;
(2-F-4-OMe-phenyl)CH$_2$NH—; (2-F-5-OMe-phenyl)CH$_2$NH—;
(2-F-6-OMe-phenyl)CH$_2$NH—; (2-Cl-3-F-phenyl)CH$_2$NH—;
(2-Cl-4-F-phenyl)CH$_2$NH—; (2-Cl-5-F-phenyl)CH$_2$NH—;
(2-Cl-6-F-phenyl)CH$_2$NH—; (2-Cl-3-CH$_3$-phenyl)CH$_2$NH—;
(2-Cl-4-CH$_3$-phenyl)CH$_2$NH—; (2-Cl-5-CH$_3$-phenyl)CH$_2$NH—;
(2-Cl-6-CH$_3$-phenyl)CH$_2$NH—; (2-Cl-3-CF$_3$-phenyl)CH$_2$NH—;
(2-Cl-4-CF$_3$-phenyl)CH$_2$NH—; (2-Cl-5-CF$_3$-phenyl)CH$_2$NH—;
(2-Cl-6-CF$_3$-phenyl)CH$_2$NH—; (2-Cl-3-OMe-phenyl)CH$_2$NH—;
(2-Cl-4-OMe-phenyl)CH$_2$NH—; (2-Cl-5-OMe-phenyl)CH$_2$NH—;
(2-Cl-6-OMe-phenyl)CH$_2$NH—; (2-CH$_3$-3-F-phenyl)CH$_2$NH—;
(2-CH$_3$-4-F-phenyl)CH$_2$NH—; (2-CH$_3$-5-F-phenyl)CH$_2$NH—;
(2-CH$_3$-6-F-phenyl)CH$_2$NH—; (2-CH$_3$-3-Cl-phenyl)CH$_2$NH—;
(2-CH$_3$-4-Cl-phenyl)CH$_2$NH—; (2-CH$_3$-5-Cl-phenyl)CH$_2$NH—;
(2-CH$_3$-6-Cl-phenyl)CH$_2$NH—; (2-CH$_3$-3-CF$_3$-phenyl)CH$_2$NH—;
(2-CH$_3$-4-CF$_3$-phenyl)CH$_2$NH—; (2-CH$_3$-5-CF$_3$-phenyl)CH$_2$NH—;
(2-CH$_3$-6-CF$_3$-phenyl)CH$_2$NH—; (2-CH$_3$-3-OMe-phenyl)CH$_2$NH—;
(2-CH$_3$-4-OMe-phenyl)CH$_2$NH—; (2-CH$_3$-5-OMe-phenyl)CH$_2$NH—;
(2-CH$_3$-6-OMe-phenyl)CH$_2$NH—; (2-CF$_3$-3-F-phenyl)CH$_2$NH—;
(2-CF$_3$-4-F-phenyl)CH$_2$NH—; (2-CF$_3$-5-F-phenyl)CH$_2$NH—;
(2-CF$_3$-6-F-phenyl)CH$_2$NH—; (2-CF$_3$-3-Cl-phenyl)CH$_2$NH—;
(2-CF$_3$-4-Cl-phenyl)CH$_2$NH—; (2-CF$_3$-5-Cl-phenyl)CH$_2$NH—;
(2-CF$_3$-6-Cl-phenyl)CH$_2$NH—; (2-CF$_3$-3-CH$_3$-phenyl)CH$_2$NH—;
(2-CF$_3$-4-CH$_3$-phenyl)CH$_2$NH—; (2-CH$_3$-5-CF$_3$-phenyl)CH$_2$NH—;
(2-CF$_3$-6-CH$_3$-phenyl)CH$_2$NH—; (2-CF$_3$-3-OMe-phenyl)CH$_2$NH—;
(2-CF$_3$-4-OMe-phenyl)CH$_2$NH—; (2-CF$_3$-5-OMe-phenyl)CH$_2$NH—;
(2-CF$_3$-6-OMe-phenyl)CH$_2$NH—; (2-OMe-3-F-phenyl)CH$_2$NH—;
(2-OMe-4-F-phenyl)CH$_2$NH—; (2-OMe-5-F-phenyl)CH$_2$NH—;
(2-OMe-6-F-phenyl)CH$_2$NH—; (2-OMe-3-Cl-phenyl)CH$_2$NH—;
(2-OMe-4-Cl-phenyl)CH$_2$NH—; (2-OMe-5-Cl-phenyl)CH$_2$NH—;
(2-OMe-6-Cl-phenyl)CH$_2$NH—; (2-OMe-4-CN-phenyl)CH$_2$NH—;
(2-OMe-4-CHO-phenyl)CH$_2$NH—; (2-OMe-3-CH$_3$-Phenyl)CH$_2$NH—;
(2-OMe-4-CH$_3$-phenyl)CH$_2$NH—; (2-OMe-5-CH$_3$-phenyl)CH$_2$NH—;
(2-OMe-6-CH$_3$-phenyl)CH$_2$NH—; (2-OMe-3-CF$_3$-phenyl)CH$_2$NH—;
(2-OMe-4-CF$_3$-phenyl)CH$_2$NH—; (2-OMe-5-CF$_3$-phenyl)CH$_2$NH—;
(2-OMe-6-CF$_3$-phenyl)CH$_2$NH—; (2-acetyl-4-Cl-phenyl)CH$_2$NH—;
(2-acetyl-4-Me-phenyl)CH$_2$NH—;
(2-acetyl-4-MeO-phenyl)CH$_2$NH—;
(2-CH$_3$CH(OH)-4-Cl-phenyl)CH$_2$NH—;
(2-CH$_3$CH(OH)-4-Me-phenyl)CH$_2$NH—;
(2-CH$_3$CH(OH)-4-MeO-phenyl)CH$_2$NH—;
(3-CF$_3$-4-Cl-phenyl)CH$_2$NH—; (3-F-4-CHO-phenyl)CH$_2$NH—;
(3-CH$_3$-4-CN-phenyl)CH$_2$NH—; (3-CH$_3$-4-MeO-phenyl)CH$_2$NH—;
(3-CH$_3$-4-Cl-phenyl)CH$_2$NH—; (3-CH$_3$-4-F-phenyl)CH$_2$NH—;
(4-F-3-CF$_3$-phenyl)CH$_2$NH—; (3-CH$_3$-4-CO$_2$-Me-phenyl)CH$_2$NH—;
(3-CF$_3$-4-C(O)CH$_3$-phenyl)CH$_2$NH—;
(3-CHO-4—OMe-phenyl)CH$_2$NH—;
(2,3,5-triCl-phenyl)CH$_2$NH—;
(2,4,5-triF-phenyl)CH$_2$NH—;
(2,6-diCl-3-Me-phenyl)CH$_2$NH—;
(3,5-diMe-4-MeO-phenyl)CH$_2$NH—; and
(2-F-3-Cl-6-CF$_3$-phenyl)CH$_2$NH—;

provided that two of $R^7$, $R^8$, and $R^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy; and n is 1 or 2.

[10a] In another preferred embodiment the present invention provides a compound of Formula (I-b):

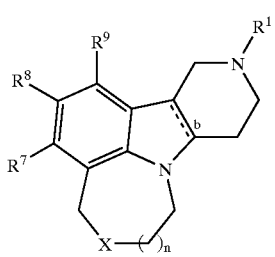

(I-b)

wherein:
b is a single bond or a double bond,
X is —S— or —O—;
R$^1$ is selected from
hydrogen, methyl, ethyl, n-propyl, n-butyl, s-butyl,
t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl,
4-methylpentyl, 2-fluoroethyl, 2,2-difluoroethyl, 2,2,2-trifluoroethyl,
2-propenyl, 2-methyl-2-propenyl, trans-2-butenyl, 3-methyl-butenyl, 3-butenyl, trans-2-pentenyl,
cis-2-pentenyl, 4-pentenyl, 4-methyl-3-pentenyl, 3,3-dichloro-2-propenyl, trans-3-phenyl-2-propenyl,
cyclopropyl, cyclobutyl, cyclopentyl, cyclohexyl, cyclopropylmethyl,
cyclobutylmethyl, cyclopentylmethyl, cyclohexylmethyl, benzyl, 2-methylbenzyl, 3-methylbenzyl, 4-methylbenzyl, 2,5-dimethylbenzyl,
2,4-dimethylbenzyl, 3,5-dimethylbenzyl,
2,4,6-trimethyl-benzyl, 3-methoxy-benzyl, 3,5-dimethoxy-benzyl,
pentafluorobenzyl, 2-phenylethyl, 1-phenyl-2-propyl, 4-phenylbutyl, 4-phenylbenzyl, 2-phenylbenzyl,
(2,3-dimethoxy-phenyl)C(=O)—, (2,5-dimethoxy-phenyl)C(=O)—, (3,4-dimethoxy-phenyl)C(=O)—, (3,5-dimethoxy-phenyl)C(=O)—, cyclopropyl-C(=O)—,
isopropyl-C(=O)—, ethyl-CO$_2$—, propyl-CO$_2$—, t-butyl-CO$_2$—,
2,6-dimethoxy-benzyl, 2,4-dimethoxy-benzyl, 2,4,6-trimethoxy-benzyl, 2,3-dimethoxy-benzyl, 2,4,5-trimethoxy-benzyl, 2,3,4-trimethoxy-benzyl, 3,4-dimethoxy-benzyl, 3,4,5-trimethoxy-benzyl, (4-fluoro-phenyl)ethyl,
—CH=CH$_2$, —CH$_2$—CH=CH$_2$, —CH=CH—CH$_3$, —C≡CH, —C≡C—CH$_3$, and —CH$_2$—C≡CH;
R$^7$, R$^8$, and R$^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl,
methylC(=O)—, ethylC(=O)—, propylC(=O)—, isopropylC(=O)—, butylC(=O)—, phenylC(=O)—,
methylCO$_2$—, ethylCO$_2$—, propylCO$_2$—, isopropylCO$_2$—, butylCO$_2$—, phenylCO$_2$—,
dimethylamino-S(=O)—, diethylamino-S(=O),
dipropylamino-S(=O)—, di-isopropylamino-S(=O)—, dibutylamino-S(=O)—, diphenylamino-S(=O)—,
dimethylamino-SO$_2$—, diethylamino-SO$_2$—,
dipropylamino-SO$_2$—, di-isopropylamino-SO$_2$—,
dibutylamino-SO$_2$—, diphenylamino-SO$_2$—,
dimethylamino-C(=O)—, diethylamino-C(=O)—,
dipropylamino-C(=O)—, di-isopropylamino-C(=O)—, dibutylamino-C(=O)—,
diphenylamino-C(=O)—, 2-chlorophenyl, 2-fluorophenyl, 2-bromophenyl,
2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl,
3-cyanophenyl, 3-methylphenyl, 3-ethylphenyl,
3-propylphenyl, 3-isopropylphenyl, 3-butylphenyl,
3-trifluoromethylphenyl, 3-methoxyphenyl,
3-isopropoxyphenyl, 3-trifluoromethoxyphenyl,
3-thiomethoxyphenyl,
4-chlorophenyl, 4-fluorophenyl, 4-bromophenyl,
4-cyanophenyl, 4-methylphenyl, 4-ethylphenyl,
4-propylphenyl, 4-isopropylphenyl, 4-butylphenyl,
4-trifluoromethylphenyl, 4-methoxyphenyl,
4 isopropoxyphenyl, 4-trifluoromethoxyphenyl,
4-thiomethoxyphenyl, 2,3-dichlorophenyl, 2,3-difluorophenyl,
2,3-dimethylphenyl, 2,3-ditrifluoromethylphenyl,
2,3-dimethoxyphenyl, 2,3-ditrifluoromethoxyphenyl,
2,4-dichlorophenyl, 2,4-difluorophenyl,
2,4-dimethylphenyl, 2,4-ditrifluoromethylphenyl,
2,4-dimethoxyphenyl, 2,4-ditrifluoromethoxyphenyl,
2,5-dichlorophenyl, 2,5-difluorophenyl,
2,5-dimethylphenyl, 2,5-ditrifluoromethylphenyl,
2,5-dimethoxyphenyl, 2,5-ditrifluoromethoxyphenyl,
2,6-dichlorophenyl, 2,6-difluorophenyl,
2,6-dimethylphenyl, 2,6-ditrifluoromethylphenyl,
2,6-dimethoxyphenyl, 2,6-ditrifluoromethoxyphenyl,
3,4-dichlorophenyl, 3,4-difluorophenyl,
3,4-dimethylphenyl, 3,4-ditrifluoromethylphenyl,
3,4-dimethoxyphenyl, 3,4-ditrifluoromethoxyphenyl,
2,4,6-trichlorophenyl, 2,4,6-trifluorophenyl,
2,4,6-trimethylphenyl, 2,4,6-tritrifluoromethylphenyl,
2,4,6-trimethoxyphenyl, 2,4,6-tritrifluoromethoxyphenyl,
2-chloro-4-CF$_3$-phenyl, 2-fluoro-3-chloro-phenyl,
2-chloro-4-CF$_3$-phenyl, 2-chloro-4-methoxy-phenyl,
2-methoxy-4-isopropyl-phenyl, 2-CF$_3$-4-methoxy-phenyl,
2-methyl-4-methoxy-5-fluoro-phenyl,
2-methyl-4-methoxy-phenyl, 2-chloro-4-CF$_3$O-phenyl,
2,4,5-trimethyl-phenyl, 2-methyl-4-chloro-phenyl,
methyl-C(=O)-NH—, ethyl-C(=O)-NH—, propyl-C(=O)-NH—,
isopropyl-C(=O)-NH—, butyl-C(=O)-NH—, phenyl-C(=O)-NH—,
4-acetylphenyl, 3-acetamidophenyl, 4-pyridyl, 2-furanyl, 2-thiophenyl, 2-naphthyl;
2-Me-5-F-phenyl, 2-F-5-Me-phenyl, 2-MeO-5-F-phenyl,
2-Me-3-Cl-phenyl, 3-NO$_2$-phenyl, 2-NO$_2$-phenyl, 2-Cl-3-Me-phenyl, 2-Me₄-EtO-phenyl, 2-Me-4-F-phenyl,
2-Cl-6-F-phenyl, 2-C$_{1-4}$ CHF$_2$)O-phenyl,
2,4-diMeO-6-F-phenyl, 2-CF$_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-CF$_3$-4-EtO-phenyl, 2-CF$_3$-4-iPrO-phenyl,
2-CF$_3$-4-Cl-phenyl, 2-CF$_3$-4-F-phenyl, 2-C$_{1-4}$-EtO-phenyl,
2-C$_{1-4}$-iPrO-phenyl, 2-Et-4-MeO-phenyl,
2-CHO-4-MeO-phenyl, 2-CH$_3$CH(OH)-4-MeO-phenyl,
2-CH$_3$CH(OH)-4-F-phenyl, 2-CH$_3$CH(OH)$_4$—Cl-phenyl,
2-CH$_3$CH(OH)-4-Me-phenyl, 2-CH$_3$CH(OMe)-4-MeO-phenyl,
2-CH$_3$C(=O)-4-MeO-phenyl, 2-CH$_3$C(=O)-4-F-phenyl,
2-CH$_3$C(=O)-4-Cl-phenyl, 2-CH$_3$C(=O)-4-Me-phenyl,
2-H$_2$C(OH)-4-MeO-phenyl, 2-H$_2$C(OMe)-4-MeO-phenyl,
2-H$_3$CCH$_2$CH(OH)-4-MeO-phenyl, 2-H$_3$CCH$_2$C(=O)-4-MeO-phenyl,
2-CH$_3$CO$_2$CH$_2$CH$_2$-4-MeO-phenyl,
(Z)-2-HOCH$_2$CH=CH-4-MeO-phenyl,
(E)-2-HOCH$_2$CH=CH-4-MeO-phenyl,
(Z)-2-CH$_3$CO$_2$CH=CH-4-MeO-phenyl,
(E)-2-CH$_3$CO$_2$CH=CH-4-MeO-phenyl,
2-CH$_3$OCH$_2$CH$_2$-4-MeO-phenyl,
2-F-4-MeO-phenyl, 2-Cl-4-F-phenyl,
(2-Cl-phenyl)-CH=CH—, (3-Cl-phenyl)-CH=CH—,
(2,6-diF-phenyl)CH=CH—, —CH$_2$CH=CH$_2$,
phenyl-CH=CH—, (2-Me-4-MeO-phenyl)-CH=CH—,
cyclohexyl, cyclopentyl, cyclohexylmethyl,
EtCO$_2$CH$_2$CH$_2$—, EtCO$_2$CH$_2$CH$_2$CH$_2$—, EtCO$_2$CH$_2$CH$_2$CH$_2$CH$_2$—,
benzyl, 2-F-benzyl, 3-F-benzyl, 4-F-benzyl,
3-MeO-benzyl, 3-OH-benzyl, 2-MeO-benzyl,
2-OH-benzyl, 2-MeOC(=O)-3-MeO-phenyl,
2-Me$_4$-CN-phenyl, 2-Me-3-CN-phenyl,
2-Me-4-MeS-phenyl, 2-CF$_3$-4-CN-phenyl,
2-CHO-phenyl, 3-CHO-phenyl, 2-HOCH$_2$-phenyl,
3-HOCH$_2$-phenyl, 3-MeOCH$_2$-phenyl,
3-Me$_2$NCH$_2$-phenyl, 3-CN-4—F-phenyl,
2-Me$_4$-H$_2$NCO-phenyl, 2-Me-4-MeOC(=O)-phenyl,
3-H$_2$NCO-4—F-phenyl, 2-Me$_2$NCH$_2$-4-MeO-phenyl-,
2-Me$_4$-CH$_3$C(=O)-phenyl, phenyl-S—, Me$_2$N—,
1-pyrrolidinyl,
phenyl-NH—, benzyl-NH—, (1-naphthyl)-NH—,
(2-naphthyl)-NH—, (2-[1,1'-biphenyl])-NH—,
(3-[1,1'-biphenyl])-NH—, (4-[1,1'-biphenyl])—NH—,
(2-F-phenyl)-NH—, (2-Cl-phenyl)-NH—,
(2-CF$_3$-phenyl)-NH—, (2-CH$_3$-phenyl)-NH—,
(2-OMe-phenyl)-NH—, (2-CN-phenyl)-NH—,
(2-OCF$_3$-phenyl)-NH—, (2-SMe-phenyl)-NH—,
(3-F-phenyl)-NH—, (3-Cl-phenyl)-NH—,
(3-CF$_3$-phenyl)-NH—, (3-CH$_3$-phenyl)-NH—,
(3-OMe-phenyl)-NH—, (3-CN-phenyl)-NH—,
(3-OCF$_3$-phenyl)-NH—, (3-SMe-phenyl)-NH—,
(4-F-phenyl)-NH—, (4-Cl-phenyl)-NH—,
(4-CF$_3$-phenyl)-NH—, (4-CH$_3$-phenyl)-NH—,
(4-OMe-phenyl)-NH—, (4-CN-phenyl)-NH—,
(4-OCF$_3$-phenyl)-NH—, (4-SMe-phenyl)-NH—,
(2,3-diCl-phenyl)-NH—, (2,4-diCl-phenyl)-NH—,
(2,5-diCl-phenyl)-NH—, (2,6-diCl-phenyl)-NH—,
(3,4-diCl-phenyl)-NH—, (3,5-diCl-phenyl)-NH—,
(2,3-diF-phenyl)-NH—, (2,4-diF-phenyl)-NH—,
(2,5-diF-phenyl)-NH—, (2,6-diF-phenyl)-NH—,
(3,4-diF-phenyl)-NH—, (3,5-diF-phenyl)-NH—,
(2,3-diCH$_3$-phenyl)-NH—, (2,4-diCH$_3$-phenyl)-NH—,
(2,5-diCH$_3$-phenyl)-NH—, (2,6-diCH$_3$-phenyl)-NH—,
(3,4-diCH$_3$-phenyl)-NH—, (3,5-diCH$_3$-phenyl)-NH—,
(2,3-diCF$_3$-phenyl)-NH—, (2,4-diCF$_3$-phenyl)-NH—,
(2,5-diCF$_3$-phenyl)-NH—, (2,6-diCF$_3$-phenyl)-NH—,
(3,4-diCF$_3$-phenyl)-NH—, (3,5-diCF$_3$-phenyl)-NH—,
(2,3-diOMe-phenyl)-NH—, (2,4-diOMe-phenyl)-NH—,
(2,5-diOMe-phenyl)-NH—, (2,6-diOMe-phenyl)-NH—,
(3,4-diOMe-phenyl)-NH—, (3,5-diOMe-phenyl)-NH—,
(2-F-3-Cl-phenyl)-NH—, (2-F-4-Cl-phenyl)-NH—,
(2-F-5-Cl-phenyl)-NH—, (2-F-6-Cl-phenyl)-NH—,
(2-F-3-CH$_3$-phenyl)-NH—, (2-F-4-CH$_3$-phenyl)-NH—,
(2-F-5-CH$_3$-phenyl)-NH—, (2-F-6-CH$_3$-phenyl)-NH—,
(2-F-3-CF$_3$-phenyl)-NH—, (2-F-4-CF$_3$-phenyl)-NH—,
(2-F-5-CF$_3$-phenyl)-NH—, (2-F-6-CF$_3$-phenyl)-NH—,
(2-F-3-OMe-phenyl)-NH—, (2-F-4-OMe-phenyl)-NH—,
(2-F-5-OMe-phenyl)-NH—, (2-F-6-OMe-phenyl)-NH—,
(2-Cl-3-F-phenyl)-NH—, (2-Cl-4-F-phenyl)-NH—,
(2-Cl-5-F-phenyl)-NH—, (2-Cl-6-F-phenyl)-NH—,
(2-Cl-3-CH$_3$-phenyl)-NH—, (2-Cl-4-CH$_3$-phenyl)-NH—,
(2-Cl-5-CH$_3$-phenyl)-NH—, (2-Cl-6-CH$_3$-phenyl)-NH—,
(2-Cl-3-CF$_3$-phenyl)-NH—, (2-Cl-4-CF$_3$-phenyl)-NH—,
(2-Cl-5-CF$_3$-phenyl)-NH—, (2-Cl-6-CF$_3$-phenyl)-NH—,
(2-Cl-3-OMe-phenyl)-NH—, (2-Cl-4-OMe-phenyl)-NH—,
(2-Cl-5-OMe-phenyl)-NH—, (2-Cl-6-OMe-phenyl)-NH—,
(2-CH$_3$-3-F-phenyl)-NH—, (2-CH$_3$-4-F-phenyl)-NH—,
(2-CH$_3$-5-F-phenyl)-NH—, (2-CH$_3$-6-F-phenyl)-NH—,
(2-CH$_3$-3-Cl-phenyl)-NH—, (2-CH$_3$-4-Cl-phenyl)-NH—,
(2-CH$_3$-5-Cl-phenyl)-NH—, (2-CH$_3$-6-Cl-phenyl)-NH—,
(2-CH$_3$-3-CF$_3$-phenyl)-NH—, (2-CH$_3$-4-CF$_3$-phenyl)-NH—,
(2-CH$_3$-5-CF$_3$-phenyl)-NH—, (2-CH$_3$-6-CF$_3$-phenyl)-NH—,
(2-CH$_3$-3-OMe-phenyl)-NH—, (2-CH$_3$-4-OMe-phenyl)-NH—,
(2-CH$_3$-5-OMe-phenyl)-NH—, (2-CH$_3$-6-OMe-phenyl)-NH—,
(2-CF$_3$-3-F-phenyl)-NH—, (2-CF$_3$-4-F-phenyl)-NH—,
(2-CF$_3$-5-F-phenyl)-NH—, (2-CF$_3$-6-F-phenyl)-NH—,
(2-CF$_3$-3-Cl-phenyl)-NH—, (2-CF$_3$-4-Cl-phenyl)-NH—,
(2-CF$_3$-5-Cl-phenyl)-NH—, (2-CF$_3$-6-Cl-phenyl)-NH—,
(2-CF$_3$-3-CH$_3$-phenyl)-NH—, (2-CF$_3$-4-CH$_3$-phenyl)-NH—, (2-CH₃-5-CF₃-phenyl)-NH—, (2-CF₃-6-CH₃-phenyl)-NH—,
(2-CF₃-3-OMe-phenyl)-NH—, (2-CF₃-4-OMe-phenyl)-NH—,
(2-CF₃-5-OMe-phenyl)-NH—, (2-CF₃-6-OMe-phenyl)-NH—,
(2-OMe-3-F-phenyl)-NH—, (2-OMe-4-F-phenyl)-NH—,
(2-OMe-5-F-phenyl)-NH—, (2-OMe-6-F-phenyl)-NH—,
(2-OMe-3-Cl-phenyl)-NH—, (2-OMe-4-Cl-phenyl)-NH—,
(2-OMe-5-Cl-phenyl)-NH—, (2-OMe-6-Cl-phenyl)-NH—,
(2-OMe-3-CH₃-phenyl)-NH—, (2-OMe-4-CH₃-phenyl)-NH—,
(2-OMe-5-CH₃-phenyl)-NH—, (2-OMe-6-CH₃-phenyl)-NH—,
(2-OMe-3-CF₃-phenyl)-NH—, (2-OMe-4-CF₃-phenyl)-NH—,
(2-OMe-5-CF₃-phenyl)-NH—, (2-OMe-6-CF₃-phenyl)-NH—(3-CF₃-4-Cl-phenyl)-NH—, (3-CF₃-4-C(O)CH₃-phenyl)-NH—, (2,3,5-triCl-phenyl)-NH—,
(3-CH₃-4-CO₂-Me-phenyl)-NH—, and
(3-CHO-4-OMe-phenyl)-NH—;

provided that two of $R^7$, $R^8$, and $R^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy; and n is 1 or 2.

[11] In another preferred embodiment the present invention provides a compound of Formula (II):

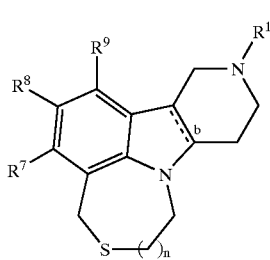

(II)

wherein:
b is a single bond, wherein the bridge hydrogens are in a cis position;
$R^1$ is selected from
hydrogen, methyl, ethyl, n-propyl, n-butyl, s-butyl,
t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl,
4-methylpentyl, 2-fluoroethyl, 2,2-difluoroethyl,
2,2,2-trifluoroethyl, 2-propenyl, 2-methyl-2-propenyl, trans-2-butenyl, 3-methyl-2-butenyl, 3-butenyl, trans-2-pentenyl, cis-2-pentenyl, 4-pentenyl,
4-methyl-3-pentenyl, 3,3-dichloro-2-propenyl,
trans-3-phenyl-2-propenyl, cyclopropyl, cyclobutyl, cyclopentyl, cyclohexyl,
cyclopropylmethyl, cyclobutylmethyl, cyclopentylmethyl, cyclohexylmethyl,
—CH=CH₂, —CH₂—CH=CH₂, —CH=CH—CH₃, —C—CH, —C=C—CH₃, and —CH₂—C≡CH;

$R^7$ and $R^9$, at each occurrence, are independently selected from hydrogen, fluoro, methyl, trifluoromethyl, and methoxy;
$R^8$ is selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl;
2-Cl-phenyl; 2-F-phenyl; 2-Br-phenyl; 2-CN-phenyl;
2-Me-phenyl; 2-CF₃-phenyl; 2-MeO-phenyl; 2-CF₃O-phenyl; 2-NO₂-phenyl; 2-MeS-phenyl; 2-CHO-phenyl; 2-HOCH₂-phenyl;
3-Cl-phenyl; 3-F-phenyl; 3-Br-phenyl; 3-CN-phenyl;
3-Me-phenyl; 3-Et-phenyl; 3-n-Pr-phenyl; 3-isoPr-phenyl;
3-n-Bu-phenyl; 3-CF₃-phenyl; 3-MeO-phenyl; 3-MeS-phenyl;
3-isopropoxyphenyl; 3-CF₃O-phenyl; 3-NO₂-phenyl;
3-CHO-phenyl; 3-HOCH₂-phenyl; 3-MeOCH₂-phenyl;
3-Me₂NCH₂-phenyl;
4-Cl-phenyl; 4-F-phenyl; 4-Br-phenyl; 4-CN-phenyl;
4-Me-phenyl; 4-Et-phenyl; 4-n-Pr-phenyl; 4-iso-Pr-phenyl;
4-n-Bu-phenyl; 4-CF₃-phenyl; 4-MeO-phenyl;
4-isopropoxyphenyl; 4-CF₃O-phenyl; 4-MeS-phenyl;
4-acetylphenyl; 3-acetamidophenyl; 4-pyridyl;
2-furanyl; 2-thiophenyl; 2-naphthyl; 1-pyrrolidinyl,
2,3-diCl-phenyl; 2,3-diF-phenyl; 2,3-diMe-phenyl;
2,3-diCF₃-phenyl; 2,3-diMeO-phenyl; 2,3-diCF₃O-phenyl;
2,4-diCl-phenyl; 2,4-diF-phenyl; 2,4-diMe-phenyl;
2,4-diCF₃-phenyl; 2,4-diMeO-phenyl; 2,4-diCF₃O-phenyl;
2,5-diCl-phenyl; 2,5-diF-phenyl; 2,5-diMe-phenyl;
2,5-diCF₃-phenyl; 2,5-diMeO-phenyl; 2,5-diCF₃O-phenyl;
2,6-diCl-phenyl; 2,6-diF-phenyl; 2,6-diMe-phenyl;
2,6-diCF₃-phenyl; 2,6-diMeO-phenyl; 2,6-diCF₃O-phenyl;
3,4-diCl-phenyl; 3,4-diF-phenyl; 3,4-diMe-phenyl;
3,4-diCF₃-phenyl; 3,4-diMeO-phenyl; 3,4-diCF₃O-phenyl;
2,4,6-triCl-phenyl; 2,4,6-triF-phenyl;
2,4,6-triMe-phenyl; 2,4,6-triCF₃-phenyl;
2,4,6-triMeO-phenyl; 2,4,6-triCF₃O-phenyl;
2,4,5-triMe-phenyl; 2,3,4-triF-phenyl;
2-Me-4-MeO-5-F-phenyl; 2,6-diCl-4-MeO-phenyl;
2,4-diMeO-6-F-phenyl; 2,6-diF-4-Cl-phenyl;
2,3,4,6-tetraF-phenyl; 2,3,4,5,6-pentaF-phenyl;
2-Cl-4-F-phenyl; 2-Cl-6-F-phenyl; 2-Cl-3-Me-phenyl;
2-Cl-4-MeO-phenyl; 2-Cl-4-EtO-phenyl;
2-Cl-4-iPrO-phenyl; 2-Cl-4-CF₃-phenyl;
2-Cl-4-CF₃O-phenyl; 2-C₁₋₄-(CHF₂)O-phenyl;
2-F-3-Cl-phenyl; 2-F-4-MeO-phenyl; 2-F-5-Me-phenyl;
2-Me-3-Cl-phenyl; 2-Me-3-CN-phenyl; 2-Me₄-Cl-phenyl;
2-Me-4-F-phenyl; 2-Me-4-CN-phenyl; 2-Me-4-MeO-phenyl;
2-Me₄-EtO-phenyl; 2-Me₄-MeS-phenyl;

2-Me₄-H₂NCO-phenyl; 2-Me₄-MeOC(=O)-phenyl;
2-Me₄-CH₃C(=O)-phenyl; 2-Me-5-F-phenyl;
2-Et-4-MeO-phenyl; 2-MeO-5-F-phenyl;
2-MeO-4-isopropyl-phenyl; 2-CF₃-4-Cl-phenyl;
2-CF₃-4-F-phenyl; 2-CF₃-4-MeO-phenyl;
2-CF₃-4-EtO-phenyl; 2-CF₃-4-iPrO-phenyl;
2-CF₃-4-CN-phenyl; 2-CF₃-6-F-phenyl;
2-CH-4-MeO-phenyl; 2-MeOC(=O)-3-MeO-phenyl;
2-CH₃CH(OH)-4-MeO-phenyl; 2-CH₃CH(OH)₄F-phenyl;
2-CH₃CH(OH)₄—Cl-phenyl; 2-CH₃CH(OH)-4-Me-phenyl;
2-CH₃CH(OMe)-4-MeO-phenyl; 2-CH₃C(=O)-4-MeO-phenyl;
2-CH₃C(=O)-4-F-phenyl; 2-CH₃C(=O)₄—Cl-phenyl;
2-CH₃C(=O)-4-Me-phenyl; 2-H₂C(OH)-4-MeO-phenyl;
2-H₂C(OMe)-4-MeO-phenyl; 2-H₃CCH₂CH(OH)-4-MeO-phenyl;
2-H₃CCH₂C(=O)-4-MeO-phenyl; 2-CH₃CO₂CH₂CH₂-4-MeO-phenyl;
(Z)-2-HOCH₂CH=CH-4-MeO-phenyl;
(E)-2-HOCH₂CH=CH-4-MeO-phenyl;
(Z)₂—CH₃CO₂CH=CH-4-MeO-phenyl;
(E)2-CH₃CO₂CH=CH-4-MeO-phenyl;
2-CH₃OCH₂CH₂-4-MeO-phenyl;
3-CN-4-F-phenyl; 3-H₂NCO-4-F-phenyl;
(2-Cl-phenyl)-CH=CH—; (3-Cl-phenyl)-CH=CH—;
(2,6-diF-phenyl)CH=CH—; phenyl-CH=CH—;
(2-Me-4-MeO-phenyl)-CH=CH—;
cyclohexyl; cyclopentyl; cyclohexylmethyl; benzyl;
2-F-benzyl; 3-F-benzyl; 4-F-benzyl; 3-MeO-benzyl;
3-OH-benzyl; 2-MeO-benzyl; 2-OH-benzyl;
tetrahydroquinolin-1-yl;
tetrahydroindolin-1-yl;
tetrahydroisoindolin-1-yl;
phenyl-S—; phenyl-NH—; pyrid-3-yl-NH—;
(4-Me-pyrid-3-yl)-NH—; (1-naphthyl)-NH—;
(2-naphthyl)-NH—; (2-Me-naphth-1-yl)-NH—;
(3-quinolinyl)-NH—;
(2-[1,1'-biphenyl])—NH—; (3-[1,1'-biphenyl])—NH—;
(4-[1,1'-biphenyl])—NH—; (2-F-phenyl)-NH—;
(2-Cl-phenyl)-NH—; (2-CF₃-phenyl)-NH—;
(2-CH₃-phenyl)-NH—; (2-OMe-phenyl)-NH—;
(2-CN-phenyl)-NH—; (2-OCF₃-phenyl)-NH—;
(2-SMe-phenyl)-NH—; (3-F-phenyl)-NH—;
(3-Cl-phenyl)-NH—; (3-CF₃-phenyl)-NH—;
(3-CH₃-phenyl)-NH—; (3-OMe-phenyl)-NH—;
(3-CN-phenyl)-NH—; (3-OCF₃-phenyl)-NH—;
(3-SMe-phenyl)-NH—; (4-F-phenyl)-NH—;
(4-Cl-phenyl)-NH—; (4-CF₃-phenyl)-NH—;
(4-CH₃-phenyl)-NH—; (4-OMe-phenyl)-NH—;
(4-CN-phenyl)-NH—; (4-OCF₃-phenyl)-NH—;
(4-SMe-phenyl)-NH—; (2,3-diCl-phenyl)-NH—;
(2,4-diCl-phenyl)-NH—; (2,5-diCl-phenyl)-NH—;
(2,6-diCl-phenyl)-NH—; (3,4-diCl-phenyl)-NH—;
(3,5-diCl-phenyl)-NH—; (2,3-diF-phenyl)-NH—;
(2,4-diF-phenyl)-NH—; (2,5-diF-phenyl)-NH—;
(2,6-diF-phenyl)-NH—; (3,4-diF-phenyl)-NH—;
(3,5-diF-phenyl)-NH—; (2,3-diCH₃-phenyl)-NH—;
(2,4-diCH₃-phenyl)-NH—; (2,5-diCH₃-phenyl)-NH—;
(2,6-diCH₃-phenyl)-NH—; (3,4-diCH₃-phenyl)-NH—;
(3,5-diCH₃-phenyl)-NH—; (2,3-diCF₃-phenyl)-NH—;
(2,4-diCF₃-phenyl)-NH—; (2,5-diCF₃-phenyl)-NH—;
(2,6-diCF₃-phenyl)-NH—; (3,4-diCF₃-phenyl)-NH—;
(3,5-diCF₃-phenyl)-NH—; (2,3-diOMe-phenyl)-NH—;
(2,4-diOMe-phenyl)-NH—; (2,5-diOMe-phenyl)-NH—;
(2,6-diOMe-phenyl)-NH—; (3,4-diOMe-phenyl)-NH—;
(3,5-diOMe-phenyl)-NH—; (2-F-3-Cl-phenyl)-NH—;
(2-F-4-Cl-phenyl)-NH—; (2-F—S-Cl-phenyl)-NH—;
(2-F-6-Cl-phenyl)-NH—; (2-F-3-CH₃-phenyl)-NH—;
(2-F-4-CH₃-phenyl)-NH—; (2-F-5-CH₃-phenyl)-NH—;
(2-F-6-CH₃-phenyl)-NH—; (2-F-3-CF₃-phenyl)-NH—;
(2-F-4-CF₃-phenyl)-NH—; (2-F-5-CF₃-phenyl)-NH—;
(2-F-6-CF₃-phenyl)-NH—; (2-F-3-OMe-phenyl)-NH—;
(2-F-4-OMe-phenyl)-NH—; (2-F-5-OMe-phenyl)-NH—;
(2-F-6-OMe-phenyl)-NH—; (2-Cl-3-F-phenyl)-NH—;
(2-Cl-4-F-phenyl)-NH—; (2-Cl-5-F-phenyl)-NH—;
(2-Cl-6-F-phenyl)-NH—; (2-Cl-3-CH₃-phenyl)-NH—;
(2-Cl-4-CH₃-phenyl)-NH—; (2-Cl-5-CH₃-phenyl)-NH—;
(2-Cl-6-CH₃-phenyl)-NH—; (2-Cl-3-CF₃-phenyl)-NH—;
(2-Cl-4-CF₃-phenyl)-NH—; (2-C₁₀.₅-CF₃-phenyl)-NH—;
(2-Cl-6-CF₃-phenyl)-NH—; (2-Cl-3-OMe-phenyl)-NH—;
(2-Cl-4-OMe-phenyl)-NH—; (2-Cl-5-OMe-phenyl)-NH—;
(2-Cl-6-OMe-phenyl)-NH—; (2-CH₃-3-F-phenyl)-NH—;
(2-CH₃-4-F-phenyl)-NH—; (2-CH₃-5-F-phenyl)-NH—;
(2-CH₃-6-F-phenyl)-NH—; (2-CH₃-3-Cl-phenyl)-NH—;
(2-CH₃-4-Cl-phenyl)-NH—; (2-CH₃-5-Cl-phenyl)-NH—;
(2-CH₃-6-Cl-phenyl)-NH—; (2-CH₃-3-CF₃-phenyl)-NH—;
(2-CH₃-4-CF₃-phenyl)-NH—; (2-CH₃-5-CF₃-phenyl)-NH—;
(2-CH₃-6-CF₃-phenyl)-NH—; (2-CH₃-3-OMe-phenyl)-NH—;
(2-CH₃-4-OMe-phenyl)-NH—; (2-CH₃-5-OMe-phenyl)-NH—;
(2-CH₃-6-OMe-phenyl)-NH—; (2-CF₃-3-F-phenyl)-NH—;
(2-CF₃-4-F-phenyl)-NH—; (2-CF₃-5-F-phenyl)-NH—;
(2-CF₃-6-F-phenyl)-NH—; (2-CF₃-3-Cl-phenyl)-NH—;
(2-CF₃-4-Cl-phenyl)-NH—; (2-CF₃-5-Cl-phenyl)-NH—;
(2-CF₃-6-Cl-phenyl)-NH—; (2-CF₃-3-CH₃-phenyl)-NH—;
(2-CF₃-4-CH₃-phenyl)-NH—; (2-CH₃-5-CF₃-phenyl)-NH—;
(2-CF₃-6-CH₃-phenyl)-NH—; (2-CF₃-3-OMe-phenyl)-NH—;
(2-CF₃-4-OMe-phenyl)-NH—; (2-CF₃-5-OMe-phenyl)-NH—;
(2-CF₃-6-OMe-phenyl)-NH—; (2-OMe-3-F-phenyl)-NH—;

(2-OMe-4-F-phenyl)-NH—; (2-OMe-5-F-phenyl)-NH—; (2-OMe-6-F-phenyl)-NH—; (2-OMe-3-Cl-phenyl)-NH—; (2-OMe-4-Cl-phenyl)-NH—; (2-OMe-5-Cl-phenyl)-NH—; (2-OMe-6-Cl-phenyl)-NH—; (2-OMe-4-CN-phenyl)-NH—; (2-OMe-4-CHO-phenyl)-NH—; (2-OMe-3-CH$_3$-phenyl)-NH—; (2-OMe-4-CH$_3$-phenyl)-NH—; (2-OMe-5-CH$_3$-phenyl)-NH—; (2-OMe-6-CH$_3$-phenyl)-NH—; (2-OMe-3-CF$_3$-phenyl)-NH—; (2-OMe-4-CF$_3$-phenyl)-NH—; (2-OMe-5-CF$_3$-phenyl)-NH—; (2-OMe-6-CF$_3$-phenyl)-NH—; (2-acetyl-4-Cl-phenyl)-NH—; (2-acetyl-4-Me-phenyl)-NH—; (2-acetyl-4-MeO-phenyl)-NH—; (2-CH$_3$CH(OH)-4-Cl-phenyl)-NH—; (2-CH$_3$CH(OH)-4-Me-phenyl)-NH—; (2-CH$_3$CH(OH)-4-MeO-phenyl)-NH—; (3-CF$_3$-4-Cl-phenyl)-NH—; (3-F-4-CHO-phenyl)-NH—; (3-CH$_3$-4-CN-phenyl)-NH—; (3-CH$_3$-4-MeO-phenyl)-NH—; (3-CH$_3$-4-Cl-phenyl)-NH—; (3-CH$_3$-4-F-phenyl)-NH—; (3-CH$_3$-4-CO$_2$-Me-phenyl)-NH—; (3-CF$_3$-4-C(O)CH$_3$-phenyl)-NH—; (3-CHO-4 OMe-phenyl)-NH—; (4-F-3-CF$_3$-phenyl)-NH—; (2,3,5-triCl-phenyl)-NH—; (2,4,5-triF-phenyl)-NH—; (2,6-diCl-3-Me-phenyl)-NH—; (3,5-diMe-4-MeO-phenyl)-NH—; (2-F-3-Cl-6-CF$_3$-phenyl)-NH—; benzyl-NH—; (3-quinolinyl)CH$_2$NH—; (2-F-phenyl)CH$_2$NH—; (2-Cl-phenyl)CH$_2$NH—; (2-CF$_3$-phenyl)CH$_2$NH—; (2-CH$_3$-phenyl)CH$_2$NH—; (2-OMe-phenyl)CH$_2$NH—; (2-CN-phenyl)CH$_2$NH—; (2-OCF$_3$-phenyl)CH$_2$NH—; (2-SMe-phenyl)CH$_2$NH—; (3-F-phenyl)CH$_2$NH—; (3-Cl-phenyl)CH$_2$NH—; (3-CF$_3$-phenyl)CH$_2$NH—; (3-CH$_3$-phenyl)CH$_2$NH—; (3-OMe-phenyl)CH$_2$NH—; (3-CN-phenyl)CH$_2$NH—; (3-OCF$_3$-phenyl)CH$_2$NH—; (3-SMe-phenyl)CH$_2$NH—; (4-F-phenyl)CH$_2$NH—; (4-Cl-phenyl)CH$_2$NH—; (4-CF$_3$-phenyl)CH$_2$NH—; (4-CH$_3$-phenyl)CH$_2$NH—; (4-OMe-phenyl)CH$_2$NH—; (4-CN-phenyl)CH$_2$NH—; (4-OCF$_3$-phenyl)CH$_2$NH—; (4-SMe-phenyl)CH$_2$NH—; (2,3-diCl-phenyl)CH$_2$NH—; (2,4-diCl-phenyl)CH$_2$NH—; (2,5-diCl-phenyl)CH$_2$NH—; (2,6-diCl-phenyl)CH$_2$NH—; (3,4-diCl-phenyl)CH$_2$NH—; (3,5-diCl-phenyl)CH$_2$NH—; (2,3-diF-phenyl)CH$_2$NH—; (2,4-diF-phenyl)CH$_2$NH—; (2,5-diF-phenyl)CH$_2$NH—; (2,6-diF-phenyl)CH$_2$NH—; (3,4-diF-phenyl)CH$_2$NH—; (3,5-diF-phenyl)CH$_2$NH—; (2,3-diCH$_3$-phenyl)CH$_2$NH—; (2,4-diCH$_3$-phenyl)CH$_2$NH—; (2,5-diCH$_3$-phenyl)CH$_2$NH—; (2,6-diCH$_3$-phenyl)CH$_2$NH—; (3,4-diCH$_3$-phenyl)CH$_2$NH—; (3,5-diCH$_3$-phenyl)CH$_2$NH—; (2,3-diCF$_3$-phenyl)CH$_2$NH—; (2,4-diCF$_3$-phenyl)CH$_2$NH—; (2,5-diCF$_3$-phenyl)CH$_2$NH—; (2,6-diCF$_3$-phenyl)CH$_2$NH—; (3,4-diCF$_3$-phenyl)CH$_2$NH—; (3,5-diCF$_3$-phenyl)CH$_2$NH—; (2,3-diOMe-phenyl)CH$_2$NH—; (2,4-diOMe-phenyl)CH$_2$NH—; (2,5-diOMe-phenyl)CH$_2$NH—; (2,6-diOMe-phenyl)CH$_2$NH—; (3,4-diOMe-phenyl)CH$_2$NH—; (3,5-diOMe-phenyl)CH$_2$NH—; (2-F-3-Cl-phenyl)CH$_2$NH—; (2-F-4-Cl-phenyl)CH$_2$NH—; (2-F-5-Cl-phenyl)CH$_2$NH—; (2-F-6-Cl-phenyl)CH$_2$NH—; (2-F-3-CH$_3$-phenyl)CH$_2$NH—; (2-F-4-CH$_3$-phenyl)CH$_2$NH—; (2-F-5-CH$_3$-phenyl)CH$_2$NH—; (2-F-6-CH$_3$-phenyl)CH$_2$NH—; (2-F-3-CF$_3$-phenyl)CH$_2$NH—; (2-F-4-CF$_3$-phenyl)CH$_2$NH—; (2-F-5-CF$_3$-phenyl)CH$_2$NH—; (2-F-6-CF$_3$-phenyl)CH$_2$NH—; (2-F-3-OMe-phenyl)CH$_2$NH—; (2-F-4-OMe-phenyl)CH$_2$NH—; (2-F-5-OMe-phenyl)CH$_2$NH—; (2-F-6-OMe-phenyl)CH$_2$NH—; (2-Cl-3-F-phenyl)CH$_2$NH—; (2-Cl-4-F-phenyl)CH$_2$NH—; (2-Cl-5-F-phenyl)CH$_2$NH—; (2-Cl-6-F-phenyl)CH$_2$NH—; (2-Cl-3-CH$_3$-phenyl)CH$_2$NH—; (2-Cl-4-CH$_3$-phenyl)CH$_2$NH—; (2-Cl-5-CH$_3$-phenyl)CH$_2$NH—; (2-Cl-6-CH$_3$-phenyl)CH$_2$NH—; (2-Cl-3-CF$_3$-phenyl)CH$_2$NH—; (2-Cl-4-CF$_3$-phenyl)CH$_2$NH—; (2-Cl-5-CF$_3$-phenyl)CH$_2$NH—; (2-Cl-6-CF$_3$-phenyl)CH$_2$NH—; (2-Cl-3-OMe-phenyl)CH$_2$NH—; (2-Cl4-OMe-phenyl)CH$_2$NH—; (2-Cl-5-OMe-phenyl)CH$_2$NH—; (2-Cl-6-OMe-phenyl)CH$_2$NH—; (2-CH$_3$-3-F-phenyl)CH$_2$NH—; (2-CH$_3$-4-F-phenyl)CH$_2$NH—; (2-CH$_3$-5-F-phenyl)CH$_2$NH—; (2-CH$_3$-6-F-phenyl)CH$_2$NH—; (2-CH$_3$-3-Cl-phenyl)CH$_2$NH—; (2-CH$_3$-4-Cl-phenyl)CH$_2$NH—; (2-CH$_3$-5-Cl-phenyl)CH$_2$NH—; (2-CH$_3$-6-Cl-phenyl)CH$_2$NH—; (2-CH$_3$-3-CF$_3$-phenyl)CH$_2$NH—; (2-CH$_3$-4-CF$_3$-phenyl)CH$_2$NH—; (2-CH$_3$-5-CF$_3$-phenyl)CH$_2$NH—; (2-CH$_3$-6-CF$_3$-phenyl)CH$_2$NH—; (2-CH$_3$-3-OMe-phenyl)CH$_2$NH—; (2-CH$_3$-4-OMe-phenyl)CH$_2$NH—; (2-CH$_3$-5-OMe-phenyl)CH$_2$NH—; (2-CH$_3$-6-OMe-phenyl)CH$_2$NH—; (2-CF$_3$-3-F-phenyl)CH$_2$NH—;

(2-CF₃-4-F-phenyl)CH₂NH—; (2-CF₃-5-F-phenyl)CH₂NH—;
(2-CF₃-6-F-phenyl)CH₂NH—; (2-CF₃-3-Cl-phenyl)CH₂NH—;
(2-CF₃-4-Cl-phenyl)CH₂NH—; (2-CF₃-5-Cl-phenyl)CH₂NH—;
(2-CF₃-6-Cl-phenyl)CH₂NH—; (2-CF₃-3-CH₃-phenyl)CH₂NH—;
(2-CF₃-4-CH₃-phenyl)CH₂NH—; (2-CH₃-5-CF₃-phenyl)CH₂NH—;
(2-CF₃-6-CH₃-phenyl)CH₂NH—; (2-CF₃-3-OMe-phenyl)CH₂NH—;
(2-CF₃-4-OMe-phenyl)CH₂NH—; (2-CF₃-5-OMe-phenyl)CH₂NH—;
(2-CF₃-4-OMe-phenyl)CH₂NH—; (2-OMe-3-F-phenyl)CH₂NH—;
(2-OMe-4-F-phenyl)CH₂NH—; (2-OMe-5-F-phenyl)CH₂NH—;
(2-OMe-6-F-phenyl)CH₂NH—; (2-OMe-3-Cl-phenyl)CH₂NH—;
(2-OMe-4-Cl-phenyl)CH₂NH—; (2-OMe-5-Cl-phenyl)CH₂NH—;
(2-OMe-6-Cl-phenyl)CH₂NH—; (2-OMe-4-CN-phenyl)CH₂NH—;
(2-OMe-4-CHO-phenyl)CH₂NH—; (2-OMe-3-CH₃-phenyl)CH₂NH—;
(2-OMe-4-CH₃-phenyl)CH₂NH—; (2-OMe-5-CH₃-phenyl)CH₂NH—;
(2-OMe-6-CH₃-phenyl)CH₂NH—; (2-OMe-3-CF₃-phenyl)CH₂NH—;
(2-OMe-4-CF₃-phenyl)CH₂NH—; (2-OMe-5-CF₃-phenyl)CH₂NH—;
(2-OMe-6-CF₃-phenyl)CH₂NH—; (2-acetyl-4-Cl-phenyl)CH₂NH—;
(2-acetyl-4-Me-phenyl)CH₂NH—;
(2-acetyl-4-MeO-phenyl)CH₂NH—;
(2-CH₃CH(OH)-4-Cl-phenyl)CH₂NH—;
(2-CH₃CH(OH)-4-Me-phenyl)CH₂NH—;
(2-CH₃CH(OH)-4-MeO-phenyl)CH₂NH—;
(3-CF₃-4-Cl-phenyl)CH₂NH—; (3-F-4-CHO-phenyl)CH₂NH—;
(3-CH₃-4-CN-phenyl)CH₂NH—; (3-CH₃-4-MeO-phenyl)CH₂NH—;
(3-CH₃-4-Cl-phenyl)CH₂NH—; (3-CH₃-4-F-phenyl)CH₂NH—;
(4-F-3-CF₃-phenyl)CH₂NH—; (3-CH₃-4-CO₂-Me-phenyl)CH₂NH—;
(3-CF₃-4-C(O)CH₃-phenyl)CH₂NH—;
(3-CHO-4-OMe-phenyl)CH₂NH—;
(2,3,5-triCl-phenyl)CH₂NH—;
(2,4,5-triF-phenyl)CH₂NH—;
(2,6-diCl-3-Me-phenyl)CH₂NH—;
(3,5-diMe-4-MeO-phenyl)CH₂NH—; and
(2-F-3-Cl-6-CF₃-phenyl)CH₂NH—;
n is 1 or 2.

[11a] In another preferred embodiment the present invention provides a compound of Formula (II):

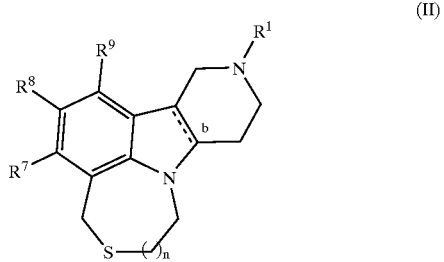

wherein:
b is a single bond, wherein the bridge hydrogens are in a cis position;
$R^1$ is selected from
hydrogen, methyl, ethyl, n-propyl, n-butyl, s-butyl,
t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl,
4-methylpentyl, 2-fluoroethyl, 2,2-difluoroethyl,
2,2,2-trifluoroethyl, 2-propenyl, 2-methyl-2-propenyl, trans-2-butenyl, 3-methyl-butenyl,
3-butenyl,
trans-2-pentenyl, cis-2-pentenyl, 4-pentenyl,
4-methyl-3-pentenyl, 3,3-dichloro-2-propenyl,
trans-3-phenyl-2-propenyl, cyclopropyl, cyclobutyl, cyclopentyl, cyclohexyl,
cyclopropylmethyl, cyclobutylmethyl, cyclopentylmethyl, cyclohexylmethyl,
—CH=CH₂, —CH₂—CH=CH₂, —CH=CH—CH₃, —CCH, —C≡C—CH₃,
and —CH₂—C≡CH;
$R^7$ and $R^9$, at each occurrence, are independently selected from hydrogen, fluoro, methyl, trifluoromethyl, and methoxy;
$R^8$ is selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl,
methylC(=O, ethylC(=O)—, propylC(=O)—, isopropylC(=O)—, butylC(=O)—, phenylC(=O)—,
methylCO₂—, ethylCO₂—, propylCO₂—, isopropylCO₂—, butylCO₂—, phenylCO₂—,
dimethylamino-S(=O)—, diethylamino-S(=O),
dipropylamino-S(=O)—, di-isopropylamino-S(=O)—, dibutylamino-S(=O),
diphenylamino-S(=O)—,
dimethylamino-SO₂—, diethylamino-SO₂—,
dipropylamino-SO₂—, di-isopropylamino-SO₂—,
dibutylamino-SO₂—, diphenylamino-SO₂—,
dimethylamino-C(=O), diethylamino-C(=O)—,
dipropylamino-C(=O), di-isopropylamino-C(=O)—, dibutylamino-C(=O)—,
diphenylamino-C(=O)—,
2-chlorophenyl, 2-fluorophenyl, 2-bromophenyl,
2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl, 3-cyanophenyl, 3-methylphenyl, 3-ethylphenyl,
3-propylphenyl, 3-isopropylphenyl, 3-butylphenyl,
3-trifluoromethylphenyl, 3-methoxyphenyl,
3-isopropoxyphenyl, 3-trifluoromethoxyphenyl,
3-thiomethoxyphenyl,
4-chlorophenyl, 4-fluorophenyl, 4-bromophenyl,
4-cyanophenyl, 4-methylphenyl, 4-ethylphenyl,
4-propylphenyl, 4-isopropylphenyl, 4-butylphenyl,
4-trifluoromethylphenyl, 4-methoxyphenyl,
4-isopropoxyphenyl, 4-trifluoromethoxyphenyl,
4-thiomethoxyphenyl,
2,3-dichlorophenyl, 2,3-difluorophenyl,
2,3-dimethylphenyl, 2,3-ditrifluoromethylphenyl,
2,3-dimethoxyphenyl, 2,3-ditrifluoromethoxyphenyl,
2,4-dichlorophenyl, 2,4-difluorophenyl,
2,4-dimethylphenyl, 2,4-ditrifluoromethylphenyl,
2,4-dimethoxyphenyl, 2,4-ditrifluoromethoxyphenyl,
2,5-dichlorophenyl, 2,5-difluorophenyl,
2,5-dimethylphenyl, 2,5-ditrifluoromethylphenyl,
2,5-dimethoxyphenyl, 2,5-ditrifluoromethoxyphenyl,
2,6-dichlorophenyl, 2,6-difluorophenyl,
2,6-dimethylphenyl, 2,6-ditrifluoromethylphenyl,
2,6-dimethoxyphenyl, 2,6-ditrifluoromethoxyphenyl,
3,4-dichlorophenyl, 3,4-difluorophenyl,
3,4-dimethylphenyl, 3,4-ditrifluoromethylphenyl,
3,4-dimethoxyphenyl, 3,4-ditrifluoromethoxyphenyl,
2,4,6-trichlorophenyl, 2,4,6-trifluorophenyl,
2,4,6-trimethylphenyl, 2,4,6-tritrifluoromethylphenyl,
2,4,6-trimethoxyphenyl, 2,4,6-tritrifluoromethoxyphenyl,
2-chloro-4-$CF_3$-phenyl, 2-fluoro-3-chloro-phenyl,
2-chloro-4-$CF_3$-phenyl, 2-chloro-4-methoxy-phenyl,
2-methoxy-4-isopropyl-phenyl, 2-$CF_3$-4-methoxy-phenyl,
2-methyl-4-methoxy-5-fluoro-phenyl,
2-methyl-4-methoxy-phenyl, 2-chloro-4-$CF_3O$-phenyl,
2,4,5-trimethyl-phenyl, 2-methyl-4-chloro-phenyl,
methyl-C(=O)-NH—, ethyl-C(=O)-NH—, propyl-C(=O)-NH—,
isopropyl-C(=O)-NH—, butyl-C(=O)-NH—, phenyl-C(=O)-NH—,
4-acetylphenyl, 3-acetamidophenyl, 4-pyridyl, 2-furanyl, 2-thiophenyl, 2-naphthyl;
2-Me-5-F-phenyl, 2-F-5-Me-phenyl, 2-MeO-5-F-phenyl,
2-Me-3-Cl-phenyl, 3-$NO_2$-phenyl, 2-$NO_2$-phenyl,
2-Cl-3-Me-phenyl, 2-$Me_4$-EtO-phenyl, 2-Me-4-F-phenyl,
2-Cl-6-F-phenyl, 2-$C_{14}$—($CHF_2$)O-phenyl,
2,4-diMeO-6-F-phenyl, 2-$CF_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-$CF_3$-4-EtO-phenyl, 2-$CF_3$-4-iPrO-phenyl,
2-$CF_3$-4-Cl-phenyl, 2-$CF_3$-4-F-phenyl, 2-Cl-4-EtO-phenyl,
2-$C_{1-4}$-iPrO-phenyl, 2-Et-4-MeO-phenyl,
2-CHO-4-MeO-phenyl, 2-$CH_3CH(OH)$-4-MeO-phenyl,
2-$CH_3CH(OH)$-4-F-phenyl, 2-$CH_3CH(OH)$-4-Cl-phenyl,
2-$CH_3CH(OH)$-4-Me-phenyl, 2-$CH_3CH(OMe)$-4-MeO-phenyl, 2-$CH_3C$(=O)-4-MeO-phenyl, 2-$CH_3C$(=O)-4-F-phenyl,
2-$CH_3C$(=O)$_4$—Cl-phenyl, 2-$CH_3C$(=O)-4-Me-phenyl,
2-$H_2C(OH)$-4-MeO-phenyl, 2-$H_2C(OMe)$-4-MeO-phenyl,
2-$H_3CCH_2CH(OH)$-4-MeO-phenyl, 2-$H_3CCH_2C$(=O)-4-MeO-phenyl,
2-$CH_3CO_2CH_2CH_2$-4-MeO-phenyl,
(Z)-2-$HOCH_2CH$=CH-4-MeO-phenyl,
(E)-2-$HOCH_2CH$=CH-4-MeO-phenyl,
(Z)-2-$CH_3CO_2CH$=CH-4-MeO-phenyl,
(E)-2-$CH_3CO_2CH$=CH-4-MeO-phenyl,
2-$CH_3OCH_2CH_2$-4-MeO-phenyl,
2-F-4-MeO-phenyl, 2-Cl-4-F-phenyl,
(2-Cl-phenyl)-CH=CH—, (3-Cl-phenyl)CH=CH—,
(2,6-diF-phenyl)-CH=CH—, —$CH_2CH$=$CH_2$,
phenyl-CH=CH—, (2-$Me_4$-MeO-phenyl)-CH=CH—,
cyclohexyl, cyclopentyl, cyclohexylmethyl,
$EtCO_2CH_2CH_2$-, $EtCO_2CH_2CH_2CH_2$—,
$EtCO_2CH_2CH_2CH_2CH_2$—,
benzyl, 2-F-benzyl, 3-F-benzyl, 4-F-benzyl,
3-MeO-benzyl, 3-OH-benzyl, 2-MeO-benzyl,
2-OH-benzyl, 2-MeOC(=O)-3-MeO-phenyl,
2-Me-4-CN-phenyl, 2-Me-3-CN-phenyl,
2-Me-4-MeS-phenyl, 2-$CF_3$—CN-phenyl,
2-CHO-phenyl, 3—CHO-phenyl, 2-$HOCH_2$-phenyl,
3-$HOCH_2$-phenyl, 3-$MeOCH_2$-phenyl,
3-$Me_2NCH_2$-phenyl, 3-CN-4-F-phenyl,
2-Me-4-$H_2NCO$-phenyl, 2-$Me_4$-MeOC(=O)-phenyl,
3-$H_2NCO$-4-F-phenyl, 2-$Me_2NCH_2$-4-MeO-phenyl-,
2-$Me_4$-$CH_3C$(=O)-phenyl, phenyl-S—, $Me_2N$—,
1-pyrrolidinyl,
phenyl-NH—, benzyl-NH—, (1-naphthyl)-NH—,
(2-naphthyl)-NH—, (2-[1,4'-biphenyl])—NH—,
(3-[1,1'-biphenyl])-NH—, (4-[1,1'-biphenyl])-NH—,
(2-F-phenyl)—NH—, (2-Cl-phenyl)—NH—,
(2-$CF_3$-phenyl)-NH—, (2-$CH_3$-phenyl)-NH—,
(2-OMe-phenyl)-NH—, (2-CN-phenyl)-NH—,
(2-$OCF_3$-phenyl)-NH—, (2-SMe-phenyl)-NH—,
(3-F-phenyl)-NH—, (3-Cl-phenyl)-NH—,
(3-$CF_3$-phenyl)-NH—, (3-$CH_3$-phenyl)-NH—,
(3-OMe-phenyl)-NH—, (3-CN-phenyl)-NH—,
(3-O $CF_3$-phenyl)-NH—, (3-SMe-phenyl)-NH—,
(4-F-phenyl)-NH—, (4-CF-phenyl, —NH—,
(4-$CF_3$-phenyl)-NH—, (4-C 23-phenyl)-Nz-,
(4-OMe-phenyl, NH—, (4-CN-phenyl)-NH—,
(4-$OCF_3$-phenyl)-NH—, (4-SMe-phenyl)-NH—,
(2,3-diCl-phenyl)-NH—, (2,4-diCl-phenyl)-NH—,
(2,5-diCl-phenyl, —NH—, (2,6-diCl-phenyl)-NH—,
(3,4-diCl-phenyl)-NH—, (3,5-diCl-phenyl)-NH—,
(2,3-diF-phenyl)-NH—, (2,4-diF-phenyl)-NH—,
(2,5-diF-phenyl)-NH—, (2,6-diF-phenyl-4 NH—,
(3,4-diF-phenyl)-NH—, (3,5-diF-phenyl)-NH—,
(2,3-di$CH_3$-phenyl)-NH—, (2,4-di$CH_3$-phenyl)-NH—,
(2,5-di$CH_3$-phenyl)-NH—, (2,6-di$CH_3$-phenyl)-NH—,
(3,4-di$CH_3$-phenyl)-NH—, (3,5-di$CH_3$-phenyl)-NH—, (2,3-diCF₃-phenyl)-NH—, (2,4-diCF₃-phenyl)-NH—,
(2,5-diCF₃-phenyl)-NH—, (2,6-diCF₃-phenyl)-NH—,
(3,4-diCF₃-phenyl)-NH—, (3,5-diCF₃-phenyl)-NH—,
(2,3-diOMe-phenyl)-NH—, (2,4-diOMe-phenyl)-NH—,
(2,5-diOMe-phenyl)-NH—, (2,6-diOMe-phenyl)-NH—,
(3,4-diOMe-phenyl)-NH—, (3,5-diOMe-phenyl)-NH—,
(2-F-3-Cl-phenyl)-NH—, (2-F-4-Cl-phenyl)-NH—,
(2-F-5-Cl-phenyl)-NH—, (2-F-6-Cl-phenyl)-NH—,
(2-F-3-CH₃-phenyl)-NH—, (2-F-4-CH₃-phenyl)-NH—,
(2-F-5-CH₃-phenyl)-NH—, (2-F-6-CH₃-phenyl)-NH—,
(2-F-3-CF₃-phenyl)-NH—, (2-F-4-CF₃-phenyl)-NH—,
(2-F-5-CF₃-phenyl)-NH—, (2-F-6-CF₃-phenyl)-NH—,
(2-F-3-OMe-phenyl)-NH—, (2-F-4-OMe-phenyl)-NH—,
(2-F—S-OMe-phenyl)-NH—, (2-F-6-OMe-phenyl)-NH—,
(2-Cl-3-F-phenyl)-NH—, (2-Cl-4-F-phenyl)-NH—,
(2-Cl-5-F-phenyl)-NH—, (2-Cl-6-F-phenyl)-NH—,
(2-Cl-3-CH₃-phenyl)-NH—, (2-Cl-4-CH₃-phenyl)-NH—,
(2-Cl-5-CH₃-phenyl)-NH—, (2-Cl-6-CH₃-phenyl)-NH—,
(2-Cl-3-CF₃-phenyl)-NH—, (2-Cl-4-CF₃-phenyl)-NH—,
(2-Cl-5-CF₃-phenyl)-NH—, (2-Cl-6-CF₃-phenyl)-NH—,
(2-Cl-3-OMe-phenyl)-NH—, (2-Cl-4-OMe-phenyl)-NH—,
(2-Cl-5-OMe-phenyl)-NH—, (2-Cl-6-OMe-phenyl)-NH—,
(2-CH₃-3-F-phenyl)-NH—, (2-CH₃-4-F-phenyl)-NH—,
(2-CH₃-5-F-phenyl)-NH—, (2-CH₃-6-F-phenyl)-NH—,
(2-CH₃-3-Cl-phenyl)-NH—, (2-CH₃-4-Cl-phenyl)-NH—,
(2-CH₃-5-Cl-phenyl)-NH—, (2-CH₃-6-Cl-phenyl)-NH—,
(2-CH₃-3-CF₃-phenyl)-NH—, (2-CH₃-4-CF₃-phenyl)-NH—,
(2-CH₃-5-CF₃-phenyl)-NH—, (2-CH₃-6-CF₃-phenyl)-NH—,
(2-CH₃-3-OMe-phenyl)-NH—, (2-CH₃-4-OMe-phenyl)-NH—,
(2-CH₃-5-OMe-phenyl)-NH—, (2-CH₃-6-OMe-phenyl)-NH—,
(2-CF₃-3-F-phenyl)-NH—, (2-CF₃-4-F-phenyl)-NH—,
(2-CF₃-5-F-phenyl)-NH—, (2-CF₃-6-F-phenyl)-NH—,
(2-CF₃-3-Cl-phenyl)-NH—, (2-CF₃-4-Cl-phenyl)-NH—,
(2-CF₃-5-Cl-phenyl)-NH—, (2-CF₃-6-Cl-phenyl)-NH—,
(2-CF₃-3-CH₃-phenyl)-NH—, (2-CF₃-4-CH₃-phenyl)-NH—,
(2-CH₃-5-CF₃-phenyl)-NH—, (2-CF₃-6-CH₃-phenyl)-NH—,
(2-CF₃-3-OMe-phenyl)-NH—, (2-CF₃-4-OMe-phenyl)-NH—,
(2-CF₃-5-OMe-phenyl)-NH—, (2-CF₃-6-OMe-phenyl)-NH—,
(2-OMe-3-F-phenyl)-NH—, (2-OMe-4-F-phenyl)-NH—,
(2-OMe-5-F-phenyl)-NH—, (2-OMe-6-F-phenyl)-NH—,
(2-OMe-3-Cl-phenyl)-NH—, (2-OMe-4-Cl-phenyl)-NH—,
(2-OMe-5-Cl-phenyl)-NH—, (2-OMe-6-Cl-phenyl)-NH—,
(2-OMe-3-CH₃-phenyl)-NH—, (2-OMe-4-CH₃-phenyl)-NH—,
(2-OMe-5-CH₃-phenyl)-NH—, (2-OMe-6-CH₃-phenyl)-NH—,
(2-OMe-3-CF₃-phenyl)-NH—, (2-OMe-4-CF₃-phenyl)-NH—,
(2-OMe-5-CF₃-phenyl)-NH—, (2-OMe-6-CF₃-phenyl)NH—,
(3-CF₃-4-Cl-phenyl)-NH—, (3-CF₃-4-C(O)CH₃-phenyl)-NH—, (2,3,5-triCl-phenyl)-NH—,
(3-CH₃-4-CO₂-Me-phenyl)-NH—, and
(3-CHO-4-OMe-phenyl)-NH—;
n is 1 or 2.

[12] In another preferred embodiment the present invention provides a compound of Formula (III):

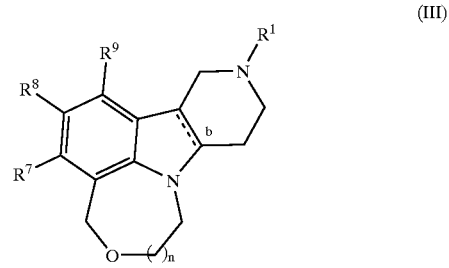

(III)

wherein:
b is a single bond, wherein the bridge hydrogens are in a cis position;
R¹ is selected from
  hydrogen, methyl, ethyl, n-propyl, n-butyl, s-butyl,
  t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl,
  4-methylpentyl, 2-fluoroethyl, 2,2-difluoroethyl,
  2,2,2-trifluoroethyl, 2-propenyl, 2-methyl-2-propenyl, trans-2-butenyl, 3-methyl-2-butenyl, 3-butenyl,
  trans-2-pentenyl, cis-2-pentenyl, 4-pentenyl,
  4-methyl-3-pentenyl, 3,3-dichloro-2-propenyl,
  trans-3-phenyl-2-propenyl, cyclopropyl, cyclobutyl, cyclopentyl, cyclohexyl,
  cyclopropylmethyl, cyclobutylmethyl, cyclopentylmethyl, cyclohexylmethyl,
  —CH=CH₂, —CH₂—CH=CH₂, —CH=CH—CH₃, —C≡CH, —C=C—CH₃,
  and —CH₂—C≡CH;
R⁷ and R⁹, at each occurrence, are independently selected from hydrogen, fluoro, methyl, trifluoromethyl, and methoxy; and
R⁸ is selected from
  hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl;
  2-Cl-phenyl; 2-F-phenyl; 2-Br-phenyl; 2-CN-phenyl;
  2-Me-phenyl; 2-CF₃-phenyl; 2-MeO-phenyl; 2-CF₃O-phenyl; 2-NO₂-phenyl; 2-MeS-phenyl; 2-CHO-phenyl; 2-HOCH₂-phenyl;
  3-Cl-phenyl; 3-F-phenyl; 3-Br-phenyl; 3-CN-phenyl;
  3-Me-phenyl; 3-Et-phenyl; 3-n-Pr-phenyl; 3-isoPr-phenyl;

3-n-Bu-phenyl; 3-CF$_3$-phenyl; 3-MeO-phenyl; 3-MeS-phenyl;
3-isopropoxyphenyl; 3-CF$_3$O-phenyl; 3-NO$_2$-phenyl;
3-CHO-phenyl; 3-HOCH$_2$-phenyl; 3-MeOCH$_2$-phenyl;
3-Me$_2$NCH$_2$-phenyl;
4-Cl-phenyl; 4-F-phenyl; 4-Br-phenyl; 4-CN-phenyl;
4-Me-phenyl; 4-Et-phenyl; 4-n-Pr-phenyl; 4-iso-Pr-phenyl;
4-n-Bu-phenyl; 4-CF$_3$-phenyl; 4-MeO-phenyl;
4-isopropoxyphenyl; 4-CF$_3$O-phenyl; 4-MeS-phenyl;
4-acetylphenyl; 3-acetamidophenyl; 4-pyridyl;
2-furanyl; 2-thiophenyl; 2-naphthyl; 1-pyrrolidinyl,
2,3-diCl-phenyl; 2,3-diF-phenyl; 2,3-diMe-phenyl;
2,3-diCF$_3$-phenyl; 2,3-diMeO-phenyl; 2,3-diCF$_3$O-phenyl;
2,4-diCl-phenyl; 2,4-diF-phenyl; 2,4-diMe-phenyl;
2,4-diCF$_3$-phenyl; 2,4-diMeO-phenyl; 2,4-diCF$_3$O-phenyl;
2,5-diCl-phenyl; 2,5-diF-phenyl; 2,5-diMe-phenyl;
2,5-diCF$_3$-phenyl; 2,5-diMeO-phenyl; 2,5-diCF$_3$O-phenyl;
2,6-diCl-phenyl; 2,6-diF-phenyl; 2,6-diMe-phenyl;
2,6-diCF$_3$-phenyl; 2,6-diMeO-phenyl; 2,6-diCF$_3$O-phenyl;
3,4-diCl-phenyl; 3,4-diF-phenyl; 3,4-diMe-phenyl;
3,4-diCF$_3$-phenyl; 3,4-diMeO-phenyl; 3,4-diCF$_3$O-phenyl;
2,4,6-triCl-phenyl; 2,4,6-triF-phenyl;
2,4,6-triMe-phenyl; 2,4,6-triCF$_3$-phenyl;
2,4,6-triMeO-phenyl; 2,4,6-triCF$_3$O-phenyl;
2,4,5-triMe-phenyl; 2,3,4-triF-phenyl;
2-Me-4-MeO-5-F-phenyl; 2,6-diCl-4-MeO-phenyl;
2,4-diMeO-6-F-phenyl; 2,6-diF-4-Cl-phenyl;
2,3,4,6-tetraF-phenyl; 2,3,4,5,6-pentaF-phenyl;
2-C14-F-phenyl; 2-Cl-6-F-phenyl; 2-Cl-3-Me-phenyl;
2-Cl-4-MeO-phenyl; 2-Cl-4-EtO-phenyl;
2-C$_{1-4}$-iPrO-phenyl; 2-Cl-4-CF$_3$-phenyl;
2-Cl-4-CF$_3$O-phenyl; 2-Cl(CHF$_2$)O-phenyl;
2-F-3-Cl-phenyl; 2-F-4-MeO-phenyl; 2-F-5-Me-phenyl;
2-Me-3-Cl-phenyl; 2-Me-3-CN-phenyl; 2-Me$_4$-Cl-phenyl;
2-Me$_4$-F-phenyl; 2-Me-4-CN-phenyl; 2-Me$_4$-MeO-phenyl;
2-Me-4-EtO-phenyl; 2-Me$_4$-MeS-phenyl;
2-Me-4-H$_2$NCO-phenyl; 2-Me$_4$-MeOC(=O)-phenyl;
2-Me-4-CH$_3$C(=O)-phenyl; 2-Me-5-F-phenyl;
2-Et 4-MeO-phenyl; 2-MeO-5-F-phenyl;
2-MeO-4-isopropyl-phenyl; 2-CF$_3$-4-Cl-phenyl;
2-CF$_3$-4-F-phenyl; 2-CF$_3$-4-MeO-phenyl;
2-CF$_3$-4-EtO-phenyl; 2-CF$_3$-4-iPrO-phenyl;
2-CF$_3$-4-CN-phenyl; 2-CF$_3$-6-F-phenyl;
2-CHO-4-MeO-phenyl; 2-MeOC(=O)-3-MeO-phenyl;
2-CH$_3$CH(OH)-4-MeO-phenyl; 2-CH$_3$CH(OH)-4-F-phenyl;
2-CH$_3$CH(OH)$_4$—Cl-phenyl; 2-CH$_3$CH(OH)-4-Me-phenyl;
2-CH$_3$CH(OMe)-4-MeO-phenyl; 2-CH$_3$C(=O)-4-MeO-phenyl;
2-CH$_3$C(=O)-4-F-phenyl; 2-CH$_3$C(=O)-4-Cl-phenyl;
2-CH$_3$C(=O)-4-Me-phenyl; 2-H$_2$C(OH)-4-MeO-phenyl;
2-H$_2$C(OMe)-4-MeO-phenyl; 2-H$_3$CCH$_2$CH(OH)-4-MeO-phenyl;
2-H$_3$CCH$_2$C(=O)-4-MeO-phenyl; 2-CH$_3$CO$_2$CH$_2$CH$_2$-4-MeO-phenyl;
(Z)-2-HOCH$_2$CH=CH-4-MeO-phenyl;
(E)-2-HOCH$_2$CH=CH-4-MeO-phenyl;
(Z)-2-CH$_3$CO$_2$CH=CH-4-MeO-phenyl;
(E)-2-CH$_3$CO$_2$CH=CH-4-MeO-phenyl;
2-CH$_3$OCH$_2$CH$_2$-4-MeO-phenyl;
3-CN-4—F-phenyl; 3-H$_2$NCO-4—F-phenyl;
(2-Cl-phenyl)CH=CH—; (3-Cl-phenyl)-CH=CH—;
(2,6-diF-phenyl)-CH=CH—; phenyl-CH=CH—;
(2-Me-4-MeO-phenyl)CH=CH—;
cyclohexyl; cyclopentyl; cyclohexylmethyl; benzyl;
2-F-benzyl; 3-F-benzyl; 4-F-benzyl; 3-MeO-benzyl;
3-OH-benzyl; 2-MeO-benzyl; 2-OH-benzyl;
tetrahydroquinolin-1-yl;
tetrahydroindolin-1-yl;
tetrahydroisoindolin-1-yl;
phenyl-S—; phenyl-NH—; pyrid-3-yl-NH—;
(4-Me-pyrid-3-yl)-NH—; (1-naphthyl)-NH—;
(2-naphthyl)-NH—; (2-Me-naphth-1-yl)-NH—;
(3-quinolinyl)-NH—;
(2-[1,1'-biphenyl])—NH—; (3-[1,1'-biphenyl])-NH—;
(4-[1,1'-biphenyl])—NH—; (2-F-phenyl)-NH—;
(2-Cl-phenyl)-NH—; (2-CF$_3$-phenyl)-NH—;
(2-CH$_3$-phenyl)-NH—; (2-OMe-phenyl)-NH—;
(2-CN-phenyl)-NH—; (2-OCF$_3$-phenyl)-NH—;
(2-SMe-phenyl)-NH—; (3-F-phenyl)-NH—;
(3-Cl-phenyl)-NH—; (3-CF$_3$-phenyl)-NH—;
(3-CH$_3$-phenyl)-NH—; (3-OMe-phenyl)-NH—;
(3-CN-phenyl)-NH—; (3-OCF$_3$-phenyl)-NH—;
(3-SMe-phenyl)-NH—; (4-F-phenyl)-NH—;
(4-Cl-phenyl)-NH—; (4-CF$_3$-phenyl)-NH—;
(4-CH$_3$-phenyl)-NH—; (4-OMe-phenyl)-NH—;
(4-CN-phenyl)-NH—; (4-OCF$_3$-phenyl)-NH—;
(4-SMe-phenyl)-NH—; (2,3-diCl-phenyl)-NH—;
(2,4-diCl-phenyl)-NH—; (2,5-diCl-phenyl)-NH—;
(2,6-diCl-phenyl)-NH—; (3,4-diCl-phenyl)-NH—;
(3,5-diCl-phenyl)-NH—; (2,3-diF-phenyl)-NH—;
(2,4-diF-phenyl)-NH—; (2,5-diF-phenyl)-NH—;
(2,6-diF-phenyl)-NH—; (3,4-diF-phenyl)-NH—;
(3,5-diCF$_3$-phenyl)-NH—; (2,3-diCH$_3$-phenyl)-NH—;
(2,4-diCH$_3$-phenyl)-NH—; (2,5-diCH$_3$-phenyl)-NH—;
(2,6-diCH$_3$-phenyl)-NH—; (3,4-diCH$_3$-phenyl)-NH—;
(3,5-diCH$_3$-phenyl)-NH—; (2,3-diCF$_3$-phenyl)-NH—;
(2,4-diCF$_3$-phenyl)-NH—; (2,5-diCF$_3$-phenyl)-NH—(2,6-diCF$_3$-phenyl)-NH—; (3,4-diCF$_3$-phenyl)-NH—;
(3,5-diCF$_3$-phenyl)-NH—; (2,3-diOMe-phenyl)-NH—;
(2,4-diOMe-phenyl)-NH—; (2,5-diOMe-phenyl)-NH—;
(2,6-diOMe-phenyl)-NH—; (3,4-diOMe-phenyl)-NH—;
(3,5-diOMe-phenyl)-NH—; (2-F-3-Cl-phenyl)-NH—;
(2-F-4-Cl-phenyl)-NH—; (2-F-5-Cl-phenyl)-NH—;
(2-F-6-Cl-phenyl)-NH—; (2-F-3-CH$_3$-phenyl)-NH—;
(2-F-4-CH$_3$-phenyl)-NH—; (2-F-5-CH$_3$-phenyl)-NH—;

(2-F-6-CH$_3$-phenyl)-NH—; (2-F-3-CF$_3$-phenyl)-NH—;
(2-F-4-CF$_3$-phenyl)-NH—; (2-F-5-CF$_3$-phenyl)-NH—;
(2-F-6-CF$_3$-phenyl)-NH—; (2-F-3-OMe-phenyl)-NH—;
(2-F-4-OMe-phenyl)-NH—; (2-F-5-OMe-phenyl)-NH—;
(2-F-6-OMe-phenyl)-NH—; (2-Cl-3-F-phenyl)-NH—;
(2-Cl-4-F-phenyl)-NH—; (2-Cl-5-F-phenyl)-NH—;
(2-Cl-6-F-phenyl)-NH—; (2-Cl-3-CH$_3$-phenyl)-NH—;
(2-Cl-4-CH$_3$-phenyl)-NH—; (2-Cl-5-CH$_3$-phenyl)-NH—;
(2-Cl-6-CH$_3$-phenyl)-NH—; (2-Cl-3-CF$_3$-phenyl)-NH—;
(2-Cl-4-CF$_3$-phenyl)-NH—; (2-Cl-5-CF$_3$-phenyl)-NH—;
(2-Cl-6-CF$_3$-phenyl)-NH—; (2-Cl-3-OMe-phenyl)-NH—;
(2-Cl-4-OMe-phenyl)-NH—; (2-Cl-5-OMe-phenyl)-NH—;
(2-Cl-6-OMe-phenyl)-NH—; (2-CH$_3$-3-F-phenyl)-NH—;
(2-CH$_3$-4-F-phenyl)-NH—; (2-CH$_3$-5-F-phenyl)-NH—;
(2-CH$_3$-6-F-phenyl)-NH—; (2-CH$_3$-3-Cl-phenyl)-NH—;
(2-CH$_3$-4-Cl-phenyl)-NH—; (2-CH$_3$-5-Cl-phenyl)-NH—;
(2-CH$_3$-6-Cl-phenyl)-NH—; (2-CH$_3$-3-CF$_3$-phenyl)-NH—;
(2-CH$_3$-4-CF$_3$-phenyl)-NH—; (2-CH$_3$-5-CF$_3$-phenyl)-NH—;
(2-CH$_3$-6-CF$_3$-phenyl)-NH—; (2-CH$_3$-3-OMe-phenyl)-NH—;
(2-CH$_3$-4-OMe-phenyl)-NH—; (2-CH$_3$-5-OMe-phenyl)-NH—;
(2-CH$_3$-6-OMe-phenyl)-NH—; (2-CF$_3$-3-F-phenyl)-NH—;
(2-CF$_3$-4-F-phenyl)-NH—; (2-CF$_3$-5-F-phenyl)-NH—;
(2-CF$_3$-6-F-phenyl)-NH—; (2-CF$_3$-3-Cl-phenyl)-NH—;
(2-CF$_3$-4-Cl-phenyl)-NH—; (2-CF$_3$-5-Cl-phenyl)-NH—;
(2-CF$_3$-6-Cl-phenyl)-NH—; (2-CF$_3$-3-CH$_3$-phenyl)-NH—;
(2-CF$_3$-4-CH$_3$-phenyl)-NH—; (2-CH$_3$-5-CF$_3$-phenyl)-NH—;
(2-CF$_3$-6-CH$_3$-phenyl)-NH—; (2-CF$_3$-3-OMe-phenyl)-NH—;
(2-CF$_3$-4-OMe-phenyl)-NH—; (2-CF$_3$-5-OMe-phenyl)-NH—;
(2-CF$_3$-6-OMe-phenyl)-NH—; (2-OMe-3-F-phenyl)-NH—;
(2-OMe-4-F-phenyl)-NH—; (2-OMe-5-F-phenyl)-NH—;
(2-OMe-6-F-phenyl)-NH—; (2-OMe-3-Cl-phenyl)-NH—;
(2-OMe-4-Cl-phenyl)-NH—; (2-OMe-5-Cl-phenyl)-NH—;
(2-OMe-6-Cl-phenyl)-NH—; (2-OMe-4-CN-phenyl)-NH—;
(2-OMe-4-CHO-phenyl)-NH—; (2-OMe-3-CH$_3$-phenyl)-NH—;
(2-OMe-4-CH$_3$-phenyl)-NH—; (2-OMe-5-CH$_3$-phenyl)-NH—;
(2-OMe-6-CH$_3$-phenyl)-NH—; (2-OMe-3-CF$_3$-phenyl)-NH—;
(2-OMe-4-CF$_3$-phenyl)-NH—; (2-OMe-5-CF$_3$-phenyl)-NH—;
(2-OMe-6-CF$_3$-phenyl)-NH—; (2-acetyl-4-Cl-phenyl)-NH—;
(2-acetyl-4-Me-phenyl)-NH—; (2-acetyl-4-MeO-phenyl)-NH—;
(2-CH$_3$CH(OH)$_4$—Cl-phenyl)-NH—;
(2-CH$_3$CH(OH)-4-Me-phenyl)-NH—;
(2-CH$_3$CH(OH) 4-MeO-phenyl)-NH—;
(3-CF$_3$-4-Cl-phenyl)-NH—; (3-F-4-CHO-phenyl)-NH—;
(3-CH$_3$-4-CN-phenyl)-NH—; (3-CH$_3$-4-MeO-phenyl)-NH—;
(3-CH$_3$-4-Cl-phenyl)-NH—; (3-CH$_3$-4-F-phenyl)-NH—;
(3-CH$_3$-4-CO$_2$-Me-phenyl)-NH—; (3-CF$_3$-4-C(O)CH$_3$-phenyl)-NH—; (3-CHO-4-OMe-phenyl)-NH—; (4-F-3-CF$_3$-phenyl)-NH—;
(2,3,5-triCl-phenyl)-NH—; (2,4,5-triF-phenyl)-NH—;
(2,6-diCl-3-Me-phenyl)-NH—; (3,5-diMe-4-MeO-phenyl)-NH—;
(2-F-3-Cl-6-CF$_3$-phenyl)-NH—;
benzyl-NH—; (3-quinolinyl)CH$_2$NH—; (2-F-phenyl)CH$_2$NH—;
(2-Cl-phenyl)CH$_2$NH—; (2-CF$_3$-phenyl)CH$_2$NH—;
(2-CH$_3$-phenyl)CH$_2$NH—; (2-OMe-phenyl)CH$_2$NH—;
(2-CN-phenyl)CH$_2$NH—; (2-OCF$_3$-phenyl)CH$_2$NH—;
(2-SMe-phenyl)CH$_2$NH—; (3-F-phenyl)CH$_2$NH—;
(3-Cl-phenyl)CH$_2$NH—; (3-CF$_3$-phenyl)CH$_2$NH—;
(3-CH$_3$-phenyl)CH$_2$NH—; (3-OMe-phenyl)CH$_2$NH—;
(3-CN-phenyl)CH$_2$NH—; (3-OCF$_3$-phenyl)CH$_2$NH—;
(3-SMe-phenyl)CH$_2$NH—; (4-F-phenyl)CH$_2$NH—;
(4-Cl-phenyl)CH$_2$NH—; (4-CF$_3$-phenyl)CH$_2$NH—;
(4-CH$_3$-phenyl)CH$_2$NH—; (4-OMe-phenyl)CH$_2$NH—;
(4-CN-phenyl)CH$_2$NH—; (4-OCF$_3$-phenyl)CH$_2$NH—;
(4-SMe-phenyl)CH$_2$NH—; (2,3-diCl-phenyl)CH$_2$NH—;
(2,4-diCl-phenyl)CH$_2$NH—; (2,5-diCl-phenyl)CH$_2$NH—;
(2,6-diCl-phenyl)CH$_2$NH—; (3,4-diCl-phenyl)CH$_2$NH—;
(3,5-diCl-phenyl)CH$_2$NH—; (2,3-diF-phenyl)CH$_2$NH—;
(2,4-diF-phenyl)CH$_2$NH—; (2,5-diF-phenyl)CH$_2$NH—;
(2,6-diF-phenyl)CH$_2$NH—; (3,4-diF-phenyl)CH$_2$NH—;
(3,5-diF-phenyl)CH$_2$NH—; (2,3-diCH$_3$-phenyl)CH$_2$NH—;
(2,4-diCH$_3$-phenyl)CH$_2$NH—; (2,5-diCH$_3$-phenyl)CH$_2$NH—;
(2,6-diCH$_3$-phenyl)CH$_2$NH—; (3,4-diCH$_3$-phenyl)CH$_2$NH—;
(3,5-diCH$_3$-phenyl)CH$_2$NH—; (2,3-diCF$_3$-phenyl)CH$_2$NH—;
(2,4-diCF$_3$-phenyl)CH$_2$NH—; (2,5-diCF$_3$-phenyl)CH$_2$NH—;
(2,6-diCF$_3$-phenyl)CH$_2$NH—; (3,4-diCF$_3$-phenyl)CH$_2$NH—;
(3,5-diCF$_3$-phenyl)CH$_2$NH—; (2,3-diOMe-phenyl)CH$_2$NH—;
(2,4-diOMe-phenyl)CH$_2$NH—; (2,5-diOMe-phenyl)CH$_2$NH—;
(2,6-diOMe-phenyl)CH$_2$NH—; (3,4-diOMe-phenyl)CH$_2$NH—;
(3,5-diOMe-phenyl)CH$_2$NH—; (2-F-3-Cl-phenyl)CH$_2$NH—;
(2-F-4-Cl-phenyl)CH$_2$NH—; (2-F-5-Cl-phenyl)CH$_2$NH—;

(2-F-6-Cl-phenyl)CH₂NH—; (2-F-3-CH₃-phenyl)CH₂NH—;
(2-F-4-CH₃-phenyl)CH₂NH—; (2-F-5-CH₃-phenyl)CH₂NH—;
(2-F-6-CH₃-phenyl)CH₂NH—; (2-F-3-CF₃-phenyl)CH₂NH—;
(2-F-4-CF₃-phenyl)CH₂NH—; (2-F-5-CF₃-phenyl)CH₂NH—;
(2-F-6-CF₃-phenyl)CH₂NH—; (2-F-3-OMe-phenyl)CH₂NH—;
(2-F-4-OMe-phenyl)CH₂NH—; (2-F-5-OMe-phenyl)CH₂NH—;
(2-F-6-OMe-phenyl)CH₂NH—; (2-Cl-3-F-phenyl)CH₂NH—;
(2-Cl-4-F-phenyl)CH₂NH—; (2-Cl-5-F-phenyl)CH₂NH—;
(2-Cl-6-F-phenyl)CH₂NH—; (2-Cl-3-CH₃-phenyl)CH₂NH—;
(2-Cl-4-CH₃-phenyl)CH₂NH—; (2-Cl-5-CH₃-phenyl)CH₂NH—;
(2-Cl-6-CH₃-phenyl)CH₂NH—; (2-Cl-3-CF₃-phenyl)CH₂NH—;
(2-Cl-4-CF₃-phenyl)CH₂NH—; (2-Cl-5-CF₃-phenyl)CH₂NH—;
(2-Cl-6-CF₃-phenyl)CH₂NH—; (2-Cl-3-OMe-phenyl)CH₂NH—;
(2-Cl-4-OMe-phenyl)CH₂NH—; (2-Cl-5-OMe-phenyl)CH₂NH—;
(2-Cl-6-OMe-phenyl)CH₂NH—; (2-CH₃-3-F-phenyl)CH₂NH—;
(2-CH₃-4-F-phenyl)CH₂NH—; (2-CH₃-5-F-phenyl)CH₂NH—;
(2-CH₃-6-F-phenyl)CH₂NH—; (2-CH₃-3-Cl-phenyl)CH₂NH—;
(2-CH₃-4-Cl-phenyl)CH₂NH—; (2-CH₃-5-Cl-phenyl)CH₂NH—;
(2-CH₃-6-Cl-phenyl)CH₂NH—; (2-CH₃-3-CF₃-phenyl)CH₂NH—;
(2-CH₃-4-CF₃-phenyl)CH₂NH—; (2-CH₃-5-CF₃-phenyl)CH₂NH—;
(2-CH₃-6-CF₃-phenyl)CH₂NH—; (2-CH₃-3-OMe-phenyl)CH₂NH—;
(2-CH₃-4-OMe-phenyl)CH₂NH—; (2-CH₃-5-OMe-phenyl)CH₂NH—;
(2-CH₃-6-OMe-phenyl)CH₂NH—; (2-CF₃-3-F-phenyl)CH₂NH—;
(2-CF₃-4-F-phenyl)CH₂NH—; (2-CF₃-5-F-phenyl)CH₂NH—;
(2-CF₃-6-F-phenyl)CH₂NH—; (2-CF₃-3-Cl-phenyl)CH₂NH—;
(2-CF₃-4-Cl-phenyl)CH₂NH—; (2-CF₃-5-Cl-phenyl)CH₂NH—;
(2-CF₃-6-Cl-phenyl)CH₂NH—; (2-CF₃-3-CH₃-phenyl)CH₂NH—;
(2-CF₃-4-CH₃-phenyl)CH₂NH—; (2-CH₃-5-CF₃-phenyl)CH₂NH—;
(2-CF₃-6-CH₃-phenyl)CH₂NH—; (2-CF₃-3-OMe-phenyl)CH₂NH—;
(2-CF₃-4-OMe-phenyl)CH₂NH—; (2-CF₃-5-OMe-phenyl)CH₂NH—;
(2-CF₃-6-OMe-phenyl)CH₂NH—; (2-OMe-3-F-phenyl)CH₂NH—;
(2-OMe-4-F-phenyl)CH₂NH—; (2-OMe-5-F-phenyl)CH₂NH—;
(2-OMe-6-F-phenyl)CH₂NH—; (2-OMe-3-Cl-phenyl)CH₂NH—;
(2-OMe-4-Cl-phenyl)CH₂NH—; (2-OMe-5-Cl-phenyl)CH₂NH—;
(2-OMe-6-Cl-phenyl)CH₂NH—; (2-OMe-4-CN-phenyl)CH₂NH—;
(2-OMe-4-CHO-phenyl)CH₂NH—; (2-OMe-3-CH₃-phenyl)CH₂NH—;
(2-OMe-4-CH₃-phenyl)CH₂NH—; (2-OMe-5-CH₃-phenyl)CH₂NH—;
(2-OMe-6-CH₃-phenyl)CH₂NH—; (2-OMe-3-CF₃-phenyl)CH₂NH—;
(2-OMe-4-CF₃-phenyl)CH₂NH—; (2-OMe-5-CF₃-phenyl)CH₂NH—;
(2-OMe-6-CF₃-phenyl)CH₂NH—; (2-acetyl-4-Cl-phenyl)CH₂NH—;
(2-acetyl-4-Me-phenyl)CH₂NH—;
(2-acetyl-4-MeO-phenyl)CH₂NH—;
(2-CH₃CH(OH)₄—Cl-phenyl)CH₂NH—;
(2-CH₃CH(OH)-4-Me-phenyl)CH₂NH—;
(2-CH₃CH(OH)-4-MeO-phenyl)CH₂NH—;
(3-CF₃-4-Cl-phenyl)CH₂NH—; (3-F-4-CHO-phenyl)CH₂NH—;
(3-CH₃-4-CN-phenyl)CH₂NH—; (3-CH₃-4-MeO-phenyl)CH₂NH—;
(3-CH₃-4-Cl-phenyl)CH₂NH—; (3-CH₃-4-F-phenyl)CH₂NH—;
(4-F-3-CF₃-phenyl)CH₂NH—; (3-CH₃-4-CO₂-Me-phenyl)CH₂NH—;
(3-CF₃-4-C(O)CH₃-phenyl)CH₂NH—;
(3-CHO-4-OMe-phenyl)CH₂NH—;
(2,3,5-triCl-phenyl)CH₂NH—;
(2,4,5-triF-phenyl)CH₂NH—;
(2,6-diCl-3-Me-phenyl)CH₂NH—;
(3,5-diMe-4-MeO-phenyl)CH₂NH—; and
(2-F-3-Cl-6-CF₃-phenyl)CH₂NH—;

n is 1 or 2.

[12a] In another preferred embodiment the present invention provides a compound of Formula (III):

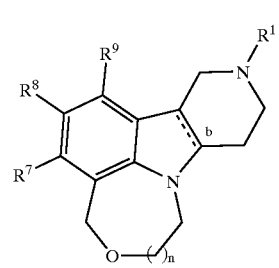

(III)

wherein:
b is a single bond, wherein the bridge hydrogens are in a cis position;
$R^1$ is selected from
hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl,
2,2,2-trifluoroethyl, 2-propenyl, 2-methyl-2-propenyl, trans-2-butenyl, 3-methyl-butenyl,
3-butenyl,
trans-2-pentenyl, cis-2-pentenyl, 4-pentenyl,
4-methyl-3-pentenyl, 3,3-dichloro-2-propenyl,
trans-3-phenyl-2-propenyl, cyclopropyl, cyclobutyl, cyclopentyl, cyclohexyl,
cyclopropylmethyl, cyclobutylmethyl, cyclopentylmethyl, cyclohexylmethyl,
—CH=CH$_2$, —CH$_2$—CH=CH$_2$, —CH=CH—CH$_3$, —C=CH, —C≡C—CH$_3$,
and —CH$_2$—C≡CH;
$R^7$ and $R^9$, at each occurrence, are independently selected from hydrogen, fluoro, methyl, trifluoromethyl, and methoxy; and
$R^8$ is selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl,
methylC(=O), ethylC(=O)—, propylC(=O)—, isopropylC(=O)—, butylC(=O)—,
phenylC(=O)—,
methylCO$_2$—, ethylCO$_2$—, propylCO$_2$—, isopropylCO$_2$—, butylCO$_2$—, phenylCO$_2$—,
dimethylamino-S(=O)—, diethylamino-S(=O)—,
dipropylamino-S(=O)—, di-isopropylamino-S(=O)—, dibutylamino-S(=O)—,
diphenylamino-S(=O)—,
dimethylamino-SO$_2$—, diethylamino-SO$_2$—,
dipropylamino-SO$_2$—, di-isopropylamino-SO$_2$—,
dibutylamino-SO$_2$—, diphenylamino-SO$_2$—,
dimethylamino-C(=O)—, diethylamino-C(=O)—,
dipropylamino-C(=O)—, di-isopropylamino-C(=O)—, dibutylamino-C(=O)—,
diphenylamino-C(=O)—,
2-chlorophenyl, 2-fluorophenyl, 2-bromophenyl,
2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl,
3-cyanophenyl, 3-methylphenyl, 3-ethylphenyl,
3-propylphenyl, 3-isopropylphenyl, 3-butylphenyl,
3-trifluoromethylphenyl, 3-methoxyphenyl,
3-isopropoxyphenyl, 3-trifluoromethoxyphenyl,
3-thiomethoxyphenyl,
4-chlorophenyl, 4-fluorophenyl, 4-bromophenyl,
4-cyanophenyl, 4-methylphenyl, 4-ethylphenyl,
4-propylphenyl, 4-isopropylphenyl, 4-butylphenyl,
4-trifluoromethylphenyl, 4-methoxyphenyl,
4-isopropoxyphenyl, 4-trifluoromethoxyphenyl,
4-thiomethoxyphenyl,
2,3-dichlorophenyl, 2,3-difluorophenyl,
2,3-dimethylphenyl, 2,3-ditrifluoromethylphenyl,
2,3-dimethoxyphenyl, 2,3-ditrifluoromethoxyphenyl,
2,4-dichlorophenyl, 2,4-difluorophenyl,
2,4-dimethylphenyl, 2,4-ditrifluoromethylphenyl,
2,4-dimethoxyphenyl, 2,4-ditrifluoromethoxyphenyl,
2,5-dichlorophenyl, 2,5-difluorophenyl,
2,5-dimethylphenyl, 2,5-ditrifluoromethylphenyl,
2,5-dimethoxyphenyl, 2,5-ditrifluoromethoxyphenyl,
2,6-dichlorophenyl, 2,6-difluorophenyl,
2,6-dimethylphenyl, 2,6-ditrifluoromethylphenyl,
2,6-dimethoxyphenyl, 2,6-ditrifluoromethoxyphenyl,
3,4-dichlorophenyl, 3,4-difluorophenyl,
3,4-dimethylphenyl, 3,4-ditrifluoromethylphenyl,
3,4-dimethoxyphenyl, 3,4-ditrifluoromethoxyphenyl,
2,4,6-trichlorophenyl, 2,4,6-trifluorophenyl,
2,4,6-trimethylphenyl, 2,4,6-tritrifluoromethylphenyl,
2,4,6-trimethoxyphenyl, 2,4,6-tritrifluoromethoxyphenyl,
2-chloro-4-CF$_3$-phenyl, 2-fluoro-3-chloro-phenyl,
2-chloro-4-CF$_3$-phenyl, 2-chloro-4-methoxy-phenyl,
2-methoxy-4-isopropyl-phenyl, 2-CF$_3$-4-methoxy-phenyl,
2-methyl-4-methoxy-5-fluorophenyl,
2-methyl-4-methoxy-phenyl, 2-chloro-4-CF$_3$O-phenyl,
2,4,5-trimethyl-phenyl, 2-methyl-4-chloro-phenyl,
methyl-C(=O)-NH—, ethyl-C(=O)-NH—, propyl-C(=O)-NH—,
isopropyl-C(=O)-NH—, butyl-C(=O)-NH—, phenyl-C(=O)-NH—,
4-acetylphenyl, 3-acetamidophenyl, 4-pyridyl, 2-furanyl, 2-thiophenyl, 2-naphthyl;
2-Me-5-F-phenyl, 2-F-5-Me-phenyl, 2-MeO-5-F-phenyl,
2-Me-3-Cl-phenyl, 3-NO$_2$-phenyl, 2-NO$_2$-phenyl,
2-Cl-3-Me-phenyl, 2-Me$_4$-EtO-phenyl, 2-Me-4-F-phenyl,
2-Cl-6-F-phenyl, 2-C$_{1-4}$-(CHF$_2$)O-phenyl,
2,4-diMeO-6-F-phenyl, 2-CF$_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-CF$_3$-4-EtO-phenyl, 2-CF$_3$-4-iPrO-phenyl,
2-CF$_3$-4-Cl-phenyl, 2-CF$_3$-4-F-phenyl, 2-C$_{1-4}$-EtO-phenyl,
2-C14-iPrO-phenyl, 2-Et-4-MeO-phenyl,
2-CHO-4-MeO-phenyl, 2-CH$_3$CH(OH)-4-MeO-phenyl,
2-CH$_3$CH(OH)-4-F-phenyl, 2-CH$_3$CH(OH)4-Cl-phenyl,
2-CH$_3$CH(OH)-4-Me-phenyl, 2-CH$_3$CH(OMe)-4-MeO-phenyl,
2-CH$_3$C(=O)-4-MeO-phenyl, 2-CH$_3$C(=O)-4-F-phenyl,
2-CH$_3$C(=O)$_4$—Cl-phenyl, 2-CH$_3$C(=O)-4-Me-phenyl,
2-H$_2$C(OH)-4-MeO-phenyl, 2-H$_2$C(OMe)-4-MeO-phenyl,
2-H$_3$CCH$_2$CH(OH)-4-MeO-phenyl, 2-H$_3$CCH$_2$C(=O)-4-MeO-phenyl,
2-CH$_3$CO$_2$CH$_2$CH$_2$-4-MeO-phenyl,
(Z)-2-HOCH$_2$CH=CH-4-MeO-phenyl,
(E)-2-HOCH$_2$CH=CH-4-MeO-phenyl,
(Z)-2-CH$_3$CO$_2$CH=CH-4-MeO-phenyl,
(E)-2-CH$_3$CO$_2$CH=CH-4-MeO-phenyl,
2-CH$_3$OCH$_2$CH$_2$-4-MeO-phenyl,
2-F-4-MeO-phenyl, 2-Cl-4-F-phenyl,
(2-Cl-phenyl)-CH=CH—, (3-Cl-phenyl)-CH=CH—,
(2,6-diF-phenyl)CH=CH—, —CH$_2$CH=CH$_2$ phenyl-CH=CH—, (2-Me$_4$-MeO-phenyl)-CH=CH—, cyclohexyl, cyclopentyl, cyclohexylmethyl,
EtCO$_2$CH$_2$CH$_2$—, EtCO$_2$CH$_2$CH$_2$CH$_2$—,
EtCO$_2$CH$_2$CH$_2$CH$_2$CH$_2$—,
benzyl, 2-F-benzyl, 3-F-benzyl, 4-F-benzyl,
3-MeO-benzyl, 3-OH-benzyl, 2-MeO-benzyl,
2-OH-benzyl, 2-MeOC(=O)-3-MeO-phenyl,
2-Me$_4$-CN-phenyl, 2-Me-3-CN-phenyl,
2-Me$_4$-MeS-phenyl, 2-CF$_3$-4-CN-phenyl,
2-CHO-phenyl, 3-CHO-phenyl, 2-HOCH$_2$-phenyl,
3-HOCH$_2$-phenyl, 3-MeOCH$_2$-phenyl,
3-Me$_2$NCH$_2$-phenyl, 3-CN-4-F-phenyl,
2-Me$_4$-H$_2$NCO-phenyl, 2-Me-4-MeOC(=O)-phenyl,
3-H$_2$NCO-4—F-phenyl, 2-Me$_2$NCH$_2$-4-MeO-phenyl-,
2-Me-4-CH$_3$C(=O)-phenyl, phenyl-S—, Me$_2$N—,
1-pyrrolidinyl,
phenyl-NH—, benzyl-NH—, (1-naphthyl)-NH—,
(2-naphthyl)-NH—, (2-[1,1'-biphenyl])-NH—,
(3-[1,1'-biphenyl])—NH—, (4-[1,1'-biphenyl])-NH—,
(2-F-phenyl)-NH—, (2-Cl-phenyl)-NH—,
(2-CF$_3$-phenyl)-NH—, (2-CH$_3$-phenyl)-NH—,
(2-OMe-phenyl)-NH—, (2-CN-phenyl)-NH—,
(2-OCF$_3$-phenyl)-NH—, (2-SMe-phenyl)-NH—,
(3-F-phenyl)-NH—, (3-Cl-phenyl)-NH—,
(3-CF$_3$-phenyl)-NH—, (3-CH$_3$-phenyl)-NH—,
(3-OMe-phenyl)-NH—, (3-CN-phenyl)-NH—,
(3-OCF$_3$-phenyl)-NH—, (3-SMe-phenyl)-NH—,
(4-F-phenyl)-NH—, (4-Cl-phenyl)-NH—,
(4-CF$_3$-phenyl)-NH—, (4-CH$_3$-phenyl)-NH—,
(4-OMe-phenyl)-NH—, (4-CN-phenyl)-NH—,
(4-OCF$_3$-phenyl)-NH—, (4-SMe-phenyl)-NH—,
(2,3-diCl-phenyl)-NH—, (2,4-diCl-phenyl)-NH—,
(2,5-diCl-phenyl)-NH—, (2,6-diCl-phenyl)-NH—,
(3,4-diCl-phenyl)-NH—, (3,5-diCl-phenyl)-NH—,
(2,3-diF-phenyl)-NH—, (2,4-diF-phenyl)-NH—,
(2,5-diF-phenyl)-NH—, (2,6-diF-phenyl)-NH—,
(3,4-diF-phenyl)-NH—, (3,5-diF-phenyl)-NH—,
(2,3-diCH$_3$-phenyl)-NH—, (2,4-diCH$_3$-phenyl)-NH—,
(2,5-diCH$_3$-phenyl)-NH—, (2,6-diCH$_3$-phenyl)-NH—,
(3,4-diCH$_3$-phenyl)-NH—, (3,5-diCH$_3$-phenyl)-NH—,
(2,3-diCF$_3$-phenyl)-NH—, (2,4-diCF$_3$-phenyl)-NH—,
(2,5-diCF$_3$-phenyl)-NH—, (2,6-diCF$_3$-phenyl)-NH—,
(3,4-diCF$_3$-phenyl)-NH—, (3,5-diCF$_3$-phenyl)-NH—,
(2,3-diOMe-phenyl)-NH—, (2,4-diOMe-phenyl)-NH—,
(2,5-diOMe-phenyl)-NH—, (2,6-diOMe-phenyl)-NH—,
(3,4-diOMe-phenyl)-NH—, (3,5-diOMe-phenyl)-NH—,
(2-F-3-Cl-phenyl)-NH—, (2-FA-Cl-phenyl)-NH—,
(2-F-5-Cl-phenyl)-NH—, (2-F-6-Cl-phenyl)-NH—,
(2-F-3-CH$_3$-phenyl)-NH—, (2-F-4-CH$_3$-phenyl)-NH—,
(2-F-5-CH$_3$-phenyl)-NH—, (2-F-6-CH$_3$-phenyl)-NH—,
(2-F-3-CF$_3$-phenyl)-NH—, (2-F-4-CF$_3$-phenyl)-NH—,
(2-F-5-CF$_3$-phenyl)-NH—, (2-F-6-CF$_3$-phenyl)-NH—,
(2-F-3-OMe-phenyl)-NH—, (2-F-4-OMe-phenyl)-NH—,
(2-F-5-OMe-phenyl)-NH—, (2-F-6-OMe-phenyl)-NH—,
(2-Cl-3-F-phenyl)-NH—, (2-C14-F-phenyl)-NH—,
(2-Cl-5-F-phenyl)-NH—, (2-Cl-6-F-phenyl)-NH—,
(2-Cl-3-CH$_3$-phenyl)-NH—, (2-C14-CH$_3$-phenyl)-NH—,
(2-Cl-5-CH$_3$-phenyl)-NH—, (2-Cl-6-CH$_3$-phenyl)-NH—,
(2-Cl-3-CF$_3$-phenyl)-NH—, (2-Cl-4-CF$_3$-phenyl)-NH—,
(2-Cl-5-CF$_3$-phenyl)-NH—, (2-Cl-6-CF$_3$-phenyl)-NH—,
(2-Cl-3-OMe-phenyl)-NH—, (2-Cl-4-OMe-phenyl)-NH—,
(2-Cl-5-OMe-phenyl)-NH—, (2-Cl-6-OMe-phenyl)-NH—,
(2-CH$_3$-3-F-phenyl)-NH—, (2-CH$_3$-4-F-phenyl)-NH—,
(2-CH$_3$-5-F-phenyl)-NH—, (2-CH$_3$-6-F-phenyl)-NH—.,
(2-CH$_3$-3-Cl-phenyl)-NH—, (2-CH$_3$-4-C1-phenyl)-NH—,
(2-CH$_3$-5-Cl-phenyl)-NH—, (2-CH$_3$-6-Cl-phenyl)-NH—,
(2-CH$_3$-3-CF$_3$-phenyl)-NH—, (2-CH$_3$-4-CF$_3$-phenyl)-NH—,
(2-CH$_3$-5-CF$_3$-phenyl)-NH—, (2-CH$_3$-6-CF$_3$-phenyl)-NH—,
(2-CH$_3$-3-OMe-phenyl)-NH—, (2-CH$_3$-4-OMe-phenyl)-NH—,
(2-CH$_3$-5-OMe-phenyl)-NH—, (2-CH$_3$-6-OMe-phenyl)-NH—,
(2-CF$_3$-3-F-phenyl)-NH—, (2-CF$_3$-4-F-phenyl)-NH—,
(2-CF$_3$-5-F-phenyl)-NH—, (2-CF$_3$-6-F-phenyl)-NH—,
(2-CF$_3$-3-Cl-phenyl)-NH—, (2-CF$_3$-4-Cl-phenyl)-NH—,
(2-CF$_3$-5-Cl-phenyl)-NH—, (2-CF$_3$-6-Cl-phenyl)-NH—,
(2-CF$_3$-3-CH$_3$-phenyl)-NH—, (2-CF$_3$-4-CH$_3$-phenyl)-NH—,
(2-CH$_3$-5-CF$_3$-phenyl)-NH—, (2-CF$_3$-6-CH$_3$-phenyl)-NH—,
(2-CF$_3$-3-OMe-phenyl)-NH—, (2-CF$_3$-4-OMe-phenyl)-NH—,
(2-CF$_3$-5-OMe-phenyl)-NH—, (2-CF$_3$-6-OMe-phenyl)-NH—,
(2-OMe-3-F-phenyl)-NH—, (2-OMe-4-F-phenyl)-NH—,
(2-OMe-5-F-phenyl)-NH—, (2-OMe-6-F-phenyl)-NH—,
(2-OMe-3-Cl-phenyl)-NH—, (2-OMe-4-Cl-phenyl)-NH—,
(2-OMe-5-Cl-phenyl)-NH—, (2-OMe-6-Cl-phenyl)-NH—,
(2-OMe-3-CH$_3$-phenyl)-NH—, (2-OMe-4-CH$_3$-phenyl)-NH—,
(2-OMe-5-CH$_3$-phenyl)-NH—, (2-OMe-6-CH$_3$-phenyl)-NH—,
(2-OMe-3-CF$_3$-phenyl)-NH—, (2-OMe-4-CF$_3$-phenyl)-NH—,
(2-OMe-5-CF$_3$-phenyl)-NH—, (2-OMe-6-CF$_3$-phenyl)-NH—(3-CF$_3$-4-Cl-phenyl)-NH—, (3-CF$_3$-4-C(O)CH$_3$-phenyl)-NH—, (2,3,5-triCl-phenyl)-NH—,
(3-CH$_3$-4-CO$_2$-Me-phenyl)-NH—, and
(3-CHO-4-OMe-phenyl)-NH—;

n is 1 or 2.

[13] In another preferred embodiment the present invention provides a compound of Formula (I-a)

(I-a)

wherein:
X is —O—, —S—, —S(=O)—, —S(=O)$_2$—, or —NR$^{10}$—;
R$^1$ is selected from
  C$_{1-6}$ alkyl substituted with Z,
  C$_{2-6}$ alkenyl substituted with Z,
  C$_{2-6}$ alkynyl substituted with Z,
  C$_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  C$_{1-6}$ alkyl substituted with 0–2 R$^2$,
  C$_{2-6}$ alkenyl substituted with 0–2 R$^2$,
  C$_{2-6}$ alkynyl substituted with 0–2 R$^2$,
  aryl substituted with 0–2 R$^2$, and
  5–6 membered heterocyclic ring system containing at least one heteroatom selected from the group consisting of N, O, and S, said heterocyclic ring system substituted with 0–2 R$^2$;
Z is selected from H,
  —CH(OH)R$^2$,
  —C(ethylenedioxy)R$^2$,
  —OR$^2$,
  —SR$^2$,
  —NR$^2$R$^3$,
  —C(O)R$^2$,
  —C(O)NR$^2$R$^3$,
  —NR$^3$C(O)R$^2$,
  —C(O)OR$^2$,
  —OC(O)R$^2$,
  —CH(=NR$^4$)NR$^2$R$^3$,
  —NHC(=NR$^4$)NR$^2$R$^3$,
  —S(O)R$^2$,
  —S(O)$_2$R$^2$,
  —S(O)$_2$NR$^2$R$^3$, and —NR$^3$S(O)$_2$R$^2$;
R$^2$, at each occurrence, is independently selected from
  C$_{1-4}$ alkyl,
  C$_{2-4}$ alkenyl,
  C$_{2-4}$ alkynyl,
  C$_{3-6}$ cycloalkyl,
  aryl substituted with 0–5 R$^{42}$;
  C$_{3-10}$ carbocyclic residue substituted with 0–3 R$^{41}$, and
  5–10 membered heterocyclic ring system containing from 1–4 heteroatoms selected from the group consisting of N, O, and S substituted with 0–3 R$^{41}$;

R$^3$, at each occurrence, is independently selected from
  25H, C$_{1-4}$ alkyl, C$_{2-4}$ alkenyl, C$_{2-4}$ alkynyl, and
  C$_{1-4}$ alkoxy;
alternatively, R$^2$ and R$^3$ join to form a 5- or 6-membered ring optionally substituted with —O— or —N(R$^4$);
R$^4$, at each occurrence, is independently selected from H, methyl, ethyl, propyl, and butyl;
R$^5$ is H, methyl, ethyl, propyl, or butyl;
R$^6$ is H, methyl, ethyl, propyl, or butyl;
R$^7$, R$^8$, and R$^9$, at each occurrence, are independently selected from
  H, halo, —CF$_3$, —OCF$_3$, —OH, —CN, —NO$_2$, —NR$^{46}$R$^{47}$,
  C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
  C$_{1-4}$ alkyl substituted with 0–2 R$^{11}$,
  C$_{3-10}$ carbocyclic residue substituted with 0–3 R$^{33}$,
  aryl substituted with 0–5 R$^{33}$,
  5–10 membered heterocyclic ring system containing from 14 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$,
  C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;
R$^{10}$ is selected from H, C$_{1-4}$ alkyl, C$_{2-4}$ alkenyl, C$_{2-4}$ alkynyl, and C$_{1-4}$ alkoxy;
R$^{11}$ is selected from
  H, halo, —CF$_3$, —CN, —NO$_2$,
  C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
  C$_{3-10}$ carbocyclic residue substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, and NR$^{14}$S(O)$_2$R$^{12}$;
R$^{12}$, at each occurrence, is independently selected from
  C$_{1-4}$alkyl,
  C$_{2-4}$ alkenyl,
  C$_{2-4}$ alkynyl,
  C$_{3-6}$ cycloalkyl,
  phenyl substituted with 0–5 R$^{33}$;
  C$_{3-10}$ carbocyclic residue substituted with 0–3 R$^{33}$, and
  5–10 membered heterocyclic ring system containing from 1–4 heteroatoms selected from the group consisting of N, O, and S substituted with 0–3 R$^{31}$;
R$^{13}$, at each occurrence, is independently selected from
  H, C$_{1-4}$ alkyl, C$_{2-4}$ alkenyl, and C$_{2-4}$ alkynyl;
alternatively, R$^{12}$ and R$^{13}$ join to form a 5- or 6-membered ring optionally substituted with —O— or —N(R$^{14}$)—;
R$^{14}$, at each occurrence, is independently selected from H and C$_{1-4}$ alkyl;
R$^{31}$, at each occurrence, is independently selected from CN, NO$_2$, —OCF$_3$, —OCH$_2$CF$_3$, —C(=O)H, —C(=O)NH$_2$, —C(=O)OCH$_3$, phenyl, C$_{2-6}$ alkenyl, C$_{2-6}$ alkynyl, C$_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O), $C_{1-4}$ alkyl-C(=O)O—, $C_{1-4}$ alkyl-C(=O)-NH—, $C_{1-4}$ alkyl-NHC(=O), ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or ($C_{1-4}$ alkyl)CO$_2$—; and $C_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or ($C_{1-4}$ alkyl)CO$_2$—;

R$^{33}$, at each occurrence, is independently selected from
H, OH, halo, CN, NO$_2$, CF$_3$, —OCF$_3$, —OCH$_2$CF$_3$, SO$_2$R$^{45}$, NR$^{46}$R$^{47}$, —C(=O)H, =O, —C(=O)NH$_2$, —C(=O)OCH$_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O), $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or ($C_{1-4}$ alkyl)CO$_2$—; and $C_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or ($C_{1-4}$ alkyl)CO$_2$—;

R$^{41}$, at each occurrence, is independently selected from
H, CF$_3$, halo, OH, CO$_2$H, SO$_2$R$^{45}$, NR$^{46}$R$^{47}$, NO$_2$, CN, =O,
$C_{2-8}$ alkenyl, $C_{2-8}$ alkynyl, $C_{1-4}$ alkoxy, $C_{1-4}$ haloalkyl
$C_{1-4}$ alkyl substituted with 0–1 R$^{43}$,
aryl substituted with 0–3 R$^{42}$, and
5–10 membered heterocyclic ring system containing from 1–4 heteroatoms selected from the group consisting of N, O, and S substituted with 0–3 R$^{44}$;

R$^{42}$, at each occurrence, is independently selected from
H, CF$_3$, halo, OH, CO$_2$H, SO$_2$R$^{45}$, SR$^{45}$, NR$^{46}$R$^{47}$, OR$^{48}$, NO$_2$, CN, CH(=NH)NH$_2$, NHC(=NH)NH$_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 R$^{43}$,
aryl substituted with 0–3 R$^{44}$, and
5–10 membered heterocyclic ring system containing from 1–4 heteroatoms selected from the group consisting of N, O, and S substituted with 0–3 R$^{44}$;

R$^{43}$ is $C_{3-6}$ cycloalkyl or aryl substituted with 0–3 R$^{44}$;
R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, $C_{1-4}$ alkyl, and $C_{1-4}$ alkoxy;
R$^{45}$ is $C_{1-4}$ alkyl;
R$^{46}$, at each occurrence, is independently selected from H and $C_{1-4}$ alkyl;
R$^{47}$, at each occurrence, is independently selected from H, $C_{1-4}$ alkyl, —C(=O)NH($C_{1-4}$ alkyl), —SO$_2$($C_{1-4}$ alkyl), —SO$_2$(phenyl), —C(=O)O($C_{1-4}$ alkyl), —C(=O)($C_{1-4}$ alkyl), and —C(=O)H;
R$^{48}$, at each occurrence, is independently selected from H, $C_{1-4}$ alkyl, —C(=O)NH($C_{1-4}$ alkyl), —C(=O)O($C_{1-4}$ alkyl), —C(=O)($C_{1-4}$ alkyl), and —C(=O)H;
k is 1 or 2; and
n is 1 or 2.

[14] In another preferred embodiment the present invention provides a compound of Formula (I-a) wherein:
X is —O—, —S—, or —NH—;
R$^1$ is selected from
$C_{2-5}$ alkyl substituted with Z,
$C_{2-5}$ alkenyl substituted with Z,
$C_{2-5}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{1-5}$ alkyl substituted with 0–2 R$^2$,
$C_{2-5}$ alkenyl substituted with 0–2 R$^2$, and
$C_{2-5}$ alkynyl substituted with 0–2 R$^2$;

Z is selected from H,
—CH(OH)R$^2$,
—C(ethylenedioxy)R$^2$,
—OR$^2$,
—SR$^2$,
—NR$^2$R$^3$,
—C(O)R$^2$,
—C(O)NR$^2$R$^3$,
—NR$^3$C(O)R$^2$,
—C(O)OR$^2$,
—OC(O)R$^2$,
—CH(=NR$^4$)NR$^2$R$^3$,
—NHC(=NR$^4$)NR$^2$R$^3$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
$C_{1-4}$ alkyl,
$C_{2-4}$ alkenyl,
$C_{2-4}$ alkynyl,
$C_{3-6}$ cycloalkyl,
aryl substituted with 0–5 R$^{42}$;
$C_{3-10}$ carbocyclic residue substituted with 0–3 R$^{41}$, and
5–10 membered heterocyclic ring system containing from 1–4 heteroatoms selected from the group consisting of N, O, and S substituted with 0–3 R$^{41}$;

R$^3$, at each occurrence, is independently selected from
H, $C_{1-4}$ alkyl, $C_{2-4}$ alkenyl, $C_{2-4}$ alkynyl, and $C_{1-4}$ alkoxy;
alternatively, R$^2$ and R$^3$ join to form a 5- or 6-membered ring optionally substituted with —O— or —N(R$^4$);
R$^4$, at each occurrence, is independently selected from H, methyl, ethyl, propyl, and butyl;
R$^5$ is H, methyl, or ethyl;
R$^6$ is H, methyl, ethyl, propyl, or butyl;
R$^7$, R$^8$, and R$^9$, at each occurrence, are independently selected from
H, halo, —CF$_3$, —OCF$_3$, —OH, —OCH$_3$, —CN, —NO$_2$, —NR$^{46}$R$^{47}$,
$C_{1-6}$ alkyl, $C_{2-6}$ alkenyl, $C_{2-6}$ alkenyl, $C_{1-4}$ haloalkyl, $C_{1-6}$ alkoxy, ($C_{1-4}$ haloalkyl)oxy,
$C_{1-4}$ alkyl substituted with 0–2 R$^{11}$,
$C_{3-10}$ carbocyclic residue substituted with 0–3 R$^{33}$,
aryl substituted with 0–5 R$^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$_2NR^{12}R^{13}$, $NR^{14}$S(O)$_2R^{12}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)NH$R^{15}$;

$R^{111}$ is selected from

H, halo, —$CF_3$, —$OCF_3$, —OH, —$OCH_3$, —CN, —$NO_2$, —$NR^{46}R^{47}$, $C_{1-6}$ alkyl, $C_{2-6}$ alkenyl, $C_{2-6}$ alkynyl, $C_{1-4}$ haloalkyl, $C_{1-6}$ alkoxy, (C14 haloalkyl)oxy, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$_2NR^{12}R^{13}$, and $NR^{14}$S(O)$_2R^{12}$;

$R^{12}$, at each occurrence, is independently selected from $C_{1-4}$ alkyl, $C_{2-4}$ alkenyl, $C_{2-4}$ alkynyl, $C_{3-6}$ cycloalkyl, phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from

H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

$R^{14}$, at each occurrence, is independently selected from H and $C_{1-4}$ alkyl;

$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O), or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{33}$, at each occurrence, is independently selected from

H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{41}$, at each occurrence, is independently selected from

H, $CF_3$, halo, OH, $CO_2H$, $SO_2R^{45}$, $NR^{46}R^{47}$, $NO_2$, CN, =O, $C_{2-8}$ alkenyl, $C_{2-8}$ alkynyl, $C_{1-4}$ alkoxy, $C_{1-4}$ haloalkyl, $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from

H, $CF_3$, halo, OH, $CO_2H$, $SO_2R^{45}$, $SR^{45}$, $NR^{46}R^{47}$, $OR^{48}$, $NO_2$, CN, CH(=NH)$NH_2$, NHC(=NH)$NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-3}$ alkyl;

$R^{47}$, at each occurrence, is independently selected from H, $C_{1-4}$ alkyl, —C(=O)NH($C_{1-14}$alkyl), —$SO_2$($C_{1-4}$ alkyl), —$SO_2$(phenyl), —C(=O)O($C_{1-4}$ alkyl), —C(=O)($C_{1-4}$ alkyl), and —C(=O)H;

$R^{48}$, at each occurrence, is independently selected from H, $C_{1-4}$ alkyl, —C(=O)NH($C_{1-4}$ alkyl), —C(=O)O($C_{1-4}$ alkyl), —C(=O)($C_{1-4}$ alkyl), and C(=O)H;

k is 1 or 2; and n is 1 or 2.

[15]In another preferred embodiment the present invention provides a compound of Formula (I-a) wherein:

X is —O— or —S—;

$R^1$ is selected from $C_{2-4}$ alkyl substituted with Z, $C_{2-4}$ alkenyl substituted with Z, $C_{2-4}$ alkynyl substituted with Z, $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{2-4}$ alkyl substituted with 0–2 $R^2$, and $C_{2-4}$ alkenyl substituted with 0–2 $R^2$;

Z is selected from H,

—CH(OH)$R^2$,

—C(ethylenedioxy)$R^2$,

—$SR^2$,

—$NR^2R^3$,

—C(O)$R^2$,

—C(O)$NR^2R^3$,

—$NR^3$C(O)$R^2$,

—C(O)O$R^2$,

—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
phenyl substituted with 0–5 R$^{42}$;
C$_{3-10}$ carbocyclic residue substituted with 0–3 R$^{41}$, and
5–10 membered heterocyclic ring system containing from 1–4 heteroatoms selected from the group consisting of N, O, and S substituted with 0–3 R$^{41}$;

R$^3$, at each occurrence, is independently selected from
H, C$_{1-4}$ alkyl, C$_{2-4}$ alkenyl, C$_{2-4}$ alkynyl, and
C$_{1-4}$ alkoxy;

alternatively, R$^2$ and R$^3$ join to form a 5- or 6-membered ring optionally substituted with —O— or —N(R$^4$)—;

R$^4$, at each occurrence, is independently selected from H, methyl, ethyl, propyl, and butyl;

R$^5$ is H;
R$^6$ is H;

R$^7$, R$^8$, and R$^9$, at each occurrence, are independently selected from
H, halo, —CF$_3$, —OCF$_3$, —OH, —OCH$_3$, —CN, —NO$_2$, C$_{1-4}$ alkyl, C$_{1-4}$ haloalkyl, C$_{1-4}$ alkoxy, (C$_{1-3}$ haloalkyl)oxy, and
C$_{1-4}$ alkyl substituted with 0–2 R$^{11}$;

R$^{11}$ is selected from
H, halo, —CF$_3$, —OCF$_3$, —OH, —OCH$_3$, —CN, —NO$_2$, C$_{1-4}$ alkyl, C$_{1-4}$ haloalkyl, C$_{1-4}$ alkoxy, and (C$_{1-3}$ haloalkyl)oxy;

R$^{33}$, at each occurrence, is independently selected from
H, OH, halo, CF$_3$, and methyl;

R$^{41}$, at each occurrence, is independently selected from
H, CF$_3$, halo, OH, CO$_2$H, SO$_2$R$^{45}$, NR$^{46}$R$^{47}$, NO$_2$, CN, —O,
C$_{2-8}$ alkenyl, C$_{2-8}$ alkynyl, C$_{1-4}$ alkoxy, C$_{1-4}$ haloalkyl,
C$_{1-4}$ alkyl substituted with 0–1 R$^{43}$,
aryl substituted with 0–3 R$^{42}$, and
5–10 membered heterocyclic ring system containing from 1–4 heteroatoms selected from the group consisting of N, O, and S substituted with 0–3 R$^{44}$;

R$^{42}$, at each occurrence, is independently selected from
H, CF$_3$, halo, OH, CO$_2$H, SO$_2$R$^{45}$, SR$^{45}$, NR$^{46}$R$^{47}$, OR$^{48}$, NO$_2$, CN, CH(=NH)NH$_2$, NHC(=NH)NH$_2$,
C$_{2-6}$ alkenyl, C$_{2-6}$ alkynyl, C$_{1-4}$ alkoxy, C$_{1-4}$ haloalkyl,
C$_{3-6}$ cycloalkyl,
C$_{1-4}$ alkyl substituted with 0–1 R$^{43}$,
aryl substituted with 0–3 R$^{44}$, and
5–10 membered heterocyclic ring system containing from 1–4 heteroatoms selected from the group consisting of N, O, and S substituted with 0–3 R$^{44}$;

R$^{43}$ is cyclopropyl, cyclobutyl, cyclopentyl, cyclohexyl, phenyl, or pyridyl, each substituted with 03 R$^{44}$;

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, methyl, ethyl, propyl, butyl, methoxy, ethoxy, propoxy, and butoxy;

R$^{45}$ is methyl, ethyl, propyl, or butyl;

R$^{46}$, at each occurrence, is independently selected from H, methyl, ethyl, propyl, and butyl;

R$^{47}$, at each occurrence, is independently selected from
H, methyl, ethyl, n-propyl, i-propyl, n-butyl, i-butyl,
—C(=O)NH(methyl), —C(=O)NH(ethyl), —SO$_2$(methyl), —SO$_2$(ethyl), —SO$_2$(phenyl), —C(=O)O(methyl), —C(=O)O(ethyl), —C(=O)(methyl), —C(=O)(ethyl), and —C(=O)H;

R$^{48}$, at each occurrence, is independently selected from
H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1; and
n is 1 or 2.

[16] In another preferred embodiment the present invention provides a compound of Formula (I-a) wherein:

X is —O— or —S—;

R$^1$ is selected from
ethyl substituted with Z,
propyl substituted with Z,
butyl substituted with Z,
propenyl substituted with Z,
butenyl substituted with Z,
ethyl substituted with R$^2$,
propyl substituted with R$^2$,
butyl substituted with R$^2$,
propenyl substituted with R$^2$, and
butenyl substituted with R$^2$;

Z is selected from H,
—CH(OH)R$^2$,
—OR$^2$,
—SR$^2$,
—NR$^2$R$^3$,
—C(O)R$^2$,
—C(O)NR$^2$R$^3$.
—NR$^3$C(O)R$^2$,
—C(O)OR$^2$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
phenyl substituted with 0–3 R$^{42}$;
naphthyl substituted with 0–3 R$^{42}$;
cyclopropyl substituted with 0–3 R$^{41}$;
cyclobutyl substituted with 0–3 R$^{41}$;
cyclopentyl substituted with 0–3 R$^{41}$;
cyclohexyl substituted with 0–3 R$^{41}$;
pyridyl substituted with 0–3 R$^{41}$;
indolyl substituted with 0–3 R$^{41}$;
indolinyl substituted with 0–3 R$^{41}$;
benzimidazolyl substituted with 0–3 R$^{41}$;
benzotriazolyl substituted with 0–3 R$^{41}$;
benzothienyl substituted with 0–3 R$^{41}$;
benzofuranyl substituted with 0–3 R$^{41}$;
phthalimid-1-yl substituted with 0–3 R$^{41}$;
inden-2-yl substituted with 0–3 R$^{41}$;
2,3-dihydro-1H-inden-2-yl substituted with 0–3 R$^{41}$;
indazolyl substituted with 0–3 R$^{41}$;
tetrahydroquinolinyl substituted with 0–3 R$^{41}$; and
tetrahydro-isoquinolinyl substituted with 0–3 R$^{41}$;

R$^3$, at each occurrence, is independently selected from
H, methyl, and ethyl;

R$^5$ is H;
R$^6$ is H;
R$^7$, R$^8$, and R$^9$, at each occurrence, are independently selected from H, F, Cl, methyl, ethyl, methoxy, —CF$_3$, and —OCF$_3$;

R⁴¹, at each occurrence, is independently selected from
H, F, Cl, Br, OH, CF₃, NO₂, CN, =O, methyl, ethyl, propyl, butyl, methoxy, and ethoxy;

R⁴², at each occurrence, is independently selected from
H, F, Cl, Br, OH, CF₃, SO₂R⁴⁵, SR⁴⁵, NR⁴⁶R⁴⁷, OR⁴⁸, NO₂, CN, =O,
methyl, ethyl, propyl, butyl, methoxy, and ethoxy;

R⁴⁵ is methyl, ethyl, propyl, or butyl;

R⁴⁶, at each occurrence, is independently selected from H, methyl, ethyl, propyl, and butyl;

R⁴⁷, at each occurrence, is independently selected from
H, methyl, ethyl, n-propyl, i-propyl, n-butyl, i-butyl, —C(=O)NH(methyl), —C(=O)NH(ethyl), —SO₂(methyl), —SO₂(ethyl), —SO₂(phenyl), —C(=O)O(methyl), —C(=O)O(ethyl), —C(=O)(methyl), —C(=O)ethyl), and —C(=O)H;

R⁴⁸, at each occurrence, is independently selected from
H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1; and
n is 1 or 2.

[17] In another preferred embodiment the present invention provides a compound of Formula (I-c):

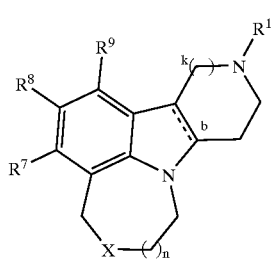

(I-c)

wherein:
b is a single bond or a double bond;
X is —S— or —O—;
R¹ is selected from
—(CH₂)₃C(=O)(4-fluoro-phenyl),
—(CH₂)₃C(=O)(4-bromo-phenyl),
—(CH₂)₃C(=O)(4-methyl-phenyl),
—(CH₂)₃C(=O)(4-methoxy-phenyl),
—(CH₂)₃C(=O)(4-(3,4-dichloro-phenyl)phenyl),
—(CH₂)₃C(=O)(3-methyl-4-fluoro-phenyl),
—(CH₂)₃C(=O)(2,3-dimethoxy-phenyl),
—(CH₂)₃C(=O)(phenyl),
—(CH₂)₃C(=O)(4-chloro-phenyl),
—(CH₂)₃C(=O)(3-methyl-phenyl),
—(CH₂)₃C(=O)(4-t-butyl-phenyl),
—(CH₂)₃C(=O)(3,4-difluoro-phenyl),
—(CH₂)₃C(=O)(2-methoxy-5-fluoro-phenyl),
—(CH₂)₃C(=O)(4-fluoro-1-naphthyl),
—(CH₂)₃C(=O)(benzyl),
—(CH₂)₃C(=O)(4-pyridyl),
—(CH₂)₃C(=O)(3-pyridyl),
—(CH₂)₃CH(OH)(4-fluoro-phenyl),
—(CH₂)₃CH(OH)(4-pyridyl),
—(CH₂)₃CH(OH)(2,3-dimethoxy-phenyl),
—(CH₂)₃S(3-fluoro-phenyl),
—(CH₂)₃S(4-fluoro-phenyl),
—(CH₂)₃ S(=O)(4-fluoro-phenyl),
—(CH₂)₃SO₂(3-fluoro-phenyl),
—(CH₂)₃ SO₂(4-fluoro-phenyl),
—(CH₂)₃O(4-fluoro-phenyl),
—(CH₂)₃O(phenyl),
—(CH₂)₃O(3-pyridyl),
—(CH₂)₃O(4-pyridyl),
—(CH₂)₃O(2-NH₂-phenyl),
—(CH₂)₃O(2-NH₂-5-F-phenyl),
—(CH₂)₃O(2-NH₂-4-F-phenyl),
—(CH₂)₃O(2-NO₂-4-F-phenyl),
—(CH₂)₃O(2-NH₂-3-F-phenyl),
—(CH₂)₃O(2-NH₂-4-Cl-phenyl),
—(CH₂)₃O(2-NH₂-4—OH-phenyl),
—(CH₂)₃O(2-NH₂-4-Br-phenyl),
—(CH₂)₃O(2-NHC(=O)Me-4-F-phenyl),
—(CH₂)₃O(2-NHC(=O)Me-phenyl),
—(CH₂)₃NH(4-fluoro-phenyl),
—(CH₂)₃N(methyl)(4-fluoro-phenyl),
—(CH₂)₃CO₂(ethyl),
—(CH₂)₃C(=O)N(methyl)(methoxy),
—(CH₂)₃C(=O)NH(4-fluoro-phenyl),
—(CH₂)₂NHC(=O)(phenyl),
—(CH₂)₂NMeC(=O)(phenyl),
—(CH₂)₂NHC(=O)(2-fluoro-phenyl),
—(CH₂)₂NMeC(=O)(2-fluoro-phenyl),
—(CH₂)₂NHC(=O)(4-fluoro-phenyl),
—(CH₂)₂NMeC(=O)(4-fluoro-phenyl),
—(CH₂)₂NHC(=O)(2,4-difluoro-phenyl),
—(CH₂)₂NMeC(=O)(2,4-difluoro-phenyl),
—(CH₂)₃(3-indolyl),
—(CH₂)₃(1-methyl-3-indolyl),
—(CH₂)₃(1-indolyl),
—(CH₂)₃(1-indolinyl),
—(CH₂)₃(1-benzimidazolyl),
—(CH₂)₃(1H-1,2,3-benzotriazol-1-yl),
—(CH₂)₃(1H-1,2,3-benzotriazol-2-yl),
—(CH₂)₂(1H-1,2,3-benzotriazol-1-yl),
—(CH₂)₂(1H-1,2,3-benzotriazol-2-yl),
—(CH₂)₃(3,4 dihydro-1(2H)-quinolinyl),
—(CH₂)₂C(=O)(4-fluoro-phenyl),
—(CH₂)₂C(=O)NH(4-fluoro-phenyl),
—CH₂CH₂(3-indolyl),
—CH₂CH₂(1-phthalimidyl),
—(CH₂)₄C(=O)N(methyl)(methoxy),
—(CH₂)₄CO₂(ethyl),
—(CH₂)₄C(=O)(phenyl),
—(CH₂)₄(cyclohexyl),
—(CH₂)₃CH(phenyl)₂,
—CH₂CH₂CH=C(phenyl)₂,
—CH₂CH₂CH=CMe(4-F-phenyl),
—(CH₂)₃CH(4-fluoro-phenyl)₂,
—CH₂CH₂CH=C(4-fluoro-phenyl)₂, —(CH$_2$)$_2$(2,3-dihydro-1H-inden-2-yl),
—(CH$_2$)$_3$C(=O)(2-NR$^2$-phenyl),
—(CH$_2$)$_3$C(=O)(2-NH$_2$-5-F-phenyl),
—(CH$_2$)$_3$C(=O)(2-NH$_2$-4—F-phenyl),
—(CH$_2$)$_3$C(=O)(2-NH$_2$-3-F-phenyl),
—(CH$_2$)$_3$C(=O)(2-NH$_2$-4-Cl-phenyl),
—(CH$_2$)$_3$C(=O)(2-NH$_2$-4—OH-phenyl),
—(CH$_2$)$_3$C(=O)(2-NH$_2$-4-Br-phenyl),
—(CH$_2$)$_3$(1H-indazol-3-yl),
—(CH$_2$)$_3$(5-F-1H-indazol-3-yl),
—(CH$_2$)$_3$(7-F-1H-indazol-3-yl),
—(CH$_2$)$_3$(6-C$_{1-1}$H-indazol-3-yl),
—(CH$_2$)$_3$ (6-Br-1H-indazol-3-yl),
—(CH$_2$)$_3$C(=O)(2-NHMe-phenyl),
—(CH$_2$)$_3$(1-benzothien-3-yl),
—(CH$_2$)$_3$(6-F-1H-indol-1-yl),
—(CH$_2$)$_3$(5-F-1H-indol-1-yl),
—(CH$_2$)$_3$(6-F-2,3-dihydro-1 H-indol-1-yl),
—(CH$_2$)$_3$(5-F-2,3-dihydro-1H-indol-1-yl),
—(CH$_2$)$_3$(6-F-1H-indol-3-yl),
—(CH$_2$)$_3$(5-F-1H-indol-3-yl),
—(CH$_2$)$_3$(5-F-1H-indol-3-yl),
—(CH$_2$)$_3$(9H-purin-9-yl),
—(CH$_2$)$_3$(7H-purin-7-yl),
—(CH$_2$)$_3$ (6-F-1H-indazol-3-yl),
—(CH$_2$)$_3$C(=O)(2-NHSO$_2$Me$_4$-F-phenyl),
—(CH$_2$)$_3$C(=O)(2-NHC(=O)Me-4-F-phenyl),
—(CH$_2$)$_3$C(=O)(2-NHC(=O)Me-phenyl),
—(CH$_2$)$_3$C(=O)(2-NHCO$_2$-Et-4-F-phenyl),
—(CH$_2$)$_3$C(=O)(2-NHC(=O)NHEt-4-F-phenyl),
—(CH$_2$)$_3$C(=O)(2-NHCHO-4-F-phenyl),
—(CH$_2$)$_3$C(=O)(2-OH-4—F-phenyl),
—(CH$_2$)$_3$C(=O)(2-MeS-4-F-phenyl),
—(CH$_2$)$_3$C(=O)(2-NHSO$_2$Me$_4$-F-phenyl),
—(CH$_2$)$_2$C(Me)CO$_2$-Me,
—(CH$_2$)$_2$C(Me)CH(OH)(4-F-phenyl)$_2$,
—(CH$_2$)$_2$C(Me)CH(OH)(4-Cl-phenyl)$_2$,
—(CH$_2$)$_2$C(Me)C(=O)(4-F-phenyl),
—(CH$_2$)$_2$C(Me)C(=O)(2-MeO4-F-phenyl),
—(CH$_2$)$_2$C(Me)C(=O)(3-Me-4-F-phenyl),
—(CH$_2$)$_2$C(Me)C(=O)(2-Me-phenyl),
—(CH$_2$)$_2$C(Me)C(=O)phenyl,

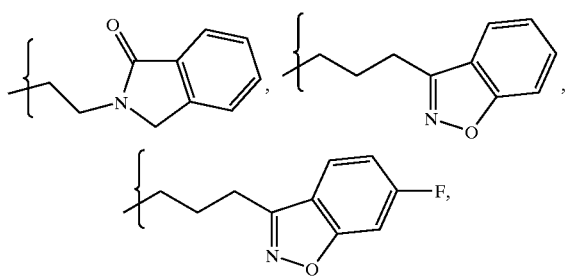

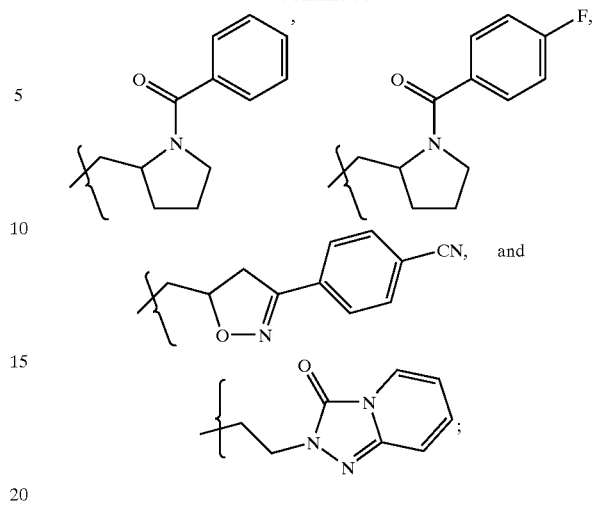

R$^7$, R$^8$, and R$^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, benzyl, HC(=O)—, methylC(=O)—, ethylC(=O)—, propylC(=O)—, isopropylC(=O)—, n-butylC(=O)—, isobutylC(=O)—, secbutylC(=O)—, tertbutylC(=O)—, phenylC(=O)—, methylC(=O)-NH—, ethylC(=O)-NH—, propylC(=O)-NH—, isopropylC(=O)-NH—, n-butylC(=O)-NH—, isobutylC(=O)-NH—, secbutylC(=O)-NH—, tertbutylC(=O)-NH—, phenylC(=O)-NH—, methylamino-, ethylamino-, propylamino-, isopropylamino-, n-butylamino-, isobutylamino-, secbutylamino-, tertbutylamino-, phenylamino-, provided that two of substituents R$^7$, R$^8$, and R$^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;

k is 1 or 2; and n is 1 or 2.

In another subgenus of the above embodiments are compounds wherein b is a single bond; more preferably, b is a single bond, wherein the bridge hydrogens are in a cis position.

In another subgenus of the above embodiments are compounds wherein X is —O—.

In another subgenus of the above embodiments are compounds wherein X is —S—.

In another subgenus of the above embodiments are compounds wherein R$^5$ is H, methyl, ethyl, propyl, or butyl; alternatively R$^5$ is H or methyl; or, alternatively R$^5$ is H.

In another subgenus of the above embodiments are compounds wherein R$^6$ is H, methyl, ethyl, propyl, or butyl; alternatively R$^6$ is H or methyl; or, alternatively R$^6$ is H.

In another subgenus of the above embodiments are compounds wherein R$^7$ and R$^9$, at each occurrence, are independently selected from H, halo, —CF$_3$, —OCF$_3$, —OH, —CN, —NO$_2$, C$_{1-4}$ alkyl, C$_{2-4}$ alkenyl, C$_{2-4}$ alkynyl, C$_{1-4}$ haloalkyl, C$_{1-4}$ alkoxy, and (C A4 haloalkyl)oxy; alternatively R$^7$ and R$^9$, at each occurrence, are independently selected from H, F, Cl, —CF$_3$, —OCF$_3$, —OH, —CN, —NO$_2$, methyl, ethyl, vinyl, allyl, methoxy, and ethoxy; or, alternatively $R^7$ and $R^9$, at each occurrence, are independently selected from H, F, Cl, —CF$_3$, —OCF$_3$, —OH, —CN, —NO$_2$, methyl, and methoxy; or, alternatively $R^7$ and $R^9$, at each occurrence, are H.

In another subgenus of the above embodiments are compounds wherein $R^8$ is methyl substituted by $R^{11}$; phenyl substituted by 0–5 $R^{33}$; —OR$^{12}$; —SR$^{12}$; or —NR$^{12}R^{13}$.

In another subgenus of the above embodiments are compounds wherein $R^8$ is methyl substituted by $R^{11}$.

In another subgenus of the above embodiments are compounds wherein $R^8$ is phenyl substituted by 0–5 $R^{33}$.

In another subgenus of the above embodiments are compounds wherein $R^8$ is —NR$^{12}R^{13}$.

In another subgenus of the above embodiments are compounds wherein $R^8$ is —OR$^{12}$.

In another subgenus of the above embodiments are compounds wherein $R^8$ is SR$^{12}$.

In another subgenus of the above embodiments are compounds wherein $R^1$ is selected from H, C$_{1-5}$ alkyl, C$_{2-5}$ alkenyl, C$_{2-5}$ alkynyl, C$_{3-6}$ cycloalkyl, —(C$_{1-3}$ alkyl)C$_{3-6}$ cycloalkyl), —(C$_{2-3}$ alkenyl)C$_{3-6}$ cycloalkyl), and —(C$_{2-3}$ alkynyl)C$_{3-6}$ cycloalkyl.

In another subgenus of the above embodiments are compounds wherein $R^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-ethylpropyl, 2-methylbutyl, 2-methylpentyl, 2-ethylbutyl, 3-ethylpentyl, 3-methylbutyl, cyclopropyl, cyclobutyl, cyclopentyl, cyclohexyl, cyclopropylmethyl, cyclobutylmethyl, cyclopentylmethyl, and cyclohexylmethyl; alternatively $R^1$ is hydrogen, methyl, ethyl, n-propyl, n-butyl, s-butyl, t-butyl, 2-propyl, 2-butyl, cyclopropylmethyl, cyclobutylmethyl, cyclopentylmethyl, or cyclohexylmethyl; or alternatively $R^1$ is hydrogen, methyl, or ethyl.

In another subgenus of the above embodiments are compounds wherein k and n, at each occurrence, are independently 1.

In an even further more preferred embodiment of the present invention, are compounds of Formula (I) selected from Table 1.

In a second embodiment, the present invention provides a pharmaceutical composition comprising a compound of Formula (I) and a pharmaceutically acceptable carrier.

In a third embodiment, the present invention provides a method for the treatment a central nervous system disorder comprising administering to a host in need of such treatment a therapeutically effective amount of a compound of Formula (I), or a pharmaceutically acceptable salt thereof, wherein the compound is a 5HT2a antagonist or a 5HT2c agonist.

In a preferred embodiment the compound is a 5HT2a antagonist.

In another preferred embodiment the compound is a 5HT2c agonist.

In a more preferred embodiment the present invention provides a method for the treatment central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility comprising administering to a host in need of such treatment a therapeutically effective amount of a compound of Formula (I).

In a further preferred embodiment the central nervous system disorder comprises obesity.

In another further preferred embodiment the central nervous system disorder comprises schizophrenia.

In another further preferred embodiment the central nervous system disorder comprises depression.

In another further preferred embodiment the central nervous system disorder comprises anxiety.

In a fourth embodiment the present invention provides novel compounds of Formula (I) or pharmaceutically acceptable salt forms thereof for use in therapy.

In a fifth embodiment the present invention provides the use of novel compounds of Formula (I) or pharmaceutically acceptable salt forms thereof for the manufacture of a medicament for the treatment of central nervous system disorders including obesity, anxiety, depression, psychosis, schizophrenia, sleep disorders, sexual disorders, migraine, conditions associated with cephalic pain, social phobias, and gastrointestinal disorders.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The numbering of the tetracyclic ring-system present in the compounds of Formula (I), as defined by nomenclature known to one skilled in the art, is shown for two examples in Formula (I'), when k is 1 and n is 1; and in Formula (I''), when k is 1 and n is 2:

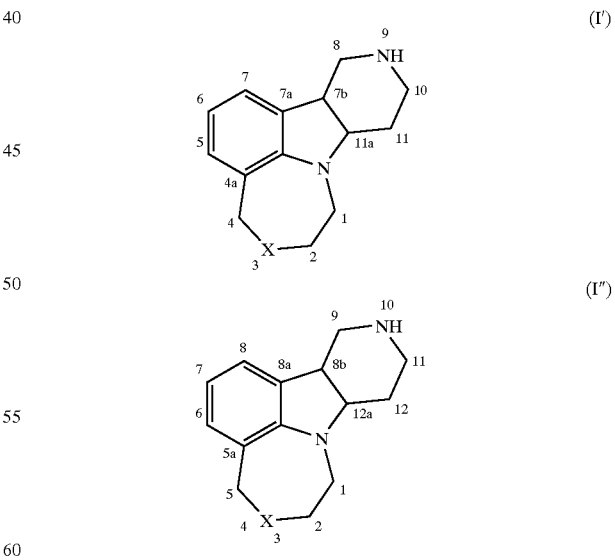

The tetracyclic ring-system present in compounds of Formula (I) occur as "cis" or "trans" isomers when the carbon-carbon bond b in Formula (I) is a single bond. As such, the terms "cis" and "trans", in conjunction with the tetracyclic ring structure, refer to the configuration of hydrogen atoms on carbon atoms 8a and 12a in Formula (I') or, for example, on carbon atoms 9a and 13a in Formula (I"), above. When both hydrogens are on the same side of the mean plane determined by the octahydro tetracyclic moiety then the configuration is designated "cis", if not, the configuration is designated "trans". It is understood that the above example is for demonstrative purposes only and not intended to limit the scope of the tetracyclic ring-system present in compounds of Formula (I). As such, it is understood that one skilled in the art of organic chemistry can apply the above numbering system to other values of k, m, and n in the scope of compounds of Formula (I) to determine the appropriate numbering. Additional Examples of the numbering of the tetracyclic ring-system are further provided below in the synthetic Examples. Lastly, it is understood that the use of "cis" or "trans" in the identification of the tetracyclic ring-system is not meant to construe the configuration of any other cis or trans geometric isomer in the molecule, for example, cis or trans butene.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^2$, $R^{11}$, $R^{33}$, $R^{41}$, $R^{42}$, etc.) occurs more than one time in any constituent or formula for a compound, its definition at each occurrence is independent of its definition at every other occurrence. Thus, for example, if a group is shown to be substituted with 0–2 $R^2$, then said group may optionally be substituted with up to two $R^2$ groups and $R^2$ at each occurrence is selected independently from the definition of $R^2$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" or "$C_{1-6}$ alkyl", denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms, for example, "$C_{2-6}$ alkenyl", and one or more unsaturated carbon-carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration having the specified number of carbon atoms, for example, "$C_{2-6}$ alkynyl", and one or more carbon-carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" is represents an alkyl group as defined above with the indicated number of carbon atoms attached through a sulpher bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=I to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic ring" or "heterocyclic ring system" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H, 6H-1,5,2-dithiazinyl, dihydrofuro

[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2, 4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, indolinyl, isoquinolinyl, quinolinyl, tetrahydroisoquinolinyl, tetrahydroquinolinyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles.

As used herein, the term "bicyclic heterocyclic ring system" is intended to mean a stable 9- to 10-membered bicyclic heterocyclic ring formed from the substituent $NR^{12}R^{13}$, which is partially unsaturated or unsaturated (aromatic), and which consists of carbon atoms, a nitrogen atom, and 1 or 2 additional heteroatoms independently selected from the group consisting of N, O and S. The additional nitrogen or sulfur heteroatoms may optionally be oxidized. The heterocyclic ring is attached to its pendant group by the nitrogen atom of the group $NR^{12}R^{13}$ and for which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. The term "bicyclic heterocyclic ring system" is intended to be a subset of the term "heterocyclic ring system". Preferred examples of a 9- to 10-membered bicyclic heterocyclic ring system are benzimidazolyl, benzimidazolinyl, benzoxazolinyl, dihydrobenzthiazolyl, dihydrodioxobenzthiazolyl, benzisoxazolinyl, 1H-indazolyl, indolyl, indolinyl, isoindolinyl, tetrahydro-isoquinolinyl, tetrahydro-quinolinyl, and benzotriazolyl.

Additionally, a subclass of preferred heterocycles are heterocycles which function as an isostere of a cyclic but non-heterocyclic substitutent such as —$CH_2$—C(=O)-phenyl. Preferred examples of such heterocycles include, but are not limited to, benzimidazolyl, benzofuranyl, benzothiophenyl, benzoxazolyl, benzthiazolyl, benzisoxazolyl, furanyl, imidazolinyl, 1H-indazolyl, indolinyl, isoindolinyl, isoquinolinyl, oxazolyl, piperidinyl, pyrazinyl, pyridinyl, pyrimidinyl, quinolinyl, thiazolyl, thiophenyl, and 1,2,3-triazolyl.

As used herein, the term "aryl", or aromatic residue, is intended to mean an aromatic moiety containing six to ten carbon atoms, such as phenyl, pyridinyl and naphthyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent Synthesis Throughout the details of the invention, the following abbreviations are used with the following meanings:

| Reagents: | |
|---|---|
| MCPBA | m-chloroperoxybenzoic acid |
| DIBAL | diisobutyl aluminum hydride |
| $Et_3N$ | triethylamine |
| TFA | trifluoroacetic acid |
| LAH | lithium aluminum hydride |
| NBS | N-bromo succinimide |
| Red-AlSodium | bis(2-methoxyethoxy)aluminum hydride |
| $Pd_2dba_3$ | Tris(dibenzylideneacetone)dipalladium(0) |
| ACE-Cl | 2-chloroethylchloroformate |
| Solvents: | |
| THF | tetrahydrofuran |
| MeOH | methanol |
| EtOH | ethanol |
| EtOAc | ethyl acetate |
| HOAc | acetic acid |
| DMF | dimethyl formamide |
| DMSO | dimethyl sulfoxide |
| DME | dimethoxyethane |
| $Et_2O$ | diethylether |
| iPrOH | isopropanol |
| MEK | methyl ethyl ketone |
| Others: | |
| Ar | aryl |
| Ph | phenyl |
| Me | methyl |
| Et | ethyl |
| NMR | nuclear magnetic resonance |
| MHz | megahertz |
| BOC | tert-butoxycarbonyl |
| CBZ | benzyloxycarbonyl |
| Bn | benzyl |
| Bu | butyl |
| Pr | propyl |
| cat. | catalytic |
| mL | milliliter |
| nM | nanometer |
| ppm | part per million |
| mmol | millimole |
| mg | milligram |
| g | gram |
| kg | kilogram |
| TLC | thin layer chromatography |
| HPLC | high pressure liquid chromatography |
| RPM | revolutions per minute |
| rt | room temperature |
| aq. | aqueous |
| sat. | saturated |

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The preparation of compounds of Formula (I) of the present invention may be carried out in a convergent or sequential synthetic manner. Detailed synthetic preparations of the compounds of Formula (I) are shown in the following reaction schemes. The skills required in preparation and purification of the compounds of Formula (I) and the intermediates leading to these compounds are known to those in the art. Purification procedures include, but are not limited to, normal or reverse phase chromatography, crystallization, and distillation.

Several methods for the preparation of the compounds of the present invention are illustrated in the schemes and examples shown below. The substitutions are as described and defined above.

Compounds of Formula (I) of this invention may be prepared as shown in Scheme 1. Thus, preparation of an aryl hydrazine (III) is accomplished, for example, by treatment of a corresponding substituted aniline (II) with $NaNO_2$ followed by reduction of the N-nitroso intermediate with a reducing agent such as LAH or zinc and an organic acid, such as acetic acid or trifluoroacetic acid at low temperature. Assembly of the core tetracyclic intermediate indole (V) is accomplished by Fischer indole cyclization of the aryl hydrazine and a suitably substituted ketone (i.e. (IV)) by methods described by, but not limited to, R. J. Sundberg, "Indoles, Best Synthetic Methods" 1996, Academic Press, San Diego, Calif. For example, treatment of the aryl hydrazine (III) as the free base or the corresponding mineral acid salt with the ketone (IV) ($R^1$=H, Bn, CBZ, $CO_2Et$, etc) in an alcoholic solvent in the presence of mineral acid affords the indoles (V) as the free bases (after treatment with aq. NaOH). Reduction of the indoles to the corresponding cis-or trans substituted dihydroindoles is accomplished by, for example, treatment with hydrogen in the presence of a catalyst such as platinum oxide or palladium on carbon, or with a metal such as zinc and a mineral acid such as hydrochloric acid, or with sodium and liquid ammonia, or with borane-amine complex such as borane-triethylamine in tetrahydofuran, or preferably by treatment with triethylsilane or $NaCNBH_3$ in an acid such as acetic or trifluoroacetic acid.

The corresponding enantiomers can be isolated by separation of the racemic mixture of (I) on a chiral stationary phase column utilizing normal or reverse phase HPLC techniques, the details of which are described in the examples. Alternatively, a diastereomeric mixture of (I) can be prepared by treatment of (I, $R^1$=H) with an appropriate chiral acid (or suitably activated derivative), for example dibenzoyl tartrate or the like (see, for example, Kinbara, K., et. al., *J Chem. Soc., Perkin Trans.* 2, 1996, 2615; and Tomori, H., et. al., *Bull. Chem. Soc. Jpn.,* 1996, 3581). The diastereomers would then be separated by traditional techniques (i.e. silica chromatography, crystallization, HPLC, etc) followed by removal of the chiral auxiliary to afford enantiomerically pure (I).

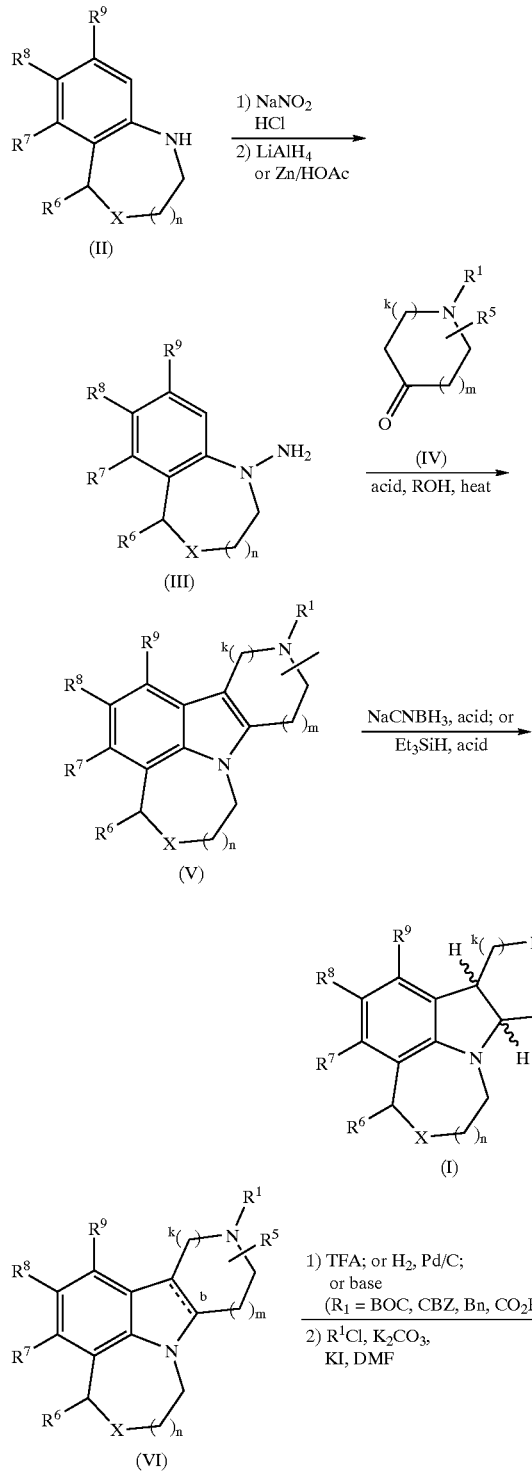

-continued

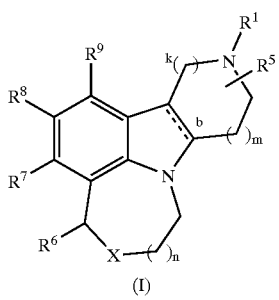

In the cases where the carboline nitrogen has been protected (VI) (i.e. R¹=Boc, Bn, CBZ, CO₂R), it may be removed under a variety of conditions as described in Greene, T. W., Wuts, P. G. W., "Protective Groups in Organic Synthesis, 2nd Edition", John Wiley and Sons, Inc., New York, pages 309–405, 1991. The free secondary amine could then be alkylated, for example, by treatment with a suitably substituted alkyl halide (R¹Cl, or R¹I) and a base to afford additional compounds of Formula (I), as described, for example, by Glennon, R. A., et. al., *Med Chem. Res.,* 1996, 197.

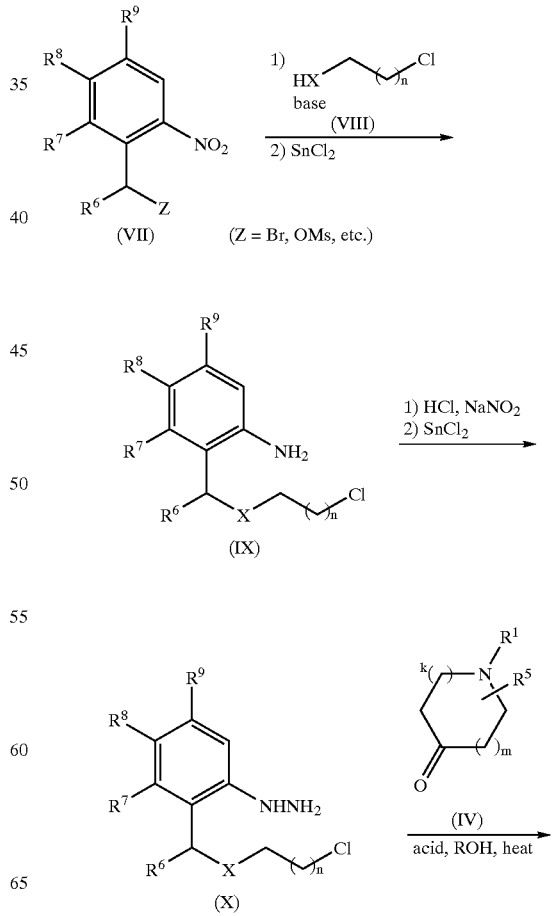

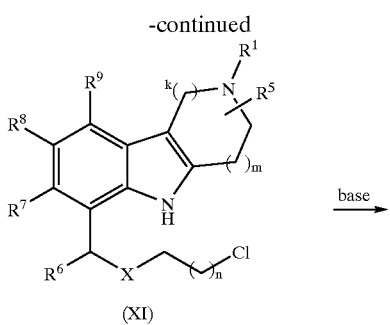

(XI)

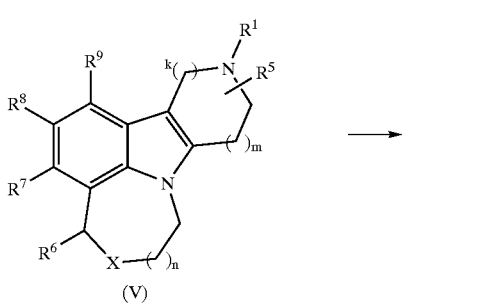

(V)

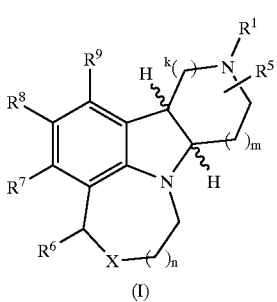

(I)

Alternatively, compounds of Formula (I) where X=O or S can be prepared as described in Scheme 2. The ortho-nitro compounds (VII) are readily available by standard procedures known to those skilled in the art. For example, where Z=Br, compounds (VII) are available by radical bromination of an appropriate ortho-nitroalkylphenyl compound. Where Z=OMs, compounds (VII) are available by reduction of an appropriate ortho-nitrophenylketone compound with sodium borohydride and conversion to the mesylate with methanesulfonyl chloride and base. Alternatively, compounds (VII) are available by addition of an appropriate alkyl Grignard or alkyllithium reagent to an appropriate ortho-nitrobenzaldehyde followed by subsequent conversion of the alcohol to a mesylate or other leaving group. Treatment of (VII) with a nucleophilic alkyl halide (X=OH, SH (VIII)) and a suitable base followed by subsequent reduction of the corresponding nitroaryl derivative affords the aniline (IX). The reduction may be accomplished with a variety of reducing agents, for example, $SnCl_2$, LAH, $NaBH_4$, $N_2H_4$, etc. or with hydrogen in the presence of a suitable catalyst, such as palladium on carbon, or platinum oxide, etc., (see Hudlicky, M., "Reductions in Organic Chemistry", Ellis Horwood, Ltd., Chichester, UK, 1984). Formation of the aryl hydrazine (X) may be accomplished as described previously in Scheme 1 or more directly by treatment of the aniline (IX) with aq. hydrochloric acid, stannous chloride and $NaNO_2$ at room temperature (see, Buck, J. S., Ide, W. S., Org. Syn., Coll. Vol., 2, 1943, 130). This primary aryl hydrazine (X) can then be cyclized under Fischer indole cyclization conditions as detailed above for compound (V), to afford the indole (XI) as the corresponding salt. Treatment of the indole (XI) with a base such potassium hydroxide or potassium t-butoxide in a solvent such as DME or THF affords the tetracyclic indole intermediates (V). These indoles can also be reduced to the corresponding cis-or trans indolines (I) as described previously in Scheme 1.

Compounds of Formula (1) where $X=NR^{10}$ can alternatively be prepared as described in Scheme 3. Treatment of hydrazino benzoic acids (XII), which are either commercially available or are readily available by standard procedures known to those skilled in the art, under the Fischer indolization conditions described earlier affords indoles (XIII). These indoles can be reduced to the corresponding cis-or trans indolines (XIV) as described previously. Amide bond formation between the carboxylic acid and an appropriate haloalkyl amine (XV) can be accomplished under a variety of amide bond forming conditions, such as with a coupling agent such as dicyclohexylcarbodiimide or carbonyl diimidazole, to give the amides (XVI). Ring closure can be accomplished by treating (XVI) with a base such as potassium hydroxide or potassium tert-butoxide with heating in the presence of potassium iodide to give a tetracyclic amide. Reduction of the amide carbonyl with a suitable reducing agent, such as borane tetrahydrofuran complex or lithium aluminum hydride, affords the tetracyclic amine (XVII). Introduction of the $R^{10}$ substituent can be readily accomplished by standard procedures, affording compounds (I). In the cases where the carboline nitrogen has been protected (XVII) (i.e. $R^1$=Boc, Bn, CBZ, $CO_2R$), it may be removed under a variety of conditions as described previously. The free secondary amine could then be alkylated, for example, by treatment with a suitably substituted alkyl halide ($R^1Cl$, or $R^1I$) and a base to afford additional compounds of Formula (I), as described in Scheme 1.

Scheme 3.

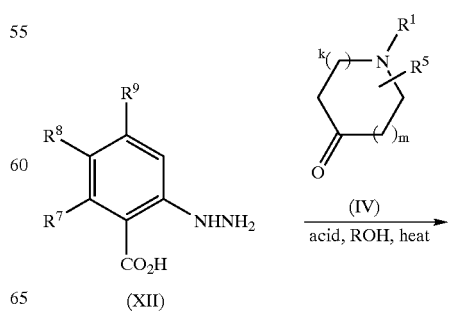

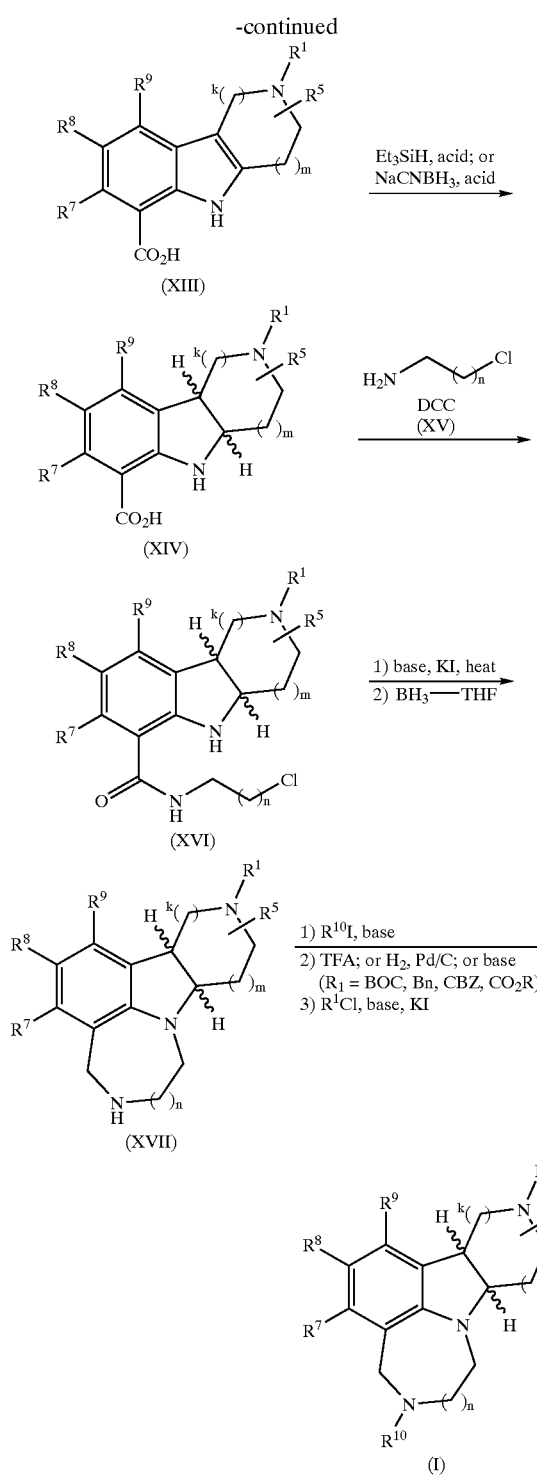

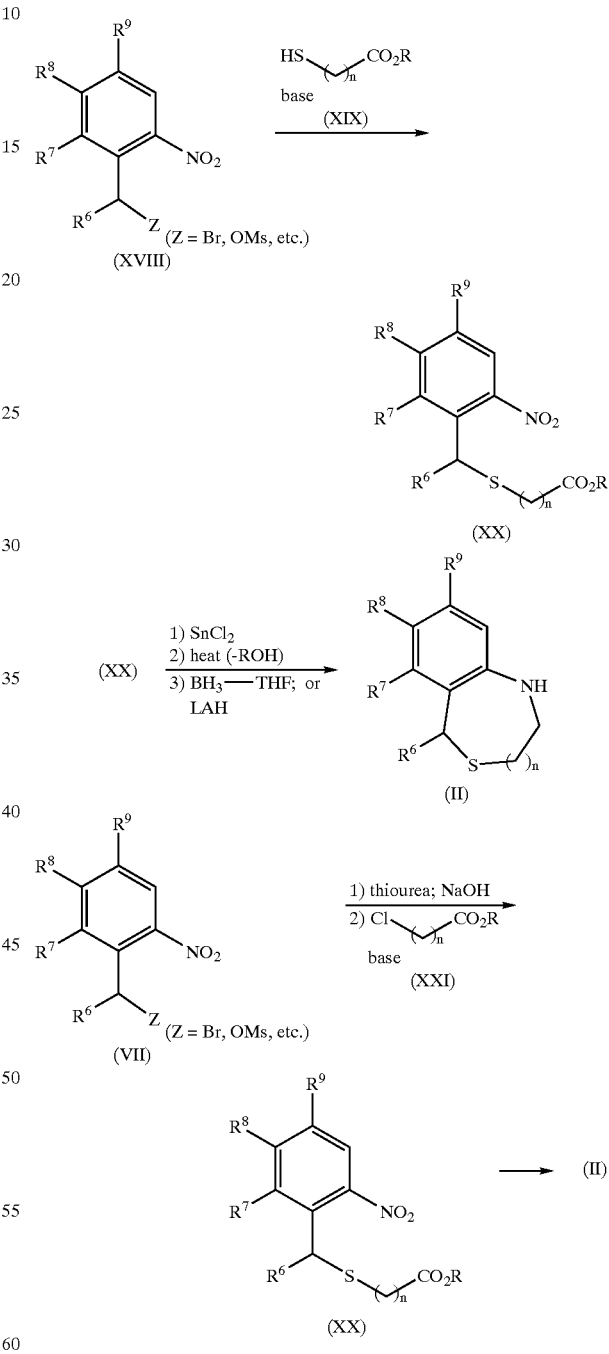

Alternatively, compounds (VII) can be converted by a variety of procedures into the corresponding benzylthiol derivatives, such as by displacement with thiourea and subsequent hydrolysis. Reaction of the intermediate sulfides with chloroester and acid derivatives (XXI) affords (XX), which can be converted as previously described into the aniline intermediates (II).

Scheme 4.

Preparation of the aniline precursors (II) to the Fischer indole cyclizations is described in the following Schemes. The preparation of compounds (II) where X=S is shown in Scheme 4. Compounds (VII) can be readily displaced with a variety of mercaptoester or acid derivatives (XIX) to afford (XX). Reduction of the nitro group by tin chloride or a variety of other well known reduction methods affords an aniline intermediate. Ring-closing condensation can occur spontaneously or under heating conditions to afford a lactam, which can be reduced with borane-tetrahydrofuran complex or LAH to give the aniline intermediates (II).

Alternatively, the anilines (II) where X=S can be prepared as described in Scheme 5. Compounds (XXII) are commercially available or are readily available by procedures described for compounds (VII) or by other procedures known to those skilled in the art. Displacement of the Z group with mercaptoesters or acids (XIX) affords compounds (XXIII). Hydrolysis of the ester forms an acid which, when treated under Friedel-Crafts acylation conditions (see Ed. G. A. Olah, "Friedel-Crafts and Related Reactions", J. Wiley and Sons, New York, 1964, Vol 3, Pts 1 and 2 or Chem. Rev., 1955, 229, or Olah, G. A., "Friedel-Crafts Chemistry", Wiley Interscience, New York, 1973, for varying conditions and protocols), i.e. strong Lewis acids (AlCl$_3$, FeCl$_3$, etc.), affords the cyclic ketones (XXIV). Incorporation of the nitrogen functionality can be accomplished in several ways. For example, Schmidt rearrangement (as described by Smith, P. A. S., *J. Am. Chem. Soc.,* 1948, 320) is effected by treatment of the carbonyl derivative (XXIV) with NaN$_3$ and methanesulfonic acid to afford the bicyclic lactam (XXV). Alternatively, this transformation may be carried out under Hoffmann rearrangement protocol (see, for example, Dike, S. Y., et. al., *Bioorg. Med. Chen Lett.,* 1991, 383), by initial formation of the oxime derivative of (XXIV) by treatment with hydroxylamine hydrochloride. Subsequent rearrangement to the lactam is efficiently accomplished by heating in polyphosphoric acid to afford the lactam (XXV). Reduction of the lactam (XXV) can be accomplished with a variety of reducing agents, for example, borane-THF complex, LAH and the like to afford the aniline intermediates (II). One skilled in the art will recognize that the intermediates (XXII) are readily available by other methods, for example by following the sequence described in the bottom of Scheme Scheme 5.

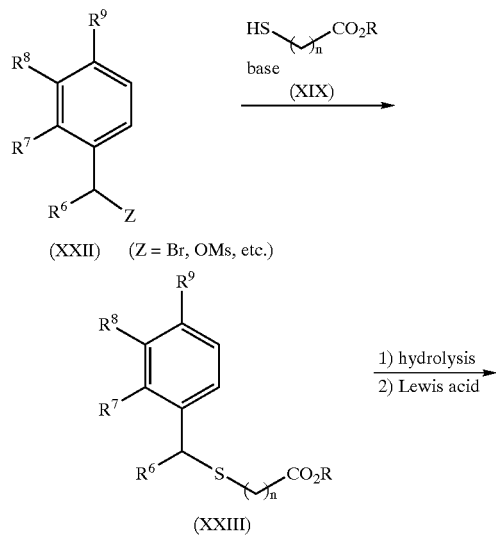

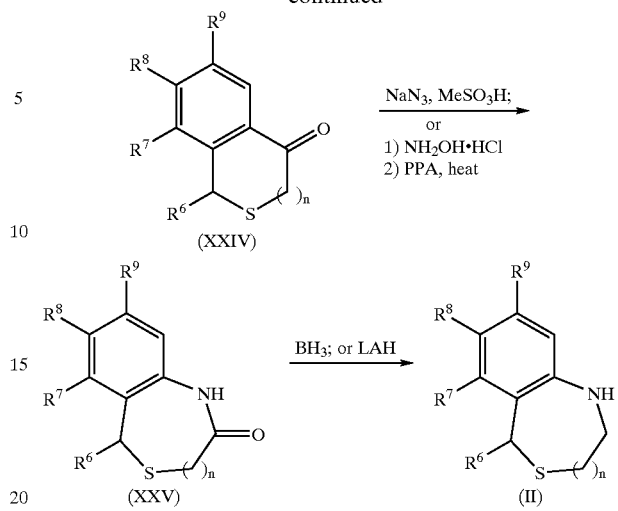

Preparation of the aniline precursors (II) to the Fischer indole cyclizations where X=O is shown in Scheme 6. 2-Aminobenzyl alcohols (XXVI) are either commercially available or are readily available by standard synthetic methods, such as by the reduction of an appropriate ketone or aldehyde or by addition of an appropriate Grignard or alkyllithium reagent to an appropriate aldehyde, whereby the amino functionality can be suitably protected or can be subsequently derived from reduction of a nitro group. N-acylation of (XXVI) with a chloroalkyl acid chloride such as (XXVII) in the presence of a base such as triethylamine, or with an appropriate chloroalkyl carboxylic acid under a variety of amide bond coupling procedures, affords an amide intermediate which can by be cyclized to the lactams (XXVIII) by treatment with a base such as sodium ethoxide. Reduction of the lactam carbonyl can be readily accomplished with a variety of reducing agents, such as LAH or borane-THF complex, as described earlier. This reduction affords the anilines (II) where X=O. Alternatively, anilines (II) where X=O can be prepared by displacing the Z group in (VII) with an appropriate hydroxy ester (XXIX) to afford (XXX), in an analogous fashion as described in Scheme 4. Also, the same compounds (XXX) are available from the readily available benzyl alcohols (XXXI) by alkylation with chloroalkyl esters (XXXII) in the presence of a base such as sodium hydride. Reduction of the nitro group of (XXX) with, for example, SnCl$_2$ followed by ring-closing condensation as described in Scheme 4 affords the lactam intermediate (XXVIII). Reduction of the lactam as described previously affords the anilines (II) where X=O.

Scheme 6.

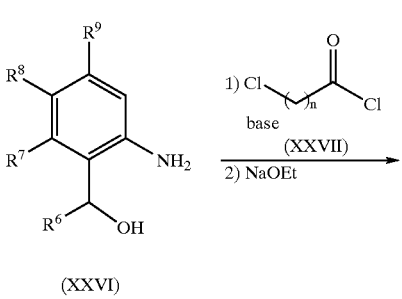
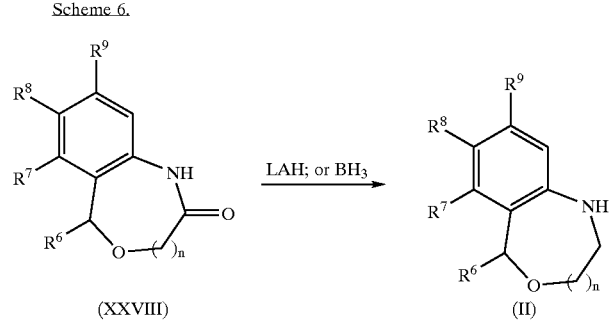

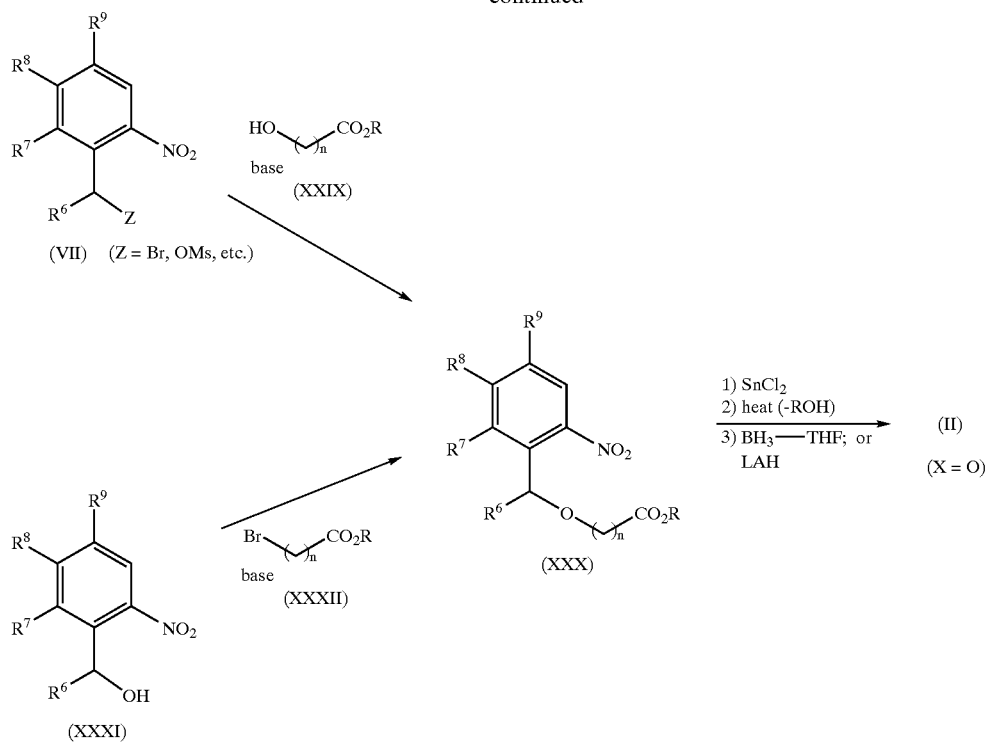

The preparation of aniline intermediates (II) where $X=NR^{10}$ is accomplished as described in Scheme 7. N-Acylation of diamines (XXXIII), readily available by standard procedures known to those skilled in the art with chloroalkyl acid chlorides (XXVII) in the presence of a base such as triethylamine affords an amide. This amide can also be formed by coupling an appropriate chloroalkyl carboxylic acid with (XXXIII) under standard amide bond coupling conditions. Heating the amide intermediate, possibly in the presence of a base, affords the lactams (XXXIV). Reduction of the lactam with LAH or borane followed by N-alkylation of the more nucleophilic ring nitrogen affords anilines (II) where $X=NR^{10}$. The group $R^{10}$ can also be a suitable protecting group, such as CBZ, $CO_2R$, etc., as long as it is compatible with the Fischer indole cyclization conditions. Subsequent deprotection and N-alkylation would provide the $N-R^{10}$ groups found in compounds of Formula (I).

Alternatively, N-alkylation of amino esters (XXXV) with compounds (VII) in the presence of a suitable base such as triethylamine or potassium carbonate would afford (XXXVI). Compounds (XXXVI) would also be available by reductive amination ($NaCNBH_3$, methanol, acetic acid) of an appropriate ortho-nitrobenzaldehyde with aminoesters (XXXV). Nitro group reduction, ring-closing condensation, amide reduction and N-alkylation with $R^{10}I$ would then afford anilines (II) where $X=NR^{10}$.

Alternatively, the anthranilic acids (XXXVII) can be coupled with an appropriate chloroalkylamine (XV) under a variety of amide bond forming conditions to afford the amides (XXXVIII). Nitro group reduction as described previously, followed by intramolecular N-alkylation, induced by heat and/or treatment with a suitable base such as triethylamine or potassium hydroxide, would afford a lactam intermediate. Reduction with borane or LAH as described previously, followed by N-alkylation with $R^{10}I$ would then afford anilines (II) where $X=NR^{10}$.

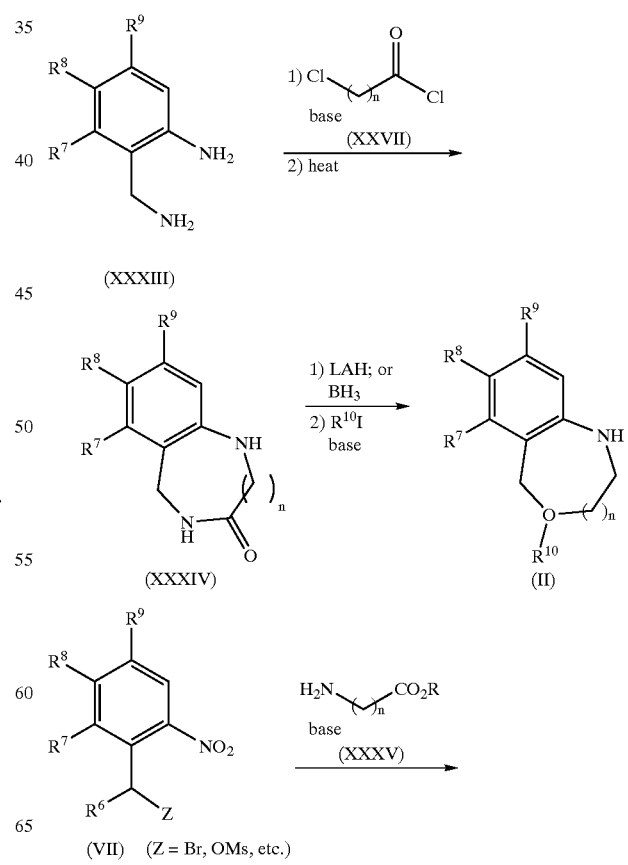

Scheme 7.

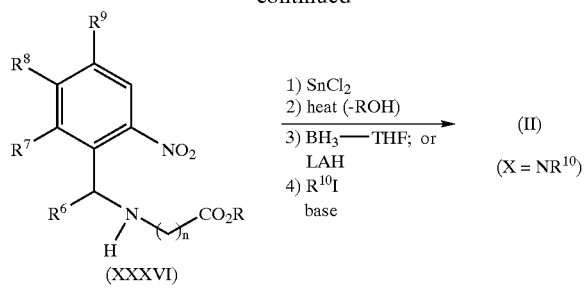

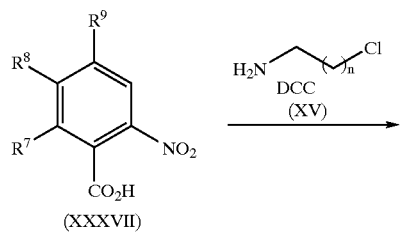

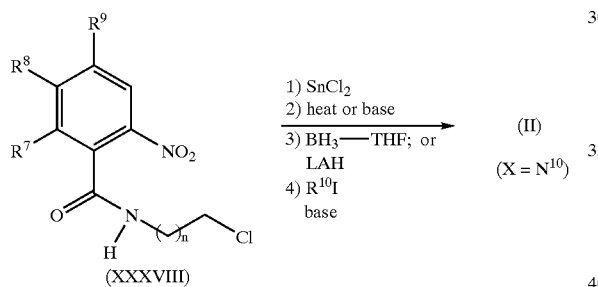

Scheme 8.

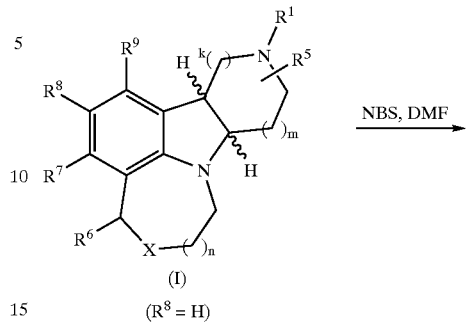

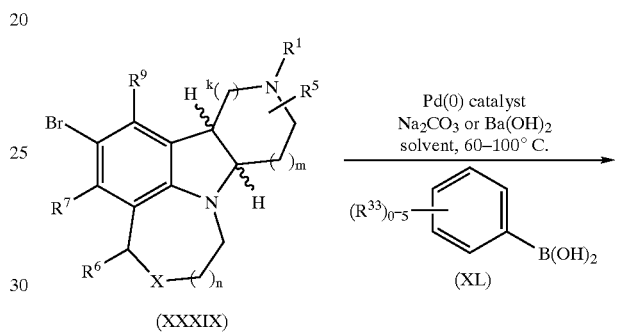

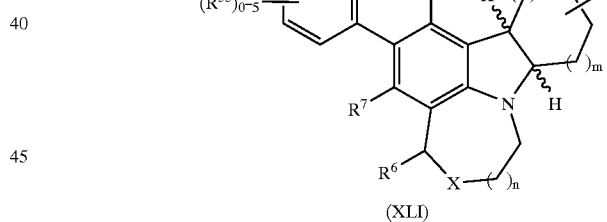

The preparation of compounds of Formula (I) with additional diversity of functionalization of the aromatic A ring of the tetracycle is shown in the following Schemes. As shown in Scheme 8, bromination of the indolines (I, $R^8$=H) when the amine is protected, for example, with the Boc or CBZ protecting groups, with, for example, NBS in DMF affords the $R^8$ brominated derivatives (XXXIX). These activated aryl derivatives (XXXIX) act as excellent counterparts for a number of important synthetic transformations.

For example, biaryl coupling is accomplished under Suzuki coupling protocol. For a review and leading references of palladium catalyzed cross coupling reactions, see Miyaura, N., Suzuki, A., *Chem. Rev.*, 1995, 2457. One such procedure entails treatment of the aryl bromide (XXX) with a functionalized aryl boronic acid (L) in the presence of a catalytic Pd(0) species, such as $Pd(PPh_3)_4$, $Pd(PPh_3)_2Cl_2$, $Pd(OAc)_2$, $Pd_2(dba)_3$ and a suitable ligand such as $PPh_3$, $AsPh_3$, etc., or other such Pd(0) catalyst, and a base such as $Na_2CO_3$, $Ba(OH)_2$ or $Et_3N$ in a suitable solvent such as DMF, toluene, THF, DME or the like, to afford the indolines (XLI).

Alternatively formation of the indole boronic ester from the bromine derivative (XXXIX) (i.e. (I, $R^8$=B(OR)$_2$) would allow for greater diversity in the subsequent coupling of this indole boronic acid with commercially available haloaromatic derivatives in a similar Suzuki coupling strategy as described above to afford the indolines (XLI). One such procedure is shown in Scheme 9. Treatment of bromides (XXXIX) with a palladium catalyst such as $Pd(PPh_3)_4$ or $Pd(PPh_3)_2Cl_2$ and a suitable base, a preferred one being potassium acetate, in the presence of diboron pinacol ester (XLII) affords the aryl boronic ester (XLIII). This boronic ester can undergo Suzuki coupling directly with a wide variety of commercially available aryl bromides (XLIV) under typical Suzuki conditions as described in Scheme 8 to afford the indolines (XLI).

Scheme 9.

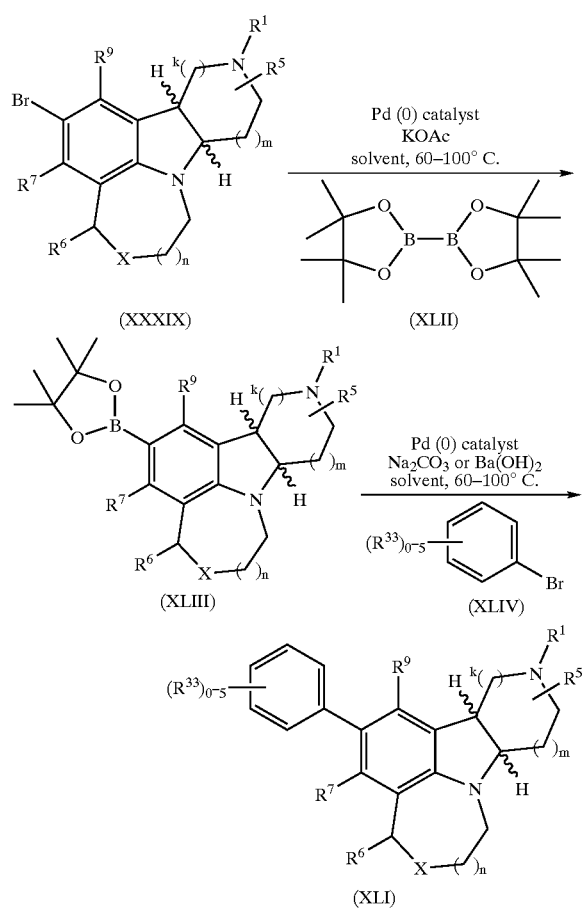

Similarly, biaryl coupling of the bromine derivatives (XLV), readily obtained by the synthetic sequence exemplified in Scheme 2, (starting with the suitably functionalized ortho-nitro compounds (VII)), is shown in Scheme 10. This approach allows for the preparation of biaryl indoles as well as the corresponding indoline derivatives. Protection of the amine functionality must be carried out if $R^1$=H (see Greene et. al for protections of amines). This is readily accomplished, for example, by treatment of bromo derivatives (XLV) with (Boc)$_2$O in aqueous sodium hydroxide and dioxane. Subsequent Suzuki coupling with a variety of aryl boronic acids is carried out as described above in Scheme 8, to afford the biaryl adducts (XLVI). This protocol is amenable to $R^7$, $R^8$, and $R^9$ bromide, iodide, triflates, and/or diazo derivatives (see Miyaura, N., Suzuki, A., *Chem. Rev.*, 1995, 2457, for a review of aryl couplings).

Scheme 10.

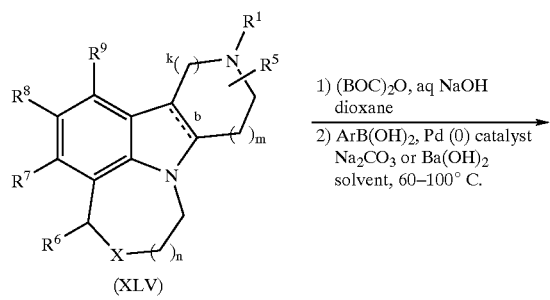

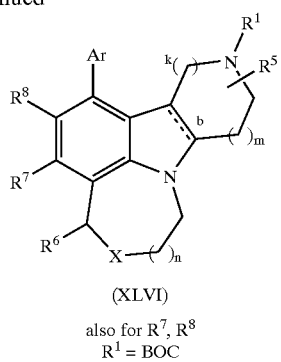

(XLVI)

also for $R^7$, $R^8$
$R^1$ = BOC

In addition, there exists a wide range of procedures and protocols for functionalizing haloaromatics, aryldiazonium and aryltriflate compounds. These procedures are well known by those in the art and described, for example, by Stanforth, S. P., *Tetrahedron*, 1998, 263; Buchwald, S. L., et. al., *J. Am. Chem. Soc.*, 1998, 9722; Stille, J. K., et. al., *J. Am. Chem. Soc.*, 1984, 7500. Among these procedures are biaryl couplings, alkylations, acylations, aminations, and amidations. The power of palladium catalyzed functionalization of aromatic cores has been 110 explored in depth in the last decade. An excellent review of this field can be found in J. Tsuji, "Palladium Reagents and Catalysts, Innovations in Organic Synthesis", J. Wiley and Sons, New York, 1995.

One such example is described in Scheme 11, where the aromatic A ring of Formula (I) is substituted with an arylamino group. Treatment of bromide (XXXIX) with benzophenone imine in the presence of a palladium (0) catalyst, such as Pd$_2$(dba)$_3$, Pd(PPh$_3$)$_4$ or Pd(PPh$_3$)$_2$Cl$_2$, and a suitable ligand such as BINAP or PPh$_3$, and a base such as NaOtBu in a suitable solvent such as DMF, toluene, THF, DME or the like, affords an imine in which nitrogen is attached to the aromatic ring. Hydrolysis of this imine, for example with hydroxylamine and sodium acetate in methanol, affords the aniline (XLVI). This aniline (XLVI) can be treated with a wide variety of commercially available aryl bromides (XLIV) in the presence of a palladium (0) catalyst, such as Pd$_2$(dba)$_3$, Pd(PPh$_3$)$_4$ or Pd(PPh$_3$)$_2$Cl$_2$, and a suitable ligand such as BINAP or PPh$_3$, and a base such as NaOtBu in a suitable solvent such as DMF, toluene, THF, DME or the like, to afford the biaryl anilines (XLVII). In analogy with Scheme 10, the chemistry described in Scheme 11 can also be applied to analogs of (XXIX) where the $R^7$ or $R^9$ groups are Br, I, OTf, etc., to afford analogs of (XLVII) where the arylamino group is on the $R^7$ or $R^9$ position.

Scheme 11.

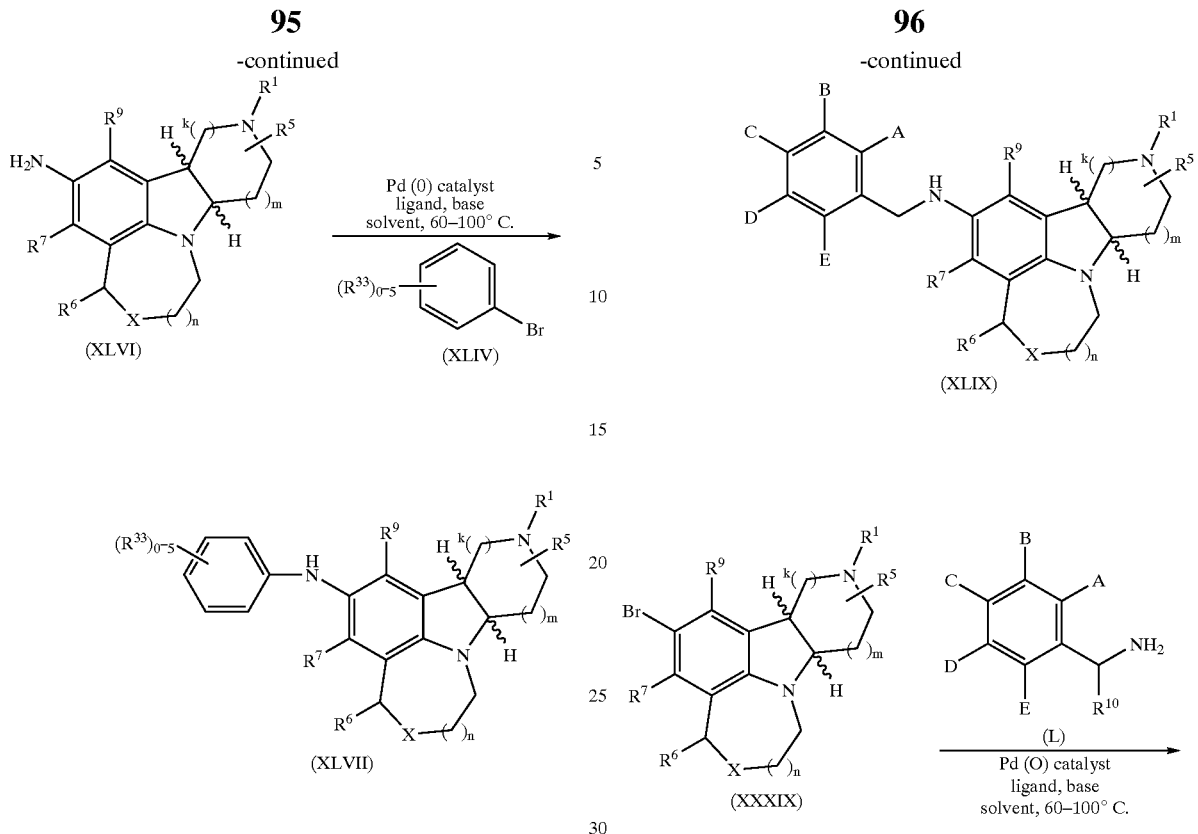

Another example is shown in Scheme 12. Treatment of the anilines (XLVI) with an appropriate benzaldehyde (XLVII) in the presence of a suitable reducing agent such as sodium triacetoxyborohydride or sodium cyanoborohydride and generally under mildly acidic conditions, such as in the presence of acetic acid, in a suitable solvent such as 1,2-dichloroethane, THF, methanol or acetonitrile, affords the benzylamine analogs (XLIX). An alternate method for preparing benzylamines (XLIX) or □-substituted benzylamines (LI) proceeds from bromides (XXXIX). Treatment of bromide (XXXIX) with benzylamines (L), which can be chiral if $R^{10}$ is an appropriate group, such as alkyl, in the presence of a palladium (0) catalyst, such as $Pd_2(dba)_3$, $Pd(PPh_3)_4$ or $Pd(PPh_3)_2C_2$, and a suitable ligand such as BINAP or $PPh_3$, and a base such as NaOtBu or $Na_2CO_3$ in a suitable solvent such as DMF, toluene, THF, DME or the like, affords the benzylamines (LI). In analogy with previous schemes, the chemistry described in Scheme 12 can also be applied to analogs of (XLVI) or (KNOX) where the $R^7$ or $R^9$ groups are $NH_2$, Br, 1, OTf, etc., to afford analogs of (XLIX) or (LI) where the benzylamino group is on the $R^7$ or $R^9$ position.

Scheme 12.

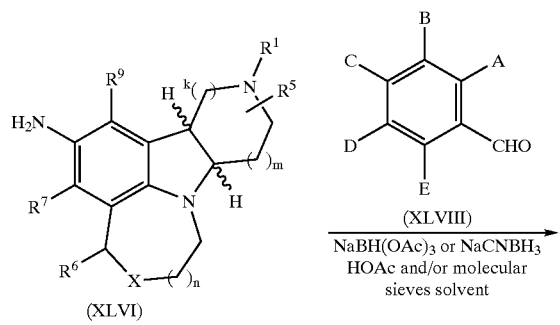

Another example is shown in Scheme 13. Treating bromides (XXXIX) with an appropriate benzylic zinc reagent (LII), which can be generated from the corresponding benzyl halide, in the presence of a palladium (O) catalyst such as $Pd(PPh_3)_4$, $Pd(PPh_3)_2C_2$, or $Pd_2(dba)_3$, and with or without a copper (I) salt, affords the derivatives (LIII) where $R^8$ is a benzyl group (see Knochel, P., et. al. Chem. Rev. 1993, 93, 2117; and Weichert, A., et. al. Syn. Lett. 1996, 473). This chemistry can also be extended to include a variety of alkylzinc and cycloalkylzinc reagents, which are available from the corresponding alkyl halides and cycloalkyl halides. In analogy with previous schemes, the chemistry described in Scheme 13 can also be applied to analogs of (XXXIX) where the $R^7$ or $R^9$ groups are Br, I, OTf, etc., to afford analogs of (LIII) where the benzyl or alkyl or cycloalkyl group is on the $R^7$ or $R^9$ position.

Scheme 13.

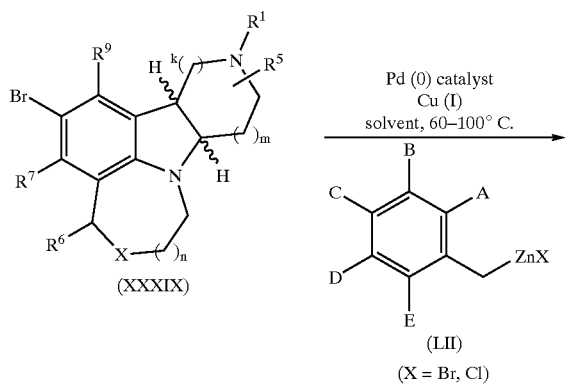

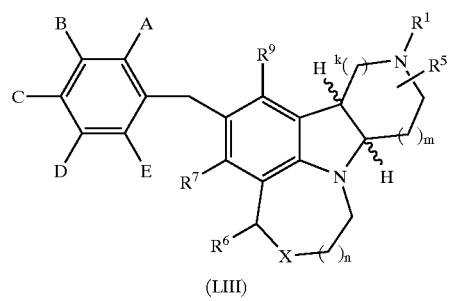

Another example is shown in Scheme 14. Compounds (XXXIX), where X is bromo or preferably iodo, can be treated with various phenols (LIV) in the presence of a base such as $Cs_2CO_3$ and a copper catalyst such as $CuPF_6(CH_3CN)_4$ at elevated temperature to afford biaryl ethers (LV) (see Sawyer, J. S. *Tetrahedron* 2000, 56, 5045). In analogy with previous schemes the chemistry described in Scheme 14 can also be applied to analogs of (XXXIX) where the $R^7$ or $R^9$ groups are Br, 1, OTf, etc., to afford analogs of (LV) where the aryloxy group is on the $R^7$ or $R^9$ position.

Scheme 14.

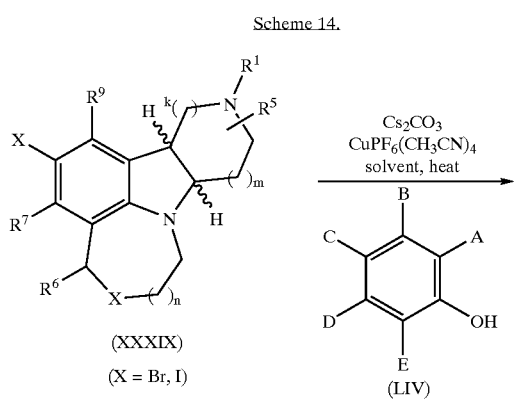

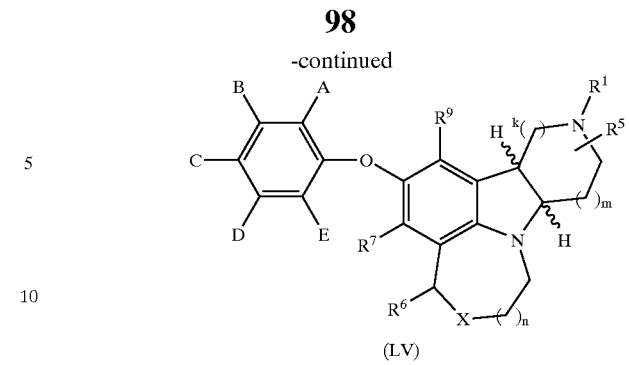

The compounds of Formula (I) with substituted $R^1$ sidechains can be prepared as described in Scheme 15. Alkylation of the indole or indoline derivatives (I, $R^1$=H) with a haloalkyl ester, such as $ClCH_2(CH_2)_pCO_2Me$, in the presence of NaI or KI and a base such as $K_2CO_3$, $Na_2CO_3$ or the like, in dioxane or THF or other such solvent while heating (see Glennon, R. A., et. al., *Med Chem. Res.*, 1996, 197) affords the $R^1$ alkylated esters. Subsequent formation of the activated amides ((LVI)) is accomplished by treatment of the ester with N,O-dimethylhydroxylamine hydrochloride and a Lewis acid such as trimethylaluminum or triethylaluminum in toluene (see, for example, Golec, J. M. C., et. al., *Tetrahedron*, 1994, 809) at 0° C. Treatment of the amide (LVI) with a variety of organometallic agents, such as Grignard reagents $R^{1a}MgBr$, alkyl and aryl lithium reagents etc. (see Sibi, M. P., et. al., *Tetrahedron Lett.*, 1992, 1941; and more generally House, H. O., *Modern Synthetic Reactions*, W. A. Benjamin, Inc., Menlo Park, Calif., 1972), in a suitable solvent such as THF, ether, etc. at low temperatures affords the substituted ketones (LVII).

Scheme 15.

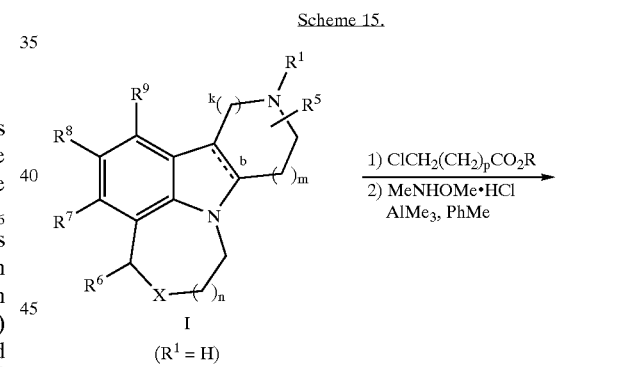

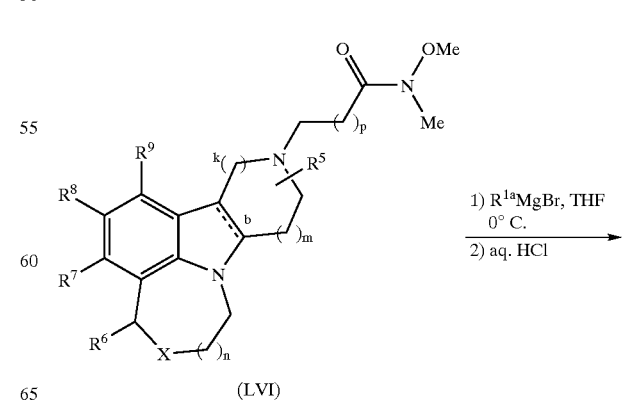

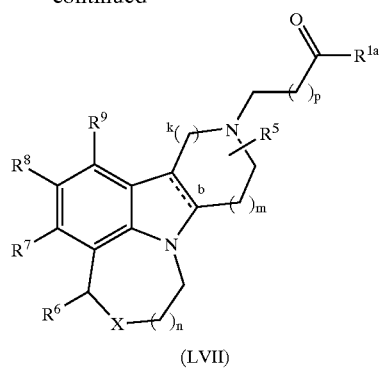

(LVII)

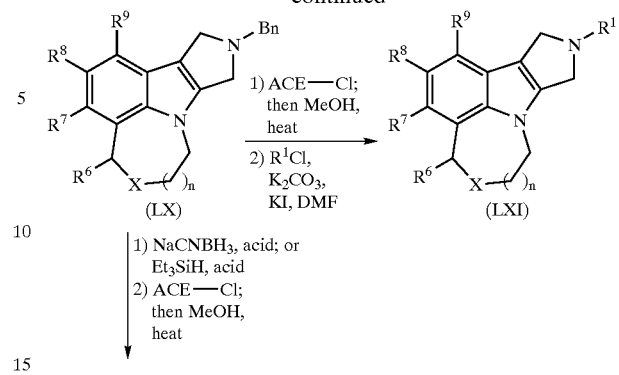

Preparation of compounds of Formula (I) where m=0, k=1 is outlined in Scheme 16 and described here. Fischer indole cyclization of the previously described hydrazine (III) with a known protected 2,3-dioxopyrrolidine (LVIII) (Carlson, E. H., et. al., J. Org. Chem., 1956, 1087) under a variety of typical cyclization conditions affords the tetracyclic indole (LIX). The reduction may be accomplished with a variety of reducing agents, for example, LAH, DIBAL, etc., to yield the pyrrole fused indole (LX). This derivative can then be deprotected and subsequently alkylated as described previously (see Greene, T. W., Wuts, P. G. W., "Protective Groups in Organic Synthesis, 2nd Edition", John Wiley and Sons, Inc., New York, 1991, and Scheme 1), to give the $R^1$ alkylated indole analogs (LXI). Alternatively, reduction of the indole (LX) to the indoline, as described previously (see Scheme 1), followed by deprotection of the benzyl group to give (LXII) and N-alkylation gives access to the corresponding $R^1$ alkylated indoline derivatives (LXIII). All the previously described methods to functionalize the aromatic ring, and to afford derivatives of varying $R^1$ sidechains are applicable to these cores.

Scheme 16.

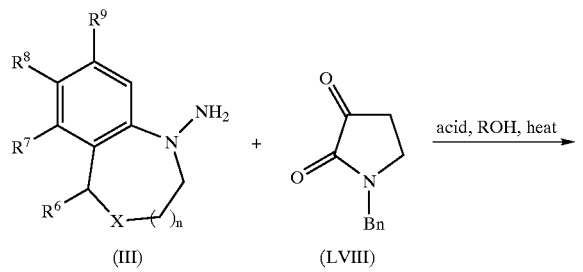

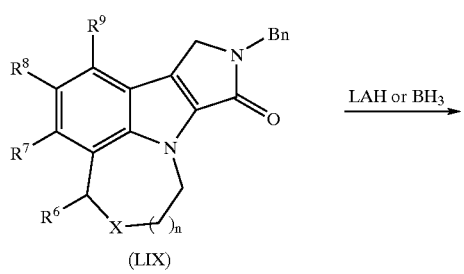

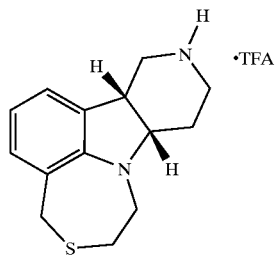

EXAMPLES

The detailed processes for preparing the compounds of Formula (I) are illustrated by the following Examples. It is, however, understood that this invention is not limited to the specific details of these Examples. The Examples as set forth below are intended to demonstrate the scope of the invention but are not intended to limit the scope of the invention.

Example 1

(7bR,11aS)-1,2,7b,8,9,10,11,11a-octahydro-4H-pyrido[4,3-b][1,4]thiazepino[6,5,4-hi]indole, trifluoroacetic acid salt Part A. 1,2,3,5-tetrahydro-4,1-benzothiazepine.

A 2-L round-bottom flask was charged with 1,5-dihydro-4,1-benzothiazepin-2(3H)-one (22.5 g, 126 mmol) followed by borane-tetrahydrofuran complex (1 M in THF, 629 mmol, 625 mL) at ambient temperature. The mixture was brought to reflux for 4 hours. The mixture was cooled to 0° C. and 100 mL of water was carefully added dropwise, resulting in the evolution of a large volume of gas. The mixture was then heated under reflux for 10 min, cooled to room temperature and extracted with ether (3×300 mL). The combined organic extracts were washed with water and brine, dried over anhydrous sodium sulfate, and filtered. After removal of solvent, the title compound was obtained as a white solid (21.5 g, 99%), which was used in the next step without further purification. $^1$H NMR (500 MHz, CDCl$_3$) δ 1.94–2.19 (m, 2H). 2.91-2.87 (m, 2H), 3.34–3.31 (b, 1H), 3.78 (s, 2H), 6.92–6.88 (m, 1H), 7.10–7.06 (m, 1 f), 7.12–7.16 (m, 1H).

Part B. 1-nitroso-1,2,3,5-tetrahydro-4,1-benzothiazepine.

A solution of 1,2,3,5-tetrahydro-4,1-benzothiazepine (12 g, 73 mmol) in acetic acid (38 mL) was chilled in an ice bath. Sodium nitrite (6.0 g, 87 mmol) in 11 mL of water was then added dropwise to the cold solution over 30 min. After the addition, the ice bath was removed and the mixture stirred for an additional 1 hour. Dilution of the suspension with cold water (60 mL) produced a pale yellow solid. The solid was collected, washed with cold water, and dried under vacuum yielding 13 g (92%) of the title compound. A second crop was obtained upon extraction of the filtrate with ether (3×50 mL). The combined organic extracts were washed with water and brine, dried over anhydrous sodium sulfate, and filtered. After removal of solvent, the second crop was obtained as a yellow oil, 0.72 g (5%). $^1$H NMR (500 MHz, DMSO-$d_6$) δ 2.9–2.85 (m, 2H), 3.40–3.34 (m, 2H), 3.9 (s, 2H), 7.24–7.20 (m, 1H), 7.45–7.35 (m, 3H).

Part C. 2,3-dihydro-4,1-benzothiazepin-[(5H)-amine.

Lithium aluminum hydride (1 M) in THF (100 mL) was cooled to 10° C. 1-nitroso-1,2,3,5-tetrahydro-4,1-benzothiazepine (13 g, 67 mmol) was dissolved in 150 mL of THF and added slowly to the cold LAH solution over 1 hour, maintaining the internal temperature between 10° C. and 20° C. Upon completion of the addition, the solution was allowed to warm to room temperature and stirred for 3 hours. Hydrated sodium sulfate (ca. 50 g) was added carefully until bubbling ceased. The resulting suspension was filtered through a pad of celite and washed with THF (10×250 mL). After removal of solvent the title compound was obtained as a brown oil 9.2 g (76%) and used without further purification. $^1$H NMR (500 MHz, CDCl$_3$) δ 2.87–2.82 (m, 2H), 3.76 (s, 2H), 4.33–4.13 (b, 2H), 7.39–7.29 (m, 3H), 7.45–7.41 (m, 3H).

Part D. 1,2,8,9,10,11-hexahydro-4H-pyrido[4,3-b[]1,4]thiazepino[6,5,4-hi]indole.

To a solution of hydrogen chloride in diethyl ether (1 M, 100 mL) was added 2,3-dihydro-4,1-benzothiazepin-1 (5H)-amine (9.2 g, 51 mmol). After stirring for 20 min, the white solid was collected and washed with ether. The resulting solid was transferred to a sealed tube with piperidone monohydrate hydrochloride (8.2 g, 53 mmol), and 2,2,2-trifluoroethanol (130 mL). The tube was flushed with nitrogen, sealed, and heated at 85° C. for 16 hours. After cooling to room temperature the suspension was concentrated, diluted with methanol, and the resulting solid collected, yielding the title compound (11.4 g, 80%) as a dark solid. $^1$H NMR (300 MHz, DMSO-D6) δ 1.98–1.92 (m, 2H), 2.12–2.08 (m, 2H), 3.04 (s, 2H), 3.25 (s, 2H), 3.42–3.38 (m, 2H), 3.62 (s, 2H), 5.83–5.72 (m, 2H), 6.17–6.06 (m, 1H).

Part E. (±)-cis-tert-butyl-1,2,7b,10,11,11a-hexahydro-4H-pyrido[4,3-b]1,4]thiazepino[6,5,4-hi]indole-9(8H) Carboxylate.

To a solution of 1,2,8,9,10,11-hexahydro-4H-pyrido[4,3-b][1,4]thiazepino[6,5,4-hi]indole (9.0 g crude, 31.9 mmol) in trifluoroacetic acid (150 mL) was added sodium cyanoborohydride (11.2 g, 179 mmol) portionwise over 2 hours at −15° C. After the addition, the mixture was stirred for 16 hours at room temperature and then carefully quenched with 6 N HCl. The resulting mixture was then heated to reflux for 1 hour. After removal of the solvents, the residue was neutralized with 6 N NaOH. Potassium carbonate (22.1 g, 160 mmol), 1,4-dioxane (150 mL), Boc$_2$O (10.5 g), and water (100 mL) were added and the mixture was stirred for 16 hours. The suspension was then extracted with ethyl acetate (250 mL each). The combined organic extracts were washed with water and brine, dried over anhydrous sodium sulfate, and filtered. After removal of solvent the residue was chromatographed (15% ethyl acetate in hexanes) yielding 5.6 g (65%) of the title compound. $^1$H NMR (300 MHz, DMSO-D6) δ 1.46 (s, 9H), 1.70–1.96 (m, 2H), 2.96–2.85 (m, 1H), 3.06–3.02 (m, 1H), 3.15–3.22 (m, 1H), 3.34–3.60 (m, 6H), 3.70–3.80 (m, 3H), 6.76–6.68 (m, 1H, 6.90–6.86 (m, 1H), 7.02–6.98 (m, 1H). LRMS (Cl, methane); 347 (M+H)$^+$.

Part F. (7bR,11aS)-1,2,7b,8,9,10,11,11a-octahydro-4H-pyrido[4,3-b][1,4]thiazepino[6,5,4-hi]indole, trifluoroacetic acid salt.

A sample of (±)Cis-tert-butyl-1,2,7b,10,11,11a-hexahydro-4H-pyrido[4,3-b][1,4]thiazepino[6,5,4-hi]indole-9(8H)-carboxylate (16.5 g) was separated by preparative HPLC (OJ column, elution with 5:95:0.05 ethanol/hexane/diethylamine) to afford, in order of elution, 6.86 g of tert-butyl (7bS,11aR)-1,2,7b,10,11,11a-hexahydro-4H-pyrido[4,3-b][1,4]thiazepino[6,5,4-hi]indole-9(8H) Carboxylate and 7.82 g of tert-butyl (7bR,11aS)-1,2,7b,10,11,11a-hexahydro-4H-pyrido[4,3-b][1,4]thiazepino[6,5,4-hi]indole-9(8H)-carboxylate. A portion of the later eluting (7bR,11aS) isomer was dissolved in CH$_2$Cl$_2$ (5 ml) at 25° C. and there was added trifluoroacetic acid (1 mL). The mixture was stirred at ambient temperature for 1 hour before saturated NaHCO$_3$ (10 mL) was added and then extracted with EtOAc (2×20 mL). The combined extracts were dried over magnesium sulfate, and concentrated. The residue was taken up in ether (2 mL) and TFA was added until a solid crashed out, which was dried in vacuo to afford the title compound of EXAMPLE 1. $^1$H NMR (CDCl$_3$, 300 MHz): δ 8.19 (m, 1H), 7.0 (m, 3H), 3.95–3.60 (m, 5H), 3.40 (m, 1H), 3.25 (m, 4H), 2.98 (m, 2H), 2.25 (m, 2H) ppm. LRMS (ES)$^+$: 247 (M+H)$^+$.

Example 2

(7bS,11aR)-1,2,7b,8,9,10,11,11a-octahydro-4H-pyrido[4,3-b][1,4]thiazepino[6,5,4-hi]indole, trifluoroacetic acid salt

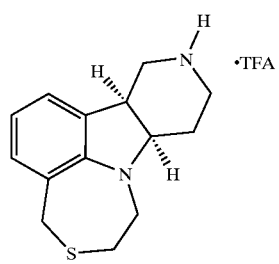

The first eluting isomer, tert-butyl (7bS,11aR)-1,2,7b,10,11,11a-hexahydro-4H-pyrido[4,3-b][1,4]thiazepino[6,5,4-hi]indole-9(8H)-carboxylate, from EXAMPLE 1, Part F was converted to the title compound of EXAMPLE 2 following the procedure described in EXAMPLE 1, Part F. $^1$H NMR (CDCl$_3$, 300 MHz): δ 8.19 (m, 1H), 7.0 (m, 3H), 3.95–3.60 (m, 5H), 3.40 (m, 1H), 3.25 (m, 4H), 2.98 (m, 2H), 2.25 (m, 2H) ppm. LRMS (ES)$^+$: 247 (M+H)$^+$.

Example 3

(7bR,11aS)-1,2,7b,8,9,10,11,11a-octahydro-4H-pyrido[4,3-b][1,4]thiazepino[6,5,4-hi]indole 3,3-dioxide, trifluoroacetic acid salt

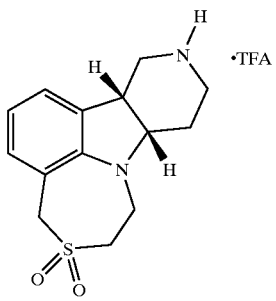

Part A. tert-butyl (7bR,11aS)-1,2,7b,10,11,11a-hexahydro-4H-pyrido[4,3-b][1,4]thiazepino[6,5,4-hi]indole-9(8H)-carboxylate 3,3-dioxide.

To a solution of tert-butyl (7bR,11aS)-1,2,7b,10,11,11a-hexahydro-4H-pyrido[4,3-b][1,4]thiazepino[6,5,4-hi]indole-9(8H)-carboxylate (65 mg, 0.19 mmol) in CH$_2$Cl$_2$ (10 mL) at 25° C. was added mCPBA (108 mg, 0.38 mmol). The mixture was stirred at ambient temperature for 2 hours before H$_2$O (10 mL) was added and then extracted with EtOAc (2×20 mL). The combined extracts were dried over magnesium sulfate, concentrated and purified by flash chromatography to give the title compound as an oil (21 mg, 30%). $^1$H NMR (CDCl$_3$, 300 MHz): δ 7.06 (d, 1H, J=7.3 Hz), 6.90 (d, 1H, J=7.3 Hz), 6.80 (t, 1H, J=7.3 Hz), 4.63 (m, 1H), 4.05 (m, 2H), 3.65 (m, 1H), 3.60–3.22 (m, 8H), 1.85 (m, 2H), 1.25 (s, 9H). LRMS (ES)$^+$: 379 (M+H)$^+$.

Part B. (7bR,11aS)-1,2,7b,8,9,10,11,11a-octahydro-4H-pyrido[4,3 b][1,4]thiazepino[6,5,4-hi]indole 3,3-dioxide, trifluoroacetic acid salt.

To a solution of tert-butyl (7bR,11aS)-1,2,7b,10,11,11a-hexahydro-4H-pyrido[4,3-b][1,4]thiazepino[6,5,4-hi] indole-9(8H)-carboxylate 3,3-dioxide (30 mg, 0.08 mmol) in CH$_2$Cl$_2$ (5 ml) at 25° C. was added TFA (1 mL). The mixture was stirred at ambient temperature for 1 hour before saturated NaHCO$_3$ (10 mL) was added and then extracted with EtOAc (2×20 mL). The combined extracts were dried over magnesium sulfate, concentrated to residue. The residue was taken up in ether (2 mL) and TFA was added until a solid crashed out, which was dried in vacuo to afford the title compound of EXAMPLE 3 (30 mg, 90%). $^1$H NMR (CDCl$_3$, 300 MHz); δ7.10 (d, 1H, J=7.3 Hz), 6.98 (d, 1H, J=7.3 Hz), 6.80 (t, 1H, J=7.3 Hz), 4.63 (d, 1H, J=15 Hz), 4.13 (d, 1H, J=15 Hz), 3.65 (m, 1H), 3.45–3.22 (m, 8H), 3.12 (m, 1H), 2.48 (m, 1H), 2.155 (m, 1H) ppm. LRMS (ES)$^+$: 279 (M+H)$^+$.

Example 4

4-(7bR,11aS)-(1,2,7b,10,11,11a-hexahydro-4H-pyrido[4,3-b][1,4]thiazepino[6,5,4-hi]indol-9(8H)-yl)-1-(4-fluorophenyl)-1-butanone

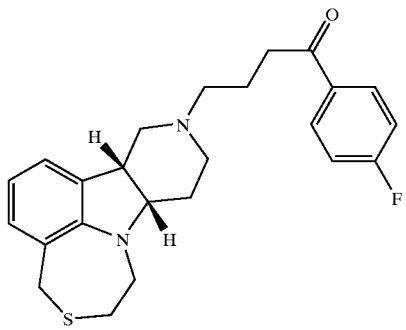

To a solution of (7bR,11aS)-1,2,7b,8,9,10,11,11a-octahydro-4H-pyrido[4,3-b][1,4]thiazepino[6,5,4-hi]indole from EXAMPLE 1 (80 mg, 0.32 mmol) in 1,4-dioxane (15 ml) at 25° C. was added 4-chloro-1-(4-fluorophenyl)butan-1-one (96 mg, 0.48 mmol), K$_2$CO$_3$ (100 mg, 0.72 mmol), and KI (32 mg, 0.19 mmol), respectively. The mixture was stirred at ambient temperature for 16 hours before H$_2$O (10 mL) was added and then extracted with EtOAc (2×20 mL). The combined extracts were dried over magnesium sulfate, concentrated, and purified by flash chromatography to give the title compound of EXAMPLE 4 as an oil (88 mg, 67%). $^1$H NMR (CDCl$_3$, 300 MHz): δ 8.01 (m, 2H), 7.15 (m, 2H), 6.96 (d, 1H, J=6.6 Hz), 6.92 (d, 1H, J 6.6 Hz), 3.82 (m, 2H), 3.25 (m, 2H), 3.19–2.60 (m, 8H), 2.42 (m, 2H), 1.95 (m, 5H). LRMS (ES)$^+$: 411 (M+H)$^+$.

Example 5

(7bR,11aS)-9-[3-(4-fluorophenoxy)propyl-1,2,7b,8,9,10,11,11a-octahydro-4H-pyrido[4,3 b][1,4]thiazepino[6,5,4-hi]indole

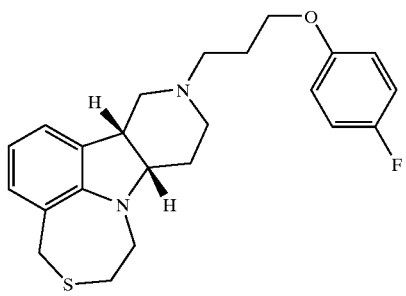

The title compound of EXAMPLE 5 was prepared from (7bR,11aS)-1,2,7b,8,9,10,11,11a-octahydro-4H-pyrido[4,3-b][1,4]thiazepino[6,5,4-hi]indole and 1-(3-chloropropoxy)-4-fluorobenzene following the procedure described in EXAMPLE 4. $^1$H NMR (CDCl$_3$, 300 MHz): δ 7.0–6.78 (m, 6H), 6.65 (t, 1H, J=7.3 Hz), 3.95 (t, 2H, J=6.2 Hz), 3.84 (dd, 2H, J=16.4 Hz), 3.59 (m, 2H), 3.25 (m, 2H), 3.15 (m, 2H), 2.85 (m, 2H), 2.65 (m, 2H), 2.45 (m, 4H), 2.30 (m, 2H) ppm. LRMS (ES)$^+$: 399 (M+H)$^+$.

Example 6

(7bR,11aS)-9-134-fluoro-2-nitrophenoxy)propyl]-1,2,7b,8,9,10,11,11a-octahydro-4H-pyrido[4,3-b][1,4]thiazepino[6,5,4-hi]indole

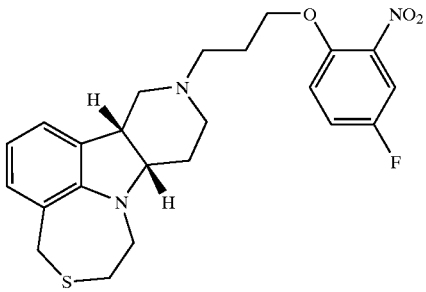

The title compound of EXAMPLE 6 was prepared from (7bR,11aS)-1,2,7b,8,9,10,11,11a-octahydro-4H-pyrido[4,3-b][1,4]thiazepino[6,5,4-hi]indole and and 1-(3-chloropropoxy)$_4$-fluoro-2-nitrobenzene following the procedure described in EXAMPLE 4. $^1$H NMR (CDCl$_3$, 300 MHz): δ 7.6 (m, 1H), 7.25 (m, 1H), 7.04 (m, 1H), 6.96 (d, 1H, J=6.6 Hz), 6.92 (d, 1H, J=6.6 Hz), 6.75 (m, 1H), 4.25 (m, 2H),3.82 (m, 2H), 3.59–3.00 (m, 8H), 2.80 (m, 2H), 2.48 (m, 2H), 2.22 (m, 2H), 1.20 (m, 2H) ppm. LRMS (ES)$^+$: 444 (M+1)$^+$.

Example 7

2-[(7bR,11aS)-1,2,7b,8,9,10,11,11a-octahydro-4H-pyrido[4,3-b][1,4]thiazepino[6,5,4-hi]indol-6-yl]benzaldehyde, trifluoroacetic acid salt

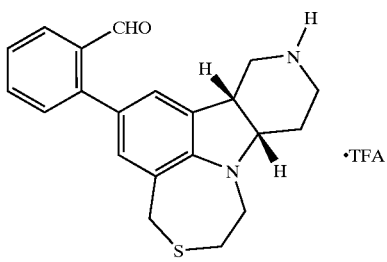

Part A. tert-butyl (7bR,11aS)-6-bromo-1,2,7b,10,11,11a-hexahydro-4H-pyrido[[4,3-b][1,4]thiazepino[6,5,4-hi]indole-9(8H)-carboxylate.

To a solution of tert-butyl (7bR,11aS)-1,2,7b,10,11,11a-hexahydro-4H-pyrido[4,3-b][1,4]thiazepino[6,5,4-hi]indole-9(8H)-carboxylate from EXAMPLE 1, Part F (3.0 g, 8.66 mmol) in 25 mL of DMF at 0° C. was added N-bromosuccinimide (1.7 g, 9.53 mmol). The reaction was stirred with slow warming to ambient temperature for 4 h. The mixture was diluted with ethyl acetate, washed with water and brine, dried (MgSO$_4$), filtered through a pad of silica gel and concentrated in vacuo to afford 3.60 g (97%) of the title compound which was used without purification. $^1$H NMR (CDCl$_3$): & 7.05 (d, 1H, J=1.9 Hz), 6.98 (d, 1H, J=1.9 Hz), 3.66–3.60 (m, 21) 3.58–3.48 (m, 3H), 3.49–3.36 (m, 4H), 3.15–3.07 (m, 1H), 3.02–2.85 (m, 2H), 1.90–1.75 (m, 2H), 1.41 (s, 9H).

Part B. tert-butyl (7bR,11aS)-6-(2-formylphenyl)-1,2,7b,10,11,11a-hexahydro-4H-pyrido[4,3-b][1,4]thiazepino[6,5,4-hi]indole-9(8H)Carboxylate.

To a solution of tert-butyl (7bR,11aS)-6-bromo-1,2,7b,10,11,11a-hexahydro-4H-pyrido[4,3-b][1,4]thiazepino[6,5,4-hi]indole-9(8H)-carboxylate (0.40 g, 0.94 mmol) in 75 mL of 1,2-dimethoxyethane and 25 mL of water was added 2-formylphenyl boronic acid (0.28 g, 1.88 mmol) and barium hydroxide octahydrate (0.88 g, 2.82 mmol). The mixture was degassed with a stream of nitrogen for 20 min and then there was added tetrakis (triphenylphosphine) palladium (0) (32 mg, 0.03 mmol) and the mixture was stirred at 100° C. for 3 h. The reaction was allowed to cool to ambient temperature and was diluted with ethyl acetate, washed with sat'd aqueous sodium bicarbonate and brine, dried (MgSO$_4$), filtered through Celite and concentrated in vacuo. The residue was purified by flash chromatography (elution with hexanes/ethyl acetate) to afford 0.10 g (24%) of the title compound. $^1$H NMR (CDCl$_3$): δ 10.00 (s, 1H), 7.96 (d, 1H, J=7.7 Hz), 7.58 (td, 1H, J=7.0, 1.5 Hz), 7.43–7.38 (m, 2H), 6.99 (broad s, 1H), 6.86 (broad s, 1H), 3.84–3.75 (m, 2H), 3.70–3.63 (m, 2H), 3.62–3.59 (m, 1H), 3.54–3.46 (m, 2H), 3.45–3.36 (m, 1H), 3.28–3.20 (m, 2H), 3.08–2.85 (m, 2H), 1.99–1.81 (m, 4H), 1.38 (s, 9H).

Part C. 2-[(7bR,11aS)-1,2,7b,8,9,10,11,11a-octahydro-4H-pyrido[4,3-b][1,4]thiazepino[6,5,4-hi]indol-6-yl]benzaldehyde, trifluoroacetic acid salt.

To a solution of tert-butyl (7bR,11aS)-62-formylphenyl) 1,2,7b,10,11,11a-hexahydro-4H-pyrido[4,3-b][1,4]thiazepino[6,5,4-hi]indole-9(8H)Carboxylate (0.10 g, 0.22 mmol) in 80 mL of methylene chloride was added 20 mL of trifluoroacetic acid and the mixture was allowed to stir at ambient temperature for 3 h. The volatiles were removed in vacuo and the residue was purified by prep HPLC (C18 reverse phase column, elution with a H$_2$O/CH$_3$CN gradient with 0.5% TFA) and lyophilized to afford 70 mg (68%) of the title compound of EXAMPLE 7. LRMS (ES$^+$): 351.0 (M+H)$^+$.

Example 8

{2-[(7bR,11aS)1,2,7b,8,9,10,11,11a-octahydro-4H-pyrido[4,3 b[1,4]thiazepino[6,5,4-hi]indol-6-yl]phenyl}methanol, trifluoroacetic acid salt

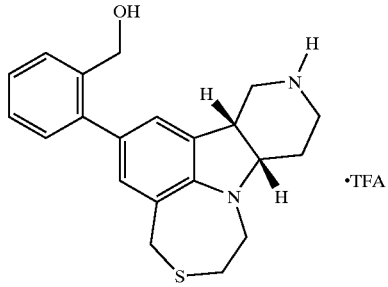

To a solution of tert-butyl (7bR,11aS)$_6$-(2-formylphenyl)-1,2,7b,10,11,11a-hexahydro-4H-pyrido[4,3-b][1,4)thiazepino[6,5,4-hi]indole-9(8H)-carboxylate from EXAMPLE 7, Part B (0.19 g, 0.44 mmol) in 10 mL of methanol was added sodium borohydride (0.07 g, 1.76 mmol). The mixture was allowed to stir at ambient temperature for 1 h and then was quenched with water and diluted with ethyl acetate. The organic layer was washed with saturated aqueous sodium bicarbonate and brine, dried (MgSO$_4$) and concentrated in vacuo. The residue was taken up in 20 mL of 4:1 methylene chloride/trifluoroacetic acid and was stirred at ambient temperature for 3 h. The volatiles were removed in vacuo and the residue was purified by prep HPLC (C18 reverse phase column, elution with a H$_2$O/CH$_3$CN gradient with 0.5% TFA) and lyophilized to afford 19 mg (10%) of the title compound of EXAMPLE 8. $^1$H NMR (DMSO-D6): δ 8.65 (broad s, 2H), 7.51 (d, 1H, J=7.0

Hz), 7.31–7.22 (m, 2H), 7.15 (d, 1H, J=7.3 Hz), 7.07 (s, 1H), 6.93 (s, 1H), 4.38 (s, 2H), 3.84 (ABq, 2H, $J_{AB}$=15.3 Hz), 3.64–3.38 (m, 4H), 3.33–3.24 (m, 1H), 3.21–3.12 (m, 2H), 3.06–2.97 (m, 2H), 2.86–2.78 (m, 1H), 2.61–2.53 (m, 1H), 2.11–2.05 (m, 1H), 1.99–1.94 (m, 1H). LRMS (ES+): 353.2 (M+H)+.

Example 9

(7bR,11aS)6-(4-methoxy-2-methylphenyl)-1,2,7b,8,9,10,11,11a-octahydro-4H-pyrido[4,3-b][1,4]thiazepino[6,5,4-hi]indole

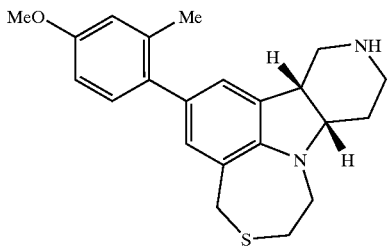

Part A. tert-butyl (7bR,11aS)-6-(4-methoxy-2-methylphenyl)-1,2,7b,10,11,11a-hexahydro-4H-pyrido[4,3-b][1,4]thiazepino[6,5,4-hi]indole-9(8H)Carboxylate.

To a solution of tert-butyl (7bR,11aS)-6-bromo-1,2,7b,10,11,11a-hexahydro-4H-pyrido[4,3-b][1,4]thiazepino[6,5,4-hi]indole-9(8H)-carboxylate from EXAMPLE 7, Part A (80 mg, 0.18 mmol) in 25 mL of DME (10 mL) was added 2-methyl 4 methoxyphenyl boronic acid (45 mg, 0.27 mmol) and TEA (0.26 mL, 1.8 mmol). The mixture was degassed with a stream of nitrogen for 20 min and then there was added Pd(dppf)$_2$ (15 mg, 0.1 mmol) and the mixture was stirred at 85° C. for 16 h. The reaction was allowed to cool to ambient temperature and was diluted with ethyl acetate, washed with sat'd aqueous sodium bicarbonate and brine, dried (MgSO$_4$), filtered through Celite and concentrated in vacuo. The residue was purified by flash chromatography (elution with hexanes/ethyl acetate) to afford (35 mg, 45% yield) of the title compound. $^1$H NMR (CDCl$_3$, 300 MHz): δ 7.13 (d, 1H, J=8.1 Hz), 6.97 (s, 1H), 6.75 (m, 3H), 3.83 (s, 3H), 3.79 (m, 1H), 3.65 (m, 2H), 3.52 (m, 3H), 3.21 (m, 2H), 3.01 (m, 2H), 2.24 (s, 3H), 1.97 (m, 2H), 1.60)m, 2H), 1.21 (s, 9H). LRMS (ES+): 467 (M+H)+.

Part B. (7bR,11aS)-6-(4-methoxy-2-methylphenyl)-1,2,7b,8,9,10,11,11a-octahydro-4H-pyrido[4,3-b][1,4]thiazepino[6,5,4-hi]indole.

To a solution of tert-butyl (7bR,11aS)-6{4-methoxy-2-methylphenyl)-1,2,7b,10,11,11a-hexahydro-4H-pyrido[4,3-b][1,4]thiazepino[6,5,4-hi]indole-9(8H)-carboxylate (34 mg, 0.07 mmol) in CH$_2$Cl$_2$ (5 ml) at 25° C. was added trifluoroacetic acid (1 mL). The mixture was stirred at ambient temperature for 1 hour before saturated NaHCO$_3$ (10 mL) was added and then extracted with EtOAc (2×20 mL). The combined extracts were dried over magnesium sulfate and concentrated to afford the title compound of EXAMPLE 9. $^1$H NMR (CDCl$_3$, 300 MHz): δ 7.16 (d, 1H, J=8.0 Hz), 6.88 (s, 1H), 6.75 (m, 3H), 3.80 (s, 3H), 3.80 (m, 1H), 3.65 (m, 1H), 3.52 (m, 1H), 3.23–2.85 (m, 6H), 2.61 (m, 1H), 2.24 (s, 3H), 2.90 (m, 4H). LRMS (ES+): 367 (M+H)+.

Example 10

(7bR,11aS)-6-(4-methoxy-2-methylphenyl)-1,2,7b,8,9,10,11,11a-octahydro-4H-pyrido[4,3-b][1,4]thiazepino[6,5,4-h]indole 3,3-dioxide, trifluoroacetic acid salt

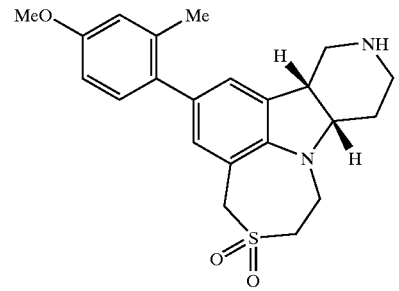

Part A. tert-butyl (7bR,11aS)-6(4-methoxy-2-methylphenyl)-1,2,7b,10,11,11a-hexahydro-4H-pyrido[4,3-b][1,4]thiazepino[6,5,4-hi]indole-9(8H)-carboxylate 3,3-dioxide.

To a solution of tert-butyl (7bR,11aS)-6-(4-methoxy-2-methylphenyl) 1,2,7b,10,11,11a-hexahydro-4H-pyrido[4,3-b](1,4]thiazepino[6,5,4-hi]indole-9(8H)-carboxylate from EXAMPLE 9, Part A (70 mg, 0.15 mmol) in a mixture of acetone (5 ml) and water (2 mL) at 25° C. was added NaIO$_4$ (321 mg, 1.5 mmol). The mixture was stirred at refluxing temperature for 16 hours and then cooled to ambient temperature before H$_2$O (10 mL) was added and then extracted with EtOAc (2×30 mL). The combined extracts were dried over magnesium sulfate and concentrated to an oil. Purification by flash chromatography afforded the title sulfone compound (28 mg, 37%) and in addition a minor amount of a sulfoxide by-product, tert-butyl (7bR,11aS)-(4-methoxy-2-methylphenyl)-1,2,7b,10,11,11a-hexahydro-4H-pyrido[4,3-b][1,4]thiazepino[6,5,4-hi]indole-9(8H)-carboxylate 3-oxide. $^1$HNMR (CDCl$_3$, 300 MHz): δ 7.26 (m, 2H), 6.90 (s, 1H), 6.81 (m, 2H), 4.83 (m, 1H), 4.06 (m, 1H), 3.82 (s, 3H), 3.80–3.22 (m, 9H), 2.24 (s, 3), 1.95 (m, 1H), 1.42 (m, 2H). LRMS (ES+): 499 (M+H)+.

Part B. (7bR,11aS)-6-(4-methoxy-2-methylphenyl)-1,2,7b,8,9,10,11,11a-octahydro-4H-pyrido[4,3-b][1,4]thiazepino [6,5,4-hi]indole 3,3-dioxide, trifluoroacetic acid salt.

To a solution of tert-butyl (7bR,11aS)-6-(4-methoxy-2-methylphenyl)-1,2,7b,10,11,11a-hexahydro-4H-pyrido[4,3-b][1,4]thiazepino[6,5,4-hi]indole-9(8H)-carboxylate 3,3-dioxide (14 mg, 0.03 mmol) in CH$_2$Cl$_2$ (5 ml) at 25° C. was added TFA (1 mL). The mixture was stirred at ambient temperature for 1 hour before saturated NaHCO$_3$ (10 mL) was added and then extracted with EtOAc (2×20 mL). The combined extracts were dried over magnesium sulfate, concentrated to residue. The residue was taken up in ether (2 mL) and TFA was added until a solid crashed out, which was dried and isolated as the title compound of EXAMPLE 10 (13 mg, 90%). $^1$H NMR (CDCl$_3$, 300 MHz): δ 7.13 (s, 1H), 7.06 (m, 2H), 6.79 (m, 2H), 4.80 (m, 1H), 4.48 (m, 1H), 3.76 (s, 3H), 3.68–3.22 (m, 8H), 3.79 (m, 1H), 2.30 (m, 1H), 2.20 (s, 3H), 2.15 (m, 1H), 1.18 (t, 1H, J=6.9 Hz) ppm. LRMS (ES+) 399 (M+H)+.

Example 11

(7bR,11aS)-6-(4-methoxy-2-methylphenyl)1,2,7b,8,9,10,11,11a-octahydro-4H-pyrido[4,3-b][1,4]thiazepino[6,5,4-hi]indole 3-oxide, trifluoroacetic acid salt

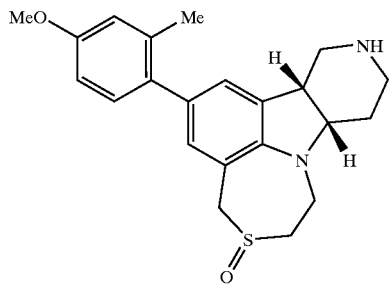

Following the deprotection procedure described in EXAMPLE 10, Part B, tert-butyl (7bR,11aS)-6-(4-methoxy-2-methylphenyl)-1,2,7b,10,11,11a-hexahydro-4H-pyrido[4,3-b][1,4]thiazepino[6,5,4-hi]indole-9(8H)-carboxylate 3-oxide was converted into the title compound of EXAMPLE 11. $^1$H NMR (CDCl$_3$, 300 MHz): δ 7.13 (m, 1H), 7.06 (m, 2H), 6.79 (m, 2H), 4.39 (m, 1H), 4.00 (m, 1H), 3.76 (s, 3H), 3.68–3.22 (m, 8H), 3.00 (m, 1H), 2.65 (m, 1H), 2.20 (s, 3H), 2.15 (m, 1H), 1.18 (t, 1H, J=6.9 Hz) ppm. LRMS (ES$^+$): 383 (M+)$^+$.

Example 12

(7bR,11aS)-6-[4-methoxy-2-(trifluoromethyl)phenyl]-1,2,7b,8,9,10,11,11a-octahydro-4H-pyrido[4,3-b 11,4]thiazepino[6,5,4-hi]indole

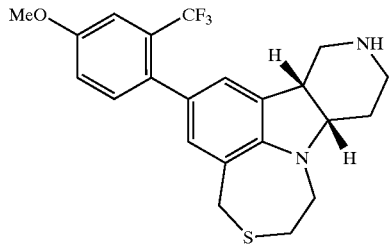

Using 4-methoxy-2-(trifluoromethyl)phenyl boronic acid and following the procedures described in EXAMPLE 9, tert-butyl (7bR,11aS)-6-bromo-1,2,7b,10,11,11a-hexahydro-4H-pyrido[4,3-b][1,4]thiazepino[6,5,4-hi]indole-9(8 carboxylate was converted into the title compound of EXAMPLE 12. $^1$H NMR (CDCl$_3$, 300 MHz): δ 7.20 (m, 3H), 7.05 (m, 21), 6.89 (s, 1H), 6.79 (s, 1H), 3.84 (s, 3H), 3.81 (m, 2H), 3.59 (m, 1H), 3.45 (m, 1H), 3.21 (m, 2H), 3.0 (m, 2H), 2.92 (m, 3H), 2.60 (m, 1H), 1.80 (m, 2H). LRMS (ES$^+$): 421 (M+H)$^+$.

Example 13

(7bR,11aS) (2,4-dichlorophenyl)-1,2,7b,8,9,10,11,11a-octahydro-4H-pyrido[4,3-b[]1,4]thiazepino[6,5,4-hi]indole

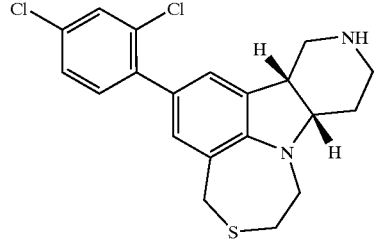

Using 2,4-dichlorophenyl boronic acid and following the procedures described in EXAMPLE 9, tert-butyl (7bR,11aS)-6-bromo-1,2,7b,10,11,11a-hexahydro-4H-pyrido[4,3-b][1,4]thiazepino[6,5,4-hi]indole-9(8H)-carboxylate was converted into the title compound of EXAMPLE 13. $^1$HNMR (CDCl$_3$, 300 MHz): δ 7.19 (m, 3H), 6.93 (s, 1H), 6.83 (s, 1H), 3.78 (m, 2H), 3.59 (m, 1H), 3.41 (m, 1H), 3.19 (m, 2H), 3.0 (m, 2H), 2.82 (m, 4H), 2.58 (m, 1H), 1.80 (m, 2H). LRMS (ES$^+$): 391 (M+H)$^+$.

Example 14

7bR,11aS)-6-(2,6-difluorophenyl)-1,2,7b,8,9,10,11,11a-octahydro-4H-pyrido[4,3-b][1,4]thiazepino[6,5,4-hi]indole

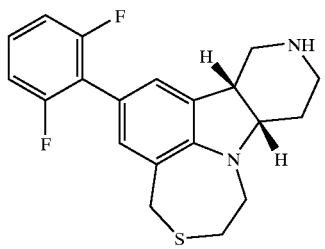

Using 2,6-difluorophenyl boronic acid and following the procedures described in EXAMPLE 9, tert-butyl (7bR,11aS)-6-bromo-1,2,7b,10,11,11a-hexahydro-4H-pyrido[4,3-b][1,4]thiazepino[6,5,4-hi]indole-9(8H)-carboxylate was converted into the title compound of EXAMPLE 14. $^1$H NMR (CDCl$_3$, 300 MHz): δ 7.19 (m, 1H), 6.93 (m, 2H), 6.83 (m, 3H), 3.81 (m, 2H), 3.59 (m, 1H), 3.41 (m, 1H), 3.21 (m, 2H), 3.0 (m, 2H), 2.82 (m, 3H), 2.60 (m, 1H), 1.80 (m, 2H). LRMS (ES$^+$): 359 (M+H)$^+$.

Example 15

3-[(7bR,11aS)-1,2,7b,8,9,10,11,11a-octahydro-4H-pyrido[4,3-b][1,4]thiazepino[6,5,4-hi]indol-6-yl] benzonitrile, trifluoroacetic acid salt

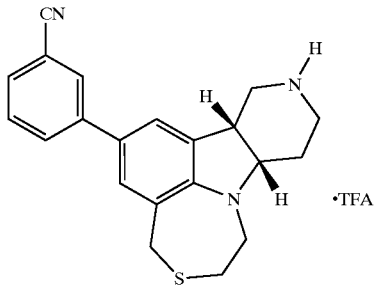

Using 3-cyanophenyl boronic acid and following the procedures described in EXAMPLE 7, tert-butyl (7bR,11aS)-6-bromo-1,2,7b,10,11,11a-hexahydro-4H-pyrido[4,3-b][1,4]thiazepino[6,5,4-hi]indole-9(8H)-carboxylate was converted into the title compound of EXAMPLE 15. $^1$H NMR (CDCl$_3$): δ 7.78 (app s, 1H), 7.73 (dt, 1H, J=7.7, 1.5 Hz), 7.58 (td, 1H, J=7.7, 1.4 Hz), 7.51 (t, 1H, J=7.7 Hz), 7.21 (d, 1H, J=1.9 Hz), 7.17 (d, 1H, J=1.8 Hz), 3.88 (ABq, 2H, J$_{AB}$=15.4 Hz), 3.70–3.61 (m, 2H), 3.60–3.53 (m, 1H), 3.42–3.30 (m, 2H), 3.29–3.12 (m, 3H), 2.95–2.85 (m, 1H), 2.77–2.68 (m, 1H), 2.30–2.18 (m, 2H). LRMS (ES$^+$): 348.2 (M+H)$^+$.

Example 16

2-[(7bR,11aS)1,2,7b,8,9,10,11,11a-octahydro-4H-pyrido[4,3-b][1,4]thiazepino[6,5,4-hi]indol-6-yl]-5-methoxybenzaldehyde, trifluoroacetic acid salt

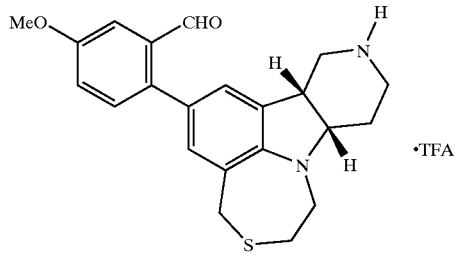

Using 4-methoxy-2-formylphenyl boronic acid and following the procedures in EXAMPLE 7, tert-butyl (7bR,11aS)-6-bromo-1,2,7b,10,11,11a-hexahydro-4H-pyrido[4,3-b][1,4]thiazepino[6,5,4-hi]indole-9(8H)-carboxylate was converted into the title compound of EXAMPLE 16. $^1$H NMR (DMSO-d6): δ 9.85 (s, 1H), 8.52 (broad s, 2H), 7.40 (app d, 1H, J=8.8 Hz), 7.32–7.25 (m, 2H), 7.10 (app s, 1H), 6.98 (d, 1H, J=1.4 Hz), 3.88 (ABq, 2H, J$_{AB}$=15.5 Hz), 3.81 (s, 3H), 3.68–3.45 (m, 3H), 3.31–3.21 (m, 1H), 3.18–3.08 (m, 1H), 3.06–2.98 (m, 2H), 2.90–2.79 (m, 1H), 2.72–2.60 (m, 2H), 2.06–1.97 (m, 2H). LRMS (ES$^+$): 381.2 (M+H)$^+$.

Example 17

{2-[(7bR,11aS)-1,2,7b,8,9,10,11,11a-octahydro-4H-pyrido[4,3-b][1,4]thiazepino[6,5,4-hi]indol-6-yl]-5-methoxyphenyl}methanol, trifluoroacetic acid salt

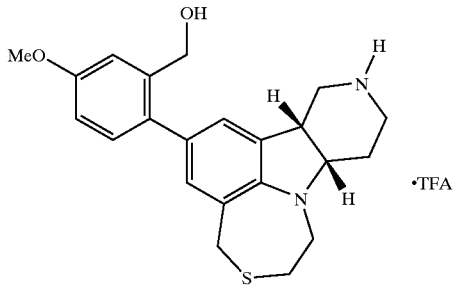

To a solution of tert-butyl (7bR,11aS)-6-(2-formyl-4-methoxyphenyl)-1,2,7b,10,11,11a-hexahydro-4H-pyrido[4,3-b][1,4]thiazepino[6,5,4-hi]indole-9(8H)—carboxylate, an intermediate from EXAMPLE 16 (0.08 g, 0.17 mmol) in 10 mL of methanol was added sodium borohydride (0.025 g, 0.66 mmol). The mixture was allowed to stir at ambient temperature for 1 h and then was quenched with water and diluted with ethyl acetate. The organic layer was washed with saturated aqueous sodium bicarbonate and brine, dried (MgSO$_4$) and concentrated in vacuo. The residue was taken up in 20 mL of 4:1 methylene chloride/trifluoroacetic acid and was stirred at ambient temperature for 3 h. The volatiles were removed in vacuo and the residue was purified by prep HPLC (C18 reverse phase column, elution with a H$_2$O/CH$_3$CN gradient with 0.5% TFA) and lyophilized to afford 18 mg (23%) of the title compound of EXAMPLE 17. $^1$H NMR (CDCl$_3$): δ 9.25 (broad s, 2H), 7.06 (d, 1H, J=8.4 Hz), 7.00–6.95 (m, 1H), 6.94 (s, 1H), 6.82 (s, 1H), 6.81–6.75 (m, 1H), 4.45 (s, 2H), 3.77 (s, 3H), 3.72 (ABq, 2H, J$_{AB}$=15.7 Hz), 3.57–3.42 (m, 3H), 3.30–3.24 (m, 1H), 3.20–2.99 (m, 4H), 2.88–2.78 (m, 1H), 2.74–2.66 (m, 1H), 2.11–2.05 (m, 1H), 1.96–1.90 (m, 1H). LRMS (ES$^+$): 383.2 (M+H)$^+$.

Example 18

4-[(7bR,11aS)-1,2,7b,8,9,10,11,11a-octahydro-4H-pyrido[4,3-b][1,4-thiazepino[6,5,4-hi]indol-6-yl]-3-(trifluoromethyl)phenyl isopropyl ether, trifluoroacetic acid salt

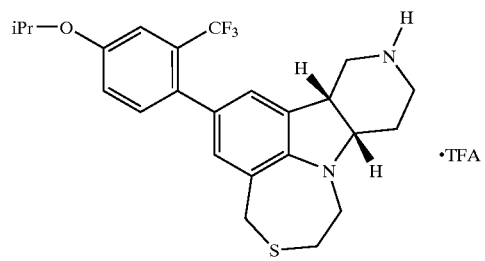

Using 4-isopropoxy-2-trifluoromethylphenyl boronic acid and following the procedures in EXAMPLE 7, tert-butyl (7bR,11aS)-6-bromo-1,2,7b,10,11,11a-hexahydro-4H-pyrido[4,3-b) [1,4]thiazepino[6,5,4-hi]indole-9(8H)-carboxylate was converted into the title compound of EXAMPLE 18. $^1$H NMR (CDCl$_3$): δ 9.53 (broad s, 1H), 9.32 (broad s, 1H), 7.20–7.14 (m, 2H), 7.01 (dd, 1H, J=8.4, 2.5 Hz), 6.92 (s, 1H), 6.87 (s, 1H), 4.60 (septet, 1H, J=6.2 Hz), 3.80 (ABq, 2H, J$_{AB}$=15.4 Hz), 3.62–3.52 (m, 3H), 3.35–3.26 (m, 2H), 3.25–3.08 (m, 3H), 2.91–2.83 (m, 1H), 2.70–2.58 (m, 1H), 2.30–2.15 (m, 2H), 1.37 (d, 6H, J=6.2 Hz). LRMS (ES+): 449.2 (M+H)+.

Example 19

5-[(7bR,11aS)-1,2,7b,8,9,10,11,11a-octahydro-4H-pyrido[4,3-b][1,4]thiazepino[6,5,4-hi]indol-6-yl]-2-fluorobenzonitride, trifluoroacetic acid salt

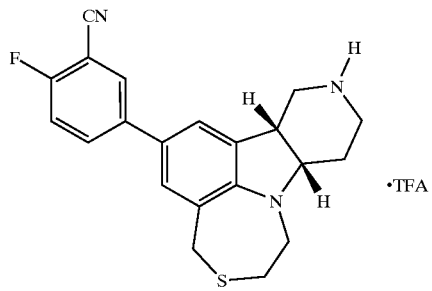

Using 4-fluoro-3-cyanophenyl boronic acid and following the procedures in EXAMPLE 7, tert-butyl (7bR,11aS)-6-bromo-1,2,7b,10,11,11a-hexahydro-4H-pyrido[4,3-b])[,4]thiazepino[6,5,4-hi]indole-9(8H)Carboxylate was converted into the title compound of EXAMPLE 19. ¹H NMR (CDCl₃): δ 9.48 (broad s, 1H), 9.39 (broad s, 1H), 7.72–7.65 (m, 2H), 7.26–7.22 (m, 1H), 7.14 (s, 1H), 7.10 (s, 1H), 3.85 (ABq, 2H, J$_{AB}$=15.8 Hz), 3.65–3.52 (m, 3H), 3.42–3.30 (m, 2H), 3.28–3.10 (m, 3H), 2.93–2.85 (m, 1H), 2.75–2.66 (m, 1H), 2.30–2.15 (m, 2H). LRMS (ES+): 366.2 (M+14)+.

Example 20

4-[(7bR,11aS)-1,2,7b,8,9,10,11,11a-octahydro-4H-pyrido[4,3-b][1,4]thiazepino[6,5,4-hi]indol-6-yl]-3(trifluoromethyl)phenyl ethyl ether, trifluoroacetic acid salt

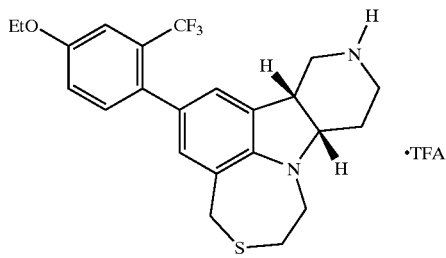

Using 4-ethoxy-2-trifluoromethylphenyl boronic acid and following the procedures in EXAMPLE 7, tert-butyl (7bR, 11aS)-6-bromo-1,2,7b,10,11,11a-hexahydro-4H-pyrido[4,3-b][1,4]thiazepino[6,5,4-hi]indole-9(8H)-carboxylate was converted into the title compound of EXAMPLE 20. ¹H NMR (CDCl₃): δ 8.70 (broad s, 2H), 7.14 (d, 1H, J=2.5 Hz), 7.10 (d, 1H, J=8.5 Hz), 6.95 (dd, 1H, J=8.4, 2.6 Hz), 6.86 (s, 1H), 6.81 (s, 1H), 4.02 (q, 2H, J=7.0 Hz), 3.74 (ABq, 2H, J$_{AB}$=15.6 Hz), 3.5845 (m, 3H), 3.35–3.27 (m, 2H), 3.22–3.00 (m, 3H), 2.89–2.78 (m, 1H), 2.70–2.58 (m, 1H), 2.20–2.10 (m, 2H), 1.38 (t, 3H, J=7.0 Hz). LRMS (ES+): 435.2 (M+H)+.

Example 21

1-{2-[(7bR,11aS)-1,2,7b,8,9,10,11,11a-octahydro-4H-pyrido[4,3-b][1,4]thiazepino[6,5,4-hi]indol-6-yl]-5-methoxyphenyl}ethanol

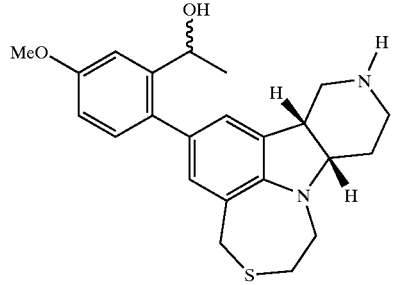

To a solution of 2-[(7bR,11aS)-1,2,7b,8,9,10,11,11a-octahydro-4H-pyrido[4,3-b)[1,4]thiazepino[6,5,4-hi]indol-6-yl]-5-methoxybenzaldehyde, the free base of EXAMPLE 16 (0.03 g, 0.08 mmol), in 5 mL of tetrahydrofuran at 0° C. was added methyl magnesium bromide (0.52 mL of a 3M solution in THF, 1.58 mmol). Stirred with warning to ambient temperature for several hours and then quenched with sat'd ammonium chloride. Extracted with ethyl acetate, washed organics with brine, dried (MgSO₄) and concentrated. The residue was purified by prep HPLC (C18 reverse phase column, elution with a H₂O/CH₃CN gradient with 0.5% TFA). Fractions containing desired compound were then immediately free based with 1 N sodium hydroxide, extracted with ethyl acetate, dried (MgSO₄) and concentrated to afford the title compound of EXAMPLE 21. LRMS (ES+): 397.1 (M+H)+.

Example 22

1-{2-[(7bR,11aS)-1,2,7b,8,9,10,11,11a-octahydro-4H-pyrido[4,3-b][1,4]thiazepino[6,5,4-hi]indol-6-yl]-5-methoxyphenyl}ethanone, trifluoroacetic acid salt

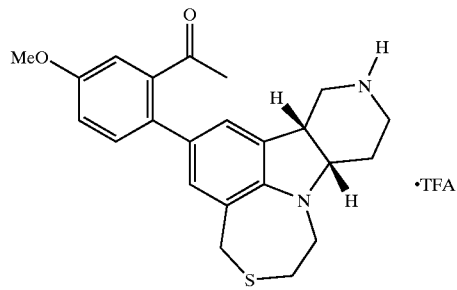

Part A. tert-butyl (7bR,11aS)-6-[2-(1-hydroxyethyl)-4-Methoxyphenyl]-1,2,7b,10,11,11a-hexahydro-4H-pyrido[4,3-b][1,4]thiazepino[6,5,4-hi]indole-9(8H)-carboxylate.

To a solution of tert-butyl (7bR,11aS)-62-formyl-4-methoxyphenyl)-1,2,7b, 10,11,11a-hexahydro-4H-pyrido[4,3-b][1,4]thiazepino[6,5,4-hi]indole-9(8H)-carboxylate, an intermediate from EXAMPLE 16 (0.176 g, 0.37 mmol), in 10 mL of tetrahydrofuran at 0° C. was added methyl magnesium bromide (0.37 mL of a 3M solution in THF, 1.10 mol). Stirred with warming to ambient temperature for several hours and then quenched with sat'd ammonium chloride. Extracted with ethyl acetate, washed organics with brine, dried (MgSO₄) and concentrated to afford 0.16 g (89%) of the title compound. LRMS (ES+): 497.5 (M+H)+.

Part B. 1-(2-[(7bR,11aS)-1,2,7b,8,9,10,11,11a-octahydro-4H-pyrido[4,3-b][1,4]thiazepino[6,5,4-hi]indol-6-yl]-5-methoxyphenyl)ethanone, trifluoroacetic acid salt.

To a solution of oxalyl chloride (0.06 mL, 0.65 mmol) in 5 mL of methylene chloride at −78° C. was added dimethyl sulfoxide (0.09 mL, 1.30 mmol). This mixture was stirred for 5 minutes and then there was added tert-butyl (7bR,11aS)-6-[2-(1-hydroxyethyl)-4-methoxyphenyl]-1,2,7b,10,11,11a-hexahydro-4H-pyrido[4,3-b][1,4]thiazepino[6,5,4-hi]indole-9(8H)-carboxylate (0.16 g, 0.33 mmol) in 3 mL of methylene chloride and the solution was stirred at −78° C. for 30 minutes. To this was added triethylamine (0.36 mL, 2.61 mmol) and the solution was stirred with warming to ambient temperature. The mixture was diluted with methylene chloride and washed with saturated ammonium chloride and brine, dried (MgSO$_4$) and concentrated to afford 0.15 g (92%) of an oil. LRMS (AP$^+$): 495.0 (M+H)$^+$. The residue was taken up in 20 mL of 4:1 methylene chloride/trifluoroacetic acid and was stirred at ambient temperature for 3 h. The volatiles were removed in vacuo and the residue was purified by prep HPLC (C18 reverse phase column, elution with a 5H$_2$O/CH$_3$CN gradient with 0.5% TFA) and lyophilized to afford 60 mg (37%) of the title compound of EXAMPLE 22. $^1$H NMR (CDCl$_3$): δ 9.20 (broad s, 2H), 7.28–7.22 (m, 1H), 7.05–6.99 (m, 2H), 6.91 (s, 1H), 6.88 (s, 1H), 3.85 (s, 3H), 3.80 (ABq, 2H, J$_{AB}$=15.3 Hz), 3.65–3.52 (m, 3H), 3.42–3.33 (m, 2H), 3.25–3.07 (m, 3H), 2.90–2.82 (m, 1H), 2.72–2.62 (m, 1H), 2.30–2.18 (m, 2H), 2.04 (s, 3H). LRMS (ES$^+$): 395.1 (M+H)$^+$.

Example 23

4-[(7bR,11aS) 1,2,7b,8,9,10,11,11a-octahydro-4H-pyrido[4,3-b][1,4]thiazepino[6,5,4-hi]indol-6-yl]-3-methylbenzonitrile, trifluoroacetic acid salt

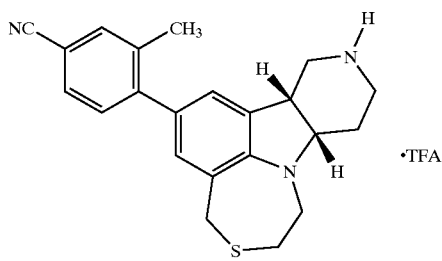

Using 2-methyl-4-cyanophenyl boronic acid and following the procedures in EXAMPLE 7, tert-butyl (7bR,11aS)$_6$-bromo-1,2,7b,10,11,11a-hexahydro-4H-pyrido[4,3-b][1,4]thiazepino[6,5,4-hi]indole-9(8H)-carboxylate was converted into the title compound of EXAMPLE 23. $^1$H NMR (CDCl$_3$): δ 8.70 (broad s, 214), 7.55 (s, 1H), 7.51 (d, 1H, J=7.7 Hz), 7.26 (app d, 1H), 6.96 (s, 1H), 6.91 (s, 1H), 3.85 (ABq, 2H, J$_{AB}$=15.7 Hz), 3.66–3.58 (m, 3H), 3.503.39 (m, 2H), 3.32–3.12 (m, 3H), 2.97–2.88 (m, 1H), 2.82–2.73 (m, 1H), 2.31 (s, 3H), 2.30–2.22 (m, 2H). LRMS (ES$^+$): 362.4 (M+H)$^+$.

Example 24

3-[(7bR,11aS)-1,2,7b,8,9,10,11,11a-octahydro-4H-pyrido[4,3-b][1,4]thiazepino[6,5,4-hi]indol-6-yl]-2-methylbenzonitrile, trifluoroacetic acid salt

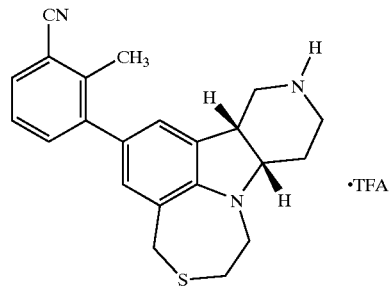

Using 2-methyl-3-cyanophenyl boronic acid and following the procedures in EXAMPLE 7, tert-butyl (7bR,11aS)-6-bromo-1,2,7b,10,11,11a-hexahydro-4H-pyrido[4,3-b][1,4]thiazepino[6,5,4-hi]indole-9(8H)-carboxylate was converted into the title compound of EXAMPLE 24. $^1$H NMR (CDCl$_3$): δ 9.50 (broad s, 1H), 9.25 (broad s, 1H), 7.60–7.55 (m, 1H), 7.39–7.34 (m, 1H), 7.28 (t, 1H, J=7.7 Hz), 6.88 (s, 1H), 6.84 (d, 1H, J=1.5 Hz), 3.81 (ABq, 2H, J$_{AB}$=15.7 Hz), 3.63–3.50 (m, 3H), 3.38–3.10 (m, 4H), 2.93–2.85 (m, 1H), 2.2.75–2.63 (m, 1H), 2.44 (s, 3H), 2.35–2.18 (m, 3H). LRMS (ES$^+$): 362.3 (M+H)$^+$.

Example 25

4-[(7bR,11aS)-1,2,7b,8,9,10,11,11a-octahydro-4H-pyrido[4,3-b][1,4]thiazepino[6,5,4-hi]indol-6-yl]-3-trifluoromethyl)benzonitrile, trifluoroacetic acid salt

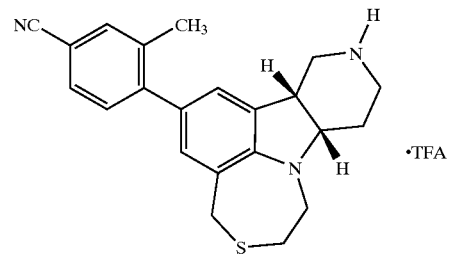

Part A. tert-butyl (7bR,11aS)-6-iodo-1,2,7b,10,11,11a-hexahydro-4H-pyrido[4,3-b[]1,4]thiazepino[6,5,4-hi]indole-9(8H)-carboxylate.

To a solution of tert-butyl (7bR,11aS)-1,2,7b,10,11,11a-hexahydro-4H-pyrido[4,3-b][1,4]thiazepino[6,5,4-hi]indole-9(8H)-carboxylate from EXAMPLE 1, Part F (0.37 g, 1.06 mmol) in 20 mL of DMF at 0° C. was added N-iodosuccinimide (0.26 g, 1.17 mmol). The reaction was stirred with slow warming to ambient temperature for 4 h. The mixture was diluted with ethyl acetate, washed with water and brine, dried (MgSO$_4$), filtered and concentrated in vacuo to afford 0.43 g (86%) of the title compound, which was used without purification. LRMS (ES+): 473.0 (M+H)+.

Part B. tert-butyl (7bR,11aS)(4,4,5,5-tetramethyl-1,3,2-dioxaborolan-2-yl) 1,2,7b,10,11,11a-hexahydro-4H-pyrido[4,3-b][1,4]thiazepino[6,5,4-hi]indole-9(8H)Carboxylate.

To a solution of tert-butyl (7bR,11aS)-6-iodo-1,2,7b,10,11,11a-hexahydro-4H-pyrido[4,3-b][1,4]thiazepino[6,5,4-hi]indole-9(8H)-carboxylate (0.20 g, 0.42 mmol) in 15 mL of DMSO was added diboron pinacol ester (0.16 g, 0.63 mmol) and potassium acetate (0.125 g, 1.27 mmol). The mixture was degassed with a stream of nitrogen for 20 min and then there was added tetrakis(triphenylphosphine)palladium (25 mg, 0.02 mmol) and the mixture was stirred at 80° C. for 16 h. The reaction was allowed to cool to ambient temperature and was diluted with ethyl acetate, washed with brine, dried (MgSO$_4$), filtered through Celite and concentrated in vacuo. The residue was purified by flash chromatography (elution with hexanes/ethyl acetate) to afford 0.13 g (65%) of the title compound. $^1$H NMR (CDCl$_3$): δ 7.43 (s, 1H), 7.35 (s, 1H), 3.82–3.75 (m, 2H), 3.68–3.58 (m, 3H), 3.50–3.38 (m, 4H), 3.26–3.20 (m, 1H), 3.08–2.98 (m, 1H), 2.92–2.85 (m, 1H), 1.92–1.80 (m, 2H), 1.42 (s, 9H), 1.32 (s, 12H).

Part C. tert-butyl (7bR,11aS)-6-[4-cyano-2-(trifluoromethyl)phenyl]-1,2,7b,10,11,11a-hexahydro-4H-pyrido[4,3-b][1,4]thiazepino[6,5,4-hi]indole 9(8H)-carboxylate.

To a solution of tert-butyl (7bR,11aS)-6-(4,4,5,5-tetramethyl-1,3,2-dioxaborolan-2-yl)-1,2,7b,10,11,11a-hexahydro-4H-pyrido[4,3-b][1,4]thiazepino[6,5,4-hi]indole-9(8H)-carboxylate (0.135 g, 0.28 mmol) in 15 mL of DMF and 2 mL of water was added 4-bromo-3-(trifluoromethyl)benzonitrile (0.143 g, 0.57 mmol) and sodium carbonate (0.15 g, 0.1.43 mmol). The mixture was degassed with a stream of nitrogen for 20 min and then there was added [1,1'-bis(diphenylphosphino)ferrocene]dichloropalladium (II) (20 mg, 0.028 mmol) and the mixture was stirred at 80° C. for 16 h. The reaction was allowed to cool to ambient temperature and was diluted with ethyl acetate, washed with sat'd aqueous sodium bicarbonate and brine, dried (MgSO$_4$), filtered through Celite and concentrated in vacuo to afford 130 mg (88%) of the title compound, which was used without purification. LRMS (ES+): 516.1 (M+H)+.

Part D. 4-[(7bR,11aS)-1,2,7b,8,9,10,11,11a-octahydro-4H-pyrido[4,3-b][1,4]thiazepino[6,5,4-hi]indolyl-6-yl]-3-(trifluoromethyl)benzonitrile, trifluoroacetic acid salt.

To a solution of tert-butyl (7bR,11aS)-6-[4-cyano-2-trifluoromethyl)phenyl]-1,2,7b,10,11,11a-hexahydro-4H-pyrido[4,3-b) [1,4]thiazepino[6,5,4-hi]indole-9(8H)-carboxylate (0.13 g, 0.25 mmol) in 20 mL of methylene chloride was added 5 mL of trifluoroacetic acid and the mixture was allowed to stir at ambient temperature for 4 h. The volatiles were removed in vacuo and the residue was purified by prep HPLC (C18 reverse phase column, elution with a H$_2$O/CH$_3$CN gradient with 0.5% TFA) and lyophilized to afford 30 mg (25%) of the title compound of EXAMPLE 25. $^1$H NMR (CDCl$_3$): δ 8.00 (s, 1H), 7.81 (d, 1H), 7.44 (d, 1H, J=8.1 Hz), 6.93 (s, 1H), 6.88 (s, 1H), 3.82 (ABq, 2H), 3.64–3.55 (m, 3H), 3.38–3.10 (m, 5H), 2.92–2.87 (m, 1H2.68–2.62 (m, 1H), 2.28–2.17 (m, 2H). LRMS (ES+): 416.3 (M+H)+.

Example 26

3-[(7bR,11aS)$_9$-(cyclobutylmethyl)-1,2,7b,8,9,10,11,11a-octahydro-4H-pyrido[4,3-b][1,4]thiazepino[6,5,4-hi]indol-6-yl]-2-methylbenzonitrile, trifluoroacetic acid salt

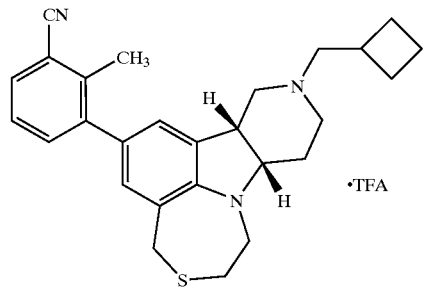

To a solution of 3-[(7bR,11aS)-1,2,7b,8,9,10,11,11a-octahydro-4H-pyrido[4,3-b][1,4]thiazepino[6,5,4-hi]indol-6-yl]-2-methylbenzonitrile from EXAMPLE 24 (48 mg, 0.13 mmol) in 5 mL of 1,4-dioxane was added (bromomethyl)Cyclobutane (0.03 mL, 0.27 mmol), N,N-diisopropylethylamine (0.23 mL, 1.33 mmol) and a catalytic amount of potassium iodide and the reaction was stirred at 100° C. for 16 h. The reaction was cooled, diluted with ethyl acetate, washed with brine, dried (MgSO$_4$) and concentrated. The residue was purified by prep HPLC (C18 reverse phase column, elution with a H$_2$O/CH$_3$CN gradient with 0.5% TFA) and lyophilized to afford 30 mg (53%) of the title compound of EXAMPLE 26. $^1$H NMR (CDCl$_3$): δ 7.59 (dd, 1H, J=7.6, 1.3 Hz), 7.37–7.33 (m, 1H), 7.29 (t, 1H, J=7.7 Hz), 6.93 (s, 1H), 6.84 (d, 1H, J=1.5 Hz), 3.84 (ABq, 2H, J$_{AB}$=15.9 Hz), 3.80–3.70 (m, 1H), 3.52–3.39 (m, 3H), 3.38–3.30 (m, 1H), 3.21–3.15 (m, 1H), 3.05–2.97 (m, 3H), 2.86–2.80 (m, 1H), 2.45 (s, 3H), 2.43–2.35 (m, 1H), 2.22–2.10 (m, 3H), 1.90–1.77 (m, 7H). LRMS (ES+): 430.5 (M+H)+.

Example 27

(7bR,11aS)-6-[2-methyl-4-(methylsulfanyl)phenyl]-1,2,7b,8,9,10,11,11a-octahydro-4H-pyrido[4,3-b[]1,4]thiazepino[6,5,4-hi]indole, trifluoroacetic acid salt

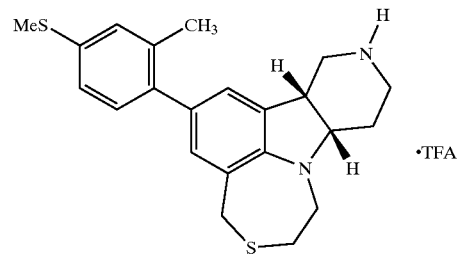

Using 4-thiomethyl-2-methylphenyl boronic acid and following the procedures in EXAMPLE 7, tert-butyl (7bR,11aS)-6-bromo-1,2,7b,10,11,11a-hexahydro-4H-pyrido[4,3-b][1,4]thiazepino[6,5,4-hi]indole-9(8H} carboxylate was converted into the title compound of EXAMPLE 27. LRMS (ES+): 383.4 (M+H)+.

Example 28

1-{2-[(7bR,11aS)-1,2,7b,8,9,10,11,11a-octahydro-4H-pyrido[4,b][1,4]thiazepino[6,5,4-hi]indol-6-yl]-fluorophenyl)ethanone, trifluoroacetic acid salt

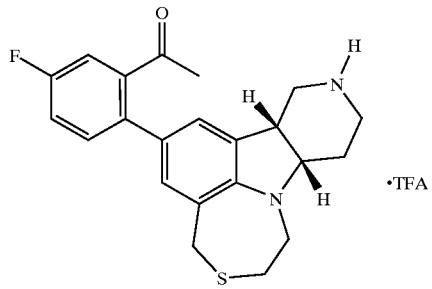

·TFA

Part A. tert-butyl (7bR,11aS)-6-[4-fluoro-2-(2-methyl-1,3-dioxolan-2-yl)phenyl]-1,2,7b,10,11,11a-hexahydro-4H-pyrido[4,3-b][1,4]thiazepino[6,5,4-h]indole-9(8H) Carboxylate.

To a solution of tert-butyl (7bR,11aS)-6-bromo-1,2,7b,10,11,11a-hexahydro-4H-pyrido[4,3-b][1,4]thiazepino[6,5,4-hi]indole-9(8H)-carboxylate (0.20 g, 0.47 mmol) in 15 mL of DME was added 4-fluoro-2-(2-methyl-1,3-dioxolan-2-yl)phenylboronic acid (0.21 g, 0.94 mmol) and 8 mL of 2M sodium carbonate. The mixture was degassed with a stream of nitrogen for 20 min and then there was added tetrakis (triphenylphospine)palladium (0) (20 mg, 0.014 mmol). The reaction was stirred at 100° for 3 h. The reaction was then cooled, diluted with ethyl acetate, washed with brine, dried (MgSO₄), filtered through a pad of Celite and concentrated to afford 0.29 g of the title compound as an oil, which was used without purification. LRMS (ES)⁺: 527.2 (M+H)⁺.

Part B. 1-{2-[(7bR,11aS)-1,2,7b,8,9,10,11,11a-octahydro-4H-pyrido[4,3-b][1,4]thiazepino[6,5,4-hi]indol-6-yl]-5-fluorophenyl}ethanone, trifluoroacetic acid salt.

To a solution of tert-butyl (7bR,11aS)-6-[4-fluoro-2-(2-methyl-1,3-dioxolan-2-yl)phenyl]-1,2,7b,10,11,11a-hexahydro-4H-pyrido[4,3-b][1,4]thiazepino[6,5,4-hi]indole-9(8H)-carboxylate (0.16 g, 0.30 mmol) in 30 mL of acetone and 30 mL of water was added p-toluenesulfonic acid monohydrate (12 mg, 0.06 mmol) and the reaction was stirred at 40° C. for 18 h. The reaction was cooled, diluted with ethyl acetate, washed with 1N aqueous sodium hydroxide and brine, dried (MgSO₄), and concentrated to an oil. LRMS (ES)⁺: 483.1 (M+H)⁺. This residue was dissolved in 5 mL of methylene chloride and then there was added 1 mL of trifluoroacetic acid and the mixture was stirred at ambient temperature for 2 h. The reaction was concentrated in vacuo and the residue was purified by prep HPLC (C18 reverse phase column, elution with a H₂O/CH₃CN gradient with 0.5% TFA) and lyophilized to afford 70 mg (60%) of the title compound of EXAMPLE 28. ¹H NMR (CDCl₃): δ 9.45 (broad s, 1H), 9.30 (broad s, 1H), 7.32–7.26 (m, 1H), 7.22–7.13 (m, 2H), 6.91 (s, 1H), 6.89 (s, 1H), 3.81 (ABq, 2H, J$_{AB}$=15.7 Hz), 3.63–3.54 (m, 3H), 3.40–3.28 (m, 2H), 3.28–3.10 (m, 3H), 2.93–2.82 (m, 1H), 2.70–2.58 (m, 1H), 2.30–2.17 (m, 2H), 2.03 (s, 3H). LRMS (ES)⁺: 383.4 (M+H)⁺.

Example 29

1-(2-[(7bR,11aS)-1,2,7b,8,9,10,11,11a-octahydro-4H-pyrido[4,3-b][1,4]thiazepino[6,5,4-hi]indol-6-yl]-5-fluorophenyl}ethanol

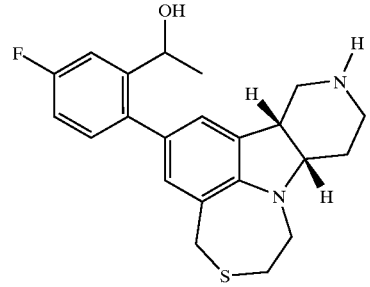

To a solution of 1-{2-[(7bR,11aS)-1,2,7b,8,9, 10,11,11a-octahydro-4H-pyrido[4,3-b][1,4]thiazepino[6,5,4-hi]indol-6-yl]-5-fluorophenyl)ethanone, the free base of EXAMPLE 28 (50 mg, 0.13 mmol) in 10 mL of methanol was added sodium borohydride (20 mg, 0.65 mmol) and the resulting mixture was stirred at ambient temperature for 3 h. The reaction was quenched with water and then diluted with ethyl acetate. The organics were washed with brine, dried (MgSO₄), and concentrated to an oil. The residue was purified by prep HPLC (C18 reverse phase column, elution with a H₂O/CH₃CN gradient with 0.5% TFA) to afford 1-{2-[(7bR,11aS)-1,2,7b,8,9,10,11,11a-octahydro-4H-pyrido[4,3-b][1,4]thiazepino[6,5,4-hi]indol-6-yl]-5-fluorophenyl}ethanol, trifluoroacetic acid salt. This material was partitioned between chloroform and saturated aqueous sodium carbonate. The organics were washed with brine, dried (K₂CO₃) and concentrated in vacuo to afford 15 mg (30%) of the title compound of EXAMPLE 29. ¹H NMR (CDCl₃): δ 7.32 (d, 1H, J=7.4 Hz), 7.15–7.08 (m, 1H), 6.97–6.90 (m, 1H), 6.82 (s, 1H), 6.74 (s, 1H), 4.97–4.93 (m, 1H), 3.88–3.70 (m, 2H), 3.65–3.60 (m, 1H), 3.50–3.40 (m, 2H), 3.24–3.05 (m, 3H), 3.00–2.80 (m, 3H), 2.62–2.50 (m, 1H), 2.40–2.30 (m, 1H), 1.93–1.78 (m, 2H), 1.40–1.34 (m, 3H). LRMS (ES)⁺: 385.4 (M+H)⁺.

Example 30

1-{2-[(7bR,11aS)-1,2,7b,8,9,10,11,11a-octahydro-4H-pyrido[4,3-b]1,4]thiazepino[6,5,4-h]indol-yl]-5-methylphenyl}ethanol, trifluoroacetic acid salt

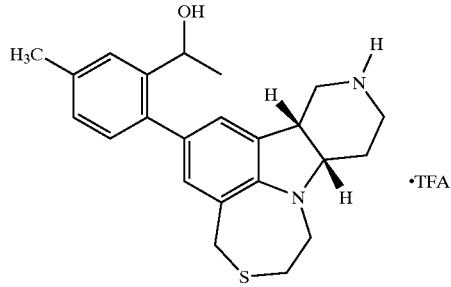

·TFA

To 2-[(7bR,11aS)-1,2,7b,8,9, 10,11,11a-octahydro-4H-pyrido[4,3-b][1,4]thiazepino[6,5,4-hi]indol-6-yl]-5-methoxybenzaldehyde, the free base of EXAMPLE 16 (98 mg, 0.27 mmol) in 10 mL of THF at 0° C. was added methyl magnesium bromide (1.8 mL of a 3M solution in THF, 5.4 mmol). The reaction was allowed to stir at 0° C. for 30 min and then with warming to room temperature. The reaction was quenched by the addition of saturated aqueous ammonium chloride and the THF was removed in vacuo. The residue was dissolved in ethyl acetate and the organics were washed with saturated sodium carbonate and brine, dried (MgSO$_4$) and concentrated. The residue was purified by prep HPLC (C18 reverse phase column, elution with a H$_2$O/CH$_3$CN gradient with 0.5% TFA) and lyophilized to afford 10 mg of the title compound of EXAMPLE 30. LRMS (ES)$^+$: 381.4 (M+H)$^+$.

Example 31

1-{2-[(7bR,11aS)-1,2,7b,8,9,10,11,11a-octahydro-4H-pyrido[4,3-b][1,4]thiazepino[6,5,4-hi]indol-6-yl]-5-chlorophenyl}ethanone, trifluoroacetic acid salt

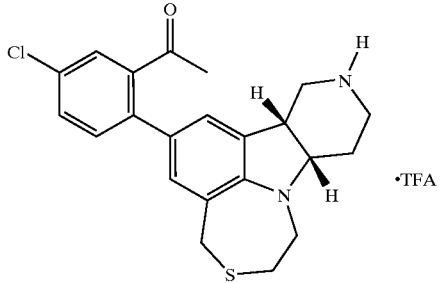

Using 4-chloro-2-acetylbromobenzene and following the procedures described in EXAMPLE 25, Parts C and D, tert-butyl (7bR,11aS)-64,4,5,5-tetramethyl-1,3,2-dioxaborolan-2-yl)-1,2,7b,10,11,11a-hexahydro-4H-pyrido[4,3-b][1,4]thiazepino[6,5,4-hi]indole-9(8H)Carboxylate from EXAMPLE 25, Part B, was converted into the title compound of EXAMPLE 31. $^1$H NMR (CD$_3$OD): δ 7.52–7.45 (m, 2H), 7.35 (d, 1H, J=8.4 Hz), 6.97 (d, 1H, J=1.8 Hz), 6.92 (d, 1H, J=1.4 Hz), 3.86 (ABq, 2H, J$_{AB}$=15.8 Hz), 3.63–3.45 (m, 3H), 3.40–3.24 (m, 4H), 3.15–3.08 (m, 1H), 2.93–2.82 (m, 1H), 2.72 (dd, 1H, J=12.6, 10.2 Hz), 2.32–2.22 (m, 1H), 2.15–2.05 (m, 1H), 2.04 (s, 3H). LRMS (ES)$^+$: 399.4 (M+H)$^+$.

Example 32

1-{2-[(7bR,11aS)-1,2,7b,8,9,10,11,11a-octahydro-4H-pyrido[4,3 b][1,4]thiazepino[6,5,4-hi]indol-6-yl]-5-chlorophenyl}ethanol

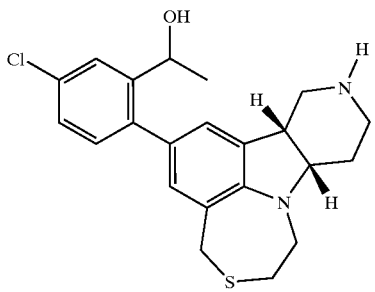

Following the procedure described in EXAMPLE 29, 1-{2-[(7bR,11aS) -1,2,7b,8,9,10,11,11a-octahydro-4H-pyrido[4,3-b][1,4]thiazepino[6,5,4-hi]indol-6-yl]-5-chlorophenyl}ethanone, the free base of EXAMPLE 31, was converted into the title compound of EXAMPLE 32. $^1$H NMR (CD$_3$OD) (some signals doubled due to diastereomers): δ 7.56 (d, 1H, J=2.2 Hz), 7.21 (dd, 1H, J=8.2, 2.4 Hz), 7.09 (d, 1H, J=8.1 Hz), 6.87 (s, 1H), 6.78 (s, 1H), 3.96–3.86 (m, 1H), 3.70–3.62 (m, 2H), 3.44–3.40 (m, 1H), 3.30–3.04 (m, 4H), 2.98–2.80 (m, 4H), 2.42 (ddd, 1H), 2.02–1.95 (m, 1H), 1.90–1.78 (m, 1H), 1.26 (dd, 3H). LRMS (ES)$^+$: 401.4 (M+H)$^+$.

Example 33

(7bR,11aS)-N-(2,4-dichlorophenyl)-1,2,7b,8,9,10,11,11a-octahydro-4H-pyrido[4,3-b][1,4]thiazepino[6,5,4-hi]indol-6-amine

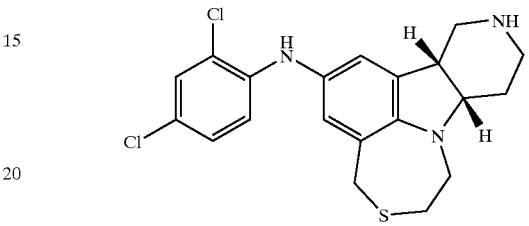

Part A. tert-butyl (7bR,11aS)$_6$-bromo-1,2,7b,10,11,11a-hexahydro-4H-pyrido[4,3-b][1,4]thiazepino[6,5,4-hi]indole-9(8H)-carboxylate.

To tert-butyl (7bR,11aS)-1,2,7b,10,11,11a-hexahydro-4H-pyrido[4,3-b)[1,4]thiazepino[6,5,4-hi]indole-9(8H)-carboxylate from EXAMPLE 1, Part F (3.4 g, 9.7 mmol) in DMF cooled to −10° C. was added N-bromosuccinimide (1.9 g, 11 mmol) in one portion, causing the solution to turn red-brown. After several minutes, the reaction was complete by TLC (20% ethyl acetate/hexanes) and the product was precipitated from the solution upon the addition of ice chips. The resulting green suspension was stirred at room temperature for 1 hour. The solid was collected, washed with water, and dried yielding 3.6 g (86%) of the title compound as a green solid. $^1$H NMR (300 MHz, CDCl$_3$) δ 1.40 (s, 9H), 1.76–1.98 (m, 2H), 2.75–3.19 (m, 6H), 3.30–3.77 (m, 6H), 7.01 (s, 1H), 7.08 (s, 1H) ppm.

Part B. tert-butyl (7bR,11aS)-amino-1,2,7b,10,11,11a-hexahydro-4H-pyrido[4,3-b][1,4]thiazepino[6,5,4-hi]indole-9(8H)-carboxylate.

To a solution of tert-butyl (7bR,11aS)-6-bromo-1,2,7b,10,11,11a-hexahydro-4H-pyrido[4,3-b](1,4]thiazepino[6,5,4-hi]indole-9(8H)-carboxylate (1.0 g, 2.4 mmol) in toluene (12 mL) was added sodium t-butoxide (0.45 g, 4.7 mmol) and benzophenone imine (0.51 g, 2.8 mmol). The resulting solution was heated to 80° C. while argon was bubbled into the solution. After 20 minutes, the solution was cooled to room temperature under argon and then Pd$_2$(dba)$_3$ (43 mg, 47 μmol) and BINAP (59 mg, 94 μmol) were added. The orange solution was returned to 80° C. for 16 hours. Dilution of the reaction mixture with ether followed by filtration through a pad of celite and removal of solvents yielded the crude imine intermediate as an orange oil. The oil was purified by column chromatography using an ethyl acetate/hexanes gradient (10–50%). The pure imine was dissolved in methanol and added to a mixture of sodium acetate (0.46 g, 5.6 mmol) and hydroxylamine hydrochloride (0.29 g, 4.2 mmol). After 1 hour at room temperature, the mixture was diluted with ether and filtered through Celite. The solution was pre-adsorbed on silica and chromatographed using an ethyl acetate/hexanes gradient (10–60%). The title compound was obtained as a tan foam 0.74 g (87%). $^1$H NMR (500 MHz, CDCl$_3$) δ 1.45 (s, 9H), 1.78–1.92 (m, 2H), 2.82–3.20 (m, 6H), 3.31–3.59 (m, 6H), 3.64–3.82 (m, 2H), 6.28 (s, 1H), 6.41 (s, 1H) ppm.

Part C. tert-butyl (7bR,11aS)₄(2,4-dichloroanilino)-1,2,7b, 10,11,11a-hexahydro-4H-pyrido[4,3-b][1,4]thiazepino[6,5,4-hi]indole-9(8H)-carboxylate.

An oven dried three-necked round bottom flask was fitted with septa, condenser, and a stopper. The flask was charged with tert-butyl (7bR,11aS)-6-amino-1,2,7b,10,11,11a-hexahydro-4H-pyrido[4,3-b][1,4]thiazepino[6,5,4-hi]indole-9(8H) carboxylate (134 mg, 0.36 mmol), 1-bromo-2,4-dichlorobenzene (70 mg, 0.31 mmol), NaOtBu (60 mg, 0.62 mmol), and anhydrous toluene (5 mL). The solution was purged with argon at 80° C. for 25 min then cooled to room temperature. While maintaining a blanket of argon, Pd₂(dba)₃ (3.4 mg, 3.7 μmol), and BINAP (7 mg, 11.2 μmol) were added quickly. The resulting mixture was heated to 80° C. for 20 hours under argon while monitoring the consumption of starting material by TLC (50% ethyl acetate/hexanes). After cooling to room temperature, the dark solution was diluted with ethyl ether (10 mL) and filtered through a pad of silica, washing with ether and ethyl acetate. The resulting solution was concentrated and chromatographed (Combiflash, 95:5 to 75:25 hexanes/ethyl acetate gradient) yielding the title compound (78 mg, 48%) as a tan solid. ¹H NMR (CDCl₃, 300 MHz) δ 1.41 (s, 9H), 1.79–1.97 (m, 2H), 2.85–3.18 (m, 6H), 3.46–3.61 (m, 4H), 3.68 (s, 2H), 5.84 (s, 1H), 6.71 (d, 1H, J=1.9 Hz), 6.79 (d, 1H, J=1.8 Hz), 6.89 (d, 1H, J=8.8 Hz), 7.01 (dd, 1H, J=2.3, 8.8 Hz), 7.29 (d, 1H, J=2.3 Hz) ppm.

Part D. (7bR,11aS)-N-(2,4-dichlorophenyl)-1,2,7b,8,9,10,11,11a-octahydro-4H-pyrido[[4,3-b][1,4]thiazepino[6,5,4-hi]indol-6-amine.

To a solution of tert-butyl (7bR,11aS)-62,4-dichloroanilino)-1,2,7b, 10,11, 11 a-hexahydro-4H-pyrido[4,3-b](1,4]thiazepino[6,5,4-hi]indole-9(8H)-carboxylate (78 mg, 0.15 mmol) in dichloromethane (5 mL) was added trifluoroacetic acid (2 mL) and the blue solution was stirred at room temperature for 2 hours. The solution was made basic with 3 N NaOH, and extracted with dichloromethane. The organic layers were combined, dried over NaSO₄ and concentrated to a yellow oil. An off-white solid was obtained upon trituration with ethyl acetate/hexanes yielding 62 mg (98%) of the title compound of EXAMPLE 33. ¹H NMR (CDCl₃, 300 MHz) δ 1.79–1.88 (m, 2H), 2.57–2.68 (m, 1H), 2.77–3.31 (m, 8H), 3.42–3.50 (m, 1H), 3.54–3.68 (m, 1H), 3.73 (s, 2H), 5.84 (s, 1H), 6.71 (d, 1H, J=1.9 Hz), 6.79 (d, 1H, J=1.8 Hz), 6.89 (d, 1H, J=8.8 Hz), 7.01 (dd, 1H, J=2.3, 8.8 Hz), 7.29 (d, 1H, J=2.3 Hz) ppm. MS/ESI m/z=406 [C₂₀H₂₁Cl₂N₃S+H]⁺.

Example 34

(7bS,11aR)-N-(2,4-dichlorophenyl)-1,2,7b,8,9,10,11,11a-octahydro-4H-pyrido[4,3-b][1,4]thiazepino[6,5,4-4-hi]indol-6-amine

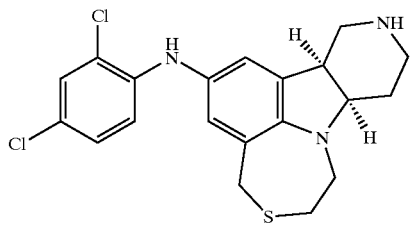

Following the procedures described in EXAMPLE 33, tert-butyl (7bS,11aR)-1,2,7b,10,11,11a-hexahydro-4H-pyrido[4,3-b][1,4]thiazepino[6,5,4-hi]indole-9(8H)-carboxylate from EXAMPLE 1, Part F was converted into the title compound of EXAMPLE 34 as a powder. ¹H NMR (CDCl₃, 300 MHz) δ 1.79–1.88 (m, 2H), 2.57–2.68 (m, 1H), 2.77–3.31 (m, 8H), 3.42–3.50 (m, 1H), 3.543.68 (m, 1H), 3.73 (s, 2H), 5.84 (s, 1H), 6.71 (d, 1H, J=1.9 Hz), 6.79 (d, 1H, J=1.8 Hz), 6.89 (d, 1H, J=8.8 Hz), 7.01 (dd, 1H, J=2.3, 8.8 Hz), 7.29 (d, 1H, J=2.3 Hz) ppm. MS/ESI m/z 406 [C₂₀H₂₁Cl₂N₃S+H]⁺.

Example 35

(7bR,11aS)-N-(4-fluoro-2-methylphenyl)-1,2,7b,8,9,10,11,11a-octahydro-4H-pyrido[4,3-b][1,4]thiazepino[6,5,4-hi]indol-6-amine

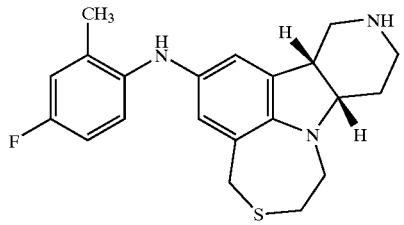

Using 2-bromo-4-fluorotoluene and following the procedures described in EXAMPLE 33, Parts C and D, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 35 as a powder. ¹H NMR (CDCl₃, 300 MHz) δ 1.79–1.88 (m, 2H), 2.20 (s, 3H), 2.57–2.68 (m, 1H), 2.77–3.08 (m, 9H), 3.12–3.23 (m, 1H), 3.37–3.42 (m, 1H), 3.543.68 (m, 1H), 3.73 (m, 3H), 4.99 (s, 1H), 6.49 (d, 1H, J=2.2 Hz), 6.60 (d, 1H, J=2.2 Hz), 6.76–7.01 (m, 3H) ppm. MS/ESI m/z=370 [C₂₁H₂₄FN₃S+H]⁺.

Example 36

(7bR,11aS)-N-(4-methoxy-2-methylphenyl)-1,2,7b,8,9,10,11,11a-octahydro-4H-pyrido[4,3-b][1,4]thiazepino[6,5,4-hi]indol-6-amine

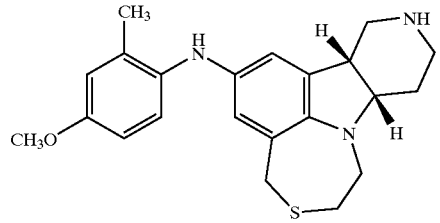

Using 2-bromo-4-methoxytoluene and following the procedures described in EXAMPLE 33, Parts C and D, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 36 as a powder. ¹H NMR (CDCl₃, 300 MHz) δ 1.24–1.28 (m, 2H), 1.82–1.85 (m, 2H), 2.21 (s, 3H), 2.57–2.64 (m, 1H), 2.82–3.03 (m, 5H), 3.14–3.21 (m, 1H), 3.34–3.39 (m, 1H), 3.54–3.60 (m, 1H), 3.65–3.74 (m, 2H), 3.78 (s, 3H), 4.95 (s, 1H), 6.40 (d, 1H, J=2 Hz), 6.50 (d, 1H, J=2 Hz), 6.68 (dd, 1H, J=2.9, 8.6 Hz), 6.76 (d, 1H, J=2.7 z), 7.03 (d, 1H, J=8.6 Hz) ppm. MS/ESI m/z=382 [C₂₂H₂₇N₃OS+H]⁺.

Example 37

(7bR,11aS)-N-(2,3-dichlorophenyl)-1,2,7b,8,9,10,11,11a-octahydro-4H-pyrido[4,3-b][1,4]thiazepino[6,5,4-hi]indol-6-amine

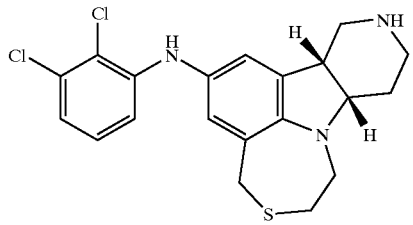

Using 1-bromo-2,3-dichlorobenzene and following the procedures described in EXAMPLE 33, Parts C and D, tert-butyl (7bR,11aS)-6-amino-1,2,7b,10,11,11a-hexahydro-4H-pyrido[4,3-b][1,4]thiazepino[6,5,4-hi]indole-9(8H) Carboxylate from EXAMPLE 33, Part B was converted into the title compound of EXAMPLE 37 as a powder. $^1$H NMR (CDCl$_3$, 300 MHz) δ 1.79–1.89 (m, 2H), 2.58–2.69 (m, 1H), 2.79–3.25 (m, 7H), 3.41–3.50 (m, 1H), 3.60–3.68 (m, 2H), 3.74 (s, 2H), 6.01 (s, 1H), 6.73 (d, 1H, J=2 Hz), 6.81–6.85 (m, 3H), 6.95–6.98 (m 1H). LRMS (ES)$^+$: 406 (M+H)$^+$.

Example 38

(7bR,11aS)-N-[2-chloro-5-(trifluoromethyl)phenyl]-1,2,7b,8,9,10,11,11a-octahydro-4H-pyrido[4,3-b][1,4]thiazepino[6,5,4-hi]indol-6-amine

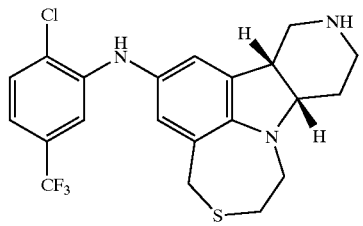

Using 3-bromo-4-chlorobenzotrifluoride and following the procedures described in EXAMPLE 33, Parts C and D, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 38 as a powder. $^1$H NMR (CDCl$_3$, 300 MHz) 1.82–1.87 (m, 4H), 2.58–2.65 (m, 1H), 2.82–3.28 (m, 6H), 3.46–3.51 (m, 1H), 3.62–3.65 (m, 1H), 3.76 (s, 2H), 6.04 (s, 1H), 6.73 s, 1H), 6.83 (s, 1H), 6.91 (d, 1H, J=8 Hz), 7.14 (s, 1H), 7.37 (d, 1H, J=8 Hz). LRMS ES)$^+$: 440 (M+H)$^+$.

Example 39

(7bR,11aS)-N-(3,4-dichlorophenyl)-1,2,7b,8,9,10,11,11a-octahydro-4H-pyrido[4,3-b][1,4]thiazepino[6,5,4-hi]indol-6-amine

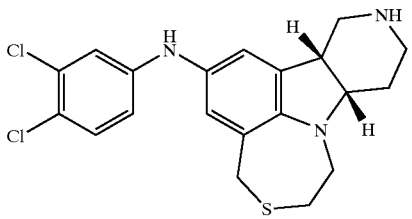

Using 3,4-dichloro-1-bromobenzene and following the procedures described in EXAMPLE 33, Parts C and D, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 39 as a powder. $^1$H NMR (CDCl$_3$, 300 MHz) δ 1.82–1.87 (m, 2H), 2.48–2.55 (m, 1H), 2.57–2.64 (m, 1H), 2.81–3.13 (m, 6H), 3.18–3.25 (m, 1H), 3.42–3.47 (m, 1H), 3.57–3.64 (m, 1H), 3.72 (s, 2H), 5.55 (s, 1H), 6.61–6.68 (m, 2H), 6.74 (s, 1H), 6.89 (d, 1H, J=3 Hz), 7.19 (d, 1H, J=9 Hz). LRMS (ES)$^+$: 406 (M+H)$^+$.

Example 40

(±)Cis-4-(1,2,7b,8,9,10,11,11a-octahydro-4H-[1,4]oxazepino[6,5,4-hi]pyrido[4,3-b]indol-6-yl)-3-(trifluoromethyl)phenyl methyl ether, trifluoroacetic acid salt

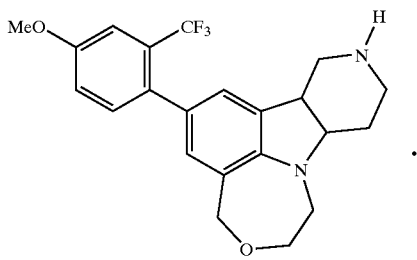

Part A. 2-chloro-N-[2-(hydroxymethyl)phenyl]acetamide.

To a solution of 2-aminobenzyl alcohol (50.00 g, 405.97 mmol) and 56.5 ml (405.97 mmol) of triethylamine in 700 ml of tetrahydrofuran at 0° C. was slowly added chloroacetyl chloride (32.33 g, 405.97 mmol) and the solution was allowed to stir overnight with warming to ambient temperature. The solution was poured through a pad of silica gel and the volatiles were removed under reduced pressure to yield 75.9 g (93%) of the title compound as a tan solid. $^1$H NMR (CDCl$_3$) δ 9.67 (broad s, 1H), 8.10(d, J=8.1 Hz, 1H),7.38(t, J=7.3, 1H),7.25(d, J=6.0 Hz, 1H),7.15(t, J=8.0 Hz, 1H), 4.77, (s, 2H), 4.11 (s, 2H). LRMS (ApcI): m/e 200.0 (M+H)$^+$.

Part B. 1,5-dihydro-4,1-benzoxazepin-2(3H)-one.

8.74 g (380.21 mmol) of sodium metal was stirred overnight in ethanol and then the solution was cooled to 0° C. and then 2-chloro-N-[2-(hydroxymethyl)phenyl]acetamide (75.9 g, 380.21 mmol) was added and the reaction was stirred at reflux overnight. The solution was filtered through a fritted filter, the solvent was reduced to a small volume and the product triturated with a 3:1 solution of EtOAc/ether solution and the product isolated by filtration to yield 34.1 g (54%) of the title compound. $^1$H NMR (DMSO-D6): δ

10.21 (s, 1H), 7.22 (t, J=6.6 Hz, 1H), 7.14, (t, J=7.7 Hz, 2H), 6.96, (t, J=7.3 Hz, 1H). LRMS (CH$_3$—CI): m/e 164.1 (M+H)$^+$.

Part C. 1,2,3,5-tetrahydro-4,1-benzoxazepine.

To a solution of 1,5-dihydro-4,1-benzoxazepin-2(3H)-one (6.09 g, 36.86 mmol) in 300 ml THF at 0° C. was slowly added lithium aluminum hydride (3.50 g, 92.17 mmol) and the reaction was refluxed for 4 h. The solution was cooled to 0° C. and quenched by dropwise addition of 3.5 ml of water, followed by 3.5 ml of 15% NaOH and 10.5 ml of water. The solution was filtered through a pad of silica gel and the volatiles were removed under reduced pressure to yield 5.31 g (95%) of the title compound. LRMS (ApcI): m/e 152.0 (M+H)$^+$.

Part D. 1-nitroso-1,2,3,5-tetrahydro-4,1-benzoxazepine.

To a solution of 1,2,3,5-tetrahydro-4,1-benzoxazepine (24.24 g, 160.32 mmol) in 200 ml of HOAc at 0° C. was added dropwise NaNO$_2$ (13.27 g, 192.38 mmol) as a solution in 20 ml of water. The solution was stirred at room temperature for 3 h, and then was diluted with EtOAc, made basic with 1 M NaOH and extracted with EtOAc. The organics were dried over MgSO$_4$, filtered through a pad of silica gel and the volatiles removed under reduced pressure to give 25.78 g (90%) of the title compound. $^1$H NMR (CDCl$_3$) δ 7.53–7.27 (m, 4H), 4.59, (s, 2H), 4.11–4.06 (m, 2H), 3.79–3.76 (m, 2H). LRMS (ApcI): m/e 179.0 (M+H)$^+$.

Part E. 2,3-dihydro-4,1-benzoxazepin-[(5H)-ylamine.

To a solution of 1-nitroso-1,2,3,5-tetrahydro-4,1-benzoxazepine. (25.78 g, 144.69 mmol) in THF at 0° C. was slowly added lithium aluminum hydride (10.98 g, 289.38 mmol) and the reaction was refluxed for 1 h and then was stirred at room temperature overnight. The reaction was cooled in an ice/water bath and the solution quenched by dropwise addition of 11 ml of water, 11 ml of 15% NaOH and 33 ml of water. The solution was dried over MgSO$_4$, filtered through a pad of silica gel and the volatiles were removed under reduced pressure to yield 16.25 g (68%) of the title compound. $^1$H NMR (300 MHz, CDCl$_3$) δ 7.31–6.90 (m, 4H), 4.56 (s, 2H), 3.90–3.76 (m, 4H), 3.21–3.18 (m, 2H). LRMS (ApcI): n/e 165.0 (M+H)$^+$.

Part F. (±)-cis-tert-butyl 1,2,7b,10,11,11a-hexahydro-4H-[1,4]oxazepino[6,5,4-hi]pyrido[4,3-b]indole-9(8H) Carboxylate.

To a solution of 2,3-dihydro-4,1-benzoxazepin-1(5H)-ylamine (11.44 g, 69.67 mmol) in 250 ml of 2,2,2-trifluoroethanol was added 4-piperidone hydrate (10.7 g, 69.67 mmol) and the mixture was heated to reflux for 2 h. 5 ml of concentrated 33% HCl was added and the mixture was stirred at reflux overnight. The volatiles were removed under reduced pressure and the residue dissolved in MeOH and triturated out with diethyl ether and dried under reduced pressure. The crude material was dissolved in 300 ml of TFA followed by the addition of triethylsilane (45.7 ml, 286.11 mmol) and the reaction was stirred overnight at room temperature. The solution was diluted with hexane and the TFA layer removed and the volatiles removed at reduced temperature. The residue was diluted with 150 ml of a saturated K$_2$CO$_3$ solution followed by the addition of 200 ml of CH$_2$Cl$_2$ and BOC anhydride (49.95 g, 228.88 mmol). The solution was then stirred overnight at ambient temperature. The organics were extracted with EtOAc and the solution dried over MgSO$_4$, filtered through a pad of silica gel and the volatiles removed. The residue was purified by first column chromatography (Silica gel; EtOAc:Hex 1:1) followed by prep HPLC (C18 reverse phase column, elution with a H$_2$O/CH$_3$CN gradient with 0.5% TFA) and lyophilized to afford 0.75 g (2%) of the title compound. $^1$H NMR (300 MHz, CDCl$_3$) δ 7.28–7.01 (m, 3H), 4.73 (AB q, J=14.7 Hz, 2H), 4.35–3.05 (broad m, 10H), 2.06, (m, 2H), 1.45 (s, 9H). LRMS (ApcI): m/e 331.1 (M+H)$^+$.

Part G. (±)-cis-tert-butyl 6-bromo-1,2,7b,10,11,11a-hexahydro-4H-[1,4]oxazepino[6,5,4-hi]pyrido[4,3-b]indole-9(8H)-carboxylate.

To a solution of (±)-cis-tert-butyl 1,2,7b,10,11,11a-hexahydro-4H-[1,4]oxazepino[6,5,4-hi]pyrido[4,3-b]indole-9(8H)-carboxylate (0.75 g, 2.26 mmol) in DMF at 0° C. was added NBS (0.44 g, 2.49 mmol) and the mixture was stirred at room temperature overnight. The solution was diluted with ethyl ether and washed 3 times with brine. The organics were dried over MgSO$_4$ and filtered through a pad of silica gel and the volatiles were removed under reduce pressure to yield 0.79 g (85%) of the title compound. $^1$H NMR (300 MHz, CDCl$_3$) δ 7.04 (d, J=1.8 Hz, 1H), 6.93 (d, J=1.8 Hz, 1H), 4.49 (AB q, 14.3 Hz, 2H), 4.10–2.69 (broad m, 10H), 1.97 (m, 2H), 1.36 (s, 9H). LRMS (ES$^+$): 410.0 (M+H)$^+$.

Part H. (±)-cis tert-butyl 6-14-methoxy-2-(trifluoromethyl) phenyl]-1,2,7b,10,11,11a-hexahydro-4H-[1,4]oxazepino[6,5,4-hi]pyrido[4,3-b]indole-9(8H)-carboxylate.

To a solution of (±)-cis-tert-butyl 6-bromo-1,2,7b,10,11,11 a-hexahydro-4H-[1,4]oxazepino[6,5,4-hi]pyrido[4,3-b]indole-9(8H)-carboxylate (0.15 g, 0.37 mmol) in 75 mL of 1,2-dimethoxyethane and 25 mL of water was added 2-trifluoromethyl-4-methoxy phenyl boronic acid (0.16 g, 0.73 mmol) and barium hydroxide octahydrate (0.35 g, 1.09 mmol). The mixture was degassed with a stream of nitrogen for 20 min and then there was added tetrakis (triphenylphosphine)palladium (13 mg, 0.01 mmol) and the mixture was stirred at 100° C. for 3 h. The reaction was allowed to cool to ambient temperature and was diluted with ethyl acetate, washed with sat'd aqueous sodium bicarbonate and brine, dried (MgSO$_4$), filtered through Celite and concentrated in vacuo. The residue was purified by flash chromatography (elution with hexanes/ethyl acetate) to afford the title compound in 70% yield. $^1$H NMR (300 MHz, CDCl$_3$) δ 7.28–6.84 (m, 5H), 4.61 (AB q, 1=4.3 Hz, 4.25-2.71 (m, 13H), 1.94 (m, 2H), 1.45 (s, 9H). LRMS (ES$^+$): 505.4 (M+H)$^+$.

Part 1. (±)-cis-4-(1,2,7b,8,9,10,11,11a-octahydro-4H-[1, 4]oxazepino[6,5,4 hi]pyrido[4,3-b]indol-6-yl)-3-(trifluoromethyl)phenyl methyl ether, trifluoroacetic acid salt.

To (±)-cis tert-butyl 6-[4-methoxy-2-(trifluoromethyl) phenyl]-1,2,7b,10,11,11a-hexahydro-4H-[1,4]oxazepino[6,5,4-hi]pyrido[4,3-b]indole-9(8H)-carboxylate (0.13 g, 0.26 mmol) was added 30 ml of TFA and stirred at room temperature for 2 h. The volatiles were removed under reduced pressure and the product purified by prep HPLC (C18 reverse phase column, elution with a H$_2$O/CH$_3$CN gradient with 0.5% TFA) and lyophilized to afford the title compound of EXAMPLE 40. $^1$H NMR (300 MHz, DMSO-D6) δ 8.79 (broad m, 2H), 7.25 (m, 3H), 7.05 (s, 1H), 6.87 (s, 1H), 4.60, (AB q, J=14.7 Hz, 2H), 4.14 (d, J=13.2 Hz, 1H), 3.83 (s, 3H), 3.66–1.99 (broad m, 9H). LRMS (ES$^+$): 405.1 (M+H)$^+$.

Example 41

(±)-cis-4(1,2,7b,8,9,10,11,11a-octahydro-4H-[1,4]oxazepino[6,5,4-hi]pyrido[4,3-b]indol-6-yl)-3-methylphenyl methyl ether, trifluoroacetic acid salt

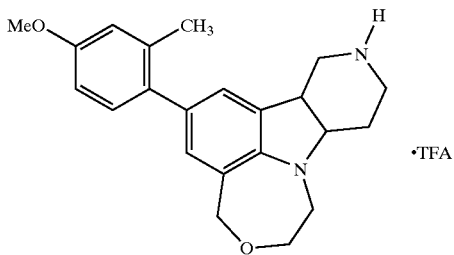

Using 2-methyl-4-methoxyphenyl boronic acid and following the procedures in EXAMPLE 26, Parts H and I, (±)-cis-tert-butyl 6-bromo-1,2,7b,10, 11,11a-hexahydro-4H-[1,4]oxazepino[6,5,4-hi]pyrido[4,3-b]indole-9(8H)-carboxylate was converted into the title compound of EXAMPLE 41. $^1$H NMR (300 MHz, DMSO-D6): δ 8.69 (broad m, 2H), 7.07 (m, 5H), 4.61, (AB q, J=14.3 Hz, 2H), 4.12 (d, J=12.8 Hz, 1H), 3.73 (s, 3H), 3.67–1.98 (broad m, 9H). LRMS (ES$^+$): 351.2 (M+H)$^+$.

Example 42

(7bR,11aS)-1,2,7b,8,9,10,11,11a-octahydro-4H-[1,4]oxazepino[6,5,4-hi]pyrido[4,3-b]indole, trifluoroacetic acid salt

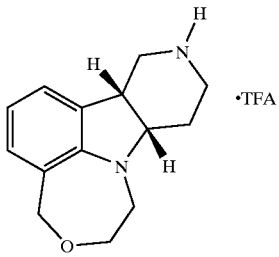

Part A. tert-butyl (7bR,11aS)-1,2,7b,10,11,11a-hexahydro-4H-[1,4]oxazepino[6,5,4-hi]pyrido[4,3-b]indole-9(8H) Carboxylate.

To a solution of 2,3-dihydro-4,1-benzoxazepin-[(5H)-ylamine from EXAMPLE 40, Part E (15.44 g, 94.03 mmol) in 400 ml of acetic acid was added 4-piperidone monohydrate HCl (21.66 g, 141.05 mmol) and the mixture was heated to 80-85° C. for 3 hrs and then the volatiles were removed in vacuo. The crude residue was dissolved in 250 ml of trifluoroacetic acid and cooled to 0° C. followed by the slow addition of NaBH$_3$CN (17.72 g, 282.11 mmol) under a flow of nitrogen. The reaction was quenched after 90 min. with NaOH and made basic (pH 10–11) with potassium carbonate. Di-tert-butyl dicarbonate (34.89 g, 159.86 mmol) was added and the reactants stirred at room temperature with the addition of 1 liter of THF overnight. The organics were extracted with ethyl acetate and the volatiles removed under vacuo. The residue was purified by column chromatography to yield the desired product as a clear oil (11.0 g, 35%). The enantiomers were separated on a chiral column (Chiralcel, OD 0.44×25 cm) at ambient temperature eluting with 0.5% aceonitrile/2.5% isopropanol/97% hexane at 1.0 ml/min and 265 nm wavelength. This purification yielded 5.0 grams or each optically pure enantiomer. The first eluting peak was identified as the title compound and has an optical rotation of +89.0 deg (DMF, 0.292 g/dl, 21° C.). LRMS (ApcI): m/e 331.1 (M+H)$^+$. The second eluting peak was identified as the enantiomer, tert-butyl (7bS,11aR)-1,2,7b,10,11,11a-hexahydro-4H-[1,4]oxazepino[6,5,4-hi]pyrido[4,3-b]indole-9(8H)Carboxylate.

Part B. (7bR,11aS)1,2,7b,8,9,10,11,11a-octahydro-4H-[1,4]oxazepino[6,5,4-hi]pyrido[4,3-b]indole, trifluoroacetic acid salt.

The first eluting peak from the chiral separation, tert-butyl (7bR,11aS)-1,2,7b,10,11,11a-hexahydro-4H-[1,4]oxazepino[6,5,4-hi]pyrido[4,3-b]indole-9(8H) carboxylate, was deprotected following the procedure described in EXAMPLE 7, Part C to afford the title compound of EXAMPLE 42. LRMS (ES$^+$): 231.2 (M+H)$^+$.

Example 43

(7bR,11aS)-6-[-4-methoxy-2-(trifluoromethyl)phenyl]-1,2,7b,8,9,10,11,11a-octahydro-4H-[1,4]oxazepino[6,5,4-hi]pyrido[4,3-b]indole, trifluoroacetic acid salt

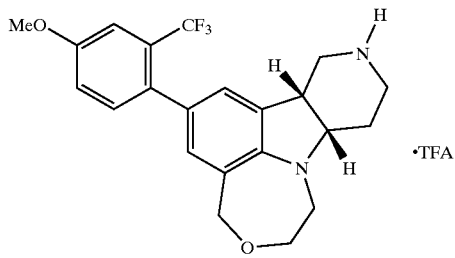

Following the procedures described in EXAMPLE 40, Parts G-I, tert-butyl (7bR,11aS),1,2,7b,10,11,11a-hexahydro-4H-[1,4]oxazepino[6,5,4-hi]pyrido[4,3-b]indole-9(8H)-carboxylate from EXAMPLE 42, Part A, was converted to the title compound of EXAMPLE 43. $^1$H NMR (300 MHz, DMSO-D6) δ 8.79 (broad m, 2H), 7.25 (m, 3H), 7.05 (s, 1H), 6.87 (s, 1H), 4.60, (AB q, J=14.7 Hz, 2H), 4.14 (d, J=13.2 Hz, 1H), 3.83 (s, 3H), 3.66–1.99 (broad m, 9H). LRMS (ESI): m/e 405.1 (M+H)$^+$.

Example 44

(7bS,11aR)-6-[4-methoxy-2-(trifluoromethyl)phenyl-1,2,7b,8,9,10,11,11a-octahydro-4H-[1,4]oxazepino[6,5,4-hi]pyrido[4,3-b]indole, trifluoroacetic acid salt

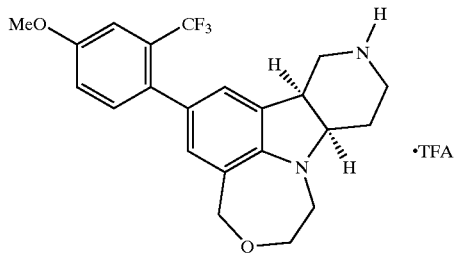

Following the procedures described in EXAMPLE 40, Parts G-1, tert-butyl (7bS,11aR)-1,2,7b,10,11,11a-hexahydro-4H-[1,4)oxazepino[6,5,4-hi]pyrido[4,3-b]indole-9(8H)-carboxylate from EXAMPLE 42, Part A, was converted to the title compound of EXAMPLE 44. $^1$H NMR (300 MHz, DMSO-D6): δ 8.79 (broad m, 2H), 7.25 (m, 3H), 7.05 (s, 1H), 6.87 (s, 1H), 4.60, (AB q, J=14.7 Hz, 2H), 4.14 (d, J=13.2 Hz, 1H), 3.83 (s, 3H), 3.66–1.99 (broad m, 9H). LRMS (ESI): m/e 405.1 (M+H)⁺.

Example 45

4-[(7bR,11aS)-1,2,7b,8,9,10,11,11a-octahydro-4H-[1,4]oxazepino[6,5,4-hi]pyrido[4,3-b]indol-6-yl]-3-methylbenzonitrile, trifluoroacetic acid salt

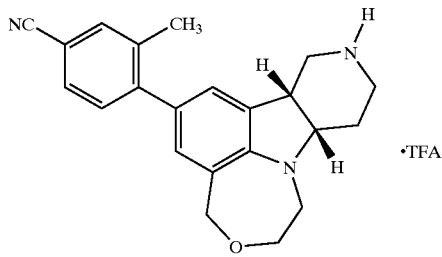

Using 4-cyano-2-methylphenyl boronic acid and following the procedures described in EXAMPLE 40, Parts G-1, tert-butyl (7bR,11aS)-1,2,7b,10,11,11a-hexahydro-4H-[1,4]oxazepino[6,5,4-hi]pyrido[4,3-b]indole-9(8H)-carboxylate from EXAMPLE 42, Part A, was converted to the title compound of EXAMPLE 45. ¹H NMR (300 MHz, DMSO-D6): δ 8.70–8.55 (broad m, 2H), 7.75 (s, 1H), 7.67 (d, J=8.1 Hz, 1H), 7.34 (d, J=8.1 Hz, 1H),7.18 (s, 1H),7.02 (s, 1H),4.81 (d, J=14.3 Hz, 1H),4.44 (d, J=14.3 Hz, 1H),4.14-1.99 (broad m, 8). LRMS (ESI): m/e 346.3 (M+H)⁺.

Example 46 and 47

4-[(7bR,11aS)-1,2,7b,8,9,10,11,11a-octahydro-4H-[1,4]oxazepino[6,5,4-hi]pyrido[4,3-b]indol-6-yl]-3-methylbenzamide, trifluoroacetic acid salt (EXAMPLE 46)

and methyl 4-[(7bR,11aS)-1,2,7b,8,9,10,11,11a-octahydro-4H-11,4)oxazepino[6,5,4-hi]pyrido[4,3-b]indol-6-yl]-3-methylbenzoate, trifluoroacetic acid salt (EXAMPLE 47)

EXAMPLE 46

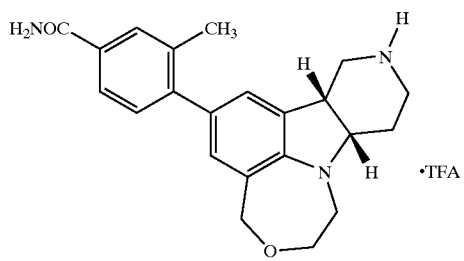

EXAMPLE 47

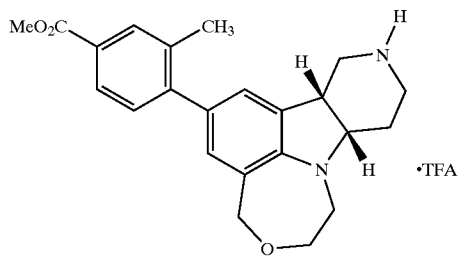

Through a solution of 4-[(7bR,11aS)-1,2,7b,8,9,10,11,11a-octahydro-4H-[1,4]oxazepino[6,5,4-hi]pyrido[4,3-b]indol-6-yl]-3-methylbenzonitrile from EXAMPLE 45 (0.15 g, 0.33 mmol) in 100 ml of MeOH at 0° C. was bubbled gaseous HCl for 10 min. The reaction was tightly stoppered, allowed to warm to ambient temperature and stirred overnight. The volatiles were removed under reduced pressure and the residue was stirred overnight at room temperature in (20 ml) of a 1:1 solution of MeOH/water. The products were separated and purified by prep HPLC (C18 reverse phase column, elution with a H₂O/CH₃CN gradient with 0.5% TFA) to yield the title products. Data for 4-[(7bR,11aS)-1,2,7b,8,9,10,11,11a-octahydro-4H-[1,4]oxazepino[6,5,4-hi]pyrido[4,3-b]indol-6-yl]-3-methylbenzamide (EXAMPLE 46). ¹H NMR (300 MHz, DMSO-D6): δ 8.60–8.50 (broad m, 2H), 7.76 (s, 1H), 7.67 (d, J=7.7 Hz, 1H), 7.20 (d, J=7.7 Hz, 1H), 7.15 (s, 1H), 6.99 (s, 1H), 4.81 (d, J=14.3 Hz, 1H), 4.44 (d, J=14.3 Hz, 1H), 4.14–1.99 (broad m, 8H). LRMS (ESI): m/e 364.3 (M+H)⁺. Data for methyl 4-[(7bR,11aS)-1,2,7b,8,9,10,11,11a-octahydro-4H-[1,4]oxazepino[6,5,4-h]pyrido[4,3-b]indol-6-yl]-3-methylbenzoate (EXAMPLE 47). ¹H NMR (300 MHz, DMSO-D6): δ 8.79–8.73 (broad m, 2H), 7.85 (s, 1H), 7.78 (d, J=8.0 Hz, 1H), 7,29 (d, J=8.0 Hz, 1H), 7.18 (s, 1H), 7.01 (s, 1H), 4.81 (d, J=14.36 Hz, 1H), 4.44(d, J=14.6 Hz, 1H), 4.14–2.01 (broad m, 8H). LRMS (ESI): m/e 379.2 (M+H)⁺.

Example 48

1-{2-[(7bR,11aS)-1,2,7b,8,9,10,11,11a-octahydro-4H-[1,4]oxazepino[6,5,4-hi]pyrido[4,3-b]indol-6-yl]-5-fluorophenyl}ethanone, trifluoroacetic acid salt

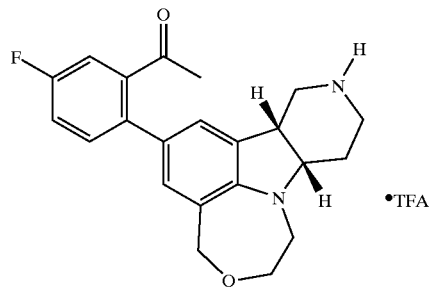

Following the procedures described in EXAMPLE 28, tert-butyl (7bR,11aS)-6-bromo-1,2,7b,10,11,11a-hexahydro-4H-[1,4]oxazepino[6,5,4-hi]pyrido[4,3-b]indole-9(8H)-carboxylate, an intermediate from EXAMPLE 43, was converted into the title compound of EXAMPLE 48. ¹H NMR (300 MHz, CD₃OD): δ 7.42–7.22 (broad m, 3H), 7.05 (d, J=1.5 Hz, 1H), 6.95 (d, J=1.5 Hz, 1H), 4.8 (d, 1H), 4.5 (d, 1H), 2.22 (dd, 1H), 3.75 (t, 1H), 3.60–3.50 (m, 3H), 3.40 (dd, 2H), 3.22 (t, 1H), 2.80 (t, 1H), 2.65 (t, 1H), 2.35 (2, 1H), 2.20–2.15 (m, 1H). LRMS (ES)+: m/e 367.3 (M+H)+.

Example 49

1-{2-[(7bR,11aS)-1,2,7b,8,9,10,11,11a-octahydro-4H-[1,4]oxazepino[6,5,4-hi]pyrido[4,3-b]indol-6-yl-5-fluorophenyl}ethanol, trifluoroacetic acid salt

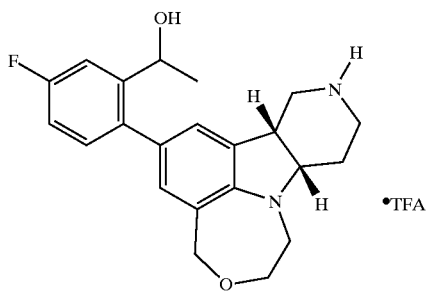

To a solution of 1-{2-[(7bR,11aS)-1,2,7b,8,9, 10,11,11a-octahydro-4H-[1,4]oxazepino[6,5,4-hi]pyrido[4,3-b]indol-6-yl]-5-fluorophenyl}ethanone from EXAMPLE 48 (0.10 g, 0.21 mmol) in 50 mL of MeOH was added NaBH$_4$ (0.04 g, 1.04 mmol) and the reaction was stirred at ambient temperature overnight. The reaction was quenched with 10% HCl and basified with 10% NaOH, the organics were extracted with ethyl acetate, dried (MgSO$_4$) and concentrated. The residue was purified by prep HPLC (C18 reverse phase column, elution with a H$_2$O/CH$_3$CN gradient with 0.5% TFA) and lyophilized to afford the title compound of EXAMPLE 49. $^1$H NMR (300 MHz, DMSO-D6): δ 8.65–8.55 (broad m, 2H), 7.31 (dd, J=2.5 Hz, 10.6 Hz, 1H), 7.10–7.05 (broad m, 3H), 6.89 (s, 1H), 4.78 (d, J=14.3 Hz, 1H), 4.71 (m, 1H), 4.43 (d, J=14.3 Hz, 1H), 4.11–1.95 (broad m, 10H), 1.18 & 1.14 (2d (diasteromers) J=6.2 Hz, 3H).
MS ESI m/e 369.2 (M+H)+

Example 50

(7bR,11aS)-6-[2-methyl-4-(methylsulfanyl)phenyl]-1,2,7b,8,9,10,11,11a-octahydro-4H-[1,4]oxazepino[6,5,4-hi]pyrido[4,3-b]indole, trifluoroacetic acid salt

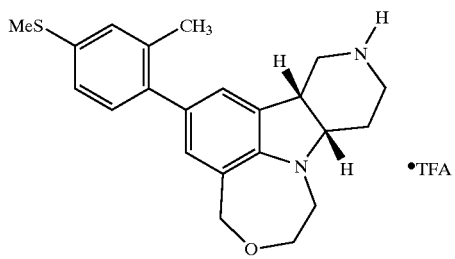

Using 2-methyl-4-(methylsulfanyl)phenylboronic acid and following the procedures described in EXAMPLE 40, Parts H and 1, tert-butyl (7bR,11aS)-6-bromo-1,2,7b,10,11, 11a-hexahydro-4H-(1,4]oxazepino[6,5,4-hi]pyrido[4,3-b] indole-9(8H) carboxylate, an intermediate from EXAMPLE 43, was converted into the title compound of EXAMPLE 50. $^1$H NMR (300 MHz, DMSO-D6): δ 8.60–8.55 (broad m, 2H), 7.14 (s, 1H), 7.10–7.08 (m, 3H), 6.93 (s, 1H), 4.79 (d, J=14.3 Hz, 1H), 4.43 (d, J=143 Hz, 1H), 4.12 (d, J=13.5 Hz 1H), 3.63–1.98 (broad m, 1H). LRMS ESI: m/e 367.3 (M+H)+.

Example 51

1-{2-[(7bR,11aS)-1,2,7b,8,9,10,11,11a-octahydro-4H-[1,4]oxazepino[6,5,4-hi]pyrido[4,3-b]indol-6-yl]-5-methylphenyl}ethanone, trifluoroacetic acid salt

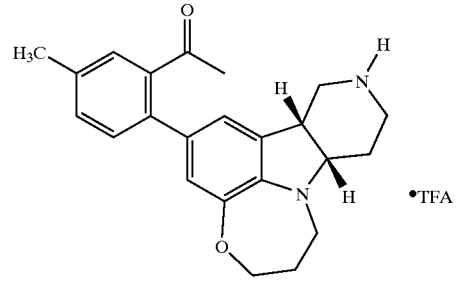

Part A. tert-butyl (7bR,11aS)$_4$-(4,4,5,5-tetramethyl-1,3,2-dioxaborolan-2-yl)-1,2,7b,10,11,11a-hexahydro-4H-[1,4] oxazepino[6,5,4-hi]pyrido[4,3-b]indole-9(8H)-carboxylate.
A solution of tert-butyl (7bR, 1 aS)-6-bromo-1,2,7b,10, 11,11a-hexahydro-4H-[1,4]oxazepino[6,5,4-hi]pyrido[4,3-b]indole-9(8H)-carboxylate (1.34 g, 3.27 mmol), diboron pinacol ester (1.24 g, 4.91 mmol) and KOAc (0.96 g, 9.82 mmol) in DMSO was degassed with nitrogen for 30 min. Tetrakis(triphenylphosphine)palladium (0) (0.19 g, 0.16 mmol) was added and the solution was heated for 2 h at 90–100° C. The solution was diluted with water and the organics extracted with Et$_2$O. The product was purified by column chromatography eluting with 1:1 hex/EtOAc to afford 0.46 g (41%) of the title compound. LRMS (ES)+: 457.4 (M+H)+.
Part B. 1-{2-[(7bR,11aS)-1,2,7b,8,9,10,11,11a-octahydro-4H-[1,4]oxazepino[6,5,4-hi]pyrido[4,3-b]indol-6-yl]-5-methylphenyl}ethanone, trifluoroacetic acid salt.
Using 1-(2-bromo-5-methylphenyl)ethanone and following the procedures described in EXAMPLE 25, Parts C and D, tert-butyl (7bR,11aS)-6-(4,4,5,5-tetramethyl-1,3,2-dioxaborolan-2-yl)-1,2,7b, 10,11,11a-hexahydro-4H-[1,4] oxazepino[6,5,4-hi]pyrido[4,3-b]indole-9(8H)-carboxylate was converted into the title compound of EXAMPLE 51. $^1$H NMR (300 MHz, CD$_3$OD): δ 7.31–7.25 (broad m, 3H), 7.04 (s, 1H), 6.92 (s, 1H), 4.81 (d, J=14.3 Hz, 1H), 4.55 (d, J=14.3 Hz, 1H), 4.20 (d, 1H), 3.75–2.10 (broad M, 11H). LRMS (ES)+: 363.3 (M+H)+.

Example 52

1-{2-[(7bR,11aS)-1,2,7b,8,9,10,11,11a-octahydro-4H-[1,4]oxazepino[6,5,4-hi]pyrido[4,3-b]indol-6-yl]-5-methylphenyl}ethanol

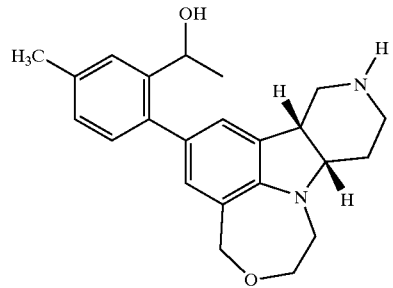

Following the procedure described in EXAMPLE 29, 1-{2-[(7bR,11aS)-1,2,7b,8,9,10,11,11a-octahydro-4H-(1,4]

oxazepino[6,5,4-hi]pyrido[4,3-b]indol-6-yl]-5-methylphenyl}ethanone from EXAMPLE 51 was converted into the title compound of EXAMPLE 52. $^1$H NMR (300 MHz DMSO-D6): δ 7.34–7.21 (broad m, 3H), 6.80 (d, J=15.0 Hz, 2H), 4.70 (d, J=14.3 Hz, 1H), 4.41 (d, J=14.3 Hz, 1H), 4.07 (d, J=12.4 Hz 1H), 3.61 (t, J=11 Hz, 1H), 3.32–1.65 (broad m, 17H). LRMS (ES)$^+$: 365.3 (M+H)$^+$.

Example 53

1-{2-[(7bR,11aS)-1,2,7b,8,9,10,11,11a-octahydro-4H-[1,4]oxazepino[6,5,4-hi]pyrido[4,3-b]indol-6-yl]-5-chlorophenyl)ethanone, trifluoroacetic acid salt

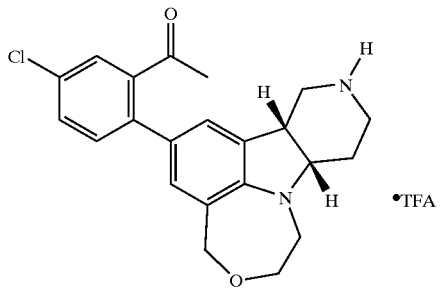

Using 4-chloro-2-acetyl bromobenzene and following the procedures described in EXAMPLE 25, Parts C and D, tert-butyl (7bR,11aS)-6-(4,4,5,5-tetramethyl-1,3,2-dioxaborolan-2-yl)-1,2,7b,10,11,11a-hexahydro-4H-[1,4]oxazepino[6,5,4-hi]pyrido[4,3-b]indole-9(8H)-carboxylate from EXAMPLE 51, Part A, was converted into the title compound of EXAMPLE 53. $^1$H NMR (300 MHz, CD$_3$OD): δ 7.52 (m, 2H), 7.35 (d, J=7.7 Hz, 1H), 7.07 (s, 1H), 6.94 (s, 1H), 4.82 (d, J=14.6 Hz, 1H), 4.51 (d, J=14.3 Hz, 1H), 4.25 (m, 1H), 3.75–2.03 (broad m, 14H). LRMS (ES)$^+$: 383.2 (M+H)$^+$.

Example 54

1-(2-[(7bR,11aS)-1,2,7b,8,9,10,11,11 a-octahydro-4H-[1,4]oxazepino[6,5,4 hi]pyrido[[4,3-b]indol-6-yl]-5-chlorophenyl}ethanol

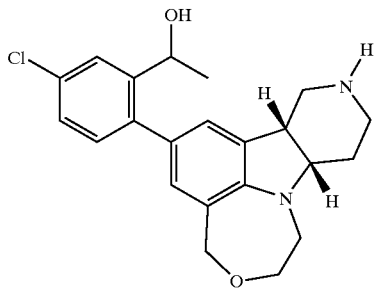

Following the procedure described in EXAMPLE 29, 1-{2-[(7bR,11aS)-1,2,7b,8,9,10,11,11a-octahydro-4H-[1,4]oxazepino[6,5,4-hi]pyrido[4,3-b]indol-6-yl]-5-chlorophenyl}ethanone from EXAMPLE 53 was converted into the title compound of EXAMPLE 54. $^1$H NMR (300 MHz, CD$_3$OD): δ 7.55 (s, 1H), 7.21 (d, J=8.5 Hz, 1H), 7.07 (d, J=8.0 Hz, 1H), 6.94 (s, 1H), 6.81 (s, 1H), 4.87 (m, 1H), 4.76 (d, 14.3 Hz, 1H), 4.50 (d, 14.3 Hz, 1H), 4.21 (m, 1H), 3.74 (t, 11.7 Hz, 1H), 3.40–1.23 (broad m, 13H). LRMS (ES)$^+$: 385.2 (M+H)$^+$.

Example 55

1-[4-[(7bR,11aS)-1,2,7b,8,9,10,11,11a-octahydro-4H-!1,4]oxazepino[6,5,4-hi]pyrido[4,3-b]indol-6-yl]-3-(trifluoromethyl)phenyl]ethanone, trifluoroacetic acid salt

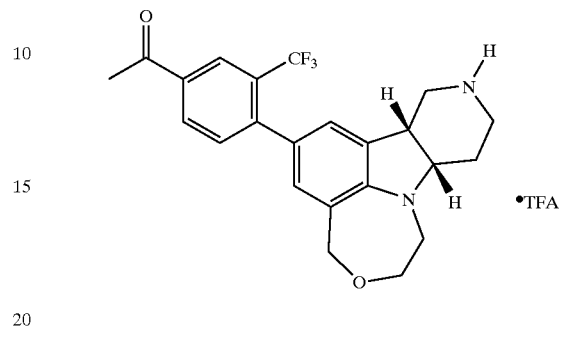

Part A. tert-butyl 6-[4-(2-methyl-1,3-dioxolan-2-yl)-2-trifluoromethyl)phenyl]-1,2,7b,10,11,11a-hexahydro-4H-[1,4]oxazepino[6,5,4-hi]pyrido[4,3-b]indole 9(8H)-carboxylate.

A solution of tert-butyl (7bR,11aS)-6-bromo-1,2,7b,10,11,11a-hexahydro-4H-[1,4]oxazepino[6,5,4-hi]pyrido[4,3-b]indole-9(8H)-carboxylate (0.16 g, 0.39 mmol), 4-(2-methyl-1,3-dioxolan-2-yl)-2-trifluoromethyl)phenylboronic acid (0.215 g, 0.78 mmol), 0.78 ml of a 2N sodium carbonate solution (1.56 mmol) and tetrakis(triphenylphosphine)palladium (0) (0.013 g, 0.012 mmol) in 100 ml of a 3:2 deoxygenated mixture of 1,2 dimethoxyethane/water was heated to reflux overnight. The solution was cooled to room temperature and diluted with 150 ml of ethyl acetate. The organics were extracted, dried over magnesium sulfate and the solution was filtered through a plug of silica gel and the volatiles were removed under reduced pressure to afford 0.20 g (90%) of the title compound which was used without purification. LRMS (ES)$^+$: 511.6 (M+H)$^+$.

Part B. 1-[4-[(7bR,11aS)-1,2,7b,8,9,10,11,11a-octahydro-4H-11,4]oxazepino[6,5,4-hi]pyrido[4,3-b]indol-6-yl]-3-(trifluoromethyl)phenyl]ethanone, trifluoroacetic acid salt.

A solution of tert-butyl 6-[42-methyl-1,3-dioxolan-2-yl)-2-(trifluoromethyl)phenyl]-1,2,7b,10,11,11a-hexahydro-4H-[1,4]oxazepino[6,5,4-hi]pyrido[4,3-b]indole-9(8H)-carboxylate (0.20 g, 0.35 mmol) and p-toluenesulfonic acid monohydrate (20 mg, 10% by weight) in 50 ml of 1:1 acetone/water was heated to 40° C. overnight. The solution was diluted with water and the organics were extracted with ethyl acetate. The organics were dried over MgSO$_4$, filtered through a pad of silica gel and the volatiles were removed under reduced pressure to afford an oil which was used without purification. LRMS (ES)$^+$: 517.2 (M+H)$^+$. The residue was dissolved in 30 ml of TFA and stirred at room temperature for 2 h. The volatiles were removed under reduced pressure and the product purified by prep HPLC (C18 reverse phase column, elution with a H$_2$O/CH$_3$CN gradient with 0.5% TFA) and lyophilized to afford the title compound of EXAMPLE 55. $^1$H NMR (300 MHz, DMSO-D6): δ 8.70–8.55 (broad m, 2H), 8.24–8.20 (m, 2H), 7.53 (d, J=7.7 Hz, 1H), 7.13 (s, 1H), 6.97 (s, 1H), 4.80 (d, J=14.1 Hz, 1H), 4.44 (d, J=14.1 Hz, 1H), 4.14 (d, J=13.2 Hz, 1H), 3.64 (t, J=11.4 Hz, 1H), 3.49–1.99 (broad m, 13H). LRMS (ES)$^+$: 417.2 (M+H)$^+$.

Example 56

(7bR,11aS)-N-(2,4-dichlorophenyl)1,2,7b,8,9,10,11,11a-octahydro-4H-[1,4]oxazepino[6,5,4-hi]pyrido[4,3-b]indol-6-amine, bis trifluoroacetic acid salt

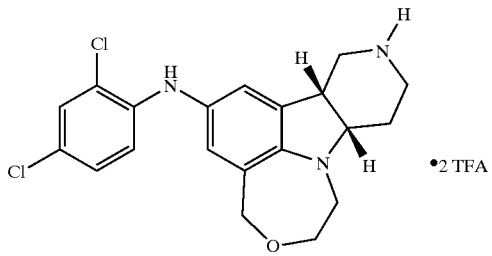

Part A. tert-butyl (7bR,11aS)-6-[(diphenylmethylene)amino]-1,2,7b,10,11,11a-hexahydro-4H-[1,4]oxazepino[6,5,4-hi]pyrido[4,3-b]indole-9(8H)-carboxylate.

A solution of tert-butyl (7bR,11aS)-6-bromo-1,2,7b,10,11,11a-hexahydro-4H-[1,4]oxazepino[6,5,4-hi]pyrido[4,3-b]indole-9(8H)-carboxylate (1.18 g, 2.88 mmol), benzophenone imine (0.62 g, 3.45 mmol), (S)-(−)-2,2'-bis(diphenylphosphino)1,1'-binaphthyl (BINAP) (0.076 g, 0.11 mmol), sodium-t-butoxide(0.69 g, 7.20 mmol) and $Pd_2DBA_3$ (0.03 g, 0.029 mmol) in 100 ml of degassed toluene was heated for 3 hrs at 90° C. The solution was filtered through a pad of silica gel and eluted with EtOAc. The volatiles were removed under reduced pressure to afford the title compound which was used without further purification. LRMS (ES)+: 510.3 $(M+H)^+$.

Part B. tert-butyl (7bR,11aS)-6-amino-1,2,7b,10,11,11a-hexahydro-4H-[1,4]oxazepino[6,5,4-hi]pyrido[4,3-b]indole-9(8H)-carboxylate.

A solution of tert-butyl $(7bR,11aS)_6$-[(diphenylmethylene)amino]-1,2,7b,10,11,11a-hexahydro-4H-[1,4]oxazepino[6,5,4-hi]pyrido[4,3-b]indole-9(8H)-carboxylate (0.96 g, 1.88 mmol), NaOAc (0.31 g, 3.76 mmol) and hydroxylamine hydrochloride (0.40 g, 5.64 mmol) in 100 ml of MeOH was stirred at ambient temperature for 30 min. The volatiles were removed under reduced pressure and the residue purified by column chromatography (eluting with a gradient of 100% diethyl ether to 100% EtOAc) to afford the title compound. LRMS $(ES)^+$: 346.3 $(M+H)^+$.

Part C. (7bR,11aS)-N-(2,4-dichlorophenyl)-1,2,7b,8,9,10,11,11a-octahydro-4H-[1,4]oxazepino[6,5,4-hi]pyrido[4,3-b]indolamine, bis trifluoroacetic acid salt.

A solution of tert-butyl (7bR,11aS)-6-amino-1,2,7b,10,11,11a-hexahydro-4H-[1,4]oxazepino[6,5,4-hi]pyrido[4,3-b]indole-9(8H)-carboxylate (0.10 g, 0.29 mmol), 1-bromo-2,4-dichlorobenzene (0.072 g, 0.318 mmol), BINAP (0.0011 g, 0.0017 mmol), sodium-t-butoxide, (0.072 g, 0.752 mmol) and $Pd_2DBA_3$ (0.0006 g, 0.00057 mmol) in 100 ml of degassed toluene was heated for 3 h at 90° C. The solution was cooled and filtered through a pad of silica gel and eluted with EtOAc. The volatiles were removed under reduced pressure and the product was purified by prep HPLC (C18 reverse phase column, elution with a $H_2O/CH_3CN$ gradient with 0.5% TFA) and lyophilized to afford a solid. LRMS $(ES)^+$: 490.2 $(M+H)^+$. This material was dissolved in 30 ml of $CH_2Cl_2$ followed by the addition of 10 ml of TFA and stirred at room temperature for 1 h, followed by removal of the volatiles under reduced pressure and the final product was purified by prep HPLC (C18 reverse phase column, elution with a $H_2O/CH_3CN$ gradient with 0.5% TFA) and lyophilized to afford the title compound of EXAMPLE 56. $^1$H NMR (300 MHz, DMSO-D6): δ 8.71–8.57 (broad m, 2H), 7.51 (m, 1H), 7.15 (d, J=8.0 Hz, 1H), 6.95 (s, 1H), 6.87 (d, J=8.8 Hz, 1H), 6.78 (s, 1H), 4.68 (d, J=14.2 Hz, 1H), 4.37 (d, J=14.2 Hz, 1H), 4.11 (d, J=12.8 Hz, 1H), 3.61 (t, J=11.7 Hz, 1H), 3.44–1.91 (broad m, 10H). LRMS $(ES)^+$: 390.2 $(M+H)^+$.

Example 57

(7bR,11aS)-N-(2,6-dichlorophenyl)-1,2,7b,8,9,10,11,11a-octahydro-41H-[1,4]oxazepino[6,5,4-hi]pyrido[4,3-b]indol-6-amine, bis trifluoroacetic acid salt

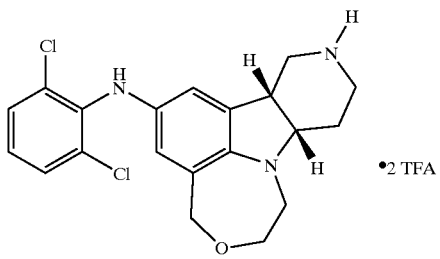

Using 2-bromo-1,3-dichlorobenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 57. $^1$H NMR (300 MHz, DMSO-D6): δ 8.68–8.50 (broad m, 2H), 7.48 (d, J=8.1 Hz, 2H), 7.16 (t, J=8.0 Hz, 1H), 6.39 (s, 1H), 6.20 (s, 1H), 4.55 (d, J=14.3 Hz, 1H), 4.31 (d, J=14.3 Hz, 1H), 4.09 (d, J=12.8, 1H), 3.56 (t, J=12.0 Hz, 1H), 3.33–1.87 (broad m, 10H). LRMS $(ES)^+$: 390.2 $(M+H)^+$.

Example 58

(7bR,11aS)-N-(2,6-difluorophenyl)-1,2,7b,8,9,10,11,11a-octahydro-4H-[1,4]oxazepino[6,5,4-hi]pyrido[4,3 b]indol-6-amine, bis trifluoroacetic acid salt

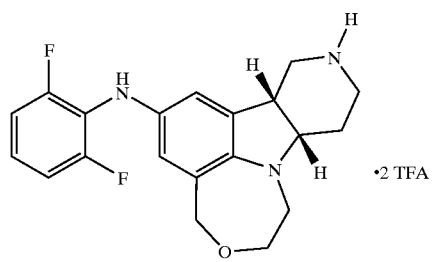

Using 2-bromo-1,3-difluorobenzene and following the procedures described in EXAMPLE 56, Part C, tert-butyl (7bR,11aS)-6-amino-1,2,7b,10,11,11a-hexahydro-4H-(1,4]oxazepino[6,5,4-hi]pyrido[4,3-b]indole-9(8H)-carboxylate from EXAMPLE 56, Part B was converted into the title compound of EXAMPLE 58. $^1$H NMR (300 MHz, DMSO-D6): δ 8.40–8.20 (broad m, 2H), 7.53 (broad s, 1H), 7.11–7.05 (broad m, 3H), 6.53 (s, 1H), 6.35 (s, 1H), 4.58 (d, J=14.7 Hz, 1), 4.32 (d, J=14.7 Hz, 1H), 4.09 (d, J=13.2 Hz, 1H), 3.60–1.85 (broad m, 1H). LRMS $(ES)^+$: 358.3 $(M+H)^+$.

Example 59

(7bR,11aS)-N-(2,5-dichlorophenyl)-1,2,7b,8,9,10,11,11a-octahydro-4H-[1,4]oxazepino[6,5,4-hi]pyrido[4,3-b]indol-6-amine, bis trifluoroacetic acid salt

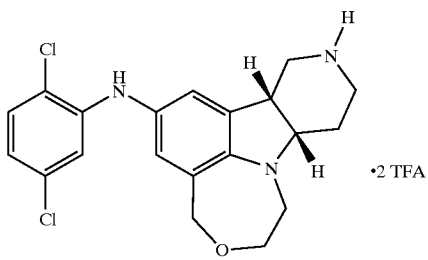

Using 1-bromo-2,5-dichlorobenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H) carboxylate from EXAMPLE 56, Part B was converted into the title compound of EXAMPLE 59. $^1$H NMR (300 MHz, DMSO-D6) δ 8.65–8.45 (broad m, 2H), 7.53 (s, 1H), 7.33 (d, J=8.4 Hz, 1H), 7.01 (s, 1H), 6.83 (s, 1H), 6.72 (m, 1H), 4.71 (d, J=14.2 Hz, 1H), 4.38 (d, J=14.2 Hz, 1H), 4.12 (d, J=13.6 Hz, 1H), 3.65–1.96 (broad m, 1H). LRMS (ES)$^+$: 390.2 M+H)$^+$.

Example 60

(7bR,11aS)-N-[2-chloro-5-trifluoromethyl)phenyl]-1,2,7b,8,9,10,11,11a-octahydro-4-[1,4]oxazepino[6,5,4-hi]pyrido[4,3 b]indolamine, bis trifluoroacetic acid salt

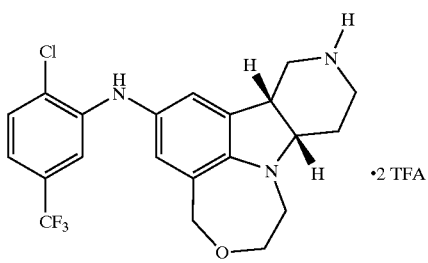

Using 1-bromo-2-chloro-5-(trifluoromethyl)benzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H) carboxylate from EXAMPLE 56, Part B was converted into the title compound of EXAMPLE 60. $^1$H NMR (300 MHz, DMSO-D6): δ 8.68–8.54 (broad m, 2H), 7.73 (s, 1H), 7.55 (d, J=8.1 Hz, 1H), 7.03–6.96 (broad m, 2H), 6.85 (s, 1H), 4.72 (d, J=14.7 Hz, 1H), 4.49 (d, J=14.7 Hz, 1H), 4.13 (d, J=13.2 Hz, 1H), 3.62 (t, J=10.9 Hz, 1H), 3.47–1.92 (broad m, 10 H). LRMS (ES)$^+$: 424.2 (M+H)$^+$.

Example 61

2-[(7bR,11aS)-1,2,7b,8,9,10,11,11a-octahydro-4H-[1,4]oxazepino[6,5,4-hi]pyrido[4,3-b]indol-6-ylamino]benzonitrile, bis trifluoroacetic acid salt

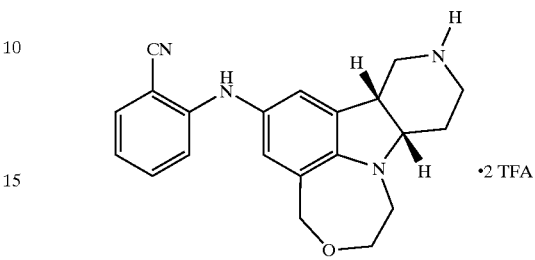

Using 2-bromobenzonitrile and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 61. $^1$H NMR (300 MHz, DMSO-D6): δ 8.70–8.56 (broad m, 2H), 8.11 (s, 1H), 7.55 (d, J=8.0 Hz, 1H), 7.38 (t, J=7.3 Hz, 1H), 6.99–6.92 (m, 2H), 6.80 (m, 2H). 4.68 (d J=14.7 Hz, 1H), 4.37 (d, J=14.7 Hz, 1H), 4.11 (d, J=12.8 Hz, 1H), 3.61 (t, 11.4 Hz, 1H), 3.44–1.91 (broad m, 10H). LRMS (ES)$^+$: 347.2 (M+H)$^+$.

Example 62

(7bR,11aS)-N-(43,4-dichlorophenyl)-1,2,7b,8,9,10,11,11a-octahydro-4H-[1,4]oxazepino[6,5,4-hi]pyrido[4,3-b]indol-6-amine, bis trifluoroacetic acid salt

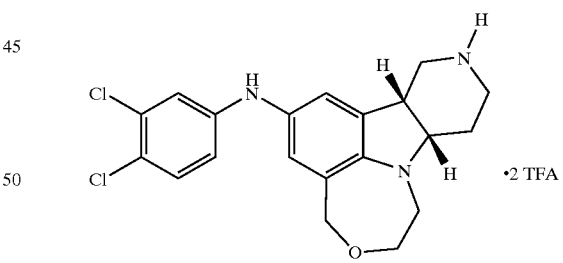

Using 1-bromo-3,4-dichlorobenzene and following the procedures described in EXAMPLE 56, Part C, tert-butyl (7bR, 1 aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 62. $^1$H NMR (300 MHz, DMSO-D6): δ 8.7–8.6 (broad m, 2H), 7.31 (d, J=8.8 Hz, 1H), 6.97–6.93 (m, 2H), 6.81–6.73 (m, 2H), 4.70 (d, J=14.2 Hz, 1H), 4.37 (d, J=14.2 1H), 4.11 (d, J=13.2 Hz, 1H), 3.60 (t, J=11.0 Hz, 1H), 3.57–1.96 (broad m, 10H). LRMS (ES)$^+$: 390.1 (M+H)$^+$.

Example 63

(7bR,11aS)-N-(2,3-dichlorophenyl)-1,2,7b,8,9,10,11,11a-octahydro-4H-[1,4]oxazepino[6,5,4-hi]pyrido[4,3-b]indol-6-amine, bis trifluoroacetic acid salt

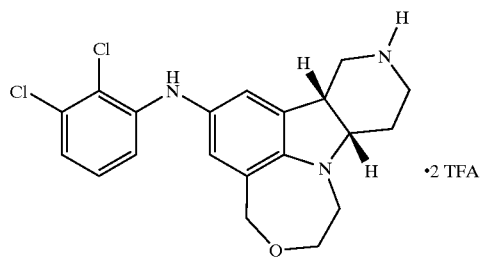

Using 1-bromo-2,3-dichlorobenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H) carboxylate from EXAMPLE 56, Part B was converted into the title compound of EXAMPLE 63. $^1$H NMR (300 MHz, DMSO-D6): δ 8.71-8.56 (broad m, 2H), 7.53 (s, 1H), 7.07 (t, J=8.0 Hz, 1H), 7.06 (s, 1H), 6.90 (d, J=7.7 Hz, 1H), 6.82 (m, 2H), 4.79 (d, J=14.3 Hz, 1H), 4.38 (d, J=14.3 Hz, 1H), 4.12 (d, J=11.5 Hz, 1H), 3.61 (t, J=11.4 Hz, 1H), 3.43–1.91 (broad m, 10H). LRMS (ES)$^+$: 390.2 (M+H)$^+$.

Example 64

(7bR,11aS)-N-(5-fluoro-2-methylphenyl)-1,2,7b,8,9,10,11,11a-octahydro-4H-[1,4]oxazepino[6,5,4-hi]pyrido[4,3-b]indol-6-amine, bis trifluoroacetic acid salt

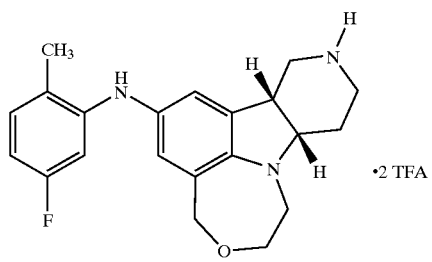

Using 1-bromo-2-methyl-5-fluorobenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 64. $^1$H NMR (300 MHz, DMSO-D6): δ 8.70–8.65 (broad m, 2H), 7.05 (t, J=7.3 Hz, 1H), 6.93 (s, 1H), 6.74 (s, 1H), 6.49 (m, 1H), 6.42 (m, 1H), 4.68 (d, J=14.6 Hz, 1H), 4.38 (d, J=14.6 Hz, 1H), 4.12 (d, J=12.8 Hz, 1H), 3.61 (t, J=11.4 Hz, 1H), 3.48–1.91 (broad m, 13H). LRMS (ES)+: 354.3 (M+H)$^+$.

Example 65

(7bR,11aS)-N-(4-fluoro-2-methylphenyl)-1,2,7b,8,9,10,11,11a-octahydro-4H-[1,4]oxazepino[6,5,4-hi]pyrido[4,3-b]indol-6-amine, bis trifluoroacetic acid salt

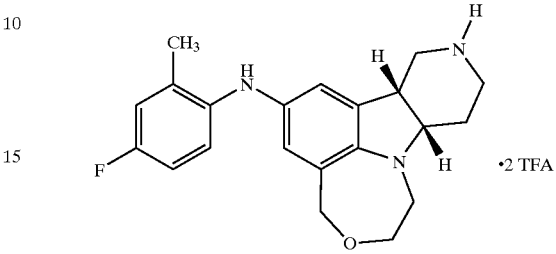

Using 1-bromo-2-methyl-5-fluorobenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 65. $^1$H NMR (300 MHz, DMSO-D6): δ 8.70–8.65 (broad m, 2H), 7.00–6.82 (m, 3H), 6.69 (s, 1H), 6.51 (s, 1H), 4.61 (d, J=14.3 Hz, 1H), 4.34 (d, J=14.3 Hz, 1H), 4.10 (d, J=12.4, 1H), 3.59 (t, J=11.7 Hz, 1H), 3.31–1.94(broad m, 10H). LRMS (ES)$^+$: 354.3 (M+H)$^+$.

Example 66

(7bR,11aS)-N-(2-fluoro-5-methylphenyl)-1,2,7b,8,9,10,11,11a-octahydro-4H-[1,4]oxazepino[16,5,4-hi]pyrido[4,3-b]indol-6-amine, bis trifluoroacetic acid salt

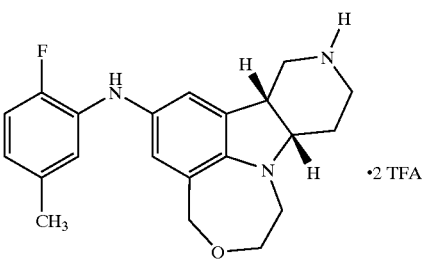

Using 1-bromo-2-fluoro-5-methylbenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 66. $^1$H NMR (300 MHz, DMSO-D6): δ 8.65–8.45 (broad m, 2H), 7.45 (broad s, 1H), 7.01 (m, 1H), 6.98 (s, 1H), 6.82 (d, J=8.4 Hz, 1H), 6.68 (s, 1H), 6.53 (m, 1H), 4.65 (d, J=14.3 Hz, 1H), 4.36 (d, J=14.3 Hz, 1H), 4.11 (d, J=13.2 Hz, 1H), 3.60 (t, J=11.0 Hz, 1H), 3.40–1.95 (broad m, 13H). LRMS (ES)+: 354.3 (M+H)$^+$.

Example 67

(7bR,11aS)-N-[3-(trifluoromethyl)phenyl]-1,2,7b,8,9,10,11,11a-octahydro-4H-[1,4]oxazepino[6,5,4-hi]pyrido[4,3-b]indol-6-amine, bis trifluoroacetic acid salt

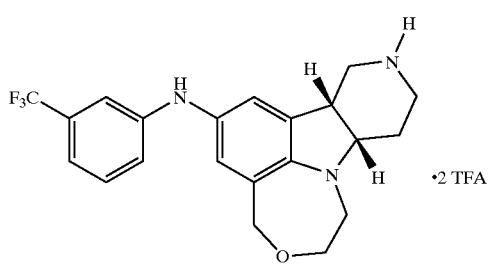

Using 1-bromo-3-(trifluoromethyl)benzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 67. $^1$H NMR (300 MHz, DMSO-D6): δ 8.18 (s, 1H), 7.32 (t, 1H, J=8.4 Hz), 7.10–6.92 (m, 4H), 6.75 (d, 1H, J=1.8 Hz), 4.71 (d, 1H, J=14.2 Hz), 4.37 (d, 1H, J=14.2 Hz), 4.11 (d, 1H, J=12.8 Hz), 3.64–1.88 (broad m, 1H). LRMS (ES)$^+$: 390.2 (M+H)$^+$.

Example 68

(7bR,11aS)-N-[4-chloro-3-(trifluoromethyl)phenyl]-1,2,7b,8,9,10,11,11a-octahydro-4H-[1,4]oxazepino[6,5,4-hi]pyrido[4,3-b]indol-6-amine, bis trifluoroacetic acid salt

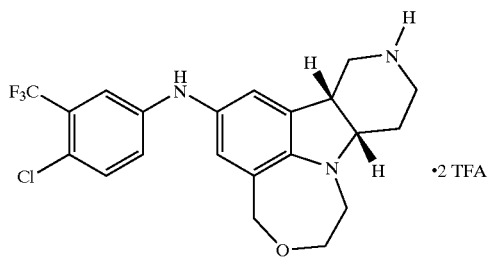

Using 1-bromo-4-chloro-3-(trifluoromethyl)benzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 68. $^1$H NMR (300 MHz, DMSO-D6): δ 8.65–8.32 (broad m, 3H), 7.39 (d, 1H, J=8.8 Hz), 7.17 (d, 1H, J=2.6 Hz), 7.05 (d, 1H, J=8.4 Hz), 6.98 (d, 1H, J=2.2 Hz), 6.75 (d, 1H, J=1.8 Hz),4.70(d, 1H, J=14.6 Hz),4.37(d, 1H, J=14.6 Hz),4.11 (d, 1H, J=13.2 Hz), 3.62 (t, 1H, J=11.7 Hz), 3.43–1.96 (broad m, 10H). LRMS (ES)+: 424.1 (M+H)$^+$.

Example 69

(7bR,11aS)-N-[3,5-(bis-trifluoromethyl)phenyl]-1,2,7b,8,9,10,11,11a-octahydro-4H-[1,4]oxazepino[6,5,4-hi]pyrido[4,3-b]indol-6-amine, bis trifluoroacetic acid salt

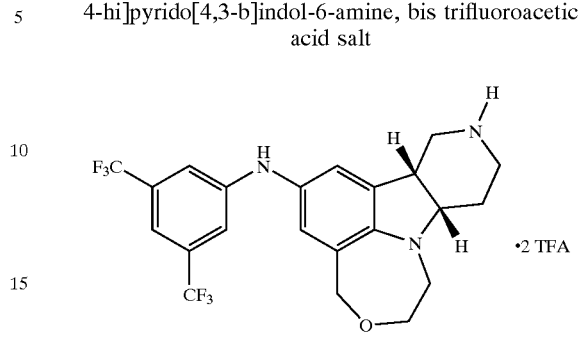

Using 1-bromo-3,5-bis(trifluoromethyl)benzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 69. $^1$H NMR (300 MHz, DMSO-D6): δ 8.61–8.45 (broad s, 3H), 7.25 (s, 2H), 7.19 (s, 1H), 7.04 (d, 1H, J=1.8 Hz), 6.81 (d, 1H, J=1.9 Hz), 4.74 (d, 1H, J=14.3 Hz), 4.38 (d, 1H, J=14.3 Hz), 4.12 (d, 1H, J=13.2 Hz), 3.61 (t, 1H, J=11.7 Hz), 3.46–1.96 (broad m, 10H). LRMS (E S)$^+$: 458.2 (M+H)$^+$.

Example 70

(±)-cis-6-(2,6-difluorophenyl)-1,2,3,4,7b,8,9,10,11,11a-decahydro[1,4]diazepino[6,7,1-hi]pyrido[4,3-b]indole

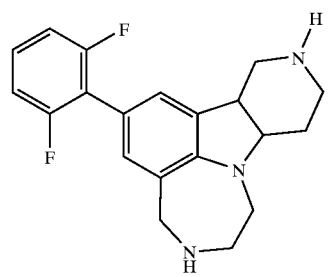

Part A. 2,3,4,5-tetrahydro-1H-pyrido[4,3-b]indole-6-carboxylic acid hydrochloride. To a suspension of 2-hydrazinic benzoic acid (19 g, 100 mmol) and 4-piperidone monohydrate hydrochloric acid (15.3 g, 100 mmol) in acetic acid (150 ml) was added concentrated hydrochloric acid (46 ml). This mixture was heated at reflux for 20 min, then at 80° C. for 18 h. After it was cooled to ~10° C. using an ice bath the solid was collected via vacuum filtration. It was rinsed with cold isopropyl alcohol (2×150 ml) and dried under vacuum at room temperature for 24 h to afford 15.3 g (61%) of the title compound as a light-gray colored powder. $^1$HNMR (300 MHz, CD$_3$OD): δ 7.84 (d, J=8.1 Hz, 1H), 7.69 (d, J=7.5 Hz, 1H), 7.13 (t, J=7.5 Hz, 1H), 4.43 (s, 2H), 3.62 (t, J=6.6 Hz, 2H), 3.20 (t, J=6.6 Hz, 2H) ppm.

Part B. (±)-cis-2-(tert-butoxycarbonyl)-2,3,4,4a,5,9b-hexahydro-1H-pyrido[4,3-b]indole-carboxylic acid.

2,3,4,5-tetrahydro-1H-pyrido[4,3-b]indole-6-carboxylic acid hydrochloride (6.9 g, 27 mmol) was suspended in trifluoroacetic acid (100 ml) and cooled to 0° C. in an ice bath. To this ice-cold suspension was added sodium cyanoborohydride (6.5 g, 94.5 mmol) in 10 portions over 30 minutes. The internal temperature was monitored to be ~ –10° C. during this addition. The resulting mixture was stirred vigorously at ~1° C. for 6 hours. Saturated aqueous potassium carbonate was added until pH of 9 while the reaction was cooled in an ice bath. Tetrahydrofuran (150 ml) was added in one portion. Di-tert-butyl dicarbonate (5.9 g, 27 mmol) was added in 4 portions over 6 minutes. Then the reaction was maintained at room temperature for 1 hour. It was diluted with water (300 ml), acidified with acetic acid until pH 6–7, extracted with chloroform (3×250 ml). The extracts were combined and dried over sodium sulfate. The drying reagent was removed by filtration and the filtrate was concentrated in vacuo. Crude product was given (12 g, >>1100%) as an orange colored foam. Four grams of this sample was purified via silica gel column chromatography eluting with 2:1 hexanes-ethyl acetate to give the title compound (1.1 g, 38%). $^1$H NMR (300 MHz, CDCl$_3$): δ 7.65 (d, J=6.1 Hz, 1H), 7.22 (d, J=6.0 Hz, 1H), 6.63 (t, J=6.0 Hz, 1H), 4.20–4.12 (m, 2H), 3.52–3.30 (m, 4H), 2.02–1.75 (m, 1H), 1.89–1.75 (m, 1H), 1.43 (s, 9H) ppm. LRMS (C1, NH$_3$): 319 (base, M+H)$^+$.

Part C. tert-butyl (±)Cis-6-{[(2-chloroethyl)amino]carbonyl}-1,3,4,4a,5,9b-hexahydro-2H-pyrido[4,3-b]indole-2-carboxylate.

(±)-cis-2-(tert-butoxycarbonyl)-2,3,4,4a,5,9b-hexahydro-1H-pyrido[4,3-b]indole-6-carboxylic acid (64 mg, 0.2 mmol) and 2-chloroethylamine hydrochloride (23 mg, 0.2 mmol) were suspended in acetonitrile (0.4 ml). With stirring N,N-diisopropylethylamine (26 mg, 0.2 mmol) was added in one portion. The resulting mixture was stirred at room temperature for 10 minutes and then cooled in an ice bath. 1,3-dicyclohexylcarbodiimide (45 mg, 0.22 mmol) was added in one portion. The reaction was then stirred between 0° C. and 10° C. for 1.5 hours, then between 10° C. and room temperature for 2.5 hours. The reaction was diluted with diethyl ether (10 ml). Solid was removed by filtration. Filtrate was concentrated in vacuo to give a yellow oil, which was then purified by silica gel column chromatography (eluting with 5:1 hexanes-ethyl acetate) to afford the title compound (34 mg, 45%) as a yellow foam. $^1$HNMR (300 MHz, CDCl$_3$): δ 7.21 (d, J=8.1 Hz, 1H), 7.13 (d, J=7.0 Hz, 1H), 6.80–6.72 (br s, 1H), 6.58 (t, J=7.7 Hz, 1H), 6.37–6.30 (br s, 1H), 4.114.03 (m, 1H), 3.82–3.15 (m, 9H), 1.90–1.60 (m, 2H), 1.41 (s, 9H) ppm. LRMS (CI, NH$_3$) 380 (30%, M+H)$^+$.

Part D. tert-butyl (±)-cis-4-oxo-1,2,3,4,7b,10,11,11a-octahydro[1,4]diazepino[6,7,1-hi]pyrido[4,3-b]indol-9(8H)-carboxylate.

tert-butyl (±)-cis-6-{[(2-chloroethyl)amino]carbonyl}-1,3,4,4a,5,9b-hexahydro-2H-pyrido[4,3-b]indole-2-carboxylate (17 mg, 0.06 mmol), potassium iodide (1 crystal) and potassium hydroxide (17 mg, 0.3 mmol) were mixed with N,N-dimethylformamide (2 ml). The mixture was then heated at reflux for 3 hours. The reaction was then diluted with diethyl ether (2 ml). The solid was removed by filtration and the filtrate was concentrated in vacuo. The resulting residue (18 mg, 88%) was the title compound. $^1$H NMR (300 MHz, CDCl$_3$): δ 7.45 (d, J=7.6 Hz, 1H), 7.14 (d, J=7.4 Hz, 1H), 6.64 (t, J=7.7 Hz, 1H), 6.39–6.32 (br s, 1H), 3.34 (dd, J=10.2, 9.2 Hz, 2H), 4.19–4.00 (m, 3H), 3.51–3.30 (m, 5H), 2.00–1.79 (m, 2H), 1.44 (s, 9H) ppm.

Part E. tert-butyl (±)-cis-6-bromo-4-oxo-1,2,3,4,7b,10,11,11a-octahydro[1,4]diazepino[6,7,1-hi]pyrido[4,3-b]indol-9(8H)Carboxylate.

tert-butyl (±)-cis-4-oxo-1,2,3,4,7b, 10,11,11a-octahydro[1,4]diazepino[6,7,1-hi]pyrido[4,3-b]indol-9(8H)-carboxylate (470 mg, 1.37 mmol) was dissolved in anhydrous N,N-methylformamide (5 ml) and cooled to 0° C. in an ice bath. Then N-bromosuccinimide (245 mg, 1.37 mmol) in anhydrous N,N-dimethylformamide (3.4 ml) was added dropwise over 15 minutes. The reaction was allowed to stir at 0° C. for 4 hours. The reaction was diluted with ethyl acetate (100 ml) and water (50 ml). Organic layer was separated and washed with water (2×100 ml) and brine (1×100 ml). The organic layer was dried over magnesium sulfate and filtered. The filtrate was concentrated under reduced pressure to give title compound as an oil (540 mg, 93.4%). $^1$H NMR (CDCl$_3$, 300 MHz): δ 7.55 (d, 1H, J=1.5 Hz); 7.19 (s, 1H); 6.42 (s-broad, 1H); 4.34 (t, 2H, J=9.4 Hz); 4.16–4.00 (m, 3H); 3.86–3.24 (m, 5H); 1.97–1.88 (m, 1H); 1.83–1.73 (m, 1H); 1.43 (s, 9H) ppm. LRMS (ApCI): 422 (base, M+H)$^+$.

Part F. (±)-cis-6-(2,6-difluorophenyl)-2,3,7b,8,9,10,11,11a-octahydro[1,4]diazepino[6,7,1-hi]pyrido[4,3-b]indol-4(1H) one.

tert-butyl (±)-cis-6-bromo-4-oxo-1,2,3,4,7b,10,11,11a-octahydro[1,4]diazepino[6,7,1-hi]pyrido[4,3-b]indol-9(8H)-carboxylate (500 mg, 1.19 mmol), triphenylphosphine (62 mg, 0.238 mmol), copper (1) bromide (34 mg, 0.238 mmol), and dichlorobis(triphenylphosphine)palladium (II) were dissolved in anhydrous N,N-dimethylformamide (20 ml) and degassed under nitrogen and stirred for 10 minutes. Then 2,6-difluorophenylstannane (1.5 eq, 497 mg) in anhydrous N,N-dimethylformamide (5 ml) was added via cannula and then heated to 60° C. for 30 minutes. Another portion of 2,6-difluorostannane (1.5 eq, 497 mg) in anhydrous N,N-dimethylformamide (2.5 ml) was added via cannula and then heated to 140° C. for 10 minutes. After 10 minutes a final portion of 2,6-difluorostannane (1.5 eq, 497 mg) in anhydrous N,N-dimethylformamide (2.5 ml) was added via cannula and reaction allowed to stir at 140° C. for 1 hour. The reaction was cooled to room temperature, diluted with ethyl acetate (200 ml) and washed with water (4×260 ml) and brine (2×150 ml). The organic layer was dried over magnesium sulfate and filtered. The filtrate was concentrated under reduced pressure to give an oil. Purified oil via silica gel column chromatography, eluting with (10%) ethyl acetate in hexanes. Fractions were collected and concentrated under reduced pressure to give an oil. This oil was purified further by high pressure liquid chromatography on a Chiralcel OD column, eluted with 2% ethyl alcohol in hexanes (0.05% diethyl amine modifier) at 7 ml/min to afford a colorless oil. The oil was dissolved in chloroform (10 ml) and cooled to 0° C. in an ice bath and trifluoroacetic acid (2 ml) was added and stirred for 3 hours, during which time reaction warmed to room temperature. This was basified with concentrated ammonium hydroxide to pH 12, then extracted with chloroform (3×20 ml). Organics were seperated and washed with brine and dried over magnesium sulfate. Organics were filtered and then concentrated under reduced pressure to give the title compound as an oil (21 mg, 5%). $^1$H NMR (CDCl$_3$, 300 MHz): δ 7.91 (d, 1H, J=1.5 Hz); 7.83 (s, 1H); 7.74 (s, 1H); 6.90 (t, 2H, J=8.1 Hz); 4.32 (t, 2H, J=9.6 Hz); 4.04 (t, 2H, J=9.54 Hz); 3.47 (s-broad, 2H); 3.31–3.04 (m, 3H); 3.08–3.04 (m, 1H); 2.23–2.10 (m, 1H); 2.08–2.03 (m, 1H) ppm.

Part G. (±)-cis-6-(2,6-difluorophenyl)-1,2,3,4,7b,8,9,10,11,11a-decahydro[1,4]diazepino[6,7,1-hi]pyrido[4,3-b]indole.

(±)-cis-6-(2,6-difluorophenyl)-2,3,7b,8,9,10,11,11a-octahydro[1,4]diazepino[6,7,1-hi]pyrido[4,3-b]indol-4 (1H)-one (16 mg, 0.045 mmol) was dissolved in borane-tetrahydrofuran complex (2 ml) and then heated to 78° C. for 12 hours. Then reaction was concentrated under reduced pressure to a residue. The residue was dissolved in concentrated hydrochloric acid (2 ml) and heated at 100° C. for 7 hours. This was cooled to room temperature and basified to pH=12. Then extracted with chloroform (3×20 ml) and concentrated under reduced pressure to give the title compound of EXAMPLE 70 (8 mg, 38%). $^1$H NMR (CDCl$_3$,300

MHz): δ 7.16–7.04 (m, 2H); 6.93–6.83 (m, 3H); 3.84–3.50 (m, 4H); 3.20–3.00 (m, 3H); 2.77–2.68 (m, 1H); 2.42 (s-broad, 4H); 2.18–1.96 (m, 2H); 1.86–1.77 (m, 1H); 1.69–1.60 (m, 1H) ppm.

Example 71

(±)-cis-6-(2,4-dichlorophenyl)-1,2,3,4,7b,8,9,10,11,11a-decahydro[1,4]diazepino[6,7,1-hi]pyrido[4,3-b]indole

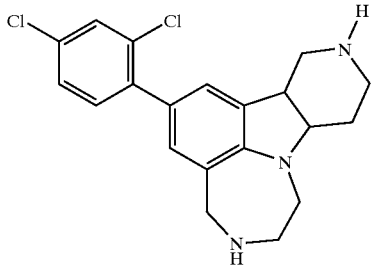

Part A. (±)Cis-6-(2,4-dichlorophenyl)-2,3,7b,8,9,10,11,11a-octahydro[1,4]diazepino[6,7,1-hi]pyrido[4,3-b]indol-4(1H)-one.

tert-butyl (±)Cis-bromo-4-oxo-1,2,3,4,7b, 10,11,11a-octahydro[1,4]diazepino[6,7,1-hi]pyrido[4,3-b]indol-9(8H)-carboxylate from EXAMPLE 70, Part E (150 mg, 0.356 mmol), 2,4-dichlorophenylboronic acid (82 mg, 0.430 mmol) and barium hydroxide (170 mg, 0.540 mmol) were dissolved in DME (7 mL) and water (4 mL), and degassed for 10 minutes under nitrogen. Tetrakis(triphenylphosphine) palladium (0) (10 mg, 0.007 mmol) was added and the reaction was heated to 90° C. for 13 h. The reaction was cooled to room temperature and diluted with ethyl acetate (20 mL) and water (20 mL). The organic layer was separated and dried over magnesium sulfate, filtered and concentrated under reduced pressure to give an oil. The oil was purified by silica gel column chromatography (13% ethyl acetate, hexanes).). Fractions were collected, concentrated to a solid, then dissolved in 20% TFA/CHCl$_3$ and stirred for 1 hour. The reaction solution was cooled to 0° C. in an ice bath, and basified to pH=10 with concentrated NH$_4$OH. This was extracted with CHCl$_3$ (3×15 ml), organics collected, dried over MgSO$_4$ and concentrated under reduced pressure to give to give the title compound. $^1$H NMR (CDCl$_3$, 300 MHz): δ 7.52 (d, 1H, J=1.8 Hz), 7.44 (d, 1H, J=1.8 Hz), 7.26–7.20 (m, 2H), 6.45 (s, 1H), 4.34 (t, 2H, J=9.2 Hz), 4.14–4.06 (m, 2H), 3.18–2.95 (m, 3H), 2.88–2.75 (m, 3H), 2.14 (s-br, 1H), 1.96–1.79 (m, 2H) ppm.

Part B. (±)-cis-6-(2,4-dichlorophenyl)-1,2,3,4,7b,8,9,10,11,11a-decahydro[1,4]diazepino[6,7,1-hi]pyrido[4,3-b]indole.

(±)-cis-62,4-dichlorophenyl)-2,3,7b,8,9,10,11,11a-octahydro[1,4]diazepino[6,7,1-hi]pyrido[4,3-b]indol-4(1H) one (43 mg, 0.111 mmol) was dissolved in borane-THF complex (3 ml, 1M) and heated at 78° C. for 2 hrs. The reaction was cooled to room temperature and concentrated under reduced pressure to a wet semi-solid. To this semi-solid was added conc. HCl (5 ml) and heated at 100° C. for 3 hours. This mixture was cooled to room temperature and basified to pH=12 with conc. NH$_4$OH, and then extracted with CHCl$_3$ (3×25 ml). The organic layer was dried over magnesium sulfate, filtered and concentrated under reduced pressure to give the title compound of EXAMPLE 71 (23 mg, 55%). $^1$H NMR (CD$_3$OD, 300 MHz): δ 7.55 (s, 1H), 7.37–7.32 (m, 3H), 7.29 (s, 1H), 4.24 (s, 2H), 4.154.05 (m, 1H), 3.87–3.80 (m, 2H), 3.60–3.37 (m, 4H), 3.22–3.16 (m, 2H), 2.91–2.83 (m, 1H), 2.21–2.16 (m, 2H) ppm.

Example 72

(7bR,11aS)-N-(1-naphthyl)-1,2,7b,8,9,10,11,11a-octahydro-4H-[1,4]oxazepino[6,5,4-hi]pyrido[[4,3-b]indol-6-amine, bis trifluoroacetic acid salt

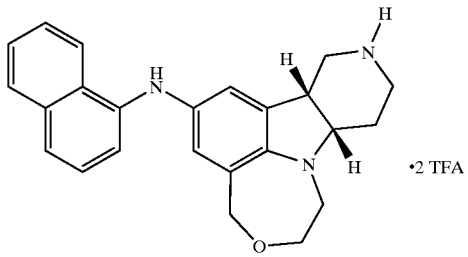

Using 1-bromonapthalene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)Carboxylate from EXAMPLE 56, Part B was converted into the title compound of EXAMPLE 72. $^1$H NMR (300 MHz, DMSO-D6): δ 8.70–8.55 (broad m, 2H), 8.20 (d, J=7.3 Hz, 1H), 7.82 (d, J=7.0 Hz, 1H), 7.47 (m, 2H), 7.31 (m, 2H), 6.98 (m, 2H), 6.79 (s, 1H), 4.66 (d, J=14.7 Hz, 1H), 4.38 (d, J=14.7 Hz, 1H), 4.13 (d, J=12.9 Hz, 1H), 3.61 (t, J=11.7 Hz, 1H), 3.41–1.96 (broad m, 10H). LRMS (ES)+: 358.3 (M+H)$^+$.

Example 73

(7bR,11aS)-N-[4-(trifluoromethyl)phenyl]-1,2,7b,8,9,10,11,11a-octahydro-4H-1,4]oxazepino[6,5,4-hi]pyrido[4,3-b]indol-6-amine, bis trifluoroacetic acid salt

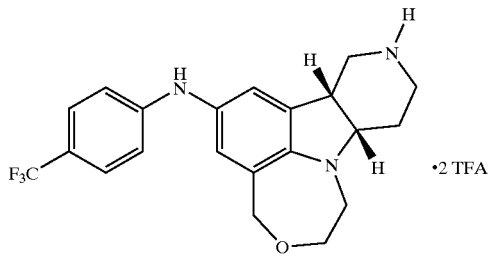

Using 1-bromo-4-(trifluoromethyl)benzene and following the procedures described in EXAMPLE 56, Part C, tert-butyl (7bR,11aS)$_6$-amino-1,2,7b,10, 11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 73. $^1$H NMR (300 MHz DMSO-D6): δ 8.65–8.50 (broad m, 2H), 8.36 (broad s, 1H), 7.41 (d, 3=8.4 Hz, 2H), 7.01 (s, 1H), 6.91 (d, J=8.5 Hz 2H), 6.78 (s, 1H), 4.71 (d, J=14.7 Hz, 1H), 4.37 (d, J=14.7 Hz, 1H), 4.11 (d, J=13.2 Hz, 1H), 3.61 (t, J=11.0 Hz, 1H), 3.41–1.96 (broad m, 10H). LRMS (ES)+: 390.1 (M+H)$^+$.

Example 74

(7bR,11aS)-N-(3,4-dimethylphenyl)-1,2,7b,8,9,10,11,11a-octahydro-4H-[1,4]oxazepino[6,5,4-hi]pyrido[4,3-b]indol-6-amine, bis trifluoroacetic acid salt

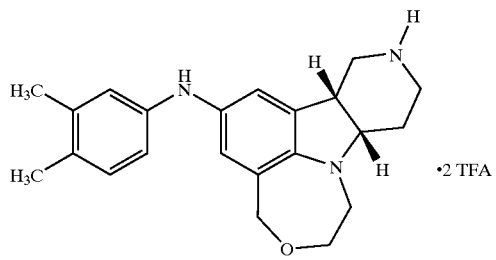

Using 4-bromo-1,2-dimethylbenzene and following the procedures described in EXAMPLE 56, Part C, tert-butyl (7bR,11)6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 74. $^1$H NMR (300 MHz, DMSO-D6): δ 8.70-8.50 (broad m, 2H), 6.90 (m, 1H), 6.84 (m, 1H), 6.70 (m, 2H), 6.51 (s, 1H), 4.60 (d, J=14.3 Hz, 1H), 4.35 (d, J=14.3 Hz, 1H), 4.10 (d, J=11.7 Hz, 1H), 3.58 (t, J=11.0 Hz, 1H), 3.29–1.93 (broad m, 16H). LRMS (ES)+: 350.2 (M+H)$^+$.

Example 75

(7bR,11aS)-N-[2-trifluoromethyl)phenyl]-1,2,7b,8,9,10,11,11a-octahydro-4H-[1,4]oxazepino[6,5,4-hi]pyrido[4,3-b]indol-6-amine, bis trifluoroacetic acid salt

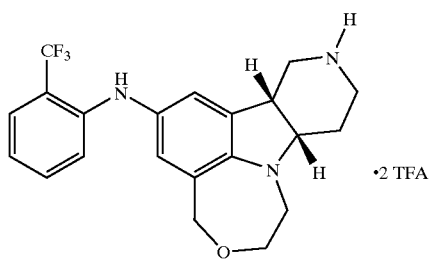

Using 1-bromo-2-(trifluoromethyl)benzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 75. $^1$H NMR (300 MHz, DMSO-D6): δ 8.75–8.55 (broad m, 2H), 7.50 (d, J=8.1 Hz, 1H), 7.36 (t, 3=7.7 Hz, 1H), 7.12 (broad s, 1H), 6.96 (m, 2H), 6.86 (t, J=7.3 Hz, 1H), 6.79 (s, 1H), 4.77 (d, J=14.3 Hz, 1H), 4.36 (d, J=14.3 Hz, 1H), 4.11 (d, J=12.8 Hz, 1H), 3.61 (t, J=11.4 Hz, 1H), 3.42–1.91 (broad m, 10H). LRMS (ES)+: 390.1 (M+H)$^+$.

Example 76

(7bR,11aS)-N-(2,3,5-trichlorophenyl)-1,2,7b,8,9,10,11,11a-octahydro-4H-[1,4]oxazepino[6,5,4-hi]pyrido[4,3-b]indol-6-amine, bis trifluoroacetic acid salt

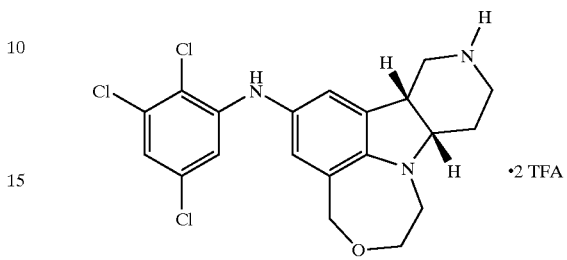

Using 1-bromo-2,3,5-trichlorobenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H) carboxylate from EXAMPLE 56, Part B was converted into the title compound of EXAMPLE 76. $^1$HNMR (300 MHz, DMSO-D6): δ 8.70–8.45 (broad m, 2H), 7.83 (s, 1H), 7.02 (m, 2H), 6.86 (d, J=1.8 Hz, 1H), 6.58 (m, 1H), 4.73 (d, J=14.6 Hz, 1H), 4.38 (d, J=14.3 Hz, 1H), 4.12 (d, J=13.2 Hz, 1H), 3.62 (t, J=11.7 Hz, 1H), 3.46–1.92 (broad m, 10H). LRMS (ES)+: 424.0 (M+H)$^+$.

Example 77

(7bR,11aS)-N-(2-naphthyl)-1,2,7b,8,9,10,11,11a-octahydro-4H-[1,4]oxazepino[6,5,4-hi]pyrido[4,3-b]indol-6-amine, bis trifluoroacetic acid salt

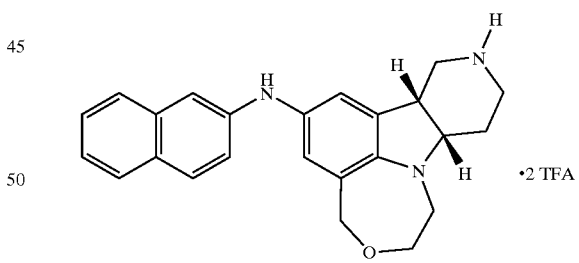

Using 2-bromonapthalene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 77. $^1$HNMR (300 MHz, DMSO-D6): δ 8.70–8.55 (broad m, 2H), 7.70 (m, 2H), 7.57 (d, J=8.4 Hz, 1H), 7.31 (t, J=7.3 Hz, 1H), 7.13 (m, 3H), 7.05 (s, 1H), 6.81 (s, 1H), 4.71 (d, J=14.7 Hz, 1H), 4.39 (d, J=14.7 Hz, 1H), 4.13 (d, J=12.9 Hz, 1H), 3.62 (t, J=11.3 Hz, 1H), 3.46–1.97 (broad m, 10H). LRMS (ES)+: 372.2 (M+H)$^+$.

Example 78

(7bR,11aS)-N-(4-chloro-2-fluorophenyl)-1,2,7b,8,9,10,11,11a-octahydro-4H-[1,4]oxazepino[6,5,4-hi]pyrido[4,3-b]indolamine, bis trifluoroacetic acid salt

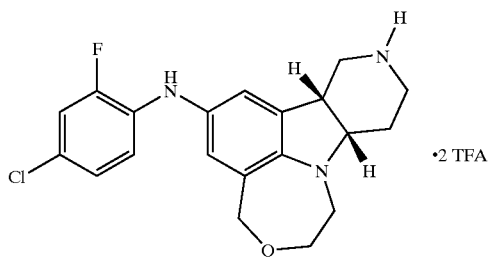

Using 1-bromo-4-chloro-2-fluorobenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 78. $^1$H NMR (300 MHz, DMSO-D6): δ 8.60–8.52 (broad m, 2H), 7.70 (broad s, 1H), 7.28 (m, 1H), 7.05–6.96 (m, 2H), 6.90 (s, 1H), 6.71 (s, 1H), 4.66 (d, J=14.3 Hz, 1H), 4.36 (d, J=14.3 Hz, 1H), 4.15 (m, 1H), 3.60 (t, J=11.4 Hz, 1H), 3.42–1.90 (broad m, 10H). LRMS (ES)+: 374.3 (M+H)$^+$.

Example 79 methyl 4-[(7bR,11aS)1,2,7b,8,9,10,11,11a-octahydro-4H-[1,4]oxazepino[6,5,4-hi]pyrido[4,3-b]indol-6-ylamino]-2-methylbenzoate, bis trifluoroacetic acid salt

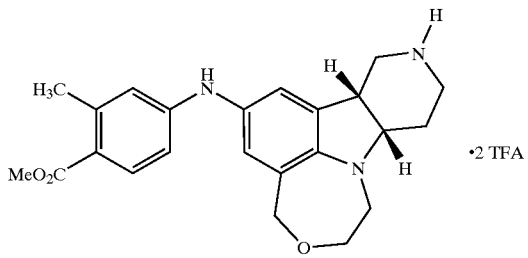

Using methyl 4-bromo-2-methylbenzoate and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 79. $^1$H NMR (300 MHz, DMSO-D6): δ 8.75-8.64 (broad m, 2H), 7.65 (s, 1H), 7.58 (d, J=6.6 Hz, 1H), 7.55 (broad s, 1H), 7.00 (s, 1H), 6.79 (m, 2H), 4.71 (d, J=14.3 Hz, 1H), 4.38 (d, J=14.3 Hz, 1H), 4.12 (d, J=12.5 Hz, 1H), 3.73 (s, 3H), 3.62 (t, J=11.8 Hz, 1H), 3.43–1.97 (broad m, 13H)). LRMS (ES)+: 394.3 (M+H)$^+$.

Example 80

(7bR,11aS)-N-(2,5-dimethoxyphenyl)-1,2,7b,8,9,10,11,11a-octahydro-4H-[1,4]oxazepino[6,5,4-hi]pyrido[4,3-b]indol-6-amine, bis trifluoroacetic acid salt

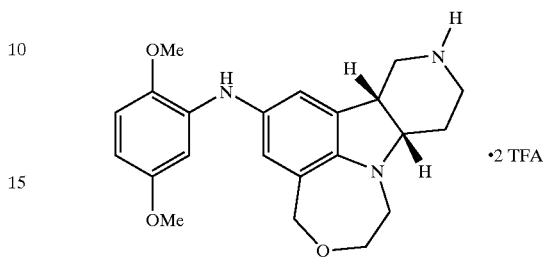

Using 2-bromo-1,4-dimethoxybenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)Carboxylate from EXAMPLE 56, Part B was converted into the title compound of EXAMPLE 80. $^1$H NMR (300 MHz, DMSO-D6): δ 8.63–8.54 (broad m, 2H), 6.97 (s, 1H), 7.09 (m, 1H), 6.82–6.76 (m, 2H), 6.46 (s, 1H), 6.23 (dd, J$_1$=2.6 Hz, J$_2$=8.5 Hz, 1H), 4.65 (d, J=14.3 Hz, 1H), 4.36 (d, J=14.3 Hz, 1H), 4.11 (d, J=13.2 Hz, 1H), 3.73 (s, 3H), 3.64–1.95 (broad m, 14H). LRMS (ES)+: 382.3 (M+H)$^+$.

Example 81

(7bR,11aS)-N-(2,4-difluorophenyl)-1,2,7b,8,9,10,11,11a-octahydro-4H-[1,4]oxazepino[6,5,4-hi]pyrido[4,3-b]indol-6-amine, bis trifluoroacetic acid salt

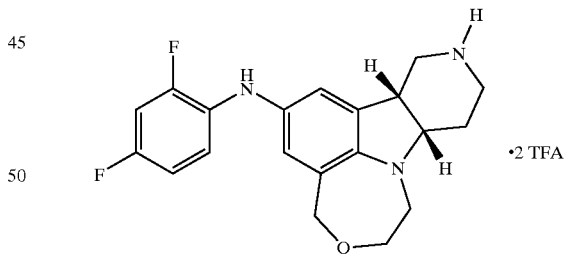

Using 1-bromo-2,4-difluorobenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)Carboxylate from EXAMPLE 56, Part B was converted into the title compound of EXAMPLE 81. $^1$HNMR (300 MHz, DMSO-D6): δ 8.62–8.49 (broad m, 2H), 7.47 (broad s, 1H), 7.18 (m, 1H), 7.09 (m, 1H), 6.86 (m, 1H), 6.80 (s, 1H), 6.61 (s, 1H), 4.64 (d, J=14.3 Hz, 1H), 4.35 (d, J=14.3 Hz, 1H), 4.10 (d, J=13.2 Hz, 1H), 3.59 (t, J=12.1 Hz, 1H), 3.38–1.90 (broad m, 10H). LRMS (ES)+: 358.3 (M+H)$^+$.

Example 82

(7bR,11aS)-N-(2,5-difluorophenyl)-1,2,7b,8,9,10,11,11a-octahydro-4H-[1,4]oxazepino[6,5,4-hi]pyrido[4,3-b]indol-6-amine, bis trifluoroacetic acid salt

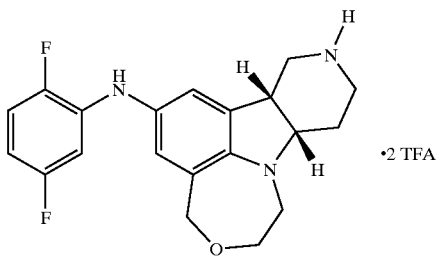

Using 2-bromo-1,4-difluorobenzene and following the procedures described in EXAMPLE 56, Part C, tert-butyl (7bR,11aS)$_6$-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 82. $^1$H NMR (300 MHz, DMSO-D6): δ 8.65–8.58 (broad m, 2H), 7.82 (broad s, 1H), 7.14 (m, 1H), 6.99 (s, 1H), 6.77 (s, 1H), 6.67 (m, 1H), 6.45 (m, 1H), 4.69 (d, J=14.3 Hz, 1H), 4.38 (d, J=14.3 Hz, 1H), 4.11 (d, J=12.8 Hz, 1H), 3.61 (t, J=11.3 Hz, 1H), 3.45–1.91 (broad m, 10 H). LRMS (S)+: 358.3 (M+H)$^+$.

Example 83

5-[(7bR,11aS)-1,2,7b,8,9,10,11,11a-octahydro-4H-[1,4]oxazepino[6,5,4-hi]pyrido[4,3-b]indol-6-ylamino]-2-methoxybenzaldehyde, bis trifluoroacetic acid salt

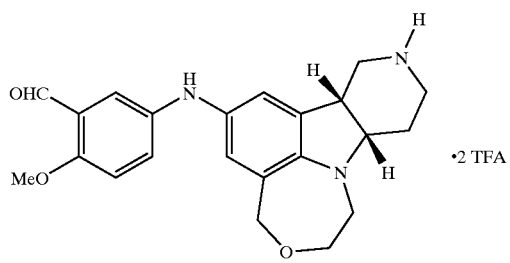

Using 5-bromo-2-methoxybenzaldehyde and following the procedures described in EXAMPLE 56, Part C, tert-butyl (7bR,11as)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 83. $^1$H NMR (300 MHz, DMSO-D6): δ 9.90 (s, 1H), 8.62–8.47 (broad m, 2H), 7.60 (m, 1H), 7.58 (t, J=1.5 Hz, 1H), 7.19 (s, 1H), 7.13 (d, J=8.5 Hz, 1H), 7.02 (t, J=8.5 Hz, 1H), 4.64 (d, J=14.3 Hz, 1H), 4.35 (d, J=14.3 Hz, 1H), 4.10 (d, J=13.2 Hz, 1H), 3.86 (s, 3H) 3.59–1.90 (broad m, 10H). LRMS (ES)+: 380.4 (M+H)$^+$.

Example 84

(7bR,11aS)-N-(4-chloro-2-methylphenyl)-1,2,7b,8,9,10,11,11a-octahydro-4H-[1,4]oxazepino[6,5,4-hi]pyrido[4,3-b]indol-4-amine, bis trifluoroacetic acid salt

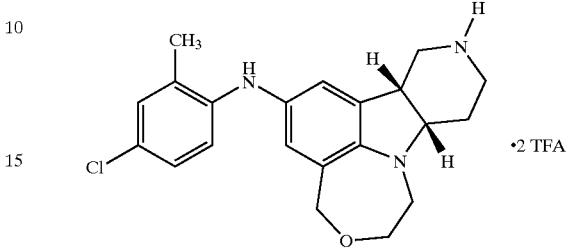

Using 1-bromo-4-chloro-2-methylbenzene and following the procedures described in EXAMPLE 56, Part C, tert-butyl (7bR,11aS)-6-amino-1,2,7b,10,11,11a-hexahydro-4H1-[1,4]oxazepino[6,5,4-hi]pyrido[4,3-b]indole-9(8H)-carboxylate from EXAMPLE 56, Part B was converted into the title compound of EXAMPLE 84. $^1$H NMR (300 MHz, DMSO-D6): δ 8.64-8.53 (broad m, 2H), 7.11 (s, 1H), 7.00 (d, J=8.4 Hz, 1H), 6.84 (m, 2H), 6.63 (s, 1H), 4.63 (d, 3=13.9 Hz, 1H), 4.34 (d, J=14.3 Hz, 1H), 4.09 (d, J=12.8 Hz, 1H), 3.58 (t, J=11.3 Hz, 1H), 3.32–1.93 (broad m, 13H). LRMS (ES)+: 370.3 (M+H)$_4$.

Example 85

(7bR,11aS)-N-[1,1'-biphenyl]-2-yl-1,2,7b,8,9,10,11,11a-octahydro-4H-[1,4]oxazepino[6,5,4-hi]pyrido[4,3-b]indol-6-amine, bis trifluoroacetic acid salt

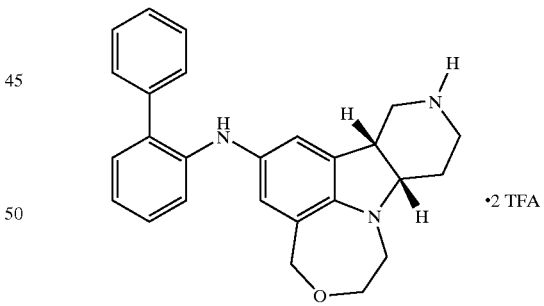

Using 2-bromo-1,1'-biphenyl and following the procedures described in EXAMPLE 56, Part C, tert-butyl (7bR,11)-amino-1,2,7b,10,11,11 a-hexahydro-4H-[1,4]oxazepino[6,5,4-hi]pyrido[4,3-b]indole-9(8H)Carboxylate from EXAMPLE 56, Part B was converted into the title compound of EXAMPLE 85. $^1$H NMR (300 MHz, DMSO-D6): δ 8.63–8.50 (broad m, 2H), 7.41–7.04 (broad m, 8H), 6.90 (t, J=7.3 Hz, 1H), 6.74 (s, 1H), 6.57 (s, 1H), 4.56 (d, J=14.3 Hz, 1H), 4.30 (d, J=14.3 Hz, 1H), 4.07 (d, J=12.5 Hz, 1H), 3.55 (t, J=11.0 Hz, 1H), 3.26–1.91 (broad m, 10H). LRMS (ES)$^+$: 398.2 (M+H)$^+$.

Example 86

4-[(7bR,11aS)-1,2,7b,8,9,10,11,11a-octahydro-4H-[1,4]oxazepino[6,5,4 hi]pyrido[4,3-b]indol-6-ylamino]-3-methoxybenzonitrile, bis-trifluoroacetic acid salt

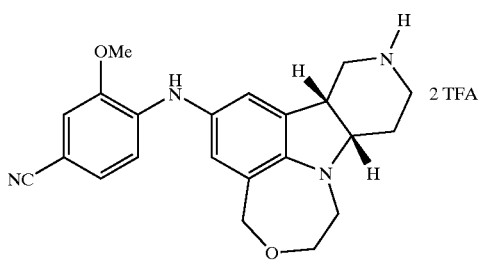

Using 4-bromo-3-methoxybenzonitrile and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 86. $^1$H NMR (dmso-D$_6$) δ: 8.6–8.5 (m, 2H), 7.32 (broad s, 1H), 7.13 (dd, 1H, J=8.3, 2.0 Hz), 7.04–6.98 (m, 3H), 6.78 (d, 1H, J=2.2 Hz), 4.52 (ABq, 2H, J$_{AB}$=14.5 Hz), 4.10 (app d, J=12.5 Hz, 1H), 3.87 (s, 3H), 3.59 (app t, 1H), 3.42–3.10 (m, 5H), 2.98–2.90 (m, 1H), 2.59 (t, 1H), 2.44–2.38 (m, 1H), 2.20–2.10 (m, 1H), 2.02–1.90 (m, 1H). LRMS (ES)+: 377.2 (M+H)$^+$.

Example 87

(7bR,11aS)-N-[2-fluoro-5-(trifluoromethyl)phenyl]-1,2,7b,8,9,10,11,11a-octahydro-4H-[1,4]oxazepino[6,5,4-hi]pyrido[4,3-b]indol-6-amine, bis-trifluoroacetic acid salt

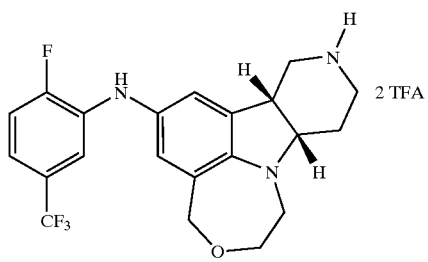

Using 3-bromo-4-fluorobenzotrifluoride and following the procedures described in EXAMPLE 56, Part C, tert-butyl (7bR,11aS)$_4$-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 87. $^1$H NMR (dmso-D$_6$) δ: 8.70–8.45 (m, 2H), 7.97 (broad s, 1H), 7.32 (dd, 1H, J=11.2, 8.3 Hz), 7.09 (dd, 1H, J=7.9, 2.0 Hz), 7.05–7.00 (m, 1H), 6.96 (d, 1H, J=2.2 Hz), 6.76 (d, 1H, J=2.2 Hz), 4.52 (ABq, 2H, J$_{AB}$=14.5 Hz), 4.10 (app d, 1H, J=12.8 Hz), 3.59 (app t, 1H), 3.42–3.25 (m, 4H), 3.21–3.15 (m, 1H), 3.02–2.93 (m, 1H), 2.59 (t, 1H), 2.44–2.36 (m, 1H), 2.20–2.10 (m, 1H), 2.02–1.90 (m, 1H). LRMS (ES)+: 408.1 (M+H)$^+$.

Example 88

4-[(7bR,11aS)1,2,7b,8,9,10,11,11a-octahydro-4H-[1,4]oxazepino[6,5,4-hi]pyrido[4,3-b]indol-6-ylamino]-3-methoxybenzaldehyde, bis-trifluoroacetic acid salt

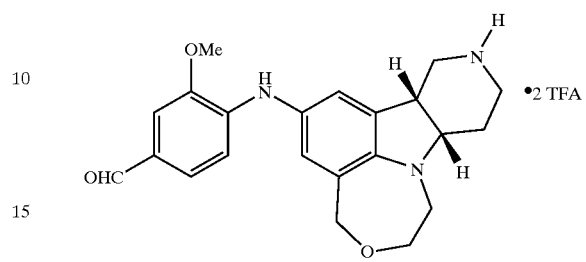

Using 4-bromo-3-methoxybenzaldehyde and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 88. $^1$H NMR (dmso-D$_6$) δ: 9.71 (s, 1H), 8.70–8.50 (m, 2H), 7.33–7.28 (m, 2H), 7.11 (d, 1H, J=8.1 Hz), 7.00 (d, 1H, J=1.4 Hz), 6.81 (d, 1H, J=1.8 Hz), 5.05 (broad s, 1H), 4.53 (ABq, 2H, J$_{AB}$=14.3 Hz), 4.12 (app d, 1H, J=12.8 Hz), 3.92 (s, 3H), 3.61 (app t, 1H), 3.42–3.25 (m, 4H), 3.24–3.18 (m, 1H), 3.02–2.93 (m, 1H), 2.61 (t, 1H), 2.45–2.38 (m, 1H), 2.20–2.10 (m, 1H), 2.05–1.92 (m, 1H). LRMS (ES)+: 380.2 (M+H)$^+$.

Example 89

(7bR,11aS)-N-(4-methyl-3-pyridinyl)-1,2,7b,8,9,10,11,11a-octahydro-4H-[1,4]oxazepino[6,5,4-hi]pyrido[4,3-b]indol-6-amine, bis-trifluoroacetic acid salt

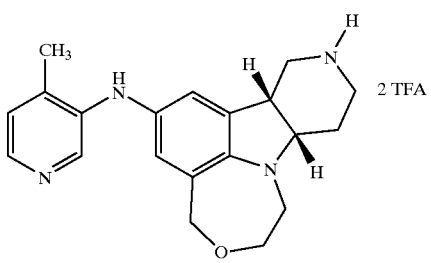

Using 3-bromo-4-methylpyridine and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 89. $^1$H NMR (dmso-D$_6$) δ: 8.90–8.70 (m, 2H), 8.12 (d, 1H, J=5.8 Hz), 8.05 (s, 1H), 8.00 (s, 1H), 7.73 (d, 1H, J=5.8 Hz), 7.08 (d, 1H, J=1.9 Hz), 6.91 (d, 1H, J=1.8 Hz), 4.57 (ABq, 2H, J$_{AB}$=14.0 Hz), 4.12 (app d, 1H, J=12.8 Hz), 3.64 (app t, 1H), 3.50–3.30 (m, 4H), 3.25–3.18 (m, 1H), 3.05–2.90 (m, 1H), 2.64 (app t, 1H), 2.42 (s, 3H), 2.45–2.38 (m, 1H), 2.22–2.12 (m, 1H), 2.05–1.95 (m, 1H). LRMS (ES)+: 337.2 (M+H)$^+$.

Example 90

(7bR,11aS)-6-(3,4-dihydro-1-(2H)-quinolinyl)-1,2,7b,8,9,10,11 a-octahydro-4H-[1,4]oxazepino[6,5,4-hi]pyrido[4,3-b]indole, bis-trifluoroacetic acid salt

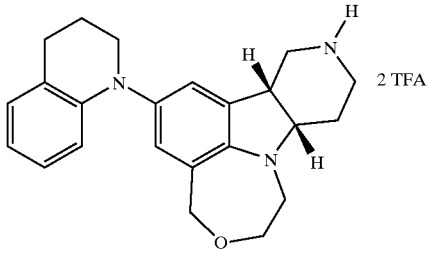

To a solution of tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B (0.40 g, 1.15 mmol), methyl 3-(2-bromophenyl)propionate (0.31 g, 1.3 mmol), BINAP (0.004 g, 0.007 mmol), sodium-t-butoxide, (0.29 g, 3.01 mmol) and Pd$_2$ DBA$_3$ (0.0021 g, 0.0023 mmol) in 10 ml of degassed toluene was heated for 3 h at 90° C. The solution was cooled and filtered through a pad of silica gel and eluted with EtOAc. The volatiles were removed under reduced pressure and the product was purified by prep HPLC (C18 reverse phase column, elution with a H$_2$O/CH$_3$CN gradient with 0.5% TFA) and lyophilized to afford an amide as an unexpected product. LRMS (ES)+: 558.1 (M+H)+. This material was dissolved in tetrahydrofuran and treated with borane THF complex (3.57 mL of a 1M solution in THF, 3.57 mmol). The resulting mixture was stirred at reflux for 3 h. The solution was cooled to 0° C., quenched with methanol and filtered through a pad of silica gel. The volatiles were removed under reduced pressure and the product was purified by prep HPLC (C18 reverse phase column, elution with a H$_2$O/CH$_3$CN gradient with 0.5% TFA) and lyophilized to afford the corresponding amine. LRMS (ES)+: 544.2 (M+H)+. To a solution of 100 mg (0.15 mmol) of this residue in 10 mL of degassed toluene was added BINAP (6.0 mg, 0.009 mmol), sodium-t-butoxide, (53 mg, 0.55 mmol) and Pd$_2$ DBA$_3$ (3.0 mg, 0.003 mmol). The reaction was stirred at 90° C. for 2 h. The solution was cooled and filtered through a pad of silica gel and eluted with EtOAc. The volatiles were removed under reduced pressure and the residue was dissolved in 4 ml of CH$_2$Cl$_2$ followed by the addition of 1 ml of TFA and stirred at room temperature for 1 h, followed by removal of the volatiles under reduced pressure. The residue was purified by prep HPLC (C18 reverse phase column, elution with a H$_2$O/CH$_3$CN gradient with 0.5% TFA) and lyophilized to afford the title compound of EXAMPLE 90. $^1$H NMR (DMSO-D6) δ: 8.70–8.50 (m, 2H), 7.03 (s, 1H), 6.92 (d, 1H, J=7.4 Hz), 6.85 (s, 1H), 6.80 (t, 1H, J=7.5 Hz), 6.51 (t, 1H, J=7.2 Hz), 6.29 (d, 1H, J=8.0 Hz), 4.55 (ABq, 2H, J$_{AB}$=14.2 Hz), 4.12 (app d, 1H, J=11.4 Hz), 3.61 (app t, 1H), 3.50–3.28 (m, 6H), 3.25–3.15 (m, 1H), 3.05–2.90 (m, 1H), 2.75 (t, 2H, J=5.8 Hz), 2.64 (app t, 1H), 2.50–2.40 (m, 1H), 2.22–2.12 (m, 1H), 2.05–1.90 (m, 3H). LRMS (ES)+: 362.2 (M+H)+.

Example 91

(7bR,11lN-(2-fluorophenyl)-1,2,7b,8,9,10,11,11a-octahydro-4H-[1,4]oxazepino[6,5,4-hi]pyrido[4,3-b]indol-6-amine, bis-trifluoroacetic acid salt

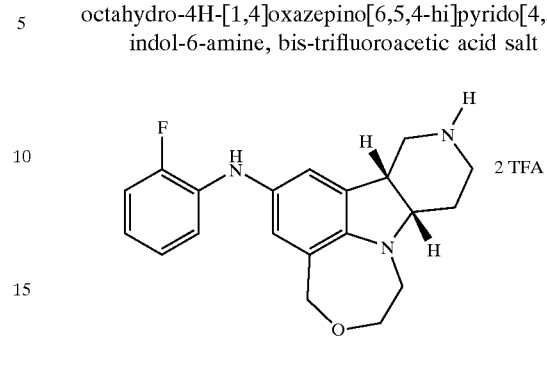

Using 1-bromo-2-fluorobenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 91. $^1$H NMR (dmso-D$_6$) δ: 8.70–8.50 (m, 2H), 7.55 (broad s, 1H), 7.15–6.95 (m, 3H), 6.90 (d, 1H, J=1.8 Hz), 6.77–6.70 (m, 1H), 6.70 (d, 1H, J=1.9 Hz), 4.51 (ABq, 2H, J$_{AB}$=14.5 Hz), 4.12 (app d, 1H, J=13.2 Hz), 3.60 (app t, 1H), 3.40–3.25 (m, 41H), 3.25–3.15 (m, 1H), 3.00–2.90 (m, 1H), 2.57 (app t, 1H), 2.45–2.38 (m, 1H), 2.20–2.10 (m, 1H), 2.05–1.90 (m, 1H). LRMS (ES)+: 340.2 (M+H)+.

Example 92

(7bR,11aS)-N-[3-fluoro-5-(trifluoromethyl)phenyl]-1,2,7b,8,9,10,11,11a-octahydro-4H-[1,4]oxazepino[6,5,4-hi]pyrido[4,3-b]indol-6-amine, bis-trifluoroacetic acid salt

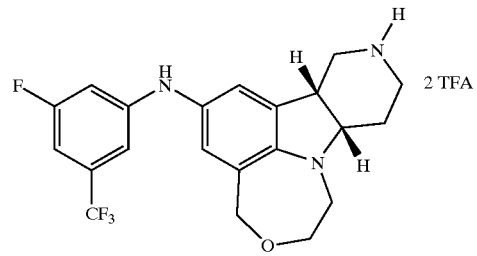

Using 3-bromo-5-fluorobenzotrifluoride and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 92. $^1$H NMR (dmso-D$_6$) δ: 8.70–8.50 (m, 2H), 8.48 (broad s, 1H), 7.02 (d, 1H, J=1.9 Hz), 6.88 (s, 1H), 6.80–6.75 (m, 4H), 4.56 (ABq, 2H, J$_{AB}$=14.5 Hz), 4.12 (app d, 1H, J=13.2 Hz), 3.62 (app t, 1H), 3.42–3.25 (m, 4H), 3.22–3.15 (m, 1H), 3.02–2.90 (m, 1H), 2.62 (app t, 1H), 2.48–2.40 (m, 1H), 2.20–2.10 (m, 1H), 2.05–1.90 (m, 1H). LRMS (ES)+: 408.4 (M+H)+.

Example 93

N$^1$-[(7bR,11aS-1,2,7b,8,9,10,1,11 a-octahydro-4H-[1,4]oxazepino[6,5,4-hi]pyrido[4,b]indol-6-yl]-N$^2$, N$^2$-dimethyl-4-(trifluoromethyl)-1,2-benzenediamine, bis-trifluoroacetic acid salt

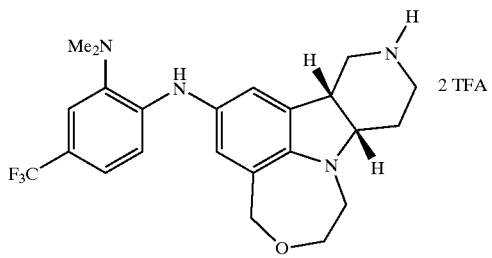

Using 4-bromo-3-(dimethylamino)benzotrifluoride and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 93. $^1$H NMR (DMSO-D6) δ: 8.70–8.50 (m, 2H), 7.10–6.92 (broad m, 4H), 6.62 (broad s, 1H), 6.43 (broad s, 1H), 4.44 (ABq, 2H, J$_{AB}$=13.6 Hz), 4.10 (app d, 1H), 3.58 (app t, 1H), 3.38–3.10 (m, 5H), 3.00–2.90 (m, 1H), 2.92 (broad s, 6H), 2.58–2.35 (m, 2H), 2.20–2.10 (m, 1H), 2.05–1.90 (m, 1H). LRMS (ES)+: 433.2 (M+H)$^+$.

Example 94

4-[(7bR,11aS)-1,2,7,b,8,9,10,11,11a-octahydro-4H-[1,4)oxazepino[6,5,4-hi]pyrido[4,3 b]indol-6-ylamino]-2-fluorobenzaldehyde, bis-trifluoroacetic acid salt

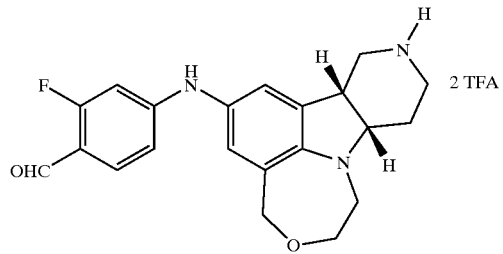

Using 4-bromo-2-fluorobenzaldehyde and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 94. $^1$H NMR (dmso-D$_6$) δ: 9.86 (s, 1H), 9.01 (s, 1H), 8.70–8.50 (m, 2H), 7.56 (t, 1H, J=8.5 Hz), 7.04 (s, 1H), 6.82 (d, 1H, J=1.9 Hz), 6.67 (dd, 1H, J=8.8, 1.8 Hz), 6.51 (dd, 1H, J=14.1, 1.8 Hz), 4.57 (ABq, 2H, J$_{AB}$=14.5 Hz), 4.09 (app d, 1H), 3.61 (m, 1H), 3.45–3.25 (m, 4H), 3.22–3.15 (m, 1H), 3.00–2.90 (m, 1H), 2.62 (t, 1H), 2.45–2.38 (m, 1H), 2.18–2.08 (m, 1H), 2.02–1.92 (m, 1H). LRMS (ES)+: 368.2 (M+H)$^+$.

Example 95

(7bR,11aS) N-[2-fluoro-3-(trifluoromethyl)phenyl]-1,2,7b,8,9,10,11,11a-octahydro-4H-[1,4]oxazepino[6,5,4-hi]pyrido[4,3-b]indol-6-amine, bis-trifluoroacetic acid salt

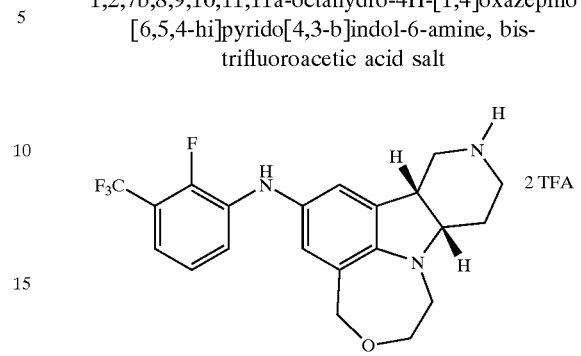

Using 3-bromo-2-fluorobenzotrifluoride and following the procedures described in EXAMPLE 56, Part C, tert-butyl (7bR,11aS)-6-amino-1,2,7b,10,11,11a-hexahydro-H-[1,4]oxazepino[6,5,4-hi]pyrido[4,3-b]indole-9(8H) Carboxylate from EXAMPLE 56, Part B was converted into the title compound of EXAMPLE 95. $^1$H NMR (dmso-D$_6$) δ: 8.70-8.50 (m, 2H), 7.93 (broad s, 1H), 7.23 (t, 1H, J=8.3 Hz), 7.11 (t, 1H, J=8.1 Hz), 7.01–6.94 (m, 2H), 6.77 (d, 1H, J=1.8 Hz), 4.52 (ABq, 2H, J$_{AB}$=14.5 Hz), 4.10 (app d, 1H, J=12.8 Hz), 3.60 (app t, 1H), 3.42–3.25 (m, 4H), 3.22–3.15 (m, 1H), 3.00–2.90 (m, 1H), 2.58 (app t, 1H), 2.48–2.40 (m, 1H), 2.20–2.10 (m, 1H), 2.05–1.90 (m, 1H). LRMS (ES)+: 408.1 (M+H)$^+$.

Example 96

(7bR,11aS)-N-[4-fluoro-3-(trifluoromethyl)phenyl-1,2,7b,8,9,10,11,11a-octahydro-4H-[1,4]oxazepino[6,5,4-hi]pyrido[4,3-b]indol-6-amine, bis-trifluoroacetic acid salt

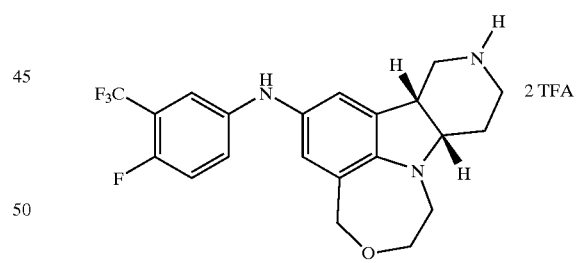

Using 5-bromo-2-fluorobenzotrifluoride and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b indole-9(8H-carboxylate from EXAMPLE 56, Part B was converted into the title compound of EXAMPLE 96. $^1$H NMR (dmso-D$_6$) δ: 8.70–8.50 (m, 2H), 8.08 (broad s, 1H), 7.23 (t, 1H, J=9.7 Hz), 7.12–7.04 (m, 2H), 6.94 (d, 1H, J=1.8 Hz), 6.71 (d, 1H, J=1.8 Hz), 4.52 (ABq, 2H, J$_{AB}$=14.1 Hz), 4.10 (app d, 1H, J=12.4 Hz), 3.59 (app t, 1H), 3.42–3.25 (m, 4H), 3.22–3.15 (m, 1H), 3.00–2.90 (m, 1H), 2.57 (app t, 1H), 2.45–2.38 (m, 1H), 2.20–2.10 (m, 1H), 2.02–1.90 (m, 1H). LRMS (ES)+: 408.1 (M+H)$^+$.

Example 97

(7bR,11aS)-6-2,3-dihydro-1H-indol-1-yl)-1,2,7b,8,9,10,11,11a-octahydro-4H-[1,4]oxazepino[[6,5,4-hi]pyrido[4,3-b]indole, bis-trifluoroacetic acid salt

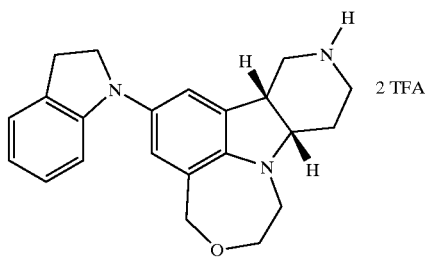

To a solution of tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B (0.155 g, 0.45 mmol) in methylene chloride was added 2-(2-bromophenyl)acetyl chloride (0.086 mL, 0.58 mmol) and 4-dimethylaminopyridine (0.137 g, 1.12 mmol). The mixture was stirred at room temperature for 24 h and then was filtered through a pad of silica gel and concentrated to afford an amide intermediate. This material was dissolved in tetrahydrofuran and treated with borane THF complex (2.69 mL of a 1 M solution in THF, 2.69 mmol). The resulting mixture was stirred at reflux for 3 h. The solution was cooled to 0° C., quenched with methanol and filtered through a pad of silica gel. The volatiles were removed under reduced pressure and the product was purified by prep HPLC (C18 reverse phase column, elution with a $H_2O/CH_3CN$ gradient with 0.5% TFA) and lyophilized to afford an amine intermediate. To a solution of 270 mg (0.51 mmol) of this residue in 20 mL of degassed toluene was added BINAP (20 mg, 0.03 mmol), sodium-t-butoxide, (127 mg, 1.32 mmol) and $Pd_2 DBA_3$ (9.0 mg, 0.01 mmol). The reaction was stirred at 90° C. for 2 h. The solution was cooled and filtered through a pad of silica gel and eluted with EtOAc. The volatiles were removed under reduced pressure and the residue was dissolved in 10 ml of $CH_2Cl_2$ followed by the addition of 3 ml of TFA and stirred at room temperature for 1 h, followed by removal of the volatiles under reduced pressure. The residue was purified by prep HPLC (C18 reverse phase column, elution with a $H_2O/CH_3CN$ gradient with 0.5% TFA) and lyophilized to afford the title compound of EXAMPLE 97. LRMS (ES)+: 348.2 (M+H)+.

Example 98

(7bR,11s)-N-[22-bromophenyl)ethyl]-1,2,7b,8,9,10,11,11a-octahydro-4H-[1,4]oxazepino[6,5,4-hi]pyrido[4,3-b]indol-6-amine, bis-trifluoroacetic acid salt

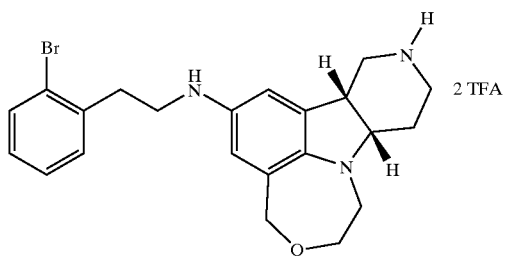

To a solution of the amine intermediate from EXAMPLE 97 (35 mg, 0.066 mmol) in 4 mL of methylene chloride was added 1 mL of trifluoroacetic acid. The reaction was stirred at room temperature for 1 h, followed by removal of the volatiles under reduced pressure. The residue was purified by prep HPLC (C18 reverse phase column, elution with a $H_2O/CH_3CN$ gradient with 0.5% TFA) and lyophilized to afford the title compound of EXAMPLE 98. LRMS (ES)+: 430.0 (M+H)+.

Example 99

(7bR,11aS)-N-(2,6-dimethylphenyl)-1,2,7b,8,9,10,11,11a-octahydro-4H-[1,4]oxazepino[6,5,4-hi]pyrido[4,3-b]indol-6-amine, bis-trifluoroacetic acid salt

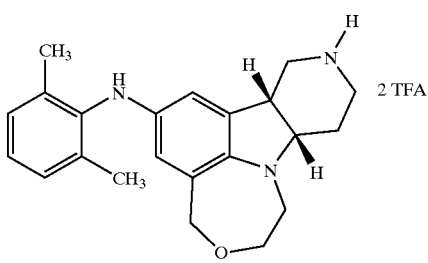

Using 2-bromo-m-xylene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 99. LRMS (ES)+: 350.2 (M+H)+.

Example 100

(7bR,11aS)-N-(2,5-dimethylphenyl)-1,2,7b,8,9,10,11,11a-octahydro-4H-[1,4]oxazepino[6,5,4-hi]pyrido[4,3-b]indolamine, bis-trifluoroacetic acid salt

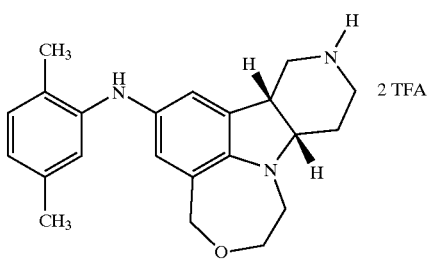

Using 2-bromo-p-xylene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8)-carboxylate from EXAMPLE 56, Part B was converted into the title compound of EXAMPLE 100. LRMS (ES)+: 350.2 (M+H)+.

Example 101

(7bR,11aS)-N-(2-methoxy-5-methylphenyl)-1,2,7b,8,9,10,11,11a-octahydro-4H-[1,4]oxazepino[6,5,4-hi]pyrido[4,3-b]indol-6-amine, bis-trifluoroacetic acid salt

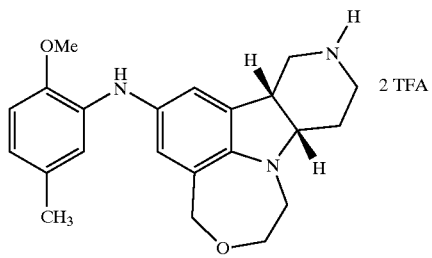

Using 3-bromo-4-methoxytoluene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8-carboxylate from EXAMPLE 56, Part B was converted into the title compound of EXAMPLE 101. $^1$H NMR (DMSO-D6) δ: 8.65–8.45 (m, 2H), 6.92 (s, 1H), 6.80–6.70 (m, 4H), 6.52 (d, 1H, J=7.7 Hz), 4.51 (ABq, 2H, $J_{AB}$=14.3 Hz), 4.11 (app d, 1H, J=11.4 Hz), 3.75 (s, 3), 3.60 (app t, 1H), 3.40–3.15 (m, 5H), 3.00–2.90 (m, 1H), 2.56 (app t, 1H), 2.45–2.38 (m, 1H), 2.20–2.10 (m, 1H), 2;13 (s, 3H), 2.02–1.90 (m, 1H). LRMS (ES)+: 366.3 M+H)$^+$.

Example 102

(7bR,11aS)-N-(1,1'-biphenyl-3-yl)-1,2,7b,8,9,10,11,11a-octahydro-4H-[1,4]oxazepino[6,5,4-hi]pyrido[4,3-b]indolamine, bis-trifluoroacetic acid salt

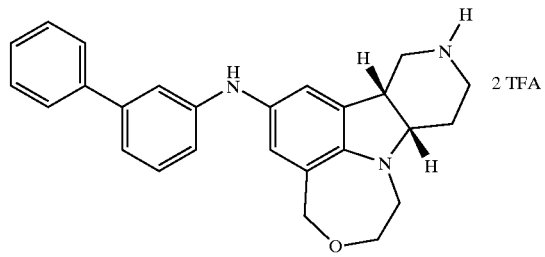

Using 3-bromo-1,1'-biphenyl and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)Carboxylate from EXAMPLE 56, Part B was converted into the title compound of EXAMPLE 102. $^1$H NMR (dmso-D$_6$) δ: 8.70–8.50 (m, 2H), 7.57–7.53 (m, 2H), 7.47–7.40 (m, 2H), 7.38–7.32 (m, 1H), 7.28–7.20 (m, 1H), 7.11 (broad s, 1H), 7.01–6.88 (m, 4H), 6.75 (broad s, 1H), 4.54 (ABq, 2H, $J_{AB}$=14.1 Hz), 4.12 (app d, 1H, J=12.8 Hz), 3.61 (app t, 1H), 3.45–3.25 (m, 4H), 3.23–3.17 (m, 1H), 3.00–2.90 (m, 1H), 2.58 (app t, 1H), 2.48–2.40 (m, 1H), 2.20–2.10 (m, 1H), 2.02–1.90 (m, 1H). LRMS (ES)+: 398.3 (M+H)$^+$.

Example 103

(7bR,11aS)-N-(2,6-dichloro-3-methylphenyl)-1,2,7b,8,9,10,11,11a-octahydro-4H-[1,4]oxazepino[6,5,4-hi]pyrido[4,3-b]indol-6-amine, bis-trifluoroacetic acid salt

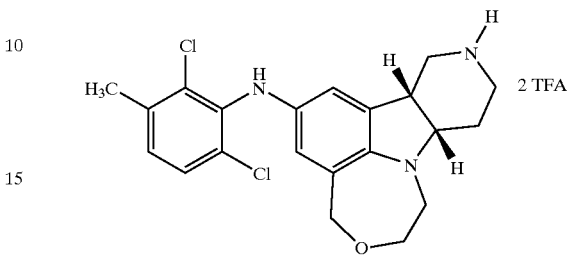

Using 3-bromo-2,4-dichlorotoluene and following the procedures described in EXAMPLE 56, Part C, tert-butyl (7bR,11aS)-6-amino-1,2,7b,10,11,11a-hexahydro-H-[1,4]oxazepino[6,5,4-hi]pyrido[4,3-b]indole-9(8H)Carboxylate from EXAMPLE 56, Part B was converted into the title compound of EXAMPLE 103. $^1$H NMR (dmso-D$_6$) δ: 8.65–8.40 (m, 2H), 7.40 (s, 1H), 7.38 (d, 1H, J=8.4 Hz), 7.16 (d, 1H, J=8.4 Hz), 6.37 (d, 1H, J=1.9 Hz), 6.18 (d, 1H, J=1.9 Hz), 4.43 (ABq, 2H, $J_{AB}$=14.3 Hz), 4.09 (app d, 1H, J=12.8 Hz), 3.56 (app t, 1H), 3.35–3.10 (m, 5H), 3.00–2.90 (m, 1H), 2.55–2.35 (m, 2H), 2.32 (s, 3H), 2.20–2.10 (m, 1H), 2.00–1.90 (m, 1H). LRMS (ES)+: 404.2 (M+H)$^+$.

Example 104

(7bR,11aS)-N-2-chloro-5-methylphenyl)-1,2,7b,8,9,10,11,11a-octahydro-4H-[1,4]oxazepino[6,5,4-hi]pyrido[4,3-b]indol-6-amine, bis-trifluoroacetic acid salt

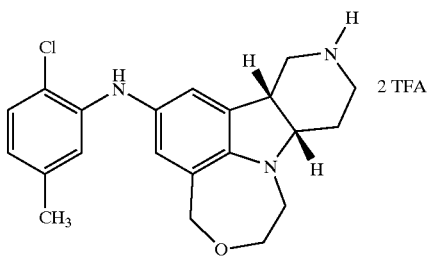

Using 3-bromo-4-chlorotoluene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 104. $^1$H NMR (dmso-D$_6$) δ: 8.70–8.50 (m, 2H), 7.19 (d, 1H, J=8.1 Hz), 7.15 (broad s, 1H), 6.96 (d, 1H, J=1.9 Hz), 6.75 (dd, 1H, J=7.0, 1.8 Hz), 6.55 (dd, 1H, J=8.0, 1.5 Hz), 4.53 (ABq, 2H, $J_{AB}$=14.5 Hz), 4.12 (app d, 1H, J=12.8 Hz), 3.65–3.55 (m, 1H), 3.42–3.25 (m, 4H), 3.23–3.27 (m, 1H), 3.00–2.90 (m, 1H), 2.60 (app t, 1H), 2.45–2.38 (m, 1H), 2.20–2.10 (m, 1H), 2.14 (s, 3H), 2.02–1.90 (m, 1H). LRMS (ES)+: 370.3 (M+H)$^+$.

Example 105

(7bR,11aS)-N-(2,4,5-trifluorophenyl)1,2,7b,8,9,10,11,11a-octahydro-4H-[1,4]oxazepino[6,5,4-hi]pyrido[4,3-b]indol-6-amine, bis-trifluoroacetic acid salt

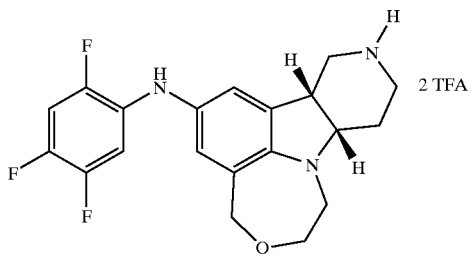

Using 1-bromo-2,4,5-trifluorobenzene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8R)-carboxylate from EXAMPLE 56, Part B was converted into the title compound of EXAMPLE 105. $^1$H NMR (dmso-D$_6$) δ: 8.62–8.45 (m, 2H), 7.73 (s, 1H), 7.52–7.40 (m, 1H), 6.99–6.89 (m, 2H), 6.72 (d, 1H, J=1.8 Hz), 4.53 (ABq, 2H, J$_{AB}$=14.3 Hz), 4.11 (app d, 1H, J=12.8 Hz), 3.65–3.55 (m, 1H), 3.42–3.25 (m, 4H), 3.23–3.27 (m, 1H), 3.00–2.90 (m, 1I4), 2.59 (app t, 1H), 2.45–2.40 (m, 1H), 2.20–2.10 (m, 1H), 2.02–1.90 (m, 1H). LRMS (ES)+: 376.2 (M+H)$^+$.

Example 106

(7bR,11aS)-N-4-methoxy-3,5-dimethylphenyl)-1,2,7b,8,9,10,11,11a-octahydro-4H-[1,4]oxazepino[6,5,4-hi]pyrido[4,3-b]indol-6-amine, bis-trifluoroacetic acid salt

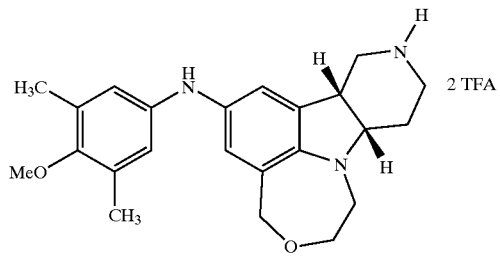

Using 5-bromo-2-methoxy-m-xylene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8S)-carboxylate from EXAMPLE 56, Part B was converted into the title compound of EXAMPLE 106. $^1$H NMR (dmso-D$_6$) δ: 8.62–8.45 (m, 2H), 6.85 (s, 1H), 6.62 (s, 1H), 6.55 (s, 2H), 4.50 (ABq, 2H, J$_{AB}$=14.5 Hz), 4.11 (app d, 1H, J=12.0 Hz), 3.63–3.55 (m, 1H), 3.55 (s, 3H), 3.40–3.15 (m, 5H), 3.00–2.90 (m, 1H), 2.60–2.37 (m, 2H), 2.20–2.10 (m, 1H), 2.11 (s, 6H), 2.02–1.90 (m, 1H). LRMS (ES)$^+$: 380.3 (M+H)$^+$.

Example 107

41(7bR,11aS)-1,2,7b,8,9,10,11,11a-octahydro-4H-[1,4]oxazepino[6,5,4-hi]pyrido[4,3-b]indol-6-ylamino]-2-methylbenzonitrile, bis-trifluoroacetic acid salt

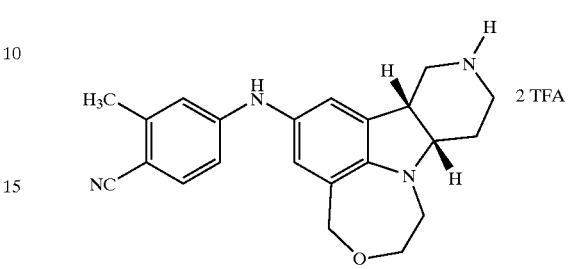

Using 4-bromo-2-methylbenzonitrile and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 107. $^1$H NMR (dmso-D$_6$) δ: 8.65–8.50 (m, 2H), 8.51 (s, 1H), 7.42 (d, 1H, J=8.4 Hz), 7.00 (d, 1H, J=1.9 Hz), 6.78 (d, 1H, J=2.2 Hz), 6.73 (s, 1H), 6.69 (d, 1H, J=8.4 Hz), 4.50 (ABq, 2H, J$_{AB}$=14.2 Hz), 4.11 (app d, 1H, J=12.4 Hz), 3.64 (app t, 1H), 3.45–3.25 (m, 4H), 3.23–3.17 (m, 1H), 3.00–2.90 (m, 1H), 2.61 (app t, 1H), 2.47–2.40 (m, 1H), 2.31 (s, 3H), 2.20–2.10 (m, 1H), 2.02–1.90 (m, 1H). LRMS (ES)+: 361.3 (M+H)$^+$.

Example 108

(7bR,11aS)-N-(4-methoxy-3-methylphenyl)-1,2,7b,8,9,10,11,11a-octahydro-4H-[1,4]oxazepino[6,5,4-hi]pyrido[4,3-b]indol-6-amine, bis-trifluoroacetic acid salt

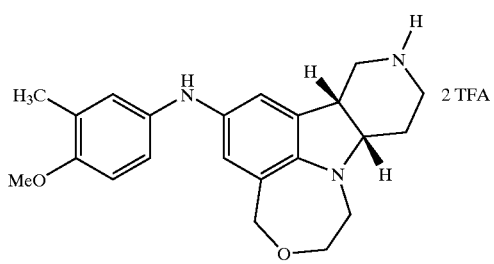

Using 5-bromo-2-methoxytoluene and following the procedures described in EXAMPLE 56, Part C, tert-butyl (7bR,11aS)-6-amino-1,2,7b,10,11,111 a-hexahydro-4H-[1,4]oxazepino[6,5,4-hi]pyrido[4,3-b]indole-9(8H)-carboxylate from EXAMPLE 56, Part B was converted into the title compound of EXAMPLE 108. LRMS (ES)+: 366.3 (M+H)$^+$.

Example 109

(7bR,11aS)-N-(4-chloro-3-methylphenyl)1,2,7b,8,9,10,11,11a-octahydro-4H-[1,4]oxazepino[6,5,4-hi]pyrido[4,3-b]indol-6-amine, bis-trifluoroacetic acid salt

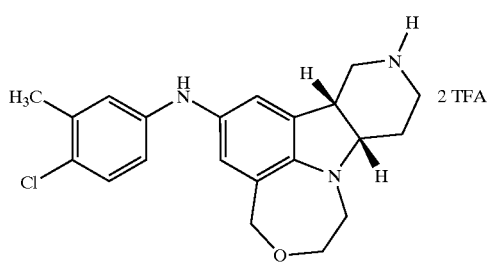

Using 5-bromo-2-chlorotoluene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 109. $^1$H NMR (DMSO-D6) δ: 8.65–8.45 (m, 2H), 7.10 (d, 1H, J=8.8 Hz), 6.90 (s, 1H), 6.78 (s, 1H), 6.70–6.63 (m, 2H), 4.50 (ABq, 2H, $J_{AB}$=14.3 Hz), 4.09 (app d, 1H, J=12.4 Hz), 3.58 (app t, 1H), 3.41–3.22 (m, 4H), 3.20–3.11 (m, 1H), 3.00–2.90 (m, 1H), 2.55 (app t, 1H), 2.47–2.40 (m, 1H), 2.20–2.10 (m, 1H), 2.18 (s, 3H), 2.00–1.90 (m, 1H). LRMS (ES)+: 370.2 (M+H)+.

Example 110

(7bR,11aS)-N-(4-fluoro-3-methylphenyl)-1,2,7b,8,9,10,11,11a-octahydro-4H-[1,4]oxazepino[6,5,4-hi]pyrido[4,3-b]indol-6-amine, bis-trifluoroacetic acid salt

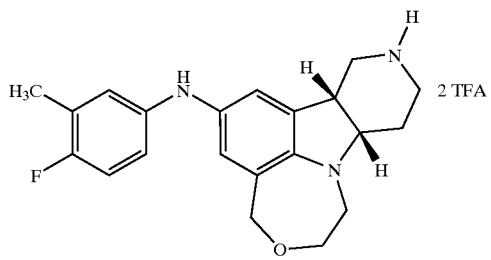

Using 5-bromo-2-fluorotoluene and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 110. $^1$H NMR (dmso-$D_6$) δ: 8.65–8.45 (m, 2H), 6.93–6.82 (m, 2H), 6.78–6.64 (m, 2H), 6.62 (s, 1H), 4.49 (ABq, 2H, $J_{AB}$=14.2 Hz), 4.09 (app d, 1H, J=12.8 Hz), 3.58 (app t, 1H), 3.40–3.10 (m, 5H), 3.00–2.85 (m, 1H), 2.53 (app t, 1H), 2.45–2.32 (m, 1H), 2.18–2.08 (m, 1H), 2.11 (s, 3H), 2.00–1.87 (m, 1H). LRMS (ES)+: 354.3 (M+H)+.

Example 111

(7bR,11aS)-N-(2-methyl-1-naphthyl)-1,2,7b,8,9,10,11,11a-octahydro-4H-[1,4]oxazepino[6,5,4-hi]pyrido[4,3-b]indol-6-amine, bis-trifluoroacetic acid salt

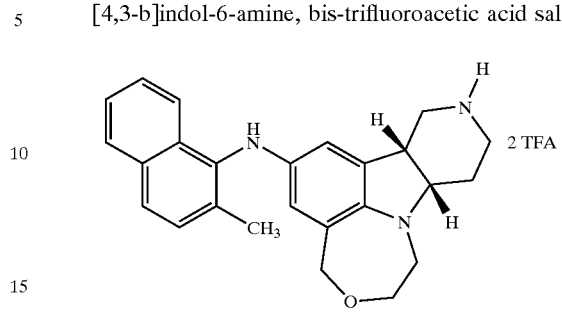

Using 1-bromo-2-methylnaphthalene and following the procedures described in EXAMPLE 56, Part C, tert-butyl (7bR,11aS)$_6$-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 111. LRMS (ES)+: 386.2 (M+H)+.

Example 112

(7bR,11aS)-N-5-fluoro-2-methoxyphenyl)-1,2,7b,8,9,10,11,11a-octahydro-4H-[1,4]oxazepino[6,5,4-hi]pyrido[4,3-b]indol-6-amine, bis-trifluoroacetic acid salt

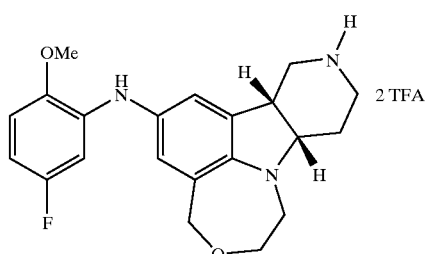

Using 2-bromo-4-fluoroanisole and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)Carboxylate from EXAMPLE 56, Part B was converted into the title compound of EXAMPLE 112. LRMS (ES)+: 370.3 (M+H)+.

Example 113

(7bR,11aS)-N-phenyl-1,2,7b,8,9,10,11,11a-octahydro-4H-[1,4]oxazepino[6,5,4-hi]pyrido[4,3-b]indol-6-amine, bis-trifluoroacetic acid salt

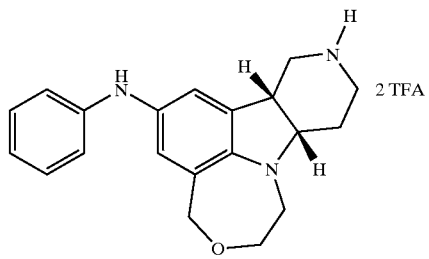

Using bromobenzene and following the procedures described in EXAMPLE 56, Part C, tert-butyl (7bR,11aS)-6-amino-1,2,7b,10,11,11a-hexahydro-4H-[1,4]oxazepino[6, 5,4-hi]pyrido[4,3-b]indole-9(8H)-carboxylate from EXAMPLE 56, Part B was converted into the title compound of EXAMPLE 113. LRMS (ES)+: 322.2 (M+H)+.

Example 114

(7bR,11aS)-N-(3-quinolinyl)-1,2,7b,8,9,10,11,11a-octahydro-4H-[1,4]oxazepino[6,5,4-hi]pyrido[4,3-b]indol-6-amine

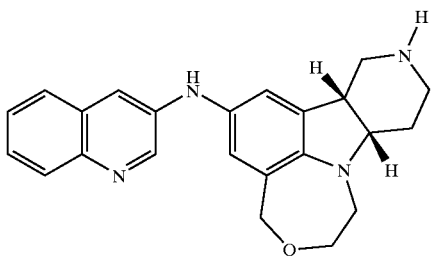

Using 3-bromoquinoline and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)Carboxylate from EXAMPLE 56, Part B was converted into (7bR,11aS)-N-(3-quinolinyl)-1,2,7b,8,9,10,11,11a-octahydro-4H-[1,4]oxazepino[6,5,4-hi]pyrido[4,3-b]indol-6-amine, bis-trifluoroacetic acid salt. This material was free-based with aq ammonium hydroxide, extracted with chloroform, washed with brine, dried ($K_2CO_3$) and concentrated to afford the title compound of EXAMPLE 114. $^1$H NMR (CDCl$_3$) δ: 8.60 (d, 1H, J=2.9 Hz), 7.95 (d, 1H, J=1.9 Hz), 7.60–7.55 (m, 1H), 7.50–7.38 (m, 3H), 6.88 (d, 1H, J=1.9 Hz), 6.81 (s, 1H), 5.99 (s, 1H4), 5.85 (broad s, 1H), 4.61 (ABq, 2H, $J_{AB}$=14.7 Hz), 4.23 (app d, 1H, J=12.4 Hz), 3.74 (app t, 1H), 3.43 (broad s, 1H), 3.30–3.00 (m, 4H), 2.75 (app t, 1H), 2.65–2.55 (m, 1H), 2.20–1.90 (m 3H). LRMS (ES)+: 373.4 (M+H)+.

Example 115

(7bR,11aS)-N-(3-pyridinyl)-1,2,7b,8,9,10,11,11a-octahydro-4H-[1,4]oxazepino[6,5,4-hi]pyrido[4,3-b]indol-6-amine

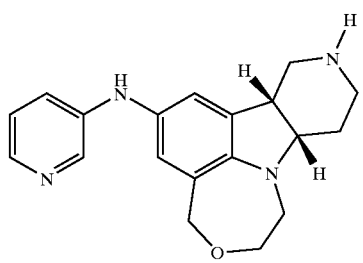

Using 3-bromopyridine and following the procedures described in EXAMPLE 56, Part C, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into (7bR,11aS)-N-(3-pyridinyl)-1,2,7b,8,9,10,11,11a-octahydro-4H-[1,4]oxazepino[6,5,4-hi]pyrido[4,3-b]indol-6-amine, bis-trifluoroacetic acid salt. This material was free-based with aq ammonium hydroxide, extracted with chloroform, washed with brine, dried ($K_2CO_3$) and concentrated to afford the title compound of EXAMPLE 115. LRMS (ES)+: 323.4 (M+H)+.

Example 116

1-{2-[(7bR,11aS)-1,2,7b,8,9,10,11,11a-octahydro-4H-[1,4]oxazepino[6,5,4-hi]pyrido[4,3-b]indol-6-ylamino]-5-methylphenyl}ethanone

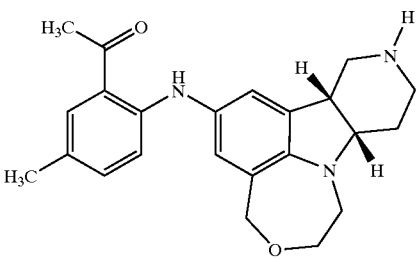

A solution of tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B (35 mg, 0.1 mmol), 2-(2-bromo-5-methylphenyl)-2-methyl-1,3-dioxolane (31 mg, 0.12 mmol), BINAP (3 mg, 0.004 mmol), sodium-t-butoxide, (24 mg, 0.25 mmol) and Pd$_2$ DBA$_3$ (1.0 mg, 0.001 mmol) in 10 ml of degassed toluene was heated for 10 h at 90° C. The solution was cooled and filtered through a pad of silica gel and eluted with EtOAc. The volatiles were removed under reduced pressure to afford a dioxolane intermediate. This intermediate was taken up in 6 mL of methylene chloride and then there was added trifluoroacetic acid (2 mL) and the reaction was allowed to stir at room temperature for 6 h and then was concentrated in vacuo. The residue was purified by preparative HPLC (C18 reverse phase column, elution with a H$_2$O/CH$_3$CN gradient with 0.5% TFA) and the product containing fractions were concentrated, free-based with aq ammonium hydroxide, extracted with chloroform, washed with brine, dried ($K_2CO_3$) and concentrated to afford the title compound of EXAMPLE 116. LRMS (ES)+: 378.4 (M+H)+.

Example 117

1-{2-[(7bR,11aS)-1,2,7b,8,9,10,11,11a-octahydro-4H-[1,4]oxazepino[6,5,4-hi]pyrido[4,3-b]indol-6-ylamino]-5-methylphenyl)ethanol

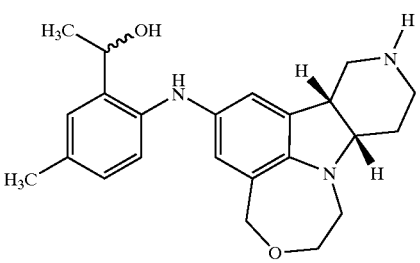

To a solution of 1-{2-[(7bR,11aS)-1,2,7b,8,9,10,11,11a-octahydro-4H-[1,4]oxazepino[6,5,4-hi]pyrido[4,3-b]indol-6-ylamino]-5-methylphenyl} ethanone from EXAMPLE 116 (20 mg, 0.05 mmol) in 5 ml methanol at 0° C. was added sodium borohydride (5.5 mg, 0.15 mmol). The solution was stirred with warming to room temperature for 2 h. The reaction was diluted with ethyl acetate, washed with water and brine, dried (MgSO$_4$) and concentrated. The residue was purified by preparative HPLC (C18 reverse phase column, elution with a H$_2$O/CH$_3$CN gradient with 0.5% TFA) and the product containing fractions were concentrated, free-based with aq ammonium hydroxide, extracted with chloroform, washed with brine, dried (K$_2$CO$_3$) and concentrated to afford the title compound of EXAMPLE 117 as a mixture of diastereomers at the alcohol center. LRMS (ES)+: 380.3 (M+H)$^+$.

Example 118

1-{2-[(7bR,11aS)-1,2,7b,8,9,10,11,11a-octahydro-4H-[1,4]oxazepino[6,5,4-hi]pyrido[4,3-b]indol-6-ylamino]-5-methoxyphenyl}ethanone

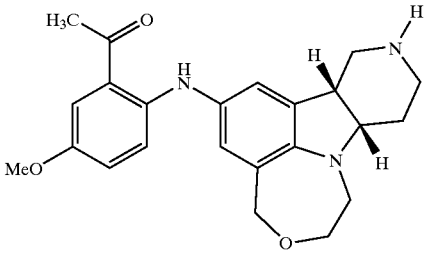

Using 2-(2-bromo-5-methoxyphenyl)-2-methyl-1,3-dioxolane and following the procedures described in EXAMPLE 116, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 118. $^1$H NMR (CDCl$_3$) o: 9.95 (s, 1H), 7.22 (d, 1H, J=2.5 Hz), 6.99–6.92 (m, 2H), 6.86 (d, 1H, J=1.8 Hz), 6.75 (d, 1H, J=1.9 Hz), 4.58 (ABq, 2H, JAB=14.2 Hz), 4.20 (app d, 1H), 3.77 (s, 3H), 3.72 (app t, 1H), 3.42–3.37 (m, 1H), 3.35–3.20 (m, 2H), 3.10 (dd, 1H), 3.01–2.90 (m, 2H), 2.71 (app t, 1H), 2.59 (s, 3H), 2.50 (app t, 1H), 2.02–1.90 (m, 2H). LRMS (ES)+: 394.4 (M+H)$^+$.

Example 119

1-{2-[(7bR,11aS)-1,2,7b,8,9,10,11,11a-octahydro-4H-11,41 oxazepino[6,5,4-hi]pyrido[4,3-b]indol-6-ylamino]-5-methoxyphenyl)ethanol

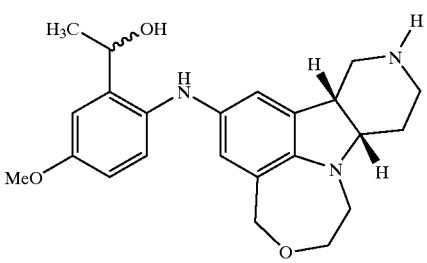

Following the procedures described in EXAMPLE 117, 1-{2-[(7bR,11aS)-1,2,7b, 8,9,10,11,11a-octahydro-4H-[1,4]oxazepino[6,5,4-hi]pyrido[4,3-b]indol-6-ylamino]-5-methoxyphenyl}ethanone from EXAMPLE 118 was converted into the title compound of EXAMPLE 119 as a mixture of diastereomers at the alcohol center. LRMS (ES)+: 396.3 (M+H)$^+$.

Example 120

2-[(7bR,11aS)-1,2,7b,8,9,10,11,11a-octahydro-4H-[1,4]oxazepino[6,5,4-hi]pyrido[4,3-b]indol-6-yl]-1H-isoindole-1,3(21)-dione, bis-trifluoroacetic acid salt

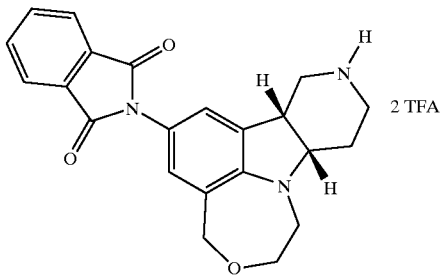

To a solution of tert-butyl (8aS,11aR)-2-amino-5,6,8a,9,11,11a-hexahydro-4H-pyrido[3,2,1-y]pyrrolo[3,4-c]quinoline-10(8H)-carboxylate from EXAMPLE 56, Part B (130 mg, 0.38 mmol) in 10 mL of toluene was added phthalic anhydride (84 mg, 0.56 mmol). The mixture was stirred at 100° C. for 3 h and then was concentrated in vacuo. The residue was dissolved in ethyl acetate and filtered through a pad of silica gel and concentrated to afford an imide intermediate. LRMS (ES)$^+$: 476.2 (M+H)$^+$. A portion of this material (35 mg, 0.07 mmol) was stirred in 4 mL of methylene chloride and 2 mL of trifluoroacetic acid at ambient temperature for 2 h. The solvent was evaporated in vacuo and the residue was purified by preparative HPLC (C18 reverse phase column, elution with a H$_2$O/CH$_3$CN gradient with 0.5% TFA) to afford the title compound of EXAMPLE 120 as a powder. $^1$H NMR (DMSO-D6) δ: 8.70–8.50 (m, 2H), 7.95–7.90 (m, 4H), 7.17 (d, 1H, J=1.9 Hz), 7.03 (d, 1H, J=2.2 Hz), 4.60 (ABq, 2H, J$_{AB}$=14.3 Hz), 4.14 (app d, 1H, J=12.4 Hz), 3.65 (app t, 1H), 3.40–3.25 (m, 4H), 3.22–3.15 (m, 1H), 3.03–2.93 (m, 1H), 2.72 (app t, 1H), 2.58–2.48 (m, 1H), 2.25–2.15 (m, 1H), 2.05–1.95 (m, 1H). LRMS (ES)+: 376.3 (M+H)$^+$.

Example 121

(7bR,11aS)-6-(1,3-dihydro-2H-isoindol-2-yl) 1,2,7b,9,18,11,11a-octahydro-4H-[1,4]oxazepino[6,5,4-hi]pyrido[4,3-b]indole, bis-trifluoroacetic acid salt

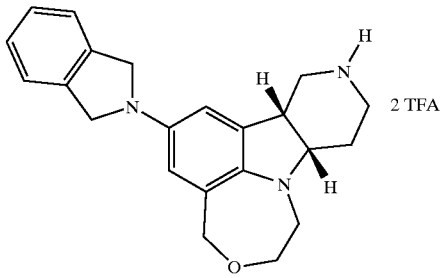

To a solution of the imide intermediate from EXAMPLE 120 (22 mg, 0.05 mmol) in 10 mL of tetrahydrofuran was added borane-THF complex (0.48 mL of 1 M borane in THF, 0.48 mmol). The mixture was stirred at 70° C. for 3 h and then was cooled to 0° C. and quenched by the slow addition of methanol. The solution was concentrated and the residue was dissolved in ethyl acetate, washed with sat'd aq NaHCO$_3$ and brine, dried (MgSO$_4$), filtered through a pad of silica gel and concentrated. The residue was taken up in 10 mL of methylene chloride and then there was added 5 mL of trifluoroacetic acid. The reaction was allowed to stir at ambient temperature for 3 h and then was concentrated in vacuo. The residue was purified by preparative HPLC (C18 reverse phase column, elution with a H$_2$O/CH$_3$CN gradient with 0.5% TFA) to afford the title compound of EXAMPLE 121 as a powder. LRMS (ES)$^+$: 348.3 (M+H)$^+$.

Example 122

(7bR,11aS)-N-benzyl-1,2,7b,8,9,10,11,11a-octahydro-4H-[1,4]oxazepino[6,5,4-hi]pyrido[4,3-b]indolamine, bis-trifluoroacetic acid salt To a solution of tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B (35 mg, 0.10 mmol) in 5 mL of 1,2-dichloroethane was added benzaldehyde (21 mg, 0.20 mmol), crushed 4A molecular sieves and three drops of glacial acetic acid. The reaction was stirred at ambient temperature for 1 h and then there was added sodium triacetoxyborohydride (64 mg, 0.30 mmol). The reaction was stirred at ambient temperature for 3 h and then was quenched by the addition of aq ammonium hydroxide. The mixture was extracted with methylene chloride, washed with brine, dried (K$_2$CO$_3$) and concentrated. The residue was purified by flash chromatography (elution with 3:1 hexane/ethyl acetate) to afford the N-BOC intermediate. This intermediate was taken up in 10 mL of methylene chloride and then there was added 5 mL of trifluoroacetic acid. The reaction was allowed to stir at ambient temperature for 3 h and then was concentrated in vacuo. The residue was purified by preparative HPLC (C18 reverse phase column, elution with a H$_2$O/CH$_3$CN gradient with 0.5% TFA) to afford the title compound of EXAMPLE 122 as a powder. $^1$H NMR (CDCl$_3$) δ: 9.45 (broad s, 1H), 9.25 (broad s, 1H), 7.35–7.22 (m, 5H), 7.03 (broad s, 1H), 6.96 (s, 1H), 4.55 (ABq, 2H, J$_{AB}$=14.8 Hz), 4.29 (s, 2H), 4.22 (app d, 1H), 3.68 (app t, 1H), 3.50–3.35 (m, 2H), 3.25–3.00 (m, 4H), 2.75 (app t, 1H), 2.50–2.37 (m, 1H), 2.22–2.10 (m, 2H). LRMS (ES)+: 336.4 (M+H)$^+$.

Example 123

(7bR,11aS)-N-(3,5-dichlorobenzyl)-1,2,7b,8,9,10,11,11a-octahydro-4H-[1,4]oxazepino[6,5,4-hi]pyrido[4,3-b]indol-6-amine, bis-trifluoroacetic acid salt

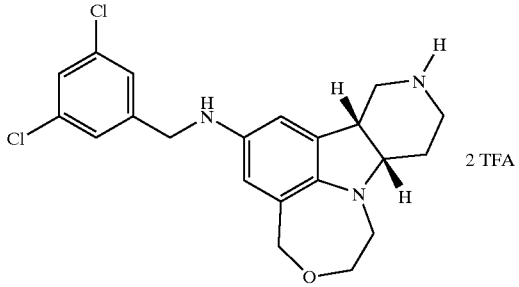

Using 3,5-dichlorobenzaldehyde and following the procedures described in EXAMPLE 122, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 123. LRMS (ES)$^+$: 404.3 (M+M)$^+$.

Example 124

(7bR,11aS)-N-(2,4-dichlorobenzyl)-1,2,7b,8,9,10,11,11a-octahydro-4H-[1,4]oxazepino[6,5,4-hi]pyrido[4,3-b]indolamine, bis-trifluoroacetic acid salt

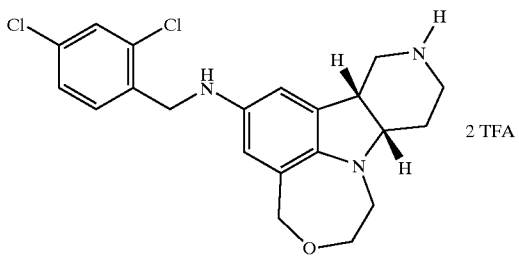

Using 2,4-dichlorobenzaldehyde and following the procedures described in EXAMPLE 122, tert-butyl (7bR, 1 aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 124. $^1$H NMR (CDCl$_3$) δ: 9.55 (broad s, 1H), 9.25 (broad s, 1H), 7.36–7.28 (m, 2H), 7.14 (dd, 1H, J=8.0, 1.8 Hz), 6.56 (broad s, 1H), 6.40 (broad s, 1H), 4.49 (ABq, 2H, J$_{AB}$=14.5 Hz), 4.30 (s, 2H), 4.15 (app d, 1H), 3.61 (app t, 1H), 3.48–3.35 (m, 2H), 3.30–3.00 (m, 4H), 2.81 (app t, 1H), 2.50–2.40 (m, 1H), 2.20–2.05 (m, 2H). LRMS (ES)$^+$: 404.3 (M+H)$^+$.

Example 125

(7bR,11aS)-N-(2,6-dichlorobenzyl)-1,2,7b,8,9,10,11,11a-octahydro-4H-[1,4]oxazepino[6,5,4-hi]pyrido[4,3-b]indol-6-amine, bis-trifluoroacetic acid salt

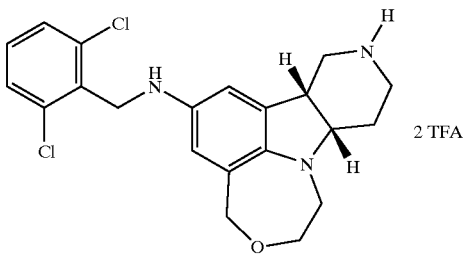

Using 2,6-dichlorobenzaldehyde and following the procedures described in EXAMPLE 122, tert-butyl (7bR,11aS)-6-amino-1,2,7b,10,11,11a-hexahydro-4H-[1,4]oxazepino[6,5,4-hi]pyrido[4,3-b]indole-9(8H) carboxylate from EXAMPLE 56, Part B was converted into the title compound of EXAMPLE 125. LRMS (ES)$^+$: 404.3 (M+H)$^+$.

Example 126

(7bR,11aS)-N-[2-fluoro-3-(trifluoromethyl)benzyl-1,2,7b,8,9,10,11,11a-octahydro-4H-[1,4]oxazepino[6,5,4-hi]pyrido[4,3-b]indol-6-amine

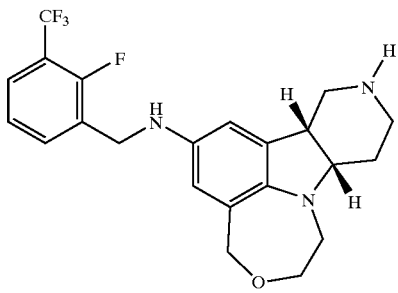

To a solution of tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B (35 mg, 0.10 mmol) in 5 mL of acetonitrile was added 2-fluoro-3-(trifluoromethyl)benzaldehyde (38 mg, 0.20 mmol) and three drops of glacial acetic acid. The reaction was stirred at ambient temperature for 1 h and then there was added sodium triacetoxyborohydride (64 mg, 0.30 mmol). The reaction was stirred at ambient temperature for 3 h and then was quenched by the addition of aq ammonium hydroxide. The mixture was extracted with methylene chloride, washed with brine, dried (K$_2$CO$_3$) and concentrated. The residue was taken up in 10 mL of methylene chloride and then there was added 5 mL of trifluoroacetic acid. The reaction was allowed to stir at ambient temperature for 3 h and then was concentrated in vacuo. The residue was purified by preparative HPLC (C18 reverse phase column, elution with a H$_2$O/CH$_3$CN gradient with 0.5% TFA) and the product containing fractions were concentrated, free-based with aq ammonium hydroxide, extracted with chloroform, washed with brine, dried (K$_2$CO$_3$) and concentrated to afford the title compound of EXAMPLE 126. $^1$H NMR (CDCl$_3$) δ: 7.55–7.40 (m, 2H), 7.12 (t, 1H, J=7.7 Hz), 6.31 (d, 1H, J=2.0 Hz), 6.15 (d, 1H, J=1.9 Hz), 4.48 (ABq, 2H, JAB 14.3 Hz), 4.32 (s, 2H), 4.12 (app d, 1H), 3.63 (app t, 1H), 3.30–3.20 (m, 2H), 3.18–2.98 (m, 4H), 2.56 (app t, 1H), 2.43 (app t, 1H), 2.05–1.92 (m, 2H). LRMS (ES)$^+$: 422.3 (M+H)$^+$.

Example 127

(7bR,11aS)-N-[2-fluoro-6-(trifluoromethyl)benzyl]-1,2,7b,8,9,10,11,11a-octahydro-4H-[1,4]oxazepino[6,5,4-hi]pyrido[[4,3-b]indol-6-amine

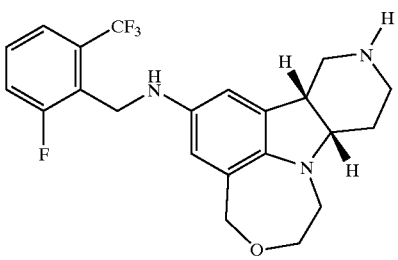

Using 2-fluoro-6-(trifluoromethyl)benzaldehyde and following the procedures described in EXAMPLE 126, tert-butyl (7bR,11aS)-amino-1,2,7b,10,11,11a-hexahydro-4H-[1,4]oxazepino[6,5,4-hi]pyrido[4,3-b]indole-9(8H) Carboxylate from EXAMPLE 56, Part B was converted into the title compound of EXAMPLE 127. $^1$H NMR (CDCl$_3$) δ: 7.42 (d, 1H, J=7.7 Hz), 7.33 (app q, 1H), 7.23 (d, 1H J=8.0 Hz), 6.45 (d, 1H, J=2.2 Hz), 6.26 (d, 1H, J=1.8 Hz), 4.52 (ABq, 2H, J$_{AB}$=14.3 Hz), 4.33 (s, 2H), 4.12 (app d, 1H, J=12.4 Hz), 3.65 (app t, 1H), 3.25–3.00 (m, 4H), 2.95–2.85 (m, 2H), 2.57 (app t, 1H), 2.42 (app t, 1H), 1.92–1.82 (m, 2H). LRMS (ES)$^+$: 422.2 (M+H)$^+$.

Example 128

(7bR,11aS)-N-[2-trifluoromethyl)benzyl]-1,2,7b,8,9,10,11,11a-octahydro-4H-[1,4]oxazepino[6,5,4-hi]pyrido[4,3-b]indol-6-amine

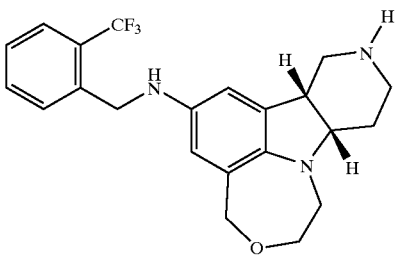

Using 2-(trifluoromethyl)benzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 128. $^1$H NMR (CDCl$_3$) δ: 7.72–7.60 (m, 2H), 7.52 (t, 1H, J=7.7 Hz), 7.38 (t, 1H, J=7.5 Hz), 6.39 (d, 1H, J=1.8 Hz), 6.21 (d, 1H, J=1.8 Hz), 4.57 (ABq, 2H, J$_{AB}$=14.3 Hz), 4.50 (s, 2H), 4.20 (app d, 1H, J=12.0 Hz), 3.74 (app t, 1H), 3.36–3.30 (m, 1H), 3.28–3.18 (m, 2H), 3.08 (dd, 1H, J=12.5, 6.2 Hz), 3.00–2.90 (m, 2H), 2.65 (app t, 1H), 2.50 (app t, 1H), 2.02–1.90 (m, 2H). LRMS (ES)$^+$: 404.3 (M+H)$^+$.

Example 129

(7bR,11aS)-N-[2,4-bis(trifluoromethyl)benzyl]-1,2,7b,8,9,10,11,11a-octahydro-4H-[1,4]oxazepino[6,5,4-hi]pyrido[4,3-b]indol-amine

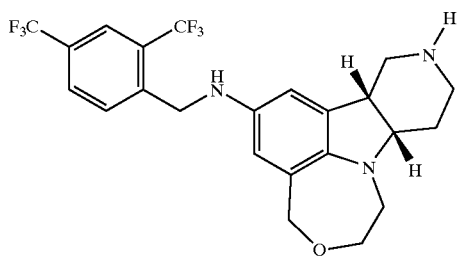

Using 2,4-bis(trifluoromethyl)benzaldehyde and following the procedures described in EXAMPLE 126, tert-butyl (7bR,11aS)-6-amino-1,2,7b,10,11,11a-hexahydro-1H-[1,4]oxazepino[6,5,4-hi]pyrido[4,3-b]indole-9(8H} carboxylate from EXAMPLE 56, Part B was converted into the title compound of EXAMPLE 129. LRMS (ES)$^+$: 472.4 (M+H)$^+$.

Example 130

(7bR,11aS)-N-[2,5-bis(trifluoromethyl)benzyl]-1,2,7b,8,9,10,11,11a-octahydro-4H-[1,4]oxazepino[6,5,4-hi]pyrido[4,3-b]indol-6-amine

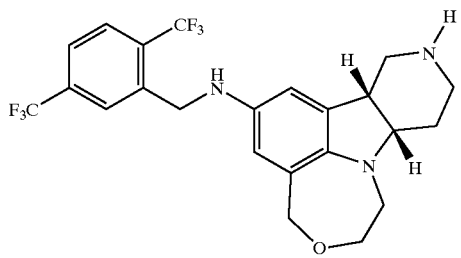

Using 2,5-bis(trifluoromethyl)benzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 130. $^1$H NMR (CDCl$_3$) δ: 7.98 (s, 1H), 7.82 (d, 1H, J=8.1 Hz), 7.64 (d, 1H, J=8.1 Hz), 6.37 (d, 1H, J=2.5 Hz), 6.18 (d, 1H, J=2.5 Hz), 4.58 (ABq, 2H, J$_{AB}$=14.1 Hz), 4.51 (s, 2H), 4.18 (app d, 1H, J=12.5 Hz), 3.90 (m, 1H), 3.74 (app t, 1H), 3.36–3.30 (m, 1H), 3.28–3.20 (m, 1H), 3.20–3.08 (m, 2H), 3.03 (dd, 1H), 2.93–2.85 (m, 2H), 2.64 (app t, 1H), 2.46 (dd, 1H, J=12.1, 10.6 Hz), 2.00–1.80 (m, 2H). LRMS (ES)+: 472.4 (M+H)$^+$.

Example 131

(7bR,11aS)-N-14-fluoro-2-(trifluoromethyl)benzyl]-1,2,7b,8,9,10,11,11a-octahydro-4H-[1,4]oxazepino[6,5,4-hi]pyrido[4,3-b]indol-6-amine

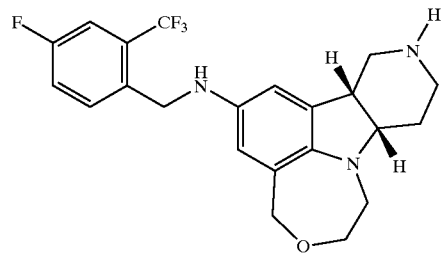

Using 4-fluoro-2-(trifluoromethyl)benzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 131. $^1$H NMR (CDCl$_3$) δ: 7.61 (dd, 1H, J=8.4, 5.5 Hz), 7.40 (dd, 1H, J=8.8, 2.8 Hz), 7.19 (td, 1H, J=8.3, 2.6 Hz), 6.35 (d, 1H, J=2.2 Hz), 6.19 (d, 1H, J=2.2 Hz), 4.56 (ABq, 2H, J$_{AB}$=14.3 Hz), 4.44 (s, 2H), 4.22 (app d, 1H, J=12.8 Hz), 3.92 (broad s, 1H), 3.71 (app t, 1H), 3.38–3.28 (m, 2H), 3.22–3.02 (m, 4H), 2.65 (app t, 1H), 2.53 (app t, 1H), 2.10–2.00 (m, 2H). LRMS (ES)$^+$: 422.3 (M+H)$^+$.

Example 132

(7bR,11aS)-N-(3-fluorobenzyl)-1,2,7b,8,9,10,11,11a-octahydro-4H-[1,4]oxazepino[6,5,4-hi]pyrido[4,3-b]indol-6-amine

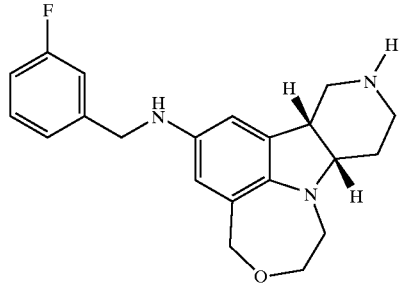

Using 3-fluorobenzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 132. LRMS (ES)$^+$: 354.4 (M+H)$^+$.

Example 133

(7bR,11aS)-N-[2-chloro-5-(trifluoromethyl)benzyl]-1,2,7b,8,9,10,11,11a-octahydro-4H-[1,4]oxazepino[6,5,4-hi pyrido[4,3-b]indol-6-amine

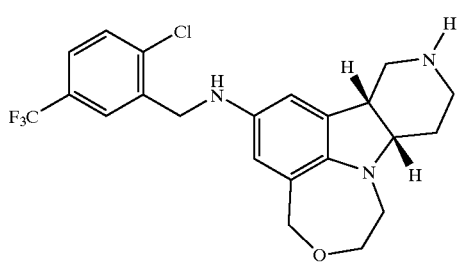

Using 2-chloro-5-(trifluoromethyl)benzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 133. $^1$H NMR (CDCl$_3$) δ: 9.45 (broad s, 1H), 9.20 (broad s, 1H), 7.68 (s, 1H), 7.52–7.45 (m, 2H), 6.41 (d, 1H, J=2.2 Hz), 6.27 (d, 1H, J=2.2 Hz), 4.55 (ABq, 2H, J$_{AB}$=14.3 Hz), 4.40 (s, 2H), 4.22 (app d, 1H, J=12.8 Hz), 3.69 (app t, 1H), 3.53–3.38 (m, 2H), 3.35–3.10 (m, 4H), 2.70–2.50 (m, 2H), 2.23–2.10 (m, 2H).

Example 134

(7bR,11aS)-N-(2-fluorobenzyl)-1,2,7b,8,9,10,11,11a-octahydro-4H-[1,4]oxazepino[6,5,4-hi]pyrido[4,3-b]indol-6-amine

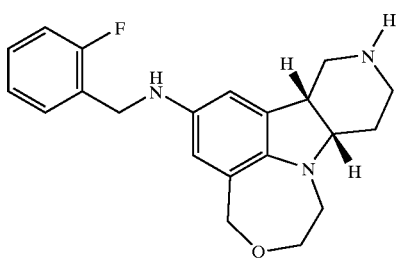

Using 2-fluorobenzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 134. LRMS (ES)+: 354.3 (M+H)$^+$.

Example 135

(7bR,11aS)-N-(2,4-dimethylbenzyl)-1,2,7b,8,9,10,11,11a-octahydro-4H-[1,4]oxazepino[6,5,4-hi]pyrido[4,3 b]indol-6-amine

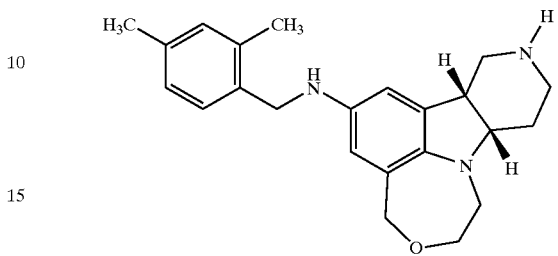

Using 2,4-dimethylbenzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 135. $^1$H NMR (CDCl$_3$) δ: 9.55 (broad s, 1H), 9.35 (broad s, 1H), 7.18 (d, 1H, J=7.7 Hz), 7.01–6.95 (m, 2H), 6.64 (s, 1H), 6.51 (s, 1H), 4.57 (ABq, 2H), 4.25–4.20 (m, 1H), 4.20 (s, 2H), 3.67 (app t, 1H), 3.50–3.10 (m, 6H), 2.70–2.50 (m, 2H), 2.30 (s, 3H), 2.27 (s, 3H), 2.23–2.10 (m, 2H).

Example 136

(7bR,11aS)-N-(4-methoxy-3-methylbenzyl)-1,2,7b,8,9,10,11,11a-octahydro-4H-[1,4]oxazepino[6,5,4-hi]pyrido[4,3-b]indol-6-amine

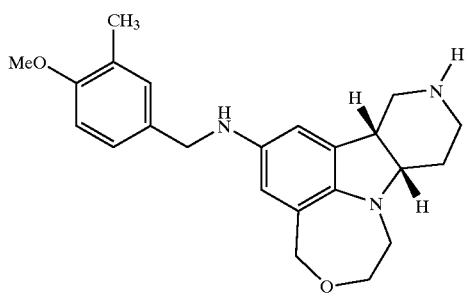

Using 3-methyl-4-methoxybenzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H) carboxylate from EXAMPLE 56, Part B was converted into the title compound of EXAMPLE 136. $^1$H NMR (CDCl$_3$) δ: 7.18–7.10 (m, 2H), 6.78 (d, 1H, J=9.2 Hz), 6.42 (d, 1H, J=1.9 Hz), 6.25 (d, 1H, J=2.2 Hz), 4.59 (ABq, 2H, J$_{AB}$=14.1 Hz), 4.20–4.10 (m, 1H), 4.13 (s, 2H), 3.83 (s, 3H), 3.74 (app t, 1H), 3.30–3.23 (m, 1H), 3.22–3.10 (m, 2H), 3.09–3.01 (m, 1H), 2.95–2.88 (m, 2H), 2.62 (app t, 1H), 2.48 (app t, 1H), 2.21 (s, 3H), 2.00–1.80 (m, 2H). LRMS (ES)$^+$: 380.4 (M+H)$^+$.

Example 137

(7bR,11aS)-N-(4-methoxy-2-methylbenzyl)-1,2,7b,8,9,10,11,11a-octahydro-4H-[1,4]oxazepino[6,5,4-hi]pyrido[4,3-b]indol-6-amine

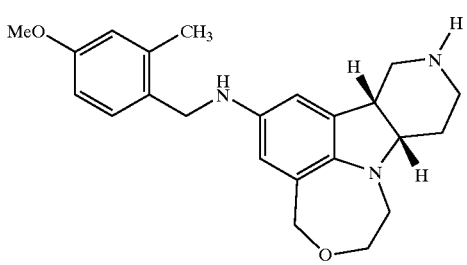

Using 2-methyl-4-methoxybenzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 137. $^1$H NMR (CDCl$_3$) δ: 7.21 (d, 1H, J=8.5 Hz), 6.75–6.68 (m, 2H), 6.59 (broad s, 1H), 6.43 (broad s, 1H), 4.58 (ABq, 2H), 4.23–4.16 (m, 1H), 4.16 (s, 2H), 3.78 (s, 3H), 3.68 (app t, 1H), 3.50–3.40 (m, 1H), 3.37–3.15 (m, 5H), 2.70–2.50 (m, 2H), 2.30 (s, 3H), 2.23–2.10 (m, 2H). LRMS (ES)$^+$: 380.4 (M+)$^+$.

Example 138

2-{[(7bR,11aS)-1,2,7b,8,9,10,11,11a-octahydro-4H-[1,4]oxazepino[6,5,4-hi]pyrido[4,3-b]indol-6-ylamino]methyl}benzonitrile

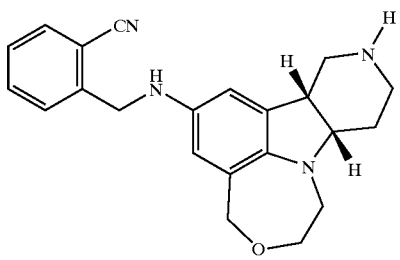

Using 2-cyanobenzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 138. $^1$H NMR (CDCl$_3$) δ: 8.42 (d, 1H), 7.67–7.50 (m, 3H), 7.19 (d, 1H, J=2.2 Hz), 6.98 (d, 1H, J=2.2 Hz), 5.32 (s, 2H), 4.65 (ABq, 2H), 4.20–4.15 (m, 1H), 3.83–3.77 (m, 1H), 3.62–3.57 (m, 1H), 3.50–3.45 (m, 1H), 3.28 (dd, 1H), 3.20 (dd, 1H), 3.03–2.96 (m, 2H), 2.90–2.78 (m, 2H), 2.05–1.98 (m, 2H).

Example 139

(7bR,11aS)-N-[4-(trifluoromethyl)benzyl]-1,2,7b,8,9,10,11,11a-octahydro-4H-[1,4]oxazepino[6,5,4-hi]pyrido[4,3-b]indol-6-amine

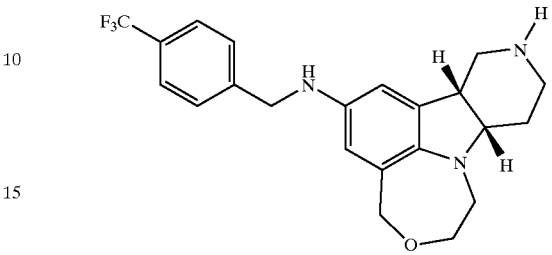

Using 2-(trifluoromethyl)benzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 139. $^1$H NMR (CDCl$_3$) δ: 9.40 (broad s, 1H), 9.20 (broad s, 1H), 7.59 (d, 2H, J=8.1 Hz), 7.50–7.42 (m, 2H), 6.37 (d, 1H, J=2.2 Hz), 6.25–6.20 (m, 1H), 4.55 (ABq, 2H, J$_{AB}$=14.4 Hz), 4.33 (s, 2H), 4.22 (app d, 1H, J=12.1 Hz), 3.68 (app t, 1H), 3.50–3.40 (m, 1H), 3.36–3.10 (m, 5H), 2.70–2.55 (m, 2H), 2.22–2.00 (m, 2H). LRMS (ES)$^+$: 404.4 (M+H)$^+$.

Example 140

(7bR,11aS)-N-(2,6-difluorobenzyl)-1,2,7b,8,9,10,11,11a-octahydro-4H-[1,4]oxazepino[6,5,4-hi]pyrido[4,3-b]indol-6-amine

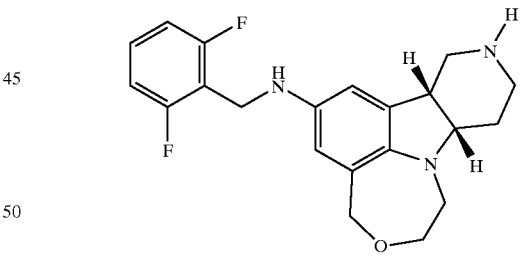

Using 2,6-difluorobenzaldehyde and following the procedures described in EXAMPLE 126, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from EXAMPLE 56, Part B was converted into the title compound of EXAMPLE 140. $^1$H NMR (CDCl$_3$) δ: 7.25–7.15 (m, 2H), 6.90–6.82 (m, 2H), 6.50 (d, 1H, J=2.2 Hz), 6.30 (d, 1H, J=2.2 Hz), 4.58 (ABq, 2H, J$_{AB}$=14.0 Hz), 4.35 (s, 2H), 4.20–4.13 (m, 1H), 3.72 (dd, 1H, J=11.5, 10.8 Hz), 3.33–3.25 (m, 1H), 3.22–3.08 (m, 2H), 3.02 (dd, 1H, J=12.4, 6.6 Hz), 2.95–2.85 (m, 2H), 2.65–2.57 (m, 1H), 2.44 (dd, 1H, J=12.3, 10.4 Hz), 1.95–1.80 (m, 2H). LRMS (ES)$^+$: 372.4 (M+H)$^+$.

Example 141

(7bR,11aS)-N-[2-fluoro-3-(trifluoromethyl)phenyl]-9-isopropyl-1,2,7b,8,9,10,11,11a-octahydro-4H-[1,4]oxazepino[6,5,4-hi]pyrido[4,3 b]indol-6-amine, bis-trifluoroacetic acid salt

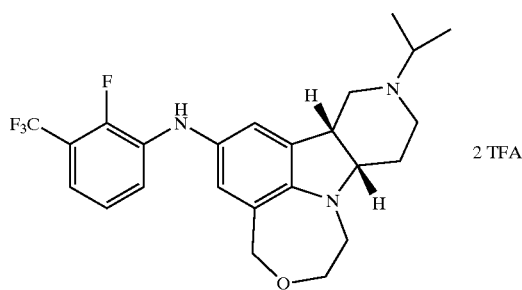

To a solution of (7bR,11aS)-N-[2-fluoro-3-trifluoromethyl)phenyl]-1,2,7b,8,9,10,11,11a-octahydro-4H-[1,4]oxazepino[6,5,4-hi]pyrido[4,3-b]indol-6-amine free base from EXAMPLE 95 (41 mg, 0.1 mmol) in 5 mL of tetrahydrofuran was added acetone (0.022 mL, 0.3 mmol). The reaction was stirred at room temperature for 4 h and then there was added sodium triacetoxyborohydride (63 mg, 0.3 mmol) and the resulting solution was allowed to stir at room temperature for 24 h. The reaction was quenched with aq NaHCO$_3$, extracted with ethyl acetate, washed with brine, dried (MgSO$_4$) and concentrated. The residue was purified by preparative HPLC (C18 reverse phase column, elution with a H$_2$O/CH$_3$CN gradient with 0.5% TFA) to afford the title compound of EXAMPLE 141. $^1$H NMR (CDCl$_3$) δ: 7.13 (t, 1H, J=8.2 Hz), 7.00–6.90 (m, 2H), 6.89 (s, 1H), 6.73 (s, 1H), 5.75 (broad s, 1H), 4.56 (ABq, 2H, J$_{AB}$=14.1 Hz), 4.21 (app d, 1H, J=11.7 Hz), 3.83–3.75 (m, 1H), 3.66 (broad t, 1H), 3.55–3.42 (m, 1H), 3.40–3.25 (m, 2H), 3.13 (app d, 1H, J=11.3 Hz), 3.05–2.92 (m, 1H), 2.71 (app t, 1H), 2.55–2.42 (m, 1H), 2.33 (app t, 1H), 2.20–2.00 (m, 2H), 1.25 (d, 6H, J=10.4 Hz). LRMS (ES)$^+$: 450.3 (M+H)$^+$.

Example 142

(7bR,11aS)-N-[2-fluoro-3-(trifluoromethyl)phenyl]-N,9-dimethyl-1,2,7b,8,9,10,11,11a-octahydro-4H-[1,4]oxazepino[6,5,4-hi]pyrido[4,3 b]indol-6-amine, bis-trifluoroacetic acid salt

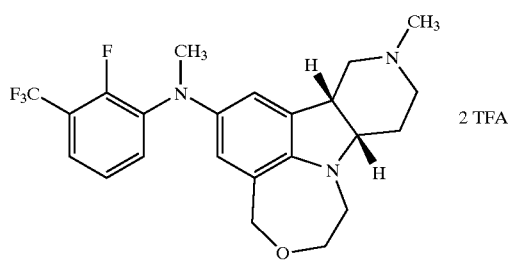

To a solution of (7bR,11aS)-N-[2-fluoro-3-(trifluoromethyl)phenyl]-1,2,7b,8,9, 10,11,11a-octahydro-4H-[1,4]oxazepino[6,5,4-hi]pyrido[4,3-b]indol-6-amine free base from EXAMPLE 95 (41 mg, 0.1 mmol) in 2 mL of 1:1 methanol/ether was added iodomethane (0.016 mL, 0.25 mmol) and potassium carbonate (41 mg, 0.30 mmol). The reaction was stirred at room temperature for 24 h and was quenched with water, extracted with ethyl acetate, washed with brine, dried (MgSO$_4$) and concentrated. The residue was purified by preparative HPLC (C18 reverse phase column, elution with a H$_2$O/CH$_3$CN gradient with 0.5% TFA) to afford the title compound of EXAMPLE 142. LRMS (ES)$^+$: 436.3 (M+H)$^+$.

Example 143

(7bR,11aS)-N-[2-fluoro-3-(trifluoromethyl)phenyl]-9-methyl-1,2,7b,8,9,10,11,11a-octahydro-4H-[1,4]oxazepino[6,5,4-hi]pyrido[4,3-b]indol-6-amine, bis-trifluoroacetic acid salt.

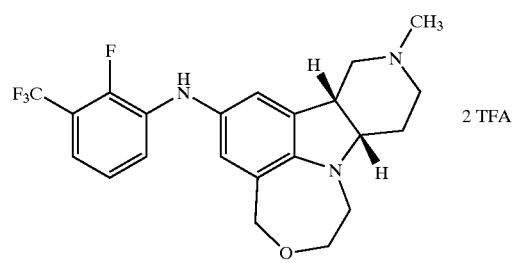

To a solution of (7bR,11aS)-N-[2-fluoro-3-(trifluoromethyl)phenyl]-1,2,7b,8,9,10,11,11a-octahydro-4H-[1,4]oxazepino[6,5,4-hi]pyrido[4,3-b]indol-4-amine free base from EXAMPLE 95 (41 mg, 0.1 mmol) in 5 mL tetrahydrofuran was added 37% aqueous formaldehyde (0.1 mL). After stirring at room temperature for 1 h there was added sodium triacetoxyborohydride (64 mg, 0.30 mmol). The reaction was stirred at room temperature for 24 h and was quenched with aq NaHCO$_3$, extracted with ethyl acetate, washed with brine, dried (MgSO$_4$) and concentrated. The residue was purified by preparative HPLC (C18 reverse phase column, elution with a H$_2$O/CH$_3$CN gradient with 0.5% TFA) to afford the title compound of EXAMPLE 143. $^1$H NMR (CDCl$_3$) δ: 7.22–7.15 (m, 1H), 7.10–6.95 (m, 2H), 6.94 (d, 1H, J=1.9 Hz), 6.81 (d, 1H, J=2.2 Hz), 5.02 (s, 1H), 4.65 (ABq, 2H, J$_{AB}$=14.5 Hz), 4.29 (app d, 1H), 4.254.20 (m, 1H), 4.154.05 (m, 2H), 3.79–3.70 (m, 1H), 3.50–3.35 (m, 3H), 3.23 (app d, 1H), 3.10–3.00 (m, 1H), 2.80 (s, 3H), 2.50–2.40 (m, 2H), 2.25–2.17 (m, 1H). LRMS (ES)$^+$: 422.3 (M+H)$^+$.

Example 144

(7bR,11aS)$_9$-ethyl-N-[2-fluoro-3-(trifluoromethyl)phenyl]-1,2,7b,8,9,10,11,11a-octahydro-4H-[1,4]oxazepino[6,5,4-hi]pyrido[4,3-b]indol-6-amine

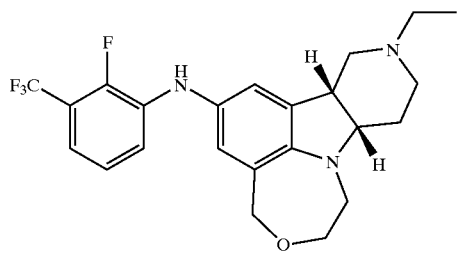

185

To a solution of (7bR,11aS)-N-[2-fluoro-3-trifluoromethyl)phenyl)-1,2,7b,8,9,10,11,11a-octahydro-4H-[1,4]oxazepino[6,5,4-hi]pyrido[4,3-b]indol-6-amine free base from EXAMPLE 95 (41 mg, 0.1 mmol) in 5 mL tetrahydrofuran was added iodoethane (0.020 mL, 0.22 mmol) and sodium carbonate (21 mg, 0.22 mmol). The reaction was stirred at 60° C. for 3 h and then was cooled, quenched with water, extracted with ethyl acetate, washed with brine, dried (MgSO$_4$) and concentrated. The residue was purified by preparative HPLC (Cl 8 reverse phase column, elution with a H$_2$O/CH$_3$CN gradient with 0.5% TFA) and the product containing fractions were concentrated, free-based with aq ammonium hydroxide, extracted with chloroform, washed with brine, dried (K$_2$CO$_3$) and concentrated to afford the title compound of EXAMPLE 144. $^1$H NMR (CDCl$_3$) δ: 7.15 (t, 1H, J=7.3 Hz), 7.05–6.95 (m, 2H), 6.91 (d, 1H, J=1.9 Hz), 6.77 (d, 1H, J=1.8 Hz), 5.73 (d, 1H, J=2.9 Hz), 4.63 (ABq, 2H, J$_{AB}$=14.3 Hz), 4.25 (app d, 1H, J=12.9 Hz), 3.75 (app t, 1H), 3.43–3.36 (m, 2H), 3.27 (dd, 1H, J=12.8, 2.9 Hz), 2.97–2.80 (m, 2H), 2.75 (app t, 1H), 2.55–2.45 (m, 2H), 2.40–2.30 (m, 1H), 2.15–2.00 (m, 2H), 1.88 (app t, 1H), 1.15 (t, 3H, J=7.2 Hz). LRMS (ES)$^+$: 436.4 (M+H)$^+$.

Example 145

(7bR,11aS)-9-(cyclobutylmethyl)-N-[2-fluoro-3-(trifluoromethyl)phenyl]-1,2,7b,8,9,10,11,11a-octahydro-4H-[1,4]oxazepino[6,5,4-hi]pyrido[4,3-b]indol-6 amine

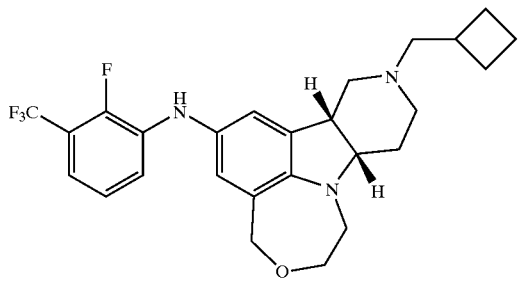

Using bromomethylcyclobutane and following the procedures described in EXAMPLE 144, (7bR,11aS)-N-[2-fluoro-3-(trifluoromethyl)phenyl]-1,2,7b,8,9,10,11,11a-octahydro-4H-[1,4]oxazepino[6,5,4-hi]pyrido[4,3-b]indol-6-anine free base from EXAMPLE 95 was converted into the title compound of EXAMPLE 145. $^1$H NMR (CDCl$_3$) δ: 7.15 (dd, 1H, J=7.8, 6.8 Hz), 7.05–6.95 (m, 2H), 6.89 (d, 1H, J=1.9 Hz), 6.77 (d, 1H, J=2.0 Hz), 5.73 (d, 1H, J=3.0 Hz), 4.63 (ABq, 2H, J$_{AB}$=14.1 Hz), 4.24 (app d, 1H, J=12.8 Hz), 3.75 (app t, 1H), 3.50–3.30 (m, 2H), 3.25 (dd, 1H, J=13.1, 2.8 Hz), 2.95–2.30 (overlapping multiplets, 7H), 2.15–1.65 (overlapping multiplets, 9H). LRMS (ES)$^+$: 476.4 (M+H)$^+$.

186

Example 146

(7bR,11aS)-N-[2-fluoro-3-(trifluoromethyl)phenyl]-9-(3-methyl-2-butenyl)-1,2,7b,8,9,10,11,11a-octahydro-4H-[1,4]oxazepino[6,5,4-hi]pyrido[4,3-b]indol-6-amine

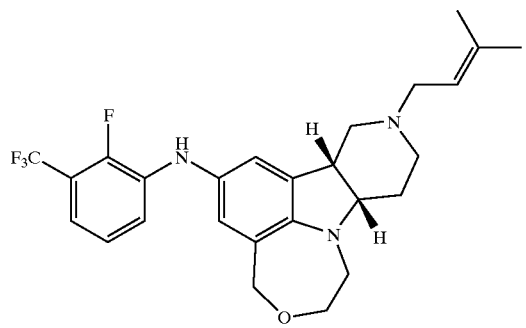

Using 4-bromo-2-methyl-2-butene and following the procedures described in EXAMPLE 144, (7bR, 1 aS)-N-[2-fluoro-3-(trifluoromethyl)phenyl]-1,2,7b,8,9,10,11,11a-octahydro-4H-[1,4]oxazepino[6,5,4-hi]pyrido[4,3-b]indol-6-amine free base from EXAMPLE 95 was converted into the title compound of EXAMPLE 146. $^1$H NMR (CDCl$_3$) δ: 7.22–7.15 (m, 1H), 7.07–6.95 (m, 2H), 6.93 (d, 1H, J=1.9 Hz), 6.79 (d, 1H, J=2.2 Hz), 5.80 (broad s, 1H), 5.36 (t, 1H, J=7.5 Hz), 4.64 (ABq, 2H, J$_{AB}$=14.3 Hz), 4.27 (app d, 1H, J=13.2 Hz), 3.85–3.70 (m, 2H), 3.54 (d, 1H, J=7.3 Hz), 3.45–3.35 (m, 3H), 3.22 (dd, 1H, J=12.8, 1.4 Hz), 2.92–2.78 (m, 2H), 2.61–2.45 (m, 1H), 2.28 (t, 1H, J=7.9 Hz), 2.18–2.12 (m, 1H), 1.81 (s, 3H), 1.67 (s, 3H). LRMS (ES)+: 476.4 (M+H)$^+$.

Example 147

(7bR,11aS)-6-[2-(trifluoromethyl)phenyl]-1,2,7b,8,9,10,11,11a-octahydro-4H-pyrido[4,3-b][1,4]thiazepino[6,5,4-hi]indole

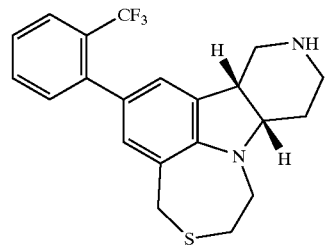

Using 2-(trifluoromethyl)phenylboronic acid and following the procedures described in EXAMPLE 7, Parts B and C, tert-butyl (7bR,11aS)-6-bromo-1,2,7b,10,11,11a-hexahydro-4H-pyrido[4,3-b][1,4]thiazepino[6,5,4-hi]indole-9(8H)-carboxylate from EXAMPLE 7, Part A was converted into the title compound of EXAMPLE 147. $^1$H NMR (CDCl$_3$) δ: 9.50 (broad s, 1H), 9.30 (broad s, 1H), 7.68 (d, 1H, J=8.1 Hz), 7.50 (t, 1H, J=7.3 Hz), 7.40 (t, 1H, J=7.3 Hz), 7.26 (d, 1H), 6.93 (s, 1H), 6.87 (s, 1H), 3.80 (ABq, 2H, J$_{AB}$=15.8 Hz), 3.61–3.45 (m, 2H), 3.37–3.05 (m, 6H), 2.90–2.80 (m, 1H), 2.70–2.57 (m, 1H), 2.25–2.10 (m, 2H). LRMS (ES)+: 391.4 (M+H)$^+$.

Example 148

(7bR,11aS)-N-(2,6-dichlorophenyl)-1,2,7b,8,9,10,11,11a-octahydro-4H-pyrido[4,3-b][1,4]thiazepino[6,5,4-hi]indol-6-amine

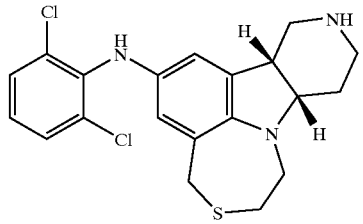

An oven-dried three-necked round bottom flask was fitted with a septa, condenser, and a stopper. The flask was charged with tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B (107 mg, 0.297 mmol), 2,6-dichlorobromobenzene (56 mg, 0.25 mmol), NaOt-Bu (71 mg, 0.74 mmol), and anhydrous toluene (6 mL). The solution was purged with argon at 80° C. for 25 min then cooled to room temperature. While maintaining a blanket of argon, Pd$_2$(dba)$_3$ (5 mg, 6 μmol), and BINAP (7 mg, 12 μmol) were added quickly. The resulting mixture was heated to 80° C. for 20 h under argon. After cooling to room temperature, the dark solution was diluted with ethyl ether (10 mL) and filtered through a pad of silica, washing with ether. The resulting solution was concentrated and the residue was chromatographed (10–12% ethyl acetate in hexanes gradient) yielding an N-BOC intermediate (90 mg, 72%) as a yellow foam: $^1$H NMR (300 MHz, CDCl$_3$) δ 1.40 (s, 9H), 1.71–1.92 (m, 2H), 2.79–3.13 (m, 3H), 3.15–3.96 (m, 9H), 5.71 (s, 1H), 6.29–6.50 (m, 2H), 6.91–7.00 (s, 1H), 7.32 (d, 2H, J=8 Hz). This intermediate (90 mg, 0.18 mmol) was dissolved in dichloromethane (8 mL) and chilled in an ice bath. Trifluoroacetic acid (2 mL) was then added and the solution was stirred at room temperature for 2 h. The solution was made basic with 3 N NaOH, and extracted with dichloromethane. The organic layers were combined, dried over NaSO$_4$ and concentrated to a yellow oil. An off-white solid was obtained upon trituration with ethyl acetate/hexanes yielding 58 mg (81%) of the title compound of EXAMPLE 148. $^1$H NMR (300 MHz, CDCl$_3$) δ 1.72–1.85 (m, 2H), 2.51–2.65 (m, 1H), 2.76–3.09 (m, 6H), 3.10–3.21 (m, 1H), 3.36–3.42 (m, 1H), 3.47–3.79 (m, 4H), 5.71 (s, 1H), 6.34 (s, 1H), 6.42 (s, 1H), 6.95 (t, 1H, J=8 Hz), 7.32 (d, 2H, J=8 Hz). LRMS (ES)$^+$: 406 (M+H)$^+$.

Example 149

(7bR,11aS)-N-(2,6-fluorophenyl)-1,2,7b,8,9,10,11,11a-octahydro-4H-pyrido[4,3-b][1,4]thiazepino[6,5,4-hi]indol-6-amine

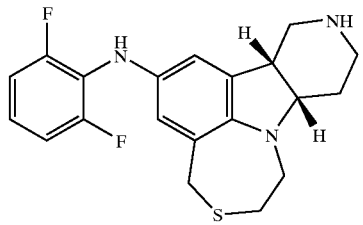

Using 2,6-difluorobromobenzene and following the procedures described in EXAMPLE 148, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 149. $^1$H NMR (300 MHz, CDCl$_3$) δ 1.71–1.80 (m, 2H), 2.52–2.64 (m, 1H), 2.81–3.08 (m, 5H), 3.16–3.77 (m, 7H), 5.33 (s, 1H), 6.43 (s, 1H), 6.51 (s, 1H), 6.91–6.94 (m, 3H). LRMS (ES)$^+$: 374 (M+H)$^+$.

Example 150

1-{2-[(7bR,11aS)1,2,7b,8,9,10,11,11a-octahydro-4H-pyrido[4,3-b][1,4]thiazepino[6,5,4-hi]indol-6-ylamino]-5-chlorophenyl}ethanone

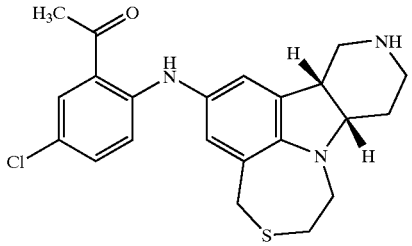

Using 2-(2-bromo-5-chlorophenyl)-2-methyl-1,3-dioxolane and following the procedures described in EXAMPLE 116, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 150. $^1$H NMR (CDCl$_3$) δ: 10.26 (s, 1H), 7.72 (d, 1H, J=2.2 Hz), 7.20 (dd, 1H, J=9.2, 2.6 Hz), 6.96 (d, 1H, J=9.2 Hz), 6.84 (d, 1H, J=1.8 Hz), 6.77 (d, 1H, J=1.9 Hz), 6.87 (s, 1H), 3.74 (ABq, 2H, J$_{AB}$=15.6 Hz), 3.63–3.57 (m, 1H), 3.50–3.42 (m, 1H), 3.40–3.30 (m, 1H), 3.20–3.02 (m, 5H), 2.98–2.90 (m, 1H), 2.66–2.58 (m, 1H), 2.61 (s, 3H), 2.05–1.97 (m, 2H). LRMS (ES)+: 391.4 (M+H)$^+$. LRMS (ES)$^+$: 414.4 (M+H)$^+$.

Example 151

1-{2-[(7bR,11aS)1,2,7b,8,9,10,11,11a-octahydro-4H-pyrido[4,3-b][1,4]thiazepino[6,5,4-hi]indol-6-ylamino]-5-chlorophenyl)ethanol

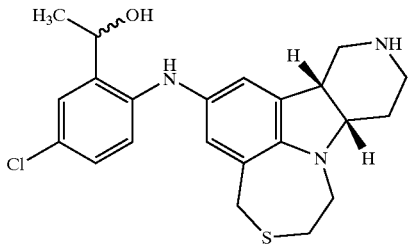

Following the procedures described in EXAMPLE 117, 1-{2-[(7bR,11aS)-1,2,7b,8,9,10,11,11a-octahydro-4H-pyrido[4,3-b][1,4]thiazepino[6,5,4-hi]indol-6-ylamino]-5-chlorophenyl}ethanone from EXAMPLE 150 was converted into the title compound of EXAMPLE 151 as a mixture of diastereomers at the alcohol center. $^1$H NMR (CDCl$_3$) δ: 7.01 (d, 1H, J=4.4 Hz), 6.98–6.90 (m, 2H), 6.58 (s, 2H), 4.79 (q, 1H, J=6.6 Hz), 4.08–4.01 (m, 2H), 3.52–3.43 (m, 1H), 3.30–3.20 (m, 1H), 3.10–3.00 (m, 1H), 2.98–2.70 (m, 6H), 2.40–2.28 (m, 1H), 1.80–1.60 (m, 2H), 1.51 (dd, 3H, J=6.2, 1.1 Hz). LRMS (ES)$^+$: 416.4 (M+H)$^+$.

Example 152

(7bR,11aS)-N-[2,6-bis(trifluoromethyl)benzyl]-1,2,7b,8,9,10,11,11a-octahydro-4H-pyrido[4,3-b][1,4]thiazepino[6,5,4-hi]indol-6-amine

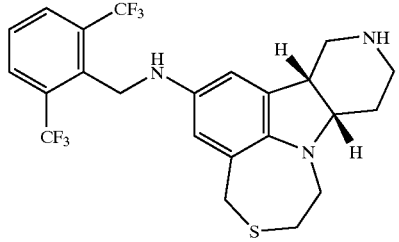

Using 2,6-bis(trifluoromethyl)benzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 152. LRMS (ES)+: 488.4 (M+H)+.

Example 153

(7bR,11aS)-N-[2-chloro-5-(trifluoromethyl)benzyl]-1,2,7b,8,9,10,11,11a-octahydro-4H-pyrido[4,3b][1,4]thiazepino[6,5,4-hi]indol-6-amine

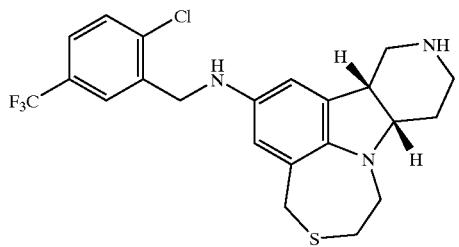

Using 2-chloro-5-(trifluoromethyl)benzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H) Carboxylate from EXAMPLE 33, Part B was converted into the title compound of EXAMPLE 153. $^1$H NMR (CDCl$_3$) δ: 9.20–9.05 (broad m, 2H), 7.67 (s, 1H), 7.52–7.40 (m, 2H), 6.43 (broad s, 1H), 6.32 (broad s, 1H), 4.39 (broad s, 2H), 4.354.10 (m, 2H), 3.75–3.30 (overlapping m, 4H), 3.30–2.79 (overlapping m, 5H), 2.65–2.50 (m, 1H), 2.20–2.05 (m, 2H). LRMS (ES)+: 454.4 (M+H)+.

Example 154

(7bR,11aS)-N-[4-fluoro-2-(trifluoromethyl)benzyl-1,2,7b,8,9,10,11,11a-octahydro-4H-pyrido[4,3-b][1,4]thiazepino[6,5,4-hi]indol-6-amine

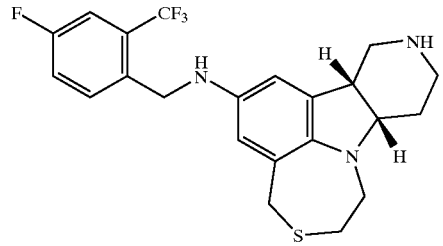

Using 4-fluoro-2-(trifluoromethyl)benzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H) Carboxylate from EXAMPLE 33, Part B was converted into the title compound of EXAMPLE 154. $^1$H NMR (CDCl$_3$) δ: 9.30 (broad s, 1H), 9.15 (broad s, 1H), 7.60–7.52 (m, 1H), 7.38–7.25 (m, 1H), 7.13 (broad t, 1H, J=8.0 Hz), 6.30–6.15 (broad m, 2H), 4.45–4.25 (broad m, 2H), 4.17–3.98 (broad m, 2H), 3.70–3.30 (m, 4H), 3.30–2.70 (broad m, 5H), 2.60–2.47 (m, 1H), 2.20–2.00 (m, 2H). LRMS (ES)+: 438.4 (M+H)+.

Example 155

(7bR,11aS)-N-(3-chloro-4-fluorobenzyl)-1,2,7b,8,9,10,11,11a-octahydro-4H-pyrido[4,3-b][1,4]thiazepino[6,5,4-hi]indol-6-amine

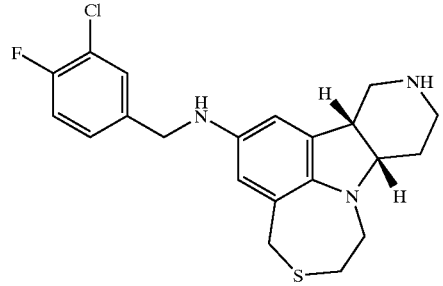

Using 4-fluoro-3-chlorobenzaldehyde and following the procedures described in EXAMPLE 126, tert-butyl (7bR,11aS)-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 155. $^1$H NMR (CDCl$_3$) δ: 7.42 (dd, 1H, 3=7.0, 2.2 Hz), 7.27–7.20 (m, 1H), 7.12 (t, 1H, J=8.6 Hz), 6.32 (d, 1H, J=2.2 Hz), 6.21 (d, 1H, J=2.2 Hz), 4.23 (broad s, 2H), 3.67 (ABq, 2H, J$_{AB}$=15.2 Hz), 3.57–3.48 (m, 1H), 3.38–3.30 (m, 2H), 3.19–3.08 (m, 1H), 3.05–2.90 (m, 4H), 2.65–2.55 (m, 2H), 2.02–1.88 (m, 2H). LRMS (ES)+: 404.4 (M+H)+.

Example 156

(7bR,11aS)-N-(3-chlorobenzyl)-1,2,7b,8,9,10,11,
11a-octahydro-4H-pyrido[4,3-b][1,4]thiazepino[6,5,
4-hi]indol-6-amine

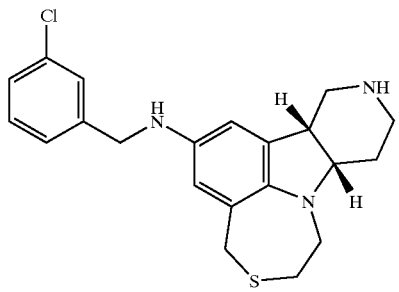

Using 3-chlorobenzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 156. $^1$H NMR (CDCl$_3$) δ: 7.37 (s, 1H), 7.29–7.20 (m, 2H), 6.34 (d, 1H, J=2.2 Hz), 6.24 (d, 1H, J=2.6 Hz), 4.25 (broad s, 2H), 3.67 (s, 2H), 3.57–3.50 (m, 1H), 3.42–3.31 (m, 2H), 3.20–2.85 (m, 6H), 2.60 (dd, 1H, J=12.8, 9.9 Hz), 2.15–1.97 (m, 2H). LRMS (ES)$^+$: 386.3 (M+H)$^+$.

Example 157

(7bR,11aS)-N-[2-(trifluoromethyl)benzyl]-1,2,7b,8,
9,10,11,11a-octahydro-4H-pyrido[4,3-b][1,4]
thiazepino[6,5,4-hi]indol-6-amine

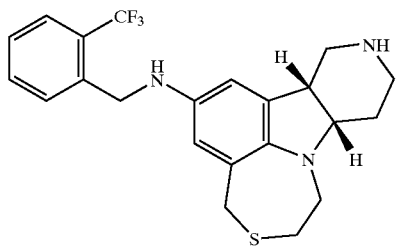

Using 2-(trifluoromethyl)benzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 157. $^1$H NMR (CDCl$_3$) δ: 7.69 (d, 1H, J=8.0 Hz), 7.64 (d, 1H, J=7.7 Hz), 7.52 (t, 1H, J=7.5 Hz), 7.38 (t, 1H, J=7.7 Hz), 6.31 (d, 1H, J=2.2 Hz), 6.22 (d, 1H, J=2.2 Hz), 4.48 (broad s, 2H), 3.67 (ABq, 2H, J$_{AB}$=15.6 Hz), 3.57–3.50 (m, 1H), 3.40–3.30 (m, 2H), 3.15–2.90 (m, 6H), 2.60 (dd, 1H, J=13.2, 9.6 Hz), 2.20–1.97 (m, 2H). LRMS (ES)$^+$: 420.4 (M+H)$^+$.

Example 158

(7bR,11aS)-N-(3,4-dichlorobenzyl)-1,2,7b,8,9,10,11,
11a-octahydro-4H-pyrido[4,3-b][1,4]thiazepino[6,5,
4-hi]indol-6-amine

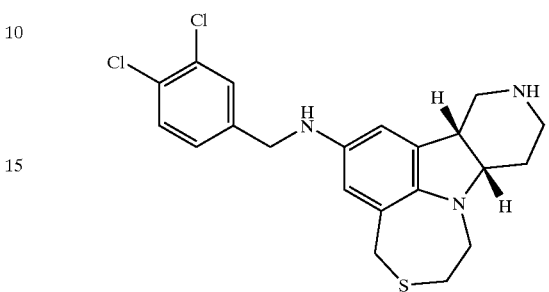

Using 3,4-dichlorobenzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 158. LRMS (ES)$^+$: 420.4 (M+H)$^+$.

Example 159

(7bR,11aS)-N-(2,5-difluorobenzyl)1,2,7b,8,9,10,11,
11a-octahydro-4H-pyrido[4,3-b][1,4]thiazepino[6,5,
4-hi]indol-6-amine

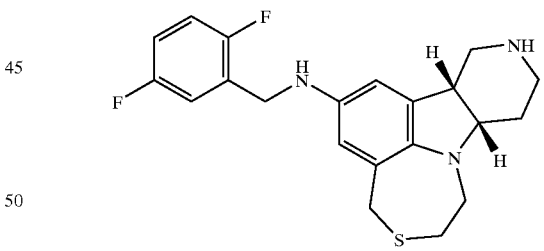

Using 2,5-difluorobenzaldehyde and following the procedures described in EXAMPLE 126, tert-butyl (7bR,11aS)$_6$-amino-1,2,7b,10,11,11a-hexahydro-4H-pyrido[4,3-b][1,4]thiazepino[6,5,4-hi]indole-9(8M carboxylate from EXAMPLE 33, Part B was converted into the title compound of EXAMPLE 159. $^1$H NMR (CDCl$_3$) δ: 7.05–6.98 (m, 1H), 6.97–6.90 (m, 1H), 6.90–6.80 (m, 1H), 6.26 (d, 1H, J=2.5 Hz), 6.14 (d, 1H, J=2.2 Hz), 4.23 (broad s, 2H), 3.59 (ABq, 2H), 3.50–3.40 (m, 1H), 3.30–3.17 (m, 2H), 3.05–2.65 (m, 61H), 2.51 (dd, 1H, J=12.7, 9.5 Hz), 1.92–1.78 (m, 2H). LRMS (ES)$^+$: 388.4 (M+H)$^+$.

Example 160

(7bR,11aS)-N-[3-chloro-2-fluoro-5-(trifluoromethyl)benzyl]-1,2,7b,8,9,10,11,11a-octahydro-4H-pyrido[4,3-b][1,4]thiazepino[6,5,4-hi]indol-6-amine

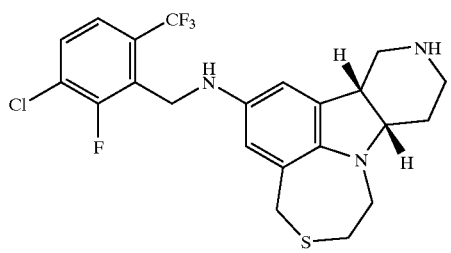

Using 3-chloro-2-fluoro-6-(trifluoromethyl)benzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 160. $^1$H NMR (CDCl$_3$) δ: 7.50–7.38 (m, 2H), 6.44 (s, 1H), 6.32 (s, 1H), 4.39 (broad s, 2H), 3.66 (s, 2H), 3.58–3.48 (m, 1H), 3.42–3.28 (m, 214), 3.25–2.79 (m, 6H), 2.55 (app t, 1H), 2.15–1.95 (m, 2H). LRMS (ES)$^+$: 472.5 (M+H)$^+$.

Example 161

(7bR,11aS)-N-(2,6-difluorobenzyl)-1,2,7b,8,9,10,11,11a-octahydro-4H-pyrido[4,3-b][1,4]thiazepino[6,5,4-hi]indol-6-amine

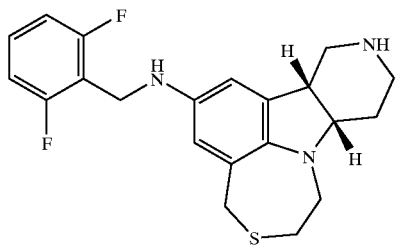

Using 2,6-difluorobenzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 161. $^1$H NMR (CDCl$_3$) δ: 7.23–7.15 (m, 1H), 6.88–6.80 (m, 2H), 6.42 (s, 1H), 6.28 (s, 1H), 4.31 (broad s, 2H), 3.64 (s, 2H), 3.55–3.45 (m, 1H), 3.37–3.23 (m, 2H), 3.15–2.80 (m, 6H), 2.60–2.50 (m, 1H), 2.05–1.82 (m, 2H). LRMS (ES)$^+$: 388.4 (M+H)$^+$.

Example 162

2-([[(7bR,11aS)-1,2,7b,8,9,10,11,11a-octahydro-4H-pyrido[4,3-b][1,4]thiazepino[6,5,4-hi]indol-6-ylamino]methyl]benzonitrile

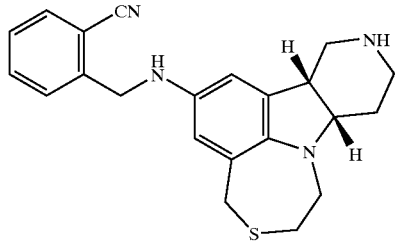

Using 2-cyanobenzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 162. $^1$H NMR (CDCl$_3$) δ: 8.14 (d, 1H, J=7.7 Hz), 7.63–7.50 (m, 3H), 6.88–6.80 (m, 2H), 7.13 (s, 1H), 6.95 (s, 1H), 4.90 (broad s, 2H), 3.81 (ABq, 2H, $J_{AB}$=15.7 Hz), 3.71–3.62 (m, 2H), 3.59–3.53 (m, 1H), 3.38–3.30 (m, 1H), 3.29–3.20 (m, if), 3.12–2.80 (m, 5H), 1.91–1.80 (m, 2H). LRMS (ES)$^+$: 377.4 (M+H)$^+$.

Example 163

(7bR,11aS)-N-(2,4-difluorobenzyl)-1,2,7b,8,9,10,11,11a-octahydro-4H-pyrido[4,3 b][1,4]thiazepino[6,5,4-hi]indol-6-amine

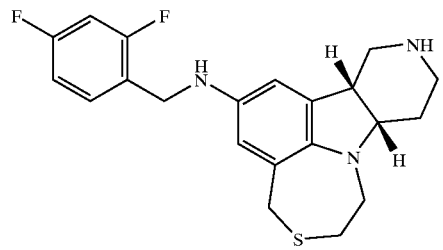

Using 2,4-difluorobenzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 163. $^1$H NMR (CDCl$_3$) δ: 7.30–7.20 (m, 1H), 6.80–6.70 (m, 2H), 6.27 (d, 1H, J=2.2 Hz), 6.15 (d, 1H, J=2.2 Hz), 4.20 (broad s, 2H), 3.59 (ABq, 2H, $J_{AB}$=15.2 Hz), 3.53–3.40 (m, 2H), 3.29–3.21 (m, 1H), 3.20–3.10 (m, 1H), 3.02–2.77 (m, 5H), 2.52 (dd, 1H, J=12.8, 9.2 Hz), 1.82–1.70 (m, 2H). LRMS (ES)$^+$: 388.4 (M+H)$^+$.

Example 164

(7bR,11aS)-N-3-quinolinylmethyl)-1,2,7b,8,9,10,11,11a-octahydro-4H-pyrido[4,3-b][1,4]thiazepino[6,5,4-hi]indol-6-amine

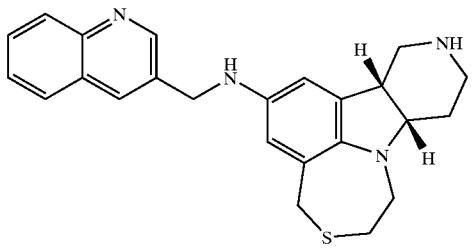

Using 3-quinolinecarboxaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 164. LRMS (ES)$^+$: 403.4 (M+H)$^+$.

Example 165

(7bR,11aS)-N-[2-(trifluoromethoxy)benzyl]-1,2,7b,8,9,10,11,11a-octahydro-4H-pyrido[4,3-b][1,4]thiazepino[6,5,4-hi]indol-6-amine

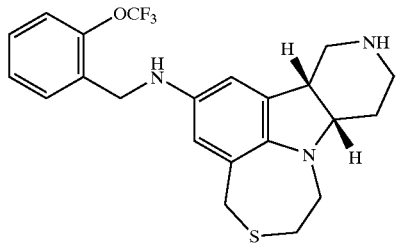

Using 2-(trifluoromethoxy)benzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 165. LRMS (ES)$^+$: 436.4 (M+H)$^+$.

EXAMPLE 166

(7bR,11aS)-N-[2-fluoro-6-(trifluoromethyl)benzyl]-1,2,7b,8,9,10,11,11a-octahydro-4H-pyrido[4,3-b][1,4]thiazepino[6,5,4-hi]indol-6-amine

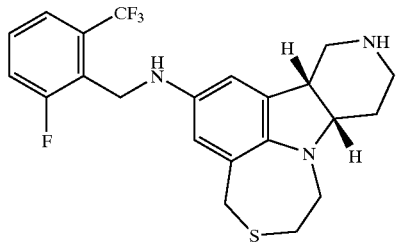

Using 2-fluoro-6-(trifluoromethyl)benzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 166.

Example 167

(7bR,11aS)-N-[2,5-bis(trifluoromethyl)benzyl]-1,2,7b,8,9,10,11,11a-octahydro-4H-pyrido[4,3-b][1,4]thiazepino[6,5,4-hi]indol-6-amine

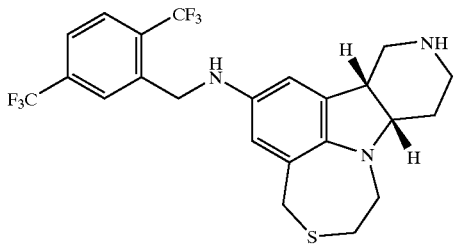

Using 2,5-bis(trifluoromethoxy)benzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 167.

Example 168

(7bR,11aS)-N-I1-(4-fluorophenyl)ethyl]-1,2,7b,8,9,10,11,11a-octahydro-4H-pyrido[4,3-b][1,4]thiazepino[6,5,4-hi]indol-6-amine

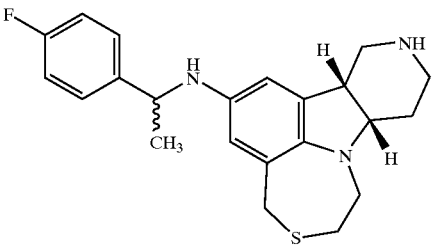

To a solution of tert-butyl (7bR,11aS)-6-bromo-1,2,7b,10,11,11a-hexahydro-4H-pyrido[4,3-b][1,4]thiazepino[6,5,4-hi]indole-9(8H)-carboxylate from EXAMPLE 7, Part A (21 mg, 0.05 mmol) in 5 mL of degassed toluene was added (±)-4-fluoro-□-methylbenzylamine (8.4 mg, 0.06 mmol), sodium tert-butoxide (12 mg, 0.13 mmol), BINAP (1.3 mg, 0.002 mmol) and Pd$_2$(dba)$_3$ (0.5 mg, 0.0005 mmol). The resulting mixture was stirred at 90° C. for 10 h and then was cooled, filtered through a pad of silica gel, eluting with ethyl acetate, and concentrated. The residue was purified by flash chromatography (elution with 2:1 hexane/ehtyl acetate) to afford an N-BOC intermediate. The residue was taken up in 2 mL of methylene chloride and then there was added 1 mL of trifluoroacetic acid. The reaction was allowed to stir at ambient temperature for 1 h and then was concentrated in vacuo. The residue was purified by preparative HPLC (C18 reverse phase column, elution with a H$_2$O/CH$_3$CN gradient with 0.5% TFA) and the product containing fractions were free-based with aq ammonium hydroxide, extracted with chloroform, washed with brine, dried (K$_2$CO$_3$) and concentrated to afford the title compound of EXAMPLE 168 as a mixture of diastereomers at the methyl center. $^1$H NMR (CDCl$_3$) δ: 7.30–7.20 (m, 2H), 6.97–6.90 (m, 2H), 6.10 (s, 1H), 6.03 (s, 1H), 4.27 (q, 1H, J=6.6 Hz), 3.52 (ABq, 2H), 3.50–3.35 (m, 1H), 3.28–3.15 (m, 2H), 3.10–2.75 (m, 5H), 2.50–2.39 (m, 1H), 1.93–1.80 (m, 2H), 1.39 (d, 3H, J=6.6 Hz). LRMS (ES)+: 384.4 (M+H)+.

Example 169

(7bR,11aS)-N-[(1S)-1-phenylethyl]-1,2,7b,8,9,10,11, 11a-octahydro-4H-pyrido[4,3-b][1,4]thiazepino[6,5, 4-hi]indol-6-amine

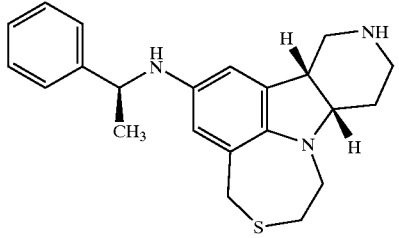

Using (S)-(-)-□-methylbenzylamine and following the procedures described in EXAMPLE 168, tert-butyl (7bR, 11aS)-6-bromo-1,2,7b,10,11,11a-hexahydro-4H-pyrido[4,3-b][1,4]thiazepino[6,5,4-hi]indole-9(8H)-carboxylate from EXAMPLE 7, Part A was converted into the title compound of EXAMPLE 169. $^1$H NMR (CDCl$_3$) δ: 7.40–7.20 (m, 5H), 6.22 (d, 1H, J=2.2 Hz), 6.14 (d, 1H, J=2.2 Hz), 4.39 (q, 1H, J=6.6 Hz), 3.62 (ABq, 2H, J$_{AB}$=15.5 Hz), 3.55–3.43 (m, 1H), 3.32–3.20 (m, 2H), 3.05–2.81 (m, 4H), 2.77–2.60 (m, 1H), 2.50 (dd, 1H, J=12.8, 9.7 Hz), 2.00–1.85 (m, 2H), 1.49 (d, 3H, J=6.6 Hz). LRMS (ES)+: 366.4 (M+H)+.

Example 170

(7bR,11aS)-N-[(1R)-1-phenylethyl]-1,2,7b,8,9,10, 11,11a-octahydro-4H-pyrido[4,3-b][1,4]thiazepino [6,5,4-hi]indol-6-amine

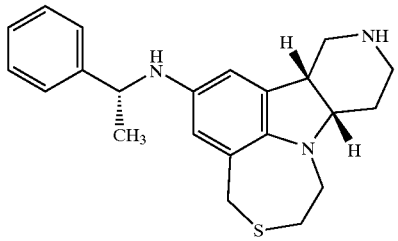

Using (R)-(-)-□-methylbenzylamine and following the procedures described in EXAMPLE 168, tert-butyl (7bR, 11aS)-6-bromo-1,2,7b,10,11,11a-hexahydro-4H-pyrido[4,3-b][1,4]thiazepino[6,5,4-hi]indole-9(8H)-carboxylate from EXAMPLE 7, Part A was converted into the title compound of EXAMPLE 170. $^1$H NMR (CDCl$_3$) δ: 7.40–7.20 (m, 5H), 6.17 (d, 1H, J=2.2 Hz), 6.10 (d, 1H, J=2.2 Hz), 4.35 (q, 1H, J=6.6 Hz), 3.56 (ABq, 2H, J$_{AB}$=15.7 Hz), 3.50–3.42 (m, 1H), 3.29–3.21 (m, 2H), 3.15–2.80 (m, 5H), 2.58–2.48 (m, 1H), 2.00–1.85 (m, 2H), 1.45 (d, 3H, J=6.6 Hz). LRMS (ES)+: 366.4 (M+H)+.

Example 171

(7bR,11aS)-N-benzyl-1,2,7b,8,9,10,11,11a-octahydro-4H-pyrido[4,3 b][1,4]thiazepino[6,5,4-hi]indol-6-amine

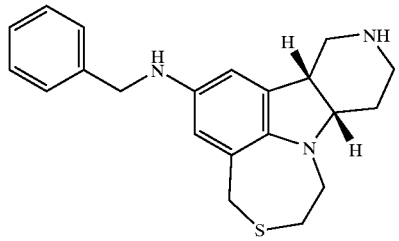

Using benzaldehyde and following the procedures described in EXAMPLE 126, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from EXAMPLE 33, Part B was converted into the title compound of EXAMPLE 171. $^1$H NMR (CDCl$_3$) δ: 7.42–7.25 (m, 5H), 6.37 (d, 1H, J=1.8 Hz), 6.26 (d, 1H, J=2.2 Hz), 4.27 (s, 2H), 3.69 (ABq, 2H, J$_{AB}$=15.2 Hz), 3.60–3.50 (m, 1H), 3.37–3.30 (m, 1H), 3.28–3.20 (m, 1H), 3.10–2.85 (m, 6H), 2.62 (dd, 1H, J=12.8, 9.1 Hz), 1.89–1.80 (m, 2H). LRMS (ES)+: 352.4 (M+H)+.

Example 172

(7bR,11aS)-N-(2-Methoxy-5-methyl-3-pyridinyl)-1, 2,7b,8,9,10,11,11a-octahydro-4H-[1,4]oxazepino[6, 5,4-hi]pyrido[4,3-b]indole-6-amine

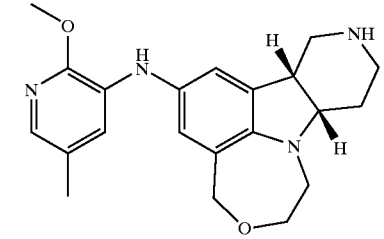

A solution of tert-butyl (7bR,11aS)-6-amino-1,2,7b,10,11, 11a-hexahydro-4H-[1,4] oxazepino[6,5,4-hi]pyrido[4,3-b] indole-9(8H)Carboxylate from Example 56, Part B (968 mg, 2.81 mmol), 3-bromo-2-methoxy-5-methylpyridine (515 mg, 2.55 mmol), and NaOt-Bu (404 mg, 4.20 mmol) in anhydrous toluene (40 mL) was stirred under an argon atmosphere in a sealable test tube. The mixture was degassed with argon at 85° C. for 30 min then cooled to 50° C. Tris(dibenzylideneacetone)dipalladium(0) (62 mg, 67 μmol) and 2,2'-bis(diphenylphosphino)-1,1'-binaphthyl (84.0 mg, 135 μmol) were added; the reaction was sealed and heated at 85° C. for 16 h. The reaction was cooled to room temperature, diluted with EtOAc, filtered through a bilayer pad of diatomaceous earth and silica gel, and concentrated. Purification of the residue by flash column chromatography (silica gel, 10–50% EtOAc/hexanes) provided tert-butyl (7bR,11aS)-6-(2-methoxy-5-methyl-3-pyridinyl) amino-1,2,7b, 10,11,11 a-hexahydro-4H-[1,4]oxazepino[6, 5,4-hi]pyrido[4,3-b]indole-9(8H)-carboxylate (1.16 g, 89%). A solution of the intermediate in CH$_2$Cl$_2$ (20 mL) at −10° C. was treated with TFA (6 mL) and stirred for 1 h. Upon concentration in vacuo, the residue was partitioned between a 1:1 solution of CH$_2$Cl$_2$/satd NaHCO$_3$ (100 mL).

199

The aqueous phase was extracted with $CH_2Cl_2$ (4×75 mL). The combined organic phases were dried over $Na_2SO_4$, filtered, and concentrated in vacuo. The residue was purified by flash column chromatography [silica gel, 5–50% (80:18:2 $CHCl_3$/MeOH/concd $NH_4OH$)/$CH_2Cl_2$] and trituration with $CH_2Cl_2$/$Et_2O$/hexanes provided the title compound of Example 172 (590 mg, 65%) as a tan solid: mp 122–124° C.; $^1H$ NMR (300 MHz, $CDCl_3$) δ 7.40 (s, 1H), 6.99 (s, 1H), 6.88 (s, 1H), 6.77 (s, 1H), 5.84 (br s, 1H), 4.75 (d, J=14.1 Hz, 1H), 4.58 (d, J=14.1 Hz, 1H), 4.34–4.16 (m, 1H), 4.01 (s, 3H), 3.89–3.69 (m, 1H), 3.58–3.39 (m, 1H), 3.38–3.13 (m, 2H), 3.11–2.99 (m, 1H), 2.98–2.85 (m, 2H), 2.81–2.68 (m, 1H), 2.61–2.42 (m, 1H), 2.19 (s, 3H), 2.01–1.77 (m, 3H); ESI MS m/z 367 $[C_{21}H_{26}N_4O_2+H]^+$.

Example 173

(7bR,11aS)-N-(2-Ethoxy-5-methyl-3-pyridinyl)-1,2, 7b,8,9,10,11,11a-octahydro-4H-[1,4]oxazepino[6,5, 4-hi]pyrido[4,3b]indole-6-amine

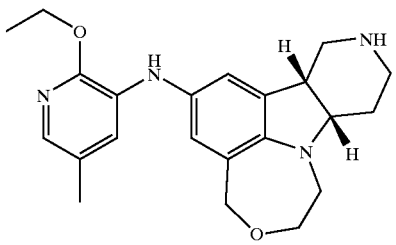

Following the same procedure described in Example 172, the title compound was prepared using tert-butyl (7bR, 11aS)-6-amino-1,2,7b,10,11,11a-hexahydro-4H-[1,4] oxazepino[6,5,4-hi]pyrido[4,3-b]indole-9(8H)-carboxylate from Example 56, Part B (579 mg, 1.68 mmol), 3-bromo-2-ethoxy-5-methylpyridine (330 mg, 1.52 mmol), NaOt-Bu (242 mg, 2.52 mmol) in anhydrous toluene (20 mL), tris(dibenzylideneacetone)dipalladium(0) (37 mg, 40 μmol), and 2,2'-bis(diphenylphosphino)-1,1'-binaphthyl (50 mg, 80 μmol) to provide the corresponding tert-butyl (7bR,11aS)-6-(2-ethoxy-5-methyl-3-pyridinyl)-amino-1,2,7b,10,11,11a-hexahydro-4H-[1,4]oxazepino[6,5,4-hi]pyrido[4,3-b] indole-9(8H)-carboxylate (680 mg) in 93% yield. A solution of the intermediate in $CH_2Cl_2$ (10 mL) was deprotected using TFA (3 mL). The crude mixture was purified by flash column chromatography [silica gel, 5–50% (80:18:2 $CHCl_3$/MeOH/concd $NH_4OH$)/$CH_2Cl_2$] and trituration with $CH_2Cl_2$/$Et_2O$/hexanes provided the title compound of Example 173 (336 mg, 62%) as a tan solid: mp 59–68° C.; $^1H$ NMR (300 MHz, $CDCl_3$) δ 7.33 (s, 1H), 6.95 (s, 1H), 6.86 (s, 1H), 6.75 (s, 1H), 5.80 (br s, 1H), 4.73 (d, J=14.2 Hz, 1H), 4.53 (d, J=14.2 Hz, 1H), 4.39 (q, J=7.0 Hz, 2H), 4.21 (d, J=12.8 Hz, 1H), 3.87–3.69 (m, 1H), 3.49–3.37 (m, 1H), 3.35–3.11 (m, 2H), 3.10–2.99 (m, 1H), 2.96–2.81 (m, 2H), 2.80–2.62 (m, 1H), 2.61–2.40 (m, 1H), 2.15 (s, 3H), 2.01–1.51 (m, 3H), 1.42 (t, J=7.0 Hz, 3H); ESI MS m/z 381 $[C_{22}H_{28}N_4O_2+H]^+$.

200

Example 174

(7bR,11aS)-N-(2-Cyano-5-methoxy-3-pyridinyl)-1, 2,7b,8,9,10,11,11a-octahydro-4H-[1,4]oxazepino[6, 5,4-hi]pyrido[4,3-b]indole-6-amine

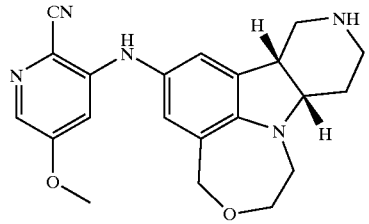

Following the same procedure described in Example 172, the title compound was prepared using tert-butyl (7bR, 11aS)-6-amino-1,2,7b,10,11,11a-hexahydro-4H-[1,4] oxazepino[6,5,4-hi]pyrido[4,3-b]indole-9(8H)-carboxylate from Example 56, Part B (130 mg, 0.377 mmol), 3-bromo-2-cyano-5-methoxypyridine (67 mg, 0.34 mmol), $CsCO_3$ (256 mg, 0.787 mmol) in anhydrous toluene (10 mL), tris(dibenzylideneacetone)dipalladium(0) (3.4 mg, 3.7 μmol), and 2,2'-bis(diphenylphosphino)-1,1'-binaphthyl (7.0 mg, 11 μmol) to provide the corresponding tert-butyl (7bR, 11aS)-6-(2-cyano-5-methoxy-3-pyridinyl)-amino-1,2,7b, 10,11,11a-hexahydro-4H-[1,4]oxazepino[6,5,4-hi]pyrido[4, 3-b]indole-9(8H)-carboxylate (146 mg) in 90% yield. A solution of the intermediate in $CH_2Cl_2$ (10 mL) was deprotected using TFA (3 mL). The crude mixture was purified by flash column chromatography [silica gel, 5–50% (80:18:2 $CHCl_3$/MeOH/concd $NH_4OH$)/$CH_2Cl_2$] and trituration with $CH_2Cl_2$/$Et_2O$/hexanes provided the title compound of Example 174 (64 mg, 56%) as a light yellow solid: mp 99–108° C.; $^1H$ NMR (300 MHz, $CDCl_3$) δ 7.78 (s, 1H), 6.88 (s, 1H), 6.77 (s, 1H), 6.60 (s, 1H), 6.11 (br s, 1H), 4.72 (d, J=14.3 Hz, 1H), 4.52 (d, J=14.3 Hz, 1H), 4.30–4.11 (m, 1H), 3.92–3.69 (m, 4H), 3.56–3.42 (m, 1H), 3.39–3.12 (m, 2H), 3.11–2.97 (m, 1H), 2.98–2.69 (m, 3H), 2.58–2.42 (m, 1H), 2.03–1.77 (m, 2H), 1.63 (br s, 1H); ESI MS m/z 378 $[C_{21}H_{23}N_5O_2+H]^+$.

Example 175

(7bR,11aS)-N-(2-Cyano-3-pyridinyl)-1,2,7b,8,9,10, 11,11a-octahydro-4H-[1,4]oxazepino[6,5,4-hi]pyrido [4,3-b]indole-6-amine, bis hydrochloride salt

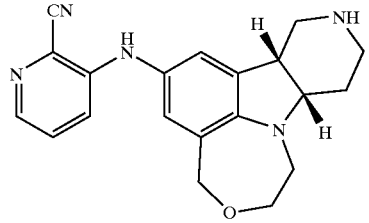

A solution of tert-butyl (7bR,11aS)-6-amino-1,2,7b,10,11, 11a-hexahydro-4H-[1,4]oxazepino[6,5,4-hi]pyrido[4,3-b]

indole-9(8H)-carboxylate from Example 56, Part B (828 mg, 2.40 mmol), 3-bromo-2-cyanopyridine (440 mg, 2.40 mmol) and cesium carbonate (1.56 g, 4.8 mmol)) in anhydrous toluene (25 mL) was stirred under an argon atmosphere in a sealable test tube. The mixture was degassed with argon. Tris(dibenzylideneacetone)dipalladium(0) (44 mg, 0.048 mmol) and 2,2'-bis(diphenylphosphino)-1,1'-binaphthyl (60 mg, 0.096 mmol) were added and the reaction was sealed and heated at 125° C. for 16 h. The reaction mixture was cooled, filtered through a pad of silica gel and concentrated in vacuo. Purification of the residue by flash column chromatography (silica gel, 10–50% EtOAc/hexanes) provided tert-butyl (7bR,11aS)-6-(2-cyano-3-pyridinyl)-amino-1,2,7b,10,11,11a-hexahydro-4H-[1,4]oxazepino[6,5,4-hi]pyrido[4,3-b]indole-9(8H)Carboxylate. This intermediate was treated with 2N HCl in ether (20 mL) and stirred at ambient temperature for 3 h. The reaction was concentrated in vacuo and the resulting solid was triturated 3 times with ether and dried in vacuo to afford 902 mg (90%) of the title compound of Example 175 as a light yellow solid. ESI MS m/z 348 $[C_{20}H_{21}N_5O+H]^+$.

Example 176

(7bR,11aS)-N-(2-Cyano-6-methyl-3-pyridinyl)-1,2,7b,8,9,10,11,11 a-octahydro-4H-[1,4]oxazepino[6,5,4-hi]pyrido[4,3-b]indole-6-amine, bis hydrochloride salt

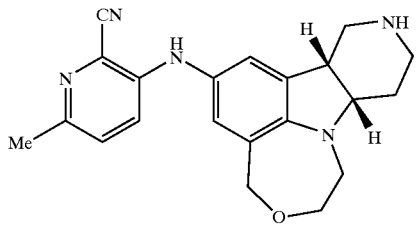

A solution of tert-butyl (7bR,11aS)-6-amino-1,2,7b,10,11,11a-hexahydro-4H-[1,4] oxazepino[6,5,4-hi]pyrido[4,3-b] indole-9(8H)-carboxylate from Example 56, Part B (300 mg, 0.89 mmol), 2-cyano-3-bromo-6-methylpyridine (200 mg, 1.02 mmol) and cesium carbonate (565 mg, 1.73 mmol) in anhydrous toluene (10 mL) was stirred under an argon atmosphere in a sealable test tube. The mixture was degassed with argon. [1,1'-Bis(diphenylphosphino)ferrocene]dichloropalladium (II), complex with dichloromethane (35 mg, 0.043 mmol) was added and the reaction was sealed and heated at 160° C. in a microwave oven for 3600 sec. The reaction mixture was cooled, filtered through a pad of silica gel and concentrated in vacuo. Purification of the residue by flash column chromatography (silica gel, 10–50% EtOAc/hexanes) provided tert-butyl (7bR,11aS)-6-(2-cyano-6-methyl-3-pyridinyl)-amino-1,2,7b,10,11,11a-hexahydro-4H-[1,4]oxazepino[6,5,4-hi]pyrido[4,3-b]indole-9(8H)-carboxylate. This intermediate was treated with 2N HCl in ether (20 mL) and stirred at ambient temperature for 3 h. The reaction was concentrated in vacuo and the resulting solid was triturated 3 times with ether and dried in vacuo to afford 84 mg (22%) of the title compound of Example 176 as an off-white solid. ESI MS m/z 362 $[C_{21}H_{23}N_5O+H]^+$.

Example 177

(7bR,11aS)-N-(5-Chloro-2-cyano-3-pyridinyl)1,2,7b,8,9,10,11,11a-octahydro-4H-[1,41 oxazepino[6,5,4-hi]pyrido[4,3-b]indole-6-amine, bis hydrochloride salt

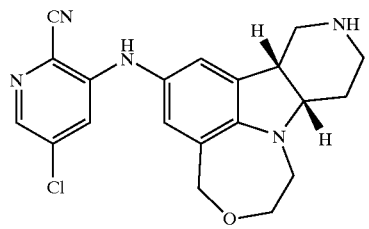

Following the procedures described in Example 176 and using 3-bromo-5-chloro-2-cyanopyridine, tert-butyl (7bR,11aS)₆-amino-1,2,7b,10,11,11a-hexahydro-4H-[1,4] oxazepino[6,5,4-hi]pyrido[4,3-b]indole-9(8H)-carboxylate from Example 56, Part B was converted into the title compound of Example 177. ESI MS m/z 382.3/384.3 $[C_{20}H_{20}ClN_5O+H]^+$.

Example 178

(7bR,11aS)-N-(2-Cyano-5-methyl-3-pyridinyl)-1,2,7b,8,9,10,11,11a-octahydro-4H-[1,4]oxazepino[6,5,4-hi]pyrido[4,3-b]indole-6-amine, bis hydrochloride salt

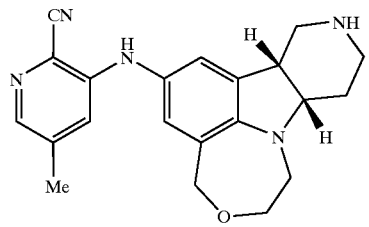

Following the procedures described in Example 176 and using 3-bromo-2-cyano-5-methylpyridine, tert-butyl (7bR,11aS)-6-amino-1,2,7b,10,11,11a-hexahydro-4H-[1,4] oxazepino[6,5,4-hi]pyrido[4,3-b]indole-9(8H)-carboxylate from Example 56, Part B was converted into the title compound of Example 178. ESI MS m/z 362.3 $[C_{21}H_{23}N_5O+H]^+$.

Example 179

(7bR,11aS)-N-(2-Cyano-5-methoxy-3-pyridinyl)-1,2,7b,8,9,10,11,11a-octahydro-4H-[1,4]oxazepino[6,5,4-hi]pyrido[4,3-b]indole-6-amine, bis hydrochloride salt

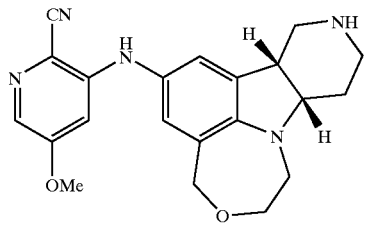

Following the procedures described in Example 176 and using 3-bromo-2-cyano-5-methoxypyridine, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from Example 56, Part B was converted into the title compound of Example 179 as a yellow solid. ESI MS m/z 378 $[C_{21}H_{23}N_5O_2+H]^+$.

Example 180

(7bR,11aS)-N-(6-Cyano-3-pyridinyl)-1,2,7b,8,9,10,11,11a-octahydro-4H-[1,4]oxazepino[6,5,4-hi]pyrido[4,3-b]indol-6-amine, bis hydrochloride salt

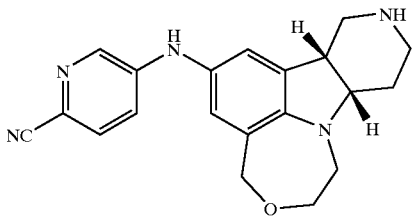

Following the procedures described in Example 176 and using 5-bromo-2-cyanopyridine, tert-butyl (7bR,11aS)-6-amino-1,2,7b,10,11,11a-hexahydro-4H-[1,4] oxazepino[6,5,4-hi]pyrido[4,3-b]indole-9(8H)-carboxylate from Example 56, Part B was converted into the title compound of Example 180 as a yellow solid. ESI MS m/z 348.3 $[C_{20}H_{21}N_5O+H]^+$.

Example 181

(7bR,11aS)-N-(6-Cyano-2-ethoxy-3-pyridinyl)-1,2,7b,8,9,10,11,11a-octahydro-4H-[1,4]oxazepino[6,5,4-hi]pyrido[4,3-b]indole-6-amine, bis hydrochloride salt

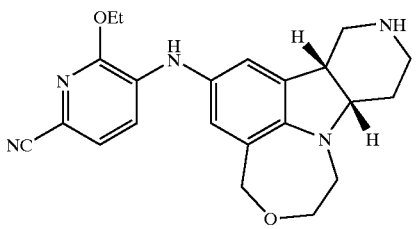

Following the procedures described in Example 176 and using 3-bromo-6-cyano-2-ethoxypyridine, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from Example 56, Part B was converted into the title compound of Example 181 as a solid. ESI MS m/z 392.3 $[C_{22}H_{25}N_5O_2+H]^+$.

Example 182

(7bR,11aS)-N-(2-Cyano-3-pyridinyl)-1,2,7b,8,9,10,11,11a-octahydro-4H-pyrido[4,3 b][1,4]thiazepino[6,5,4-hi]indole-6-amine, bis hydrochloride salt

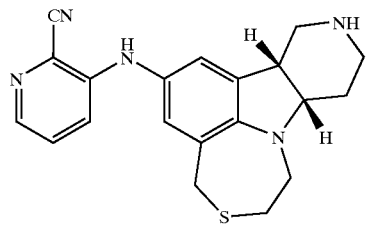

Following the procedures described in Example 176 and using 3-bromo-2-cyanopyridine, tert-butyl (7bR,11aS)-6-amino-1,2,7b,10,11,11a-hexahydro-4H-pyrido[4,3-b][1,4]thiazepino[6,5,4-hi]indole-9(8H)-carboxylate from Example 33, Part B was converted into the title compound of Example 182 as a solid. ESI MS m/z 364.2 $[C_{20}H_{21}N_5S+H]^+$.

Example 183

(7bR,11aS)-N-[2-Cyano-5-(trifluoromethyl)-3-pyridinyl]-1,2,7b,8,9,10,11,11a-octahydro-4H-pyrido[4,3-b][1,4]thiazepino[6,5,4-hi]indole-6-amine, bis hydrochloride salt

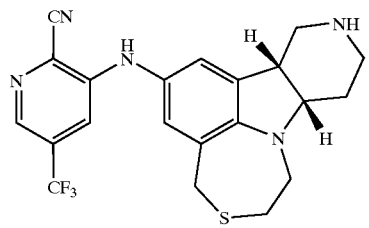

Following the procedures described in Example 176 and using 3-bromo-5-trifluoromethyl-pyridine-2-carbonitrile, tert-butyl (7bR,11aS)-6-amino-1,2,7b,10,11,11a-hexahydro-4H-pyrido[4,3-b][1,4]thiazepino[6,5,4-hi]indole-9(8H) carboxylate from Example 33, Part B was converted into the title compound of Example 183 as a solid. ESI MS m/z 432.2 $[C_{21}H_{20}F_3N_5S+H]^+$.

Example 184

(7bR,11aS)-N-[2-Cyano-6-methyl-3-pyridinyl]-1,2,
7b,8,9,10,11,11a-octahydro-4H-pyrido[4,3-b][1,4]
thiazepino[6,5,4-hi]indole-amine, his hydrochloride
salt

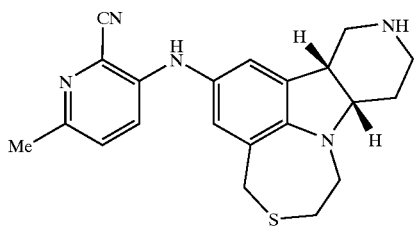

Following the procedures described in Example 176 and using 3-bromo-6-methyl-2-cyanopyridine, tert-butyl (7bR, 11aS)-6-amino-1,2,7b,10,11,11a-hexahydro-4H-pyrido[4,3-b][1,4]thiazepino[6,5,4-hi]indole-9(8H)-carboxylate from Example 33, Part B was converted into the title compound of Example 184 as a solid. ESI MS m/z 378.2 $[C_{21}H_{23}N_5S+H]^+$.

Example 185

(7bR,11aS)-N-[2-Cyano-5-methyl-3-pyridinyl-1,2,
7b,8,9,10,11,11a-octahydro-4H-pyrido[4,3-b][1,4]
thiazepino[6,5,4-hi]indole-6-amine, bis
hydrochloride salt

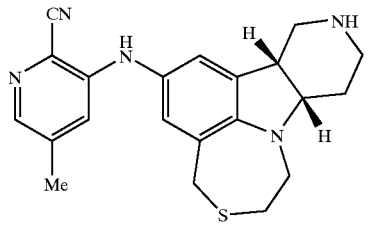

Following the procedures described in Example 176 and using 3-bromo-5-methyl-2-cyanopyridine, tert-butyl (7bR, 11aS)-6-amino-1,2,7b,10,11,11a-hexahydro-4H-pyrido[4,3-b][1,4]thiazepino[6,5,4-hi]indole-9(8H)-carboxylate from Example 33, Part B was converted into the title compound of Example 185 as a solid. ESI MS m/z 378.2 $[C_{21}H_{23}N_5S+H]^+$.

Example 186

(7bR,11aS)-N-[2-Ethoxy-3-pyridinyl]-1,2,7b,8,9,10,
11,11a-octahydro-4H-pyrido[4,3-b][1,4]thiazepino
[6,5,4-hi]indole-6-amine, bis hydrochloride salt

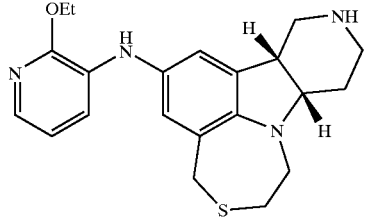

Following the procedures described in Example 175 and using 3-bromo-2-ethoxypyridine, sodium tert-butoxide as the base and [1,1'-bis(diphenylphosphino)ferrocene] dichloropalladium (II), complex with dichloromethane, as the palladium source, tert-butyl (7bR,11aS)-6-amino-1,2,7b, 10,11,11a-hexahydro-4H-pyrido[4,3-b][1,4]thiazepino[6,5, 4-hi]indole-9(8H)-carboxylate from Example 33, Part B was converted into the title compound of Example 186 as a solid. ESI MS m/z 383.2 $[C_{21}H_{26}N_4OS+H]^+$.

Example 187

(7bR,11aS)-N-(2-Ethoxy-3-pyridinyl)-1,2,7b,8,9,10,
11,11a-octahydro-4H-[1,4] oxazepino[6,5,4-hi]
pyrido[4,3-b]indole-6-amine, bis hydrochloride salt

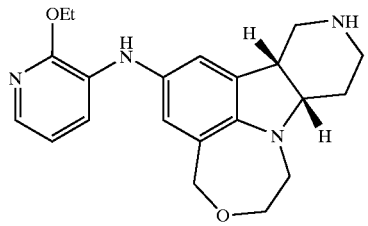

Following the procedures described in Example 175 and using 3-bromo-2-ethoxypyridine, tert-butyl (7bR,11aS)-6-amino-1,2,7b,10,11,11a-hexahydro-4H-[1,4] oxazepino[6,5, 4-hi]pyrido[4,3-b]indole-9(8H)-carboxylate from Example 56, Part B was converted into the title compound of Example 187 as a solid. ESI MS m/z 367.2 $[C_{21}H_{26}N_4O_2+H]^+$.

Example 188

(7bR,11aS)-N-(2-Isopropoxy-3-pyridinyl)-1,2,7b,8,
9,10,11,11a-octahydro-4H-[1,4] oxazepino[6,5,4-hi]
pyrido[4,3-b]indole-6-amine, bis hydrochloride salt

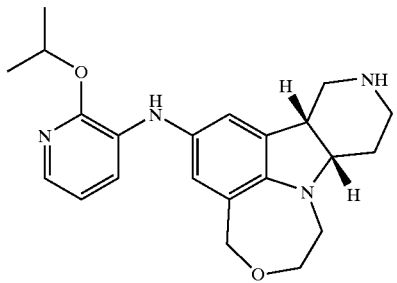

Following the procedures described in Example 175 and using 3-bromo-2-isopropoxypyridine, tert-butyl (7bR, 11aS)-6-amino-1,2,7b,10,11,11a-hexahydro-4H-[1,4] oxazepino[6,5,4-hi]pyrido[4,3-b]indole-9(8H)-carboxylate from Example 56, Part B was converted into the title compound of Example 188 as a solid. ESI MS m/z 381 $[C_{22}H_{28}N_4O_2+H]^+$.

Example 189

(7bR,11aS)-N-2-Isopropoxy-5-methyl-3-pyridinyl]-1,2,7b,8,9,10,11,11a-octahydro-4H-[1,4]oxazepino[6,5,4-hi]pyrido[4,3-b]indole-6-amine, bis hydrochloride salt

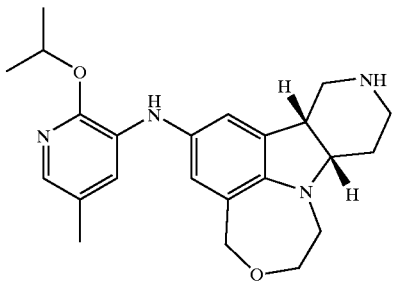

Following the procedures described in Example 175 and using 3-bromo-2-isopropoxy-5-methylpyridine and [1,1'-bis(diphenylphosphino)ferrocene]dichloropalladium (II), complex with dichloromethane, as the palladium source, tert-butyl (7bR,11aS)$_6$-amino-1,2,7b,10,11,11a-hexahydro-4H-[1,4]oxazepino[6,5,4-hi]pyrido[4,3-b]indole-9(8H)-carboxylate from Example 56, Part B was converted into the title compound of Example 189 as a solid. ESI MS m/z 395.4 $[C_{23}H_{30}N_4O_2+H]^+$.

Example 190

(7bR,11aS)-N-[6-Methoxy-5-methyl-3-pyridinyl]-1,2,7b,8,9,10,11,11a-octahydro-4H-[1,4]oxazepino[6,5,4-hi]pyrido[4,3-b]indole-6-amine, bis hydrochloride salt

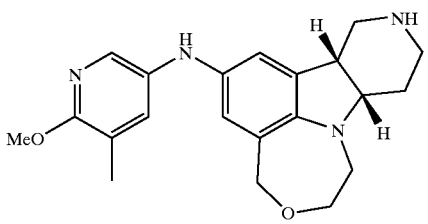

Following the procedures described in Example 176 and using 3-bromo-6-methoxy-5-methylpyridine and potassium tert-butoxide as the base, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from Example 56, Part B was converted into the title compound of Example 190 as a solid. ESI MS m/z 381.3 $[C_{21}H_{26}N_4OS+H]^+$.

Example 191

(7bR,11aS)-N-[6-Isopropoxy-3-pyridinyl]-1,2,7b,8,9,10,11,11a-octahydro-4H-[1,4]oxazepino[6,5,4-hi]pyrido[4,3-b]indole-6-amine, bis hydrochloride salt

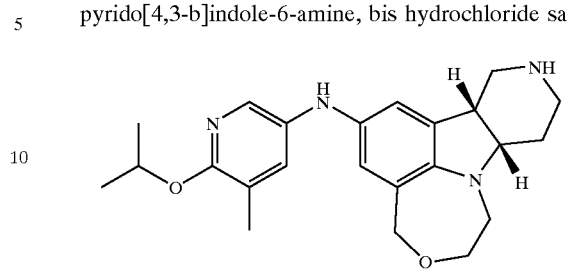

Following the procedures described in Example 176 and using 3-bromo-6-isopropoxy-5-methylpyridine and potassium tert-butoxide as the base, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from Example 56, Part B was converted into the title compound of Example 191 as a solid. ESI MS m/z 395.4 $[C_{23}H_{30}N_4O_2+H]^+$.

Example 192

(7bR,11aS)-N-[2-(2,2,2-Trifluoroethoxy)-3-pyridinyl]-1,2,7b,8,9,10,11,11a-octahydro-4H-[1,4]oxazepino[6,5,4-hi]pyrido[4,3 b]indole-6-amine, bis hydrochloride salt

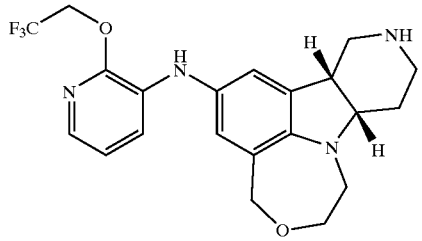

Following the procedures described in Example 176 and using 3-bromo-2-(2,2,2-trifluoroethoxy)pyridine and potassium tert-butoxide as the base, tert-butyl (7bR,11aS)-6-amino-1,2,7b, 10,11,11a-hexahydro-4H-[1,4]oxazepino[6,5,4-hi] pyrido[4,3-b]indole-9(8H)-carboxylate from Example 56, Part B was converted into the tide compound of Example 192 as a solid. ESI MS m/z 421.3 $[C_{21}H_{23}F_3N_4O_2+H]^+$.

Example 193

(7bR,11aS)-N-[2(2,2,2-Trifluoroethoxy)-5-methyl-3-pyridinyl]-1,2,7b,8,9,10,11,11a-octahydro-4H-[1,4]oxazepino[6,5,4-hi]pyrido[4,3-b]indole-6-amine, bis hydrochloride salt

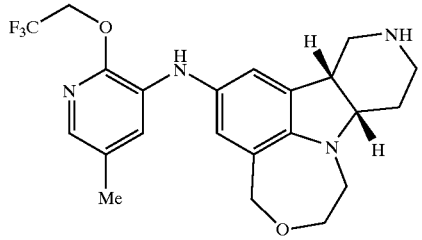

Following the procedures described in Example 176 and using 3-bromo-2-(2,2,2-trifluoroethoxy)pyridine and potassium tert-butoxide as the base, tert-butyl (7bR,11aS)-6-amino-1,2,7b,10,11,11a-hexahydro-4H-[1,4]oxazepino[6,5,4-hi] pyrido[4,3-b]indole-9(8H)-carboxylate from Example 56, Part B was converted into the title compound of Example 193 as a solid. ESI MS m/z 435.4 $[C_{22}H_{25}F_3N_4O_2+H]^+$.

Example 194

(7bR,11aS)-N-[2-(2-Methoxyethoxy)$_3$-pyridinyl]-1,2,7b,8,9,10,11,11a-octahydro-4H-[1,4]oxazepino[6,5,4-hi]pyrido[4,3 b]indole-6-amine, bis hydrochloride salt

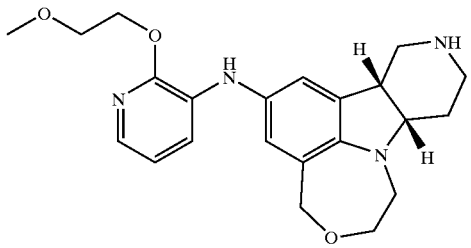

Following the procedures described in Example 176 and using 3-bromo-2-(2-methoxyethoxy)pyridine and potassium tert-butoxide as the base, tert-butyl (7bR,11aS)-6-amino-1,2,7b,10,11,11a-hexahydro-4H-[1,4]oxazepino[6,5,4-hi] pyrido[4,3-b]indole-9(8H)-carboxylate from Example 56, Part B was converted into the title compound of Example 194 as a solid. ESI MS m/z 397.4 $[C_{22}H_{28}N_4O_3+H]^+$.

Example 195

(7bR,11aS)-N-[2-Propoxy-3-pyridinyl]-1,2,7b,8,9,10,11,11a-octahydro-4H-[1,4]oxazepino[6,5,4-hi] pyrido[4,3-b]indole-6-amine, bis hydrochloride salt

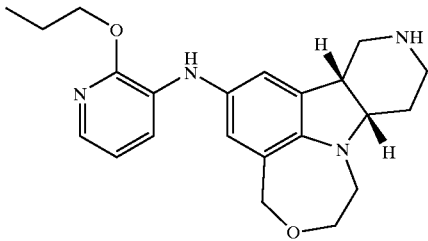

Following the procedures described in Example 176 and using 3-bromo-2-propoxypyridine and potassium tert-butoxide as the base, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from Example 56, Part B was converted into the title compound of Example 195 as a solid. ESI MS m/z 381.4 $[C_{22}H_{28}N_4O_2+H]^+$.

Example 196
(7bR,11aS)-N-[2-Ethoxymethyl-3-pyridinyl]-1,2,7b,8,9,10,11,11a-octahydro-4H-[1,4]oxazepino[6,5,4-hi]pyrido[4,3-b]indole-6-amine, bis hydrochloride salt

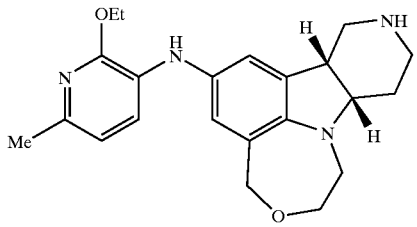

Following the procedures described in Example 176 and using 3-bromo-2-ethoxy-6-methylpyridine and potassium tert-butoxide as the base, tert-butyl (7bR,11aS)-6-amino-1,2,7b,10,11,11a-hexahydro-4H-[1,4]oxazepino[6,5,4-hi] pyrido[4,3-b]indole-9(8H)-carboxylate from Example 56, Part B was converted into the title compound of Example 196 as a solid. ESI MS m/z 381.4 $[C_{22}H_2N_4O_2+H]^+$.

EXAMPLE 197
(7bR,11aS)-N-[6-Methoxy-4-methyl-3-pyridinyl]-1,2,7b,8,9,10,11,11a-octahydro-4H-[1,4]oxazepino[6,5,4-hi]pyrido[4,3-b]indole-6-amine, bis hydrochloride salt

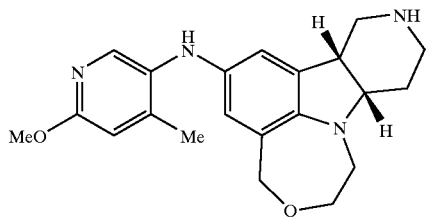

Following the procedures described in Example 176 and using 3-bromo-6-methoxy-4-methylpyridine and potassium tert-butoxide as the base, tert-butyl (7bR,11aS)-6 amino-1,2,7b,10,11,11a-hexahydro-4H-[1,4]oxazepino[6,5,4-hi] pyrido[4,3-b]indole-9(8)Carboxylate from Example 56, Part B was converted into the title compound of Example 197 as a solid. ESI MS m/z 367.3 $[C_{21}H_{26}N_4O_2+H]^+$.

Example 198
(7bR,11aS)-N-[2-Ethoxy-6-trifluoromethyl-3-pyridinyl]-1,2,7b,8,9,10,11,11a-octahydro-4H-[1,4]oxazepino[6,5,4-hi]pyrido[4,3-b]indole-6-amine, bis hydrochloride salt

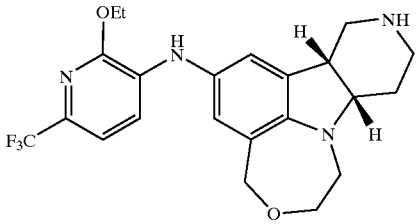

Following the procedures described in Example 175 and using 3-bromo-2-ethoxy-6 (trifluoromethyl)pyridine and [1,1'-bis(diphenylphosphino)ferrocene]dichloropalladium (II), complex with dichloromethane, as the palladium source, tert-butyl (7bR,11aS)-6-amino-1,2,7b,10,11,11a-hexahydro-4H-[1,4]oxazepino[6,5,4-hi]pyrido[4,3-b] indole-9(8H)-carboxylate from Example 56, Part B was converted into the title compound of Example 198 as a solid. ESI MS m/z 435.4 $[C_{22}H_{25}F_3N_4O_2+H]^+$.

Example 199

(7bR,11aS)-N-[2-Ethoxy-5-trifluoromethyl-3-pyridinyl]-1,2,7b,8,9,10,11,11a-octahydro-4H-[1,4]oxazepino[6,5,4-hi]pyrido[4,3-b]indole-6-amine, bis hydrochloride salt

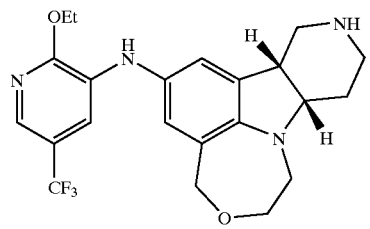

Following the procedures described in Example 175 and using 3-bromo-2-ethoxy-5-(trifluoromethyl)pyridine and [1,1'-bis(diphenylphosphino)ferrocene]dichloropalladium (II), complex with dichloromethane, as the palladium source, tert-butyl (7bR,11aS)-6-amino-1,2,7b,10,11,11a-hexahydro-4H-[1,4]oxazepino[6,5,4-hi]pyrido[4,3-b]indole-9(8H)-carboxylate from Example 56, Part B was converted into the title compound of Example 199 as a solid. ESI MS m/z 435.3 $[C_{22}H_{25}F_3N_4O_2+H]^+$.

The following Table provides representative EXAMPLES, the syntheses of which are described above, of the compounds of Formula (I) of the present invention.

TABLE 1

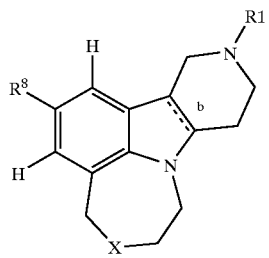

| Ex# | X | b | R⁸ | R¹ |
|---|---|---|---|---|
| 1 | S | sgl-cis | H | H |
| 2 | S | sgl-cis | H | H |
| 3 | SO₂ | sgl-cis | H | H |
| 4 | S | sgl-cis | H | —(CH₂)₃C(=O)-(4-F-phenyl) |
| 5 | S | sgl-cis | H | —(CH₂)₃O-(4-F-phenyl) |
| 6 | S | sgl-cis | H | —(CH₂)₃O-(2-NO₂-4-F-phenyl) |
| 7 | S | sgl-cis | 2-CHO-phenyl | H |
| 8 | 5 | sgl-cis | 2-(CH₂OH)-phenyl | H |
| 9 | S | sgl-cis | 2-Me-4-OMe-phenyl | H |
| 10 | SO₂ | sgl-cis | 2-Me-4-OMe-phenyl | H |
| 11 | SO | sgl-cis | 2-Me-4-OMe-phenyl | H |
| 12 | S | sgl-cis | 2-CF₃-4-OMe-phenyl | H |
| 13 | S | sgl-cis | 2,4-dichloro-phenyl | H |
| 14 | S | sgl-cis | 2,6-difluoro-phenyl | H |
| 15 | S | sgl-cis | 3-CN-phenyl | H |
| 16 | S | sgl-cis | 2-CHO-4-OMe-phenyl | H |
| 17 | S | sgl-cis | 2-(CH₂OH)-4-OMe-phenyl | H |
| 18 | S | sgl-cis | 2-CF₃-4-(O-i-Pr)-phenyl | H |
| 19 | S | sgl-cis | 3-CN-4-fluoro-phenyl | H |
| 20 | S | sgl-cis | 2-CF₃-4-OEt-phenyl | H |
| 21 | S | sgl-cis | 2-[CH(OH)CH₃]-4-OMe-phenyl | H |
| 22 | S | sgl-cis | 2-[C(=O)CH₃]-4-OMe-phenyl | H |
| 23 | S | sgl-cis | 2-Me-4-CN-phenyl | H |
| 24 | S | sgl-cis | 2-Me-3-CN-phenyl | H |
| 25 | S | sgl-cis | 2-CF₃-4-CN-phenyl | H |
| 26 | S | sgl-cis | 2-Me-3-CN-phenyl | —CH₂-cyclobutyl |
| 27 | S | sgl-cis | 2-Me-4-SMe-phenyl | H |
| 28 | S | sgl-cis | 2-[C(=O)CH₃]-4-F-phenyl | H |
| 29 | S | sgl-cis | 2-[CH(OH)CH₃]-4-F-phenyl | H |

TABLE 1-continued

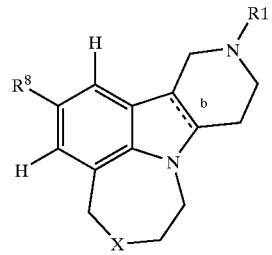

| Ex# | X | b | R8 | R1 |
|---|---|---|---|---|
| 30 | S | sgl-cis | 2-[CH(OH)CH$_3$]-4-Me-phenyl | H |
| 31 | S | sgl-cis | 2-[C(=O)CH$_3$]-4-Cl-phenyl | H |
| 32 | S | sgl-cis | 2-[CH(OH)CH$_3$]-4-Cl-phenyl | H |
| 33 | S | sgl-cis | (2,4-dichlorophenyl)-NH— | H |
| 34 | S | sgl-cis | (2,4-dichlorophenyl)-NH— | H |
| 35 | S | sgl-cis | (2-Me-4-F-phenyl)-NH— | H |
| 36 | S | sgl-cis | (2-Me-4-OMe-phenyl)-NH— | H |
| 37 | S | sgl-cis | (2,3-dichlorophenyl)-NH— | H |
| 38 | S | sgl-cis | (2-Cl-5-CF$_3$-phenyl)-NH— | H |
| 39 | S | sgl-cis | (3,4-dichlorophenyl)-NH— | H |
| 40 | O | sgl-cis | 2-CF$_3$-4-OMe-phenyl | H |
| 41 | O | sgl-cis | 2-Me-4-OMe-phenyl | H |
| 42 | O | sgl-cis | H | H |
| 43 | O | sgl-cis | 2-CF$_3$-4-OMe-phenyl | H |
| 44 | O | sgl-cis | 2-CF$_3$-4-OMe-phenyl | H |
| 45 | O | sgl-cis | 2-Me-4-CN-phenyl | H |
| 46 | O | sgl-cis | 2-Me-4-(CONH$_2$)-phenyl | H |
| 47 | O | sgl-cis | 2-Me-4-(CO$_2$Me)-phenyl | H |
| 48 | O | sgl-cis | 2-[C(=O)CH$_3$]-4-F-phenyl | H |
| 49 | O | sgl-cis | 2-[CH(OH)CH$_3$]-4-F-phenyl | H |
| 50 | O | sgl-cis | 2-Me-4-SMe-phenyl | H |
| 51 | O | sgl-cis | 2-[C(=O)CH$_3$]-4-Me-phenyl | H |
| 52 | O | sgl-cis | 2-[CH(OH)CH$_3$]-4-Me-phenyl | H |
| 53 | O | sgl-cis | 2-[C(=O)CH$_3$]-4-Cl-phenyl | H |
| 54 | O | sgl-cis | 2-[CH(OH)CH$_3$]-4-Cl-phenyl | H |
| 55 | O | sgl-cis | 2-CF$_3$-4-[C(=O)CH$_3$]-phenyl | H |
| 56 | O | sgl-cis | (2,4-dichlorophenyl)-NH— | H |
| 57 | O | sgl-cis | (2,6-dichlorophenyl)-NH— | H |
| 58 | O | sgl-cis | (2,6-difluorophenyl)-NH— | H |
| 59 | O | sgl-cis | (2,5-dichlorophenyl)-NH— | H |
| 60 | O | sgl-cis | (2-Cl-5-CF$_3$-phenyl)-NH— | H |
| 61 | O | sgl-cis | (2-CN-phenyl)-NH— | H |
| 62 | O | sgl-cis | (3,4-dichlorophenyl)-NH— | H |
| 63 | O | sgl-cis | (2,3-dichlorophenyl)-NH— | H |
| 64 | O | sgl-cis | (2-Me-5-F-phenyl)-NH— | H |
| 65 | O | sgl-cis | (2-Me-4-F-phenyl)-NH— | H |
| 66 | O | sgl-cis | (2-F-5-Me-phenyl)-NH— | H |
| 67 | O | sgl-cis | (3-CF$_3$-phenyl)-NH— | H |
| 68 | O | sgl-cis | (3-CF$_3$-4-Cl-phenyl)-NH— | H |
| 69 | O | sgl-cis | (3,5-bis-CF$_3$-phenyl)-NH— | H |
| 70 | NH | sgl-cis | 2,6-difluoro-phenyl | H |
| 71 | NH | sgl-cis | 2,4-dichloro-phenyl | H |
| 72 | O | sgl-cis | 1-napthyl-NH— | H |
| 73 | O | sgl-cis | (4-CF$_3$-phenyl)-NH— | H |
| 74 | O | sgl-cis | (3,4-dimethylphenyl)-NH— | H |
| 75 | O | sgl-cis | (2-CF$_3$-phenyl)-NH— | H |
| 76 | O | sgl-cis | (2,3,5-trichlorophenyl)-NH— | H |
| 77 | O | sgl-cis | 2-napthyl-NH— | H |
| 78 | O | sgl-cis | (2-F-4-Cl-phenyl)-NH— | H |
| 79 | O | sgl-cis | (3-Me-4-CO$_2$Me-phenyl)-NH— | H |
| 80 | O | sgl-cis | (2,5-dimethoxyphenyl)-NH— | H |
| 81 | O | sgl-cis | (2,4-difluorophenyl)-NH— | H |
| 82 | O | sgl-cis | (2,5-difluorophenyl)-NH— | H |
| 83 | O | sgl-cis | (3-CHO-4-OMe-phenyl)-NH— | H |
| 84 | O | sgl-cis | (2-Me-4-Cl-phenyl)-NH— | H |
| 85 | O | sgl-cis | 2-(1,1'-biphenyl)-NH— | H |
| 86 | O | sgl-cis | (2-OMe-4-CN-phenyl)-NH— | H |
| 87 | O | sgl-cis | (2-F-5-CF$_3$-phenyl)-NH— | H |
| 88 | O | sgl-cis | (2-OMe-4-CHO-phenyl)-NH— | H |
| 89 | O | sgl-cis | (4-CH$_3$-pyrid-3-yl)-NH— | H |

TABLE 1-continued

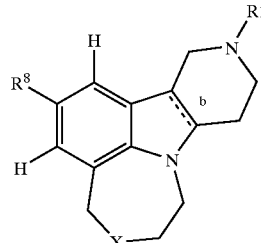

| Ex# | X | b | R⁸ | R¹ |
|---|---|---|---|---|
| 90 | O | sgl-cis | 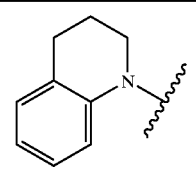 | H |
| 91 | O | sgl-cis | (2-F-phenyl)-NH— | H |
| 92 | O | sgl-cis | (3-F-5-CF₃-phenyl)-NH— | H |
| 93 | O | sgl-cis | (2-NMe₂-4-CF₃-phenyl)-NH— | H |
| 94 | O | sgl-cis | (3-F-4-CHO-phenyl)-NH— | H |
| 95 | O | sgl-cis | (2-F-3-CF₃-phenyl)-NH— | H |
| 96 | O | sgl-cis | (4-F-3-CF₃-phenyl)-NH— | H |
| 97 | O | sgl-cis | 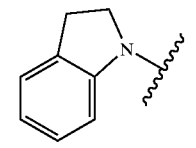 | H |
| 98 | O | sgl-cis | (2-Br-phenyl)CH₂CH₂—NH— | H |
| 99 | O | sgl-cis | (2,6-dimethylphenyl)-NH— | H |
| 100 | O | sgl-cis | (2,5-dimethylphenyl)-NH— | H |
| 101 | O | sgl-cis | (2-OMe-5-CH₃-phenyl)-NH— | H |
| 102 | O | sgl-cis | 3-(1,1'-biphenyl)-NH— | H |
| 103 | O | sgl-cis | (2,6-dichloro-3-CH₃-phenyl)-NH— | H |
| 104 | O | sgl-cis | (2-Cl-5-CH₃-phenyl)-NH— | H |
| 105 | O | sgl-cis | (2,4,5-trifluorophenyl)-NH— | H |
| 106 | O | sgl-cis | (3,5-dimethyl-4-OMe-phenyl)-NH— | H |
| 107 | O | sgl-cis | (3-CH₃-4-CN-phenyl)-NH— | H |
| 108 | O | sgl-cis | (3-CH₃-4-OMe-phenyl)-NH— | H |
| 109 | O | sgl-cis | (3-CH₃-4-Cl-phenyl)-NH— | H |
| 110 | O | sgl-cis | (3-CH₃-4-F-phenyl)-NH— | H |
| 111 | O | sgl-cis | 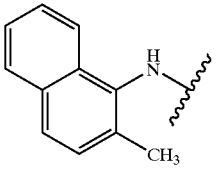 | H |
| 112 | O | sgl-cis | (2-OMe-5-F-phenyl)-NH— | H |
| 113 | O | sgl-cis | Phenyl-NH— | H |
| 114 | O | sgl-cis | 3-quinolinyl-NH— | H |
| 115 | O | sgl-cis | 3-pyridyl-NH— | H |
| 116 | O | sgl-cis | (2-acetyl-4-Me-phenyl)-NH— | H |
| 117 | O | sgl-cis | (2-CH(OH)CH₃-4-Me-phenyl)-NH— | H |
| 118 | O | sgl-cis | (2-acetyl-4-OMe-phenyl)-NH— | H |
| 119 | O | sgl-cis | (2-CH(OH)CH₃-4-OMe-phenyl)-NH— | H |
| 120 | O | sgl-cis | 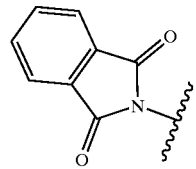 | H |

TABLE 1-continued

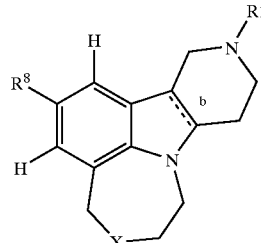

| Ex# | X | b | R⁸ | R¹ |
|---|---|---|---|---|
| 121 | O | sgl-cis | (isoindoline-N-yl) | H |
| 122 | O | sgl-cis | Phenyl-CH$_2$—NH— | H |
| 123 | O | sgl-cis | (3,5-dichlorophenyl)-CH$_2$—NH— | H |
| 124 | O | sgl-cis | (2,4-dichlorophenyl)-CH$_2$—NH— | H |
| 125 | O | sgl-cis | (2,6-dichlorophenyl)-CH$_2$—NH— | H |
| 126 | O | sgl-cis | (2-F-3-CF$_3$-phenyl)-CH$_2$—NH— | H |
| 127 | O | sgl-cis | (6-F-2-CF$_3$-phenyl)-CH$_2$—NH— | H |
| 128 | O | sgl-cis | (2-CF$_3$-phenyl)-CH$_2$—NH— | H |
| 129 | O | sgl-cis | (2,4-bis-CF$_3$-phenyl)-CH$_2$—NH— | H |
| 130 | O | sgl-cis | (2,5-bis-CF$_3$-phenyl)-CH$_2$—NH— | H |
| 131 | O | sgl-cis | (4-F-2-CF$_3$-phenyl)-CH$_2$—NH— | H |
| 132 | O | sgl-cis | (3-F-phenyl)-CH$_2$—NH— | H |
| 133 | O | sgl-cis | (2-Cl-5-CF$_3$-phenyl)-CH$_2$—NH— | H |
| 134 | O | sgl-cis | (2-F-phenyl)-CH$_2$—NH— | H |
| 135 | O | sgl-cis | (2,4-dimethylphenyl)-CH$_2$—NH— | H |
| 136 | O | sgl-cis | (3-CH$_3$-4-OMe-phenyl)-CH$_2$—NH— | H |
| 137 | O | sgl-cis | (2-CH$_3$-4-OMe-phenyl)-CH$_2$—NH— | H |
| 138 | O | sgl-cis | (2-CN-phenyl)-CH$_2$—NH— | H |
| 139 | O | sgl-cis | (4-CF$_3$-phenyl)-CH$_2$—NH— | H |
| 140 | O | sgl-cis | (2,6-difluorophenyl)-CH$_2$—NH— | H |
| 141 | O | sgl-cis | (2-F-3-CF$_3$-phenyl)—NH— | i-Pr |
| 142 | O | sgl-cis | (2-F-3-CF$_3$-phenyl)-N(CH$_3$)— | CH$_3$ |
| 143 | O | sgl-cis | (2-F-3-CF$_3$-phenyl)—NH— | CH$_3$ |
| 144 | O | sgl-cis | (2-F-3-CF$_3$-phenyl)—NH— | —CH$_2$CH$_3$ |
| 145 | O | sgl-cis | (2-F-3-CF$_3$-phenyl)—NH— | —CH$_2$-cyclobutyl |
| 146 | O | sgl-cis | (2-F-3-CF$_3$-phenyl)—NH— | —CH$_2$CH=C(CH$_3$)$_2$ |
| 147 | S | sgl-cis | 2-CF$_3$-phenyl | H |
| 148 | S | sgl-cis | (2,6-dichlorophenyl)—NH— | H |
| 149 | S | sgl-cis | (2,6-difluorophenyl)—NH— | H |
| 150 | S | sgl-cis | (2-acetyl-4-Cl-phenyl)—NH— | H |
| 151 | S | sgl-cis | (2-CH(OH)CH$_3$-4-Cl-phenyl)—NH— | H |
| 152 | S | sgl-cis | (2,6-bis-CF$_3$-phenyl)-CH$_2$—NH— | H |
| 153 | S | sgl-cis | (2Cl-5-CF$_3$-phenyl)-CH$_2$—NH— | H |
| 154 | S | sgl-cis | (4-F-2-CF$_3$-phenyl)-CH$_2$—NH— | H |
| 155 | S | sgl-cis | (3-Cl-4-F-phenyl)-CH$_2$—NH— | H |
| 156 | S | sgl-cis | (3-Cl-phenyl)-CH$_2$NH— | H |
| 157 | S | sgl-cis | (2-CF$_3$-phenyl)-CH$_2$—NH— | H |
| 158 | S | sgl-cis | (3,4-dichlorophenyl)-CH$_2$—NH— | H |
| 159 | S | sgl-cis | (2,5-difluorophenyl)-CH$_2$—NH— | H |
| 160 | S | sgl-cis | (2-F-3-Cl-6-CF$_3$-phenyl)-CH$_2$—NH— | H |
| 161 | S | sgl-cis | (2,6-difluorophenyl)-CH$_2$—NH— | H |
| 162 | S | sgl-cis | (2-CN-phenyl)-CH$_2$—NH— | H |
| 163 | S | sgl-cis | (2,4-difluorophenyl)-CH$_2$—NH— | H |
| 164 | S | sgl-cis | (3-quinolinyl)-CH$_2$—NH— | H |
| 165 | S | sgl-cis | (2-OCF$_3$-phenyl)-CH$_2$—NH— | H |
| 166 | S | sgl-cis | (6-F-2-CF$_3$-phenyl)-CH$_2$—NH— | H |
| 167 | S | sgl-cis | (2,5-bis-CF$_3$-phenyl)-CH$_2$—NH— | H |
| 168 | S | sgl-cis | (+/−)-(4-F-phenyl)-CH(CH$_3$)—NH— | H |
| 169 | S | sgl-cis | (S)-phenyl-CH(CH$_3$)—NH— | H |
| 170 | S | sgl-cis | (R)-phenyl-CH(CH$_3$)—NH— | H |
| 171 | S | sgl-cis | Phenyl-CH$_2$—NH— | H |

Utility

The compounds of the present invention have therapeutic utility for illnesses or disorders involving the neurotransmitter serotonin (5-hydroxy tryptamine or 5-HT) and either agonism or antagonism of 5-HT2 receptors, as demonstrated by the assays described below. Therapeutic utility for these illnesses or disorders could involve numerous biological processes affected by serotonin including, but not limited to, appetite, mood, sleep, sexual activity, and arterial constriction. These biological processes may also be important to numerous central nervous system (CNS) disorders including those related to the affective disorders of depression, anxiety, psychosis, and schizophrenia, as well as, disorders of food intake such as anorexia, bulemia, and obesity. The compounds of the present invention potentially have therapeutic utility in other conditions in which serotonin has been implicated, such as migraine, attention deficit disorder or attention deficit hyperactivity disorder, addictive behavior, and obsessive-compulsive disorder, as well as, conditions associated with cephalic pain, social phobias, and gastrointestinal disorders such as dysfunction of the gastrointestinal tract motility. Lastly, compounds of the present invention potentially have therapeutic utility in neurodegenerative diseases and traumatic conditions represented by the examples of Alzheimer's disease and brain/spinal cord trauma The pharmacological analysis of each compound for either antogonism or agonism of at 5-HT2A and 5-HT2C receptors consisted of in vitro and in vivo studies. In vitro analyses included $K_i$ determinations at 5-HT2A and 5-HT2C receptors and an assessment of functional (i.e., agonism or antagonism) activity at each receptor class by IP3 hydrolysis assays. Additional receptor assays were conducted to evaluate receptor specificity of 5-HT2A and 5-HT2C receptors over monoamine and nuisance receptors (e.g. histamine, dopamine, and muscarinic). A compound is considered active as a 5-HT2A antagonist or a 5-HT2C agonist if it has an $IC_{50}$ value or a $K_i$ value of less than about 50 micromolar; preferably less than about 0.1 micromolar; more preferably less than about 0.01 micromolar. Using the assays disclosed herein, compounds of the present invention have been shown to have an $IC_{50}$ value of less than about 50 micromolar for 5-HT2A antagonism or 5-HT2C agonism.

In vivo assays assessed compound activity in a variety of behavioral paradigms including quipazine head twitch, acute and chronic feeding models, anxiety and depression models (learned-helplessness, elevated plus maze, Geller-Siefter, conditioned taste aversion, taste reactivity, satiety sequence). In aggregate, these models reflect activity as a 5-HT2A antagonist (quipazine head twitch; depression models) or 5-HT2C agonist (feeding models, anxiety models, depression models) and provide some indication as to bioavailability, metabolism and pharmacokinetics.

Radioligand binding experiments were conducted on recombinant human 5-HT2A and 5-HT2C receptors expressed in HEK293E cells. The affinities of compounds of the present invention to bind at these receptors is determined by their capacity to compete for $[^{125}I]$-1-(2,5-dimethoxy-4-iodophenyl)-2-amino-propane (DOI) binding at the 5-HT2A or 5-HT2C. General references for binding assays include 1) Lucaites VL, Nelson DL, Wainscott DB, Baez M (1996) Receptor subtype and density determine the coupling repertoire of the 5-HT2 receptor subfamily. Life Sci., 59(13): 1081–95. J Med Chem 1988 January; 31(1): 5–7; 2) Glennon RA, Seggel MR, Soine WH, Herrick-Davis K, Lyon RA, Titeler M (1988) [125I]-1-(2,5-dimethoxy-4-iodophenyl)-2-amino-propane: an iodinated radioligand that specifically labels the agonist high-affinity state of 5-HT2 serotonin receptors. J. Med. Chem. 31(1): 5–7 and 3) Leonhardt S, Gorospe E, Hoffman BJ, Teitler M (1992) Molecular pharmacological differences in the interaction of serotonin with 5-hydroxytryptamine1C and 5-hydroxytryptamine2 receptors. Mol Pharmacol., 42(2): 328–35.

The functional properties of compounds (efficacy and potency) were determined in whole cells expressing 5-HT2A or 5-HT2C receptors by assessing their ability to stimulate or inhibit receptor-mediated phosphoinositol hydrolysis. The procedures used are described below.

In Vitro Binding Assays

Stable Expression of 5-HT2A and 5-HT2C Receptors in HEK293E Cells.

Stable cell lines were generated by transfecting 293EBNA cells with plasmids containing human 5-HT2A, 5-HT2B, or 5-HT2C (VNV edited isoform) cDNA using calcium phosphate. These plasmids also contained the cytomegalovirus (CMV) immediate early promoter to drive receptor expression and EBV oriP for their maintenance as an extrachromosomal element, and the hph gene from *E. Coli* to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% $CO_2$) for 10 days. The 5-HT2A cells were adapted to spinner culture for bulk processing whereas it was necessary to maintain the other lines as adherent cultures. On the day of harvest, cells were washed in phosphate-buffered saline (PBS), counted, and stored at –800C.

Membrane Preparation

On the day of assay, pellets of whole cells (containing approximately 1×108 cells) expressing the 5-HT2A or 5-HT2C receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., IL) using bovine serum albumin as the standard.

Radioligand Binding Assays for the 5-HT2A and 5-HT2C Receptors.

Radioligand binding studies were conducted to determine the binding affinities (KI values) of compounds for the human recombinant 5-HT2A, 5-HT2B, and 5-HT2C receptors (Fitzgerald et al., 1999). Assays were conducted in disposable polypropylene 96well plates (Costar Corp., Cambridge, Mass.) and were initiated by the addition of 5-HT2A, 5-HT2B, or 5-HT2C membrane homogenate in tissue buffer (10–30 (g/well) to assay buffer (50 mM Tris HCl, 0.5 mM EDTA, 10 mM pargyline, 10 mM $MgSO_4$, 0.05% ascorbic acid, pH 7.5) containing $[^{125}I]DOI$ for the 5-HT2A and 5-HT2C receptors (0.3–0.5 nM, final) or $[^3H]$ LSD (2–2.5 nM, final) for the 5-HT2B receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (cell harvester; Inotech Biosystems Inc., Lansing, Mich.) over GFF glass-fiber filters that had been pre-soaked in 0.3% polyethyleneimine. Filters were washed in ice-cold 50 mM Tris HCl buffer (pH 7.5) and then counted in a gamma counter for the 5-HT2A and 5-HT2C assays, or by liquid scintillation spectroscopy for the 5-HT2B assay.

Phosphoinositide Hydrolysis Studies.

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT2A, 5-HT2B, or 5-HT2C receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 (g/ml hygromycin B, and 250(g/ml G418. Following a 2448 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H]inositol for 16–18 hr. Following this incubation, the cells were washed with DMEM (without serum or inositol) containing 10 mM LiCl and 10 (M pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AGI-X8 resin), and counted by liquid scintillation spectroscopy as described previously (Egan et al., 1998).

Data Analyses

The equilibrium apparent dissociation constants (Ki's) from the competition experiments were calculated using an iterative nonlinear regression curve-fitting program (GraphPad Prism; San Diego, Calif.). For the PI hydrolysis experiments, EC50's were calculated using a one-site 'pseudo' Hill model: $y=((Rmax-Rmin)/(1+R/EC50)nH))+Rmax$ where R=response (Deltagraph, Monterey, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

In Vivo Experiments for Serotonergie Ligands.

Preclinical Efficacy, Potency, and Side Effect Liability.

a) Anti-Serotonin Efficacy.

Antagonism of Quipazine-Induced Head Twitch in Rat. Quipazine, an agonist at 5-HT receptors, produces a characteristic head twitch response in rats. 5-HT receptor antagonists effectively antagonize this 5-HT agonist-induced behavioral effect (Lucki et al., 1984). Accordingly, the quipazine-induced head twitch model in rat can function as an in vivo behavioral correlate to 5-HT receptor binding. Compounds are administered 30 minutes before behavioral testing (and 25 minutes before quipazine), and a dose-related antagonism of the quipazine response is determined.

b) Antipsychotic Efficacy.

Inhibition of the Conditioned Avoidance Response (CAR) in Rat. Rats are trained to consistently avoid (by climbing onto a pole suspended from the ceiling of the test chamber) an electric foot shock (0.75 mA) delivered to the grid floor of the testing chamber. All antipsychotic drugs effectively inhibit this conditioned avoidance response (Arnt, 1982). The ability of a compound to inhibit this response is used to determine the antipsychotic efficacy of potential drug candidates.

c) Extrapyramidal Side Effect Liability.

Induction of Catalepsy in Rat. Typical antipsychotic drugs produce extrapyramidal side effects (EPS) at clinically effective doses. The most widely accepted preclinical indicator of EPS liability in humans is a drug-induced catalepsy syndrome in rat (Costall and Naylor, 1975), a condition whereby the animal will remain immobile in an externally imposed posture (analogous to a catatonic stupor in humans). Rats are tested for induction of catalepsy in a dose-response test after oral administration of compounds.

d) CNS Penetration; In vivo Brain Receptor Occupancy.

In Vivo Binding. To determine the level of in vivo receptor occupancy, an in vivo receptor binding protocol is used. This procedure uses an appropriate radioligand to label the receptor of interest. For example, to measure both Dopamine D2 and 5-HT2A receptors in vivo, one can use $^3$H—N-methyl spiperone ($^3$H —NMSP), (Frost, et. al. 1987) The procedure uses rats (or mice) fasted overnight. To measure the effects of compounds on the receptors of interest, compounds are dosed, usually p.o. for example in 2 microliters/gram body weight in 0.25% Methocel suspension. The radiolabeled compound (in this example, $^3$H—NMSP) is administered by i.v. tail vein injection (10 microcuries label/200 gram rat). Time course experiments are used to determine the optimal time of binding for both the radiolabeled and unlabeled compound. These optimal time frames are used for all subsequent dose-response experiments. After the appropriate time frame of compound/radioligand exposure, the animals are sacrificed and the relevant brain regions dissected (frontal cortex for 5-HT2A and striatum for D2 receptors) and examined for their content of radioactivity. The level of non-specific binding is determined by examining a brain region known not to contain the receptor of interest (in this case the cerebellum) or by administering an excess of compound known pharmacologically to interact with the receptor.

REFERENCES

Arnt, J. Acta Pharmacol. et Toxicol. 1982: 51, 321–329.

Berridge M. J., Downes P. C., Hanley M. R. (1982) Lithium amplifies agonist-dependent phosphotidyinositol response in brain and salivary glands. Biochem. J., 206, 587–595.

Costall, B and Naylor, RJ. Psychopharmacology. 1975: 43, 69–74.

Egan C. T., Herrick-Davis K., Miller K., Glennon R. A., and Teitler M. (1998) Agonist activity of LSD and lisuride at cloned 5-HT2A and 5-HT2C receptors. Psychopharmacology, 136, 409–414.

Fitzgerald LW, Conklin DS, Krause CM, Marshall AP, Patterson JP, Tran DP, Iyer G, Kostich WA, Largent BL, Hartig PR (1999) High-affinity agonist binding correlates with efficacy (intrinsic activity) at the human serotonin 5-HT2A and 5-HT2C receptors: evidence favoring the ternary complex and two-state models of agonist action. J. Neurochem., 72, 2127–2134.

Frost, J. J., Smith, A. C., Kuhar, M. J., Dannals, R. F., Wagner, H. N., 1987, In Vivo Binding of 3H—N-Methylspiperone to Dopamine and Serotonin Receptors. Life Sciences, 40:987–995.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9, 301–308.

Lucki, I, Nobler, M. S., Frazer, A., 1984, Differential actions of serotonin antagonists on two behavioral models of serotonin receptor activation in the rat. J. Pharmacol. Exp. Ther. 228(1): 133–139.

Dosage and Formulation

The serotonin agonist and serotonin antagonist compounds of this invention can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.1 to about 30 mg/kg. Advantageously, compounds of the present invention may be administered in a single daily dose, or the total daily dosage may be administered in divided doses of two, three, or four times daily.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences, supra*, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

What is claimed is:

1. A compound of the formula (I):

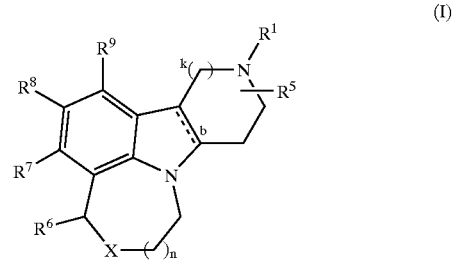

or stereoisomers or pharmaceutically acceptable salt forms thereof, wherein:

b is a single bond or a double bond;

X is —O—, —S—, —S(=O), —S(=O)$_2$—, or —NR$^{10}$—;

R$^1$ is selected from
H,
C(=O)R$^2$,
C(=O)OR$^2$,
C$_{1-8}$ alkyl,
C$_{2-8}$ alkenyl,
C$_{2-8}$ alkynyl,
C$_{3-7}$ cycloalkyl,
C$_{1-6}$ alkyl substituted with Z,
C$_{2-6}$ alkenyl substituted with Z,
C$_{2-6}$ alkyl substituted with Z,
C$_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
C$_{1-3}$ alkyl substituted with Y,
C$_{2-3}$ alkenyl substituted with Y,
C$_{2-3}$ alkynyl substituted with Y,
C$_{1-6}$ alkyl substituted with 0–2 R$^2$, $C_{2-6}$ alkenyl substituted with 0–2 $R^2$,
$C_{2-6}$ alkynyl substituted with 0–2 $R^2$,
aryl substituted with 0–2 $R^2$, and
5–6 membered heterocyclic ring system containing at least one heteroatom selected from the group consisting of N, O, and S, said heterocyclic ring system substituted with 0–2 $R^2$;

Y is selected from
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{3-6}$ cycloalkyl substituted with —($C_{1-3}$ alkyl)-Z,
aryl substituted with —($C_{1-3}$ alkyl)-Z, and
5–6 membered heterocyclic ring system containing at least one heteroatom selected from the group consisting of N, O, and S, said heterocyclic ring system substituted with —($C_{1-3}$ alkyl)-Z;

Z is selected from H,
—CH(OH)$R^2$,
—C(ethylenedioxy)$R^2$,
—O$R^2$,
—S$R^2$,
—N$R^2R^3$,
—C(O)$R^2$,
—C(O)N$R^2R^3$,
—N$R^3$C(O)$R^2$,
—C(O)O$R^2$,
—OC(O)$R^2$,
—CH(=N$R^4$)N$R^2R^3$,
—NHC(=N$R^4$)N$R^2R^3$,
—S(O)$R^2$,
—S(O)$_2R^2$,
—S(O)$_2$N$R^2R^3$, and —N$R^3$S(O)$_2R^2$;

$R^2$, at each occurrence, is independently selected from
halo,
$C_{1-3}$ haloalkyl,
$C_{1-4}$ alkyl,
$C_{2-4}$ alkenyl,
$C_{2-4}$ alkynyl,
$C_{3-6}$ cycloalkyl,
aryl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H and $C_{1-4}$ alkyl;

$R^5$ is H or $C_{1-4}$ alkyl;
$R^6$ is H or $C_{1-4}$ alkyl;

$R^7$ and $R^9$, at each occurrence, are independently selected from
H, halo, —CF$_3$, —OCF$_3$, —OH, —CN, —NO$_2$, —N$R^{46}R^{47}$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^1$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, N$R^{12}R^{13}$, C(O)H, C(O)$R^{12}$, C(O)N$R^{12}R^{13}$, N$R^{14}$C(O)$R^{12}$, C(O)O$R^{12}$, OC(O)$R^{12}$, OC(O)O$R^{12}$, CH(=N$R^{14}$)N$R^{12}R^{13}$, NHC(=N$R^{14}$)N$R^{12}R^{13}$, S(O)$R^{12}$, S(O)$_2R^{12}$, S(O)N$R^{12}R^{13}$, S(O)$_2$N$R^{12}R^{13}$, N$R^{14}$S(O)$R^{12}$, N$R^{14}$S(O)$_2R^{12}$, N$R^{12}$C(O)$R^{15}$, N$R^{12}$C(O)O$R^{15}$, N$R^{12}$S(O)$_2R^{15}$, and N$R^{12}$C(O)NH$R^{15}$;

$R^8$ is selected from
H, halo, —CF$_3$, —OCF$_3$, —OH, —CN, —NO$_2$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, N$R^{12}R^{13}$, C(O)H, C(O)$R^{12}$, C(O)N$R^{12}R^{13}$, N$R^{14}$C(O)$R^{12}$, C(O)O$R^{12}$, OC(O)$R^{12}$, OC(O)O$R^{12}$, CH(=N$R^{14}$)N$R^{12}R^{13}$, NHC(=N$R^{14}$)N$R^{12}R^{13}$, S(O)$R^{12}$, S(O)$_2R^{12}$, S(O)N$R^{12}R^{13}$, S(O)$_2$N$R^{12}R^{13}$, N$R^{14}$S(O)$R^{12}$, N$R^{14}$S(O)$_2R^{12}$, N$R^{12}$C(O)$R^{15}$, N$R^{12}$C(O)O$R^{15}$, N$R^{12}$S(O)$_2R^{15}$, and N$R^{12}$C(O)NH$R^{15}$;

$R^{10}$ is selected from H,
$C_{1-4}$ alkyl substituted with 0–2 $R^{10A}$,
$C_{2-4}$ alkenyl substituted with 0–2 $R^{10A}$,
$C_{2-4}$ alkynyl substituted with 0–1 $R^{10A}$, and
$C_{1-4}$ alkoxy;

$R^{10A}$ is selected from
$C_{1-4}$alkoxy,
$C_{3-6}$ carbocyclic residue substituted with 0–3 $R^{33}$,
phenyl substituted with 0–3 $R^{33}$, and
5–6 membered heterocyclic ring system containing 1, 2, or 3 heteroatoms selected from the group consisting of N, O, and S; substituted with 0–2 $R^{44}$;

$R^{111}$ is selected from
H, halo, —CF$_3$, —CN, —NO$_2$, $C_{1-6}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, N$R^{12}R^{13}$, C(O)H, C(O)$R^{12}$, C(O)N$R^{12}R^{13}$, N$R^{14}$C(O)$R^{12}$, C(O)O$R^{12}$, OC(O)$R^{12}$, OC(O)O$R^{12}$, CH(=N$R^{14}$)N$R^{12}R^{13}$, NHC(=N$R^{14}$)N$R^{12}R^{13}$, S(O)$R^{12}$, S(O)$_2R^{12}$, S(O)N$R^{12}R^{13}$, S(O)$_2$N$R^{12}R^{13}$, N$R^{14}$S(O)$R^{12}$, N$R^{14}$S(O)$_2R^{12}$, N$R^{12}$C(O)$R^{15}$,
N$R^{12}$C(O)O$R^{15}$, N$R^{12}$S(O)$_2R^{15}$, and N$R^{12}$C(O)NH$R^{15}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and 5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$);

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$, $SO_2R^{45}$, $NR^{46}R^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, $C_{1-3}$ alkyloxy-, and =O;

$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{33}$, at each occurrence, is independently selected from H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, C14 alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O), ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{41}$, at each occurrence, is independently selected from H, $CF_3$, halo, OH, $CO_2H$, $SO_2R^{45}$, $NR^{46}R^{47}$, $NO_2$, CN, =O;

$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —C(=O)NH($C_{1-4}$ alkyl), —$SO_2(C_{1-4}$ alkyl), —C(=O)O($C_{1-4}$ alkyl), —C(=O)($C_{1-4}$ alkyl), and —C(=O)H;

k is 1 or 2;

m is 0 or 1; and n is 1 or 2;

provided that when b is a double bond; n is 1; m is 1; k is 1; X is —O—, —S—, —S(=O)—, or —$SO_2$—; and the three substituents of $R^7$, $R^8$, and $R^9$, consist of i) three hydrogens, ii) two hydrogens and one chloro, or iii) two hydrogens and one methyl; then $R^1$ must contain the substituent Z or Y.

2. A compound of claim 1 of Formula (I-a):

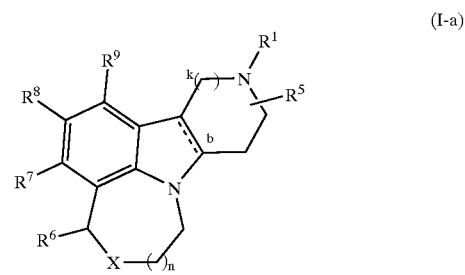

(I-a)

wherein:

X is —O—, —S—, —S(=O)—, —S(=O)$_2$—, or —$NR^{10}$—;

$R^1$ is selected from
H,
C(=O)$R^2$,
C(=O)O$R^2$,
$C_{1-8}$ alkyl,
$C_{2-8}$ alkenyl,
$C_{2-8}$ alkynyl,
$C_{3-7}$ cycloalkyl,
$C_{1-6}$ alkyl substituted with 0–2 $R^2$,
$C_{2-6}$ alkenyl substituted with 0–2 $R^2$,
$C_{2-6}$ alkynyl substituted with 0–2 $R^2$,
aryl substituted with 0–2 $R^2$, and
5–6 membered heterocyclic ring system containing at least one heteroatom selected from the group consisting of N, O, and S, said heterocyclic ring system substituted with 0–2 $R^2$;

$R^2$, at each occurrence, is independently selected from F, Cl, $CH_2F$, $CHF_2$, $CF_3$, $C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^5$ is H, methyl, ethyl, propyl, or butyl;

$R^6$ is H, methyl, ethyl, propyl, or butyl;

$R^7$ and $R^9$, at each occurrence, are independently selected from
H, halo, —$CF_3$, —$OCF_3$, —OH, —CN, —$NO_2$, —$NR^{46}R^{47}$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^8$ is selected from
H, halo, —$CF_3$, —$OCF_3$, —OH, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^{10}$ is selected from H, $C_{1-4}$ alkyl, $C_{2-4}$ alkenyl, $C_{2-4}$ alkynyl, and $C_{1-4}$ alkoxy;

$R^{11}$ is selected from
H, halo, —$CF_3$, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{2}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$,
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3-$R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from
H, OH, halo, CN, $NO_2$, $CF_3$, $SO_2R^{45}$, $NR^{46}R^{47}$, —C(=O)H,
$C_{1-4}$ alkyl, $C_{2-4}$ alkenyl, $C_{2-4}$ alkynyl, $C_{1-4}$ haloalkyl, $C_{1-3}$ haloalkyl-oxy-, $C_{1-3}$ alkyloxy- and =O;

$R^{31}$, at each occurrence, is independently selected from
CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O), $C_{1-4}$ alkyl-C(=O)O—, $C_{1-4}$ alkyl-C(=O)-NH—, Cl alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O), or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O), or ($C_{1-4}$ alkyl)$CO_2$—;

$R^{33}$, at each occurrence, is independently selected from
H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—;

$R^{41}$, at each occurrence, is independently selected from H, $CF_3$, halo, OH, $CO_2H$, $SO_2R^{45}$, $NR^{46}R^{47}$, $NO_2$, CN; $C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $NR^{46}R^{47}$, $NO_2$, CN, $CH(=NH)NH_2$, $NHC(=NH)NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;
$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;
$R^{45}$ is $C_{1-4}$ alkyl;
$R^{46}$, at each occurrence, is independently selected from H and $C_{1-4}$ alkyl;
$R^{47}$, at each occurrence, is independently selected from H and $C_{1-4}$ alkyl;
k is 1 or 2; and
n is 1 or 2.

3. A compound of claim 2 wherein:
X is —O—, —S—, or —NH—;
$R^1$ is selected from
H,
$C(=O)R^2$,
$C(=O)OR^2$,
$C_{1-6}$ alkyl,
$C_{2-6}$ alkenyl,
$C_{2-6}$ alkynyl,
$C_{3-6}$ cycloalkyl,
$C_{1-4}$ alkyl substituted with 0–2 $R^2$,
$C_{2-4}$ alkenyl substituted with 0–2 $R^2$, and
$C_{2-4}$ alkynyl substituted with 0–2 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^5$ is H, methyl, ethyl, propyl, or butyl;
$R^6$ is H, methyl, ethyl, propyl, or butyl;
$R^7$ and $R^9$, at each occurrence, are independently selected from
H, halo, —$CF_3$, —$OCF_3$, —OH, —CN, —$NO_2$, —$NR^{46}R^{47}$,
$C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^8$ is selected from
H, halo, —$CF_3$, —$OCF_3$, —OH, —CN, —$NO_2$,
$C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —CN, —$NO_2$, $C_{1-6}$ alkyl,
$C_{2-6}$ alkenyl, $C_{2-6}$ alkynyl, $C_{1-4}$ haloalkyl, $C_{1-6}$ alkoxy, $C_{3-10}$ cycloalkyl,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^{12}$, at each occurrence, is independently selected from
$C_{1-4}$ alkyl substituted with 0–1 $R^{12a}$,
$C_{2-4}$ alkenyl substituted with O—$R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H, methyl, ethyl, propyl, and butyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, F, Cl, CN, $NO_2$, $CF_3$, $SO_2R^{45}$, $NR^{46}R^{47}$, —C(=O)H,
methyl, ethyl, methoxy, ethoxy, trifluoromethyl, trifluoromethoxy and =O;

$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)}, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—;

$R^{33}$, at each occurrence, is independently selected from H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}C(=O)$, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—;

$R^{41}$, at each occurrence, is independently selected from H, $CF_3$, halo, OH, $CO_2H$, $SO_2R^{45}$, $NR^{46}R^{47}$, $NO_2$, CN, $C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-14}$ alkoxy, $C_{1-14}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 03 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2; and n is 1 or 2.

4. A compound of claim 2 wherein:

X is —S—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic residue substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^6$ is H;

$R^7$ and $R^9$, at each occurrence, are independently selected from
H, halo, —$CF_3$, —$OCF_3$, —OH, —CN, —$NO_2$, —$NR^{46}R^{47}$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^8$ is selected from
H, halo, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic residue substituted with 0–3 $R^{33}$,
aryl substituted with 0–5 $R^{33}$, and 5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with O—$R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$,
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{33}$, at each occurrence, is independently selected from H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-14}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl) $CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl) $CO_2$—;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, $CF_3$, halo, OH, $CO_2H$, $SO_2R^{45}$, $NR^{46}R^{47}$, $NO_2$, CN, CH(=NH)$NH_2$, NHC(=NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1; and n is 1 or 2.

5. A compound of claim 2 wherein:
X is —S—;
$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic residue substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^6$ is H;

$R^7$ and $R^9$, at each occurrence, are independently selected from
H, F, Cl, —$CH_3$, —$OCH_3$, —$CF_3$, —$OCF_3$, —CN, and —$NO_2$, $R^8$ is selected from
H, F, Cl, Br, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;

237

OR$^{12}$, SR$^2$, NR$^{12}$,R$^{13}$, NR$^{12}$C(O)R$^{15}$, NR$^{12}$C(O)OR$^{15}$,
  NR$^{12}$S(O)$_2$R$^{15}$, and NR$^{12}$C(O)NHR$^{15}$;

R$^{11}$ is selected from
  H, halo, —CF$_3$, —CN, —NO$_2$,
  C$_{1-4}$ alkyl, C$_{2-4}$ alkenyl, C$_{2-4}$ alkynyl, C$_{1-4}$ haloalkyl,
    C$_{1-4}$ alkoxy, (C$_{1-4}$ haloalkyl)oxy,
  C$_{3-10}$ cycloalkyl substituted with 0–2 R$^{33}$,
  C$_{3-10}$ carbocyclic residue substituted with 0–3 R$^{33}$,
  aryl substituted with 0–5 R$^{33}$, and
  5–6 membered heterocyclic ring system containing 1, 2, or 3 heteroatoms selected from the group consisting of N, O, and S substituted with 0–3 R$^{31}$;

R$^{12}$, at each occurrence, is independently selected from
  C$_{1-4}$ alkyl substituted with 0–1 R$^{12a}$,
  C$_{2-4}$ alkenyl substituted with O—R$^{12a}$,
  C$_{2-4}$ alkynyl substituted with O—R$^{12a}$,
  C$_{3-6}$ cycloalkyl substituted with 0–3 R$^{33}$,
  aryl substituted with 0–5 R$^{33}$;
  C$_{3-10}$ carbocyclic residue substituted with 0–3 R$^{33}$, and
  5–10 membered heterocyclic ring system containing from 1–4 heteroatoms selected from the group consisting of N, O, and S substituted with 0–3 R$^{31}$;

R$^{12a}$, at each occurrence, is independently selected from
  phenyl substituted with 0–5 R$^{33}$;
  C$_{3-10}$ carbocyclic residue substituted with 0–3 R$^{33}$, and
  5–10 membered heterocyclic ring system containing from 1–4 heteroatoms selected from the group consisting of N, O, and S substituted with 0–3 R$^{31}$;

R$^{13}$, at each occurrence, is independently selected from
  H, C$_{1-4}$ alkyl, C$_{2-4}$ alkenyl, and C$_{2-4}$ alkynyl;
alternatively, R$^{12}$ and R$^{13}$ join to form a 5- or 6-membered ring optionally substituted with —O— or —N(R$^{14}$)—;
alternatively, R$^{12}$ and R$^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, quinolinyl, tetrahydroquinolinyl, isoquinolinyl, tetrahydroisoquinolinyl; wherein said bicyclic heterocyclic ring system is substituted with 0–1 R$^{16}$;

R$^{14}$, at each occurrence, is independently selected from H, methyl, ethyl, propyl, and butyl;

R$^{15}$, at each occurrence, is independently selected from H, methyl, ethyl, propyl, and butyl;

R$^{16}$, at each occurrence, is independently selected from H, OH, F, Cl, CN, NO$_2$, methyl, ethyl, methoxy, ethoxy, trifluoromethyl, and trifluoromethoxy;

R$^{31}$, at each occurrence, is independently selected from CN, NO$_2$, —OCF$_3$, —OCH$_2$CF$_3$, —C(=O)H, —C(=O)NH$_2$, —C(=O)OCH$_3$, phenyl, C$_{2-6}$ alkenyl, C$_{2-6}$ alkynyl, C$_{3-6}$ cycloalkyl, C$_{1-4}$ haloalkyl, C$_{1-4}$ haloalkyl-oxy-, C$_{1-4}$ alkyloxy-, C$_{1-4}$ alkylthio-, C$_{1-4}$ alkyl-C(=O)—, C$_{1-4}$ alkyl-OC(=O)—, C$_{1-4}$ alkyl-C(=O)O—, C$_{1-4}$ alkyl-C(=O)-NH—, C$_{1-4}$ alkyl-NHC(=O)—, (C$_{1-4}$ alkyl)$_2$NC(=O)—, C$_{3-6}$ cycloalkyl-oxy-, C$_{3-6}$ cycloalkylmethyl-oxy-; C$_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O), or (C$_{1-4}$ alkyl)CO$_2$—; and C$_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O), or (C$_{1-4}$ alkyl)CO$_2$—;

R$^{33}$, at each occurrence, is independently selected from H, OH, halo, CN, NO$_2$, CF$_3$, —OCF$_3$, —OCH$_2$CF$_3$, SO$_2$R$^{45}$, NR$^{46}$R$^{47}$, —C(=O)H, =O, —C(=O)

238

NH$_2$, —C(=O)OCH$_3$, phenyl, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyl-oxy-, C$_{1-4}$ alkyloxy-, C$_{1-4}$ alkylthio-, C$_{1-4}$ alkyl-C(=O), C$_{1-4}$ alkyl-OC(=O)—, C$_{1-4}$ alkyl-C(=O)O—, C$_{1-4}$ alkyl-C(=O)-NH—, C$_{1-4}$ alkyl-NHC(=O)—, (C$_{1-4}$ alkyl)$_2$NC(=O)—, C$_{3-6}$ cycloalkyl-oxy-, C$_{3-6}$ cycloalkylmethyl-oxy-; C$_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—; and C$_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—;

R$^{41}$, at each occurrence, is independently selected from H, CF$_3$, halo, OH, CO$_2$H, SO$_2$R$^{45}$, NR$^{46}$R$^{47}$, NO$_2$, CN, C$_{2-4}$ alkenyl, C$_{2-4}$ alkynyl, C$_{1-3}$ alkoxy, C$_{1-3}$ haloalkyl, and C$_{1-3}$ alkyl;

R$^{42}$, at each occurrence, is independently selected from H, CF$_3$, halo, OH, CO$_2$H, SO$_2$R$^{45}$, NR$^{46}$R$^{47}$, NO$_2$, CN, CH(=NH)NH$_2$, NHC(=NH)NH$_2$,
  C$_{2-4}$ alkenyl, C$_{2-4}$ alkynyl, C$_{1-3}$ alkoxy, C$_{1-3}$ haloalkyl, C$_{3-6}$ cycloalkyl, and C$_{1-3}$ alkyl;

R$^{43}$ is cyclopropyl, cyclobutyl, cyclopentyl, cyclohexyl, phenyl, or pyridyl, each substituted with 0–3 R$^{44}$;

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, methyl, ethyl, propyl, butyl, methoxy, ethoxy, propoxy, and butoxy;

R$^{45}$ is methyl, ethyl, propyl, or butyl;

R$^{46}$, at each occurrence, is independently selected from H, methyl, ethyl, propyl, and butyl;

R$^{47}$, at each occurrence, is independently selected from from H, methyl, ethyl, propyl, and butyl;

k is 1; and n is 1 or 2.

6. A compound of claim 2 wherein:

X is —S—;

R$^1$ is selected from H,
  C$_{1-5}$ alkyl substituted with 0–1 R$^2$,
  C$_{2-5}$ alkenyl substituted with 0–1 R$^2$, and
  C$_{2-3}$ alkynyl substituted with 0–1 R$^2$;

R$^2$ is C$_{3-6}$ cycloalkyl;

R$^5$ is H, methyl, ethyl, or propyl;

R$^6$ is H;

R$^7$ and R$^9$, at each occurrence, are independently selected from H, F, Cl, —CH$_3$, —OCH$_3$, —CF$_3$, —OCF$_3$, —CN, and —NO$_2$;

R$^8$ is selected from R$^{11}$;
  methyl substituted with R$^{11}$;
  phenyl substituted with 0–3 R$^{33}$;
  pyridyl substituted with 0–2 R$^{33}$;
  OR$^{12}$, SR$^{12}$, NR$^{12}$R$^{13}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{11}$ is selected from
  phenyl-substituted with 0–5 fluoro;
  pyridyl substituted with 0–2 R$^{33}$;
  naphthyl-substituted with 0–2 R$^{33}$;
  2-(H$_3$CCH$_2$C(=O))-phenyl-substituted with R$^{33}$;
  2-(H$_3$CC(=O))-phenyl-substituted with R$^{33}$;
  2-(HC(=O))phenyl-substituted with R$^{33}$;
  2-(H$_3$CCH(OH))-phenyl-substituted with R$^{33}$;
  2-(H$_3$CCH$_2$CH(OH))-phenyl-substituted with R$^{33}$;
  2-(HOCH$_2$)-phenyl-substituted with R$^{33}$;

2-(HOCH$_2$CH$_2$)-phenyl-substituted with R$^{33}$;
2-(H$_3$COCH$_2$)-phenyl-substituted with R$^{33}$;
2-(H$_3$COCH$_2$CH$_2$)-phenyl-substituted with R$^{33}$;
2-(H$_3$CCH(OMe))-phenyl-substituted with R$^{33}$;
2-(H$_3$COC(=O))-phenyl-substituted with R$^{33}$;
2-(HOCH$_2$CH=CH)-phenyl-substituted with R$^{33}$;
2-((MeOC=O)CH=CH)-phenyl-substituted with R$^{33}$;
2-(methyl)phenyl-substituted with R$^{33}$;
2-(ethyl)-phenyl-substituted with R$^{33}$;
2-(i-propyl)phenyl-substituted with R$^{33}$;
2-(F$_3$C)-phenyl-substituted with R$^{33}$;
2-(NC)-phenyl-substituted with R$^{33}$;
2-(H$_3$CO)phenyl-substituted with R$^{33}$;
2-(fluoro)-phenyl-substituted with R$^{33}$;
2-(chloro)-phenyl-substituted with R$^{33}$;
3-(NC)-phenyl-substituted with R$^{33}$;
3-(H$_3$CO)-phenyl-substituted with R$^{33}$;
3-(fluoro)-phenyl-substituted with R$^{33}$;
3-(chloro)-phenyl-substituted with R$^{33}$;
3-(H$_3$C)-phenyl-substituted with R$^{33}$;
3-(F$_3$C)-phenyl-substituted with R$^{33}$;
3-(H$_3$CS)-phenyl-substituted with R$^{33}$;
4-(NC)-phenyl-substituted with R$^{33}$;
4-(fluoro)-phenyl-substituted with R$^{33}$;
4-(chloro)-phenyl-substituted with R$^{33}$;
4-(H$_3$CS)-phenyl-substituted with R$^{33}$;
4-(H$_3$CO)-phenyl-substituted with R$^{33}$;
4-(ethoxy)-phenyl-substituted with R$^{33}$;
4-(i-propoxy)-phenyl-substituted with R$^{33}$;
4-(i-butoxy)phenyl-substituted with R$^{33}$;
4-(H$_3$CCH$_2$CH$_2$C(=O))-phenyl-substituted with R$^{33}$;
4-((H$_3$C)$_2$CHC(=O))-phenyl-substituted with R$^{33}$;
4-(H$_3$CCH$_2$C(=O))-phenyl-substituted with R$^{33}$;
4-(H$_3$CC(=O))-phenyl-substituted with R$^{33}$;
4-(H$_3$CCH$_2$CH$_2$CH(OH)}phenyl-substituted with R$^{33}$;
4-((H$_3$C)$_2$CHCH(OH))-phenyl-substituted with R$^{33}$;
4-(H$_3$CCH$_2$CH(OH))-phenyl-substituted with R$^{33}$;
4-(H$_3$CCH(OH))-phenyl-substituted with R$^{33}$;
4-(cyclopropyloxy)-phenyl-substituted with R$^{33}$;
4-(cyclobutyloxy)-phenyl-substituted with R$^{33}$; and
4-(cyclopentyloxy)-phenyl-substituted with R$^{33}$;

R$^{12}$ is selected from
methyl substituted with R$^{11}$;
phenyl substituted with 0–5 fluoro;
pyridyl substituted with 0–2 R$^{33}$;
naphthyl substituted with 0–2 R$^{33}$;
2-(H$_3$CCH$_2$C(=O))-phenyl-substituted with R$^{33}$;
2-(H$_3$CC(=O))-phenyl-substituted with R$^{33}$;
2-(HC(=O))phenyl-substituted with R$^{33}$;
2-(H$_3$CCH(OH))-phenyl-substituted with R$^{33}$;
2-(H$_3$CCH$_2$CH(OH))-phenyl-substituted with R$^{33}$;
2-(HOCH$_2$)-phenyl-substituted with R$^{33}$;
2-(HOCH$_2$CH$_2$)-phenyl-substituted with R$^{33}$;
2-(H$_3$COCH$_2$)-phenyl-substituted with R$^{33}$;
2-(H$_3$COCH$_2$CH$_2$)phenyl-substituted with R$^{33}$;
2-(H$_3$CCH(OMe))-phenyl-substituted with R$^{33}$;
2-(H$_3$COC(=O))-phenyl-substituted with R$^{33}$;
2-(HOCH$_2$CH=CH)-phenyl-substituted with R$^{33}$;
2-((MeOC=O)CH=CH)-phenyl-substituted with R$^{33}$;
2-(methyl)-phenyl-substituted with R$^{33}$;
2-(ethyl)-phenyl-substituted with R$^{33}$;
2-(propyl)-phenyl-substituted with R$^{33}$;
2-(F$_3$C)phenyl-substituted with R$^{33}$;
2-(NC)-phenyl-substituted with R$^{33}$;
2-(H$_3$CO)-phenyl-substituted with R$^{33}$;
2-(fluoro)-phenyl-substituted with R$^{33}$;
2-(chloro)-phenyl-substituted with R$^{33}$;
3-(NC)-phenyl-substituted with R$^{33}$;
3-(H$_3$CO)-phenyl-substituted with R$^{33}$;
3-(fluoro)-phenyl-substituted with R$^{33}$;
3-(chloro)-phenyl-substituted with R$^{33}$;
3-(H$_3$C)-phenyl-substituted with R$^{33}$;
3-(F$_3$C)-phenyl-substituted with R$^{33}$;
3-(H$_3$CS)-phenyl-substituted with R$^{33}$;
4-(fluoro)-phenyl-substituted with R$^{33}$;
4-(chloro)-phenyl-substituted with R$^{33}$;
4-(H$_3$CS)-phenyl-substituted with R$^{33}$;
4-(H$_3$CO)-phenyl-substituted with R$^{33}$;
4-(ethoxy)-phenyl-substituted with R$^{33}$;
4-(i-propoxy)-phenyl-substituted with R$^{33}$;
4-(i-butoxy)phenyl-substituted with R$^{33}$;
4-(H$_3$CCH$_2$CH$_2$C(=O))-phenyl-substituted with R$^{33}$;
4-((H$_3$C)$_2$CHC(=O))-phenyl-substituted with R$^{33}$;
4-(H$_3$CCH$_2$C(=O))-phenyl-substituted with R$^{33}$;
4-(H$_3$CC(=O))-phenyl-substituted with R$^{33}$;
4-(H$_3$CCH$_2$CH$_2$CH(OH))-phenyl-substituted with R$^{33}$;
4-((H$_3$C)$_2$CHCH(OH))-phenyl-substituted with R$^{33}$;
4-(H$_3$CCH$_2$CH(OH))-phenyl-substituted with R$^{33}$;
4-(H$_3$CCH(OH))-phenyl-substituted with R$^{33}$;
4-(cyclopropyloxy)-phenyl-substituted with R$^{33}$;
4-(cyclobutyloxy)-phenyl-substituted with R$^{33}$; and
4-(cyclopentyloxy)-phenyl-substituted with R$^{33}$;

R$^{13}$ is H, methyl, or ethyl;

alternatively, R$^{12}$ and R$^{13}$ join to form a 5- or 6-membered ring selected from pyrrolyl, pyrrolidinyl, imidazolyl, piperidinyl, piperizinyl, methylpiperizinyl, and morpholinyl;

alternatively, R$^{12}$ and R$^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 R$^{16}$;

R$^{15}$ is H, methyl, ethyl, propyl, or butyl;

R$^{16}$ at each occurrence, is independently selected from H, OH, F, Cl, CN, NO$_2$, methyl, ethyl, methoxy, ethoxy, trifluoromethyl, and trifluoromethoxy;

R$^{33}$, at each occurrence, is independently selected from H, F, Cl, —CH$_3$, —CH$_2$CH$_3$, —OCH$_3$, —SCH$_3$, —CF$_3$, —OCF$_3$, —CN, and —NO$_2$;

k is 1; and n is 1 or 2.

7. A compound of claim 2 wherein:

X is —O—;

R$^1$ is selected from
H,
C$_{1-4}$ alkyl,
C$_{2-4}$ alkenyl,
C$_{2-4}$ alkynyl,
C$_{3-4}$ cycloalkyl,
C$_{1-3}$ alkyl substituted with 0–1 R$^2$,
C$_{2-3}$ alkenyl substituted with 0–1 R$^2$, and
C$_{2-3}$ alkynyl substituted with 0–1 R$^2$;

R$^2$, at each occurrence, is independently selected from
C$_{1-4}$ alkyl,
C$_{2-4}$ alkenyl,
C$_{2-4}$ alkynyl, $C_{3-6}$ cycloalkyl,
phenyl substituted with 0–5 $R^{42}$;
$C_{3-6}$ carbocyclic residue substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^6$ is H;

$R^7$ and $R^9$, at each occurrence, are independently selected from
H, halo, —$CF_3$, —$OCF_3$, —OH, —CN, —$NO_2$, —$NR^{46}R^{47}$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^8$ is selected from
H, halo, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with O—$R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a S— or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one 0, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-$C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—;

$R^{33}$, at each occurrence, is independently selected from H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, $CF_3$, halo, OH, $CO_2H$, $SO_2R^{45}$, $NR^{46}R^{47}$, $NO_2$, CN, CH(=NH)$NH_2$, NHC(—NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1; and n is 1 or 2.

8. A compound of claim 2 wherein

X is —O—;

$R^1$ is selected from
- H,
- $C_{1-4}$ alkyl,
- $C_{2-4}$ alkenyl,
- $C_{2-4}$ alkynyl,
- $C_{3-4}$ cycloalkyl,
- $C_{1-3}$ alkyl substituted with 0–1 $R^2$,
- $C_{2-3}$ alkenyl substituted with 0–1 $R^2$, and
- $C_{2-3}$ alkynyl substituted with 0–1 $R^2$;

$R^2$, at each occurrence, is independently selected from
- $C_{1-4}$ alkyl,
- $C_{2-4}$ alkenyl,
- C24 alkynyl,
- $C_{3-6}$ cycloalkyl,
- phenyl substituted with 0–5 $R^{42}$;
- $C_{3-6}$ carbocyclic residue substituted with 0–3 $R^{41}$, and
- 5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^6$ is H;

$R^7$ and $R^9$, at each occurrence, are independently selected from H, F, Cl, —CH$_3$, —OCH$_3$, —CF$_3$, —OCF$_3$, —CN, and —NO$_2$;

$R^8$ is selected from
- H, F, Cl, Br, —CF$_3$, —OCF$_3$, —OH, —CN, —NO$_2$,
- $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
- $C_{3-10}$ cycloalkyl substituted with 0–2 $R^{33}$,
- $C_{1-4}$ alkyl substituted with 0–2 $R^{11}$,
- $C_{2-4}$ alkenyl substituted with 0–2 $R^{11}$,
- $C_{2-4}$ alkynyl substituted with 0–1 $R^{11}$,
- $C_{3-10}$ carbocyclic residue substituted with 0–3 $R^{33}$,
- aryl substituted with 0–5 $R^{33}$,
- 5–6 membered heterocyclic ring system containing 1, 2, or 3 heteroatoms selected from the group consisting of N, O, and S substituted with 0–3 $R^{31}$;
- $OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
- H, halo, —CF$_3$, —CN, —NO$_2$,
- $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
- $C_{3-10}$ cycloalkyl substituted with 0–2 $R^{33}$,
- $C_{3-10}$ carbocyclic residue substituted with 0–3 $R^{33}$,
- aryl substituted with 0–5 $R^{33}$, and
- 5–6 membered heterocyclic ring system containing 1, 2, or 3 heteroatoms selected from the group consisting of N, O, and S substituted with 0–3 $R^{31}$;

$R^{12}$, at each occurrence, is independently selected from
- $C_{1-4}$ alkyl substituted with 0–1 $R^{12a}$,
- $C_{2-4}$ alkenyl substituted with 0–1 $R^{12a}$,
- $C_{2-4}$ alkynyl substituted with 0–1 $R^{12a}$,
- $C_{3-6}$ cycloalkyl substituted with 0–3 $R^{33}$,
- aryl substituted with 0–5 $R^{33}$;
- $C_{3-10}$ carbocyclic residue substituted with 0–3 $R^{33}$, and
- 5–10 membered heterocyclic ring system containing from 1–4 heteroatoms selected from the group consisting of N, O, and S substituted with 0–3 $R^{31}$;

$R^{12a}$, at each occurrence, is independently selected from
- phenyl substituted with 0–5 $R^{33}$;
- $C_{3-10}$ carbocyclic residue substituted with 0–3 $R^{33}$, and
- 5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, quinolinyl, tetrahydroquinolinyl, isoquinolinyl, tetrahydroisoquinolinyl; wherein said bicyclic heterocyclic ring system is substituted with 0–1 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, NO$_2$, methyl, ethyl, methoxy, ethoxy, trifluoromethyl, and trifluoromethoxy;

$R^{31}$, at each occurrence, is independently selected from CN, NO$_2$, —OCF$_3$, —OCH$_2$CF$_3$, —C(=O)H, —C(=O)NH$_2$, —C(=O)OCH$_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, Cl alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —SO$_2R^{45}$, —NR$^{46}R^{47}$, NR$^{46}R^{47}$C(=O)—, or ($C_{1-4}$ alkyl)CO$_2$—; and $C_{2-6}$ alkenyl substituted with OH, methoxy, ethoxy, propoxy, butoxy, —SO$_2R^{45}$, —NR$^{46}R^{47}$, NR$^{46}R^{47}$C(=O)—, or ($C_{1-4}$ alkyl)CO$_2$—;

$R^{33}$, at each occurrence, is independently selected from H, OH, halo, CN, NO$_2$, CF$_3$, —OCF$_3$, —OCH$_2$CF$_3$, SO$_2R^{45}$, NR$^{46}R^{47}$, —C(=O)H, =O, —C(=O)NH$_2$, —C(=O)OCH$_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —SO$_2R^{45}$, —NR$^{46}R^{47}$, NR$^{46}R^{47}$C(=O)—, or ($C_{1-4}$ alkyl)CO$_2$—; and $C_{2-6}$ alkenyl substituted with OH, methoxy, ethoxy, propoxy, butoxy, —SO$_2R^{45}$, —NR$^{46}R^{47}$, NR$^{46}R^{47}$C(=O), or ($C_{1-4}$ alkyl)CO$_2$—;

$R^{41}$, at each occurrence, is independently selected from H, CF$_3$, halo, OH, CO$_2$H, SO$_2R^{45}$, NR$^{46}R^{47}$, NO$_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, CF$_3$, halo, OH, CO$_2$H, SO$_2R^{45}$, NR$^{46}R^{47}$, NO$_2$, CN, CH(=NH)NH$_2$, NHC(=NH)NH$_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1; and n is 1 or 2.

9. A compound of claim 2 wherein:

X is —O—;

$R^1$ is selected from H,
  $C_{1-5}$ alkyl substituted with 0–1 $R^2$,
  $C_{2-5}$ alkenyl substituted with 0–1 $R^2$, and
  $C_{2-3}$ alkynyl substituted with 0–1 $R^2$;

$R^2$ is $C_{3-6}$ cycloalkyl;

$R^5$ is H, methyl, ethyl, or propyl;

$R^6$ is H;

$R^7$ and $R^9$, at each occurrence, are independently selected from H, F, Cl, —$CH_3$, —$OCH_3$, —$CF_3$, —$OCF_3$, —CN, and —$NO_2$;

$R^8$ is selected from $R^{11}$;
  methyl substituted with $R^{11}$;
  phenyl substituted with 0–3 $R^{33}$;
  pyridyl substituted with 0–2 $R^{33}$;
  $OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
  phenyl-substituted with 0–5 fluoro;
  pyridyl substituted with 0–2 $R^{33}$;
  naphthyl-substituted with 0–2 $R^{33}$;
  2-($H_3CCH_2C$(=O))-phenyl-substituted with $R^{33}$;
  2-($H_3CC$(=O))-phenyl-substituted with $R^{33}$;
  2-(HC(=O))-phenyl-substituted with $R^{33}$;
  2-($H_3CCH(OH)$)-phenyl-substituted with $R^{33}$;
  2-($H_3CCH_2CH(OH)$)-phenyl-substituted with $R^{33}$;
  2-($HOCH_2$)-phenyl-substituted with $R^{33}$;
  2-($HOCH_2CH_2$)-phenyl-substituted with $R^{33}$;
  2-($H_3COCH_2$)-phenyl-substituted with $R^{33}$;
  2-($H_3COCH_2CH_2$)-phenyl-substituted with $R^{33}$;
  2-($H_3CCH(OMe)$)-phenyl-substituted with $R^{33}$;
  2-($H_3COC$(=O))-phenyl-substituted with $R^{33}$;
  2-($HOCH_2CH$=CH)-phenyl-substituted with $R^{33}$;
  2-((MeOC(=O)CH=CH)-phenyl-substituted with $R^{33}$;
  2-(methyl)-phenyl-substituted with $R^{33}$;
  2-(ethyl)-phenyl-substituted with $R^{33}$;
  2-(i-propyl)-phenyl-substituted with $R^{33}$;
  2-($F_3C$)-phenyl-substituted with $R^{33}$;
  2-(NC)-phenyl-substituted with $R^{33}$;
  2-($H_3CO$)-phenyl-substituted with $R^{33}$;
  2-(fluoro)-phenyl-substituted with $R^{33}$;
  2-(chloro)-phenyl-substituted with $R^{33}$;
  3-(NC)-phenyl-substituted with $R^{33}$;
  3-($H_3CO$)-phenyl-substituted with $R^{33}$;
  3-(fluoro)-phenyl-substituted with $R^{33}$;
  3-(chloro)-phenyl-substituted with $R^{33}$;
  3-($H_3C$)-phenyl-substituted with $R^{33}$;
  3-($F_3C$)-phenyl-substituted with $R^{33}$;
  3-($H_3CS$)-phenyl-substituted with $R^{33}$;
  4-(NC)-phenyl-substituted with $R^{33}$;
  4-(fluoro)-phenyl-substituted with $R^{33}$;
  4-(chloro)-phenyl-substituted with $R^{33}$;
  4-($H_3CS$)-phenyl-substituted with $R^{33}$;
  4-($H_3CO$)phenyl-substituted with $R^{33}$;
  4-(ethoxy)phenyl-substituted with $R^{33}$;
  4-(i-propoxy)-phenyl-substituted with $R^{33}$;
  4-(i-butoxy)-phenyl-substituted with $R^{33}$;
  4-($H_3CCH_2CH_2C$(=O))-phenyl-substituted with $R^{33}$;
  (($H_3C)_2CHC$(=O))-phenyl-substituted with $R^{33}$;
  4-($H_3CCH_2C$(=O))-phenyl-substituted with $R^{33}$;
  4-($H_3CC$(=O))-phenyl-substituted with $R^{33}$;
  4-($H_3CCH_2CH_2CH(OH)$)-phenyl-substituted with $R^{33}$;
  4-(($H_3C)_2CHCH(OH)$)-phenyl-substituted with $R^{33}$;
  4-($H_3CCH_2CH(OH)$)-phenyl-substituted with $R^{33}$;
  4-($H_3CCH(OH)$)-phenyl-substituted with $R^{33}$;
  4-(cyclopropyloxy)-phenyl-substituted with $R^{33}$;
  4-(cyclobutyloxy)-phenyl-substituted with $R^{33}$; and
  4-(cyclopentyloxy)-phenyl-substituted with $R^{33}$;

$R^{12}$ is selected from
  methyl substituted with $R^{11}$;
  phenyl substituted with 0–5 fluoro;
  pyridyl substituted with 0–2 $R^{33}$;
  naphthyl substituted with 0–2 $R^{33}$;
  2-($H_3CCH_2C$(=O))-phenyl-substituted with $R^{33}$;
  2-($H_3CC$(=O))-phenyl-substituted with $R^{33}$;
  2-(HC(=O))-phenyl-substituted with $R^{33}$;
  2-($H_3CCH(OH)$)-phenyl-substituted with $R^{33}$;
  2-($H_3CCH_2CH(OH)$)-phenyl-substituted with $R^{33}$;
  2-($HOCH_2$)-phenyl-substituted with $R^{33}$;
  2-($HOCH_2CH_2$)-phenyl-substituted with $R^{33}$;
  2-($H_3COCH_2$)-phenyl-substituted with $R^{33}$;
  2-($H_3COCH_2CH_2$)-phenyl-substituted with $R^{33}$;
  2-($H_3CCH(OMe)$)-phenyl-substituted with $R^{33}$;
  2-($H_3COC$(=O))-phenyl-substituted with $R^{33}$;
  2-($HOCH_2CH$=CH)phenyl-substituted with $R^{33}$;
  2-((MeOC(=O)CH=CH)-phenyl-substituted with $R^{33}$;
  2-(methyl)phenyl-substituted with $R^{33}$;
  2-(ethyl)-phenyl-substituted with $R^{33}$;
  2-(i-propyl)-phenyl-substituted with $R^{33}$;
  2-($F_3C$)-phenyl-substituted with $R^{33}$;
  2-(NC)phenyl-substituted with $R^{33}$;
  2-($H_3CO$)phenyl-substituted with $R^{33}$;
  2-(fluoro)-phenyl-substituted with $R^{33}$;
  2-(chloro)-phenyl-substituted with $R^{33}$;
  3-(NC)-phenyl-substituted with $R^{33}$;
  3-($H_3CO$)-phenyl-substituted with $R^{33}$;
  3-(fluoro)-phenyl-substituted with $R^{33}$;
  3-(chloro)-phenyl-substituted with $R^{33}$;
  3-($H_3C$)-phenyl-substituted with $R^{33}$;
  3-($F_3C$)-phenyl-substituted with $R^{33}$;
  3-($H_3CS$)-phenyl-substituted with $R^{33}$;
  4-(fluoro)-phenyl-substituted with $R^{33}$;
  4-(chloro)-phenyl-substituted with $R^{33}$;
  4-($H_3CS$)-phenyl-substituted with $R^{33}$;
  4-($H_3CO$)-phenyl-substituted with $R^{33}$;
  4-(ethoxy)-phenyl-substituted with $R^{33}$;
  4-(i-propoxy)-phenyl-substituted with $R^{33}$;
  4-(i-butoxy)-phenyl-substituted with $R^{33}$;
  4-($H_3CCH_2CH_2C$(=O))-phenyl-substituted with $R^{33}$;
  4-(($H_3C)_2CHC$(=O))-phenyl-substituted with $R^{33}$;
  4-($H_3CCH_2C$(=O))-phenyl-substituted with $R^{33}$;
  4-($H_3CC$(=O))-phenyl-substituted with $R^{33}$;
  4-($H_3CCH_2CH_2CH(OH)$)-phenyl-substituted with $R^{33}$;
  4-(($H_3C)_2CHCH(OH)$)-phenyl-substituted with $R^{33}$;
  4-($H_3CCH_2CH(OH)$)-phenyl-substituted with $R^{33}$;
  4-($H_3CCH(OH)$)-phenyl-substituted with $R^{33}$;

4-(cyclopropyloxy)-phenyl-substituted with $R^{33}$;
4-(cyclobutyloxy)phenyl-substituted with $R^{33}$; and
4-(cyclopentyloxy)-phenyl-substituted with $R^{33}$;

$R^{13}$ is H, methyl, or ethyl;

alternatively, $R^{12}$ and $R^{13}$ join to form a 5- or 6 membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl quinolinyl, tetrahydroquinolinyl, isoquinolinyl, and tetrahydroisoquinolinyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{33}$, at each occurrence, is independently selected from H, F, Cl, $-CH_3$, $-CH_2CH_3$, $-OCH_3$, $-SCH_3$, $-CF_3$, $-OCF_3$, $-CN$, and $-NO_2$;

k is 1; and n is 1 or 2.

10. A compound of claim 2 of Formula (I-b)

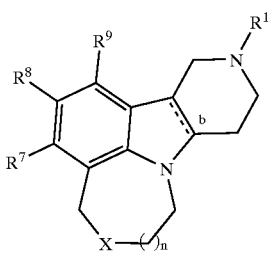

(I-b)

wherein:

b is a single bond or a double bond;

X is —S— or —O—;

$R^1$ is selected from
hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl,
4-methylpentyl, 2-fluoroethyl, 2,2-difluoroethyl, 2,2,2-trifluoroethyl,
2-propenyl, 2-methyl-2-propenyl, trans-2-butenyl, 3-methyl-2-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl,
cyclobutylmethyl, cyclopentylmethyl, cyclohexylmethyl,
benzyl, 2-methylbenzyl, 3-methylbenzyl, 4-methylbenzyl, 2,5-dimethylbenzyl, 2,4-dimethylbenzyl,
3,5-dimethylbenzyl, 2,4,6-trimethyl-benzyl,
3-methoxy-benzyl, 3,5-dimethoxy-benzyl, pentafluorobenzyl, 2-phenylethyl, 1-phenyl-2-propyl,
4-phenylbutyl, 4-phenylbenzyl, 2-phenylbenzyl,
2,6-dimethoxy-benzyl, 2,4-dimethoxy-benzyl,
2,4,6-trimethoxy-benzyl, 2,3-dimethoxy-benzyl,
2,4,5-trimethoxy-benzyl, 2,3,4-trimethoxy-benzyl,
3,4-dimethoxy-benzyl, 3,4,5-trimethoxy-benzyl,
(4-fluoro-phenyl)ethyl,
$-CH=CH_2$, $-CH_2-CH=CH_2$, $-CH=CH-CH_3$, $-C\equiv CH$, $-C\equiv C-CH_3$, and $-CH_2-C\equiv CH$;

$R^7$, $R^8$, and $R^9$, at each occurrence, are independently selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl;

2-Cl-phenyl; 2-F-phenyl; 2-Br-phenyl; 2-CN-phenyl;
2-Me-phenyl; 2-$CF_3$-phenyl; 2-MeO-phenyl; 2-$CF_3$O-phenyl; 2-$NO_2$-phenyl; 2-MeS-phenyl; 2-CHO-phenyl; 2-HOCH$_2$-phenyl;

3-Cl-phenyl; 3-F-phenyl; 3-Br-phenyl; 3-CN-phenyl;
3-Me-phenyl; 3-Et-phenyl; 3-n-Pr-phenyl; 3-isoPr-phenyl;

3-n-Bu-phenyl; 3-$CF_3$-phenyl; 3-MeO-phenyl; 3-MeS-phenyl;

3-isopropoxyphenyl; 3-$CF_3$O-phenyl; 3-$NO_2$-phenyl;
3-CHO-phenyl; 3-HOCH$_2$-phenyl; 3-MeOCH$_2$-phenyl;

3-Me$_2$NCH$_2$-phenyl;

4-Cl-phenyl; 4-F-phenyl; 4-Br-phenyl; 4-CN-phenyl;
4-Me-phenyl; 4-Et-phenyl; 4-n-Pr-phenyl;
4-iso-Pr-phenyl; 4-n-Bu-phenyl; 4-$CF_3$-phenyl;
4-MeO-phenyl; 4-isopropoxyphenyl; 4-$CF_3$O-phenyl;
4-MeS-phenyl;

4-acetylphenyl; 3-acetamidophenyl; 4-pyridyl;
2-furanyl; 2-thiophenyl; 2-naphthyl; 1-pyrrolidinyl,
2,3-diCl-phenyl; 2,3-diF-phenyl; 2,3-diMe-phenyl;
2,3-di$CF_3$-phenyl; 2,3-diMeO-phenyl; 2,3-di$CF_3$O-phenyl;

2,4-diCl-phenyl; 2,4-diF-phenyl; 2,4-diMe-phenyl;
2,4-di$CF_3$-phenyl; 2,4-diMeO-phenyl; 2,4-di$CF_3$O-phenyl;

2,5-diCl-phenyl; 2,5-diF-phenyl; 2,5-diMe-phenyl;
2,5-di$CF_3$-phenyl; 2,5-diMeO-phenyl; 2,5-di$CF_3$O-phenyl;

2,6-diCl-phenyl; 2,6-diF-phenyl; 2,6-diMe-phenyl;
2,6-di$CF_3$-phenyl; 2,6-diMeO-phenyl; 2,6-di$CF_3$O-phenyl;

3,4-diCl-phenyl; 3,4-diF-phenyl; 3,4-diMe-phenyl;
3,4-di$CF_3$-phenyl; 3,4-diMeO-phenyl; 3,4-di$CF_3$O-phenyl;

2,4,6-triCl-phenyl; 2,4,6-triF-phenyl;
2,4,6-triMe-phenyl; 2,4,6-tri$CF_3$-phenyl;
2,4,6-triMeO-phenyl; 2,4,6-tri$CF_3$O-phenyl;
2,4,5-triMe-phenyl; 2,3,4-triF-phenyl;
2-Me$_4$-MeO-5-F-phenyl; 2,6-diCl-4-MeO-phenyl;
2,4-diMeO-6-F-phenyl; 2,6-diF-4-Cl-phenyl;
2,3,4,6-tetraF-phenyl; 2,3,4,5,6-pentaF-phenyl;

2-Cl-4-F-phenyl; 2-Cl-6-F-phenyl; 2-Cl-3-Me-phenyl;
2-Cl-4-MeO-phenyl; 2-$C_{1-4}$-EtO-phenyl;
2-Cl-4-iPrO-phenyl; 2-Cl-4-$CF_3$-phenyl;
2-Cl-4-$CF_3$O-phenyl; 2-$C_{1-4}$CHF$_2$)O-phenyl;

2-F-3-Cl-phenyl; 2-F-4-MeO-phenyl; 2-F-5-Me-phenyl;

2-Me-3-Cl-phenyl; 2-Me-3-CN-phenyl; 2-Me$_4$-Cl-phenyl;

2-Me$_4$-F-phenyl; 2-Me$_4$-CN-phenyl; 2-Me$_4$-MeO-phenyl;

2-Me$_4$-EtO-phenyl; 2-Me$_4$-MeS-phenyl;

2-Me₄-H₂NCO-phenyl; 2-Me₄-MeOC(=O)phenyl;
2-Me-4-CH₃C(=O)-phenyl; 2-Me-5-F-phenyl;
2-Et-4-MeO-phenyl; 2-MeO-5-F-phenyl;
2-MeO-4-isopropyl-phenyl; 2-CF₃-4-Cl-phenyl;
2-CF₃-4-F-phenyl; 2-CF₃-4-MeO-phenyl;
2-CF₃-4-EtO-phenyl; 2-CF₃-4-iPrO-phenyl;
2-CF₃-4-CN-phenyl; 2-CF₃-6-F-phenyl;
2-CHO-4-MeO-phenyl; 2-MeOC(=O)-3-MeO-phenyl;
2-CH₃CH(OH)-4-MeO-phenyl; 2-CH₃CH(OH)-4-F-phenyl;
2-CH₃CH(OH)₄—Cl-phenyl; 2-CH₃CH(OH)-4-Me-phenyl;
2-CH₃CH(OMe)-4-MeO-phenyl; 2-CH₃C(=O)-4-MeO-phenyl;
2-CH₃C(=O)-4-F-phenyl; 2-CH₃C(=O)₄—Cl-phenyl;
2-CH₃C(=O)-4-Me-phenyl; 2-H₂C(OH)-4-MeO-phenyl;
2-H₂C(OMe)-4-MeO-phenyl; 2-H₃CCH₂CH(OH)-4-MeO-phenyl;
2-H₃CCH₂C(=O)-4-MeO-phenyl;
2-CH₃CO₂CH₂CH₂-4-MeO-phenyl;
(Z)-2-HOCH₂CH=CH-4-MeO-phenyl;
(E)-2-HOCH₂CH=CH-4-MeO-phenyl;
(Z)-2-CH₃CO₂CH=CH-4-MeO-phenyl;
(E)-2-CH₃CO₂CH=CH-4-MeO-phenyl;
2-CH₃OCH₂CH₂-4-MeO-phenyl;
3-CN-4-F-phenyl; 3-H₂NCO-4-F-phenyl;
(2-Cl-phenyl)-CH=CH—; (3-Cl-phenyl)-CH=CH—;
(2,6-diF-phenyl)-CH=CH—; phenyl-CH=CH—;
(2-Me₄-MeO-phenyl)-CH=CH—;
cyclohexyl; cyclopentyl; cyclohexylmethyl; benzyl;
2-F-benzyl; 3-F-benzyl; 4-F-benzyl; 3-MeO-benzyl;
3-OH-benzyl; 2-MeO-benzyl; 2-OH-benzyl;
tetrahydroquinolin-1-yl;
tetrahydroindolin-1-yl;
tetrahydroisoindolin-1-yl;
phenyl-S—; phenyl-NH—; pyrid-3-yl-NH—;
(4-Me-pyrid-3-yl)-NH—; (1-naphthyl)-NH—;
(2-naphthyl)-NH—; (2-Me-naphth-1-yl)-NH—;
(3-quinolinyl)-NH—;
(2-[1,1'-biphenyl])-NH—; (3-[1,1'-biphenyl])—NH—;
(4-[1,1'-biphenyl])—NH—; (2-F-phenyl)-NH—;
(2-Cl-phenyl)-NH—; (2-CF₃-phenyl)-NH—;
(2-CH₃-phenyl)-NH—; (2-OMe-phenyl)-NH—;
(2-CN-phenyl)-NH—; (2-OCF₃-phenyl)-NH—;
(2-SMe-phenyl)-NH—; (3-F-phenyl)-NH—;
(3-Cl-phenyl)-NH—; (3-CF₃-phenyl)-NH—;
(3-CH₃-phenyl)-NH—; (3-OMe-phenyl)-NH—;
(3-CN-phenyl)-NH—; (3-OCF₃-phenyl)-NH—;
(3-SMe-phenyl)-NH—; (4-F-phenyl)-NH—;
(4-Cl-phenyl)-NH—; (4-CF₃-phenyl)-NH—;
(4-CH₃-phenyl)-NH—; (4-OMe-phenyl)-NH—;
(4-CN-phenyl)-NH—; (4-OCF₃-phenyl)-NH—;
(4-SMe-phenyl)-NH—; (2,3-diCl-phenyl)-NH—;
(2,4-diCl-phenyl)-NH—; (2,5-diCl-phenyl)-NH—;
(2,6-diCl-phenyl)-NH—; (3,4-diCl-phenyl)-NH—;
(3,5-diCl-phenyl)-NH—; (2,3-diF-phenyl)-NH—;
(2,4-diF-phenyl)-NH—; (2,5-diF-phenyl)-NH—;
(2,6-diF-phenyl)-NH—; (3,4-diF-phenyl)-NH—;
(3,5-diF-phenyl)-NH—; (2,3-diCH₃-phenyl)-NH—;
(2,4-diCH₃-phenyl)-NH—; (2,5-diCH₃-phenyl)-NH—;
(2,6-diCH₃-phenyl)-NH—; (3,4-diCH₃-phenyl)-NH—;
(3,5-diCH₃-phenyl)-NH—; (2,3-diCF₃-phenyl)-NH—;
(2,4-diCF₃-phenyl)-NH—; (2,5-diCF₃-phenyl)-NH—;
(2,6-diCF₃-phenyl)-NH—; (3,4-diCF₃-phenyl)-NH—;
(3,5-diCF₃-phenyl)-NH—; (2,3-diOMe-phenyl)-NH—;
(2,4-diOMe-phenyl)-NH—; (2,5-diOMe-phenyl)-NH—;
(2,6-diOMe-phenyl)-NH—; (3,4-diOMe-phenyl)-NH—;
(3,5-diOMe-phenyl)-NH—; (2-F-3-Cl-phenyl)-NH—;
(2-F-4-Cl-phenyl)-NH—; (2-F-5-Cl-phenyl)-NH—;
(2-F-6-Cl-phenyl)-NH—; (2-F-3-CH₃-phenyl)-NH—;
(2-F-4-CH₃-phenyl)-NH—; (2-F-5-CH₃-phenyl)-NH—;
(2-F-6-CH₃-phenyl)-NH—; (2-F-3-CF₃-phenyl)-NH—;
(2-F-4-CF₃-phenyl)-NH—; (2-F-5-CF₃-phenyl)-NH—;
(2-F-6-CF₃-phenyl)-NH—; (2-F-3-OMe-phenyl)-NH—;
(2-F-4-OMe-phenyl)-NH—; (2-F-5-OMe-phenyl)-NH—;
(2-F-6-OMe-phenyl)-NH—; (2-Cl-3-F-phenyl)-NH—;
(2-Cl-4-F-phenyl)-NH—; (2-Cl-5-F-phenyl)-NH—;
(2-Cl-6-F-phenyl)-NH—; (2-Cl-3-CH₃-phenyl)-NH—;
(2-Cl-4-CH₃-phenyl)-NH—; (2-Cl-5-CH₃-phenyl)-NH—;
(2-Cl-6-CH₃-phenyl)-NH—; (2-Cl-3-CF₃-phenyl)-NH—;
(2-Cl-4-CF₃-phenyl)-NH—; (2-Cl-5-CF₃-phenyl)-NH—;
(2-Cl-6-CF₃-phenyl)-NH—; (2-Cl-3-OMe-phenyl)-NH—;
(2-Cl-4-OMe-phenyl)-NH—; (2-Cl-5-OMe-phenyl)-NH—;
(2-Cl-6-OMe-phenyl)-NH—; (2-CH₃-3-F-phenyl)-NH—;
(2-CH₃-4-F-phenyl)-NH—; (2-CH₃-5-F-phenyl)-NH—;
(2-CH₃-6-F-phenyl)-NH—; (2-CH₃-3-Cl-phenyl)-NH—;
(2-CH₃-4-Cl-phenyl)-NH—; (2-CH₃-5-Cl-phenyl)-NH—;
(2-CH₃-6-Cl-phenyl)-NH—; (2-CH₃-3-CF₃-phenyl)-NH—;
(2-CH₃-4-CF₃-phenyl)-NH—; (2-CH₃-5-CF₃-phenyl)-NH—;
(2-CH₃-6-CF₃-phenyl)-NH—; (2-CH₃-3-OMe-phenyl)-NH—;
(2-CH₃-4-OMe-phenyl)-NH—; (2-CH₃-5-OMe-phenyl)-NH—;
(2-CH₃-6-OMe-phenyl)-NH—; (2-CF₃-3-F-phenyl)-NH—;
(2-CF₃-4-F-phenyl)-NH—; (2-CF₃-5-F-phenyl)-NH—;
(2-CF₃-6-F-phenyl)-NH—; (2-CF₃-3-Cl-phenyl)-NH—;
(2-CF₃-4-Cl-phenyl)-NH—; (2-CF₃-5-Cl-phenyl)-NH—;
(2-CF₃-6-Cl-phenyl)-NH—; (2-CF₃-3-CH₃-phenyl)-NH—;
(2-CF₃-4-CH₃-phenyl)-NH—; (2-CH₃-5-CF₃-phenyl)-NH—;
(2-CF₃-6-CH₃-phenyl)-NH—; (2-CF₃-3-OMe-phenyl)-NH—;
(2-CF₃-4-OMe-phenyl)-NH—; (2-CF₃-5-OMe-phenyl)-NH—;
(2-CF₃-6-OMe-phenyl)-N H—; (2-OMe-3-F-phenyl)-NH—;

(2-OMe-4-F-phenyl)-NH—; (2-OMe-5-F-phenyl)-NH—;
(2-OMe-6-F-phenyl)-NH—; (2-OMe-3-Cl-phenyl)-NH—;
(2-OMe-4-Cl-phenyl)-NH—; (2-OMe-5-Cl-phenyl)-NH—;
(2-OMe-6-Cl-phenyl)-NH—N; (2-OMe-4-CN-phenyl)-NH—;
(2-OMe-4-CHO-phenyl)-NH—; (2-OMe-3-CH$_3$-phenyl)-NH—;
(2-OMe-4-CH$_3$-phenyl)-NH—; (2-OMe-5-CH$_3$-phenyl)-NH—;
(2-OMe-6-CH$_3$-phenyl)-NH—; (2-OMe-3-CF$_3$-phenyl)-NH—;
(2-OMe-4-CF$_3$-phenyl)-NH—; (2-OMe-5-CF$_3$-phenyl)-NH—;
(2-OMe-6-CF$_3$-phenyl)-NH—; (2-acetyl-4-Cl-phenyl)-NH—;
(2-acetyl-4-Me-phenyl)-NH—; (2-acetyl-4-MeO-phenyl)-NH—;
(2-CH$_3$CH(OH)-4-Cl-phenyl)-NH—;
(2-CH$_3$CH(OH)-4-Me-phenyl)-NH—;
(2-CH$_3$CH(OH)-4-MeO-phenyl)-NH—;
(3-CF$_3$-4-Cl-phenyl)-NH—; (3-F-4-CHO-phenyl)-NH—;
(3-CH$_3$-4-CN-phenyl)-NH—; (3-CH$_3$-4-MeO-phenyl)-NH—;
(3-CH$_3$-4-Cl-phenyl)-NH—; (3-CH$_3$-4-F-phenyl)-NH—;
(3-CH$_3$-4-CO$_2$-Me-phenyl)-NH—; (3-CF$_3$-4-C(O)CH$_3$-phenyl)-NH—; (3-CHO-4-OMe-phenyl)-NH—; (4-F-3-CF$_3$-phenyl)-NH—;
(2,3,5-triCl-phenyl)-NH—; (2,4,5-triF-phenyl)-NH—;
(2,6-diCl-3-Me-phenyl)-NH—; (3,5-diMe-4-MeO-phenyl)-NH—;
(2-F-3-Cl-6-CF$_3$-phenyl)-NH—;
benzyl-NH—; (3-quinolinyl)CH$_2$NH—; (2-F-phenyl)CH$_2$NH—;
(2-Cl-phenyl)CH$_2$NH—; (2-CF$_3$-phenyl)CH$_2$NH—;
(2-CH$_3$-phenyl)CH$_2$NH—; (2-OMe-phenyl)CH$_2$NH—;
(2-CN-phenyl)CH$_2$NH—; (2-OCF$_3$-phenyl)CH$_2$NH—;
(2-SMe-phenyl)CH$_2$NH—; (3-F-phenyl)CH$_2$NH—;
(3-Cl-phenyl)CH$_2$NH—; (3-CF$_3$-phenyl)CH$_2$NH—;
(3-CH$_3$-phenyl)CH$_2$NH—; (3-OMe-phenyl)CH$_2$NH—;
(3-CN-phenyl)CH$_2$NH—; (3-OCF$_3$-phenyl)CH$_2$NH—;
(3-SMe-phenyl)CH$_2$NH—; (4-F-phenyl)CH$_2$NH—;
(4-Cl-phenyl)CH$_2$NH—; (4-CF$_3$-phenyl)CH$_2$NH—;
(4-CH$_3$-phenyl)CH$_2$NH—; (4-OMe-phenyl)CH$_2$NH—;
(4-CN-phenyl)CH$_2$NH—; (4-OCF$_3$-phenyl)CH$_2$NH—;
(4-SMe-phenyl)CH$_2$NH—; (2,3-diCl-phenyl)CH$_2$NH—;
(2,4-diCl-phenyl)CH$_2$NH—; (2,5 diCl-phenyl)CH$_2$NH—;
(2,6-diCl-phenyl)CH$_2$NH—; (3,4-diCl-phenyl)CH$_2$NH—;
(3,5-diCl-phenyl)CH$_2$NH—; (2,3-diF-phenyl)CH$_2$NH—;
(2,4-diF-phenyl)CH$_2$NH—; (2,5-diF-phenyl)CH$_2$NH—;
(2,6-diF-phenyl)CH$_2$NH—; (3,4-diF-phenyl)CH$_2$NH—;
(3,5-diF-phenyl)CH$_2$NH—; (2,3-diCH$_3$-phenyl)CH$_2$NH—;
(2,4-diCH$_3$-phenyl)CH$_2$NH—; (2,5-diCH$_3$-phenyl)CH$_2$NH—;
(2,6-diCH$_3$-phenyl)CH$_2$NH—; (3,4-diCH$_3$-phenyl)CH$_2$NH—;
(3,5-diCH$_3$-phenyl)CH$_2$NH—; (2,3-diCF$_3$-phenyl)CH$_2$NH—;
(2,4-diCF$_3$-phenyl)CH$_2$NH—; (2,5-diCF$_3$-phenyl)CH$_2$NH—;
(2,6-diCF$_3$-phenyl)CH$_2$NH—; (3,4-diCF$_3$-phenyl)CH$_2$NH—;
(3,5-diCF$_3$-phenyl)CH$_2$NH—; (2,3-diOMe-phenyl)CH$_2$NH—;
(2,4-diOMe-phenyl)CH$_2$NH—; (2,5-diOMe-phenyl)CH$_2$NH—;
(2,6-diOMe-phenyl)CH$_2$NH—; (3,4-diOMe-phenyl)CH$_2$NH—;
(3,5-diOMe-phenyl)CH$_2$NH—; (2-F-3-Cl-phenyl)CH$_2$NH—;
(2-F-4-Cl-phenyl)CH$_2$NH—; (2-F-5-Cl-phenyl)CH$_2$NH—;
(2-F-6-Cl-phenyl)CH$_2$NH—; (2-F-3-CH$_3$-phenyl)CH$_2$NH—;
(2-F-4-CH$_3$-phenyl)CH$_2$NH—; (2-F-5-CH$_3$-phenyl)CH$_2$NH—;
(2-F-6-CH$_3$-phenyl)CH$_2$NH—; (2-F-3-CF$_3$-phenyl)CH$_2$NH—;
(2-F-4-CF$_3$-phenyl)CH$_2$NH—; (2-F-5-CF$_3$-phenyl)CH$_2$NH—;
(2-F-6-CF$_3$-phenyl)CH$_2$NH—; (2-F-3-OMe-phenyl)CH$_2$NH—;
(2-F-4-OMe-phenyl)CH$_2$NH—; (2-F-5-OMe-phenyl)CH$_2$NH—;
(2-F-6-OMe-phenyl)CH$_2$NH—; (2-Cl-3-F-phenyl)CH$_2$NH—;
(2-Cl-4-F-phenyl)CH$_2$NH—; (2-Cl-5-F-phenyl)CH$_2$NH—;
(2-Cl-6-F-phenyl)CH$_2$NH—; (2-Cl-3-CH$_3$-phenyl)CH$_2$NH—;
(2-Cl-4-CH$_3$-phenyl)CH$_2$NH—; (2-Cl-5-CH$_3$-phenyl)CH$_2$NH—;
(2-Cl-6-CH$_3$-phenyl)CH$_2$NH—; (2-Cl-3-CF$_3$-phenyl)CH$_2$NH—;
(2-Cl-4-CF$_3$-phenyl)CH$_2$NH—; (2-Cl-5-CF$_3$-phenyl)CH$_2$NH—;
(2-Cl-6-CF$_3$-phenyl)CH$_2$NH—; (2-Cl-3-OMe-phenyl)CH$_2$NH—;
(2-Cl-4-OMe-phenyl)CH$_2$NH—; (2-Cl-5-OMe-phenyl)CH$_2$NH—;
(2-Cl-6-OMe-phenyl)CH$_2$NH—; (2-CH$_3$-3-F-phenyl)CH$_2$NH—;
(2-CH$_3$-4-F-phenyl)CH$_2$NH—; (2-CH$_3$-5-F-phenyl)CH$_2$NH—;
(2-CH$_3$-6-F-phenyl)CH$_2$NH—; (2-CH$_3$-3-Cl-phenyl)CH$_2$NH—;
(2-CH$_3$-4-Cl-phenyl)CH$_2$NH—; (2-CH$_3$-5-Cl-phenyl)CH$_2$NH—;
(2-CH$_3$-6-Cl-phenyl)CH$_2$NH—; (2-CH$_3$-3-CF$_3$-phenyl)CH$_2$NH—;
(2-CH$_3$-4-CF$_3$-phenyl)CH$_2$NH—; (2-CH$_3$-5-CF$_3$-phenyl)CH$_2$NH—;
(2-CH$_3$-6-CF$_3$-phenyl)CH$_2$NH—; (2-CH$_3$-3-OMe-phenyl)CH$_2$NH—;
(2-CH$_3$-4-OMe-phenyl)CH$_2$NH—; (2-CH$_3$-5-OMe-phenyl)CH$_2$NH—;
(2-CH$_3$-6-OMe-phenyl)CH$_2$NH—; (2-CF$_3$-3-F-phenyl)CH$_2$NH—;

(2-CF$_3$-4-F-phenyl)CH$_2$NH—; (2-CF$_3$-5-F-phenyl)CH$_2$NH—;
(2-CF$_3$-6-F-phenyl)CH$_2$NH—; (2-CF$_3$-3-Cl-phenyl)CH$_2$NH—;
(2-CF$_3$-4-Cl-phenyl)CH$_2$NH—; (2-CF$_3$-5-Cl-phenyl)CH$_2$NH—;
(2-CF$_3$-6-Cl-phenyl)CH$_2$NH—; (2-CF$_3$-3-CH$_3$-phenyl)CH$_2$NH—;
(2-CF$_3$-4-CH$_3$-phenyl)CH$_2$NH—; (2-CH$_3$-5-CF$_3$-phenyl)CH$_2$NH—;
(2-CF$_3$-6-CH$_3$-phenyl)CH$_2$NH—; (2-CF$_3$-3-OMe-phenyl)CH$_2$NH—;
(2-CF$_3$-4-OMe-phenyl)CH$_2$NH—; (2-CF$_3$-5-OMe-phenyl)CH$_2$NH—;
(2-CF$_3$-6-OMe-phenyl)CH$_2$NH—; (2-OMe-3-F-phenyl)CH$_2$NH—;
(2-OMe-4-F-phenyl)CH$_2$NH—; (2-OMe-5-F-phenyl)CH$_2$NH—;
(2-OMe-6-F-phenyl)CH$_2$NH—; (2-OMe-3-Cl-phenyl)CH$_2$NH—;
(2-OMe-4-Cl-phenyl)CH$_2$NH—; (2-OMe-5-Cl-phenyl)CH$_2$NH—;
(2-OMe-6-Cl-phenyl)CH$_2$NH—; (2-OMe-4-CN-phenyl)CH$_2$NH—;
(2-OMe-4-CHO-phenyl)CH$_2$NH—; (2-OMe-3-CH$_3$-phenyl)CH$_2$NH—;
(2-OMe-4-CH$_3$-phenyl)CH$_2$NH—; (2-OMe-5-CH$_3$-phenyl)CH$_2$NH—;
(2-OMe-6-CH$_3$-phenyl)CH$_2$NH—; (2-OMe-3-CF$_3$-phenyl)CH$_2$NH—;
(2-OMe-4-CF$_3$-phenyl)CH$_2$NH—; (2-OMe-5-CF$_3$-phenyl)CH$_2$NH—;
(2-OMe-6-CF$_3$-phenyl)CH$_2$NH—; (2-acetyl-4-Cl-phenyl)CH$_2$NH—;
(2-acetyl-4-Me-phenyl)CH$_2$NH—;
(2-acetyl-4-MeO-phenyl)CH$_2$NH—;
(2-CH$_3$CH(OH)$_4$—Cl-phenyl)CH$_2$NH—;
(2-CH$_3$CH(OH)-4-Me-phenyl)CH$_2$NH—;
(2-CH$_3$CH(OH)-4-MeO-phenyl)CH$_2$NH—;
(3-CF$_3$-4-Cl-phenyl)CH$_2$NH—; (3-F-4-CHO-phenyl)CH$_2$NH—;
(3-CH$_3$-4-CN-phenyl)CH$_2$NH—; (3-CH$_3$-4-MeO-phenyl)CH$_2$NH—;
(3-CH$_3$-4-Cl-phenyl)CH$_2$NH—; (3-CH$_3$-4-F-phenyl)CH$_2$NH—;
(4-F-3-CF$_3$-phenyl)CH$_2$NH—; (3-CH$_3$-4-CO$_2$-Me-phenyl)CH$_2$NH—;
(3-CF$_3$-4-C(O)CH$_3$-phenyl)CH$_2$NH—;
(3-CHO-4-OMe-phenyl)CH$_2$NH—;
(2,3,5-triCl-phenyl)CH$_2$NH—;
(2,4,5-triF-phenyl)CH$_2$NH—;
(2,6-diCl-3-Me-phenyl)CH$_2$NH—;
(3,5-diMe-4-MeO-phenyl)CH$_2$NH—; and
(2-F-3-Cl-6-CF$_3$-phenyl)CH$_2$NH—;

provided that two of R$^7$, R$^8$, and R$^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy; and n is 1 or 2.

11. A compound of claim 10 of Formula (II)

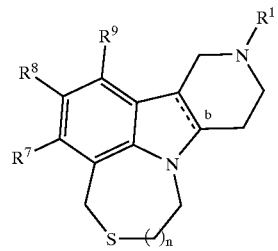

(II)

wherein:
b is a single bond, wherein the bridge hydrogens are in a cis position;
R$^1$ is selected from
hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl,
4-methylpentyl, 2-fluoroethyl, 2,2-difluoroethyl, 2,2,2-trifluoroethyl, 2-propenyl, 2-methyl-2-propenyl, trans-2-butenyl, 3-methyl-2-butenyl, 3-butenyl, trans-2-pentenyl, cis-2-pentenyl, 4-pentenyl,
4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl,
—CH=CH$_2$, —CH$_2$—CH=CH$_2$, —CH=CH—CH$_3$, —CECH, —C≡C—CH$_3$,
and —CH$_2$—C≡CH;
R$^7$ and R$^9$, at each occurrence, are independently selected from hydrogen, fluoro, methyl, trifluoromethyl, and methoxy;
R$^8$ is selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl;
2-Cl-phenyl; 2-F-phenyl; 2-Br-phenyl; 2-CN-phenyl; 2-Me-phenyl; 2-CF$_3$-phenyl; 2-MeO-phenyl; 2-CF$_3$O-phenyl; 2-NO$_2$-phenyl; 2-MeS-phenyl; 2-CHO-phenyl; 2-HOCH$_2$-phenyl;
3-Cl-phenyl; 3-F-phenyl; 3-Br-phenyl; 3-CN-phenyl; 3-Me-phenyl; 3-Et-phenyl; 3-n-Pr-phenyl; 3-isoPr-phenyl;
3-n-Bu-phenyl; 3-CF$_3$-phenyl; 3-MeO-phenyl; 3-MeS-phenyl;
3-isopropoxyphenyl; 3-CF$_3$O-phenyl; 3-NO$_2$-phenyl; 3-CHO-phenyl; 3-HOCH$_2$-phenyl; 3-MeOCH$_2$-phenyl;
3-Me$_2$NCH$_2$-phenyl;
4-Cl-phenyl; 4-F-phenyl; 4-Br-phenyl; 4-CN-phenyl; 4-Me-phenyl; 4-Et-phenyl; 4-n-Pr-phenyl; 4-iso-Pr-phenyl;
4-n-Bu-phenyl; 4-CF$_3$-phenyl; 4-MeO-phenyl; 4-isopropoxyphenyl; 4-CF$_3$O-phenyl; 4-MeS-phenyl; 4-acetylphenyl; 3-acetamidophenyl; 4-pyridyl; 2-furanyl; 2-thiophenyl; 2-naphthyl; 1-pyrrolidinyl,
2,3-diCl-phenyl; 2,3-diF-phenyl; 2,3-diMe-phenyl; 2,3-diCF$_3$-phenyl; 2,3-diMeO-phenyl; 2,3-diCF$_3$O-phenyl;
2,4-diCl-phenyl; 2,4-diF-phenyl; 2,4-diMe-phenyl;

2,4-diCF$_3$-phenyl; 2,4-diMeO-phenyl; 2,4-diCF$_3$O-phenyl;
2,5-diCl-phenyl; 2,5-diF-phenyl; 2,5-diMe-phenyl;
2,5-diCF$_3$-phenyl; 2,5-diMeO-phenyl; 2,5-diCF$_3$O-phenyl;
2,6-diCl-phenyl; 2,6-diF-phenyl; 2,6-diMe-phenyl;
2,6-diCF$_3$-phenyl; 2,6-diMeO-phenyl; 2,6-diCF$_3$O-phenyl;
3,4-diCl-phenyl; 3,4-diF-phenyl; 3,4-diMe-phenyl;
3,4-diCF$_3$-phenyl; 3,4-diMeO-phenyl; 3,4-diCF$_3$O-phenyl;
2,4,6-triCl-phenyl; 2,4,6-triF-phenyl;
2,4,6-triMe-phenyl; 2,4,6-triCF$_3$-phenyl;
2,4,6-triMeO-phenyl; 2,4,6-triCF$_3$O-phenyl;
2,4,5-triMe-phenyl; 2,3,4-triF-phenyl;
2-Me$_4$-MeO-5-F-phenyl; 2,6-diCl-4-MeO-phenyl;
2,4-diMeO-6-F-phenyl; 2,6-diF-4-Cl-phenyl;
2,3,4,6-tetraF-phenyl; 2,3,4,5,6-pentaF-phenyl;
2-Cl-4-F-phenyl; 2-Cl-6-F-phenyl; 2-Cl-3-Me-phenyl;
2-Cl-4-MeO-phenyl; 2-C$_{1-4}$-EtO-phenyl;
2-C$_{1-4}$-iPrO-phenyl; 2-C$_{14}$CF$_3$-phenyl;
2-C14-CF$_3$O-phenyl; 2-C$_{14}$—(CHF$_2$)O-phenyl;
2-F-3-Cl-phenyl; 2-F-4-MeO-phenyl; 2-F-5-Me-phenyl;
2-Me-3-Cl-phenyl; 2-Me-3-CN-phenyl; 2-Me$_4$-Cl-phenyl;
2-Me-4F-phenyl; 2-Me-4-CN-phenyl; 2-Me$_4$-MeO-phenyl;
2-Me4-EtO-phenyl; 2-Me$_4$-MeS-phenyl;
2-Me-4-H$_2$NCO-phenyl; 2-Me$_4$-MeOC(=O)-phenyl;
2-Me4-CH$_3$C(=O)-phenyl; 2-Me-5-F-phenyl;
2-Et-4-MeO-phenyl; 2-MeO-5-F-phenyl;
2-MeO-4-isopropyl-phenyl; 2-CF$_3$-4-Cl-phenyl;
2-CF$_3$-4-F-phenyl; 2-CF$_3$-4-MeO-phenyl;
2-CF$_3$-4-EtO-phenyl; 2-CF$_3$-4-iPrO-phenyl;
, 2-CF$_3$-4-CN-phenyl; 2-CF$_3$-6-F-phenyl;
2-CHO-4-MeO-phenyl; 2-MeOC(=O)$_3$-MeO-phenyl;
2-CH$_3$CH(OH)-4-MeO-phenyl; 2-CH$_3$CH(OH)-4-F-phenyl;
2-CH$_3$CH(OH)-4-Cl-phenyl; 2-CH$_3$CH(OH)-4-Me-phenyl;
2-CH$_3$CH(OMe)-4-MeO-phenyl; 2-CH$_3$C(=O)-4-MeO-phenyl;
2-CH$_3$C(=O)-4-F-phenyl; 2-CH$_3$C(=O)$_4$—Cl-phenyl;
2-CH$_3$C(=O)-4-Me-phenyl; 2-H$_2$C(OH)-4-MeO-phenyl;
2-H$_2$C(OMe)-4-MeO-phenyl; 2-H$_3$CCH$_2$CH(OH)-4-MeO-phenyl;
2-H$_3$CCH$_2$C(=O)-4-MeO-phenyl;
2-CH$_3$CO$_2$CH$_2$CH$_2$-4-MeO-phenyl;
(Z)-2-HOCH$_2$CH=CH-4-MeO-phenyl;
(E)-2-HOCH$_2$CH=CH-4-MeO-phenyl;
(Z)-2-CH$_3$CO$_2$CH=CH-4-MeO-phenyl;
(E)-2-CH$_3$CO$_2$CH=CH-4-MeO-phenyl;
2-CH$_3$OCH$_2$CH$_2$-4-MeO-phenyl;
3-CN-4-F-phenyl; 3-H$_2$NCO-4-F-phenyl;
(2-Cl-phenyl)-CH=CH—; (3-Cl-phenyl)-CH=CH—;
(2,6-diF-phenyl)CH=CH—; phenyl-CH=CH—;
(2-Me$_4$-MeO-phenyl)-CH=CH—;
cyclohexyl; cyclopentyl; cyclohexylmethyl; benzyl;
2-F-benzyl; 3-F-benzyl; 4-F-benzyl; 3-MeO-benzyl;
3-OH-benzyl; 2-MeO-benzyl; 2-OH-benzyl;
tetrahydroquinolin-1-yl;
tetrahydroindolin-1-yl;
tetrahydroisoindolin-1-yl;
phenyl-S—; phenyl-NH—; pyrid-3-yl-NH—;
(4-Me-pyrid-3-yl)-NH—; (1-naphthyl)-NH—;
(2-naphthyl)-NH—; (2-Me-naphth-1-yl)-NH—;
(3-quinolinyl)-NH—;
(2-[1,1'-biphenyl])-NH—; (3-[1,1'-biphenyl])—NH—;
(4-[1,1'-biphenyl])-NH—; (2-F-phenyl)-NH—;
(2-Cl-phenyl)-NH—; (2-CF$_3$-phenyl)-NH—;
(2-CH$_3$-phenyl)-NH—; (2-OMe-phenyl)-NH—;
(2-CN-phenyl)-NH—; (2-OCF$_3$-phenyl)-NH—;
(2-SMe-phenyl)-NH—; (3-F-phenyl)-NH—;
(3-Cl-phenyl)-NH—; (3-CF$_3$-phenyl)-NH—;
(3-CH$_3$-phenyl)-NH—; (3-OMe-phenyl)-NH—;
(3-CN-phenyl)-NH—; (3-OCF$_3$-phenyl)-NH—;
(3-SMe-phenyl)-NH—; (4-F-phenyl)-NH—;
(4-Cl-phenyl)-NH—; (4-CF$_3$-phenyl)-NH—;
(4-CH$_3$-phenyl)-NH—; (4-OMe-phenyl)-NH—;
(4-CN-phenyl)-NH—; (4-OCF$_3$-phenyl)-NH—;
(4-SMe-phenyl)-NH—; (2,3-diCl-phenyl)-NH—;
(2,4-diCl-phenyl)-NH—; (2,5-diCl-phenyl)-NH—;
(2,6-diCl-phenyl)-NH—; (3,4-diCl-phenyl)-NH—;
(3,5-diCl-phenyl)-NH—; (2,3-diF-phenyl)-NH—;
(2,4-diF-phenyl)-NH—; (2,5-diF-phenyl)-NH—;
(2,6-diF-phenyl)-NH—; (3,4-diF-phenyl)-NH—;
(3,5-diF-phenyl)-NH—; (2,3-diCH$_3$-phenyl)-NH—;
(2,4-diCH$_3$-phenyl)-NH—; (2,5-diCH$_3$-phenyl)-NH—;
(2,6-diCH$_3$-phenyl)-NH—; (3,4-diCH$_3$-phenyl)-NH—;
(3,5-diCH$_3$-phenyl)-NH—; (2,3-diCF$_3$-phenyl)-NH—;
(2,4-diCF$_3$-phenyl)-NH—; (2,5-diCF$_3$-phenyl)-NH—;
(2,6-diCF$_3$-phenyl)-NH—; (3,4-diCF$_3$-phenyl)-NH—;
(3,5-diCF$_3$-phenyl)-NH—; (2,3-diOMe-phenyl)-NH—;
(2,4-diOMe-phenyl)-NH—; (2,5-diOMe-phenyl)-NH—;
(2,6-diOMe-phenyl)-NH—; (3,4-diOMe-phenyl)-NH—;
(3,5-diOMe-phenyl)-NH—; (2-F-3-Cl-phenyl)-NH—;
(2-F-4-Cl-phenyl)-NH—; (2-F-5-Cl-phenyl)-NH—;
(2-F-6-Cl-phenyl)-NH—; (2-F-3-CH$_3$-phenyl)-NH—;
(2-F-4-CH$_3$-phenyl)-NH—; (2-F-5-CH$_3$-phenyl)-NH—;
(2-F-6-CH$_3$-phenyl)-NH—; (2-F-3-CF$_3$-phenyl)-NH—;
(2-F-4-CF$_3$-phenyl)-NH—; (2-F-5-CF$_3$-phenyl)-NH—;
(2-F-6-CF$_3$-phenyl)-NH—; (2-F-3-OMe-phenyl)-NH—;
(2-F-4-OMe-phenyl)-NH—; (2-F-5-OMe-phenyl)-NH—;
(2-F-6-OMe-phenyl)-NH—; (2-Cl-3-F-phenyl)-NH—;
(2-Cl-4-F-phenyl)-NH—; (2-Cl-5-F-phenyl)-NH—;
(2-Cl-6-F-phenyl)-NH—; (2-Cl-3-CH$_3$-phenyl)-NH—;
(2-C14-CH$_3$-phenyl)-NH—; (2-Cl-5-CH$_3$-phenyl)-NH—;
(2-Cl-6-CH$_3$-phenyl)-NH—; (2-Cl-3-CF$_3$-phenyl)-NH—;
(2-C14-CF$_3$-phenyl)-NH—; (2-Cl-5-CF$_3$-phenyl)-NH—;
(2-Cl-6-CF$_3$-phenyl)-NH—; (2-Cl-3-OMe-phenyl)-NH—;
(2-C14-OMe-phenyl)-NH—; (2-Cl-5-OMe-phenyl)-NH—;
(2-Cl-6-OMe-phenyl)-NH—; (2-CH$_3$-3-F-phenyl)-NH—;
(2-CH$_3$-4-F-phenyl)-NH—; (2-CH$_3$-5-F-phenyl)-NH—;
(2-CH$_3$-6-F-phenyl)-NH—; (2-CH$_3$-3-Cl-phenyl)-NH—;

(2-CH₃-4-Cl-phenyl)-NH—; (2-CH₃-5-Cl-phenyl)-NH—;
(2-CH₃-6-Cl-phenyl)-NH—; (2-CH₃-3-CF₃-phenyl)-NH—;
(2-CH₃-4-CF₃-phenyl)-NH—; (2-CH₃-5-CF₃-phenyl)-NH—;
(2-CH₃-6-CF₃-phenyl)-NH—; (2-CH₃-3-OMe-phenyl)-NH—;
(2-CH₃-4-OMe-phenyl)-NH—; (2-CH₃-5-OMe-phenyl)-NH—;
(2-CH₃-6-OMe-phenyl)-NH—; (2-CF₃-3-F-phenyl)-NH—;
(2-CF₃-4-F-phenyl)-NH—; (2-CF₃-5-F-phenyl)-NH—;
(2-CF₃-6-F-phenyl)-NH—; (2-CF₃-3-Cl-phenyl)-NH—;
(2-CF₃-4-Cl-phenyl)-NH—; (2-CF₃-5-Cl-phenyl)-NH—;
(2-CF₃-6-Cl-phenyl)-NH—; (2-CF₃-3-CH₃-phenyl)-NH—;
(2-CF₃-4-CH₃-phenyl)-NH—; (2-CH₃-5-CF₃-phenyl)-NH—;
(2-CF₃-6-CH₃-phenyl)-NH—; (2-CF₃-3-OMe-phenyl)-NH—;
(2-CF₃-4-OMe-phenyl)-NH—; (2-CF₃-5-OMe-phenyl)-NH—;
(2-CF₃-6-OMe-phenyl)-NH—; (2-OMe-3-F-phenyl)-NH—;
(2-OMe-4-F-phenyl)-NH—; (2-OMe-5-F-phenyl)-NH—;
(2-OMe-6-F-phenyl)-NH—; (2-OMe-3-Cl-phenyl)-NH—;
(2-OMe-4-Cl-phenyl)-NH—; (2-OMe-5-Cl-phenyl)-NH—;
(2-OMe-6-Cl-phenyl)-NH—; (2-OMe-4-CN-phenyl)-NH—;
(2-OMe-4-CHO-phenyl)-NH—; (2-OMe-3-CH₃-phenyl)-NH—;
(2-OMe-4-CH₃-phenyl)-NH—; (2-OMe-5-CH₃-phenyl)-NH—;
(2-OMe-6-CH₃-phenyl)-NH—; (2-OMe-3-CF₃-phenyl)-NH—;
(2-OMe-4-CF₃-phenyl)-NH—; (2-OMe-5-CF₃-phenyl)-NH—;
(2-OMe-6-CF₃-phenyl)-NH— (2-acetyl-4-Cl-phenyl)-NH—;
(2-acetyl-4-Me-phenyl)-NH—; (2-acetyl-4-MeO-phenyl)-NH—;
(2-CH₃CH(OH)-4-Cl-phenyl)-NH—;
(2-CH₃CH(OH)-4-Me-phenyl)-NH—;
(2-CH₃CH(OH)-4-MeO-phenyl)-NH—;
(3-CF₃-4-Cl-phenyl)-NH—; (3-F-4-CHO-phenyl)-NH—;
(3-CH₃-4-CN-phenyl)-NH—; (3-CH₃-4-MeO-phenyl)-NH—;
(3-CH₃-4-Cl-phenyl)-NH—; (3-CH₃-4-F-phenyl)-NH—;
(3-CH₃-4-CO₂-Me-phenyl)-NH—; (3-CF₃-4-C(O)CH₃-phenyl)-NH—; (3-CHO-4—OMe-phenyl)-NH—; (4-F-3-CF₃-phenyl)-NH—;
(2,3,5-triCl-phenyl)-NH—; (2,4,5-triF-phenyl)-NH—;
(2,6-diCl-3-Me-phenyl)-NH—; (3,5-diMe-4-MeO-phenyl)-NH—;
(2-F-3-Cl-6-CF₃-phenyl)-NH—;
benzyl-NH—; (3-quinolinyl)CH₂NH—; (2-F-phenyl)CH₂NH—;
(2-Cl-phenyl)CH₂NH—; (2-CF₃-phenyl)CH₂NH—;
(2-CH₃-phenyl)CH₂NH—; (2-OMe-phenyl)CH₂NH—;
(2-CN-phenyl)CH₂NH—; (2-OCF₃-phenyl)CH₂NH—;
(2-SMe-phenyl)CH₂NH—; (3-F-phenyl)CH₂NH—;
(3-Cl-phenyl)CH₂NH—; (3-CF₃-phenyl)CH₂NH—;
(3-CH₃-phenyl)CH₂NH—; (3-OMe-phenyl)CH₂NH—;
(3-CN-phenyl)CH₂NH—; (3-OCF₃-phenyl)CH₂NH—;
(3-SMe-phenyl)CH₂NH—; (4-F-phenyl)CH₂NH—;
(4-Cl-phenyl)CH₂NH—; (4-CF₃-phenyl)CH₂NH—;
(4-CH₃-phenyl)CH₂NH—; (4-OMe-phenyl)CH₂NH—;
(4-CN-phenyl)CH₂NH—; (4-OCF₃-phenyl)CH₂NH—;
(4-SMe-phenyl)CH₂NH—; (2,3-diCl-phenyl)CH₂NH—;
(2,4-diCl-phenyl)CH₂NH—; (2,5-diCl-phenyl)CH₂NH—;
(2,6-diCl-phenyl)CH₂NH—; (3,4-diCl-phenyl)CH₂NH—;
(3,5-diCl-phenyl)CH₂NH—; (2,3-diF-phenyl)CH₂NH—;
(2,4-diF-phenyl)CH₂NH—; (2,5-diF-phenyl)CH₂NH—;
(2,6-diF-phenyl)CH₂NH—; (3,4-diF-phenyl)CH₂NH—;
(3,5-diF-phenyl)CH₂NH—; (2,3-diCH₃-phenyl)CH₂NH—;
(2,4-diCH₃-phenyl)CH₂NH—; (2,5-diCH₃-phenyl)CH₂NH—;
(2,6-diCH₃-phenyl)CH₂NH—; (3,4-diCH₃-phenyl)CH₂NH—;
(3,5-diCH₃-phenyl)CH₂NH—; (2,3-diCF₃-phenyl)CH₂NH—;
(2,4-diCF₃-phenyl)CH₂NH—; (2,5-diCF₃-phenyl)CH₂NH—;
(2,6-diCF₃-phenyl)CH₂NH—; (3,4-diCF₃-phenyl)CH₂NH—;
(3,5-diCF₃-phenyl)CH₂NH—; (2,3-diOMe-phenyl)CH₂NH—;
(2,4-diOMe-phenyl)CH₂NH—; (2,5-diOMe-phenyl)CH₂NH—;
(2,6-diOMe-phenyl)CH₂NH—; (3,4-diOMe-phenyl)CH₂NH—;
(3,5-diOMe-phenyl)CH₂NH—; (2-F-3-Cl-phenyl)CH₂NH—;
(2-F-4-Cl-phenyl)CH₂NH—; (2-F-5-Cl-phenyl)CH₂NH—;
(2-F-6-Cl-phenyl)CH₂NH—; (2-F-3-CH₃-phenyl)CH₂NH—;
(2-F-4-CH₃-phenyl)CH₂NH—; (2-F-5-CH₃-phenyl)CH₂NH—;
(2-F-6-CH₃-phenyl)CH₂NH—; (2-F-3-CF₃-phenyl)CH₂NH—;
(2-F-4-CF₃-phenyl)CH₂NH—; (2-F-5-CF₃-phenyl)CH₂NH—;
(2-F-6-CF₃-phenyl)CH₂NH—; (2-F-3-OMe-phenyl)CH₂NH—;
(2-F-4-OMe-phenyl)CH₂NH—; (2-F-5-OMe-phenyl)CH₂NH—;
(2-F-6-OMe-phenyl)CH₂NH—; (2-Cl-3-F-phenyl)CH₂NH—;
(2-Cl-4-F-phenyl)CH₂NH—; (2-Cl-5-F-phenyl)CH₂NH—;
(2-Cl-6-F-phenyl)CH₂NH—; (2-Cl-3-CH₃-phenyl)CH₂NH—;

(2-Cl-4-CH₃-phenyl)CH₂NH—; (2-Cl-5-CH₃-phenyl)CH₂NH—;
(2-Cl-6-CH₃-phenyl)CH₂NH—; (2-Cl-3-CF₃-phenyl)CH₂NH—;
(2-Cl-4-CF₃-phenyl)CH₂NH—; (2-Cl-5-CF₃-phenyl)CH₂NH—;
(2-Cl-6-CF₃-phenyl)CH₂NH—; (2-Cl-3-OMe-phenyl)CH₂NH—;
(2-Cl-4-OMe-phenyl)CH₂NH—; (2-Cl-5-OMe-phenyl)CH₂NH—;
(2-Cl-6-OMe-phenyl)CH₂NH—; (2-CH₃-3-F-phenyl)CH₂NH—;
(2-CH₃-4-F-phenyl)CH₂NH—; (2-CH₃-5-F-phenyl)CH₂NH—;
(2-CH₃-6-F-phenyl)CH₂NH—; (2-CH₃-3-Cl-phenyl)CH₂NH—;
(2-CH₃-4-Cl-phenyl)CH₂NH—; (2-CH₃-5-Cl-phenyl)CH₂NH—;
(2-CH₃-6-Cl-phenyl)CH₂NH—; (2-CH₃-3-CF₃-phenyl)CH₂NH—;
(2-CH₃-4-CF₃-phenyl)CH₂NH—; (2-CH₃-5-CF₃-phenyl)CH₂NH—;
(2-CH₃-6-CF₃-phenyl)CH₂NH—; (2-CH₃-3-OMe-phenyl)CH₂NH—;
(2-CH₃-4-OMe-phenyl)CH₂NH—; (2-CH₃-5-OMe-phenyl)CH₂NH—;
(2-CH₃-6-OMe-phenyl)CH₂NH—; (2-CF₃-3-F-phenyl)CH₂NH—;
(2-CF₃-4-F-phenyl)CH₂NH—; (2-CF₃-5-F-phenyl)CH₂NH—;
(2-CF₃-6-F-phenyl)CH₂NH—; (2-CF₃-3-Cl-phenyl)CH₂NH—;
(2-CF₃-4-Cl-phenyl)CH₂NH—; (2-CF₃-5-Cl-phenyl)CH₂NH—;
(2-CF₃-6-Cl-phenyl)CH₂NH—; (2-CF₃-3-CH₃-phenyl)CH₂NH—;
(2-CF₃-4-CH₃-phenyl)CH₂NH—; (2-CH₃-5-CF₃-phenyl)CH₂NH—;
(2-CF₃-6-CH₃-phenyl)CH₂NH—; (2-CF₃-3-OMe-phenyl)CH₂NH—;
(2-CF₃-4-OMe-phenyl)CH₂NH—; (2-CF₃-5-OMe-phenyl)CH₂NH—;
(2-CF₃-6-OMe-phenyl)CH₂NH—; (2-OMe-3-F-phenyl)CH₂NH—;
(2-OMe-4-F-phenyl)CH₂NH—; (2-OMe-5-F-phenyl)CH₂NH—;
(2-OMe-6-F-phenyl)CH₂NH—; (2-OMe-3-Cl-phenyl)CH₂NH—;
(2-OMe-4-Cl-phenyl)CH₂NH—; (2-OMe-5-Cl-phenyl)CH₂NH—;
(2-OMe-6-Cl-phenyl)CH₂NH—; (2-OMe-4-CN-phenyl)CH₂NH—;
(2-OMe-4-CHO-phenyl)CH₂NH—; (2-OMe-3-CH₃-phenyl)CH₂NH—;
(2-OMe-4-CH₃-phenyl)CH₂NH—; (2-OMe-5-CH₃-phenyl)CH₂NH—;
(2-OMe-6-CH₃-phenyl)CH₂NH—; (2-OMe-3-CF₃-phenyl)CH₂NH—;
(2-OMe-4-CF₃-phenyl)CH₂NH—; (2-OMe-5-CF₃-phenyl)CH₂NH—;
(2-OMe-6-CF₃-phenyl)CH₂NH—; (2-acetyl-4-Cl-phenyl)CH₂NH—;
(2-acetyl-4-Me-phenyl)CH₂NH—;
(2-acetyl-4-MeO-phenyl)CH₂NH—;
(2-CH₃CH(OH)₄—Cl-phenyl)CH₂NH—;
(2-CH₃CH(OH)-4-Me-phenyl)CH₂NH—;
(2-CH₃CH(OH)4-MeO-phenyl)CH₂NH—;
-362(3-CF₃-4-Cl-phenyl)CH₂NH—; (3-F-4-CHO-phenyl)CH₂NH—;
(3-CH₃-4-CN-phenyl)CH₂NH—; (3-CH₃-4-MeO-phenyl)CH₂NH—;
(3-CH₃-4-Cl-phenyl)CH₂NH—; (3-CH₃-4-F-phenyl)CH₂NH—;
(4-F-3-CF₃-phenyl)CH₂NH—; (3-CH₃-4-CO₂-Me-phenyl)CH₂NH—;
(3-CF₃-4-C(O)CH₃-phenyl)CH₂NH—;
(3-CHO-4-OMe-phenyl)CH₂NH—;
(2,3,5-triCl-phenyl)CH₂NH—;
(2,4,5-triF-phenyl)CH₂NH—;
(2,6-diCl-3-Me-phenyl)CH₂NH—;
(3,5-diMe-4-MeO-phenyl)CH₂NH—; and
(2-F-3-Cl-6-CF₃-phenyl)CH₂NH—;

n is 1 or 2.

12. A compound of claim 10 of Formula (III)

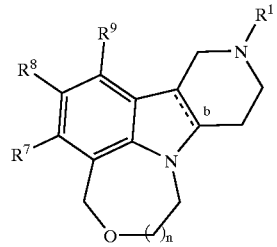

(III)

wherein:
b is a single bond, wherein the bridge hydrogens are in a cis position;
$R^1$ is selected from
hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl,
4-methylpentyl, 2-fluoroethyl, 2,2-difluoroethyl, 2,2,2-trifluoroethyl, 2-propenyl, 2-methyl-2-propenyl, trans-2-butenyl, 3-methyl-2-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl,
—CH=CH₂, —CH₂—CH=CH₂, —CH=CH—CH₃, —C=CH, —C≡C—CH₃, and —CH₂—C≡CH;
$R^7$ and $R^9$, at each occurrence, are independently selected from hydrogen, fluoro, methyl, trifluoromethyl, and methoxy; and
$R^8$ is selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl;
2-Cl-phenyl; 2-F-phenyl; 2-Br-phenyl; 2-CN-phenyl; 2-Me-phenyl; 2-CF₃-phenyl; 2-MeO-phenyl; 2-CF₃O-phenyl; 2-NO₂-phenyl; 2-MeS-phenyl; 2-CHO-phenyl; 2-HOCH₂-phenyl;
3-Cl-phenyl; 3-F-phenyl; 3-Br-phenyl; 3-CN-phenyl; 3-Me-phenyl; 3-Et-phenyl; 3-n-Pr-phenyl; 3-isoPr-phenyl;
3-n-Bu-phenyl; 3-CF₃-phenyl; 3-MeO-phenyl; 3-MeS-phenyl;

3-isopropoxyphenyl; 3-CF$_3$O-phenyl; 3-NO$_2$-phenyl;
3-CHO-phenyl; 3-HOCH$_2$-phenyl; 3-MeOCH$_2$-phenyl;
3-Me$_2$NCH$_2$-phenyl;
4-Cl-phenyl; 4-F-phenyl; 4-Br-phenyl; 4-CN-phenyl;
4-Me-phenyl; 4-Et-phenyl; 4-n-Pr-phenyl; 4-iso-Pr-phenyl;
4-n-Bu-phenyl; 4-CF$_3$-phenyl; 4-MeO-phenyl;
4-isopropoxyphenyl; 4-CF$_3$O-phenyl; 4-MeS-phenyl;
4-acetylphenyl; 3-acetamidophenyl; 4-pyridyl;
2-furanyl; 2-thiophenyl; 2-naphthyl; 1-pyrrolidinyl,
2,3-diCl-phenyl; 2,3-diF-phenyl; 2,3-diMe-phenyl;
2,3-diCF$_3$-phenyl; 2,3-diMeO-phenyl; 2,3-diCF$_3$O-phenyl;
2,4-diCl-phenyl; 2,4-diF-phenyl; 2,4-diMe-phenyl;
2,4-diCF$_3$-phenyl; 2,4-diMeO-phenyl; 2,4-diCF$_3$O-phenyl;
2,5-diCl-phenyl; 2,5-diF-phenyl; 2,5-diMe-phenyl;
2,5-diCF$_3$-phenyl; 2,5-diMeO-phenyl; 2,5-diCF$_3$O-phenyl;
2,6-diCl-phenyl; 2,6-diF-phenyl; 2,6-diMe-phenyl;
2,6-diCF$_3$-phenyl; 2,6-diMeO-phenyl; 2,6-diCF$_3$O-phenyl;
3,4-diCl-phenyl; 3,4-diF-phenyl; 3,4-diMe-phenyl;
3,4-diCF$_3$-phenyl; 3,4-diMeO-phenyl; 3,4-diCF$_3$O-phenyl;
2,4,6-triCl-phenyl; 2,4,6-triF-phenyl;
2,4,6-triMe-phenyl; 2,4,6-triCF$_3$-phenyl;
2,4,6-triMe-phenyl; 2,4,6-triCF$_3$O-phenyl;
2,4,5-triMe-phenyl; 2,3,4-triF-phenyl;
2-Me-4-MeO-5-F-phenyl; 2,6-diCl-4-MeO-phenyl;
2,4-diMeO-6-F-phenyl; 2,6-diF-4-Cl-phenyl;
2,3,4,6-tetraF-phenyl; 2,3,4,5,6-pentaF-phenyl;
2-Cl-4-F-phenyl; 2-Cl-6-F-phenyl; 2-Cl-3-Me-phenyl;
2-Cl-4-MeO-phenyl; 2-C$_{1-4}$-EtO-phenyl;
2-Cl-4-iPrO-phenyl; 2-C14-CF$_3$-phenyl;
2-Cl-4-CF$_3$O-phenyl; 2-C14-(CHF$_2$)O-phenyl;
2-F-3-Cl-phenyl; 2-F-4-MeO-phenyl; 2-F-5-Me-phenyl;
2-Me-3-Cl-phenyl; 2-Me-3-CN-phenyl; 2-Me-4-Cl-phenyl;
2-Me-4-F-phenyl; 2-Me-CN-phenyl; 2-Me-4-MeO-phenyl;
2-Me$_4$-EtO-phenyl; 2-Me$_4$-MeS-phenyl;
2-Me$_4$-H$_2$NCO-phenyl; 2-Me$_4$-MeOC(=O)-phenyl;
2-Me4-CH$_3$C(=O)-phenyl; 2-Me-5-F-phenyl;
2-Et-4-MeO-phenyl; 2-MeO-5-F-phenyl;
2-MeO-4-isopropyl-phenyl; 2-CF$_3$-4-Cl-phenyl;
2-CF$_3$-4-F-phenyl; 2-CF$_3$-4-MeO-phenyl;
2-CF$_3$-4-EtO-phenyl; 2-CF$_3$-4-iPrO-phenyl;
2-CF$_3$-4-CN-phenyl; 2-CF$_3$-6-F-phenyl;
2-CHO-4-MeO-phenyl; 2-MeOC(=O)-3-MeO-phenyl;
2-CH$_3$CH(OH)-4-MeO-phenyl; 2-CH$_3$CH(OH)-4-F-phenyl;
2-CH$_3$CH(OH)-4-Cl-phenyl; 2-CH$_3$CH(OH)-4-Me-phenyl;
2-CH$_3$CH(OMe)-4-MeO-phenyl; 2-CH$_3$C(=O)-4-MeO-phenyl;
2-CH$_3$C(=O)-4-F-phenyl; 2-CH$_3$C(=O)-4-Cl-phenyl;
2-CH$_3$C(=O)-4-Me-phenyl; 2-H$_2$C(OH)-4-MeO-phenyl;
2-H$_2$C(OMe)-4-MeO-phenyl; 2-H$_3$CCH$_2$CH(OH)-4-MeO-phenyl;
2-H$_3$CCH$_2$C(=O)-4-MeO-phenyl;
2-CH$_3$CO$_2$CH$_2$CH$_2$-4-MeO-phenyl;
(Z)-2-HOCH$_2$CH=CH-4-MeO-phenyl;
(E)$_2$—HOCH$_2$CH=CH-4-MeO-phenyl;
(Z)-2-CH$_3$CO$_2$CH=CH-4-MeO-phenyl;
(E)-2-CH$_3$CO$_2$CH=CH-4-MeO-phenyl;
2-CH$_3$OCH$_2$CH$_2$-4-MeO-phenyl;
3-CN-4-F-phenyl; 3-H$_2$NCO-4-F-phenyl;
(2-Cl-phenyl)-CH=CH—; (3-Cl-phenyl)-CH—CH—;
(2,6-diF-phenyl)-CH=CH—; phenyl-CH=CH—;
(2-Me$_4$-MeO-phenyl)-CH=CH—;
cyclohexyl; cyclopentyl; cyclohexylmethyl; benzyl;
2-F-benzyl; 3-F-benzyl; 4-F-benzyl; 3-MeO-benzyl;
3-OH-benzyl; 2-MeO-benzyl; 2-OH-benzyl;
tetrahydroquinolin-1-yl;
tetrahydroindolin-1-yl;
tetrahydroisoindolin-1-yl;
phenyl-S—; phenyl-NH—; pyrid-3-yl-NH—;
(4-Me-pyrid-3-yl)-NH—; (1-naphthyl)-NH—;
(2-naphthyl)-NH—; (2-Me-naphth-1-yl)-NH—;
(3-quinolinyl)-NH—;
(2-[1,1'-biphenyl])—NH—; (3-[1,1'-biphenyl])—NH—;
(4-[1,1'-biphenyl])—NH—; (2-F-phenyl)-NH—;
(2-Cl-phenyl)-NH—; (2-CF$_3$-phenyl)-NH—;
(2-CH$_3$-phenyl)-NH—; (2-OMe-phenyl)-NH—;
(2-CN-phenyl)-NH—; (2-OCF$_3$-phenyl)-NH—;
(2-SMe-phenyl)-NH—; (3-F-phenyl)-NH—;
(3-Cl-phenyl)-NH—; (3-CF$_3$-phenyl)-NH—;
(3-CH$_3$-phenyl)-NH—; (3-OMe-phenyl)-NH—;
(3-CN-phenyl)-NH—; (3-OCF$_3$-phenyl)-NH—;
(3-SMe-phenyl)-NH—; (4-F-phenyl)-NH—;
(4-Cl-phenyl)-NH—; (4-CF$_3$-phenyl)-NH—;
(4-CH$_3$-phenyl)-NH—; (4-OMe-phenyl)-NH—;
(4-CN-phenyl)-NH—; (4-OCF$_3$-phenyl)-NH—;
(4-SMe-phenyl)-NH—; (2,3-diCl-phenyl)-NH—;
(2,4-diCl-phenyl)-NH—; (2,5-diCl-phenyl)-NH—;
(2,6-diCl-phenyl)-NH—; (3,4-diCl-phenyl)-NH—;
(3,5-diCl-phenyl)-NH—; (2,3-diF-phenyl)-NH—;
(2,4-diF-phenyl)-NH—; (2,5-diF-phenyl)-NH—;
(2,6-diF-phenyl)-NH—; (3,4-diF-phenyl)-NH—;
(3,5-diF-phenyl)-NH—; (2,3-diCH$_3$-phenyl)-NH—;
(2,4-diCH$_3$-phenyl)-NH—; (2,5-diCH$_3$-phenyl)-NH—;
(2,6-diCH$_3$-phenyl)-NH—; (3,4-diCH$_3$-phenyl)-NH—;
(3,5-diCH$_3$-phenyl)-NH—; (2,3-diCF$_3$-phenyl)-NH—;
(2,4-diCF$_3$-phenyl)-NH—; (2,5-diCF$_3$-phenyl)-NH—;
(2,6-diCF$_3$-phenyl)-NH—; (3,4-diCF$_3$-phenyl)-NH—;
(3,5-diCF$_3$-phenyl)-NH—; (2,3-diOMe-phenyl)-NH—;
(2,4-diOMe-phenyl)-NH—; (2,5-diOMe-phenyl)-NH—;
(2,6-diOMe-phenyl)-NH—; (3,4-diOMe-phenyl)-NH—;
(3,5-diOMe-phenyl)-NH—; (2-F-3-Cl-phenyl)-NH—;
(2-F-4-Cl-phenyl)-NH—; (2-F-5-Cl-phenyl)-NH—;
(2-F-6-Cl-phenyl)-NH—; (2-F-3-CH$_3$-phenyl)-NH—;
(2-F-4-CH$_3$-phenyl)-NH—; (2-F-5-CH$_3$-phenyl)-NH—;
(2-F-6-CH$_3$-phenyl)-NH—; (2-F-3-CF$_3$-phenyl)-NH—;
(2-F-4-CF$_3$-phenyl)-NH—; (2-F-5-CF$_3$-phenyl)-NH—;
(2-F-6-CF$_3$-phenyl)-NH—; (2-F-3-OMe-phenyl)-NH—;
(2-F-4-OMe-phenyl)-NH—; (2-F-5-OMe-phenyl)-NH—;
(2-F-6-OMe-phenyl)-NH—; (2-Cl-3-F-phenyl)-NH—;

(2-Cl-4-F-phenyl)-NH—; (2-Cl-5-F-phenyl)-NH—;
(2-Cl-6-F-phenyl)-NH—; (2-Cl-3-CH$_3$-phenyl)-NH—;
(2-Cl-4-CH$_3$-phenyl)-NH—; (2-Cl-5-CH$_3$-phenyl)-NH—;
(2-Cl-6-CH$_3$-phenyl)-NH—; (2-Cl-3-CF$_3$-phenyl)-NH—;
(2-Cl-4-CF$_3$-phenyl)-NH—; (2-Cl-5-CF$_3$-phenyl)-NH—;
(2-Cl-6-CF$_3$-phenyl)-NH—; (2-Cl-3-OMe-phenyl)-NH—;
(2-Cl-4-OMe-phenyl)-NH—; (2-Cl-5-OMe-phenyl)-NH—;
(2-Cl-6-OMe-phenyl)-NH—; (2-CH$_3$-3-F-phenyl)-NH—;
(2-CH$_3$-4-F-phenyl)-NH—; (2-CH$_3$-5-F-phenyl)-NH—;
(2-CH$_3$-6-F-phenyl)-NH—; (2-CH$_3$-3-Cl-phenyl)-NH—;
(2-CH$_3$-4-Cl-phenyl)-NH—; (2-CH$_3$-5-Cl-phenyl)-NH—;
(2-CH$_3$-6-Cl-phenyl)-NH—; (2-CH$_3$-3-CF$_3$-phenyl)-NH—;
(2-CH$_3$-4-CF$_3$-phenyl)-NH—; (2-CH$_3$-5-CF$_3$-phenyl)-NH—;
(2-CH$_3$-6-CF$_3$-phenyl)-NH—; (2-CH$_3$-3-OMe-phenyl)-NH—;
(2-CH$_3$-4-OMe-phenyl)-NH—; (2-CH$_3$-5-OMe-phenyl)-NH—;
(2-CH$_3$-6-OMe-phenyl)-NH—; (2-CF$_3$-3-F-phenyl)-NH—;
(2-CF$_3$-4-F-phenyl)-NH—; (2-CF$_3$-5-F-phenyl)-NH—;
(2-CF$_3$-6-F-phenyl)-NH—; (2-CF$_3$-3-Cl-phenyl)-NH—;
(2-CF$_3$-4-Cl-phenyl)-NH—; (2-CF$_3$-5-Cl-phenyl)-NH—;
(2-CF$_3$-6-Cl-phenyl)-NH—; (2-CF$_3$-3-CH$_3$-phenyl)-NH—;
(2-CF$_3$-4-CH$_3$-phenyl)-NH—; (2-CH$_3$-5-CF$_3$-phenyl)-NH—;
(2-CF$_3$-6-CH$_3$-phenyl)-NH—; (2-CF$_3$-3-OMe-phenyl)-NH—;
(2-CF$_3$-4-OMe-phenyl)-NH—; (2-CF$_3$-5-OMe-phenyl)-NH—;
(2-CF$_3$-6-OMe-phenyl)-NH—; (2-OMe-3-F-phenyl)-NH—;
(2-OMe-4-F-phenyl)-NH—; (2-OMe-5-F-phenyl)-NH—;
(2-OMe-6-F-phenyl)-NH—; (2-OMe-3-Cl-phenyl)-NH—;
(2-OMe-4-Cl-phenyl)-NH—; (2-OMe-5-Cl-phenyl)-NH—;
(2-OMe-6-Cl-phenyl)-NH—; (2-OMe-4-CN-phenyl)-NH—;
(2-OMe-4-CHO-phenyl)-NH—; (2-OMe-3-CH$_3$-phenyl)-NH—;
(2-OMe-4-CH$_3$-phenyl)-NH—; (2-OMe-5-CH$_3$-phenyl)-NH—;
(2-OMe-6-CH$_3$-phenyl)-NH—; (2-OMe-3-CF$_3$-phenyl)-NH—;
(2-OMe-4-CF$_3$-phenyl)-NH—; (2-OMe-5-CF$_3$-phenyl)-NH—;
(2-OMe-6-CF$_3$-phenyl)-NH—; (2-acetyl-4-Cl-phenyl)-NH—;
(2-acetyl-4-Me-phenyl)-NH—; (2-acetyl-4-MeO-phenyl)-NH—;
(2-CH$_3$CH(OH)$_4$—Cl-phenyl)-NH—;
(2-CH$_3$CH(OH)-4-Me-phenyl)-NH—;
(2-CH$_3$CH(OH)-4-MeO-phenyl)-NH—;
(3-CF$_3$-4-Cl-phenyl)-NH—; (3-F-4-CHO-phenyl)-NH—;
(3-CH$_3$-4-CN-phenyl)-NH—; (3-CH$_3$-4-MeO-phenyl)-NH—;
(3-CH$_3$-4-Cl-phenyl)-NH—; (3-CH$_3$-4-F-phenyl)-NH—;
(3-CH$_3$-4-CO$_2$-Me-phenyl)-NH—; (3-CF$_3$-4-C(O)CH$_3$-phenyl)-NH—; (3-CHO-4—OMe-phenyl)-NH—; (4-F-3-CF$_3$-phenyl)-NH—;
(2,3,5-triCl-phenyl)-NH—; (2,4,5-triF-phenyl)-NH—;
(2,6-diCl-3-Me-phenyl)-NH—; (3,5-Me4-MeO-phenyl)-NH—;
(2-F-3-Cl-6-CF$_3$-phenyl)-NH—;
benzyl-NH—; (3-quinolinyl)CH$_2$NH—; (2-F-phenyl)CH$_2$NH—;
(2-Cl-phenyl)CH$_2$NH—; (2-CF$_3$-phenyl)CH$_2$NH—;
(2-CH$_3$-phenyl)CH$_2$NH—; (2-OMe-phenyl)CH$_2$NH—;
(2-CN-phenyl)CH$_2$NH—; (2-OCF$_3$-phenyl)CH$_2$NH—;
(2-SMe-phenyl)CH$_2$NH—; (3-F-phenyl)CH$_2$NH—;
(3-Cl-phenyl)CH$_2$NH—; (3-CF$_3$-phenyl)CH$_2$NH—;
(3-CH$_3$-phenyl)CH$_2$NH—; (3-OMe-phenyl)CH$_2$NH—;
(3-CN-phenyl)CH$_2$NH—; (3-OCF$_3$-phenyl)CH$_2$NH—;
(3-SMe-phenyl)CH$_2$NH—; (4-F-phenyl)CH$_2$NH—;
(4-Cl-phenyl)CH$_2$NH—; (4-CF$_3$-phenyl)CH$_2$NH—;
(4-CH$_3$-phenyl)CH$_2$NH—; (4-OMe-phenyl)CH$_2$NH—;
(4-CN-phenyl)CH$_2$NH—; (4-OCF$_3$-phenyl)CH$_2$NH—;
(4-SMe-phenyl)CH$_2$NH—; (2,3-diCl-phenyl)CH$_2$NH—;
(2,4-diCl-phenyl)CH$_2$NH—; (2,5-diCl-phenyl)CH$_2$NH—;
(2,6-diCl-phenyl)CH$_2$NH—; (3,4-diCl-phenyl)CH$_2$NH—;
(3,5-diCl-phenyl)CH$_2$NH—; (2,3-diF-phenyl)CH$_2$NH—;
(2,4-diF-phenyl)CH$_2$NH—; (2,5-diF-phenyl)CH$_2$NH—;
(2,6-diF-phenyl)CH$_2$NH—; (3,4-diF-phenyl)CH$_2$NH—;
(3,5-diF-phenyl)CH$_2$NH—; (2,3-diCH$_3$-phenyl)CH$_2$NH—;
(2,4-diCH$_3$-phenyl)CH$_2$NH—; (2,5-diCH$_3$-phenyl)CH$_2$NH—;
(2,6-diCH$_3$-phenyl)CH$_2$NH—; (3,4-diCH$_3$-phenyl)CH$_2$NH—;
(3,5-diCH$_3$-phenyl)CH$_2$NH—; (2,3-diCF$_3$-phenyl)CH$_2$NH—;
(2,4-diCF$_3$-phenyl)CH$_2$NH—; (2,5-diCF$_3$-phenyl)CH$_2$NH—;
(2,6-diCF$_3$-phenyl)CH$_2$NH—; (3,4-diCF$_3$-phenyl)CH$_2$NH—;
(3,5-diCF$_3$-phenyl)CH$_2$NH—; (2,3-diOMe-phenyl)CH$_2$NH—;
(2,4-diOMe-phenyl)CH$_2$NH—; (2,5-diOMe-phenyl)CH$_2$NH—;
(2,6-diOMe-phenyl)CH$_2$NH—; (3,4-diOMe-phenyl)CH$_2$NH—;
(3,5-diOMe-phenyl)CH$_2$NH—; (2-F-3-Cl-phenyl)CH$_2$NH—;
(2-F-4-Cl-phenyl)CH$_2$NH—; (2-F-5-Cl-phenyl)CH$_2$NH—;

(2-F-6-Cl-phenyl)CH$_2$NH—; (2-F-3-CH$_3$-phenyl)CH$_2$NH—;
(2-F-4-CH$_3$-phenyl)CH$_2$NH—; (2-F-5-CH$_3$-phenyl)CH$_2$NH—,
(2-F-6-CH$_3$-phenyl)CH$_2$NH—; (2-F-3-CF$_3$-phenyl)CH$_2$NH—;
(2-F-4-CF$_3$-phenyl)CH$_2$NH—; (2-F-5-CF$_3$-phenyl)CH$_2$NH—;
(2-F-3-phenyl)CH$_2$NH—; (2-F-3-OMe-phenyl)CH$_2$NH—;
(2-F-4-OMe-phenyl)CH$_2$NH—; (2-F-5-OMe-phenyl)CH$_2$NH—;
(2-F-6-OMe-phenyl)CH$_2$NH—; (2-Cl-3-F-phenyl)CH$_2$NH—;
(2-Cl-4-F-phenyl)CH$_2$NH—; (2-Cl-5-F-phenyl)CH$_2$NH—;
(2-Cl-6-F-phenyl)CH$_2$NH—; (2-Cl-3-CH$_3$-phenyl)CH$_2$NH—;
(2-Cl-4-CH$_3$-phenyl)CH$_2$NH—; (2-Cl-5-CH$_3$-phenyl)CH$_2$NH—;
(2-Cl-6-CH$_3$-phenyl)CH$_2$NH—; (2-Cl-3-CF$_3$-phenyl)CH$_2$NH—;
(2-Cl-4-CF$_3$-phenyl)CH$_2$NH—; (2-Cl-5-CF$_3$-phenyl)CH$_2$NH—;
(2-Cl-6-CF$_3$-phenyl)CH$_2$NH—; (2-Cl-3-OMe-phenyl)CH$_2$NH—;
(2-Cl-4-OMe-phenyl)CH$_2$NH—; (2-Cl-5-OMe-phenyl)CH$_2$NH—;
(2-Cl-6-OMe-phenyl)CH$_2$NH—; (2-CH$_3$-3-F-phenyl)CH$_2$NH—;
(2-CH$_3$-4-F-phenyl)CH$_2$NH—; (2-CH$_3$-5-F-phenyl)CH$_2$NH—;
(2-CH$_3$-6-F-phenyl)CH$_2$NH—; (2-CH$_3$-3-Cl-phenyl)CH$_2$NH—;
(2-CH$_3$-4-Cl-phenyl)CH$_2$NH—; (2-CH$_3$-5-Cl-phenyl)CH$_2$NH—;
(2-CH$_3$-6-Cl-phenyl)CH$_2$NH—; (2-CH$_3$-3-CF$_3$-phenyl)CH$_2$NH—;
(2-CH$_3$-4-CF$_3$-phenyl)CH$_2$NH—; (2-CH$_3$-5-CF$_3$-phenyl)CH$_2$NH—;
(2-CH$_3$-6-CF$_3$-phenyl)CH$_2$NH—; (2-CH$_3$-3-OMe-phenyl)CH$_2$NH—;
(2-CH$_3$-4-OMe-phenyl)CH$_2$NH— (2-CH$_3$-5-OMe-phenyl)CH$_2$NH—;
(2-CH$_3$-6-OMe-phenyl)CH$_2$NH—; (2-CF$_3$-3-F-phenyl)CH$_2$NH—;
(2-CF$_3$-4-F-phenyl)CH$_2$NH—; (2-CF$_3$-5-F-phenyl)CH$_2$NH—;
(2-CF$_3$-6-F-phenyl)CH$_2$NH—; (2-CF$_3$-3-Cl-phenyl)CH$_2$NH—;
(2-CF$_3$-4-Cl-phenyl)CH$_2$NH—; (2-CF$_3$-5-Cl-phenyl)CH$_2$NH—;
(2-CF$_3$-6-Cl-phenyl)CH$_2$NH—; (2-CF$_3$-3-CH$_3$-phenyl)CH$_2$NH—;
(2-CF$_3$-4-CH$_3$-phenyl)CH$_2$NH—; (2-CH$_3$-5-CF$_3$-phenyl)CH$_2$NH—;
(2-CF$_3$-6-CH$_3$-phenyl)CH$_2$NH—; (2-CF$_3$-3-OMe-phenyl)CH$_2$NH—;
(2-CF$_3$-4-OMe-phenyl)CH$_2$NH—; (2-CF$_3$-5-OMe-phenyl)CH$_2$NH—;
(2-CF$_3$-6-OMe-phenyl)CH$_2$NH—; (2-OMe-3-F-phenyl)CH$_2$NH—;
(2-OMe-4-F-phenyl)CH$_2$NH—; (2-OMe-5-F-phenyl)CH$_2$NH—;
(2-OMe-6-F-phenyl)CH$_2$NH—; (2-OMe-3-Cl-phenyl)CH$_2$NH—;
(2-OMe-4-Cl-phenyl)CH$_2$NH—; (2-OMe-5-Cl-phenyl)CH$_2$NH—;
(2-OMe-6-Cl-phenyl)CH$_2$NH—; (2-OMe-4-CN-phenyl)CH$_2$NH—;
(2-OMe-4-CHO-phenyl)CH$_2$NH—; (2-OMe-3-CH$_3$-phenyl)CH$_2$NH—;
(2-OMe-4-CH$_3$-phenyl)CH$_2$NH—; (2-OMe-5-CH$_3$-phenyl)CH$_2$NH—;
(2-OMe-6-CH$_3$-phenyl)CH$_2$NH—; (2-OMe-3-CF$_3$-phenyl)CH$_2$NH—;
(2-OMe-4-CF$_3$-phenyl)CH$_2$NH—; (2-OMe-5-CF$_3$-phenyl)CH$_2$NH—;
(2-OMe-6-CF$_3$-phenyl)CH$_2$NH—; (2-acetyl-4-Cl-phenyl)CH$_2$NH—;
(2-acetyl-4-Me-phenyl)CH$_2$NH—;
(2-acetyl-4-MeO-phenyl)CH$_2$NH—;
(2-CH$_3$CH(OH)-4-Cl-phenyl)CH$_2$NH—;
(2-CH$_3$CH(OH)-4-Me-phenyl)CH$_2$NH—;
(2-CH$_3$CH(OH)-4-MeO-phenyl)CH$_2$NH—;
(3-CF$_3$-4-Cl-phenyl)CH$_2$NH—; (3-F-4-CHO-phenyl)CH$_2$NH—;
(3-CH$_3$-4-CN-phenyl)CH$_2$NH—; (3-CH$_3$-4-MeO-phenyl)CH$_2$NH—;
(3-CH$_3$-4-Cl-phenyl)CH$_2$NH—; (3-CH$_3$-4-F-phenyl)CH$_2$NH—;
(4-F-3-CF$_3$-phenyl)CH$_2$NH—; (3-CH$_3$-4-CO$_2$-Me-phenyl)CH$_2$NH—;
(3-CF$_3$-4-C(O)CH$_3$-phenyl)CH$_2$NH—;
(3-CHO-4-OMe-phenyl)CH$_2$NH—;
(2,3,5-triCl-phenyl)CH$_2$NH—;
(2,4,5-triF-phenyl)CH$_2$NH—;
(2,6-diCl-3-Me-phenyl)CH$_2$NH—;
(3,5-Me4-MeO-phenyl)CH$_2$NH—; and
(2-F-3-Cl-6-CF$_3$-phenyl)CH$_2$NH—;

n is 1 or 2.

13. A compound of claim 1 of formula (I-a)

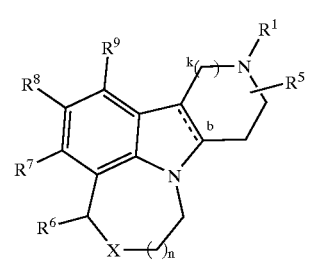

(I-a)

wherein:

X is —O—, —S—, —S(=O)—, —S(=O)$_2$—, or —NR$^{10}$—;

R$^1$ is selected from
- C$_{1-6}$ alkyl substituted with Z,
- C$_{2-6}$ alkenyl substituted with Z,
- C$_{2-6}$ alkynyl substituted with Z,
- C$_{3-6}$ cycloalkyl substituted with Z,
- aryl substituted with Z,
- 5–6 membered heterocyclic ring system containing at least one heteroatom selected from the group consisting of N, O, and S, said heterocyclic ring system substituted with Z;
- C$_{1-6}$ alkyl substituted with O$_2$ R$^2$,
- C$_{2-6}$ alkenyl substituted with 0–2 R$^2$,
- C$_{2-6}$ alkynyl substituted with 0–2 R$^2$,
- aryl substituted with 0–2 R$^2$, and
- 5–6 membered heterocyclic ring system containing at least one heteroatom selected from the group consisting of N, O, and S, said heterocyclic ring system substituted with 0–2 R$^2$;

Z is selected from H,
—CH(OH)R$^2$,
—C(ethylenedioxy)R$^2$,
—OR$^2$,
—SR$^2$,
—NR$^2$R$^3$,
—C(O)R$^2$,
—C(O)NR$^2$R$^3$,
—NR$^3$C(O)R$^2$,
—C(O)OR$^2$,
—OC(O)R$^2$,
—CH(=NR$^4$)NR$^2$R$^3$,
—NHC(=NR$^4$)NR$^2$R$^3$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
C$_{1-4}$ alkyl,
C$_{2-4}$ alkenyl,
C$_{2-4}$ alkynyl,
C$_{3-6}$ cycloalkyl,
aryl substituted with 0–5 R$^{42}$;
C$_{3-10}$ carbocyclic residue substituted with 0–3 R$^{41}$, and
5–10 membered heterocyclic ring system containing from 1–4 heteroatoms selected from the group consisting of N, O, and S substituted with 0–3 R$^{41}$;

R$^3$, at each occurrence, is independently selected from
H, C$_{1-4}$ alkyl, C$_{2-4}$ alkenyl, C$_{2-4}$ alkynyl, and
C$_{1-4}$ alkoxy;
alternatively, R$^2$ and R$^3$ join to form a 5- or 6-membered ring optionally substituted with —O— or —N(R$^4$);

R$^4$, at each occurrence, is independently selected from H, methyl, ethyl, propyl, and butyl;

R$^5$ is H, methyl, ethyl, propyl, or butyl;

R$^6$ is H, methyl, ethyl, propyl, or butyl;

R$^7$, R$^8$, and R$^9$, at each occurrence, are independently selected from
H, halo, —CF$_3$, —OCF$_3$, —OH, —CN, —NO$_2$, —NR$^{46}$R$^{47}$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{1-4}$ alkyl substituted with 0–2 R$^{11}$,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{10}$ is selected from H, C$_{1-4}$ alkyl, C$_{2-4}$ alkenyl, C$_{2-4}$ alkynyl, and C$_{1-4}$ alkoxy;

R$^{11}$ is selected from
H, halo, —CF$_3$, —CN, —NO$_2$,
C$_{1-8}$ alkyl, C$_{2-8}$ alkenyl, C$_{2-8}$ alkynyl, C$_{1-4}$ haloalkyl, C$_{1-6}$ alkoxy, C$_{3-10}$ cycloalkyl,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, and NR$^{14}$S(O)$_2$R$^{12}$;

R$^2$, at each occurrence, is independently selected from
C$_{1-4}$ alkyl,
C$_{2-4}$ alkenyl,
C24 alynyl,
C$_{3-6}$ cycloalkyl,
phenyl substituted with 0–5 R$^{33}$;
C$_{3-10}$ carbocyclic residue substituted with 0–3 R$^{33}$, and
5–10 membered heterocyclic ring system containing from 1–4 heteroatoms selected from the group consisting of N, O, and S substituted with 0–3 R$^{31}$;

R$^{13}$, at each occurrence, is independently selected from
H, C$_{1-4}$ alkyl, C$_{2-4}$ alkenyl, and C$_{2-4}$ alkynyl;
alternatively, R$^{12}$ and R$^{13}$ join to form a 5- or 6-membered ring optionally substituted with —O— or —N(R$^{14}$)—;

R$^{14}$, at each occurrence, is independently selected from H and C$_{1-4}$ alkyl;

R$^{31}$, at each occurrence, is independently selected from
CN, NO$_2$, —OCF$_3$, —OCH$_2$CF$_3$, —C(=O)H, —C(=O)NH$_2$, —C(=O)OCH$_3$, phenyl, C$_{2-6}$ alkenyl, C$_{2-6}$ alkynyl, C$_{3-6}$ cycloalkyl, C$_{1-4}$ haloalkyl, C$_{1-4}$ haloalkyl-oxy-, C$_{1-4}$ alkyloxy-, C$_{1-4}$ alkylthio-, C$_{1-4}$ alkyl-C(=O)—, C$_{1-4}$ alkyl-OC(=O)—, C$_{1-4}$ alkyl-C(=O)O—, C$_{1-4}$ alkyl-C(=O)-NH—, C$_{1-4}$ alkyl-NHC(=O)—, (C$_{1-4}$ alkyl)$_2$NC(=O)—, C$_{3-6}$ cycloalkyl-oxy-, C$_{3-6}$ cycloalkylmethyl-oxy-; C$_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—; and C$_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—;

R$^{33}$, at each occurrence, is independently selected from
H, OH, halo, CN, NO$_2$, CF$_3$, —OCF$_3$, —OCH$_2$CF$_3$, SO$_2$R$^{45}$, NR$^{46}$R$^{47}$, —C(=O)H, =O, —C(=O)NH$_2$, —C(=O)OCH$_3$, phenyl, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyl-oxy-, C$_{1-4}$ alkyloxy-, C$_{1-4}$ alkylthio-, C$_{1-4}$ alkyl-C(=O)—, C$_{1-4}$ alkyl-OC(=O)—, CIA alkyl-C(=O)O—, C$_{1-4}$ alkyl-C(=O)-NH—, C$_{1-4}$ alkyl-NHC(=O)—, (C$_{1-4}$ alkyl)$_2$NC(=O)—, C$_{3-6}$ cycloalkyl-oxy-, C$_{3-6}$ cycloalkylmethyl-oxy-; C$_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—; and C$_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—;

R$^{41}$, at each occurrence, is independently selected from
H, CF$_3$, halo, OH, CO$_2$H, SO$_2$R$^{45}$, NR$^{46}$R$^{47}$, NO$_2$, CN, =O,
C$_{2-8}$ alkenyl, C$_{2-8}$ alkynyl, C$_{1-4}$ alkoxy, C$_{1-4}$ haloalkyl
C$_{1-4}$ alkyl substituted with 0–1 R$^{43}$,
aryl substituted with 0–3 R$^{42}$, and
5–10 membered heterocyclic ring system containing from 1–4 heteroatoms selected from the group consisting of N, O, and S substituted with 0–3 R$^{44}$;

R$^{42}$, at each occurrence, is independently selected from
H, CF$_3$, halo, OH, CO$_2$H, SO$_2$R$^{45}$, SR$^{45}$, NR$^{46}$R$^{47}$, OR$^{48}$, NO$_2$, CN, CH(=NH)NH$_2$, NHC(=NH)NH$_2$,
C$_{2-6}$ alkenyl, C$_{2-6}$ alkynyl, C$_{1-4}$ alkoxy, C$_{1-4}$ haloalkyl, C$_{3-6}$ cycloalkyl,
C$_{1-4}$ alkyl substituted with 0–3 R$^{43}$,
aryl substituted with 0–3 R$^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H, Cl alkyl, —C(=O)NH($C_{1-4}$ alkyl), —$SO_2$($C_{1-4}$ alkyl), —$SO_2$(phenyl), —C(=O)O($C_{1-4}$ alkyl), —C(=O)($C_{1-4}$ alkyl), and —C(=O)H;

$R^{48}$, at each occurrence, is independently selected from H, $C_{1-4}$ alkyl, —C(=O)NH($C_{1-4}$ alkyl), —C(=O)O($C_{1-4}$ alkyl), —C(=O)($C_{1-4}$ alkyl), and —C(=O)H;

k is 1 or 2; and n is 1 or 2.

14. A compound of claim 13 wherein:

X is —O—, —S—, or —NH—;

$R^1$ is selected from
  $C_{2-5}$ alkyl substituted with Z,
  $C_{2-5}$ alkenyl substituted with Z,
  $C_{2-5}$ alkynyl substituted with Z,
  $C_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  $C_{1-5}$ alkyl substituted with 0–2 $R^2$,
  $C_{2-5}$ alkenyl substituted with 0–2 $R^2$, and
  $C_{2-5}$ alkynyl substituted with 0–2 $R^2$;

Z is selected from H,
  —CH(OH)$R^2$,
  —C(ethylenedioxy)$R^2$,
  —$SR^2$,
  —$NR^2R^3$,
  —C(O)$R^2$,
  —C(O)$NR^2R^3$,
  —$NR^3$C(O)$R^2$,
  —C(O)$OR^2$,
  —OC(O)$R^2$,
  —CH(—$NR^4$)$NR^2R^3$,
  —NHC(=$NR^4$)$NR^2R^3$,
  —S(O)$R^2$,
  —S(O)$_2R^2$,
  —S(O)$_2NR^2R^3$, and —$NR^3$S(O)$_2R^2$;

$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  aryl substituted with 0–5 $R^{42}$;
  $C_{3-10}$ carbocyclic residue substituted with 0–3 $R^{41}$, and
  5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$);

$R^4$, at each occurrence, is independently selected from H, methyl, ethyl, propyl, and butyl;

$R^5$ is H, methyl, or ethyl;

$R^6$ is H, methyl, ethyl, propyl, or butyl;

$R^7$, $R^8$, and $R^9$, at each occurrence, are independently selected from
  H, halo, —$CF_3$, —$OCF_3$, —OH, —$OCH_3$, —CN, —$NO_2$, —$NR^{46}R^{47}$,
  $C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
  $C_{1-4}$ alkyl substituted with 0–2 $R^{11}$,
  $C_{3-10}$ carbocyclic residue substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$_2NR^{12}R^{13}$, $NR^{14}$S(O)$_2R^{12}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^1$ 5;

$R^{11}$ is selected from
  H, halo, —$CF_3$, —$OCF_3$, —OH, —$OCH_3$, —CN, —$NO_2$, —$NR^{46}R^{47}$,
  $C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
  $C_{3-10}$ carbocyclic residue substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, C(O)$R^{12}$, C(O)$NR^{12}R^{13}$, $NR^{14}$C(O)$R^{12}$,
  C(O)$OR^{12}$, OC(O)$R^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$_2NR^{12}R^{13}$, and $NR^{14}$S(O)$_2R^{12}$;

$R^{12}$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

$R^{14}$, at each occurrence, is independently selected from H and $C_{1-4}$ alkyl;

$R^{31}$, at each occurrence, is independently selected from CN, $NO_2$, —$OCF_3$, —$OCH_2CF_3$, —C(=O)H, —C(=O)$NH_2$, —C(=O)$OCH_3$, phenyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{33}$, at each occurrence, is independently selected from
H, OH, halo, CN, $NO_2$, $CF_3$, —$OCF_3$, —$OCH_2CF_3$, $SO_2R^{45}$, $NR^{46}R^{47}$, —C(=O)H, =O, —C(=O)$NH_2$, —C(=O)$OCH_3$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-OC(=O)—, $C_{1-4}$ alkyl-C(=O)O—, $C_{1-4}$ alkyl-C(=O)-NH—, $C_{1-4}$ alkyl-NHC(=O)—, ($C_{1-4}$ alkyl)$_2$NC(=O)—, $C_{3-6}$ cycloalkyl-oxy-, $C_{3-6}$ cycloalkylmethyl-oxy-; $C_{1-6}$ alkyl substituted with OH, methoxy, ethoxy, propoxy, butoxy, —$SO_2R^{45}$, —$NR^{46}R^{47}$, $NR^{46}R^{47}$C(O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{41}$, at each occurrence, is independently selected from
H, $CF_3$, halo, OH, $CO_2H$, $SO_2R^{45}$, $NR^{46}R^{47}$, $NO_2$, CN, =O,
$C_{2-8}$ alkenyl, $C_{2-8}$ alkynyl, $C_{1-4}$ alkoxy, $C_{1-4}$haloalkyl, $C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SR^{45}$, $NR^{46}R^{47}$, $OR^{48}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-3}$ alkyl;

$R^{47}$, at each occurrence, is independently selected from H, $C_{1-4}$ alkyl, —C(=O)NH($C_{1-4}$ alkyl), —$SO_2$($C_{1-4}$ alkyl), —$SO_2$(phenyl), —C(=O)O($C_{1-4}$ alkyl), —C(=O)($C_{1-4}$ alkyl), and —C(=O)H;

$R^{48}$, at each occurrence, is independently selected from H, $C_{1-4}$ alkyl, —C(=O)NH($C_{1-4}$ alkyl), —C(=O)O($C_{1-4}$ alkyl), —C(=O)($C_{1-4}$ alkyl), and —C(=O)H;

k is 1 or 2; and
n is 1 or 2.

15. A compound of claim 13 wherein:
X is —O— or —S—;
$R^1$ is selected from
$C_{2-4}$ alkyl substituted with Z,
$C_{2-4}$ alkenyl substituted with Z,
$C_{2-4}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{2-4}$ alkyl substituted with 0–2 $R^2$, and
$C_{2-4}$ alkenyl substituted with 0–2 $R^2$;

Z is selected from H,
—CH(0H)$R^2$,
—C(ethylenedioxy)$R^2$,
—$SR^2$,
—$NR^2R^3$,
—C(O)$R^2$,
—C(O)$NR^2R^3$,
—$NR^3$C(O)$R^2$,
—C(O)$OR^2$,
—S(O)$R^2$,
—S(O)$_2R^2$,
—S(O)$_2NR^2R^3$, and —$NR^3$S(O)$_2R^2$;

$R^2$, at each occurrence, is independently selected from
phenyl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^3$, at each occurrence, is independently selected from
H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H, methyl, ethyl, propyl, and butyl;

$R^5$ is H;

$R^6$ is H;

$R^7$, $R^8$, and $R^9$, at each occurrence, are independently selected from
H, halo, —$CF_3$, —$OCF_3$, —OH, —$OCH_3$, —CN, —$NO_2$,
$C_{1-4}$ alkyl, $C_{1-4}$ haloalkyl, $C_{1-4}$ alkoxy, ($C_{1-3}$ haloalkyl)oxy, and
$C_{1-4}$ alkyl substituted with 0–2 $R^{11}$;

$R^{11}$ is selected from
H, halo, —$CF_3$, —$OCF_3$, —OH, —$OCH_3$, —CN, —$NO_2$,
$C_{1-4}$ alkyl, $C_{1-4}$ haloalkyl, $C_{1-4}$ alkoxy, and ($C_{1-3}$ haloalkyl)oxy;

$R^{33}$, at each occurrence, is independently selected from
H, OH, halo, $CF_3$, and methyl;

$R^{41}$, at each occurrence, is independently selected from
H, $CF_3$, halo, OH, $CO_2H$, $SO_2R^{45}$, $NR^{46}R^{47}$, $NO_2$, CN, =O,
$C_{2-8}$ alkenyl, $C_{2-8}$ alkynyl, $C_{1-4}$ alkoxy, $C_{1-4}$ haloalkyl,
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SR^{45}$, $NR^{46}R^{47}$, $OR^{48}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted With 0–3 $R^{44}$, and
5–10 membered heterocyclic ring system containing from 1–4 heteroatoms selected from the group consisting of N, O, and S substituted with 0–3 $R^{44}$;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

R$^{45}$ is methyl, ethyl, propyl, or butyl;

R$^{46}$, at each occurrence, is independently selected from H, methyl, ethyl, propyl, and butyl;

R$^{47}$, at each occurrence, is independently selected from H, methyl, ethyl, n-propyl, i-propyl, n-butyl, i-butyl, —C(=O)NH(methyl), —C(=O)NH(ethyl), —SO$_2$(methyl), —SO$_2$(ethyl), —SO$_2$(phenyl), —C(=O)O(methyl), —C(=O)O(ethyl), —C(=O)(methyl), —C(=O)(ethyl), and —C(=O)H;

R$^{48}$, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1; and n is 1 or 2.

16. A compound of claim 13 wherein:

X is —O— or —S—;

R$^1$ is selected from
ethyl substituted with Z,
propyl substituted with Z,
butyl substituted with Z,
propenyl substituted with Z,
butenyl substituted with Z,
ethyl substituted with R$^2$,
propyl substituted with R$^2$,
butyl substituted with R$^2$,
propenyl substituted with R$^2$, and
butenyl substituted with R$^2$;

Z is selected from H,
—CH(OH)R$^2$,
—SR$^2$,
—NR$^2$R$^3$,
—C(O)R$^2$,
—C(O)NR$^2$R$^3$,
—NR$^3$C(O)R$^2$,
—C(O)OR$^2$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
phenyl substituted with 0–3 R$^{42}$;
naphthyl substituted with 0–3 R$^{42}$;
cyclopropyl substituted with 0–3 R$^{41}$;
cyclobutyl substituted with 0–3 R$^{41}$;
cyclopentyl substituted with 0–3 R$^{41}$;
cyclohexyl substituted with 0–3 R$^{41}$;
pyridyl substituted with 0–3 R$^{41}$;
indolyl substituted with 0–3 R$^{41}$;
indolinyl substituted with 0–3 R$^{41}$;
benzimidazolyl substituted with 0–3 R$^{41}$;
benzotriazolyl substituted with 0–3 R$^{41}$;
benzothienyl substituted with 0–3 R$^{41}$;
benzofuranyl substituted with 0–3 R$^{41}$;
phthalimid-1-yl substituted with 0–3 R$^{41}$;
inden-2-yl substituted with 0–3 R$^{41}$;
2,3-dihydro-1H-inden-2-yl substituted with 0–3 R$^{41}$;
indazolyl substituted with 0–3 R$^{41}$;
tetrahydroquinolinyl substituted with 0–3 R$^{41}$; and
tetrahydro-isoquinolinyl substituted with 0–3 R$^{41}$;

R$^3$, at each occurrence, is independently selected from H, methyl, and ethyl;

R$^5$ is H;

R$^6$ is H;

R$^7$, R$^8$, and R$^9$, at each occurrence, are independently selected from H, F, Cl, methyl, ethyl, methoxy, —CF$_3$, and —OCF$_3$;

R$^{41}$, at each occurrence, is independently selected from H, F, Cl, Br, OH, CF$_3$, NO$_2$, CN, =O, methyl, ethyl, propyl, butyl, methoxy, and ethoxy;

R$^{42}$, at each occurrence, is independently selected from H, F, Cl, Br, OH, CF$_3$, SO$_2$R$^{45}$, SR$^{45}$, NR$^{46}$R$^{47}$, OR$^{48}$, NO$_2$, CN, =O, methyl, ethyl, propyl, butyl, methoxy, and ethoxy;

R$^{45}$ is methyl, ethyl, propyl, or butyl;

R$^{46}$, at each occurrence, is independently selected from H, methyl, ethyl, propyl, and butyl;

R$^{47}$, at each occurrence, is independently selected from H, methyl, ethyl, n-propyl, i-propyl, n-butyl, i-butyl, —C(=O)NH(methyl), —C(=O)NH(ethyl), —SO$_2$(methyl), —SO$_2$(ethyl), —SO$_2$(phenyl), —C(=O)O(methyl), —C(=O)O(ethyl), —C(=O)(methyl), —C(=O)(ethyl), and —C(=O)H;

R$^{48}$, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1; and n is 1 or 2.

17. A compound of claim 13 of Formula (I-c)

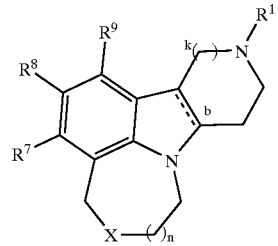

(I-c)

wherein:
b is a single bond or a double bond;
X is —S— or —O—;
R$^1$ is selected from
—(CH$_2$)$_3$C(=O)(4-fluoro-phenyl),
—(CH$_2$)$_3$C(=O)(4-bromo-phenyl),
—(CH$_2$)$_3$C(=O)(4-methyl-phenyl),
—(CH$_2$)$_3$C(=O)(4-methoxy-phenyl),
—(CH$_2$)$_3$C(=O)(4-(3,4-dichloro-phenyl)phenyl),
—(CH$_2$)$_3$C(=O)(3-methyl-4-fluoro-phenyl),
—(CH$_2$)$_3$C(=O)(2,3-dimethoxy-phenyl),
—(CH$_2$)$_3$C(=O)(Phenyl),
—(CH$_2$)$_3$C(=O)(4-chloro-phenyl),
—(CH$_2$)$_3$C(=O)(3-methyl-phenyl),
—(CH$_2$)$_3$C(=O)(4-t-butyl-phenyl),
—(CH$_2$)$_3$C(=O)(3,4-difluoro-phenyl),
—(CH$_2$)$_3$C(=O)(2-methoxy-5-fluoro-phenyl),
—(CH$_2$)$_3$C(=O)(4-fluoro-1-naphthyl),
—(CH$_2$)$_3$C(=O)(benzyl),
—(CH$_2$)$_3$C(=O)(4-pyridyl),
—(CH$_2$)$_3$C(=O)(3-pyridyl),
—(CH$_2$)$_3$CH(OH)(4-fluoro-phenyl),
—(CH$_2$)$_3$CH(OH)(4-pyridyl),
—(CH$_2$)$_3$CH(OH)(2,3-dimethoxy-phenyl),
—(CH$_2$)$_3$S(3-fluoro-phenyl), —(CH₂)₃S(4-fluoro-phenyl),
—(CH₂)₃S(=O)(4-fluoro-phenyl),
—(CH₂)₃SO₂(3-fluoro-phenyl),
—(CH₂)₃SO₂(4-fluoro-phenyl),
—(CH₂)₃O(4-fluoro-phenyl),
—(CH₂)₃O(phenyl),
—(CH₂)₃O(3-pyridyl),
—(CH₂)₃O(4-pyridyl),
—(CH₂)₃O(2-NH₂-phenyl),
—(CH₂)₃O(2-NH₂-5-F-phenyl),
—(CH₂)₃O(2-NH₂-4-F-phenyl),
—(CH₂)₃O(2-NO₂₋₄—F-phenyl),
—(CH₂)₃O(2-NH₂-3-F-phenyl),
—(CH₂)₃O(2-NH₂-4-Cl-phenyl),
—(CH₂)₃O(2-NH₂-4-OH-phenyl),
—(CH₂)₃O(2-NH₂-4-Br-phenyl),
—(CH₂)₃O(2-NHC(=O)Me-4-F-phenyl),
—(CH₂)₃O(2-NHC(=O)Me-phenyl),
—(CH₂)₃NH(4-fluoro-phenyl),
—(CH₂)₃N(methyl)(4-fluoro-phenyl),
—(CH₂)₃CO₂(ethyl),
—(CH₂)₃C(=O)N(methyl)(methoxy),
—(CH₂)₃C(=O)NH(4-fluoro-phenyl),
—(CH₂)₂NHC(=O)(phenyl),
—(CH₂)₂NMeC(=O)(phenyl),
—(CH₂)₂NHC(=O)(2-fluoro-phenyl),
—(CH₂)₂NMeC(=O)(2-fluoro-phenyl),
—(CH₂)₂NHC(=O)(4-fluoro-phenyl),
—(CH₂)₂NMeC(=O)(4-fluoro-phenyl),
—(CH₂)₂NHC(=O)(2,4-difluoro-phenyl),
—(CH₂)₂NMeC(=O)(2,4-difluoro-phenyl),
—(CH₂)₃(3-indolyl),
—(CH₂)₃(1-methyl-3-indolyl),
—(CH₂)₃(1-indolyl),
—(CH₂)₃(1-indolinyl),
—(CH₂)₃ (1-benzimidazolyl),
—(CH₂)₃(1H-1,2,3-benzotriazol-1-yl),
—(CH₂)₃(1H-1,2,3-benzotriazol-2-yl),
—(CH₂)₂(1H-1,2,3-benzotriazol-1-yl),
—(CH₂)₂(1H-1,2,3-benzotriazol-2-yl),
—(CH₂)₃(3,4 dihydro-1 (2H)-quinolinyl),
—(CH₂)₂C(=O)(4-fluoro-phenyl),
—(CH₂)₂C(=O)NH(4-fluoro-phenyl),
—(CH₂CH₂(3-indolyl),
—(CH₂CH₂(1-phthalimidyl),
—(CH₂)₄C(=O)N(methyl)(methoxy),
—(CH₂)₄CO₂(ethyl),
—(CH₂)₄C(=O)(phenyl),
—(CH₂)₄(cyclohexyl),
—(CH₂)₃CH(phenyl)₂,
—(CH₂CH₂CH=C(phenyl)₂,
—(CH₂CH₂CH=CMe(4-F-phenyl),
—(CH₂)₃CH(4-fluoro-phenyl)₂,
—(CH₂CH₂CH=C(4-fluoro-phenyl)₂,
—(CH₂)₂(2,3-dihydro-1H-inden-2-yl),
—(CH₂)₃C(=O)(2-NH₂-phenyl),
—(CH₂)₃C(=O)(2-NH₂-5-F-phenyl),
—(CH₂)₃C(=O)(2—NH₂-4-F-phenyl),
—(CH₂)₃C(=O)(2-NH₂-3-F-phenyl),
—(CH₂)₃C(=O)(2-NH₂-4-Cl-phenyl),
—(CH₂)₃C(=O)(2-NH₂-4-OH-phenyl),
—(CH₂)₃C(=O)(2-NH₂-4-Br-phenyl),
—(CH₂)₃(1H-indazol-3-yl),
—(CH₂)₃(5-F-1H-indazol-3-yl),
—(CH₂)₃(7-F-1H-indazol-3-yl),
—(CH₂)₃(6-C₁₋₁H-indazol-3-yl),
—(CH₂)₃(6-Br-1H-indazol-3-yl), —(CH₂)₃C(=O)(2-NHMe-phenyl),
—(CH₂)₃(1-benzothien-3-yl),
—(CH₂)₃(6-F-1H-indol-1-yl),
—(CH₂)₃(5-F-1H-indol-1-yl),
—(CH₂)₃(6-F-2,3-dihydro-1H-indol-1-yl),
—(CH₂)₃(5-F-2,3-dihydro-1H-indol-1-yl),
—(CH₂)₃(6-F-1H-indol-3-yl),
—(CH₂)₃(5-F-1H-indol-3-yl),
—(CH₂)₃(5-F-1H-indol-3-yl),
—(CH₂)₃(9H-purin-9-yl),
—(CH₂)₃(7H-purin-7-yl),
—(CH₂)₃(6-F-1H-indazol-3-yl),
—(CH₂)₃C(=O)(2-NHSO₂Me₄-F-phenyl),
—(CH₂)₃C(=O)(2-NHC(=O)Me-4-F-phenyl),
—(CH₂)₃C(=O)(2-NHC(=O)Me-phenyl),
—(CH₂)₃C(=O)(2-NHCO₂-Et-4-F-phenyl),
—(CH₂)₃C(=O)(2-NHC(=O)NHEt-4-F-phenyl),
—(CH₂)₃C(=O)(2—NHCHO-4-F-phenyl),
—(CH₂)₃C(=O)(2-OH-4-F-phenyl),
—(CH₂)₃C(=O)(2-MeS-4-F-phenyl),
—(CH₂)₃C(=O)(2-NHSO₂Me₄-F-phenyl),
—(CH₂)₂C(Me)CO₂Me,
—(CH₂)₂C(Me)CH(OH)(4-F-phenyl)₂,
—(CH₂)₂C(Me)CH(OH)(4-Cl-phenyl)₂,
—(CH₂)₂C(Me)C(=O)(4-F-phenyl),
—(CH₂)₂C(Me)C(=O)(2-MeO-4-F-phenyl),
—(CH₂)₂C(Me)C(=O)(3-Me-4-F-phenyl),
—(CH₂)₂C(Me)C(=O)(2-Me-phenyl),
—(CH₂)₂C(Me)C(=O)phenyl,

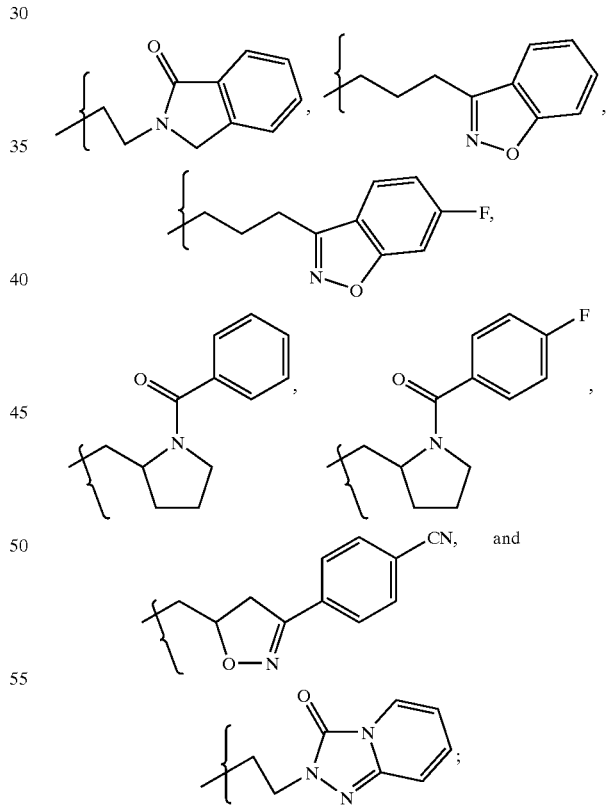

R⁷, R⁸, and R⁹, at each occurrence, are independently selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, benzyl, HC(=O)—, methylC(=O)—, ethylC(=O)—, propylC(=O)—, isopropylC(=O)—, n-butylC(=O)—, isobutylC(=O)—, secbutylC(=O)—, tertbutylC(=O), phenylC(=O)—, methylC(=O)-NH—, ethylC(=O)NH—, propylC(=O)-NH—, isopropylC(=O)-NH—, n-butylC(=O)-NH—, isobutylC(=O)-NH—, secbutylC(=O)-NH—, tertbutylC(=O)-NH—, phenylC(=O)-NH—, methylamino-, ethylamino-, propylamino-, isopropylamino-, n-butylamino-, isobutylamino-, secbutylamino-, tertbutylamino-, phenylamino-, provided that two of substituents $R^7$, $R^8$, and $R^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;

k is 1 or 2; and n is 1 or 2.

18. A compound of claim 1 wherein b is a single bond.

19. A pharmaceutical composition comprising a pharmaceutically acceptable carrier and a therapeutically effective amount of a compound of claim 1 or a pharmaceutically acceptable salt thereof.

20. A method for treating a human suffering from a disorder associated with 5HT2C receptor modulation comprising administering to a patient in need thereof a therapeutically effective amount of a compound of claim 1, or a pharmaceutically acceptable salt thereof.

21. A method of claim 20 for treating a human suffering from a disorder associated with 5HT2C receptor modulation wherein the compound is a 5HT2C agonist.

22. A method for treating a human suffering from a disorder associated with 5HT2A receptor modulation comprising administering to a patient in need thereof a therapeutically effective amount of a compound of claim 1, or a pharmaceutically acceptable salt thereof.

23. A method of claim 22 for treating a human suffering from a disorder associated with 5HT2A receptor modulation wherein the compound is a 5HT2A antagonist.

24. A method for treating obesity comprising administering to a patient in need thereof a therapeutically effective amount of a compound of claim 1, or a pharmaceutically acceptable salt thereof.

25. A method for treating schizophrenia comprising administering to a patient in need thereof a therapeutically effective amount of compound of claim 1, or a pharmaceutically acceptable salt thereof.

26. A method for treating depression comprising administering to a patient in need thereof a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 6,849,619 B2
DATED : February 1, 2005
INVENTOR(S) : Robichaud et al.

It is certified that error appears in the above-identified patent and that said Letters Patent is hereby corrected as shown below:

Column 226,
Line 45, delete "$R^{111}$ is selected from" and insert -- $R^{11}$ is selected from -- therefor.

Signed and Sealed this

Seventeenth Day of May, 2005

JON W. DUDAS
*Director of the United States Patent and Trademark Office*

UNITED STATES PATENT AND TRADEMARK OFFICE
Certificate

Patent No. 6,849,619 B2                                                                                                  Patented: February 1, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Parthasarathi Rajagopalan, Madras (IN); Albert J. Robichaud, Ringoes, NJ (US); John M. Fevig, Doylestown, PA (US); Ian S. Mitchell, Lafayette, CO (US); Taekyu Lee, Doylestown, PA (US); Wenting Chen, Langhorne, PA (US); and Joseph Cacciola, Newark, DE (US).

Signed and Sealed this Fifteenth Day of April 2014.

*EMILY BERNHARDT*
*Supervisory Patent Examiner*
Art Unit 1624
Technology Center 1600

UNITED STATES PATENT AND TRADEMARK OFFICE
Certificate

Patent No. 6,849,619 B2                                                                 Patented: February 1, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Parthasarathi Rajagopalan, Madras (IN); Albert J. Robichaud, Ringoes, NJ (US); John M. Fevig, Doylestown, PA (US); Ian S. Mitchell, Lafayette, CO (US); Taekyu Lee, Doylestown, PA (US); Wenting Chen, Langhorne, PA (US); and Joseph Cacciola, Newark, DE (US).

Signed and Sealed this Thirteenth Day of May 2014.

JAMES WILSON
*Supervisory Patent Examiner*
Art Unit 1624
Technology Center 1600